US009012189B2

(12) United States Patent
Bastian et al.

(10) Patent No.: US 9,012,189 B2
(45) Date of Patent: Apr. 21, 2015

(54) MODIFIED ALCOHOL DEHYDROGENASES FOR THE PRODUCTION OF FUELS AND CHEMICALS

(75) Inventors: Sabine Bastian, Pasadena, CA (US); Frances Arnold, La Cañada, CA (US); Peter Meinhold, Denver, CO (US)

(73) Assignees: Gevo, Inc., Englewood, CO (US); The California Institute of Technology, Pasadena, CA (US)

( * ) Notice: Subject to any disclaimer, the term of this patent is extended or adjusted under 35 U.S.C. 154(b) by 597 days.

(21) Appl. No.: 13/025,805

(22) Filed: Feb. 11, 2011

(65) Prior Publication Data
US 2011/0201072 A1   Aug. 18, 2011

Related U.S. Application Data

(60) Provisional application No. 61/304,069, filed on Feb. 12, 2010, provisional application No. 61/308,568, filed on Feb. 26, 2010, provisional application No. 61/282,641, filed on Mar. 10, 2010, provisional application No. 61/352,133, filed on Jun. 7, 2010, provisional application No. 61/411,885, filed on Nov. 9, 2010, provisional application No. 61/430,801, filed on Jan. 7, 2011.

(51) Int. Cl.
*C12P 7/16*  (2006.01)
*C12N 15/81* (2006.01)
*C12N 9/04*  (2006.01)

(52) U.S. Cl.
CPC .............. *C12N 15/81* (2013.01); *C12N 9/0006* (2013.01); *C12P 7/16* (2013.01); *C12Y 102/01005* (2013.01); *C12Y 101/01* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 6,753,314 B1 * | 6/2004 | Giot et al. ............... | 424/1.69 |
| 8,017,376 B2 | 9/2011 | Dundon et al. | |
| 8,133,715 B2 * | 3/2012 | Buelter et al. ........... | 435/254.11 |
| 8,153,415 B2 * | 4/2012 | Buelter et al. ........... | 435/254.11 |
| 8,158,404 B2 * | 4/2012 | Lies et al. ............... | 435/254.2 |
| 2007/0092957 A1 | 4/2007 | Donaldson et al. | |
| 2011/0076733 A1 | 3/2011 | Urano et al. | |

FOREIGN PATENT DOCUMENTS

| WO | WO 2009/086423 A2 | 7/2009 |
|---|---|---|
| WO | WO 2012/027642 A1 | 3/2012 |

OTHER PUBLICATIONS

Bastian et al.*
"Request for *Inter Partes* Reexamination of U.S. Patent No. 8,133,715 Under 35 U.S.C. § 311 and 37 C.F.R. § 1.913," 3131 pages, U.S. Reexamination Control No. 95/002,159 (filed Sep. 7, 2012).
"Request for *Inter Partes* Reexamination of U.S. Patent No. 8,158,404 Under 35 U.S.C. § 311 and 37 C.F.R. § 1.913," 2583 pages, U.S. Reexamination Control No. 95/002,177 (filed Sep. 11, 2012).
"Request for *Inter Partes* Reexamination of U.S. Patent No. 8,153,415 Under 35 U.S.C. § 311 and 37 C.F.R. § 1.913,"3262 pages, U.S. Reexamination Control No. 95/002,174 (filed Sep. 10, 2012).
Overkamp et al., "Metabolic Engineering of Glycerol Production in *Saccaromyces cerevisiae*," *AEM* 68(6):2814-2821, American Society for Microbiology, United States (2002).
Van Maris et al., "Directed Evolution of Pyruvate Decarboxylase-Negative *Saccharomyces cerevisiae*, Yielding a $C_2$-Independent, Glucose-Tolerant, and P-yruvate-Hyperpproducing Yeast," *Appl. Environ. Microbiol.* 70(1):159-166, American Society for Microbiology, United States (2004).
Würdig et al., "Vorkommen, Nachweis und Bestimmung von 2-und 3-methyl-2,3-dihydroxybuttersä und 2-hydroxyglutarav im Wein," *Vitis* 8:216-230, Bundesanstalt fur Zuechtungsforschung an Kulturpflanzen, Germany (1969).
"Order Granting Inter Partes Reexamination of U.S. Patent No. 8,133,715," 35 pages, U.S. Reexamination Control No. 95/002,159 (mailed Dec. 3, 2012).
"Order Granting Inter Partes Reexamination of U.S. Patent No. 8,158,404," 20 pages, U.S. Reexamination Control No. 95/002,177 (mailed Dec. 10, 2012).
"Order Granting Inter Partes Reexamination of U.S. Patent No. 8,153,415," 38 pages, U.S. Reexamination Control No. 95/002,174 (mailed Dec. 7, 2012).
Written Opinion for International Application No. PCT/US2011/024482, 10 pages (mailed Apr. 9, 2012).
Scannell et al., "Independent sorting-out of thousands of duplicated gene pairs in two yeast species descended from a whole-genome duplication." PNAS 2007, Vo. 104(20): 8397-8402.
"Office Action in *Inter Partes* Reexamination of U.S. Patent No. 8,133,715," 46 pages, U.S. Reexamination Control No. 95/002,159 (mailed Jun. 14, 2013).
"Office Action in *Inter Partes* Reexamination of U.S. Patent No. 8,158,404," 28 pages, U.S. Reexamination Control No. 95/002,177 (mailed Jun. 14, 2013).
"Office Action in *Inter Partes* Reexamination of U.S. Patent No. 8,153,415," 47 pages, U.S. Reexamination Control No. 95/002,174 (mailed Jun. 14, 2013).

* cited by examiner

*Primary Examiner* — Hope Robinson
(74) *Attorney, Agent, or Firm* — Cooley LLP

(57) ABSTRACT

The present invention relates to recombinant microorganisms comprising biosynthetic pathways and methods of using said recombinant microorganisms to produce various beneficial metabolites. In various aspects of the invention, the recombinant microorganisms may further comprise one or more modifications resulting in the reduction or elimination of 3 keto-acid (e.g., acetolactate and 2-aceto-2-hydroxybutyrate) and/or aldehyde-derived by-products. In various embodiments described herein, the recombinant microorganisms may be microorganisms of the *Saccharomyces* clade, Crabtree-negative yeast microorganisms, Crabtree-positive yeast microorganisms, post-WGD (whole genome duplication) yeast microorganisms, pre-WGD (whole genome duplication) yeast microorganisms, and non-fermenting yeast microorganisms.

10 Claims, 22 Drawing Sheets

EC 1.1.1.30

EC 1.1.1.31

EC 1.1.1.103

EC 1.1.1.217

```
SEQUENCE LISTING

<160> NUMBER OF SEQ ID NOS: 268

<210> SEQ ID NO 1
<211> LENGTH: 267
<212> TYPE: PRT
<213> ORGANISM: Saccharomyces cerevisiae

<400> SEQUENCE: 1

Met Ser Gln Gly Arg Lys Ala Ala Glu Arg Leu Ala Lys Lys Thr Val
1               5                   10                  15

Leu Ile Thr Gly Ala Ser Ala Gly Ile Gly Lys Ala Thr Ala Leu Glu
            20                  25                  30

Tyr Leu Glu Ala Ser Asn Gly Asp Met Lys Leu Ile Leu Ala Ala Arg
```

```
                35                  40                  45
Arg Leu Glu Lys Leu Glu Glu Leu Lys Lys Thr Ile Asp Gln Glu Phe
 50                  55                  60

Pro Asn Ala Lys Val His Val Ala Gln Leu Asp Ile Thr Gln Ala Glu
65                  70                  75                  80

Lys Ile Lys Pro Phe Ile Glu Asn Leu Pro Gln Glu Phe Lys Asp Ile
                85                  90                  95

Asp Ile Leu Val Asn Asn Ala Gly Lys Ala Leu Gly Ser Asp Arg Val
                100                 105                 110

Gly Gln Ile Ala Thr Glu Asp Ile Gln Asp Val Phe Asp Thr Asn Val
                115                 120                 125

Thr Ala Leu Ile Asn Ile Thr Gln Ala Val Leu Pro Ile Phe Gln Ala
130                 135                 140

Lys Asn Ser Gly Asp Ile Val Asn Leu Gly Ser Ile Ala Gly Arg Asp
145                 150                 155                 160

Ala Tyr Pro Thr Gly Ser Ile Tyr Cys Ala Ser Lys Phe Ala Val Gly
                165                 170                 175

Ala Phe Thr Asp Ser Leu Arg Lys Glu Leu Ile Asn Thr Lys Ile Arg
                180                 185                 190

Val Ile Leu Ile Ala Pro Gly Leu Val Glu Thr Glu Phe Ser Leu Val
                195                 200                 205

Arg Tyr Arg Gly Asn Glu Glu Gln Ala Lys Asn Val Tyr Lys Asp Thr
210                 215                 220

Thr Pro Leu Met Ala Asp Asp Val Ala Asp Leu Ile Val Tyr Ala Thr
225                 230                 235                 240

Ser Arg Lys Gln Asn Thr Val Ile Ala Asp Thr Leu Ile Phe Pro Thr
                245                 250                 255

Asn Gln Ala Ser Pro His His Ile Phe Arg Gly
                260                 265

<210> SEQ ID NO 2
<211> LENGTH: 267
<212> TYPE: PRT
<213> ORGANISM: Kabatiella polyspora

<400> SEQUENCE: 2

Met Ser Gln Gly Arg Lys Ala Ser Glu Arg Leu Ala Gly Lys Thr Val
1               5                   10                  15

Leu Ile Thr Gly Ala Ser Ser Gly Ile Gly Lys Ala Thr Ala Leu Glu
                20                  25                  30

Tyr Leu Asp Ala Ser Asn Gly His Met Lys Leu Ile Leu Val Ala Arg
                35                  40                  45

Arg Leu Glu Lys Leu Gln Glu Leu Lys Glu Thr Ile Cys Lys Glu Tyr
 50                  55                  60

Pro Glu Ser Lys Val His Val Glu Glu Leu Asp Ile Ser Asp Ile Asn
65                  70                  75                  80

Arg Ile Pro Glu Phe Ile Ala Lys Leu Pro Glu Glu Phe Lys Asp Ile
                85                  90                  95

Asp Ile Leu Ile Asn Asn Ala Gly Lys Ala Leu Gly Ser Asp Thr Ile
                100                 105                 110

Gly Asn Ile Glu Asn Glu Asp Ile Lys Gly Met Phe Glu Thr Asn Val
                115                 120                 125

Phe Gly Leu Ile Cys Leu Thr Gln Ala Val Leu Pro Ile Phe Lys Ala
                130                 135                 140
```

```
Lys Asn Gly Gly Asp Ile Val Asn Leu Gly Ser Ile Ala Gly Ile Glu
145                 150                 155                 160

Ala Tyr Pro Thr Gly Ser Ile Tyr Cys Ala Thr Lys Phe Ala Val Lys
                165                 170                 175

Ala Phe Thr Glu Ser Leu Arg Lys Glu Leu Ile Asn Thr Lys Ile Arg
            180                 185                 190

Val Ile Glu Ile Ala Pro Gly Met Val Asn Thr Glu Phe Ser Val Ile
        195                 200                 205

Arg Tyr Lys Gly Asp Gln Glu Lys Ala Asp Lys Val Tyr Glu Asn Thr
    210                 215                 220

Thr Pro Leu Tyr Ala Asp Asp Ile Ala Asp Leu Ile Val Tyr Thr Thr
225                 230                 235                 240

Ser Arg Lys Ser Asn Thr Val Ile Ala Asp Val Leu Val Phe Pro Thr
                245                 250                 255

Cys Gln Ala Ser Ala Ser His Ile Tyr Arg Gly
                260                 265

<210> SEQ ID NO 3
<211> LENGTH: 267
<212> TYPE: PRT
<213> ORGANISM: Saccharomyces castellii

<400> SEQUENCE: 3

Met Ser Gln Gly Pro Lys Ala Ala Glu Arg Leu Asn Glu Lys Ile Val
1               5                   10                  15

Phe Ile Thr Gly Ala Ser Ala Gly Ile Gly Gln Ala Thr Ala Leu Glu
            20                  25                  30

Tyr Met Asp Ala Ser Asn Gly Thr Val Lys Leu Val Leu Val Ala Arg
        35                  40                  45

Arg Leu Glu Lys Leu Gln Gln Leu Lys Glu Val Ile Glu Ala Lys Tyr
    50                  55                  60

Pro Lys Ser Lys Val Tyr Ile Gly Lys Leu Asp Val Thr Glu Leu Glu
65                  70                  75                  80

Thr Ile Gln Pro Phe Leu Asp Asn Leu Pro Glu Glu Phe Lys Asp Ile
                85                  90                  95

Asp Ile Leu Ile Asn Asn Ala Gly Lys Ala Leu Gly Ser Asp Arg Val
            100                 105                 110

Gly Asp Ile Asp Ile Lys Asp Val Lys Gly Met Met Asp Thr Asn Val
        115                 120                 125

Leu Gly Leu Ile Asn Val Thr Gln Ala Val Leu His Ile Phe Gln Lys
    130                 135                 140

Lys Asn Ser Gly Asp Ile Val Asn Leu Gly Ser Val Ala Gly Arg Asp
145                 150                 155                 160

Ala Tyr Pro Thr Gly Ser Ile Tyr Cys Ala Ser Lys Phe Ala Val Arg
                165                 170                 175

Ala Phe Thr Glu Ser Leu Arg Arg Glu Leu Ile Asn Thr Lys Ile Arg
            180                 185                 190

Val Ile Leu Ile Ala Pro Gly Ile Val Glu Thr Glu Phe Ser Val Val
        195                 200                 205

Arg Tyr Lys Gly Asp Asn Glu Arg Ala Lys Ser Val Tyr Asp Gly Val
    210                 215                 220

His Pro Leu Glu Ala Asp Asp Val Ala Asp Leu Ile Val Tyr Thr Thr
225                 230                 235                 240

Ser Arg Lys Gln Asn Thr Val Ile Ala Asp Thr Leu Ile Phe Pro Thr
                245                 250                 255
```

Ser Gln Gly Ser Ala Phe His Val His Arg Asp
            260                 265

<210> SEQ ID NO 4
<211> LENGTH: 268
<212> TYPE: PRT
<213> ORGANISM: Candida glabrata

<400> SEQUENCE: 4

Met Ser Gln Gly Arg Lys Ala Ala Glu Arg Leu Gln Gly Lys Ile Ala
1               5                   10                  15

Phe Ile Thr Gly Ala Ser Ala Gly Ile Gly Lys Ala Thr Ala Ile Glu
            20                  25                  30

Tyr Leu Asp Ala Ser Asn Gly Ser Val Lys Leu Val Leu Gly Ala Arg
        35                  40                  45

Arg Met Glu Lys Leu Glu Glu Leu Lys Lys Glu Leu Leu Ala Gln Tyr
    50                  55                  60

Pro Asp Ala Lys Ile His Ile Gly Lys Leu Asp Val Thr Asp Phe Glu
65                  70                  75                  80

Asn Val Lys Gln Phe Leu Ala Asp Leu Pro Glu Glu Phe Lys Asp Ile
                85                  90                  95

Asp Ile Leu Ile Asn Asn Ala Gly Lys Ala Leu Gly Ser Asp Lys Val
            100                 105                 110

Gly Asp Ile Asp Pro Glu Asp Ile Ala Gly Met Val Asn Thr Asn Val
        115                 120                 125

Leu Ala Leu Ile Asn Leu Thr Gln Leu Leu Pro Leu Phe Lys Lys
    130                 135                 140

Lys Asn Ser Gly Asp Ile Val Asn Leu Gly Ser Ile Ala Gly Arg Asp
145                 150                 155                 160

Ala Tyr Pro Thr Gly Ala Ile Tyr Cys Ala Thr Lys His Ala Val Arg
                165                 170                 175

Ala Phe Thr Gln Ser Leu Arg Lys Glu Leu Ile Asn Thr Asp Ile Arg
            180                 185                 190

Val Ile Glu Ile Ala Pro Gly Met Val Glu Thr Glu Phe Ser Val Val
        195                 200                 205

Arg Tyr Lys Gly Asp Lys Ser Lys Ala Asp Asp Val Tyr Arg Gly Thr
    210                 215                 220

Thr Pro Leu Tyr Ala Asp Asp Ile Ala Asp Leu Ile Val Tyr Ser Thr
225                 230                 235                 240

Ser Arg Lys Pro Asn Met Val Val Ala Asp Val Leu Val Phe Pro Thr
                245                 250                 255

His Gln Ala Ser Ala Ser His Ile Tyr Arg Gly Asp
            260                 265

<210> SEQ ID NO 5
<211> LENGTH: 267
<212> TYPE: PRT
<213> ORGANISM: Saccharomyces bayanus

<400> SEQUENCE: 5

Met Ser Gln Gly Arg Lys Ala Ala Glu Arg Leu Ala Asn Lys Thr Val
1               5                   10                  15

Leu Ile Thr Gly Ala Ser Ala Gly Ile Gly Lys Ala Thr Ala Leu Glu
            20                  25                  30

Tyr Leu Glu Ala Ser Asn Gly Asn Met Lys Leu Ile Leu Ala Ala Arg
        35                  40                  45

```
Arg Leu Glu Lys Leu Glu Glu Leu Lys Lys Thr Ile Asp Glu Glu Phe
     50                  55                  60

Pro Asn Ala Lys Val His Val Gly Gln Leu Asp Ile Thr Gln Ala Glu
 65                  70                  75                  80

Lys Ile Lys Pro Phe Ile Glu Asn Leu Pro Glu Ala Phe Lys Asp Ile
                 85                  90                  95

Asp Ile Leu Ile Asn Asn Ala Gly Lys Ala Leu Gly Ser Glu Arg Val
                100                 105                 110

Gly Glu Ile Ala Thr Gln Asp Ile Gln Asp Val Phe Asp Thr Asn Val
             115                 120                 125

Thr Ala Leu Ile Asn Val Thr Gln Ala Val Leu Pro Ile Phe Gln Ala
130                 135                 140

Lys Asn Ser Gly Asp Ile Val Asn Leu Gly Ser Val Ala Gly Arg Asp
145                 150                 155                 160

Ala Tyr Pro Thr Gly Ser Ile Tyr Cys Ala Ser Lys Phe Ala Val Gly
                165                 170                 175

Ala Phe Thr Asp Ser Leu Arg Lys Glu Leu Ile Asn Thr Lys Ile Arg
             180                 185                 190

Val Ile Leu Ile Ala Pro Gly Leu Val Glu Thr Glu Phe Ser Leu Val
         195                 200                 205

Arg Tyr Arg Gly Asn Glu Glu Gln Ala Lys Asn Val Tyr Lys Asp Thr
     210                 215                 220

Thr Pro Leu Met Ala Asp Asp Val Ala Asp Leu Ile Val Tyr Ser Thr
225                 230                 235                 240

Ser Arg Lys Gln Asn Thr Val Val Ala Asp Thr Leu Ile Phe Pro Thr
                245                 250                 255

Asn Gln Ala Ser Pro Tyr His Ile Phe Arg Gly
            260                 265

<210> SEQ ID NO 6
<211> LENGTH: 273
<212> TYPE: PRT
<213> ORGANISM: Zygosaccharomyces rouxii

<400> SEQUENCE: 6

Met Ser Gln Gly Val Lys Ala Ala Glu Arg Leu Ala Gly Lys Thr Val
 1               5                  10                  15

Phe Ile Thr Gly Ala Ser Ala Gly Ile Gly Gln Ala Thr Ala Lys Glu
             20                  25                  30

Tyr Leu Asp Ala Ser Asn Gly Gln Ile Lys Leu Ile Leu Ala Ala Arg
         35                  40                  45

Arg Leu Glu Lys Leu His Glu Phe Lys Glu Gln Thr Thr Lys Ser Tyr
     50                  55                  60

Pro Ser Ala Gln Val His Ile Gly Lys Leu Asp Val Thr Ala Ile Asp
 65                  70                  75                  80

Thr Ile Lys Pro Phe Leu Asp Lys Leu Pro Lys Glu Phe Gln Asp Ile
                 85                  90                  95

Asp Ile Leu Ile Asn Asn Ala Gly Lys Ala Leu Gly Thr Asp Lys Val
                100                 105                 110

Gly Asp Ile Ala Asp Glu Asp Val Glu Gly Met Phe Asp Thr Asn Val
             115                 120                 125

Leu Gly Leu Ile Lys Val Thr Gln Ala Val Leu Pro Ile Phe Lys Arg
130                 135                 140

Lys Asn Ser Gly Asp Val Val Asn Ile Ser Ser Val Ala Gly Arg Glu
```

```
            145                 150                 155                 160
Ala Tyr Pro Gly Gly Ser Ile Tyr Cys Ala Thr Lys His Ala Val Lys
                165                 170                 175

Ala Phe Thr Glu Ser Leu Arg Lys Glu Leu Val Asp Thr Lys Ile Arg
                180                 185                 190

Val Met Ser Ile Asp Pro Gly Asn Val Glu Thr Glu Phe Ser Met Val
                195                 200                 205

Arg Phe Arg Gly Asp Thr Glu Lys Ala Lys Val Tyr Gln Asp Thr
            210                 215                 220

Val Pro Leu Tyr Ala Asp Asp Ile Ala Asp Leu Ile Val Tyr Ala Thr
225                 230                 235                 240

Ser Arg Lys Gln Asn Thr Val Ile Ala Asp Thr Leu Ile Phe Ser Ser
                245                 250                 255

Asn Gln Ala Ser Pro Tyr His Leu Tyr Arg Gly Ser Gln Asp Lys Thr
                260                 265                 270

Asn

<210> SEQ ID NO 7
<211> LENGTH: 268
<212> TYPE: PRT
<213> ORGANISM: Kluyveromyces lactis

<400> SEQUENCE: 7

Met Ser Gln Gly Arg Lys Ala Ala Glu Arg Leu Gln Asn Lys Thr Ile
1               5                   10                  15

Phe Ile Thr Gly Ala Ser Ala Gly Ile Gly Gln Ala Thr Ala Leu Glu
                20                  25                  30

Tyr Leu Asp Ala Ala Asn Gly Asn Val Lys Leu Ile Leu Ala Ala Arg
            35                  40                  45

Arg Leu Ala Lys Leu Glu Glu Leu Lys Glu Lys Ile Asn Ala Glu Tyr
        50                  55                  60

Pro Gln Ala Lys Val Tyr Ile Gly Gln Leu Asp Val Thr Glu Thr Glu
65                  70                  75                  80

Lys Ile Gln Pro Phe Ile Asp Asn Leu Pro Glu Glu Phe Lys Asp Ile
                85                  90                  95

Asp Ile Leu Ile Asn Asn Ala Gly Lys Ala Leu Gly Ser Asp Val Val
                100                 105                 110

Gly Thr Ile Ser Ser Glu Asp Ile Lys Gly Met Ile Asp Thr Asn Val
            115                 120                 125

Val Ala Leu Ile Asn Val Thr Gln Ala Val Leu Pro Ile Phe Lys Ala
        130                 135                 140

Lys Asn Ser Gly Asp Ile Val Asn Leu Gly Ser Val Ala Gly Arg Asp
145                 150                 155                 160

Ala Tyr Pro Thr Gly Ser Ile Tyr Cys Ala Ser Lys His Ala Val Arg
                165                 170                 175

Ala Phe Thr Gln Ser Leu Arg Lys Glu Leu Ile Asn Thr Gly Ile Arg
                180                 185                 190

Val Ile Glu Ile Ala Pro Gly Asn Val Glu Thr Glu Phe Ser Leu Val
            195                 200                 205

Arg Tyr Lys Gly Asp Ala Asp Arg Ala Lys Gln Val Tyr Lys Gly Thr
        210                 215                 220

Thr Pro Leu Tyr Ala Asp Asp Ile Ala Asp Leu Ile Val Tyr Ala Thr
225                 230                 235                 240

Ser Arg Lys Pro Asn Thr Val Ile Ala Asp Val Leu Val Phe Ala Ser
```

```
                        245                 250                 255
Asn Gln Ala Ser Pro Tyr His Ile Tyr Arg Gly Glu
                260                 265

<210> SEQ ID NO 8
<211> LENGTH: 267
<212> TYPE: PRT
<213> ORGANISM: Ashbya gossypii

<400> SEQUENCE: 8

Met Ser Leu Gly Arg Lys Ala Ala Glu Arg Leu Ala Asn Lys Ile Val
1               5                   10                  15

Leu Val Thr Gly Ala Ser Ala Gly Ile Gly Arg Ala Thr Ala Ile Asn
            20                  25                  30

Tyr Ala Asp Ala Thr Asp Gly Ala Ile Lys Leu Ile Leu Val Ala Arg
        35                  40                  45

Arg Ala Glu Lys Leu Thr Ser Leu Lys Gln Glu Ile Glu Ser Lys Tyr
    50                  55                  60

Pro Asn Ala Lys Ile His Val Gly Gln Leu Asp Val Thr Gln Leu Asp
65                  70                  75                  80

Gln Ile Arg Pro Phe Leu Glu Gly Leu Pro Glu Glu Phe Arg Asp Ile
                85                  90                  95

Asp Ile Leu Ile Asn Asn Ala Gly Lys Ala Leu Gly Thr Glu Arg Val
            100                 105                 110

Gly Glu Ile Ser Met Asp Asp Ile Gln Glu Val Phe Asn Thr Asn Val
        115                 120                 125

Ile Gly Leu Val His Leu Thr Gln Glu Val Leu Pro Ile Met Lys Ala
    130                 135                 140

Lys Asn Ser Gly Asp Ile Val Asn Val Gly Ser Ile Ala Gly Arg Glu
145                 150                 155                 160

Ala Tyr Pro Gly Gly Ser Ile Tyr Cys Ala Thr Lys His Ala Val Lys
                165                 170                 175

Ala Phe Thr Arg Ala Met Arg Lys Glu Leu Ile Ser Thr Lys Ile Arg
            180                 185                 190

Val Phe Glu Ile Ala Pro Gly Ser Val Glu Thr Glu Phe Ser Met Val
        195                 200                 205

Arg Met Arg Gly Asn Glu Glu Asn Ala Lys Lys Val Tyr Gln Gly Phe
    210                 215                 220

Glu Pro Leu Asp Gly Asp Asp Ile Ala Asp Thr Ile Val Tyr Ala Thr
225                 230                 235                 240

Ser Arg Arg Ser Asn Thr Val Val Ala Glu Met Val Val Tyr Pro Ser
                245                 250                 255

Ala Gln Gly Ser Leu Tyr Asp Thr His Arg Asn
            260                 265

<210> SEQ ID NO 9
<211> LENGTH: 268
<212> TYPE: PRT
<213> ORGANISM: Saccharomyces kluyveri

<400> SEQUENCE: 9

Met Ser Gln Gly Arg Arg Ala Ala Glu Arg Leu Ala Asn Lys Thr Val
1               5                   10                  15

Phe Ile Thr Gly Ala Ser Ala Gly Ile Gly Gln Ala Thr Ala Leu Glu
            20                  25                  30

Tyr Cys Asp Ala Ser Asn Gly Lys Ile Asn Leu Val Leu Ser Ala Arg
```

```
                35                  40                  45
Arg Leu Glu Lys Leu Gln Glu Leu Lys Asp Lys Ile Thr Lys Glu Tyr
 50                  55                  60

Pro Glu Ala Lys Val Tyr Ile Gly Val Leu Asp Val Thr Glu Thr Glu
65                  70                  75                  80

Lys Ile Lys Pro Phe Leu Asp Gly Leu Pro Glu Glu Phe Lys Asp Ile
                85                  90                  95

Asp Ile Leu Ile Asn Asn Ala Gly Lys Ala Leu Gly Ser Asp Pro Val
                100                 105                 110

Gly Thr Ile Lys Thr Glu Asp Ile Glu Gly Met Ile Asn Thr Asn Val
                115                 120                 125

Leu Ala Leu Ile Asn Ile Thr Gln Ala Val Leu Pro Ile Phe Lys Ala
        130                 135                 140

Lys Asn Phe Gly Asp Ile Val Asn Leu Gly Ser Val Ala Gly Arg Asp
145                 150                 155                 160

Ala Tyr Pro Thr Gly Ala Ile Tyr Cys Ala Ser Lys His Ala Val Arg
                165                 170                 175

Ala Phe Thr Gln Ser Leu Arg Lys Glu Leu Val Asn Thr Asn Ile Arg
                180                 185                 190

Val Ile Glu Ile Ala Pro Gly Asn Val Glu Thr Glu Phe Ser Leu Val
        195                 200                 205

Arg Tyr Lys Gly Asp Thr Asp Arg Ala Lys Lys Val Tyr Glu Gly Thr
210                 215                 220

Asn Pro Leu Tyr Ala Asp Asp Ile Ala Asp Leu Ile Val Tyr Ala Thr
225                 230                 235                 240

Ser Arg Lys Pro Asn Thr Val Ile Ala Asp Val Leu Val Phe Ala Ser
                245                 250                 255

Asn Gln Ala Ser Pro Tyr His Ile Tyr Arg Gly Asp
                260                 265

<210> SEQ ID NO 10
<211> LENGTH: 267
<212> TYPE: PRT
<213> ORGANISM: Kluyveromyces thermotolerans

<400> SEQUENCE: 10

Met Ser Gln Gly Arg Ala Ala Glu Arg Leu Ala Gly Lys Thr Val
1               5                   10                  15

Phe Ile Thr Gly Ala Ser Ala Gly Ile Gly Gln Ala Thr Ala Gln Glu
                20                  25                  30

Tyr Leu Glu Ala Ser Glu Gly Lys Ile Lys Leu Ile Leu Ala Ala Arg
        35                  40                  45

Arg Leu Asp Lys Leu Glu Glu Ile Lys Ala Lys Val Ser Lys Asp Phe
 50                  55                  60

Pro Glu Ala Gln Val His Ile Gly Gln Leu Asp Val Thr Gln Thr Asp
65                  70                  75                  80

Lys Ile Gln Pro Phe Val Asp Asn Leu Pro Glu Glu Phe Lys Asp Ile
                85                  90                  95

Asp Ile Leu Ile Asn Asn Ala Gly Lys Ala Leu Gly Ser Asp Pro Val
                100                 105                 110

Gly Thr Ile Asp Pro Asn Asp Ile Gln Gly Met Ile Gln Thr Asn Val
                115                 120                 125

Ile Gly Leu Ile Asn Val Thr Gln Ala Val Leu Pro Ile Phe Lys Ala
        130                 135                 140
```

```
Lys Asn Ser Gly Asp Ile Val Asn Leu Gly Ser Val Ala Gly Arg Glu
145                 150                 155                 160

Ala Tyr Pro Thr Gly Ser Ile Tyr Cys Ala Thr Lys His Ala Val Arg
                165                 170                 175

Ala Phe Thr Gln Ser Leu Arg Lys Glu Leu Ile Asn Thr Asn Ile Arg
            180                 185                 190

Val Ile Glu Val Ala Pro Gly Asn Val Glu Thr Glu Phe Ser Leu Val
        195                 200                 205

Arg Tyr Lys Gly Asp Ser Lys Ala Lys Lys Val Tyr Glu Gly Thr
    210                 215                 220

Gln Pro Leu Tyr Ala Asp Asp Ile Ala Asp Leu Ile Val Tyr Ala Thr
225                 230                 235                 240

Ser Arg Lys Pro Asn Thr Val Ile Ala Asp Val Leu Val Phe Ala Ser
                245                 250                 255

Asn Gln Ala Ser Pro Tyr His Ile Tyr Arg Gly
                260                 265
```

<210> SEQ ID NO 11
<211> LENGTH: 267
<212> TYPE: PRT
<213> ORGANISM: Kluyveromyces waltii

<400> SEQUENCE: 11

```
Met Ser Gln Gly Arg Lys Ala Ser Glu Arg Leu Ala Gly Lys Thr Val
1               5                   10                  15

Leu Ile Thr Gly Ala Ser Ala Gly Ile Gly Gln Ala Thr Ala Leu Glu
            20                  25                  30

Tyr Leu Asp Ala Ser Asn Gly Asn Ile Lys Leu Ile Leu Ala Ala Arg
        35                  40                  45

Arg Leu Glu Lys Leu Lys Glu Ile Lys Ser Gln Phe Glu Lys Asp Phe
    50                  55                  60

Pro Glu Ala Lys Val Tyr Ile Gly Gln Leu Asp Val Thr His Thr Asp
65                  70                  75                  80

Glu Ile Lys Pro Phe Ile Asp Asn Leu Pro Glu Glu Phe Lys Asp Ile
                85                  90                  95

Asp Ile Leu Ile Asn Asn Ala Gly Lys Ala Leu Gly Ser Asp Pro Val
            100                 105                 110

Gly Thr Ile Asp Ala Ser Asp Ile Glu Gly Met Ile Gln Thr Asn Val
        115                 120                 125

Val Ala Leu Ile Asn Met Thr Gln Ala Val Leu Pro Ile Phe Lys Ala
    130                 135                 140

Lys Asn Ala Gly Asp Ile Val Asn Leu Gly Ser Val Ala Gly Arg Glu
145                 150                 155                 160

Ala Tyr Pro Thr Gly Ser Ile Tyr Cys Ala Thr Lys His Ala Val Arg
                165                 170                 175

Ala Phe Thr Gln Ser Leu Arg Lys Glu Leu Ile Asn Thr Asn Ile Arg
            180                 185                 190

Val Ile Glu Ile Ala Pro Gly Asn Val Glu Thr Glu Phe Ser Leu Val
        195                 200                 205

Arg Tyr Lys Gly Asp Pro Glu Lys Ala Lys Lys Val Tyr Glu Gly Thr
    210                 215                 220

Thr Pro Leu Tyr Ala Asp Asp Ile Ala Asp Leu Ile Val Tyr Ala Thr
225                 230                 235                 240

Ser Arg Lys Ser Asn Thr Val Ile Ala Asp Val Leu Val Phe Ala Ser
                245                 250                 255
```

```
Asn Gln Ala Ser Pro Tyr His Ile Tyr Arg Gly
            260                 265

<210> SEQ ID NO 12
<211> LENGTH: 269
<212> TYPE: PRT
<213> ORGANISM: Pichia stipitis

<400> SEQUENCE: 12

Met Ser Phe Gly Lys Lys Ala Ala Glu Arg Leu Ala Asn Lys Ile Ile
1               5                   10                  15

Leu Ile Thr Gly Ala Ser Ser Gly Ile Gly Glu Ala Thr Ala Arg Glu
            20                  25                  30

Phe Ala Ser Ala Ala Asn Gly Asn Ile Arg Leu Ile Leu Thr Ala Arg
        35                  40                  45

Arg Lys Glu Lys Leu Ala Gln Leu Ser Asp Ser Leu Thr Lys Glu Phe
    50                  55                  60

Pro Thr Ile Lys Ile His Ser Ala Lys Leu Asp Val Thr Glu His Asp
65                  70                  75                  80

Gly Ile Lys Pro Phe Ile Ser Gly Leu Pro Lys Asp Phe Ala Asp Ile
                85                  90                  95

Asp Val Leu Ile Asn Asn Ala Gly Lys Ala Leu Gly Lys Ala Ser Val
            100                 105                 110

Gly Glu Ile Ser Asp Ser Asp Ile Gln Gly Met Met Gln Thr Asn Val
        115                 120                 125

Leu Gly Leu Ile Asn Met Thr Gln Ala Val Ile Pro Ile Phe Lys Ala
    130                 135                 140

Lys Asn Ser Gly Asp Ile Val Asn Ile Gly Ser Ile Ala Gly Arg Asp
145                 150                 155                 160

Pro Tyr Pro Gly Gly Ser Ile Tyr Cys Ala Ser Lys Ala Ala Val Lys
                165                 170                 175

Phe Phe Ser His Ser Leu Arg Lys Glu Leu Ile Asn Thr Arg Ile Arg
            180                 185                 190

Val Leu Glu Val Asp Pro Gly Ala Val Leu Thr Glu Phe Ser Leu Val
        195                 200                 205

Arg Phe His Gly Asp Gln Gly Ala Ala Asp Ala Val Tyr Glu Gly Thr
    210                 215                 220

Gln Pro Leu Asp Ala Ser Asp Ile Ala Glu Val Ile Val Phe Gly Ile
225                 230                 235                 240

Thr Arg Lys Gln Asn Thr Val Ile Ala Glu Thr Leu Val Phe Pro Ser
                245                 250                 255

His Gln Ala Ser Ala Ser His Val Tyr Lys Ala Pro Lys
            260                 265

<210> SEQ ID NO 13
<211> LENGTH: 270
<212> TYPE: PRT
<213> ORGANISM: Debaryomyces hansenii

<400> SEQUENCE: 13

Met Ser Tyr Gly Ser Lys Ala Ala Glu Arg Val Ala Asn Lys Ile Val
1               5                   10                  15

Leu Ile Thr Gly Ala Ser Ser Gly Ile Gly Glu Ala Thr Ala Lys Glu
            20                  25                  30

Ile Ala Ser Ala Ala Asn Gly Asn Leu Lys Leu Val Leu Cys Ala Arg
        35                  40                  45
```

```
Arg Lys Glu Lys Leu Asp Asn Leu Ser Lys Glu Leu Thr Asp Lys Tyr
     50                  55                  60

Ser Ser Ile Lys Val His Val Ala Gln Leu Asp Val Ser Lys Leu Glu
65                  70                  75                  80

Thr Ile Lys Pro Phe Ile Asn Asp Leu Pro Lys Glu Phe Ser Asp Val
                 85                  90                  95

Asp Val Leu Val Asn Asn Ala Gly Leu Ala Leu Gly Arg Asp Glu Val
             100                 105                 110

Gly Thr Ile Asp Thr Asp Asp Met Leu Ser Met Phe Gln Thr Asn Val
            115                 120                 125

Leu Gly Leu Ile Thr Ile Thr Gln Ala Val Leu Pro Ile Met Lys Lys
    130                 135                 140

Lys Asn Ser Gly Asp Val Val Asn Ile Gly Ser Ile Ala Gly Arg Asp
145                 150                 155                 160

Ser Tyr Pro Gly Gly Gly Ile Tyr Cys Pro Thr Lys Ala Ser Val Lys
                165                 170                 175

Ser Phe Ser Gln Val Leu Arg Lys Glu Leu Ile Ser Thr Lys Ile Arg
            180                 185                 190

Val Leu Glu Val Asp Pro Gly Asn Val Glu Thr Glu Phe Ser Asn Val
        195                 200                 205

Arg Phe Lys Gly Asp Met Glu Lys Ala Lys Ser Val Tyr Ala Gly Thr
    210                 215                 220

Glu Pro Leu Leu Ser Glu Asp Val Ala Glu Val Val Phe Gly Leu
225                 230                 235                 240

Thr Arg Lys Gln Asn Thr Val Ile Ala Glu Thr Leu Val Phe Ser Thr
                245                 250                 255

Asn Gln Ala Ser Ser Ser His Leu Tyr Arg Glu Ser Asp Lys
            260                 265                 270

<210> SEQ ID NO 14
<211> LENGTH: 269
<212> TYPE: PRT
<213> ORGANISM: Pichia pastoris

<400> SEQUENCE: 14

Met Ser Tyr Gly Leu Ala Ala Ala Ser Arg Leu Ala Gly Lys Val Ile
1               5                   10                  15

Leu Ile Thr Gly Ala Ser Ser Gly Ile Gly Glu Ala Thr Ala Leu Glu
            20                  25                  30

Tyr Ala Asn Ala Ala Lys Gly Glu Ile Lys Leu Ala Leu Ser Ala Arg
        35                  40                  45

Arg Phe Glu Lys Leu Glu Gly Leu Lys Glu Lys Leu Thr Thr Gln Trp
    50                  55                  60

Pro Asn Ile Lys Val His Ile Ala Leu Leu Asp Val Ser Asn Ile Ala
65                  70                  75                  80

Lys Leu Thr Glu Tyr Val Glu Ser Leu Pro Glu Glu Phe Lys Ala Val
                85                  90                  95

Asp Val Leu Val Asn Asn Ala Gly Lys Ala Leu Gly Ile Asp Arg Val
            100                 105                 110

Gly Gln Ile Leu Gln Glu Asp Ile Asp Gly Met Phe Gln Thr Asn Val
        115                 120                 125

Ile Gly Leu Ile Ser Leu Thr Gln Leu Ile Leu Pro Gly Met Lys Ala
    130                 135                 140

Arg Asn Arg Gly Asp Ile Ile Gln Leu Gly Ser Ile Ala Gly Arg Asp
```

```
                145                 150                 155                 160
        Pro Tyr Pro Gly Gly Gly Ile Tyr Cys Ala Thr Lys Ala Ala Val Arg
                            165                 170                 175

Ser Phe Ser His Ser Leu Arg Lys Glu Leu Ile Asp Thr Lys Ile Arg
                            180                 185                 190

Val Ile Glu Ile Asp Pro Gly Ala Val Gln Thr Glu Phe Ser Leu Val
                        195                 200                 205

Arg Tyr Lys Gly Ser Lys Glu Ser Ala Ser Lys Val Tyr Glu Gly Ala
                    210                 215                 220

Glu Pro Leu Asn Ala Leu Asp Ile Ala Glu Leu Ile Val Phe Ala Ser
        225                 230                 235                 240

Thr Arg Arg Glu Asn Thr Val Val Ala Glu Thr Leu Val Phe Pro Thr
                            245                 250                 255

Asn Gln Ala Gly Ala Gly Tyr Val Tyr Arg Lys Lys Asp
                            260                 265

<210> SEQ ID NO 15
<211> LENGTH: 268
<212> TYPE: PRT
<213> ORGANISM: Candida dubliniensis

<400> SEQUENCE: 15

Met Ser Phe Gly Arg Lys Ala Ala Glu Arg Leu Ala Asn Arg Ser Ile
        1               5                   10                  15

Leu Ile Thr Gly Ala Ser Ser Gly Ile Gly Glu Ala Cys Ala Lys Val
                        20                  25                  30

Phe Ala Glu Ala Ser Asn Gly Gln Val Lys Leu Val Leu Gly Ala Arg
                    35                  40                  45

Arg Lys Glu Arg Leu Val Lys Leu Ser Asp Thr Leu Ile Lys Gln Tyr
                50                  55                  60

Pro Asn Ile Lys Ile His His Asp Phe Leu Asp Val Thr Ile Lys Asp
        65                  70                  75                  80

Ser Ile Ser Lys Phe Ile Ala Gly Ile Pro His Glu Phe Glu Pro Asp
                        85                  90                  95

Val Leu Ile Asn Asn Ser Gly Lys Ala Leu Gly Lys Glu Glu Val Gly
                    100                 105                 110

Glu Leu Lys Asp Glu Asp Ile Thr Glu Met Phe Asp Thr Asn Val Ile
                115                 120                 125

Gly Val Ile Arg Met Thr Gln Ala Val Leu Pro Leu Leu Lys Lys Lys
        130                 135                 140

Pro Tyr Ala Asp Val Val Phe Ile Gly Ser Ile Ala Gly Arg Val Pro
        145                 150                 155                 160

Tyr Lys Asn Gly Gly Gly Tyr Cys Ala Ser Lys Ala Ala Val Arg Ser
                            165                 170                 175

Phe Thr Asp Thr Phe Arg Lys Glu Thr Ile Asn Thr Gly Ile Arg Val
                        180                 185                 190

Ile Glu Val Asp Pro Gly Ala Val Leu Thr Glu Phe Ser Val Val Arg
                    195                 200                 205

Tyr Lys Gly Asp Thr Asp Ala Ala Asp Ala Val Tyr Thr Gly Thr Glu
                210                 215                 220

Pro Leu Thr Pro Glu Asp Val Ala Glu Val Val Phe Ala Ser Ser
        225                 230                 235                 240

Arg Lys Gln Asn Thr Val Ile Ala Asp Thr Leu Ile Phe Pro Asn His
                            245                 250                 255
```

Gln Ala Ser Pro Asp His Val Tyr Arg Lys Pro Asn
            260                 265

<210> SEQ ID NO 16
<211> LENGTH: 268
<212> TYPE: PRT
<213> ORGANISM: Candida albicans

<400> SEQUENCE: 16

Met Ser Phe Gly Arg Lys Ala Ala Glu Arg Leu Ala Asn Arg Ser Ile
1               5                   10                  15

Leu Ile Thr Gly Ala Ser Ser Gly Ile Gly Glu Ala Cys Ala Lys Val
            20                  25                  30

Phe Ala Glu Ala Ser Asn Gly Gln Ile Lys Leu Ile Leu Gly Ala Arg
        35                  40                  45

Arg Lys Glu Arg Leu Ile Lys Leu Ser Asp Thr Leu Ile Lys Gln Tyr
    50                  55                  60

Pro Asn Ile Lys Ile His His Asp Phe Leu Asp Val Thr Ile Lys Asp
65                  70                  75                  80

Ser Ile Ser Lys Phe Ile Ala Gly Ile Pro Thr Asp Phe Glu Pro Asp
                85                  90                  95

Val Leu Ile Asn Asn Ser Gly Lys Ala Leu Gly Lys Glu Gln Val Gly
            100                 105                 110

Glu Leu Lys Asp Glu Asp Ile Thr Glu Met Leu Asp Thr Asn Val Val
        115                 120                 125

Gly Val Ile Arg Met Thr Gln Ala Val Leu Pro Leu Leu Lys Lys Lys
    130                 135                 140

Asn Tyr Ala Asp Val Val Phe Ile Gly Ser Ile Ala Gly Arg Val Ala
145                 150                 155                 160

Tyr Lys Asn Gly Gly Tyr Cys Ala Ser Lys Ala Ala Val Arg Ser
                165                 170                 175

Phe Val Asp Thr Phe Arg Lys Glu Thr Ile Asp Thr Gly Ile Arg Val
            180                 185                 190

Ile Glu Val Asp Pro Gly Ala Val Leu Thr Glu Phe Ser Val Val Arg
        195                 200                 205

Tyr Lys Gly Asp Thr Glu Ala Ala Asp Ala Val Tyr Thr Gly Thr Glu
    210                 215                 220

Pro Leu Thr Pro Glu Asp Val Ala Glu Val Val Phe Ala Ala Ser
225                 230                 235                 240

Arg Lys Gln Asn Thr Val Ile Ala Asp Thr Leu Ile Phe Pro Asn His
                245                 250                 255

Gln Ala Ser Pro Asp His Val Tyr Arg Lys Pro Asn
            260                 265

<210> SEQ ID NO 17
<211> LENGTH: 268
<212> TYPE: PRT
<213> ORGANISM: Yarrowia lipolytica

<400> SEQUENCE: 17

Met Ser Phe Gly Asp Lys Ala Ala Ala Arg Leu Ala Gly Lys Thr Val
1               5                   10                  15

Phe Val Thr Gly Ala Ser Ser Gly Ile Gly Gln Ala Thr Val Leu Ala
            20                  25                  30

Leu Ala Glu Ala Ala Lys Gly Asp Leu Lys Phe Val Leu Ala Ala Arg
        35                  40                  45

```
Arg Thr Asp Arg Leu Asp Glu Leu Lys Lys Lys Leu Glu Thr Asp Tyr
    50                  55                  60

Lys Gly Ile Gln Val Leu Pro Phe Lys Leu Asp Val Ser Lys Val Glu
 65                  70                  75                  80

Glu Thr Glu Asn Ile Val Ser Lys Leu Pro Lys Glu Phe Ser Glu Val
                 85                  90                  95

Asp Val Leu Ile Asn Asn Ala Gly Met Val His Gly Thr Glu Lys Val
                100                 105                 110

Gly Ser Ile Asn Gln Asn Asp Ile Glu Ile Met Phe His Thr Asn Val
                115                 120                 125

Leu Gly Leu Ile Ser Val Thr Gln Gln Phe Val Gly Glu Met Arg Lys
    130                 135                 140

Arg Asn Lys Gly Asp Ile Val Asn Ile Gly Ser Ile Ala Gly Arg Glu
145                 150                 155                 160

Pro Tyr Val Gly Gly Ile Tyr Cys Ala Thr Lys Ala Ala Val Arg
                165                 170                 175

Ser Phe Thr Glu Thr Leu Arg Lys Glu Asn Ile Asp Thr Arg Ile Arg
                180                 185                 190

Val Ile Glu Val Asp Pro Gly Ala Val Glu Thr Glu Phe Ser Val Val
                195                 200                 205

Arg Phe Arg Gly Asp Lys Ser Lys Ala Asp Ala Val Tyr Ala Gly Thr
    210                 215                 220

Glu Pro Leu Val Ala Asp Ile Ala Glu Phe Ile Thr Tyr Thr Leu
225                 230                 235                 240

Thr Arg Arg Glu Asn Val Val Ile Ala Asp Thr Leu Ile Phe Pro Asn
                245                 250                 255

His Gln Ala Ser Pro Thr His Val Tyr Arg Lys Asn
                260                 265

<210> SEQ ID NO 18
<211> LENGTH: 270
<212> TYPE: PRT
<213> ORGANISM: Issatchenkia orientalis

<400> SEQUENCE: 18

Met Phe Gly Asn Ile Ser Gln Arg Leu Ala Gly Lys Asn Ile Leu Ile
 1               5                  10                  15

Thr Gly Ala Ser Thr Gly Ile Gly Tyr His Thr Ala Lys Tyr Phe Ala
                 20                  25                  30

Glu Ala Ala Asn Gly Asp Leu Lys Leu Val Leu Ala Ala Arg Arg Lys
                 35                  40                  45

Glu Lys Leu Glu Ala Leu Lys Ala Asp Leu Leu Ala Lys Tyr Pro Ser
    50                  55                  60

Ile Lys Val His Ile Glu Ser Leu Asp Val Ser Lys Thr Glu Thr Ile
 65                  70                  75                  80

Ala Pro Phe Leu Lys Gly Leu Pro Glu Glu Phe Ser Ile Val Asp Val
                 85                  90                  95

Leu Val Asn Asn Ala Gly Lys Ala Leu Gly Leu Asp Pro Ile Gly Ser
                100                 105                 110

Val Asp Pro Lys Asp Val Asp Glu Met Phe Gln Thr Asn Val Leu Gly
                115                 120                 125

Met Ile Gln Leu Thr Gln Leu Val Val Gln Gln Met Lys Glu Arg Asn
    130                 135                 140

Ser Gly Asp Ile Val Gln Leu Gly Ser Val Ala Gly Arg Asn Pro Tyr
145                 150                 155                 160
```

```
Pro Gly Gly Gly Ile Tyr Cys Ala Ser Lys Ala Ala Leu Arg Ser Phe
                165                 170                 175

Thr His Val Leu Arg Glu Leu Ile Asn Thr Lys Ile Arg Val Ile
            180                 185                 190

Glu Ile Glu Pro Gly Asn Val Ala Thr Glu Glu Phe Ser Leu Thr Arg
            195                 200                 205

Phe Lys Gly Asp Lys Ser Lys Ala Glu Lys Val Tyr Glu Gly Thr Glu
        210                 215                 220

Pro Leu Tyr Gly Thr Asp Ile Ala Glu Leu Ile Leu Phe Ala Val Ser
225                 230                 235                 240

Arg Pro Gln Asn Thr Val Ile Ala Glu Thr Leu Val Phe Ala Ser Asn
                245                 250                 255

Gln Ala Ser Ala Tyr His Ile Phe Arg Gly Ser Leu Asp Lys
            260                 265                 270

<210> SEQ ID NO 19
<211> LENGTH: 271
<212> TYPE: PRT
<213> ORGANISM: Aspergillus nidulans

<400> SEQUENCE: 19

Met Ala Ser Ala Met Ala Lys Arg Leu Glu Gly Lys Thr Ile Ile
1               5                   10                  15

Thr Gly Ala Ser Ser Gly Ile Gly Arg Ser Thr Ala Arg Glu Phe Ala
            20                  25                  30

Arg Thr Ala Pro Lys Asp Leu Lys Leu Ile Val Thr Ala Arg Arg Ile
            35                  40                  45

Asp Ala Leu Glu Glu Leu Ala Lys Glu Ile Lys Glu Glu Val Gly Glu
        50                  55                  60

Gly Val Lys Thr Leu Pro Val Lys Leu Asp Val Ser Asn Pro Glu Glu
65                  70                  75                  80

Val Lys Asn Phe Val Pro Ser Leu Pro Ala Glu Phe Gln Asp Ile Asp
                85                  90                  95

Ile Leu Val Asn Asn Ala Gly Leu Val Lys Gly Val Ala Gln Ala Pro
            100                 105                 110

Asn Ile Asp Pro Glu Asp Ile Asn Ile Met Phe Ala Thr Asn Val Thr
        115                 120                 125

Gly Leu Ile Asn Leu Thr Gln Ala Val Leu Pro Ile Phe Lys Lys Arg
130                 135                 140

Ser Asp Gly Gly Arg Gly Asp Ile Ile Asn Ile Gly Ser Ile Ala Gly
145                 150                 155                 160

Arg Glu Pro Tyr Pro Gly Gly Ser Ile Tyr Cys Ser Thr Lys Ala Ala
                165                 170                 175

Val Lys Ser Phe Thr Glu Ala Leu Arg Lys Glu Leu Ile Ser Thr Arg
            180                 185                 190

Ile Arg Val Ile Glu Ile Asp Pro Gly Gln Val Glu Thr Glu Phe Ser
        195                 200                 205

Ile Val Arg Phe Tyr Gly Asp Lys Ser Lys Ala Asn Ala Val Tyr Ala
        210                 215                 220

Asn Cys Glu Pro Leu Thr Pro Asp Asp Ile Ala Glu Val Ile Val Phe
225                 230                 235                 240

Ala Ala Gly Arg Arg Glu Asn Val Val Ile Ala Asp Thr Leu Ile Phe
                245                 250                 255

Pro Ser His Gln Ala Ser Pro Gly His Leu Tyr Lys Lys Pro Gln
```

```
                    260                 265                 270

<210> SEQ ID NO 20
<211> LENGTH: 278
<212> TYPE: PRT
<213> ORGANISM: Aspergillus niger

<400> SEQUENCE: 20

Met Ala Thr Ala Met Ala Lys Arg Leu Glu Gly Lys Thr Ile Leu Val
1               5                   10                  15

Thr Gly Ala Ser Ser Gly Ile Gly Arg Ser Thr Ala Lys Glu Phe Ala
            20                  25                  30

Arg Thr Ser Pro Lys Asp Leu Lys Ile Ile Val Thr Ala Arg Arg Ile
        35                  40                  45

Asp Ser Leu Gln Glu Leu Ala Lys Glu Ile Lys Glu Glu Val Gly Glu
    50                  55                  60

Gly Val Lys Val Leu Pro Val Gln Leu Asp Val Ser Asn Pro Glu Asp
65                  70                  75                  80

Ile Lys Lys Phe Val Pro Ser Leu Pro Glu Glu Phe Lys Glu Ile Asp
                85                  90                  95

Val Leu Val Asn Asn Ala Gly Leu Val Lys Gly Val Ala Lys Ala Pro
            100                 105                 110

Glu Ile Ala Pro Glu Asp Ile Asn Val Met Phe Ser Thr Asn Val Thr
        115                 120                 125

Gly Leu Ile Asn Met Thr Gln Ala Ile Leu Pro Ile Phe Lys Lys Arg
    130                 135                 140

Ala Asp Gly Gly Arg Gly Asp Ile Ile Asn Ile Gly Ser Ile Ala Gly
145                 150                 155                 160

Arg Glu Ala Tyr Pro Gly Gly Ser Ile Tyr Cys Ala Thr Lys Ala Ala
                165                 170                 175

Ile Arg Ser Phe Thr Asp Ala Leu Arg Lys Glu Leu Ile Ala Thr Arg
            180                 185                 190

Ile Arg Ile Ile Glu Ile Asp Pro Gly Gln Val Glu Thr Glu Phe Ser
        195                 200                 205

Val Val Arg Phe Tyr Gly Asp Lys Ala Lys Ala Asp Ala Val Tyr Ala
    210                 215                 220

Gly Cys Glu Pro Leu Thr Pro Asp Asp Ile Ala Glu Val Val Phe
225                 230                 235                 240

Ala Ala Gly Arg Arg Glu Asn Val Val Ile Ala Asp Thr Leu Ile Phe
                245                 250                 255

Pro Ser His Gln Val Ser Gln Thr Ser His Thr Gly Leu Asn Ser Ile
            260                 265                 270

Ala Asp Gly Thr Val Thr
        275

<210> SEQ ID NO 21
<211> LENGTH: 270
<212> TYPE: PRT
<213> ORGANISM: Neurospora crassa

<400> SEQUENCE: 21

Met Ser Ser Ala Val Ala Lys Arg Leu Ala Gly Lys Thr Ile Val Ile
1               5                   10                  15

Thr Gly Ala Ser Ser Gly Ile Gly Arg Ser Thr Ala Phe Glu Phe Ala
            20                  25                  30

Arg Thr Ala Pro Asn His Gly Leu Lys Leu Ile Leu Thr Ala Arg Arg
```

```
                35                  40                  45
Val Asp Ala Leu Glu Gln Ile Ala Lys Glu Ile Arg Gln Glu Val Gly
 50                  55                  60

Glu Gly Val Gln Val Leu Pro Val Lys Leu Asp Val Ser Gln Pro Glu
 65                  70                  75                  80

Glu Val Arg Gly Phe Val Gly Asn Leu Pro Glu Trp Arg Asp Ile
                 85                  90                  95

His Val Leu Val Asn Asn Ala Gly Leu Val Lys Gly Ala Pro Ser Ile
                100                 105                 110

Ala Glu Glu Asp Ile Asn Val Met Phe Ala Thr Asn Val Thr Gly Leu
                115                 120                 125

Ile Asn Met Thr Gln Ala Ile Leu Pro Ile Phe Lys Ala Arg Gly Ser
            130                 135                 140

Glu Gly Gly Ser Gly Asp Ile Val Asn Ile Gly Ser Ile Ala Gly Arg
145                 150                 155                 160

Glu Pro Tyr Ala Gly Gly Ser Ile Tyr Cys Ala Thr Lys Ala Ala Val
                165                 170                 175

Arg Ser Phe Thr Asp Ala Leu Arg Lys Glu Leu Ile Ala Thr Arg Ile
                180                 185                 190

Arg Val Met Glu Ile Asp Pro Gly Gln Val Glu Thr Glu Phe Ser Val
            195                 200                 205

Val Arg Phe Tyr Gly Asp Lys Asn Lys Ala Asp Ala Val Tyr Ala Gly
210                 215                 220

Val Asp Pro Leu Thr Pro Asp Asp Ile Ala Glu Ile Val Val Phe Val
225                 230                 235                 240

Val Thr Arg Arg Glu Asn Val Val Ala Asp Thr Leu Val Phe Pro
                245                 250                 255

Ser His Gln Ala Gly Ala Gly Ile Met His Arg Lys Ser Thr
                260                 265                 270

<210> SEQ ID NO 22
<211> LENGTH: 259
<212> TYPE: PRT
<213> ORGANISM: Schizosaccharomyces pombe

<400> SEQUENCE: 22

Met Ser Arg Leu Asp Gly Lys Thr Ile Leu Ile Thr Gly Ala Ser Ser
 1               5                  10                  15

Gly Ile Gly Lys Ser Thr Ala Phe Glu Ile Ala Lys Val Ala Lys Val
                20                  25                  30

Lys Leu Ile Leu Ala Ala Arg Arg Phe Ser Thr Val Glu Glu Ile Ala
            35                  40                  45

Lys Glu Leu Glu Ser Lys Tyr Glu Val Ser Val Leu Pro Leu Lys Leu
 50                  55                  60

Asp Val Ser Asp Leu Lys Ser Ile Pro Gly Val Ile Glu Ser Leu Pro
 65                  70                  75                  80

Lys Glu Phe Ala Asp Ile Asp Val Leu Ile Asn Asn Ala Gly Leu Ala
                85                  90                  95

Leu Gly Thr Asp Lys Val Ile Asp Leu Asn Ile Asp Asp Ala Val Thr
                100                 105                 110

Met Ile Thr Thr Asn Val Leu Gly Met Met Ala Met Thr Arg Ala Val
            115                 120                 125

Leu Pro Ile Phe Tyr Ser Lys Asn Lys Gly Asp Ile Leu Asn Val Gly
            130                 135                 140
```

```
Ser Ile Ala Gly Arg Glu Ser Tyr Val Gly Ser Val Tyr Cys Ser
145                 150                 155                 160

Thr Lys Ser Ala Leu Ala Gln Phe Thr Ser Ala Leu Arg Lys Glu Thr
            165                 170                 175

Ile Asp Thr Arg Ile Arg Ile Met Glu Val Asp Pro Gly Leu Val Glu
            180                 185                 190

Thr Glu Phe Ser Val Val Arg Phe His Gly Asp Lys Gln Lys Ala Asp
            195                 200                 205

Asn Val Tyr Lys Asn Ser Glu Pro Leu Thr Pro Glu Asp Ile Ala Glu
        210                 215                 220

Val Ile Leu Phe Ala Leu Thr Arg Arg Glu Asn Val Val Ile Ala Asp
225                 230                 235                 240

Thr Leu Val Phe Pro Ser His Gln Gly Gly Ala Asn His Val Tyr Arg
            245                 250                 255

Lys Gln Ala

<210> SEQ ID NO 23
<211> LENGTH: 268
<212> TYPE: PRT
<213> ORGANISM: Kluyveromyces marxianus

<400> SEQUENCE: 23

Met Ser Gln Gly Arg Arg Ala Ala Glu Arg Leu Gln Asn Lys Thr Ile
1               5                   10                  15

Phe Ile Thr Gly Ala Ser Ala Gly Ile Gly Glu Ala Thr Ala Leu Glu
            20                  25                  30

Tyr Leu Asp Ala Ala Asn Gly Asn Val Lys Leu Val Leu Ala Ala Arg
        35                  40                  45

Arg Leu Ser Lys Leu Gln Ala Leu Lys Asp Lys Ile Ala Ala Glu Tyr
    50                  55                  60

Pro Glu Ala Lys Val Tyr Ile Gly Glu Leu Asp Val Thr Glu Thr Glu
65                  70                  75                  80

Lys Ile Lys Pro Phe Ile Gln Gly Leu Pro Glu Glu Phe Lys Asp Ile
                85                  90                  95

Asp Ile Leu Ile Asn Asn Ala Gly Lys Ala Leu Gly Val Asp Pro Val
            100                 105                 110

Gly Ala Ile Asp Ser Glu Asp Ile Lys Gly Met Ile Asp Thr Asn Val
        115                 120                 125

Leu Gly Leu Ile Asn Val Thr Gln Ala Val Leu Pro Ile Phe Lys Ala
    130                 135                 140

Lys Asn Ser Gly Asp Ile Val Asn Leu Gly Ser Val Ala Gly Arg Glu
145                 150                 155                 160

Ala Tyr Pro Asn Gly Ser Ile Tyr Cys Ala Thr Lys His Ala Val Arg
                165                 170                 175

Ala Phe Thr Gln Ser Leu Arg Lys Glu Leu Ile Asn Thr Lys Ile Arg
            180                 185                 190

Val Ile Glu Ile Ala Pro Gly Asn Val Glu Thr Glu Phe Ser Tyr Val
        195                 200                 205

Arg Tyr Lys Gly Asp Thr Asp Ala Ala Lys Lys Val Tyr Lys Gly Thr
    210                 215                 220

Thr Pro Leu Tyr Ala Asp Asp Ile Ala Asp Leu Ile Val Tyr Ala Thr
225                 230                 235                 240

Ser Arg Lys Gln Asn Thr Val Ile Ala Asp Val Leu Val Phe Ala Thr
                245                 250                 255
```

Asn Gln Ala Ser Pro Tyr His Ile Tyr Arg Gly Glu
        260                 265

<210> SEQ ID NO 24

<400> SEQUENCE: 24

000

<210> SEQ ID NO 25
<211> LENGTH: 500
<212> TYPE: PRT
<213> ORGANISM: Saccharomyces cerevisiae

<400> SEQUENCE: 25

Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Thr Glu Asp
50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
        290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val

```
            325                 330                 335
Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
            355                 360                 365

Gly Ala Lys Ile Leu Thr Gly Gly Glu Lys Val Gly Asp Lys Gly Tyr
            370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
                420                 425                 430

Gly Ser Gly Ile Glu Thr Glu Ser Leu Ser Thr Gly Leu Lys Val Ala
                435                 440                 445

Lys Met Leu Lys Ala Gly Thr Val Trp Ile Asn Thr Tyr Asn Asp Phe
            450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500

<210> SEQ ID NO 26
<211> LENGTH: 499
<212> TYPE: PRT
<213> ORGANISM: Saccharomyces castellii

<400> SEQUENCE: 26

Met Thr Lys Ile Asn Phe Glu Ala Ala Glu Pro Ala Thr Ile Thr Leu
1               5                   10                  15

Pro Asn Gly Ile Thr Tyr Asn Gln Pro Thr Gly Leu Phe Ile Asn Asn
                20                  25                  30

Glu Phe Met Lys Ser Gln Asp Tyr Lys Thr Ile Lys Val Glu Asn Pro
            35                  40                  45

Ala Thr Ala Glu Ile Val Cys Glu Val Ser Ser Gly Thr Ser Glu Asp
        50                  55                  60

Val Glu Tyr Ala Val Glu Ser Ala Glu His Ala Phe Asn Asp Thr Asp
65                  70                  75                  80

Trp Ala Thr Gln Asp Pro Lys Ile Arg Gly Arg Tyr Leu Ser Lys Leu
                85                  90                  95

Ala Asp Leu Met Glu Glu Asn Leu Glu Leu Met Ala Ser Ile Glu Thr
            100                 105                 110

Leu Asp Asn Gly Lys Thr Leu Ala Leu Ser Arg Gly Asp Val Gly Leu
        115                 120                 125

Ala Ile Asn Cys Ile Arg Asp Ala Ala Ser Tyr Ala Asp Lys Ile Asn
    130                 135                 140

Gly Arg Thr Ile Asn Ser Gly Asp Gly Tyr Met Asn Phe Thr Val Lys
145                 150                 155                 160

Glu Pro Ile Gly Val Cys Gly Gln Ile Ile Pro Trp Asn Phe Pro Leu
                165                 170                 175

Met Met Leu Ser Trp Lys Ile Ala Pro Ala Leu Ala Met Gly Asn Val
            180                 185                 190
```

-continued

```
Ile Ile Leu Lys Pro Ala Ser Ala Thr Pro Leu Asn Ala Leu Phe Phe
        195                 200                 205

Ala Ser Leu Cys Lys Lys Val Gly Ile Pro Ala Gly Val Val Asn Ile
    210                 215                 220

Ile Pro Gly Pro Gly Arg Thr Val Gly Asn Ala Ile Thr Thr His Pro
225                 230                 235                 240

Arg Ile Arg Lys Ala Ala Phe Thr Gly Ser Thr Glu Ile Gly Lys Asp
                245                 250                 255

Ile Ala Ile Lys Ala Ser Gly Ser Asn Leu Lys Lys Ile Thr Leu Glu
            260                 265                 270

Leu Gly Gly Lys Ser Ala His Leu Val Phe Asp Asp Ala Asn Ile Glu
        275                 280                 285

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Lys Leu Met Pro Ala Phe Lys Lys Tyr Val Glu Asn Leu Lys Val Gly
                325                 330                 335

Asp Pro Phe Asp Glu Ser Asn Phe Gln Gly Ala Ile Thr Asn Arg Glu
            340                 345                 350

Gln Tyr Glu Thr Ile Leu Lys Tyr Ile Lys Ile Gly Lys Glu Glu Gly
        355                 360                 365

Ala Lys Ile Leu Thr Gly Gly Glu Thr Ile Gly Asn Lys Gly Tyr Phe
    370                 375                 380

Ile Lys Pro Thr Ile Phe Tyr Asp Val Lys Glu Asp Met Glu Ile Val
385                 390                 395                 400

Arg Glu Glu Ile Phe Gly Pro Val Val Thr Val Ser Lys Phe Lys Asp
                405                 410                 415

Ile Glu Asp Gly Val Ala Met Ala Asn Ala Ser Glu Phe Gly Leu Gly
            420                 425                 430

Ala Gly Ile Glu Thr Glu Asn Leu Ser Thr Ala Leu Lys Val Ala Lys
        435                 440                 445

Met Leu Lys Ser Gly Thr Val Trp Ile Asn Thr Tyr Asn Asp Phe Asp
    450                 455                 460

Ser Arg Val Pro Phe Gly Gly Val Lys Gln Ser Gly Tyr Gly Arg Glu
465                 470                 475                 480

Met Gly Glu Glu Val Tyr Asp Cys Tyr Thr Glu Val Lys Ala Ile Arg
                485                 490                 495

Ile Lys Leu

<210> SEQ ID NO 27
<211> LENGTH: 497
<212> TYPE: PRT
<213> ORGANISM: Candida glabrata

<400> SEQUENCE: 27

Met Ala Tyr Lys Thr Ala Ala Thr Lys Thr Ile Lys Leu Pro Asn Gly
1               5                   10                  15

Leu Thr Tyr Glu Gln Pro Thr Gly Leu Phe Ile Asn Asn Glu Phe Val
            20                  25                  30

Glu Ser Ser Asp Gly Lys Thr Met Thr Ile Glu Asn Pro Ser Thr Gln
        35                  40                  45

Glu Pro Ile Val Asp Val Phe Ser Ala Thr Lys Glu Asp Val Asp Tyr
    50                  55                  60
```

-continued

```
Ala Val Asp Cys Ala Glu Arg Ala Phe Glu Lys Ser Asp Trp Ala Thr
 65                  70                  75                  80

Gln Asp Pro Lys Val Arg Ala Arg Tyr Leu Ser Lys Leu Ala Asp Leu
                 85                  90                  95

Met Glu Glu Gln Leu Glu Leu Ile Ala Ser Ile Glu Thr Leu Asp Asn
            100                 105                 110

Gly Lys Thr Ile Ala Leu Ser Arg Gly Asp Val Gln Leu Ser Ile Asn
        115                 120                 125

Cys Ile Arg Asp Ala Ala Ser Tyr Ala Asp Lys Val Asp Gly Arg Ser
    130                 135                 140

Ile Asp Thr Gly Asp Gly Tyr Met Asn Tyr Thr Ile Arg Glu Pro Ile
145                 150                 155                 160

Gly Val Cys Ala Gln Ile Ile Pro Trp Asn Phe Pro Leu Met Met Leu
                165                 170                 175

Ser Trp Lys Val Gly Pro Ala Leu Ala Met Gly Asn Cys Ile Val Leu
            180                 185                 190

Lys Pro Ala Ser Ala Thr Pro Leu Asn Ala Leu Tyr Phe Ser Ser Leu
        195                 200                 205

Cys Lys Gln Val Gly Ile Pro Ala Gly Val Val Asn Ile Ile Pro Gly
    210                 215                 220

Pro Gly Gly Met Val Gly Thr Ala Leu Thr Thr His Pro Lys Val Arg
225                 230                 235                 240

Lys Val Ala Phe Thr Gly Ser Thr Asp Ile Gly Lys Asp Ile Ala Val
                245                 250                 255

Lys Ala Ser Ala Ser Asn Leu Lys Lys Ile Thr Leu Glu Leu Gly Gly
            260                 265                 270

Lys Ser Ala His Leu Val Phe Asn Asp Ala Asn Leu Glu Lys Thr Leu
        275                 280                 285

Pro Asn Leu Val Asn Gly Ile Phe Lys Asn Ala Gly Gln Ile Cys Ser
    290                 295                 300

Ser Gly Ser Arg Ile Tyr Ala Gln Ala Gly Ile Tyr Asp Arg Leu Leu
305                 310                 315                 320

Lys Glu Phe Lys Ala Tyr Ile Glu Lys Asn Ile Lys Val Gly Asn Pro
                325                 330                 335

Phe Asp Glu Ser Asn Phe Gln Gly Ala Ile Thr Asn Lys Glu Gln Tyr
            340                 345                 350

Asn Thr Ile Leu Lys Tyr Ile Asn Ile Gly Lys Glu Glu Gly Ala Lys
        355                 360                 365

Val Leu Thr Gly Gly Glu Thr Ala Ala Glu Lys Gly Tyr Phe Ile Lys
    370                 375                 380

Pro Thr Val Phe Tyr Asp Val Lys Glu Asp Met Arg Val Val Lys Glu
385                 390                 395                 400

Glu Ile Phe Gly Pro Cys Val Thr Ile Ser Lys Phe Glu Glu Ile Glu
                405                 410                 415

Asp Gly Val Ala Met Ala Asn Asp Ser Glu Phe Gly Leu Gly Ala Gly
            420                 425                 430

Ile Glu Thr Glu Asn Leu Ser Thr Ala Leu Lys Val Ala Lys Met Leu
        435                 440                 445

His Ser Gly Thr Val Trp Ile Asn Thr Tyr Asn Asp Phe Asp Ser Arg
    450                 455                 460

Val Pro Phe Gly Gly Tyr Lys Gln Ser Gly Tyr Gly Arg Glu Met Gly
465                 470                 475                 480

Ser Glu Val Tyr Glu Cys Tyr Thr Gln Thr Lys Ala Val Arg Ile Lys
```

Leu

<210> SEQ ID NO 28
<211> LENGTH: 500
<212> TYPE: PRT
<213> ORGANISM: Saccharomyces bayanus

<400> SEQUENCE: 28

Met Thr Lys Leu His Phe Asp Thr Ala Glu Ala Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Thr Lys Ala Gln Asp Gly Lys Thr Tyr Pro Val Glu Asp Pro
        35                  40                  45

Ser Thr Glu Asn Thr Ile Cys Glu Val Ser Ser Ala Thr Thr Glu Asp
    50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ser
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Ile Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Thr Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Ser Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Ile Asp Ser Ser Glu Ser Asn Leu Lys Lys Ile Thr Leu Glu
            260                 265                 270

Leu Gly Gly Lys Ser Ala His Leu Val Phe Asp Asp Ala Asp Ile Lys
        275                 280                 285

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu

```
                355                 360                 365
Gly Ala Lys Ile Leu Thr Gly Gly Glu Lys Val Gly Asp Lys Gly Tyr
        370                 375                 380

Phe Ile Arg Pro Thr Val Phe Tyr Asp Val Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Ala Met Ala Asn Ser Ser Glu Phe Gly Leu
            420                 425                 430

Gly Ser Gly Ile Glu Thr Glu Ser Leu Ser Thr Gly Leu Lys Val Ala
                435                 440                 445

Lys Met Leu Lys Ala Gly Thr Val Trp Ile Asn Thr Tyr Asn Asp Phe
        450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500

<210> SEQ ID NO 29
<211> LENGTH: 507
<212> TYPE: PRT
<213> ORGANISM: Kluyveromyces lactis

<400> SEQUENCE: 29

Met Ser Ser Thr Ile Ala Glu Lys Leu Asn Leu Lys Ile Val Glu Gln
1               5                   10                  15

Asp Ala Val Ser Ile Thr Leu Pro Asn Gly Leu Thr Tyr Gln Gln Pro
            20                  25                  30

Thr Gly Leu Phe Ile Asn Asn Gln Phe Ile Lys Ser Gln Asp Gly Lys
        35                  40                  45

Thr Leu Lys Val Glu Asn Pro Ser Thr Glu Glu Ile Ile Val Glu Val
    50                  55                  60

Gln Ser Ala Thr Ser Gln Asp Val Glu Tyr Ala Val Glu Ala Ala Asp
65                  70                  75                  80

Ala Ala Phe Asn Ser Glu Trp Ser Thr Met Asp Pro Lys Lys Arg Gly
                85                  90                  95

Ser Leu Leu Phe Lys Leu Ala Asp Leu Ile Glu Ala Gln Lys Glu Leu
            100                 105                 110

Ile Ala Ser Ile Glu Ser Ala Asp Asn Gly Lys Thr Leu Ala Leu Ala
        115                 120                 125

Arg Gly Asp Val Gly Leu Val Ile Asp Tyr Ile Arg Ser Ala Ala Gly
    130                 135                 140

Tyr Ala Asp Lys Leu Gly Gly Arg Thr Ile Asn Thr Gly Asp Gly Tyr
145                 150                 155                 160

Ala Asn Phe Thr Tyr Lys Glu Pro Leu Gly Val Cys Gly Gln Ile Ile
                165                 170                 175

Pro Trp Asn Phe Pro Leu Met Met Leu Ser Trp Lys Ile Ala Pro Ala
            180                 185                 190

Leu Val Ala Gly Asn Thr Val Ile Leu Lys Pro Ala Ser Pro Thr Pro
        195                 200                 205

Leu Asn Ala Leu Phe Phe Ala Ser Leu Cys Lys Glu Ala Gly Ile Pro
    210                 215                 220
```

```
Ala Gly Val Val Asn Ile Val Pro Gly Pro Gly Arg Ser Val Gly Asp
225                 230                 235                 240

Thr Ile Thr Asn His Pro Lys Ile Arg Lys Ile Ala Phe Thr Gly Ser
            245                 250                 255

Thr Asp Ile Gly Arg Asp Val Ala Ile Lys Ala Ala Gln Ser Asn Leu
            260                 265                 270

Lys Lys Val Thr Leu Glu Leu Gly Lys Ser Ala His Leu Val Phe
        275                 280                 285

Glu Asp Ala Asn Ile Lys Lys Thr Ile Pro Asn Leu Val Asn Gly Ile
        290                 295                 300

Phe Lys Asn Ala Gly Gln Ile Cys Ser Ser Gly Ser Arg Ile Tyr Val
305                 310                 315                 320

Gln Asp Thr Ile Tyr Asp Gln Leu Leu Ser Glu Phe Lys Thr Tyr Leu
            325                 330                 335

Glu Thr Glu Ile Lys Val Gly Ser Pro Phe Asp Glu Ser Asn Phe Gln
            340                 345                 350

Ala Ala Ile Asn Asn Lys Ala Gln Phe Glu Thr Ile Leu Asn Tyr Ile
            355                 360                 365

Asp Ile Gly Lys Lys Glu Gly Ala Ser Ile Leu Thr Gly Gly Glu Arg
        370                 375                 380

Val Gly Asn Lys Gly Tyr Phe Ile Lys Pro Thr Val Phe Tyr Asn Val
385                 390                 395                 400

Lys Glu Asp Met Arg Ile Val Lys Glu Ile Phe Gly Pro Val Val
            405                 410                 415

Thr Ile Ser Lys Phe Ser Thr Val Asp Glu Ala Val Ala Leu Ala Asn
            420                 425                 430

Asp Ser Glu Phe Gly Leu Gly Ala Gly Ile Glu Thr Glu Asn Ile Ser
        435                 440                 445

Val Ala Leu Lys Val Ala Lys Arg Leu Lys Ala Gly Thr Val Trp Ile
        450                 455                 460

Asn Thr Tyr Asn Asp Phe Asp Ala Ala Val Pro Phe Gly Gly Tyr Lys
465                 470                 475                 480

Gln Ser Gly Tyr Gly Arg Glu Met Gly Glu Glu Ala Phe Glu Ser Tyr
            485                 490                 495

Thr Gln Ile Lys Ala Val Arg Ile Lys Leu Asp
            500                 505

<210> SEQ ID NO 30
<211> LENGTH: 526
<212> TYPE: PRT
<213> ORGANISM: Kluyveromyces thermotolerans

<400> SEQUENCE: 30

Met Asn Tyr Ala Cys Leu Arg Ser Gly Ser Ser Met Leu Gly Met Val
1               5                   10                  15

Lys Ala Ala Arg Ser Phe Ser Ile Ser Ala Arg Ala Leu Ser Ala Arg
            20                  25                  30

Ala Lys Ala Asp Phe Val Lys Ile Thr Thr Pro Asn Gly His Thr Tyr
        35                  40                  45

Glu Gln Pro Thr Gly Leu Phe Ile Asn Asn Glu Phe Leu Lys Ser Gln
    50                  55                  60

Lys Gly Glu Thr Ile Thr Val Glu Asp Pro Ser Thr Glu Gln Lys Ile
65                  70                  75                  80

Val Glu Val Gln Ser Gly Thr Lys Glu Asp Val Glu Tyr Ala Val Glu
            85                  90                  95
```

```
Cys Ala Glu Lys Ala Phe Asn Ser Ser Trp Ser Thr Gly Asp Pro Arg
            100                 105                 110

Asn Arg Ala Arg Ser Leu Leu Lys Leu Ala Asp Leu Val Glu Glu Arg
            115                 120                 125

Lys Glu Leu Ile Ala Ser Ile Glu Ser Met Asp Asn Gly Lys Thr Leu
        130                 135                 140

Ala Leu Ala Arg Gly Asp Val Gly Ile Val Ile Asn Phe Leu Arg Ser
145                 150                 155                 160

Ala Ala Gly Tyr Ala Asp Lys Leu Asp Gly Arg Ser Ile Asn Thr Gly
                165                 170                 175

Asp Gly Tyr Val Asn Tyr Thr Ile Arg Glu Pro Val Gly Val Cys Gly
            180                 185                 190

Gln Ile Ile Pro Trp Asn Phe Pro Leu Met Met Leu Ser Trp Lys Ile
        195                 200                 205

Ala Pro Ala Leu Ala Ala Gly Asn Thr Val Ile Leu Lys Pro Ala Ser
        210                 215                 220

Pro Thr Pro Leu Asn Ala Leu Tyr Phe Ala Ser Leu Cys Lys Glu Ala
225                 230                 235                 240

Gly Ile Pro Ala Gly Val Val Asn Ile Ile Pro Gly Pro Gly Arg Gly
                245                 250                 255

Val Gly Glu Thr Leu Thr Thr His Pro Lys Ile Arg Lys Ile Ala Phe
            260                 265                 270

Thr Gly Ser Thr Gly Thr Gly Lys Gly Ile Ala Val Lys Ala Ala Gln
        275                 280                 285

Ser Asn Leu Lys Lys Val Thr Leu Glu Leu Gly Gly Lys Ser Ala His
        290                 295                 300

Leu Val Phe Asn Asp Ala Asn Ile Glu Lys Thr Leu Pro Asn Leu Val
305                 310                 315                 320

Asn Gly Ile Phe Leu Asn Ala Gly Gln Ile Cys Ser Ser Gly Ser Arg
                325                 330                 335

Ile Tyr Val Gln Glu Gly Ile Tyr Asp Lys Leu Leu Pro Ala Phe Arg
            340                 345                 350

Lys Tyr Val Glu Glu Lys Ile Thr Val Gly Ser Pro Phe Asp Glu Asn
        355                 360                 365

Asn Phe Gln Gly Ala Ile Asn Asn Lys Ala Gln Phe Glu Thr Ile Met
        370                 375                 380

Asn Tyr Val Gly Ile Gly Lys Ser Glu Gly Ala Lys Val Leu Thr Gly
385                 390                 395                 400

Gly Glu Lys Val Asn Asp Lys Gly Tyr Phe Ile Arg Pro Thr Ile Phe
                405                 410                 415

Tyr Asp Val Glu Glu Asp Met Arg Ile Val Lys Glu Glu Val Phe Gly
            420                 425                 430

Pro Val Val Thr Ile Ser Lys Phe Lys Glu Ile Glu Asp Gly Val Ala
        435                 440                 445

Met Ala Asn Asp Ser Glu Phe Gly Leu Gly Ala Gly Ile Gln Thr Glu
        450                 455                 460

Asn Val Ser Thr Ala Leu Lys Val Ser Lys Met Leu Lys Ala Gly Ile
465                 470                 475                 480

Val Trp Val Asn Thr Tyr Asn Asp Phe Asp Ser Ser Val Pro Phe Gly
                485                 490                 495

Gly Cys Lys Gln Ser Gly Tyr Gly Arg Glu Met Gly Ile Glu Ala Phe
            500                 505                 510
```

Glu Ala Tyr Thr Ser Val Lys Ala Val Arg Ile Lys Leu Ala
        515                 520                 525

<210> SEQ ID NO 31
<211> LENGTH: 526
<212> TYPE: PRT
<213> ORGANISM: Kluyveromyces waltii

<400> SEQUENCE: 31

Met Asn Lys Met Ser Leu Lys Asn Ala Ser Thr Met Leu Arg Met Ala
1               5                   10                  15

Lys Tyr Ala Arg Asn Phe Ser Val Ser Ser Arg Ile Leu Ser Ala Lys
            20                  25                  30

Met Lys Ala Asp Phe Val Lys Val Thr Thr Pro Asn Gly Leu Thr Tyr
        35                  40                  45

Glu Gln Pro Thr Gly Leu Phe Ile Asn Asn Glu Phe Val Lys Ser His
    50                  55                  60

Asn Gly Ala Thr Ile Ala Val Glu Asp Pro Ala Thr Glu Lys Lys Ile
65                  70                  75                  80

Val Glu Val Gln Ser Gly Thr Lys Glu Asp Val Glu Tyr Ala Val Glu
                85                  90                  95

Cys Ala Glu Lys Ala Phe Asn Ser Ser Trp Ser Thr Gly Asp Pro Arg
            100                 105                 110

Val Arg Ala Arg Ala Leu Leu Lys Leu Ala Asp Leu Ile Glu Gln Arg
        115                 120                 125

Lys Glu Leu Ile Ser Ser Ile Glu Cys Met Asp Asn Gly Lys Ala Leu
    130                 135                 140

Phe Leu Ala Lys Asn Asp Val Arg Ile Val Ile Asp Tyr Ile Arg Ser
145                 150                 155                 160

Ser Ala Gly Phe Ala Asp Lys Leu Asp Gly Arg Thr Ile Asn Thr Gly
                165                 170                 175

Asp Gly Tyr Val Asn Tyr Thr Leu Arg Glu Pro Val Gly Val Cys Gly
            180                 185                 190

Gln Ile Ile Pro Trp Asn Phe Pro Leu Leu Met Leu Ser Trp Lys Ile
        195                 200                 205

Ala Pro Ala Leu Ala Ala Gly Asn Thr Val Ile Leu Lys Pro Ala Ser
    210                 215                 220

Pro Thr Pro Leu Asn Ala Leu Tyr Phe Ala Ser Leu Cys Lys Glu Ala
225                 230                 235                 240

Gly Ile Pro Ala Gly Val Val Asn Ile Ile Pro Gly Pro Gly Arg Asp
                245                 250                 255

Val Gly Glu Thr Leu Thr Thr His Pro Lys Ile Arg Lys Ile Ala Phe
            260                 265                 270

Thr Gly Ser Thr Gly Thr Gly Lys Gly Ile Ala Val Lys Ala Ala Gln
        275                 280                 285

Ser Asn Leu Lys Lys Val Thr Leu Glu Leu Gly Gly Lys Ser Ala His
    290                 295                 300

Met Val Phe Asn Asp Ala Asn Leu Glu Lys Thr Ile Pro Asn Leu Val
305                 310                 315                 320

Asn Gly Ile Phe Leu Asn Ala Gly Gln Ile Cys Ser Ser Gly Ser Arg
                325                 330                 335

Ile Tyr Val Gln Glu Gly Ile Tyr Asp Lys Leu Leu Pro Ala Phe Lys
            340                 345                 350

Lys Tyr Val Glu Glu Val Ile Thr Val Gly Ser Pro Phe Asp Glu Ser
        355                 360                 365

```
Asn Phe Gln Gly Ala Ile Asn Lys Ala Gln Phe Asp Thr Ile Met
    370                 375                 380

Asn Tyr Val Gly Ile Gly Lys Glu Glu Gly Ala Lys Val Leu Thr Gly
385                 390                 395                 400

Gly Lys Arg Ser Gly Asp Gln Gly Tyr Phe Ile Arg Pro Thr Ile Phe
                405                 410                 415

Tyr Asp Val Asn Glu Asp Met Arg Ile Val Lys Glu Glu Ile Phe Gly
            420                 425                 430

Pro Val Val Thr Ile Ser Lys Phe Lys Glu Ile Glu Asp Gly Val Ala
        435                 440                 445

Met Ala Asn Asn Ser Glu Phe Gly Leu Gly Ala Gly Ile Gln Thr Glu
    450                 455                 460

Ser Val Ser Thr Ala Leu Lys Val Ser Lys Met Leu Lys Ala Gly Thr
465                 470                 475                 480

Val Trp Val Asn Thr Tyr Asn Asp Phe Asp Ser Ser Val Pro Phe Gly
                485                 490                 495

Gly Cys Lys Gln Ser Gly Tyr Gly Ser Glu Met Gly Ile Glu Ala Phe
                500                 505                 510

Asp Ser Tyr Thr Thr Lys Ala Val Arg Ile Lys Leu Ala
            515                 520                 525

<210> SEQ ID NO 32
<211> LENGTH: 500
<212> TYPE: PRT
<213> ORGANISM: Saccharomyces cerevisiae

<400> SEQUENCE: 32

Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
                20                  25                  30

Lys Phe Met Lys Ala Gln Asp Gly Lys Thr Tyr Pro Val Glu Asp Pro
            35                  40                  45

Ser Thr Glu Asn Thr Val Cys Glu Val Ser Ser Ala Thr Thr Glu Asp
        50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
```

```
            210                 215                 220
Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
                260                 265                 270

Leu Gly Gly Lys Ser Ala His Leu Val Phe Asp Asp Ala Asn Ile Lys
                275                 280                 285

Lys Thr Leu Pro Asn Leu Val Asn Gly Ile Phe Lys Asn Ala Gly Gln
                290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
                340                 345                 350

Gln Gln Phe Asp Thr Ile Met Asn Tyr Ile Asp Ile Gly Lys Lys Glu
                355                 360                 365

Gly Ala Lys Ile Leu Thr Gly Gly Glu Lys Val Gly Asp Lys Gly Tyr
                370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
                420                 425                 430

Gly Ser Gly Ile Glu Thr Glu Ser Leu Ser Thr Gly Leu Lys Val Ala
                435                 440                 445

Lys Met Leu Lys Ala Gly Thr Val Trp Ile Asn Thr Tyr Asn Asp Phe
                450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
                500

<210> SEQ ID NO 33
<211> LENGTH: 500
<212> TYPE: PRT
<213> ORGANISM: Saccharomyces cerevisiae

<400> SEQUENCE: 33

Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
                20                  25                  30

Lys Phe Met Lys Ala Gln Asp Gly Lys Thr Tyr Pro Val Glu Asp Pro
                35                  40                  45

Ser Thr Glu Asn Thr Val Cys Glu Val Ser Ser Ala Thr Thr Glu Asp
                50                  55                  60

Val Glu Tyr Ala Ile Glu Cys Ala Asp Arg Ala Phe His Asp Thr Glu
65                  70                  75                  80
```

```
Trp Ala Thr Gln Asp Pro Arg Glu Arg Gly Arg Leu Leu Ser Lys Leu
             85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
            115                 120                 125

Ala Ile Asn Cys Leu Arg Asp Ala Ala Tyr Ala Asp Lys Val Asn
130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
            195                 200                 205

Ala Ser Leu Cys Lys Lys Val Gly Ile Pro Ala Gly Val Val Asn Ile
            210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
            275                 280                 285

Lys Thr Leu Pro Asn Leu Val Asn Gly Ile Phe Lys Asn Ala Gly Gln
290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
            355                 360                 365

Gly Ala Lys Ile Leu Thr Gly Gly Glu Lys Val Gly Asp Lys Gly Tyr
            370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
            435                 440                 445

Lys Met Leu Lys Ala Gly Thr Val Trp Ile Asn Thr Tyr Asn Asp Phe
450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
```

<210> SEQ ID NO 34
<211> LENGTH: 500
<212> TYPE: PRT
<213> ORGANISM: Saccharomyces cerevisiae

<400> SEQUENCE: 34

```
Met Thr Lys Leu His Phe Asp Thr Ala Glu Pro Val Lys Ile Thr Leu
  1               5                  10                  15

Pro Asn Gly Leu Thr Tyr Glu Gln Pro Thr Gly Leu Phe Ile Asn Asn
             20                  25                  30

Lys Phe Met Lys Ala Gln Asp Gly Lys Thr Tyr Pro Val Glu Asp Pro
         35                  40                  45

Ser Thr Glu Asn Thr Val Cys Glu Val Ser Ser Ala Thr Thr Glu Asp
 50                  55                  60

Val Glu Tyr Ala Ile Glu Cys Ala Asp Arg Ala Phe His Asp Thr Glu
 65                  70                  75                  80

Trp Ala Thr Gln Asp Pro Arg Glu Arg Gly Arg Leu Leu Ser Lys Leu
                 85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
            115                 120                 125

Ala Ile Asn Cys Leu Arg Asp Ala Ala Ala Tyr Ala Asp Lys Val Asn
130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
            195                 200                 205

Ala Ser Leu Cys Lys Lys Val Gly Ile Pro Ala Gly Val Val Asn Ile
        210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365
```

```
Gly Ala Lys Ile Leu Thr Gly Gly Glu Lys Val Gly Asp Lys Gly Tyr
        370             375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
        420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
        500

<210> SEQ ID NO 35
<211> LENGTH: 501
<212> TYPE: PRT
<213> ORGANISM: Saccharomyces cerevisiae

<400> SEQUENCE: 35

Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
                20                  25                  30

Lys Phe Met Lys Ala Gln Asp Gly Lys Thr Tyr Pro Val Glu Asp Pro
            35                  40                  45

Ser Thr Glu Asn Thr Val Cys Glu Val Ser Ser Ala Thr Thr Glu Asp
        50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
                100                 105                 110

Leu Asp Asn Gly Lys Thr Leu Ala Phe Lys Ala Arg Gly Asp Val Thr
            115                 120                 125

Ile Ala Ile Asn Cys Leu Arg Asp Ala Ala Tyr Ala Asp Lys Val
        130                 135                 140

Asn Gly Arg Thr Ile Asn Thr Gly Asp Gly Tyr Met Asn Phe Thr Thr
145                 150                 155                 160

Leu Glu Pro Ile Gly Val Cys Gly Gln Ile Ile Pro Trp Asn Phe Pro
                165                 170                 175

Ile Met Met Leu Ala Trp Lys Ile Ala Pro Ala Leu Ala Met Gly Asn
            180                 185                 190

Val Cys Ile Leu Lys Pro Ala Ala Val Thr Pro Leu Asn Ala Leu Tyr
        195                 200                 205

Phe Ala Ser Leu Cys Lys Lys Val Gly Ile Pro Ala Gly Val Val Asn
    210                 215                 220

Ile Val Pro Gly Pro Gly Arg Thr Val Gly Ala Ala Leu Thr Asn Asp
225                 230                 235                 240
```

Pro Arg Ile Arg Lys Leu Ala Phe Thr Gly Ser Thr Glu Val Gly Lys
            245                 250                 255

Ser Val Ala Val Asp Ser Ser Glu Ser Asn Leu Lys Lys Ile Thr Leu
            260                 265                 270

Glu Leu Gly Gly Lys Ser Ala His Leu Val Phe Asp Asp Ala Asn Ile
            275                 280                 285

Lys Lys Thr Leu Pro Asn Leu Val Asn Gly Ile Phe Lys Asn Ala Gly
            290                 295                 300

Gln Ile Cys Ser Ser Gly Ser Arg Ile Tyr Val Gln Glu Gly Ile Tyr
305                 310                 315                 320

Asp Glu Leu Leu Ala Ala Phe Lys Ala Tyr Leu Glu Thr Glu Ile Lys
            325                 330                 335

Val Gly Asn Pro Phe Asp Lys Ala Asn Phe Gln Gly Ala Ile Thr Asn
            340                 345                 350

Arg Gln Gln Phe Asp Thr Ile Met Asn Tyr Ile Asp Ile Gly Lys Lys
            355                 360                 365

Glu Gly Ala Lys Ile Leu Thr Gly Gly Glu Lys Val Gly Asp Lys Gly
            370                 375                 380

Tyr Phe Ile Arg Pro Thr Val Phe Tyr Asp Val Asn Glu Asp Met Arg
385                 390                 395                 400

Ile Val Lys Glu Glu Ile Phe Gly Pro Val Val Thr Val Ala Lys Phe
            405                 410                 415

Lys Thr Leu Glu Glu Gly Val Glu Met Ala Asn Ser Ser Glu Phe Gly
            420                 425                 430

Leu Gly Ser Gly Ile Glu Thr Glu Ser Leu Ser Thr Gly Leu Lys Val
            435                 440                 445

Ala Lys Met Leu Lys Ala Gly Thr Val Trp Ile Asn Thr Tyr Asn Asp
            450                 455                 460

Phe Asp Ser Arg Val Pro Phe Gly Gly Val Lys Gln Ser Gly Tyr Gly
465                 470                 475                 480

Arg Glu Met Gly Glu Glu Val Tyr His Ala Tyr Thr Glu Val Lys Ala
            485                 490                 495

Val Arg Ile Lys Leu
            500

<210> SEQ ID NO 36
<211> LENGTH: 500
<212> TYPE: PRT
<213> ORGANISM: Saccharomyces cerevisiae

<400> SEQUENCE: 36

Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
            35                  40                  45

Ser Thr Glu Asn Thr Val Cys Glu Val Ser Ser Ala Thr Thr Glu Asp
            50                  55                  60

Val Glu Tyr Ala Ile Glu Cys Ala Asp Arg Thr Phe His Asp Thr Glu
65                  70                  75                  80

Trp Ala Thr Gln Asp Pro Arg Glu Arg Gly Arg Leu Leu Ser Lys Leu
            85                  90                  95

Ala Asp Glu Leu Glu Ser Gln Ile Asp Leu Val Ser Ser Ile Glu Ala

```
            100                 105                 110
Leu Asp Asn Gly Lys Thr Leu Ala Leu Ala Arg Gly Asp Val Thr Ile
        115                 120                 125

Ala Ile Asn Cys Leu Arg Asp Ala Ala Tyr Ala Asp Lys Val Asn
130                 135                 140

Gly Arg Thr Ile Asn Thr Gly Asp Gly Tyr Met Asn Phe Thr Thr Leu
145                 150                 155                 160

Glu Pro Val Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
                180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
        210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
                260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
        290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
                340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
                420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
        450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500

<210> SEQ ID NO 37
```

<211> LENGTH: 500
<212> TYPE: PRT
<213> ORGANISM: Saccharomyces cerevisiae

<400> SEQUENCE: 37

```
Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Pro Glu Asp
50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
370                 375                 380

Phe Ile Arg Pro Thr Val Phe Tyr Asp Val Asn Glu Asp Met Arg Ile
```

```
                385                 390                 395                 400
Val Lys Glu Glu Ile Phe Gly Pro Val Thr Val Ala Lys Phe Lys
                405                 410                 415

Thr Leu Glu Glu Gly Val Glu Met Ala Asn Ser Ser Glu Phe Gly Leu
                420                 425                 430

Gly Ser Gly Ile Glu Thr Glu Ser Leu Ser Thr Gly Leu Lys Val Ala
                435                 440                 445

Lys Met Leu Lys Ala Gly Thr Val Trp Ile Asn Thr Tyr Asn Asp Phe
                450                 455                 460

Asp Ser Arg Val Pro Phe Gly Val Lys Gln Ser Gly Tyr Gly Arg
465                 470                 475                 480

Glu Met Gly Glu Val Tyr His Ala Tyr Thr Glu Val Lys Ala Val
                485                 490                 495

Arg Ile Lys Leu
                500

<210> SEQ ID NO 38
<211> LENGTH: 497
<212> TYPE: PRT
<213> ORGANISM: Pichia pastoris

<400> SEQUENCE: 38

Met Ser Glu Phe Val Ala Lys Ile Asn Ile Pro Thr Ile Ala Glu Pro
1               5                   10                  15

Val Glu Val Pro Thr Gly Leu Phe Ile Asn Asn Glu Trp Val Ala Ala
                20                  25                  30

Lys Ser Gly Lys Thr Phe Ala Val Thr Ser Pro Ile Asp Glu Ser His
                35                  40                  45

Leu Thr Asp Leu Gln Met Ala Gly Ala Asp Val Asp Ile Ala Thr
                50                  55                  60

Asp Phe Ala Tyr Lys Ala Phe Tyr Lys His Lys Phe Val Glu Pro Ser
65                  70                  75                  80

Val Arg Gly Arg Trp Leu Tyr Lys Leu Ala Glu Leu Phe Glu Glu His
                85                  90                  95

Lys Asp Thr Ile Ala Lys Leu Glu Ser Leu Asp Asn Gly Lys Ala Leu
                100                 105                 110

His Cys Ala Gln Phe Asp Leu Asn Leu Val Val Glu Tyr Leu Arg Ser
                115                 120                 125

Cys Ala Gly Tyr Ala Asp Lys Val Asp Gly Arg Thr Ile Asn Thr Gly
                130                 135                 140

Lys Asp His Leu Asn Phe Thr Lys Arg Glu Pro Leu Gly Val Cys Gly
145                 150                 155                 160

Gln Ile Ile Pro Trp Asn Phe Pro Ile Leu Met Trp Ala Trp Lys Ile
                165                 170                 175

Gly Pro Ala Leu Ala Thr Gly Asn Ala Val Val Leu Lys Pro Ala Ser
                180                 185                 190

Ala Thr Pro Leu Thr Ala Leu Tyr Ala Thr Lys Leu Val Lys Glu Ala
                195                 200                 205

Gly Ile Pro Ala Gly Leu Val Asn Ile Val Pro Gly Ser Gly Arg Gly
                210                 215                 220

Cys Gly Asn Ala Ile Leu Gln His Pro Lys Ile Lys Lys Ile Ala Phe
225                 230                 235                 240

Thr Gly Ser Thr Ala Val Gly Ile Asp Val Met Val Ala Ala Ala Thr
                245                 250                 255
```

Phe Asn Leu Lys Lys Val Thr Leu Glu Leu Gly Gly Lys Ser Pro Asn
            260                 265                 270

Ile Val Phe Asp Asp Cys Glu Leu Glu Ser Thr Ile Gln Asn Leu Ile
            275                 280                 285

Thr Gly Ile Phe Phe Asn Gly Gly Glu Val Cys Cys Ala Gly Ser Arg
        290                 295                 300

Ile Tyr Val Gln Glu Gly Ile Tyr Glu Gln Val Leu Ser Lys Phe Lys
305                 310                 315                 320

Glu Glu Ile Ser Lys Leu Lys Val Gly Asn Pro Phe Glu Glu Gly Thr
                325                 330                 335

Tyr Gln Gly Ala Gln Ala Thr Pro Asp Gln Phe Glu Cys Val Leu Gly
            340                 345                 350

Tyr Ile Glu Arg Ala Lys Lys Ala Gly Ala Lys Leu Leu Thr Gly Gly
            355                 360                 365

Asn Arg Ile Gly Thr Lys Gly Tyr Phe Val Glu Pro Thr Val Phe Tyr
        370                 375                 380

Asp Cys Asp Glu Asp Leu Glu Ile Val Lys Asp Glu Ile Phe Gly Pro
385                 390                 395                 400

Val Ala Ser Ile Gly Lys Phe Lys Asp Val Ala Glu Leu Val Glu Lys
                405                 410                 415

Ala Asn Asn Ser Glu Tyr Gly Leu Ala Ala Gly Ile His Thr Gln Asp
            420                 425                 430

Leu Asn Lys Ala Phe Gly Val Ala Asp Gln Leu Glu Ala Gly Ser Val
            435                 440                 445

Trp Ile Asn Thr Tyr Asn Asp Leu His Gln Ser Val Pro Phe Gly Gly
        450                 455                 460

Tyr Lys Thr Ser Gly Ile Gly Arg Glu Met Gly Leu Glu Ala Phe Asp
465                 470                 475                 480

Asn Tyr Thr Gln Val Lys Ala Val Arg Thr Arg Leu Asn Val Pro Thr
                485                 490                 495

Ala

<210> SEQ ID NO 39
<211> LENGTH: 507
<212> TYPE: PRT
<213> ORGANISM: Kluyveromyces marxianus

<400> SEQUENCE: 39

Met Ser Ser Ser Leu Ala Glu Lys Leu Asn Val Lys Ile Val Glu Gln
1               5                   10                  15

Lys Pro Val Thr Val Thr Leu Pro Asn Gly Leu Thr Tyr Glu Gln Pro
            20                  25                  30

Thr Gly Leu Phe Ile Asn Asn Gln Phe Ile Arg Ser Gln Asp Gly Ser
        35                  40                  45

Thr Leu Lys Val Glu Asn Pro Ser Thr Glu Glu Ile Ile Val Glu Val
    50                  55                  60

Gln Ser Ala Thr Ala Gln Asp Val Glu Tyr Ala Val Glu Ser Ala Glu
65                  70                  75                  80

Ala Ala Phe Asn Ser Glu Trp Ser Ser Met Asp Pro Arg Asn Arg Ala
                85                  90                  95

Ala Tyr Leu Val Lys Leu Ala Asn Leu Ile Glu Glu Lys Lys Glu Leu
            100                 105                 110

Ile Ala Ser Ile Glu Ser Thr Asp Asn Gly Lys Ala Leu Ala Leu Ala
        115                 120                 125

Arg Gly Asp Val Gly Leu Val Ile Asp Tyr Ile Arg Ser Ala Ala Gly
    130                 135                 140

Tyr Ala Asp Lys Leu Gly Gly Arg Thr Ile Asp Thr Gly Asp Gly Tyr
145                 150                 155                 160

Ala Asn Phe Thr Tyr Arg Glu Pro Ile Gly Val Cys Gly Gln Ile Ile
                165                 170                 175

Pro Trp Asn Phe Pro Leu Met Met Leu Ser Trp Lys Ile Ala Pro Ala
            180                 185                 190

Leu Val Ala Gly Asn Thr Val Ile Leu Lys Pro Ala Ser Pro Thr Pro
        195                 200                 205

Leu Asn Ala Leu Phe Phe Ala Ser Leu Cys Lys Glu Ala Gly Ile Pro
    210                 215                 220

Ala Gly Val Val Asn Ile Val Pro Gly Pro Gly Arg Ser Val Gly Asp
225                 230                 235                 240

Thr Ile Thr Asn His Pro Lys Ile Arg Lys Ile Ala Phe Thr Gly Ser
                245                 250                 255

Thr Asp Ile Gly Arg Asp Val Ala Ile Lys Ala Ala Gln Ser Asn Leu
            260                 265                 270

Lys Lys Val Thr Leu Glu Leu Gly Gly Lys Ser Ala His Leu Val Phe
        275                 280                 285

Ala Asp Ala Asn Ile Lys Lys Thr Ile Pro Asn Leu Val Asn Gly Ile
    290                 295                 300

Phe Lys Asn Ala Gly Gln Ile Cys Ser Ser Gly Ser Arg Ile Tyr Val
305                 310                 315                 320

Gln Asp Thr Ile Tyr Asp Glu Leu Leu Ser Glu Phe Lys Lys Tyr Leu
                325                 330                 335

Glu Thr Glu Ile Lys Val Gly Ser Pro Phe Asp Glu Ser Asn Phe Gln
            340                 345                 350

Ala Ala Ile Thr Asn Lys Ala Gln Phe Glu Thr Ile Leu Asn Tyr Ile
        355                 360                 365

Asp Ile Gly Lys Lys Glu Gly Ala Lys Ile Leu Thr Gly Gly Glu Arg
    370                 375                 380

Val Gly Asn Lys Gly Tyr Phe Ile Arg Pro Thr Val Phe Tyr Asp Val
385                 390                 395                 400

Lys Glu Asp Met Arg Ile Val Lys Glu Glu Ile Phe Gly Pro Val Val
                405                 410                 415

Thr Ile Ser Lys Phe Ser Thr Val Asp Glu Ala Val Ala Leu Ala Asn
            420                 425                 430

Asp Ser Glu Phe Gly Leu Gly Ala Gly Ile Glu Thr Gly Asn Leu Ser
        435                 440                 445

Val Ala Leu Lys Val Ala Lys Arg Leu His Ala Gly Thr Val Trp Ile
    450                 455                 460

Asn Thr Tyr Asn Asp Phe Asp Ala Ala Val Pro Phe Gly Gly Tyr Lys
465                 470                 475                 480

Gln Ser Gly Tyr Gly Arg Glu Met Gly Glu Ala Phe Glu Ser Tyr
                485                 490                 495

Thr Gln Val Lys Ala Val Arg Ile Lys Leu Glu
            500                 505

<210> SEQ ID NO 40
<211> LENGTH: 503
<212> TYPE: PRT
<213> ORGANISM: Schizosaccharomyces pombe

<400> SEQUENCE: 40

```
Met Ser Thr Lys Leu Val Asp His Val Glu Ile Thr Val Pro Thr Gly
1               5                   10                  15

Lys Thr Tyr Ile Gln Pro Val Gly Leu Phe Ile Asn Asn Gln His Val
            20                  25                  30

Asp Ser Val His Gly Gly Arg Val Lys Val Tyr Ser Pro Ser Thr Glu
        35                  40                  45

Lys Leu Ile Cys Glu Val Ala Asp Ala Asp Glu Glu Asp Val Asp Ile
    50                  55                  60

Ala Val Lys Val Ala Arg Ala Ala Phe Gln Thr Asp Ala Pro Trp Arg
65                  70                  75                  80

Lys Phe Ser Ser Ala Gln Arg Gly Arg Cys Leu Ser Arg Leu Ala Asp
                85                  90                  95

Cys Ile Glu Gln Asn Leu Glu Tyr Leu Ala Ser Ile Glu Thr Leu Asp
            100                 105                 110

Asn Gly Lys Ser Ile Thr Leu Ala Arg Gly Asp Val Gln Ala Ala Ala
        115                 120                 125

Asp Cys Phe Arg Tyr Tyr Gly Gly Trp Ala Asp Lys Asp Tyr Gly Gln
130                 135                 140

Thr Ile Glu Thr Asp Ile Lys Arg Phe Ala Tyr Thr Arg His Glu Pro
145                 150                 155                 160

Ile Gly Val Cys Gly Gln Ile Ile Pro Trp Asn Phe Pro Phe Leu Met
                165                 170                 175

Cys Ala Trp Lys Ile Ala Pro Ala Val Ala Cys Gly Asn Thr Ile Ile
            180                 185                 190

Leu Lys Thr Ala Glu Leu Thr Pro Leu Ser Ala Leu Cys Leu Thr Lys
        195                 200                 205

Phe Val Pro Glu Cys Gly Phe Pro Pro Gly Val Ile Asn Val Leu Ser
210                 215                 220

Gly Asp Gly Arg Arg Cys Gly Asn Ala Ile Ser Ser His Met Asp Ile
225                 230                 235                 240

Asp Lys Val Ala Phe Thr Gly Ser Thr Gly Val Gly Arg Met Val Met
                245                 250                 255

Arg Ala Ala Ala Ser Ser Asn Leu Lys Lys Val Thr Leu Glu Leu Gly
            260                 265                 270

Gly Lys Ser Pro Asn Ile Val Phe Asn Asp Ala Asp Leu Asp Ser Ala
        275                 280                 285

Ala Val Trp Thr Asn Tyr Gly Ile Phe Tyr Asn Ser Gly Gln Val Cys
        290                 295                 300

Cys Ala Gly Ser Arg Val Tyr Val Gln Glu Asp Val Tyr Asp Glu Phe
305                 310                 315                 320

Ile Lys Arg Met Val Ala Lys Ala Lys Thr Leu Lys Val Gly Asp Pro
            325                 330                 335

Phe Ala Glu Asp Thr Phe Gln Gly Ala Gln Val Ser Lys Gln Gln Tyr
        340                 345                 350

Glu Arg Ile Val Ser Tyr Ile Glu Ser Gly Ile Ala His Gly Ala Lys
        355                 360                 365

Leu Glu Ile Gly Gly Lys Arg His Gly Asn Leu Gly Tyr Phe Val Glu
370                 375                 380

Pro Thr Ile Leu Ser Asn Val Thr Glu Asp Met Ala Val Gly Lys Glu
385                 390                 395                 400

Glu Ile Phe Gly Pro Val Leu Ala Val Ile Lys Phe Lys Thr Ile Glu
            405                 410                 415
```

```
Glu Ala Ile Arg Arg Gly Asn Asn Ser Thr Tyr Gly Leu Ala Ala Gly
            420                 425                 430

Val His Thr Asn Asn Ile Thr Asn Ala Ile Lys Val Ser Asn Ala Leu
            435                 440                 445

Glu Ala Gly Thr Val Trp Val Asn Cys Tyr Asn Leu Leu His His Gln
        450                 455                 460

Ile Pro Phe Gly Gly Tyr Lys Glu Ser Gly Ile Gly Arg Glu Leu Gly
465                 470                 475                 480

Ser Tyr Gly Leu Thr Asn Tyr Thr Gln Thr Lys Ala Val His Ile Asn
                485                 490                 495

Leu Gly Met Asp Ser Pro Ile
            500
```

<210> SEQ ID NO 41
<211> LENGTH: 496
<212> TYPE: PRT
<213> ORGANISM: Schizosaccharomyces pombe

<400> SEQUENCE: 41

```
Met Ser Glu Asp Leu Phe Val Ser Ile Asn Phe Pro Asn Gly Lys Ser
1               5                  10                  15

Val Lys Gln Pro Ile Gly Leu Tyr Ile Asn Gly Glu Trp His Lys Ser
            20                  25                  30

Ala Glu Thr Trp Glu Thr Val Asp Pro Ser Ile Glu Glu Val Ile Ala
        35                  40                  45

Lys Val Tyr Leu Ala Gly Glu Lys Glu Ile Asp Tyr Ala Val Lys Ser
    50                  55                  60

Ala Lys Glu Ala Phe Lys Thr Trp Lys Lys Val Pro Gly Ser Glu Lys
65                  70                  75                  80

Gly Glu Leu Leu Met Lys Leu Ala Glu Leu Thr Glu Lys His Ala Asp
                85                  90                  95

Thr Leu Ala Ala Ile Glu Ala Met Asp Ser Gly Lys Pro Leu Val Ser
            100                 105                 110

Asn Ala Arg Gly Asp Val Asp Gly Thr Ile Ala Leu Leu Arg Tyr Cys
        115                 120                 125

Ala Gly Trp Ala Asp Lys Ile Tyr Gly Gln Val Ile Pro Thr Gly Pro
    130                 135                 140

Glu Lys Leu Ala Tyr Ala Lys Arg Thr Pro Ile Gly Val Cys Gly Gln
145                 150                 155                 160

Ile Val Pro Trp Asn Tyr Pro Leu Asn Met Ala Gly Trp Lys Ile Ala
                165                 170                 175

Pro Ala Leu Ala Ala Gly Asn Cys Ile Ile Lys Ser Ala Glu Thr
            180                 185                 190

Thr Pro Leu Ser Leu Leu Tyr Phe Ala Thr Leu Val Glu Glu Ala Gly
        195                 200                 205

Phe Pro Lys Gly Val Val Asn Ile Ile Ser Gly Leu Gly Thr Val Ala
    210                 215                 220

Gly Ser Tyr Met Ala Lys His Pro Gly Ile Asp Lys Ile Ala Phe Thr
225                 230                 235                 240

Gly Ser Thr Lys Val Gly Val Ile Val Gln Gln Leu Ala Ala Ser Asn
                245                 250                 255

Leu Lys Ala Val Thr Leu Glu Cys Gly Gly Lys Ser Pro Phe Leu Val
            260                 265                 270

Phe Glu Asp Ala Asp Leu Asp Gln Ala Val Lys Trp Ala Ala Leu Gly
        275                 280                 285
```

```
Ile Met Tyr Asn Ser Gly Gln Ile Cys Thr Ser Asn Ser Arg Ile Tyr
    290                 295                 300

Val Gln Asp Ser Val Tyr Asp Lys Phe Ile Glu Leu Phe Lys Lys His
305                 310                 315                 320

Val Ile Gln Asp Tyr Ile Val Gly Met Pro Phe Asp Asp Asn Thr Val
                325                 330                 335

Val Gly Pro Val Val Asn Lys Thr Gln Tyr Asn Arg Ile Lys Asn Tyr
            340                 345                 350

Ile Glu Gln Gly Lys Lys Glu Gly Ala Lys Leu Val Leu Gly Asp Glu
        355                 360                 365

Pro Leu Pro Leu Lys Gln Gly Tyr Phe Ile Ser Pro Thr Ile Phe Ala
    370                 375                 380

Asp Cys Ser Glu Asn Met Thr Ile Val Lys Glu Ile Phe Gly Pro
385                 390                 395                 400

Val Val Ala Ile Ser Lys Phe Lys Thr Glu Asp Glu Ala Ile Glu Lys
                405                 410                 415

Ala Asn Asn Thr Thr Tyr Gly Leu Ala Ala Met Cys Phe Thr Lys Asp
            420                 425                 430

Leu Glu Arg Ala His Arg Val Ser Asp Glu Leu Glu Ala Gly Met Val
        435                 440                 445

Phe Ile Asn Ser Thr Glu Asn Ser Asp Ile Gln Ala Pro Phe Gly Gly
    450                 455                 460

Ile Lys Met Ser Gly Ile Gly Asn Glu Leu Gly Ser Asn Gly Ile Glu
465                 470                 475                 480

Met Tyr Thr Gln Ile Lys Ala Val His Ile Asn Phe Asn Asn Lys Leu
                485                 490                 495

<210> SEQ ID NO 42
<211> LENGTH: 1716
<212> TYPE: DNA
<213> ORGANISM: Bacillus subtilis

<400> SEQUENCE: 42
atgttgacta aagctacaaa agagcagaaa tcattggtga aaaatagggg tgcagaactt      60
gttgtggact gtttggtaga acagggcgta acacatgttt ttggtatccc aggtgcaaaa     120
atcgacgccg tgtttgatgc attacaagac aagggtccag aaattattgt tgctagacat     180
gagcaaaatg ccgcatttat ggcgcaagct gtaggtaggc ttacaggtaa acctggtgtt     240
gtcctagtta cgtctggccc aggagcctcc aatttagcaa ctggtctatt gacagctaat     300
actgagggag atcctgtagt tgcgttagcc ggtaatgtaa ttagagctga taggcttaag     360
agaactcacc agtctctaga caacgctgct ttattccaac cgatcaccaa gtactcagta     420
gaggtacaag acgtaaagaa tatacctgaa gctgtgacaa acgcatttcg tatagcttct     480
gctggtcagg ctggtgccgc gtttgtttct tttcctcaag acgttgtcaa tgaagtgacc     540
aatactaaaa acgttagagc ggttgcagcc cctaaactag gtccagccgc agacgacgca     600
attagcgctg caattgctaa aattcagacg gcgaaactac cagtagtcct tgtcggtatg     660
aagggcggaa gaccagaagc aataaaaagct gttcgtaagt tattgaagaa agtccaatta     720
ccttttcgttg agacttacca agcagcaggt actttatcta gagatttaga ggatcagtat     780
tttggaagga taggtctatt tagaaaccaa ccaggagatt tactattaga caagctgat     840
gttgtactta ctatccggtta tgatcctata gagtatgacc caaagtttg gaacataaat     900
ggggatagaa caattataca tctagacgag ataatcgccg acatcgatca cgcttatcaa     960
```

-continued

```
ccagatttag aactaatcgg agatatcccg tcaacaatca atcatattga acatgatgct    1020
gtaaaggttg agttcgctga acgtgagcag aaaatcttat ctgatctaaa gcaatatatg    1080
catgagggtg aacaagttcc agcagactgg aaatctgacc gtgcacatcc tttggaaatc    1140
gttaaggaac taagaaatgc ggtcgatgat catgtgactg ttacatgtga tatcggttca    1200
catgcaattt ggatgtcacg ttattttagg agctacgaac cattaacttt aatgatatct    1260
aacgggatgc aaactctggg ggttgcactt ccttgggcta ttggcgctag tttagttaag    1320
cccggtgaga aggtggtatc ggtatcaggt gatggtggct ttctgttttc ggctatggaa    1380
ttagaaactg cagtccgttt aaaagctccc attgtgcata ttgtctggaa tgattctact    1440
tacgacatgg ttgcttttca acagttgaag aaatacaata gaacttcggc tgtagacttt    1500
ggtaacatcg atattgtgaa atatgctgag tcttttggcg caacaggcct gagggtggaa    1560
agtccagatc agttagctga tgtgttgaga caagggatga atgccgaggg accggtaatc    1620
atagatgtgc cagttgacta ctcagacaat attaatttgg cttctgataa acttcctaaa    1680
gagtttggcg agctaatgaa gaccaaagcc ttataa                              1716
```

<210> SEQ ID NO 43
<211> LENGTH: 571
<212> TYPE: PRT
<213> ORGANISM: Bacillus subtilis

<400> SEQUENCE: 43

```
Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240
```

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
        290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
                340                 345                 350

Leu Ser Asp Leu Lys Gln Tyr Met His Glu Gly Glu Gln Val Pro Ala
            355                 360                 365

Asp Trp Lys Ser Asp Arg Ala His Pro Leu Glu Ile Val Lys Glu Leu
        370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
                420                 425                 430

Ala Ile Gly Ala Ser Leu Val Lys Pro Gly Glu Lys Val Val Ser Val
            435                 440                 445

Ser Gly Asp Gly Gly Phe Leu Phe Ser Ala Met Glu Leu Glu Thr Ala
        450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
        530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 44
<211> LENGTH: 1476
<212> TYPE: DNA
<213> ORGANISM: Escherichia coli

<400> SEQUENCE: 44
atggcgaatt atttcaacac tctgaacctg cgtcaacaac tggcgcaact gggtaagtgc      60
cgtttcatgg gtcgtgacga gtttgcggac ggtgcttctt atctgcaagg caagaaggtt     120
gttattgttg gttgcggtgc gcaaggcctg aatcaaggtc tgaatatgcg cgacagcggc     180
ctggacatta gctatgcgct gcgcaaggag gctatcgcgg aaaaacgtgc tagctggcgc     240

```
aaggctactg agaacggctt caaggttggc acctatgagg agctgattcc gcaagctgac    300
ctggttatca atctgacccc agataaagtg catagcgacg ttgttcgtac tgttcaaccg    360
ctgatgaagg atggtgctgc tctgggttat agccacggct ttaacattgt tgaggtaggt    420
gaacaaattc gcaaggacat tactgttgtt atggtggctc caaagtgtcc gggtactgag    480
gttcgcgagg aatataagcg cggttttggt gttccaaccc tgatcgcggt gcatccagag    540
aatgacccaa agggtgaggg tatggctatc gcgaaggcgt gggctgcggc gactggcggc    600
catcgcgctg gcgttctgga gagcagcttt gtggctgagg ttaagagcga tctgatgggt    660
gaacagacta ttctgtgtgg tatgctgcaa gcgggtagcc tgctgtgttt tgataaactg    720
gttgaggagg gcactgaccc ggcgtatgcg gagaagctga tccaatttgg ctgggagact    780
attactgagc gcctgaagca aggtggtatt actctgatga tggatcgcct gagcaatcca    840
gctaagctgc gcgcgtacgc tctgagcgag caactgaagg aaattatggc accgctgttt    900
caaaagcaca tggatgatat cattagcggt gagtttagca gcggcatgat ggctgattgg    960
gcgaatgacg acaaaaagct gctgacttgg cgcgaggaaa ctggtaagac tgctttcgag   1020
actgctccac aatacgaggg taagattggt gaacaagaat attttgacaa gggtgttctg   1080
atgatcgcta tggttaaggc tggtgtggag ctggcttttg agactatggt tgacagcggt   1140
attatcgagc aaagcgcgta ctacgagagc ctgcatgaac tgccactgat cgcgaatact   1200
attgcgcgca acgcctgta tgagatgaat gttgtgatta gcgacactgc ggaatatggc   1260
aattacctgt ttagctatgc gtgcgttcca ctgctgaagc cattcatggc ggaactgcag   1320
ccaggtgatc tgggcaaggc gatcccagag ggtgctgttg acaatggtca gctgcgcgac   1380
gttaatgagg ctatccgttc tcacgctatc gaacaagttg gcaaaaagct gcgtggttac   1440
atgaccgaca tgaagcgcat cgcggtggct ggctaa                              1476
```

<210> SEQ ID NO 45
<211> LENGTH: 493
<212> TYPE: PRT
<213> ORGANISM: Escherichia coli

<400> SEQUENCE: 45

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu

```
              145                 150                 155                 160
Val Arg Glu Glu Tyr Lys Arg Gly Phe Gly Val Pro Thr Leu Ile Ala
                    165                 170                 175

Val His Pro Glu Asn Asp Pro Lys Gly Glu Gly Met Ala Ile Ala Lys
                    180                 185                 190

Ala Trp Ala Ala Ala Thr Gly Gly His Arg Ala Gly Val Leu Glu Ser
                    195                 200                 205

Ser Phe Val Ala Glu Val Lys Ser Asp Leu Met Gly Glu Gln Thr Ile
                    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                    245                 250                 255

Gly Trp Glu Thr Ile Thr Glu Ala Leu Lys Gln Gly Gly Ile Thr Leu
                    260                 265                 270

Met Met Asp Arg Leu Ser Asn Pro Ala Lys Leu Arg Ala Tyr Ala Leu
                    275                 280                 285

Ser Glu Gln Leu Lys Glu Ile Met Ala Pro Leu Phe Gln Lys His Met
                    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                    325                 330                 335

Thr Ala Phe Glu Thr Ala Pro Gln Tyr Glu Gly Lys Ile Gly Glu Gln
                    340                 345                 350

Glu Tyr Phe Asp Lys Gly Val Leu Met Ile Ala Met Val Lys Ala Gly
                    355                 360                 365

Val Glu Leu Ala Phe Glu Thr Met Val Asp Ser Gly Ile Ile Glu Glu
                    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                    405                 410                 415

Ala Glu Tyr Gly Asn Tyr Leu Phe Ser Tyr Ala Cys Val Pro Leu Leu
                    420                 425                 430

Lys Pro Phe Met Ala Glu Leu Gln Pro Gly Asp Leu Gly Lys Ala Ile
                    435                 440                 445

Pro Glu Gly Ala Val Asp Asn Gly Gln Leu Arg Asp Val Asn Glu Ala
450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly Leu Glu
                    485                 490

<210> SEQ ID NO 46
<211> LENGTH: 1476
<212> TYPE: DNA
<213> ORGANISM: Escherichia coli

<400> SEQUENCE: 46
atggccaact attttaacac attaaatttg agacaacaat tggctcaact gggtaagtgc     60
agatttatgg aagggacga gtttgctgat ggtgcttctt atctgcaagg aaagaaagta    120
gtaattgttg gctgcggtgc tcagggtcta aaccaaggtt taaacatgag agattcaggt    180
```

```
ctggatattt cgtatgcatt gaggaaagag tctattgcag aaaaggatgc cgattggcgt    240
aaagcgacgg aaaatgggtt caaagttggt acttacgaag aactgatccc tcaggcagat    300
ttagtgatta acctaacacc agataaggtt cactcagacg tagtaagaac agttcaaccg    360
ctgatgaagg atggggcagc tttaggttac tctcatggct taatatcgt tgaagtgggc     420
gagcagatca gaaaaggtat aacagtcgta atggttgcgc caaagtgccc aggtacggaa    480
gtcagagagg agtacaagag gggttttggt gtacctacat tgatcgccgt acatcctgaa    540
aatgacccca aacgtgaagg tatggcaata gcgaaggcat gggcagccgc aaccggaggt    600
catagagcgg gtgtgttaga gagttctttc gtagctgagg tcaagagtga cttaatgggt    660
gaacaaacca ttctgtgcgg aatgttgcag gcagggtctt tactatgctt tgataaattg    720
gtcgaagagg gtacagatcc tgcctatgct gaaaagttga tacaatttgg ttgggagaca    780
atcaccgagg cacttaaaca aggtggcata acattgatga tggatagact ttcaaatccg    840
gccaagctaa gagcctacgc cttatctgag caactaaaag agatcatggc accattattc    900
caaaagcaca tggacgatat tatctccggt gagttttcct caggaatgat ggcagattgg    960
gcaaacgatg ataaaaagtt attgacgtgg agagaagaaa ccggcaagac ggcattcgag   1020
acagccccac aatacgaagg taaaattggt gaacaagaat actttgataa gggagtattg   1080
atgatagcta tggtgaaggc aggggtagaa cttgcattcg aaactatggt tgactccggt   1140
atcattgaag aatctgcata ctatgagtct ttgcatgaat tgccttttgat agcaaatact   1200
attgcaagaa aaagacttta cgagatgaat gttgtcatat cagacactgc agaatatggt   1260
aattacttat ttagctacgc gtgtgtcccg ttgttagagc ccttcatggc cgagttacaa   1320
cctggtgatt tggggaaggc tattccggaa ggagcggttg acaatggcca actgagagac   1380
gtaaatgaag ctattcgttc gcatgctata gaacaggtgg gtaaaaagct gagaggatat   1440
atgaccgata tgaaaagaat tgcagtggca ggatga                             1476
```

<210> SEQ ID NO 47
<211> LENGTH: 491
<212> TYPE: PRT
<213> ORGANISM: Escherichia coli

<400> SEQUENCE: 47

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ser Ile Ala Glu Lys Asp Ala Asp Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140
```

| Lys | Gly | Ile | Thr | Val | Val | Met | Val | Ala | Pro | Lys | Cys | Pro | Gly | Thr | Glu |
| --- | --- | --- | --- | --- | --- | --- | --- | --- | --- | --- | --- | --- | --- | --- | --- |
| 145 | | | | 150 | | | | | 155 | | | | | 160 | |

| Val | Arg | Glu | Glu | Tyr | Lys | Arg | Gly | Phe | Gly | Val | Pro | Thr | Leu | Ile | Ala |
| --- | --- | --- | --- | --- | --- | --- | --- | --- | --- | --- | --- | --- | --- | --- | --- |
| | | | | 165 | | | | | 170 | | | | | 175 | |

| Val | His | Pro | Glu | Asn | Asp | Pro | Lys | Arg | Glu | Gly | Met | Ala | Ile | Ala | Lys |
| --- | --- | --- | --- | --- | --- | --- | --- | --- | --- | --- | --- | --- | --- | --- | --- |
| | | | 180 | | | | | 185 | | | | | 190 | | |

| Ala | Trp | Ala | Ala | Ala | Thr | Gly | Gly | His | Arg | Ala | Gly | Val | Leu | Glu | Ser |
| --- | --- | --- | --- | --- | --- | --- | --- | --- | --- | --- | --- | --- | --- | --- | --- |
| | | | 195 | | | | | 200 | | | | | 205 | | |

| Ser | Phe | Val | Ala | Glu | Val | Lys | Ser | Asp | Leu | Met | Gly | Glu | Gln | Thr | Ile |
| --- | --- | --- | --- | --- | --- | --- | --- | --- | --- | --- | --- | --- | --- | --- | --- |
| | | 210 | | | | | 215 | | | | | 220 | | | |

| Leu | Cys | Gly | Met | Leu | Gln | Ala | Gly | Ser | Leu | Leu | Cys | Phe | Asp | Lys | Leu |
| --- | --- | --- | --- | --- | --- | --- | --- | --- | --- | --- | --- | --- | --- | --- | --- |
| 225 | | | | 230 | | | | | 235 | | | | | 240 | |

| Val | Glu | Glu | Gly | Thr | Asp | Pro | Ala | Tyr | Ala | Glu | Lys | Leu | Ile | Gln | Phe |
| --- | --- | --- | --- | --- | --- | --- | --- | --- | --- | --- | --- | --- | --- | --- | --- |
| | | | | 245 | | | | | 250 | | | | | 255 | |

| Gly | Trp | Glu | Thr | Ile | Thr | Glu | Ala | Leu | Lys | Gln | Gly | Gly | Ile | Thr | Leu |
| --- | --- | --- | --- | --- | --- | --- | --- | --- | --- | --- | --- | --- | --- | --- | --- |
| | | | 260 | | | | | 265 | | | | | 270 | | |

| Met | Met | Asp | Arg | Leu | Ser | Asn | Pro | Ala | Lys | Leu | Arg | Ala | Tyr | Ala | Leu |
| --- | --- | --- | --- | --- | --- | --- | --- | --- | --- | --- | --- | --- | --- | --- | --- |
| | | 275 | | | | | 280 | | | | | 285 | | | |

| Ser | Glu | Gln | Leu | Lys | Glu | Ile | Met | Ala | Pro | Leu | Phe | Gln | Lys | His | Met |
| --- | --- | --- | --- | --- | --- | --- | --- | --- | --- | --- | --- | --- | --- | --- | --- |
| 290 | | | | 295 | | | | | 300 | | | | | | |

| Asp | Asp | Ile | Ile | Ser | Gly | Glu | Phe | Ser | Ser | Gly | Met | Met | Ala | Asp | Trp |
| --- | --- | --- | --- | --- | --- | --- | --- | --- | --- | --- | --- | --- | --- | --- | --- |
| 305 | | | | | 310 | | | | | 315 | | | | | 320 |

| Ala | Asn | Asp | Asp | Lys | Lys | Leu | Leu | Thr | Trp | Arg | Glu | Thr | Gly | Lys |
| --- | --- | --- | --- | --- | --- | --- | --- | --- | --- | --- | --- | --- | --- | --- |
| | | | | 325 | | | | | 330 | | | | | 335 |

| Thr | Ala | Phe | Glu | Thr | Ala | Pro | Gln | Tyr | Glu | Gly | Lys | Ile | Gly | Glu | Gln |
| --- | --- | --- | --- | --- | --- | --- | --- | --- | --- | --- | --- | --- | --- | --- | --- |
| | | | 340 | | | | | 345 | | | | | 350 | | |

| Glu | Tyr | Phe | Asp | Lys | Gly | Val | Leu | Met | Ile | Ala | Met | Val | Lys | Ala | Gly |
| --- | --- | --- | --- | --- | --- | --- | --- | --- | --- | --- | --- | --- | --- | --- | --- |
| | | | 355 | | | | | 360 | | | | | 365 | | |

| Val | Glu | Leu | Ala | Phe | Glu | Thr | Met | Val | Asp | Ser | Gly | Ile | Ile | Glu | Glu |
| --- | --- | --- | --- | --- | --- | --- | --- | --- | --- | --- | --- | --- | --- | --- | --- |
| | 370 | | | | | 375 | | | | | 380 | | | | |

| Ser | Ala | Tyr | Tyr | Glu | Ser | Leu | His | Glu | Leu | Pro | Leu | Ile | Ala | Asn | Thr |
| --- | --- | --- | --- | --- | --- | --- | --- | --- | --- | --- | --- | --- | --- | --- | --- |
| 385 | | | | | 390 | | | | | 395 | | | | | 400 |

| Ile | Ala | Arg | Lys | Arg | Leu | Tyr | Glu | Met | Asn | Val | Val | Ile | Ser | Asp | Thr |
| --- | --- | --- | --- | --- | --- | --- | --- | --- | --- | --- | --- | --- | --- | --- | --- |
| | | | | 405 | | | | | 410 | | | | | 415 | |

| Ala | Glu | Tyr | Gly | Asn | Tyr | Leu | Phe | Ser | Tyr | Ala | Cys | Val | Pro | Leu | Leu |
| --- | --- | --- | --- | --- | --- | --- | --- | --- | --- | --- | --- | --- | --- | --- | --- |
| | | | 420 | | | | | 425 | | | | | 430 | | |

| Glu | Pro | Phe | Met | Ala | Glu | Leu | Gln | Pro | Gly | Asp | Leu | Gly | Lys | Ala | Ile |
| --- | --- | --- | --- | --- | --- | --- | --- | --- | --- | --- | --- | --- | --- | --- | --- |
| | | | 435 | | | | | 440 | | | | | 445 | | |

| Pro | Glu | Gly | Ala | Val | Asp | Asn | Gly | Gln | Leu | Arg | Asp | Val | Asn | Glu | Ala |
| --- | --- | --- | --- | --- | --- | --- | --- | --- | --- | --- | --- | --- | --- | --- | --- |
| | 450 | | | | | 455 | | | | | 460 | | | | |

| Ile | Arg | Ser | His | Ala | Ile | Glu | Gln | Val | Gly | Lys | Lys | Leu | Arg | Gly | Tyr |
| --- | --- | --- | --- | --- | --- | --- | --- | --- | --- | --- | --- | --- | --- | --- | --- |
| 465 | | | | | 470 | | | | | 475 | | | | | 480 |

| Met | Thr | Asp | Met | Lys | Arg | Ile | Ala | Val | Ala | Gly |
| --- | --- | --- | --- | --- | --- | --- | --- | --- | --- | --- |
| | | | | 485 | | | | | 490 | |

<210> SEQ ID NO 48
<211> LENGTH: 1647
<212> TYPE: DNA
<213> ORGANISM: Lactococcus lactis

<400> SEQUENCE: 48

| atgtatactg | ttggtgatta | tctgctggac | cgtctgcatg | aactgggtat | cgaagaaatc | 60 |
|---|---|---|---|---|---|---|
| ttcggcgttc | cgggtgatta | caatctgcag | ttcctggatc | agatcatctc | tcataaagac | 120 |
| atgaaatggg | tgggtaacgc | taacgaactg | aacgcaagct | acatggcaga | tggttatgca | 180 |

-continued

```
cgtaccaaga aagccgcggc atttctgacc actttcggtg ttggcgaact gagcgccgtc    240
aacggtctgg cgggctccta cgccgaaaac ctgccggtgg tggagatcgt aggcagccca    300
acgagcaaag ttcagaacga aggtaaattc gtccaccaca ctctggctga cggcgatttc    360
aaacacttca tgaaaatgca tgaacctgtg actgcggcac gtacgctgct gactgcagag    420
aacgctactg tggaaatcga ccgcgttctg tctgcgctgc tgaaagaacg caaaccagtt    480
tacatcaacc tgcctgtgga tgttgcggca gctaaagcgg aaaaaccgag cctgccgctg    540
aagaaagaaa actccacttc taacactagc gaccaggaaa tcctgaacaa atccaggag    600 tctctgaaaa cgcaaagaa accaatcgtg atcaccggcc acgaaatcat ttcttttggt    660
ctggagaaga ccgtgaccca attcatcagc aaaaccaaac tgccgattac caccctgaac    720
ttcggcaagt cctctgttga cgaggctctg ccgtctttcc tgggcatcta acggtact    780 ctgagcgaac cgaacctgaa agaatttgtt gaatctgcgg acttcatcct gatgctgggc    840
gttaaactga ccgactcttc taccggtgca ttcactcacc atctgaacga aaacaaatg    900 attagcctga acatcgacga gggtaaaatc ttcaacgagc gtatccagaa cttcgacttc    960
gaaagcctga tcagctctct gctggacctg tccgaaatcg agtataaagg caaatacatt   1020
gacaaaaagc aagaagattt cgtaccatct aacgcactgc tgtcccagga tcgcctgtgg   1080
caggccgtgg agaacctgac ccagagcaat gaaaccatcg tggcggaaca aggtacgagc   1140 ttttttcggcg cgtcttctat ctttctgaaa tccaaaagcc attttatcgg tcagccgctg   1200
tggggtagca ttggctatac tttcccggca gcgctgggct ctcagatcgc tgataaagaa   1260
tctcgtcatc tgctgttcat cggtgacggt tccctgcagc tgaccgtaca ggaactgggt   1320
ctggcaattc gtgaaaagat caacccgatt gcttcatta ttaacaatga cggctacacc   1380
gttgagcgtg agatccacgg tccgaaccag tcttacaacg atatccctat gtggaactac   1440
tctaaactgc cggagtcctt cggcgcaact gaggaccgtg ttgtgtctaa aattgtgcgt   1500
accgaaaacg aatttgtgag cgtgatgaaa gaggcccagg ccgatccgaa ccgtatgtac   1560
tggatcgaac tgatcctggc gaagaaggc gcaccgaagg tactgaagaa atgggcaag   1620 ctgtttgctg aacagaataa atcctaa                                        1647
```

<210> SEQ ID NO 49
<211> LENGTH: 548
<212> TYPE: PRT
<213> ORGANISM: Lactococcus lactis

<400> SEQUENCE: 49

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110
```

```
His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
                180                 185                 190

Glu Ile Leu Asn Lys Ile Gln Glu Ser Leu Lys Asn Ala Lys Lys Pro
                195                 200                 205

Ile Val Ile Thr Gly His Glu Ile Ile Ser Phe Gly Leu Glu Lys Thr
210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
                275                 280                 285

Gly Ala Phe Thr His His Leu Asn Glu Asn Lys Met Ile Ser Leu Asn
                290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
                355                 360                 365

Ser Asn Glu Thr Ile Val Ala Glu Gln Gly Thr Ser Phe Phe Gly Ala
                370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
                435                 440                 445

Pro Ile Cys Phe Ile Ile Asn Asn Asp Gly Tyr Thr Val Glu Arg Glu
                450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
                515                 520                 525
```

Glu Gly Ala Pro Lys Val Leu Lys Lys Met Gly Lys Leu Phe Ala Glu
    530                 535                 540

Gln Asn Lys Ser
545

<210> SEQ ID NO 50
<211> LENGTH: 1713
<212> TYPE: DNA
<213> ORGANISM: Lactococcus lactis

<400> SEQUENCE: 50

| | | | | | |
|---|---|---|---|---|---|
| atggagttta | agtataacgg | caaagttgaa | tctgttgaac | tgaataagta | cagcaaaacg | 60 |
| ttgacacaag | atcccacaca | acccgccaca | caggcaatgt | attacggcat | cgggtttaaa | 120 |
| gacgaagatt | tcaagaaagc | tcaagtgggt | atagtgtcga | tggactggga | tggaaatcca | 180 |
| tgcaacatgc | atttaggaac | ccttggatca | agattaaaa | gctcagtaaa | tcagacagat | 240 |
| ggtctgatcg | gcttacaatt | tcatacgata | ggagtttctg | atgggatagc | aaatggaaag | 300 |
| ttgggaatga | gatactccct | tgtttccaga | gaagttatag | ctgactctat | tgaaaccaac | 360 |
| gctggcgctg | aatactatga | tgcaattgta | gccatcccag | ttgtgacaa | aaatatgcca | 420 |
| ggttctatta | ttggtatggc | aagacttaat | aggccaagca | ttatggtgta | tggaggaaca | 480 |
| atagaacacg | gtaatataa | aggtgagaaa | ttgaacatcg | tatcggcttt | tgaatctcta | 540 |
| ggccagaaaa | ttaccggcaa | tatctctgat | gaagattatc | acggtgttat | ttgtaatgct | 600 |
| attcctggtc | aaggggcatg | tggggggatg | tacacagcta | ataccttagc | tgccgctatc | 660 |
| gaaacactag | gtatgtcatt | gccgtattct | tcttcgaacc | ctgcagtatc | tcaagaaaaa | 720 |
| caagaagaat | gtgatgagat | tggattagcc | attaagaatc | ttttggaaaa | agacatcaag | 780 |
| cctagtgata | taatgactaa | ggaggcgttc | gagaacgcta | ttaccattgt | gatggtcttg | 840 |
| gggggtagta | ctaatgctgt | cttgcatatt | attgcaatgg | ctaacgcgat | aggtgtcgaa | 900 |
| ataactcagg | atgacttcca | aagaattagt | gacattactc | agtactaggt | gattttaaa | 960 |
| ccttcaggta | aatatatgat | ggaagatttg | cataaaattg | gaggcttgcc | agcagtgctt | 1020 |
| aagtaccttc | taaaggaagg | aaaattgcat | ggtgactgcc | ttactgtgac | gggtaaaaca | 1080 |
| ttagccgaga | atgtcgagac | tgccctagac | ttggatttcg | actcacaaga | tatcatgagg | 1140 |
| ccactaaaga | atcctatcaa | ggccaccggc | cacttgcaga | ttctgtacgg | taatttagct | 1200 |
| caaggggggtt | ccgtagcaaa | aattagcggt | aagaaggag | agttcttcaa | aggcactgcc | 1260 |
| agagtctttg | atggtgaaca | acattttatc | gacggcatag | aatctggtcg | tttgcatgct | 1320 |
| ggagatgtag | cggtaattag | gaatataggt | cccgtcggcg | gacctggtat | gcccgaaatg | 1380 |
| ctgaagccta | catcagcatt | aattggtgcg | ggtttaggga | aaagttgcgc | gttaattacg | 1440 |
| gatggtagat | ctccggtgg | cactcacggt | tttgttgtcg | gccatattgt | gcctgaagcc | 1500 |
| gttgagggtg | gactaatcgg | cttagttgaa | gatgacgata | taatagagat | agatgcagtc | 1560 |
| aacaactcta | tatccctgaa | agtttccgat | gaagaaatcg | caaagagaag | agctaattat | 1620 |
| cagaagccaa | ctccgaaagc | caccagggga | gttttggcaa | aattcgctaa | attaacccgt | 1680 |
| cctgcatcgg | aagggtgtgt | tactgatctg | taa | | | 1713 |

<210> SEQ ID NO 51
<211> LENGTH: 570
<212> TYPE: PRT
<213> ORGANISM: Lactococcus lactis

<400> SEQUENCE: 51

```
Met Glu Phe Lys Tyr Asn Gly Lys Val Glu Ser Val Glu Leu Asn Lys
1               5                   10                  15

Tyr Ser Lys Thr Leu Thr Gln Asp Pro Thr Gln Pro Ala Thr Gln Ala
            20                  25                  30

Met Tyr Tyr Gly Ile Gly Phe Lys Asp Glu Asp Phe Lys Lys Ala Gln
        35                  40                  45

Val Gly Ile Val Ser Met Asp Trp Asp Gly Asn Pro Cys Asn Met His
50                  55                  60

Leu Gly Thr Leu Gly Ser Lys Ile Lys Ser Val Asn Gln Thr Asp
65                  70                  75                  80

Gly Leu Ile Gly Leu Gln Phe His Thr Ile Gly Val Ser Asp Gly Ile
                85                  90                  95

Ala Asn Gly Lys Leu Gly Met Arg Tyr Ser Leu Val Ser Arg Glu Val
            100                 105                 110

Ile Ala Asp Ser Ile Glu Thr Asn Ala Gly Ala Glu Tyr Tyr Asp Ala
            115                 120                 125

Ile Val Ala Ile Pro Gly Cys Asp Lys Asn Met Pro Gly Ser Ile Ile
130                 135                 140

Gly Met Ala Arg Leu Asn Arg Pro Ser Ile Met Val Tyr Gly Gly Thr
145                 150                 155                 160

Ile Glu His Gly Glu Tyr Lys Gly Glu Lys Leu Asn Ile Val Ser Ala
                165                 170                 175

Phe Glu Ser Leu Gly Gln Lys Ile Thr Gly Asn Ile Ser Asp Glu Asp
            180                 185                 190

Tyr His Gly Val Ile Cys Asn Ala Ile Pro Gly Gln Gly Ala Cys Gly
            195                 200                 205

Gly Met Tyr Thr Ala Asn Thr Leu Ala Ala Ala Ile Glu Thr Leu Gly
210                 215                 220

Met Ser Leu Pro Tyr Ser Ser Asn Pro Ala Val Ser Gln Glu Lys
225                 230                 235                 240

Gln Glu Glu Cys Asp Glu Ile Gly Leu Ala Ile Lys Asn Leu Leu Glu
            245                 250                 255

Lys Asp Ile Lys Pro Ser Asp Ile Met Thr Lys Glu Ala Phe Glu Asn
                260                 265                 270

Ala Ile Thr Ile Val Met Val Leu Gly Gly Ser Thr Asn Ala Val Leu
            275                 280                 285

His Ile Ile Ala Met Ala Asn Ala Ile Gly Val Glu Ile Thr Gln Asp
            290                 295                 300

Asp Phe Gln Arg Ile Ser Asp Ile Thr Pro Val Leu Gly Asp Phe Lys
305                 310                 315                 320

Pro Ser Gly Lys Tyr Met Met Glu Asp Leu His Lys Ile Gly Gly Leu
            325                 330                 335

Pro Ala Val Leu Lys Tyr Leu Leu Lys Glu Gly Lys Leu His Gly Asp
            340                 345                 350

Cys Leu Thr Val Thr Gly Lys Thr Leu Ala Glu Asn Val Glu Thr Ala
            355                 360                 365

Leu Asp Leu Asp Phe Asp Ser Gln Asp Ile Met Arg Pro Leu Lys Asn
370                 375                 380

Pro Ile Lys Ala Thr Gly His Leu Gln Ile Leu Tyr Gly Asn Leu Ala
385                 390                 395                 400

Gln Gly Gly Ser Val Ala Lys Ile Ser Gly Lys Glu Gly Glu Phe Phe
                405                 410                 415
```

```
Lys Gly Thr Ala Arg Val Phe Asp Gly Glu Gln His Phe Ile Asp Gly
                420                 425                 430

Ile Glu Ser Gly Arg Leu His Ala Gly Asp Val Ala Val Ile Arg Asn
            435                 440                 445

Ile Gly Pro Val Gly Gly Pro Gly Met Pro Glu Met Leu Lys Pro Thr
        450                 455                 460

Ser Ala Leu Ile Gly Ala Gly Leu Gly Lys Ser Cys Ala Leu Ile Thr
465                 470                 475                 480

Asp Gly Arg Phe Ser Gly Thr His Gly Phe Val Val Gly His Ile
                485                 490                 495

Val Pro Glu Ala Val Glu Gly Gly Leu Ile Gly Leu Val Glu Asp Asp
            500                 505                 510

Asp Ile Ile Glu Ile Asp Ala Val Asn Asn Ser Ile Ser Leu Lys Val
        515                 520                 525

Ser Asp Glu Glu Ile Ala Lys Arg Arg Ala Asn Tyr Gln Lys Pro Thr
530                 535                 540

Pro Lys Ala Thr Arg Gly Val Leu Ala Lys Phe Ala Lys Leu Thr Arg
545                 550                 555                 560

Pro Ala Ser Glu Gly Cys Val Thr Asp Leu
                565                 570

<210> SEQ ID NO 52
<211> LENGTH: 1701
<212> TYPE: DNA
<213> ORGANISM: Saccharomyces cerevisiae

<400> SEQUENCE: 52
atgaagaagc tcaacaagta ctcgtatatc atcactgaac ctaagggcca aggtgcgtcc      60
caggccatgc tttatgccac cggtttcaag aaggaagatt tcaagaagcc tcaagtcggg     120
gttggttcct gttggtggtc cggtaaccca tgtaacatgc atctattgga cttgaataac     180
agatgttctc aatccattga aaaagcgggt ttgaaagcta tgcagttcaa caccatcggt     240
gtttcagacg gtatctctat gggtactaaa ggtatgagat actcgttaca aagtagagaa     300
atcattgcag actcctttga accatcatg atggcacaac tacgatgc taacatcgcc        360
atcccatcat gtgacaaaaa catgcccggt gtcatgatgg ccatgggtag acataacaga     420
ccttccatca tggtatatgg tggtactatc ttgcccggtc atccaacatg tggttcttcg     480
aagatctcta aaaacatcga tatcgtctct gcgttccaat cctacggtga atatatttcc     540
aagcaattca ctgaagaaga agagaagat gttgtggaac atgcatgccc aggtcctggt     600
tcttgtggtg gtatgtatac tgccaacaca atggcttctg ccgctgaagt gctaggtttg     660
accattccaa actcctcttc cttcccagcc gtttccaagg agaagttagc tgagtgtgac     720
aacattggtg aatacatcaa gaagacaatg gaattgggta ttttacctcg tgatatcctc     780
acaaaagagg ctttttgaaaa cgccattact tatgtcgttg caaccggtgg gtccactaat     840
gctgttttgc atttggtggc tgttgctcac tctgcgggtg tcaagttgtc accagatgat     900
ttccaaagaa tcagtgatac tacaccattg atcggtgact caaaccttc tggtaaatac     960
gtcatggccg atttgattaa cgttggtggt acccaatctg tgattaagta tctatatgaa    1020
aacaacatgt tgcacggtaa cacaatgact gttaccggtg acactttggc agaacgtgca    1080
aagaaagcac aagcctacc tgaaggacaa gagattatta gccactctc ccacccaatc      1140
aaggccaacg tcacttgca aattctgtac ggttcattgg caccaggtgg agctgtgggt    1200
aaaattaccg gtaaggaagg tacttacttc aagggtagag cacgtgtgtt cgaagaggaa    1260
```

```
ggtgccttta ttgaagcctt ggaaagaggt gaaatcaaga agggtgaaaa aaccgttgtt    1320
gttatcagat atgaaggtcc aagaggtgca ccaggtatgc ctgaaatgct aaagccttcc    1380
tctgctctga tgggttacgg tttgggtaaa gatgttgcat tgttgactga tggtagattc    1440
tctggtggtt ctcacgggtt cttaatcggc acattgttc  ccgaagccgc tgaaggtggt    1500
cctatcgggt tggtcagaga cggcgatgag attatcattg atgctgataa taacaagatt    1560
gacctattag tctctgataa ggaaatggct aacgtaaac  aaagttgggt tgcacctcca    1620
cctcgttaca caagaggtac tctatccaag tatgctaagt tggtttccaa cgcttccaac    1680
ggttgtgttt tagatgcttg a                                              1701
```

<210> SEQ ID NO 53
<211> LENGTH: 566
<212> TYPE: PRT
<213> ORGANISM: Saccharomyces cerevisiae

<400> SEQUENCE: 53

```
Met Lys Lys Leu Asn Lys Tyr Ser Tyr Ile Ile Thr Glu Pro Lys Gly
1               5                   10                  15

Gln Gly Ala Ser Gln Ala Met Leu Tyr Ala Thr Gly Phe Lys Lys Glu
            20                  25                  30

Asp Phe Lys Lys Pro Gln Val Gly Val Gly Ser Cys Trp Trp Ser Gly
        35                  40                  45

Asn Pro Cys Asn Met His Leu Leu Asp Leu Asn Asn Arg Cys Ser Gln
    50                  55                  60

Ser Ile Glu Lys Ala Gly Leu Lys Ala Met Gln Phe Asn Thr Ile Gly
65                  70                  75                  80

Val Ser Asp Gly Ile Ser Met Gly Thr Lys Gly Met Arg Tyr Ser Leu
                85                  90                  95

Gln Ser Arg Glu Ile Ile Ala Asp Ser Phe Glu Thr Ile Met Met Ala
            100                 105                 110

Gln His Tyr Asp Ala Asn Ile Ala Ile Pro Ser Cys Asp Lys Asn Met
        115                 120                 125

Pro Gly Val Met Met Ala Met Gly Arg His Asn Arg Pro Ser Ile Met
    130                 135                 140

Val Tyr Gly Gly Thr Ile Leu Pro Gly His Pro Thr Cys Gly Ser Ser
145                 150                 155                 160

Lys Ile Ser Lys Asn Ile Asp Ile Val Ser Ala Phe Gln Ser Tyr Gly
                165                 170                 175

Glu Tyr Ile Ser Lys Gln Phe Thr Glu Glu Arg Glu Asp Val Val
            180                 185                 190

Glu His Ala Cys Pro Gly Pro Gly Ser Cys Gly Gly Met Tyr Thr Ala
        195                 200                 205

Asn Thr Met Ala Ser Ala Ala Glu Val Leu Gly Leu Thr Ile Pro Asn
    210                 215                 220

Ser Ser Ser Phe Pro Ala Val Ser Lys Glu Lys Leu Ala Glu Cys Asp
225                 230                 235                 240

Asn Ile Gly Glu Tyr Ile Lys Lys Thr Met Glu Leu Gly Ile Leu Pro
                245                 250                 255

Arg Asp Ile Leu Thr Lys Glu Ala Phe Glu Asn Ala Ile Thr Tyr Val
            260                 265                 270

Val Ala Thr Gly Gly Ser Thr Asn Ala Val Leu His Leu Val Ala Val
        275                 280                 285
```

Ala His Ser Ala Gly Val Lys Leu Ser Pro Asp Asp Phe Gln Arg Ile
    290                 295                 300

Ser Asp Thr Thr Pro Leu Ile Gly Asp Phe Lys Pro Ser Gly Lys Tyr
305                 310                 315                 320

Val Met Ala Asp Leu Ile Asn Val Gly Gly Thr Gln Ser Val Ile Lys
                325                 330                 335

Tyr Leu Tyr Glu Asn Asn Met Leu His Gly Asn Thr Met Thr Val Thr
                340                 345                 350

Gly Asp Thr Leu Ala Glu Arg Ala Lys Lys Ala Pro Ser Leu Pro Glu
                355                 360                 365

Gly Gln Glu Ile Ile Lys Pro Leu Ser His Pro Ile Lys Ala Asn Gly
    370                 375                 380

His Leu Gln Ile Leu Tyr Gly Ser Leu Ala Pro Gly Gly Ala Val Gly
385                 390                 395                 400

Lys Ile Thr Gly Lys Glu Gly Thr Tyr Phe Lys Gly Arg Ala Arg Val
                405                 410                 415

Phe Glu Glu Glu Gly Ala Phe Ile Glu Ala Leu Glu Arg Gly Glu Ile
                420                 425                 430

Lys Lys Gly Glu Lys Thr Val Val Ile Arg Tyr Glu Gly Pro Arg
    435                 440                 445

Gly Ala Pro Gly Met Pro Glu Met Leu Lys Pro Ser Ser Ala Leu Met
450                 455                 460

Gly Tyr Gly Leu Gly Lys Asp Val Ala Leu Leu Thr Asp Gly Arg Phe
465                 470                 475                 480

Ser Gly Gly Ser His Gly Phe Leu Ile Gly His Ile Val Pro Glu Ala
                485                 490                 495

Ala Glu Gly Gly Pro Ile Gly Leu Val Arg Asp Gly Asp Glu Ile Ile
                500                 505                 510

Ile Asp Ala Asp Asn Asn Lys Ile Asp Leu Leu Val Ser Asp Lys Glu
    515                 520                 525

Met Ala Gln Arg Lys Gln Ser Trp Val Ala Pro Pro Arg Tyr Thr
530                 535                 540

Arg Gly Thr Leu Ser Lys Tyr Ala Lys Leu Val Ser Asn Ala Ser Asn
545                 550                 555                 560

Gly Cys Val Leu Asp Ala
                565

<210> SEQ ID NO 54
<211> LENGTH: 771
<212> TYPE: DNA
<213> ORGANISM: Drosophila melanogaster

<400> SEQUENCE: 54
atgtcgttta ctttgaccaa caagaacgtg attttcgttg ccggtctggg aggcattggt    60
ctggacacca gcaaggagct gctcaagcgc gatctgaaga acctggtgat cctcgaccgc   120
attgagaacc cggctgccat tgccgagctg aaggcaatca atccaaaggt gaccgtcacc   180
ttctacccct atgatgtgac cgtgcccatt gccgagacca ccaagctgct gaagaccatc   240
ttcgcccagc tgaagaccgt cgatgtcctg atcaacggag ctggtatcct ggacgatcac   300
cagatcgagc gcaccattgc cgtcaactac actggcctgg tcaacaccac gacggccatt   360
ctggacttct gggacaagcg caagggcggt cccgtggta tcatctgcaa cattggatcc   420
gtcactggat tcaatgccat ctaccaggtg cccgtctact ccggcaccaa ggccgccgtg   480
gtcaacttca ccagctccct ggcgaaactg gccccattta ccggcgtgac ggcttacact   540

-continued

```
gtgaaccccg gcatcacccg caccaccctg gtgcacacgt tcaactcctg gttggatgtt    600
gagcctcagg ttgccgagaa gctcctggct catcccaccc agccctcgtt ggcctgcgcc    660
gagaacttcg tcaaggctat cgagctgaac cagaacggag ccatctggaa actggacttg    720
ggcaccctgg aggccatcca gtggaccaag cactgggact ccggcatcta a             771
```

<210> SEQ ID NO 55
<211> LENGTH: 256
<212> TYPE: PRT
<213> ORGANISM: Drosophila melanogaster

<400> SEQUENCE: 55

```
Met Ser Phe Thr Leu Thr Asn Lys Asn Val Ile Phe Val Ala Gly Leu
1               5                   10                  15

Gly Gly Ile Gly Leu Asp Thr Ser Lys Glu Leu Leu Lys Arg Asp Leu
            20                  25                  30

Lys Asn Leu Val Ile Leu Asp Arg Ile Glu Asn Pro Ala Ala Ile Ala
        35                  40                  45

Glu Leu Lys Ala Ile Asn Pro Lys Val Thr Val Thr Phe Tyr Pro Tyr
    50                  55                  60

Asp Val Thr Val Pro Ile Ala Glu Thr Thr Lys Leu Leu Lys Thr Ile
65                  70                  75                  80

Phe Ala Gln Leu Lys Thr Val Asp Val Leu Ile Asn Gly Ala Gly Ile
                85                  90                  95

Leu Asp Asp His Gln Ile Glu Arg Thr Ile Ala Val Asn Tyr Thr Gly
            100                 105                 110

Leu Val Asn Thr Thr Thr Ala Ile Leu Asp Phe Trp Asp Lys Arg Lys
        115                 120                 125

Gly Gly Pro Gly Gly Ile Ile Cys Asn Ile Gly Ser Val Thr Gly Phe
    130                 135                 140

Asn Ala Ile Tyr Gln Val Pro Val Tyr Ser Gly Thr Lys Ala Ala Val
145                 150                 155                 160

Val Asn Phe Thr Ser Ser Leu Ala Lys Leu Ala Pro Ile Thr Gly Val
                165                 170                 175

Thr Ala Tyr Thr Val Asn Pro Gly Ile Thr Arg Thr Thr Leu Val His
            180                 185                 190

Thr Phe Asn Ser Trp Leu Asp Val Glu Pro Gln Val Ala Glu Lys Leu
        195                 200                 205

Leu Ala His Pro Thr Gln Pro Ser Leu Ala Cys Ala Glu Asn Phe Val
    210                 215                 220

Lys Ala Ile Glu Leu Asn Gln Asn Gly Ala Ile Trp Lys Leu Asp Leu
225                 230                 235                 240

Gly Thr Leu Glu Ala Ile Gln Trp Thr Lys His Trp Asp Ser Gly Ile
                245                 250                 255
```

<210> SEQ ID NO 56
<211> LENGTH: 1023
<212> TYPE: DNA
<213> ORGANISM: Lactococcus lactis

<400> SEQUENCE: 56

```
atgaaagcag cagtagtaag acacaatcca gatggttatg cggaccttgt tgaaaaggaa    60
cttcgagcaa tcaaacctaa tgaagctttg cttgacatgg agtattgtgg agtctgtcat   120
accgatttgc acgttgcagc aggtgattat ggcaacaaag cagggactgt tcttggtcat   180
```

```
gaaggaattg gaattgtcaa agaaattgga gctgatgtaa gctcgcttca agttggtgat      240
cgggtttcag tggcttggtt ctttgaagga tgtggtcact gtaatactg tgtatctggt       300 aatgaaactt tttgtcgaga agttaaaaat gcaggatatt cagttgatgg cggaatggct      360
gaagaagcaa ttgttgttgc cgattatgct gtcaaagttc ctgacggact tgacccaatt      420
gaagctagct caattacttg tgctggagta acaacttaca aagcaatcaa agtatcagga      480
gtaaaacctg gtgattggca agtaattttt ggtgctggag gacttggaaa tttagcaatt      540
caatatgcta aaaatgtttt tggagcaaaa gtaattgctg ttgatattaa tcaagataaa      600
ttaaatttag ctaaaaaaat tggagctgat gtgattatca attctggtga tgtaaatcca      660
gttgatgaaa ttaaaaaaat aactggcggc ttaggggtgc aaagtgcaat agtttgtgct      720
gttgcaagga ttgcttttga acaagcggtt gcttctttga aacctatggg caaaatggtt      780
gctgtggcac ttcccaatac tgagatgact ttatcagttc aacagttgt ttttgacgga       840 gtggaggttg caggttcact tgtcggaaca agacttgact tggcagaagc ttttcaattt      900
ggagcagaag gtaaggtaaa accaattgtt gcgacacgca aactgaagaa atcaatgat       960 attattgatg aaatgaaggc aggaaaaatt gaaggccgaa tggtcattga tttactaaa      1020 taa                                                                   1023

<210> SEQ ID NO 57
<211> LENGTH: 340
<212> TYPE: PRT
<213> ORGANISM: Lactococcus lactis

<400> SEQUENCE: 57

Met Lys Ala Ala Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Tyr Gly Asn Lys Ala Gly Thr Val Leu Gly His Glu Gly Ile Gly
    50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Tyr Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Ile Ile Asn Ser Gly Asp Val Asn Pro Val Asp Glu Ile
    210                 215                 220
```

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Leu Pro Asn Thr Glu Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335

Asp Phe Thr Lys
            340

<210> SEQ ID NO 58
<211> LENGTH: 1041
<212> TYPE: DNA
<213> ORGANISM: Lactococcus lactis

<400> SEQUENCE: 58
atgaaggctg cagttgtccg tcacaatcct gatgggtacg ctgatcttgt agaaaaagag     60
ttgagggcca ttaagccaaa tgaggcattg ttggatatgg aatactgcgg tgtctgtcac    120
actgacctac atgttgctgc cggagattac ggcaacaagg cagggacagt tttaggacat    180
gaaggtatag gtattgtgaa agagattggt gccgatgtta gttctctcca agtaggtgat    240
agagtgagtg ttgcttggtt tttcgaaggg tgtggacatt gcgaatactg tgtgtcaggt    300
aacgagacat tttgccgaga agtcaaaaac gctggttata gcgttgatgg tggaatggca    360
gaggaagcaa tcgtggttgc agattatgcc gtcaaagtcc cagatggcct agatccaata    420
gaagcatcat ctataacttg tgcaggcgtc accacttaca aagctatcaa ggtgtctggc    480
gttaagccag agactggca gttatcttc ggagctggtg gcctgggcaa cttagctatc    540
cagtacgcca aaacgtatt tggtgcgaag gtgatcgctg tagatatcaa tcaagataag    600
ctcaatcttg ccaaaaagat aggtgctgat gtcatcatta ctctggtga cgttaaccct    660 gtagacgaaa tcaaaaagat cactggcggt ttaggtgttc aatccgcgat tgtatgtgcc    720
gttgcgagaa ttgcattcga gcaggctgta gcctcactaa agcctatggg caaaatggta    780
gccgttgctt tgccaaacac agaaatgaca ttatctgtgc caacagtcgt gtttgatgga    840
gttgaagtag caggtagtct tgttggaaca agactcgatt tggccgaagc tttccaattc    900
ggtgcagaag ggaaggttaa gcctattgtc gctaccagaa agttggagga aatcaatgac    960
atcattgatg agatgaaggc ggggaagatt gaaggtagaa tggttataga cttcacgaag   1020
caccaccacc accaccacta a                                             1041

<210> SEQ ID NO 59
<211> LENGTH: 346
<212> TYPE: PRT
<213> ORGANISM: Lactococcus lactis

<400> SEQUENCE: 59

Met Lys Ala Ala Val Val Arg His Asn Pro Asp Gly Tyr Ala Asp Leu
1               5                   10                  15

| Val | Glu | Lys | Glu | Leu | Arg | Ala | Ile | Lys | Pro | Asn | Glu | Ala | Leu | Leu | Asp |
| | | 20 | | | | | 25 | | | | | 30 | | | |

Met Glu Tyr Cys Gly Val Cys His Thr Asp Leu His Val Ala Ala Gly
        35                  40                  45

Asp Tyr Gly Asn Lys Ala Gly Thr Val Leu Gly His Glu Gly Ile Gly
50                      55                  60

Ile Val Lys Glu Ile Gly Ala Asp Val Ser Ser Leu Gln Val Gly Asp
65                   70                 75              80

Arg Val Ser Val Ala Trp Phe Phe Glu Gly Cys Gly His Cys Glu Tyr
            85                  90              95

Cys Val Ser Gly Asn Glu Thr Phe Cys Arg Glu Val Lys Asn Ala Gly
          100                105              110

Tyr Ser Val Asp Gly Gly Met Ala Glu Glu Ala Ile Val Ala Asp
        115                120              125

Tyr Ala Val Lys Val Pro Asp Gly Leu Asp Pro Ile Glu Ala Ser Ser
    130                135              140

Ile Thr Cys Ala Gly Val Thr Thr Tyr Lys Ala Ile Lys Val Ser Gly
145                  150              155            160

Val Lys Pro Gly Asp Trp Gln Val Ile Phe Gly Ala Gly Leu Gly
          165              170              175

Asn Leu Ala Ile Gln Tyr Ala Lys Asn Val Phe Gly Ala Lys Val Ile
        180                185              190

Ala Val Asp Ile Asn Gln Asp Lys Leu Asn Leu Ala Lys Lys Ile Gly
        195              200              205

Ala Asp Val Ile Ile Asn Ser Gly Asp Val Asn Pro Val Asp Glu Ile
    210                215              220

Lys Lys Ile Thr Gly Gly Leu Gly Val Gln Ser Ala Ile Val Cys Ala
225                  230              235            240

Val Ala Arg Ile Ala Phe Glu Gln Ala Val Ala Ser Leu Lys Pro Met
          245              250              255

Gly Lys Met Val Ala Val Ala Leu Pro Asn Thr Glu Met Thr Leu Ser
        260              265              270

Val Pro Thr Val Val Phe Asp Gly Val Glu Val Ala Gly Ser Leu Val
    275                280              285

Gly Thr Arg Leu Asp Leu Ala Glu Ala Phe Gln Phe Gly Ala Glu Gly
    290                295              300

Lys Val Lys Pro Ile Val Ala Thr Arg Lys Leu Glu Glu Ile Asn Asp
305                  310              315            320

Ile Ile Asp Glu Met Lys Ala Gly Lys Ile Glu Gly Arg Met Val Ile
          325              330              335

Asp Phe Thr Lys His His His His His His
        340                345

<210> SEQ ID NO 60
<211> LENGTH: 1041
<212> TYPE: DNA
<213> ORGANISM: Lactococcus lactis

<400> SEQUENCE: 60

```
atgaaggctg cagttgtccg tcacaatcct gatgggtacg ctgatcttgt agaaaaagag        60
ttgagggcca ttaagccaaa tgaggcattg ttggatatgg aatactgcgg tgtctgtcac       120
actgacctac atgttgctgc cggagatttc ggcaacaagg cagggacagt tttaggacat       180
gaaggtatag gtattgtgaa agagattggt gccgatgtta gttctctcca gtaggtgat       240
```

```
agagtgagtg ttgcttggtt tttcgaaggg tgtggacatt gcgaatactg tgtgtcaggt    300
aacgagacat tttgccgaga agtcaaaaac gctggttata gcgttgatgg tggaatggca    360
gaggaagcga tcgtggttgc agattatgcc gttaaagtcc cagatggcct agatccaata    420
gaagcatcat ctataacttg tgcaggcgtc accacttaca aagctatcaa ggtgtctggc    480
gttaagccag gagactggca agttatcttc ggagctggtg gcctgggcaa cttagctatc    540
cagtacgcca aaaacgtatt tggtgcgaag gtgatcgctg tagatatcaa tcaagataag    600
ctcaatcttg ccaaaaagat aggtgctgat gtcacaatta actctggtga cgttaaccct    660
gtagacgaaa tcaaaaagat cactggcggt ttaggtgttc aatccgcgat gtatgtgcc     720 gttgcgagaa ttgcattcga gcaggctgta gcctcactaa agcctatggg caaaatggta    780
gccgttgctg taccaaacac agaaatgaca ttatctgtgc caacagtcgt gtttgatgga    840
gttgaagtag caggtagtct tgttggaaca agactcgatt tggccgaagc tttccaattc    900
ggtgcagaag gaaggttaa gcctattgtc gctaccagaa agttggagga aatcaatgac     960
atcattgatg agatgaaggc ggggaagatt gaaggtagaa tggttataga cttcacgaag   1020
caccaccacc accaccacta a                                             1041

<210> SEQ ID NO 61
<211> LENGTH: 346
<212> TYPE: PRT
<213> ORGANISM: Lactococcus lactis

<400> SEQUENCE: 61

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Tyr Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Thr Ile Asn Ser Gly Asp Val Asn Pro Val Asp Glu Ile
    210                 215                 220
```

```
Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
            245                 250                 255

Gly Lys Met Val Ala Val Ala Val Pro Asn Thr Glu Met Thr Leu Ser
        260                 265                 270

Val Pro Thr Val Val Phe Asp Gly Val Glu Val Ala Gly Ser Leu Val
    275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335

Asp Phe Thr Lys His His His His His His
            340                 345
```

```
<210> SEQ ID NO 62
<211> LENGTH: 24
<212> TYPE: DNA
<213> ORGANISM: Artificial Sequence
<220> FEATURE:
<223> OTHER INFORMATION: primer oGV698

<400> SEQUENCE: 62
actcgccgat agtggaaacc gacg                                          24

<210> SEQ ID NO 63
<211> LENGTH: 21
<212> TYPE: DNA
<213> ORGANISM: Artificial Sequence
<220> FEATURE:
<223> OTHER INFORMATION: primer oGV1965

<400> SEQUENCE: 63
caaactgtga tggacgacac c                                             21

<210> SEQ ID NO 64
<211> LENGTH: 23
<212> TYPE: DNA
<213> ORGANISM: Artificial Sequence
<220> FEATURE:
<223> OTHER INFORMATION: primer oGV2631

<400> SEQUENCE: 64
caatacgtta tgccgtaatg aag                                           23

<210> SEQ ID NO 65
<211> LENGTH: 38
<212> TYPE: DNA
<213> ORGANISM: Artificial Sequence
<220> FEATURE:
<223> OTHER INFORMATION: primer oGV2632

<400> SEQUENCE: 65 gcttttacc cattattgat atagtgttta agcgaatg                            38

<210> SEQ ID NO 66
<211> LENGTH: 36
<212> TYPE: DNA
<213> ORGANISM: Artificial Sequence
<220> FEATURE:
<223> OTHER INFORMATION: primer oGV2633
```

<400> SEQUENCE: 66
cactatatca ataatgggta aaaagcctga actcac                                36

<210> SEQ ID NO 67
<211> LENGTH: 21
<212> TYPE: DNA
<213> ORGANISM: Artificial Sequence
<220> FEATURE:
<223> OTHER INFORMATION: primer oGV2634

<400> SEQUENCE: 67
ttattccttt gccctcggac g                                                21

<210> SEQ ID NO 68
<211> LENGTH: 20
<212> TYPE: DNA
<213> ORGANISM: Artificial Sequence
<220> FEATURE:
<223> OTHER INFORMATION: primer oGV2680

<400> SEQUENCE: 68
tgcactgctg tcttcacttc                                                  20

<210> SEQ ID NO 69
<211> LENGTH: 18
<212> TYPE: DNA
<213> ORGANISM: Artificial Sequence
<220> FEATURE:
<223> OTHER INFORMATION: primer oGV2796

<400> SEQUENCE: 69
tgtcagcgct tcagactc                                                    18

<210> SEQ ID NO 70
<211> LENGTH: 22
<212> TYPE: DNA
<213> ORGANISM: Artificial Sequence
<220> FEATURE:
<223> OTHER INFORMATION: primer oGV2797

<400> SEQUENCE: 70
aagtattttt aaggattcgc tc                                               22

<210> SEQ ID NO 71
<211> LENGTH: 45
<212> TYPE: DNA
<213> ORGANISM: Artificial Sequence
<220> FEATURE:
<223> OTHER INFORMATION: primer oGV2798

<400> SEQUENCE: 71
cttcattacg gcataacgta ttgaagtatt tttaaggatt cgctc                      45

<210> SEQ ID NO 72
<211> LENGTH: 45
<212> TYPE: DNA
<213> ORGANISM: Artificial Sequence
<220> FEATURE:
<223> OTHER INFORMATION: primer oGV2800

<400> SEQUENCE: 72
cgtccgaggg caaaggaata agatagttat cattatgtaa gtgcg                      45

<210> SEQ ID NO 73

```
<211> LENGTH: 18
<212> TYPE: DNA
<213> ORGANISM: Artificial Sequence
<220> FEATURE:
<223> OTHER INFORMATION: primer oGV2801

<400> SEQUENCE: 73
gggagtttag caatcagc                                              18

<210> SEQ ID NO 74
<211> LENGTH: 19
<212> TYPE: DNA
<213> ORGANISM: Artificial Sequence
<220> FEATURE:
<223> OTHER INFORMATION: primer oGV2802

<400> SEQUENCE: 74
tggttgaccc gcaaacttc                                             19

<210> SEQ ID NO 75
<211> LENGTH: 21
<212> TYPE: DNA
<213> ORGANISM: Artificial Sequence
<220> FEATURE:
<223> OTHER INFORMATION: primer oGV2803

<400> SEQUENCE: 75
acaatctccc tgtctcctcc c                                          21

<210> SEQ ID NO 76
<211> LENGTH: 24
<212> TYPE: DNA
<213> ORGANISM: Artificial Sequence
<220> FEATURE:
<223> OTHER INFORMATION: primer oGV2804

<400> SEQUENCE: 76
aaggtgattt ggcacaaatt ttac                                       24

<210> SEQ ID NO 77
<211> LENGTH: 25
<212> TYPE: DNA
<213> ORGANISM: Artificial Sequence
<220> FEATURE:
<223> OTHER INFORMATION: primer oGV2805

<400> SEQUENCE: 77
ggtacaattc tgtcctgaat tgtag                                      25

<210> SEQ ID NO 78
<211> LENGTH: 21
<212> TYPE: DNA
<213> ORGANISM: Artificial Sequence
<220> FEATURE:
<223> OTHER INFORMATION: primer oGV2806

<400> SEQUENCE: 78
aggtcctaga aatcccttaa g                                          21

<210> SEQ ID NO 79
<211> LENGTH: 46
<212> TYPE: DNA
<213> ORGANISM: Artificial Sequence
<220> FEATURE:
<223> OTHER INFORMATION: primer oGV2808

<400> SEQUENCE: 79
```

```
cttcattacg gcataacgta ttgcgatatc agtatacaag gtaggc                    46

<210> SEQ ID NO 80
<211> LENGTH: 44
<212> TYPE: DNA
<213> ORGANISM: Artificial Sequence
<220> FEATURE:
<223> OTHER INFORMATION: primer oGV2810

<400> SEQUENCE: 80
cgtccgaggg caaaggaata aggatttaag atgagtggta ttgg                      44

<210> SEQ ID NO 81
<211> LENGTH: 22
<212> TYPE: DNA
<213> ORGANISM: Artificial Sequence
<220> FEATURE:
<223> OTHER INFORMATION: primer oGV2811

<400> SEQUENCE: 81
tgttcgtaac ttttgtcatc ac                                              22

<210> SEQ ID NO 82
<211> LENGTH: 19
<212> TYPE: DNA
<213> ORGANISM: Artificial Sequence
<220> FEATURE:
<223> OTHER INFORMATION: primer oGV2812

<400> SEQUENCE: 82
tcagcatgcg gaacaattg                                                  19

<210> SEQ ID NO 83
<211> LENGTH: 21
<212> TYPE: DNA
<213> ORGANISM: Artificial Sequence
<220> FEATURE:
<223> OTHER INFORMATION: primer oGV2813

<400> SEQUENCE: 83
tccacacggt atcatacgat c                                               21

<210> SEQ ID NO 84
<211> LENGTH: 21
<212> TYPE: DNA
<213> ORGANISM: Artificial Sequence
<220> FEATURE:
<223> OTHER INFORMATION: primer oGV2814

<400> SEQUENCE: 84
gcggtcgaca agttcaatat g                                               21

<210> SEQ ID NO 85
<211> LENGTH: 22
<212> TYPE: DNA
<213> ORGANISM: Artificial Sequence
<220> FEATURE:
<223> OTHER INFORMATION: primer oGV2815

<400> SEQUENCE: 85
tactgagccg ccaaccttag ta                                              22

<210> SEQ ID NO 86
<211> LENGTH: 21
<212> TYPE: DNA
```

```
<213> ORGANISM: Artificial Sequence
<220> FEATURE:
<223> OTHER INFORMATION: primer oGV2816

<400> SEQUENCE: 86
cataactata cccgtacgca g                                             21

<210> SEQ ID NO 87
<211> LENGTH: 45
<212> TYPE: DNA
<213> ORGANISM: Artificial Sequence
<220> FEATURE:
<223> OTHER INFORMATION: primer oGV2818

<400> SEQUENCE: 87
cttcattacg gcataacgta ttgagcgtag atctactgaa catgc                   45

<210> SEQ ID NO 88
<211> LENGTH: 40
<212> TYPE: DNA
<213> ORGANISM: Artificial Sequence
<220> FEATURE:
<223> OTHER INFORMATION: primer oGV2820

<400> SEQUENCE: 88
cgtccgaggg caaaggaata acatgagatt gtcaaagagg                         40

<210> SEQ ID NO 89
<211> LENGTH: 20
<212> TYPE: DNA
<213> ORGANISM: Artificial Sequence
<220> FEATURE:
<223> OTHER INFORMATION: primer oGV2821

<400> SEQUENCE: 89
caccaggctt attgatgacc                                               20

<210> SEQ ID NO 90
<211> LENGTH: 18
<212> TYPE: DNA
<213> ORGANISM: Artificial Sequence
<220> FEATURE:
<223> OTHER INFORMATION: primer oGV2822

<400> SEQUENCE: 90
cattaccggc agttgctc                                                 18

<210> SEQ ID NO 91
<211> LENGTH: 20
<212> TYPE: DNA
<213> ORGANISM: Artificial Sequence
<220> FEATURE:
<223> OTHER INFORMATION: primer oGV2824

<400> SEQUENCE: 91
tatgacagtg cctatcaagc                                               20

<210> SEQ ID NO 92
<211> LENGTH: 19
<212> TYPE: DNA
<213> ORGANISM: Artificial Sequence
<220> FEATURE:
<223> OTHER INFORMATION: primer oGV2825

<400> SEQUENCE: 92
aatgggttct accagtatc                                                19
```

<210> SEQ ID NO 93
<211> LENGTH: 20
<212> TYPE: DNA
<213> ORGANISM: Artificial Sequence
<220> FEATURE:
<223> OTHER INFORMATION: primer oGV2826

<400> SEQUENCE: 93
aagccgggaa cgtgcgtaac                                               20

<210> SEQ ID NO 94
<211> LENGTH: 43
<212> TYPE: DNA
<213> ORGANISM: Artificial Sequence
<220> FEATURE:
<223> OTHER INFORMATION: primer oGV2827

<400> SEQUENCE: 94
cttcattacg gcataacgta ttgggaacgc gtaatggtgc ttg                     43

<210> SEQ ID NO 95
<211> LENGTH: 41
<212> TYPE: DNA
<213> ORGANISM: Artificial Sequence
<220> FEATURE:
<223> OTHER INFORMATION: primer oGV2828

<400> SEQUENCE: 95
cgtccgaggg caaaggaata acccgagttg actgctcatt g                       41

<210> SEQ ID NO 96
<211> LENGTH: 20
<212> TYPE: DNA
<213> ORGANISM: Artificial Sequence
<220> FEATURE:
<223> OTHER INFORMATION: primer oGV2829

<400> SEQUENCE: 96
aatactcgcc gaggcgtagg                                               20

<210> SEQ ID NO 97
<211> LENGTH: 20
<212> TYPE: DNA
<213> ORGANISM: Artificial Sequence
<220> FEATURE:
<223> OTHER INFORMATION: primer oGV2830

<400> SEQUENCE: 97
ttggagctgg gaggtaaatc                                               20

<210> SEQ ID NO 98
<211> LENGTH: 20
<212> TYPE: DNA
<213> ORGANISM: Artificial Sequence
<220> FEATURE:
<223> OTHER INFORMATION: primer oGV2831

<400> SEQUENCE: 98
tgcggctaac ccatattgag                                               20

<210> SEQ ID NO 99
<211> LENGTH: 20
<212> TYPE: DNA
<213> ORGANISM: Artificial Sequence
<220> FEATURE:

```
<223> OTHER INFORMATION: primer oGV2832

<400> SEQUENCE: 99
tacgctgagc gtagtacaac                                                    20

<210> SEQ ID NO 100
<211> LENGTH: 22
<212> TYPE: DNA
<213> ORGANISM: Artificial Sequence
<220> FEATURE:
<223> OTHER INFORMATION: primer oGV2833

<400> SEQUENCE: 100
taaagcgctg ggtggacaac cg                                                 22

<210> SEQ ID NO 101
<211> LENGTH: 20
<212> TYPE: DNA
<213> ORGANISM: Artificial Sequence
<220> FEATURE:
<223> OTHER INFORMATION: primer oGV2834

<400> SEQUENCE: 101
gcaccgagac gtcattgttg                                                    20

<210> SEQ ID NO 102
<211> LENGTH: 43
<212> TYPE: DNA
<213> ORGANISM: Artificial Sequence
<220> FEATURE:
<223> OTHER INFORMATION: primer oGV2835

<400> SEQUENCE: 102
cttcattacg gcataacgta ttgtaaacac gccaggcttg acc                          43

<210> SEQ ID NO 103
<211> LENGTH: 41
<212> TYPE: DNA
<213> ORGANISM: Artificial Sequence
<220> FEATURE:
<223> OTHER INFORMATION: primer oGV2836

<400> SEQUENCE: 103
cgtccgaggg caaaggaata atccattcgg tggtgttaag c                            41

<210> SEQ ID NO 104
<211> LENGTH: 20
<212> TYPE: DNA
<213> ORGANISM: Artificial Sequence
<220> FEATURE:
<223> OTHER INFORMATION: primer oGV2837

<400> SEQUENCE: 104
atggcgaaat ggcagtactc                                                    20

<210> SEQ ID NO 105
<211> LENGTH: 18
<212> TYPE: DNA
<213> ORGANISM: Artificial Sequence
<220> FEATURE:
<223> OTHER INFORMATION: primer oGV2838

<400> SEQUENCE: 105
accaacgacc caagaatc                                                      18
```

```
<210> SEQ ID NO 106
<211> LENGTH: 18
<212> TYPE: DNA
<213> ORGANISM: Artificial Sequence
<220> FEATURE:
<223> OTHER INFORMATION: primer oGV2839

<400> SEQUENCE: 106
ctttgcgaca gtgacaac                                                  18

<210> SEQ ID NO 107
<211> LENGTH: 21
<212> TYPE: DNA
<213> ORGANISM: Artificial Sequence
<220> FEATURE:
<223> OTHER INFORMATION: primer oGV2840

<400> SEQUENCE: 107
cctcacgtaa gggcatgata g                                              21

<210> SEQ ID NO 108
<211> LENGTH: 22
<212> TYPE: DNA
<213> ORGANISM: Artificial Sequence
<220> FEATURE:
<223> OTHER INFORMATION: primer oGV2841

<400> SEQUENCE: 108
gcattgcagc ggtattgtca gg                                             22

<210> SEQ ID NO 109
<211> LENGTH: 20
<212> TYPE: DNA
<213> ORGANISM: Artificial Sequence
<220> FEATURE:
<223> OTHER INFORMATION: primer oGV2842

<400> SEQUENCE: 109
cagcagccac atagtatacc                                                20

<210> SEQ ID NO 110
<211> LENGTH: 43
<212> TYPE: DNA
<213> ORGANISM: Artificial Sequence
<220> FEATURE:
<223> OTHER INFORMATION: primer oGV2843

<400> SEQUENCE: 110
cttcattacg gcataacgta ttgagccgtc gtttgacatg ttg                      43

<210> SEQ ID NO 111
<211> LENGTH: 41
<212> TYPE: DNA
<213> ORGANISM: Artificial Sequence
<220> FEATURE:
<223> OTHER INFORMATION: primer oGV2844

<400> SEQUENCE: 111
cgtccgaggg caaaggaata acgctccatt tggagggatc g                        41

<210> SEQ ID NO 112
<211> LENGTH: 20
<212> TYPE: DNA
<213> ORGANISM: Artificial Sequence
<220> FEATURE:
<223> OTHER INFORMATION: primer oGV2845
```

```
<400> SEQUENCE: 112
gaatgcgctt gctgctaggg                                               20

<210> SEQ ID NO 113
<211> LENGTH: 22
<212> TYPE: DNA
<213> ORGANISM: Artificial Sequence
<220> FEATURE:
<223> OTHER INFORMATION: primer oGV2846

<400> SEQUENCE: 113
cagctcttgc tgcaggtaac ac                                            22

<210> SEQ ID NO 114
<211> LENGTH: 22
<212> TYPE: DNA
<213> ORGANISM: Artificial Sequence
<220> FEATURE:
<223> OTHER INFORMATION: primer oGV2847

<400> SEQUENCE: 114
ggcacaatct tggagccgtt ag                                            22

<210> SEQ ID NO 115
<211> LENGTH: 20
<212> TYPE: DNA
<213> ORGANISM: Artificial Sequence
<220> FEATURE:
<223> OTHER INFORMATION: primer oGV2848

<400> SEQUENCE: 115
accaagccat caaggttgtc                                               20

<210> SEQ ID NO 116
<211> LENGTH: 22
<212> TYPE: DNA
<213> ORGANISM: Artificial Sequence
<220> FEATURE:
<223> OTHER INFORMATION: primer oGV2849

<400> SEQUENCE: 116
tgggtgatgg tttggcgaat gc                                            22

<210> SEQ ID NO 117
<211> LENGTH: 28
<212> TYPE: DNA
<213> ORGANISM: Artificial Sequence
<220> FEATURE:
<223> OTHER INFORMATION: primer oGV2896

<400> SEQUENCE: 117
gaaatgatga catgtggaaa tataacag                                      28

<210> SEQ ID NO 118
<211> LENGTH: 22
<212> TYPE: DNA
<213> ORGANISM: Artificial Sequence
<220> FEATURE:
<223> OTHER INFORMATION: primer 893

<400> SEQUENCE: 118
ggatgtgaag tcgttgacac ag                                            22

<210> SEQ ID NO 119
<211> LENGTH: 20
```

-continued

```
<212> TYPE: DNA
<213> ORGANISM: Artificial Sequence
<220> FEATURE:
<223> OTHER INFORMATION: primer 2231

<400> SEQUENCE: 119
ttgaaacgtt gggtccatac                                              20

<210> SEQ ID NO 120
<211> LENGTH: 20
<212> TYPE: DNA
<213> ORGANISM: Artificial Sequence
<220> FEATURE:
<223> OTHER INFORMATION: primer 2232

<400> SEQUENCE: 120
ttcaccgtgt gctagagaac                                              20

<210> SEQ ID NO 121
<211> LENGTH: 28
<212> TYPE: DNA
<213> ORGANISM: Artificial Sequence
<220> FEATURE:
<223> OTHER INFORMATION: primer 2862

<400> SEQUENCE: 121
ttatacagga aacttaatag aacaaatc                                     28

<210> SEQ ID NO 122
<211> LENGTH: 20
<212> TYPE: DNA
<213> ORGANISM: Artificial Sequence
<220> FEATURE:
<223> OTHER INFORMATION: primer 2867

<400> SEQUENCE: 122
tgaaacagca tggcgcatag                                              20

<210> SEQ ID NO 123
<211> LENGTH: 42
<212> TYPE: DNA
<213> ORGANISM: Artificial Sequence
<220> FEATURE:
<223> OTHER INFORMATION: primer 2869

<400> SEQUENCE: 123
ctgtgtcaac gacttcacat ccgaggtaac gaggaacaag cc                     42

<210> SEQ ID NO 124
<211> LENGTH: 21
<212> TYPE: DNA
<213> ORGANISM: Artificial Sequence
<220> FEATURE:
<223> OTHER INFORMATION: primer 2870

<400> SEQUENCE: 124
tttcgccggt atattccgta g                                            21

<210> SEQ ID NO 125
<211> LENGTH: 45
<212> TYPE: DNA
<213> ORGANISM: Artificial Sequence
<220> FEATURE:
<223> OTHER INFORMATION: primer 2891

<400> SEQUENCE: 125
```
gttctattaa gtttcctgta taacggcatt gttcaccaga atgtc       45

<210> SEQ ID NO 126
<211> LENGTH: 20
<212> TYPE: DNA
<213> ORGANISM: Artificial Sequence
<220> FEATURE:
<223> OTHER INFORMATION: primer 2902

<400> SEQUENCE: 126
tcccgacggc tgctagaatg       20

<210> SEQ ID NO 127
<211> LENGTH: 20
<212> TYPE: DNA
<213> ORGANISM: Artificial Sequence
<220> FEATURE:
<223> OTHER INFORMATION: primer 2904

<400> SEQUENCE: 127
cgctccccat taattataca       20

<210> SEQ ID NO 128
<211> LENGTH: 20
<212> TYPE: DNA
<213> ORGANISM: Artificial Sequence
<220> FEATURE:
<223> OTHER INFORMATION: primer 2913

<400> SEQUENCE: 128
gaaaggctct tggcagtgac       20

<210> SEQ ID NO 129
<211> LENGTH: 20
<212> TYPE: DNA
<213> ORGANISM: Artificial Sequence
<220> FEATURE:
<223> OTHER INFORMATION: primer 2914

<400> SEQUENCE: 129
gccctggtgc aattagaatg       20

<210> SEQ ID NO 130
<211> LENGTH: 20
<212> TYPE: DNA
<213> ORGANISM: Artificial Sequence
<220> FEATURE:
<223> OTHER INFORMATION: primer 2915

<400> SEQUENCE: 130
tgcagagggt gatgagtaag       20

<210> SEQ ID NO 131
<211> LENGTH: 20
<212> TYPE: DNA
<213> ORGANISM: Artificial Sequence
<220> FEATURE:
<223> OTHER INFORMATION: primer 2916

<400> SEQUENCE: 131
ggccaaaggt aaggagaacg       20

<210> SEQ ID NO 132
<211> LENGTH: 25
<212> TYPE: DNA
<213> ORGANISM: Artificial Sequence

```
<220> FEATURE:
<223> OTHER INFORMATION: primer 821

<400> SEQUENCE: 132
cgggtaatta acgacaccct agagg                                           25

<210> SEQ ID NO 133
<211> LENGTH: 26
<212> TYPE: DNA
<213> ORGANISM: Artificial Sequence
<220> FEATURE:
<223> OTHER INFORMATION: primer 2320

<400> SEQUENCE: 133
ggctgtgtag aagtactcgc cgatag                                          26

<210> SEQ ID NO 134
<211> LENGTH: 58
<212> TYPE: DNA
<213> ORGANISM: Artificial Sequence
<220> FEATURE:
<223> OTHER INFORMATION: primer 3065

<400> SEQUENCE: 134
aaaaaggagt agaaacattt tgaagctatg cgttgataag ggcaacaacg ttagtatc       58

<210> SEQ ID NO 135
<211> LENGTH: 60
<212> TYPE: DNA
<213> ORGANISM: Artificial Sequence
<220> FEATURE:
<223> OTHER INFORMATION: primer 3066

<400> SEQUENCE: 135
atactaacgt tgttgcccct tatcaacgca tagcttcaaaa tgtttctact cctttttac     60

<210> SEQ ID NO 136
<211> LENGTH: 58
<212> TYPE: DNA
<213> ORGANISM: Artificial Sequence
<220> FEATURE:
<223> OTHER INFORMATION: primer 3067

<400> SEQUENCE: 136
tcaaattttt cttttttttc tgtacagtta cccaagctgt tttgcctatt ttcaaagc       58

<210> SEQ ID NO 137
<211> LENGTH: 57
<212> TYPE: DNA
<213> ORGANISM: Artificial Sequence
<220> FEATURE:
<223> OTHER INFORMATION: primer 3068

<400> SEQUENCE: 137
gctttgaaaa taggcaaaac agcttgggta actgtacaga aaaaaagaa aaatttg         57

<210> SEQ ID NO 138
<211> LENGTH: 29
<212> TYPE: DNA
<213> ORGANISM: Artificial Sequence
<220> FEATURE:
<223> OTHER INFORMATION: primer 3069

<400> SEQUENCE: 138
agttcaaatc agttcgagga taatttaag                                       29
```

-continued

<210> SEQ ID NO 139
<211> LENGTH: 32
<212> TYPE: DNA
<213> ORGANISM: Artificial Sequence
<220> FEATURE:
<223> OTHER INFORMATION: primer 3070

<400> SEQUENCE: 139
ttaataaatg ctcaaaagaa aaaggctgg cg                           32

<210> SEQ ID NO 140
<211> LENGTH: 22
<212> TYPE: DNA
<213> ORGANISM: Artificial Sequence
<220> FEATURE:
<223> OTHER INFORMATION: primer 3103

<400> SEQUENCE: 140
accggtgctt ctgcaggtat tg                                     22

<210> SEQ ID NO 141
<211> LENGTH: 22
<212> TYPE: DNA
<213> ORGANISM: Artificial Sequence
<220> FEATURE:
<223> OTHER INFORMATION: primer 3106

<400> SEQUENCE: 141
atgcttggtt ggaagcaaat ac                                     22

<210> SEQ ID NO 142
<211> LENGTH: 22
<212> TYPE: DNA
<213> ORGANISM: Artificial Sequence
<220> FEATURE:
<223> OTHER INFORMATION: primer 3498

<400> SEQUENCE: 142
atgtctcaag gtagaagagc tg                                     22

<210> SEQ ID NO 143
<211> LENGTH: 52
<212> TYPE: DNA
<213> ORGANISM: Artificial Sequence
<220> FEATURE:
<223> OTHER INFORMATION: primer 3137

<400> SEQUENCE: 143
ggagtagaaa cattttgaag ctatgtatat cttctgaatc aattgcaccg ac    52

<210> SEQ ID NO 144
<211> LENGTH: 55
<212> TYPE: DNA
<213> ORGANISM: Artificial Sequence
<220> FEATURE:
<223> OTHER INFORMATION: primer 3140

<400> SEQUENCE: 144 caaattttc ttttttttct gtacagagag gtatgattaa taccaatgtc ttggg  55

<210> SEQ ID NO 145
<211> LENGTH: 22
<212> TYPE: DNA
<213> ORGANISM: Artificial Sequence
<220> FEATURE:
<223> OTHER INFORMATION: primer 3499

```
<400> SEQUENCE: 145
tcattcacca cggtaaatgt gg                                              22

<210> SEQ ID NO 146
<211> LENGTH: 52
<212> TYPE: DNA
<213> ORGANISM: Artificial Sequence
<220> FEATURE:
<223> OTHER INFORMATION: primer 3138

<400> SEQUENCE: 146
gtcggtgcaa ttgattcaga agatatacat agcttcaaaa tgtttctact cc             52

<210> SEQ ID NO 147
<211> LENGTH: 57
<212> TYPE: DNA
<213> ORGANISM: Artificial Sequence
<220> FEATURE:
<223> OTHER INFORMATION: primer 3139

<400> SEQUENCE: 147
gtattaatca tacctctctg tacagaaaaa aagaaaaat ttgaaatata aataacg          57

<210> SEQ ID NO 148
<211> LENGTH: 35
<212> TYPE: DNA
<213> ORGANISM: Artificial Sequence
<220> FEATURE:
<223> OTHER INFORMATION: primer 3501

<400> SEQUENCE: 148
gaaggaaatt ccagtctcct agttcctttg aacac                                35

<210> SEQ ID NO 149
<211> LENGTH: 26
<212> TYPE: DNA
<213> ORGANISM: Artificial Sequence
<220> FEATURE:
<223> OTHER INFORMATION: primer 2320

<400> SEQUENCE: 149
ggctgtgtag aagtactcgc cgatag                                          26

<210> SEQ ID NO 150
<211> LENGTH: 34
<212> TYPE: DNA
<213> ORGANISM: Artificial Sequence
<220> FEATURE:
<223> OTHER INFORMATION: primer 3500

<400> SEQUENCE: 150
cagaacaatc aatcaacgaa cgaacgaccc accc                                 34

<210> SEQ ID NO 151
<211> LENGTH: 25
<212> TYPE: DNA
<213> ORGANISM: Artificial Sequence
<220> FEATURE:
<223> OTHER INFORMATION: primer 821

<400> SEQUENCE: 151
cgggtaatta acgacaccct agagg                                           25

<210> SEQ ID NO 152
```

```
<211> LENGTH: 29
<212> TYPE: DNA
<213> ORGANISM: Artificial Sequence
<220> FEATURE:
<223> OTHER INFORMATION: primer 3141

<400> SEQUENCE: 152
aaggagatgc ttggtttgta gcaaacacc                                     29

<210> SEQ ID NO 153
<211> LENGTH: 58
<212> TYPE: DNA
<213> ORGANISM: Artificial Sequence
<220> FEATURE:
<223> OTHER INFORMATION: primer oGV3065

<400> SEQUENCE: 153
aaaaaggagt agaaacattt tgaagctatg cgttgataag ggcaacaacg ttagtatc     58

<210> SEQ ID NO 154
<211> LENGTH: 60
<212> TYPE: DNA
<213> ORGANISM: Artificial Sequence
<220> FEATURE:
<223> OTHER INFORMATION: primer oGV3066

<400> SEQUENCE: 154
atactaacgt tgttgccctt atcaacgcat agcttcaaaa tgtttctact ccttttttac   60

<210> SEQ ID NO 155
<211> LENGTH: 58
<212> TYPE: DNA
<213> ORGANISM: Artificial Sequence
<220> FEATURE:
<223> OTHER INFORMATION: primer oGV3067

<400> SEQUENCE: 155
tcaaattttt cttttttttc tgtacagtta cccaagctgt tttgcctatt ttcaaagc     58

<210> SEQ ID NO 156
<211> LENGTH: 57
<212> TYPE: DNA
<213> ORGANISM: Artificial Sequence
<220> FEATURE:
<223> OTHER INFORMATION: primer oGV3068

<400> SEQUENCE: 156
gctttgaaaa taggcaaaac agcttgggta actgtacaga aaaaaagaa aaatttg       57

<210> SEQ ID NO 157
<211> LENGTH: 22
<212> TYPE: DNA
<213> ORGANISM: Artificial Sequence
<220> FEATURE:
<223> OTHER INFORMATION: primer oGV3103

<400> SEQUENCE: 157
accggtgctt ctgcaggtat tg                                            22

<210> SEQ ID NO 158
<211> LENGTH: 22
<212> TYPE: DNA
<213> ORGANISM: Artificial Sequence
<220> FEATURE:
<223> OTHER INFORMATION: primer oGV3106

<400> SEQUENCE: 158
```

```
atgcttggtt ggaagcaaat ac                                              22
```

<210> SEQ ID NO 159
<211> LENGTH: 20
<212> TYPE: DNA
<213> ORGANISM: Artificial Sequence
<220> FEATURE:
<223> OTHER INFORMATION: primer oGV1321

<400> SEQUENCE: 159

```
aatcatatcg aacacgatgc                                                 20
```

<210> SEQ ID NO 160
<211> LENGTH: 20
<212> TYPE: DNA
<213> ORGANISM: Artificial Sequence
<220> FEATURE:
<223> OTHER INFORMATION: primer oGV1324

<400> SEQUENCE: 160

```
agctggtctg gtgattctac                                                 20
```

<210> SEQ ID NO 161
<211> LENGTH: 780
<212> TYPE: DNA
<213> ORGANISM: Schizosaccharomyces pombe

<400> SEQUENCE: 161

```
atgagccgtt tggatggaaa aacgatttta atcactggtg cctcttctgg aattggaaaa     60
agcactgctt ttgaaattgc caaagttgcc aaagtaaaac ttattttggc tgctcgcaga    120
ttttctaccg ttgaagaaat tgcaaaggag ttagaatcga aatatgaagt atcggttctt    180
cctcttaaat tggatgtttc tgatttgaag tctattcctg gggtaattga gtcattgcca    240
aaggaatttg ctgatatcga tgtcttgatt aataatgctg gacttgctct aggtaccgat    300
aaagtcattg atcttaatat tgatgacgcc gttaccatga ttactaccaa tgttcttggt    360
atgatggcta tgactcgtgc ggttcttcct atattctaca gcaaaaacaa gggtgatatt    420
ttgaacgttg gcagtattgc cggcagagaa tcatacgtag gcggctccgt ttactgctct    480
accaagtctg cccttgctca attcacttcc gctttgcgta aggagactat tgacactcgc    540
attcgtatta tggaggttga tcctggcttg gtcgaaaccg aattcagcgt tgtgagattc    600
cacggagaca acaaaaggc tgataatgtt tacaaaaata gtgagccttt gacacccgaa    660
gacattgctg aggtgattct ttttgccctc actcgcagag aaaacgtcgt tattgccgat    720
acacttgttt cccatcccca tcaaggtggt gccaatcatg tgtacagaaa gcaagcgtag    780
```

<210> SEQ ID NO 162
<211> LENGTH: 23
<212> TYPE: DNA
<213> ORGANISM: Artificial Sequence
<220> FEATURE:
<223> OTHER INFORMATION: primer oGV3490

<400> SEQUENCE: 162

```
gtcaagattg ttgaacaaaa gcc                                             23
```

<210> SEQ ID NO 163
<211> LENGTH: 60
<212> TYPE: DNA
<213> ORGANISM: Artificial Sequence
<220> FEATURE:

```
<223> OTHER INFORMATION: primer oGV3492

<400> SEQUENCE: 163
gagtaaaaaa ggagtagaaa cattttgaag ctatggttta gtggggttgg ggaagctggc    60

<210> SEQ ID NO 164
<211> LENGTH: 59
<212> TYPE: DNA
<213> ORGANISM: Artificial Sequence
<220> FEATURE:
<223> OTHER INFORMATION: primer oGV3493

<400> SEQUENCE: 164 caaattttc ttttttttct gtacaggcca acatcaagaa gactattcca aacttggtc     59

<210> SEQ ID NO 165
<211> LENGTH: 25
<212> TYPE: DNA
<213> ORGANISM: Artificial Sequence
<220> FEATURE:
<223> OTHER INFORMATION: primer oGV3495

<400> SEQUENCE: 165
tgtatgattc gaaagcttct tcacc                                          25

<210> SEQ ID NO 166
<211> LENGTH: 60
<212> TYPE: DNA
<213> ORGANISM: Artificial Sequence
<220> FEATURE:
<223> OTHER INFORMATION: primer oGV3491

<400> SEQUENCE: 166
gccagcttcc ccaaccccac taaaccatag cttcaaaatg tttctactcc ttttttactc    60

<210> SEQ ID NO 167
<211> LENGTH: 59
<212> TYPE: DNA
<213> ORGANISM: Artificial Sequence
<220> FEATURE:
<223> OTHER INFORMATION: primer oGV3494

<400> SEQUENCE: 167
gaccaagttt ggaatagtct tcttgatgtt ggcctgtaca gaaaaaaag aaaaatttg      59

<210> SEQ ID NO 168
<211> LENGTH: 21
<212> TYPE: DNA
<213> ORGANISM: Artificial Sequence
<220> FEATURE:
<223> OTHER INFORMATION: primer oGV3497

<400> SEQUENCE: 168
ttactcgagc ttgattctga c                                              21

<210> SEQ ID NO 169
<211> LENGTH: 26
<212> TYPE: DNA
<213> ORGANISM: Artificial Sequence
<220> FEATURE:
<223> OTHER INFORMATION: primer oGV2320

<400> SEQUENCE: 169
ggctgtgtag aagtactcgc cgatag                                         26
```

```
<210> SEQ ID NO 170
<211> LENGTH: 21
<212> TYPE: DNA
<213> ORGANISM: Artificial Sequence
<220> FEATURE:
<223> OTHER INFORMATION: primer oGV3496

<400> SEQUENCE: 170
atgtcttcat cactagcaga g                                      21

<210> SEQ ID NO 171
<211> LENGTH: 25
<212> TYPE: DNA
<213> ORGANISM: Artificial Sequence
<220> FEATURE:
<223> OTHER INFORMATION: primer oGV0821

<400> SEQUENCE: 171
cgggtaatta acgacaccct agagg                                  25

<210> SEQ ID NO 172
<211> LENGTH: 23
<212> TYPE: DNA
<213> ORGANISM: Artificial Sequence
<220> FEATURE:
<223> OTHER INFORMATION: primer oGV0706

<400> SEQUENCE: 172
ggttggtatt ccagctggtg tcg                                    23

<210> SEQ ID NO 173
<211> LENGTH: 24
<212> TYPE: DNA
<213> ORGANISM: Artificial Sequence
<220> FEATURE:
<223> OTHER INFORMATION: primer oGV3502

<400> SEQUENCE: 173
gaaacacagt ggattagtgc tgtc                                   24

<210> SEQ ID NO 174
<211> LENGTH: 60
<212> TYPE: DNA
<213> ORGANISM: Artificial Sequence
<220> FEATURE:
<223> OTHER INFORMATION: primer oGV3504

<400> SEQUENCE: 174
gaagagtaaa aaaggagtag aaacattttg aagctatgct ctttgtaatt gttgttggtg    60

<210> SEQ ID NO 175
<211> LENGTH: 60
<212> TYPE: DNA
<213> ORGANISM: Artificial Sequence
<220> FEATURE:
<223> OTHER INFORMATION: primer oGV3505

<400> SEQUENCE: 175 caaattttc ttttttttct gtacaaacag agtccatccg tttgaaactg attgcatgtc    60

<210> SEQ ID NO 176
<211> LENGTH: 22
<212> TYPE: DNA
<213> ORGANISM: Artificial Sequence
<220> FEATURE:
<223> OTHER INFORMATION: primer oGV3507
```

<400> SEQUENCE: 176
tcaaattcta ttatcgcgcg gg         22

<210> SEQ ID NO 177
<211> LENGTH: 60
<212> TYPE: DNA
<213> ORGANISM: Artificial Sequence
<220> FEATURE:
<223> OTHER INFORMATION: primer oGV3503

<400> SEQUENCE: 177
caccaacaac aattacaaag agcatagctt caaaatgttt ctactccttt tttactcttc         60

<210> SEQ ID NO 178
<211> LENGTH: 60
<212> TYPE: DNA
<213> ORGANISM: Artificial Sequence
<220> FEATURE:
<223> OTHER INFORMATION: primer oGV3506

<400> SEQUENCE: 178
gacatgcaat cagtttcaaa cggatggact ctgtttgtac agaaaaaaaa gaaaaatttg         60

<210> SEQ ID NO 179
<211> LENGTH: 26
<212> TYPE: DNA
<213> ORGANISM: Artificial Sequence
<220> FEATURE:
<223> OTHER INFORMATION: primer oGV3509

<400> SEQUENCE: 179
ctcctccgtt gcagaacaag gctttg         26

<210> SEQ ID NO 180
<211> LENGTH: 26
<212> TYPE: DNA
<213> ORGANISM: Artificial Sequence
<220> FEATURE:
<223> OTHER INFORMATION: primer oGV2320

<400> SEQUENCE: 180
ggctgtgtag aagtactcgc cgatag         26

<210> SEQ ID NO 181
<211> LENGTH: 26
<212> TYPE: DNA
<213> ORGANISM: Artificial Sequence
<220> FEATURE:
<223> OTHER INFORMATION: primer oGV3508

<400> SEQUENCE: 181
cggtgttaag tgccagaaat tggttg         26

<210> SEQ ID NO 182
<211> LENGTH: 25
<212> TYPE: DNA
<213> ORGANISM: Artificial Sequence
<220> FEATURE:
<223> OTHER INFORMATION: primer oGV0821

<400> SEQUENCE: 182
cgggtaatta acgacaccct agagg         25

<210> SEQ ID NO 183
<211> LENGTH: 27

```
<212> TYPE: DNA
<213> ORGANISM: Artificial Sequence
<220> FEATURE:
<223> OTHER INFORMATION: primer oGV3510

<400> SEQUENCE: 183
cggcgtactc gacgtcttga gaagtag                                          27

<210> SEQ ID NO 184
<211> LENGTH: 1023
<212> TYPE: DNA
<213> ORGANISM: Lactococcus lactis

<400> SEQUENCE: 184
atgaaagcag cagtagtaag acacaatcca gatggttatg cggaccttgt tgaaaaggaa      60
cttcgagcaa tcaaacctaa tgaagctttg cttgacatgg agtattgtgg agtctgtcat     120
accgatttgc acgttgcagc aggtgattat ggcaacaaag cagggactgt tcttggtcat     180
gaaggaattg gaattgtcaa agaaattgga gctgatgtaa gctcgcttca agttggtgat     240
cgggtttcag tggcttggtt ctttgaagga tgtggtcact gtgaatactg tgtatctggt     300
aatgaaactt tttgtcgaga agttaaaaat gcaggatatt cagttgatgg cggaatggct     360
gaagaagcaa ttgttgttgc cgattatgct gtcaaagttc ctgacggact tgacccaatt     420
gaagctagct caattacttg tgctggagta acaacttaca aagcaatcaa agtatcagga     480
gtaaaacctg gtgattggca gtaattttt ggtgctggag acttggaaa tttagcaatt     540 caatatgcta aaaatgtttt tggagcaaaa gtaattgctg ttgatattaa tcaagataaa     600
ttaaatttag ctaaaaaaat tggagctgat gtgattatca attctggtga tgtaaatcca     660
gttgatgaaa ttaaaaaaat aactggcggc ttaggggtgc aaagtgcaat agtttgtgct     720
gttgcaagga ttgcttttga acaagcggtt gcttctttga aacctatggg caaaatggtt     780
gctgtggcac ttcccaatac tgagatgact ttatcagttc aacagttgt ttttgacgga     840 gtggaggttg caggttcact tgtcggaaca agacttgact tggcagaagc ttttcaattt     900
ggagcagaag gtaaggtaaa accaattgtt gcgacacgca aactggaaga atcaatgat     960 attattgatg aaatgaaggc aggaaaaatt gaaggccgaa tggtcattga ttttactaaa    1020
taa                                                                 1023

<210> SEQ ID NO 185
<211> LENGTH: 340
<212> TYPE: PRT
<213> ORGANISM: Lactococcus lactis

<400> SEQUENCE: 185

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Tyr Gly Asn Lys Ala Gly Thr Val Leu Gly His Glu Gly Ile Gly
    50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95
```

```
Cys Val Ser Gly Asn Glu Thr Phe Cys Arg Glu Val Lys Asn Ala Gly
            100                 105                 110

Tyr Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Ile Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Leu Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335

Asp Phe Thr Lys
            340

<210> SEQ ID NO 186
<211> LENGTH: 1041
<212> TYPE: DNA
<213> ORGANISM: Lactococcus lactis

<400> SEQUENCE: 186
atgaaggctg cagttgtccg tcacaatcct gatgggtacg ctgatcttgt agaaaaagag      60
ttgagggcca ttaagccaaa tgaggcattg ttggatatgg aatactgcgg tgtctgtcac     120
actgacctac atgttgctgc cggagattac ggcaacaagg cagggacagt tttaggacat     180
gaaggtatag gtattgtgaa agagattggt gccgatgtta gttctctcca agtaggtgat     240
agagtgagtg ttgcttggtt tttcgaaggg tgtggacatt gcgaatactg tgtgtcaggt     300
aacgagacat tttgccgaga agtcaaaaac gctggttata cgttgatgg tggaatggca     360 gaggaagcaa tcgtggttgc agattatgcc gtcaaagtcc agatggcct agatccaata     420 gaagcatcat ctataacttg tgcaggcgtc accacttaca aagctatcaa ggtgtctggc     480
gttaagccag agactggca agttatcttc ggagctggtg gcctgggcaa cttagctatc     540
cagtacgcca aaaacgtatt tggtgcgaag gtgatcgctg tagatatcaa tcaagataag     600
ctcaatcttg ccaaaaagat aggtgctgat gtcatcatta actctggtga cgttaaccct     660
gtagacgaaa tcaaaaagat cactggcggt ttaggtgttc aatccgcgat tgtatgtgcc     720
```

```
gttgcgagaa ttgcattcga gcaggctgta gcctcactaa agcctatggg caaaatggta    780
gccgttgctt tgccaaacac agaaatgaca ttatctgtgc caacagtcgt gtttgatgga    840
gttgaagtag caggtagtct tgttggaaca agactcgatt tggccgaagc tttccaattc    900
ggtgcagaag gaaggttaa gcctattgtc gctaccagaa agttggagga aatcaatgac    960
atcattgatg agatgaaggc ggggaagatt gaaggtagaa tggttataga cttcacgaag   1020
caccaccacc accaccacta a                                              1041

<210> SEQ ID NO 187
<211> LENGTH: 346
<212> TYPE: PRT
<213> ORGANISM: Lactococcus lactis

<400> SEQUENCE: 187
```

| | | | | | | | | | | | | | | |
|---|---|---|---|---|---|---|---|---|---|---|---|---|---|---|
| Met | Lys | Ala | Ala | Val | Val | Arg | His | Asn | Pro | Asp | Gly | Tyr | Ala | Asp | Leu |
| 1 | | | | 5 | | | | | 10 | | | | | 15 | |
| Val | Glu | Lys | Glu | Leu | Arg | Ala | Ile | Lys | Pro | Asn | Glu | Ala | Leu | Leu | Asp |
| | | | 20 | | | | | 25 | | | | | 30 | | |
| Met | Glu | Tyr | Cys | Gly | Val | Cys | His | Thr | Asp | Leu | His | Val | Ala | Ala | Gly |
| | | | 35 | | | | | 40 | | | | | 45 | | |
| Asp | Tyr | Gly | Asn | Lys | Ala | Gly | Thr | Val | Leu | Gly | His | Glu | Gly | Ile | Gly |
| | | 50 | | | | | 55 | | | | | 60 | | | |
| Ile | Val | Lys | Glu | Ile | Gly | Ala | Asp | Val | Ser | Ser | Leu | Gln | Val | Gly | Asp |
| 65 | | | | | 70 | | | | | 75 | | | | | 80 |
| Arg | Val | Ser | Val | Ala | Trp | Phe | Phe | Glu | Gly | Cys | Gly | His | Cys | Glu | Tyr |
| | | | | 85 | | | | | 90 | | | | | 95 | |
| Cys | Val | Ser | Gly | Asn | Glu | Thr | Phe | Cys | Arg | Glu | Val | Lys | Asn | Ala | Gly |
| | | | 100 | | | | | 105 | | | | | 110 | | |
| Tyr | Ser | Val | Asp | Gly | Gly | Met | Ala | Glu | Glu | Ala | Ile | Val | Val | Ala | Asp |
| | | | 115 | | | | | 120 | | | | | 125 | | |
| Tyr | Ala | Val | Lys | Val | Pro | Asp | Gly | Leu | Asp | Pro | Ile | Glu | Ala | Ser | Ser |
| | | 130 | | | | | 135 | | | | | 140 | | | |
| Ile | Thr | Cys | Ala | Gly | Val | Thr | Thr | Tyr | Lys | Ala | Ile | Lys | Val | Ser | Gly |
| 145 | | | | | 150 | | | | | 155 | | | | | 160 |
| Val | Lys | Pro | Gly | Asp | Trp | Gln | Val | Ile | Phe | Gly | Ala | Gly | Gly | Leu | Gly |
| | | | | 165 | | | | | 170 | | | | | 175 | |
| Asn | Leu | Ala | Ile | Gln | Tyr | Ala | Lys | Asn | Val | Phe | Gly | Ala | Lys | Val | Ile |
| | | | 180 | | | | | 185 | | | | | 190 | | |
| Ala | Val | Asp | Ile | Asn | Gln | Asp | Lys | Leu | Asn | Leu | Ala | Lys | Lys | Ile | Gly |
| | | | 195 | | | | | 200 | | | | | 205 | | |
| Ala | Asp | Val | Ile | Ile | Asn | Ser | Gly | Asp | Val | Asn | Pro | Val | Asp | Glu | Ile |
| | | 210 | | | | | 215 | | | | | 220 | | | |
| Lys | Lys | Ile | Thr | Gly | Gly | Leu | Gly | Val | Gln | Ser | Ala | Ile | Val | Cys | Ala |
| 225 | | | | | 230 | | | | | 235 | | | | | 240 |
| Val | Ala | Arg | Ile | Ala | Phe | Glu | Gln | Ala | Val | Ala | Ser | Leu | Lys | Pro | Met |
| | | | | 245 | | | | | 250 | | | | | 255 | |
| Gly | Lys | Met | Val | Ala | Val | Ala | Leu | Pro | Asn | Thr | Glu | Met | Thr | Leu | Ser |
| | | | 260 | | | | | 265 | | | | | 270 | | |
| Val | Pro | Thr | Val | Val | Phe | Asp | Gly | Val | Glu | Val | Ala | Gly | Ser | Leu | Val |
| | | | 275 | | | | | 280 | | | | | 285 | | |
| Gly | Thr | Arg | Leu | Asp | Leu | Ala | Glu | Ala | Phe | Gln | Phe | Gly | Ala | Glu | Gly |
| | | 290 | | | | | 295 | | | | | 300 | | | |
| Lys | Val | Lys | Pro | Ile | Val | Ala | Thr | Arg | Lys | Leu | Glu | Glu | Ile | Asn | Asp |

```
305                 310                 315                 320
Ile Ile Asp Glu Met Lys Ala Gly Lys Ile Glu Gly Arg Met Val Ile
                325                 330                 335
Asp Phe Thr Lys His His His His His His
            340                 345
```

<210> SEQ ID NO 188
<211> LENGTH: 1041
<212> TYPE: DNA
<213> ORGANISM: Lactococcus lactis

<400> SEQUENCE: 188

```
atgaaggctg cagttgtccg tcacaatcct gatgggtacg ctgatcttgt agaaaaagag      60
ttgagggcca ttaagccaaa tgaggcattg ttggatatgg aatactgcgg tgtctgtcac     120
actgacctac atgttgctgc cggagattac ggcaacaagg cagggacagt tttaggacat     180
gaaggtatag gtattgtgaa agagattggt gccgatgtta gttctctcca agtaggtgat     240
agagtgagtg ttgcttggtt tttcgaaggg tgtggacatt gcgaatactg tgtgtcaggt     300
aacgagacat tttgccgaga agtcaaaaac gctggttata gcgttgatgg tggaatggca     360
gaggaagcga tcgtggttgc agattatgcc gttaaagtcc cagatggcct agatccaata     420
gaagcatcat ctataacttg tgcaggcgtc accacttaca aagctatcaa ggtgtctggc     480
gttaagccag agactggca gttatcttc ggagctggtg gcctgggcaa cttagctatc     540
cagtacgcca aaacgtatt tggtgcgaag gtgatcgctg tagatatcaa tcaagataag     600
ctcaatcttg ccaaaaagat aggtgctgat gtcatcatta actctggtga cgtttaccct     660
gtagacgaaa tcaaaaagat cactggcggt ttaggtgttc aatccgcgat tgtatgtgcc     720
gttgcgagaa ttgcattcga gcaggctgta gcctcactaa agcctatggg caaaatggta     780
gccgttgctg tgccaaacac agaaatgaca ttatctgtgc caacagtcgt gtttgatgga     840
gttgaagtag caggtagtct tgttggaaca agactcgatt tggccgaagc tttccaattc     900
ggtgcagaag ggaaggttaa gccattgtc gctaccagaa agttggagga aatcaatgac     960
atcattgatg agatgaaggc ggggaagatt gaaggtagaa tggttataga cttcacgaag    1020
caccaccacc accaccacta a                                              1041
```

<210> SEQ ID NO 189
<211> LENGTH: 346
<212> TYPE: PRT
<213> ORGANISM: Lactococcus lactis

<400> SEQUENCE: 189

```
Met Lys Ala Ala Val Val Arg His Asn Pro Asp Gly Tyr Ala Asp Leu
1               5                   10                  15
Val Glu Lys Glu Leu Arg Ala Ile Lys Pro Asn Glu Ala Leu Leu Asp
            20                  25                  30
Met Glu Tyr Cys Gly Val Cys His Thr Asp Leu His Val Ala Ala Gly
        35                  40                  45
Asp Tyr Gly Asn Lys Ala Gly Thr Val Leu Gly His Glu Gly Ile Gly
    50                  55                  60
Ile Val Lys Glu Ile Gly Ala Asp Val Ser Ser Leu Gln Val Gly Asp
65                  70                  75                  80
Arg Val Ser Val Ala Trp Phe Phe Glu Gly Cys Gly His Cys Glu Tyr
                85                  90                  95
Cys Val Ser Gly Asn Glu Thr Phe Cys Arg Glu Val Lys Asn Ala Gly
```

|     |     |     |     | 100 |     |     |     | 105 |     |     |     | 110 |     |     |
| --- | --- | --- | --- | --- | --- | --- | --- | --- | --- | --- | --- | --- | --- | --- |
| Tyr | Ser | Val | Asp | Gly | Gly | Met | Ala | Glu | Glu | Ala | Ile | Val | Val | Ala | Asp |
|     |     |     |     | 115 |     |     |     |     | 120 |     |     |     |     | 125 |     |
| Tyr | Ala | Val | Lys | Val | Pro | Asp | Gly | Leu | Asp | Pro | Ile | Glu | Ala | Ser | Ser |
|     |     |     | 130 |     |     |     |     | 135 |     |     |     |     | 140 |     |     |
| Ile | Thr | Cys | Ala | Gly | Val | Thr | Thr | Tyr | Lys | Ala | Ile | Lys | Val | Ser | Gly |
| 145 |     |     |     |     | 150 |     |     |     |     | 155 |     |     |     |     | 160 |
| Val | Lys | Pro | Gly | Asp | Trp | Gln | Val | Ile | Phe | Gly | Ala | Gly | Leu | Gly |
|     |     |     |     | 165 |     |     |     |     | 170 |     |     |     |     | 175 |
| Asn | Leu | Ala | Ile | Gln | Tyr | Ala | Lys | Asn | Val | Phe | Gly | Ala | Lys | Val | Ile |
|     |     |     | 180 |     |     |     |     | 185 |     |     |     |     | 190 |     |     |
| Ala | Val | Asp | Ile | Asn | Gln | Asp | Lys | Leu | Asn | Leu | Ala | Lys | Lys | Ile | Gly |
|     |     | 195 |     |     |     |     | 200 |     |     |     |     | 205 |     |     |     |
| Ala | Asp | Val | Ile | Ile | Asn | Ser | Gly | Asp | Val | Tyr | Pro | Val | Asp | Glu | Ile |
|     | 210 |     |     |     |     | 215 |     |     |     |     | 220 |     |     |     |     |
| Lys | Lys | Ile | Thr | Gly | Gly | Leu | Gly | Val | Gln | Ser | Ala | Ile | Val | Cys | Ala |
| 225 |     |     |     |     | 230 |     |     |     |     | 235 |     |     |     |     | 240 |
| Val | Ala | Arg | Ile | Ala | Phe | Glu | Gln | Ala | Val | Ala | Ser | Leu | Lys | Pro | Met |
|     |     |     |     | 245 |     |     |     |     | 250 |     |     |     |     | 255 |     |
| Gly | Lys | Met | Val | Ala | Val | Ala | Val | Pro | Asn | Thr | Glu | Met | Thr | Leu | Ser |
|     |     |     | 260 |     |     |     |     | 265 |     |     |     |     | 270 |     |     |
| Val | Pro | Thr | Val | Val | Phe | Asp | Gly | Val | Glu | Val | Ala | Gly | Ser | Leu | Val |
|     |     | 275 |     |     |     |     | 280 |     |     |     |     | 285 |     |     |     |
| Gly | Thr | Arg | Leu | Asp | Leu | Ala | Glu | Ala | Phe | Gln | Phe | Gly | Ala | Glu | Gly |
|     | 290 |     |     |     |     | 295 |     |     |     |     | 300 |     |     |     |     |
| Lys | Val | Lys | Pro | Ile | Val | Ala | Thr | Arg | Lys | Leu | Glu | Glu | Ile | Asn | Asp |
| 305 |     |     |     |     | 310 |     |     |     |     | 315 |     |     |     |     | 320 |
| Ile | Ile | Asp | Glu | Met | Lys | Ala | Gly | Lys | Ile | Glu | Gly | Arg | Met | Val | Ile |
|     |     |     |     | 325 |     |     |     |     | 330 |     |     |     |     | 335 |     |
| Asp | Phe | Thr | Lys | His | His | His | His | His | His |     |     |     |     |     |     |
|     |     |     | 340 |     |     |     |     | 345 |     |     |     |     |     |     |     |

<210> SEQ ID NO 190
<211> LENGTH: 1041
<212> TYPE: DNA
<213> ORGANISM: Lactococcus lactis

<400> SEQUENCE: 190

| atgaaggctg cagttgtccg tcacaatcct gatgggtacg ctgatcttgt agaaaaagag | 60 |
| ttgagggcca ttaagccaaa tgaggcattg ttggatatgg aatactgcgg tgtctgtcac | 120 |
| actgacctac atgttgctgc cggagatttc ggcaacaagg cagggacagt tttaggacat | 180 |
| gaaggtatag gtattgtgaa agagattggt gccgatgtta gttctctcca gtaggtgat | 240 |
| agagtgagtg ttgcttggtt tttcgaaggg tgtggacatt gcgaatactg tgtgtcaggt | 300 |
| aacgagacat tttgccgaga agtcaaaaac gctggttata gcgttgatgg tggaatggca | 360 |
| gaggaagcga tcgtggttgc agattatgcc gttaaagtcc cagatggcct agatccaata | 420 |
| gaagcatcat ctataacttg tgcaggcgtc accacttaca agctatcaa ggtgtctggc | 480 |
| gttaagccag agactggca gttatcttc ggagctggtg gcctgggcaa cttagctatc | 540 |
| cagtacgcca aaaacgtatt tggtgcgaag gtgatcgctg tagatatcaa tcaagataag | 600 |
| ctcaatcttg ccaaaaagat aggtgctgat gtcacaatta actctggtga cgttaaccct | 660 |
| gtagacgaaa tcaaaaagat cactggcggt ttaggtgttc aatccgcgat tgtatgtgcc | 720 |

```
gttgcgagaa ttgcattcga gcaggctgta gcctcactaa agcctatggg caaaatggta        780
gccgttgctc tgccaaacac agaaatgaca ttatctgtgc aacagtcgt gtttgatgga         840 gttgaagtag caggtagtct tgttggaaca agactcgatt tggccgaagc tttccaattc        900
ggtgcagaag ggaaggttaa gcctattgtc gctaccagaa agttggagga aatcaatgac        960
atcattgatg agatgaaggc ggggaagatt gaaggtagaa tggttataga cttcacgaag       1020
caccaccacc accaccacta a                                                 1041

<210> SEQ ID NO 191
<211> LENGTH: 346
<212> TYPE: PRT
<213> ORGANISM: Lactococcus lactis

<400> SEQUENCE: 191

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Tyr Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Thr Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Leu Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320
```

Ile Ile Asp Glu Met Lys Ala Gly Lys Ile Glu Gly Arg Met Val Ile
                325                 330                 335

Asp Phe Thr Lys His His His His His
            340                 345

<210> SEQ ID NO 192
<211> LENGTH: 1041
<212> TYPE: DNA
<213> ORGANISM: Lactococcus lactis

<400> SEQUENCE: 192
atgaaggctg cagttgtccg tcacaatcct gatgggtacg ctgatcttgt agaaaaagag    60
ttgagggcca ttaagccaaa tgaggcattg ttggatatgg aatactgcgg tgtctgtcac   120
actgacctac atgttgctgc cggagatttc ggcaacaagg cagggacagt tttaggacat   180
gaaggtatag gtattgtgaa agagattggt gccgatgtta gttctctcca agtaggtgat   240
agagtgagtg ttgcttggtt tttcgaaggg tgtggacatt gcgaatactg tgtgtcaggt   300
aacgagacat tttgccgaga agtcaaaaac gctggttata gcgttgatgg tggaatggca   360
gaggaagcga tcgtggttgc agattatgcc gttaaagtcc cagatggcct agatccaata   420
gaagcatcat ctataacttg tgcaggcgtc accacttaca aagctatcaa ggtgtctggc   480
gttaagccag agactggca agttatcttc ggagctggtg gcctgggcaa cttagctatc   540
cagtacgcca aaacgtatt tggtgcgaag gtgatcgctg tagatatcaa tcaagataag   600
ctcaatcttg ccaaaaagat aggtgctgat gtcacaatta actctggtga cgttaaccct   660
gtagacgaaa tcaaaaagat cactggcggt ttaggtgttc aatccgcgat tgtatgtgcc   720
gttgcgagaa ttgcattcga gcaggctgta gcctcactaa agcctatggg caaaatggta   780
gccgttgctg taccaaacac agaaatgaca ttatctgtgc caacagtcgt gtttgatgga   840
gttgaagtag caggtagtct tgttggaaca agactcgatt tggccgaagc tttccaattc   900
ggtgcagaag ggaaggttaa gcctattgtc gctaccagaa agttgaagga aatcaatgac   960
atcattgatg agatgaaggc ggggaagatt gaaggtagaa tggttataga cttcacgaag  1020
caccaccacc accaccacta a                                            1041

<210> SEQ ID NO 193
<211> LENGTH: 346
<212> TYPE: PRT
<213> ORGANISM: Lactococcus lactis

<400> SEQUENCE: 193

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Tyr Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Leu Gly
                165                 170                 175

Asn Leu Ala Ile Gln Tyr Ala Lys Asn Val Phe Gly Ala Lys Val Ile
                180                 185                 190

Ala Val Asp Ile Asn Gln Asp Lys Leu Asn Leu Ala Lys Lys Ile Gly
            195                 200                 205

Ala Asp Val Thr Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Val Pro Asn Thr Glu Met Thr Leu Ser
                260                 265                 270

Val Pro Thr Val Val Phe Asp Gly Val Glu Val Ala Gly Ser Leu Val
            275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335

Asp Phe Thr Lys His His His His His His
            340                 345

<210> SEQ ID NO 194
<211> LENGTH: 1041
<212> TYPE: DNA
<213> ORGANISM: Lactococcus lactis

<400> SEQUENCE: 194
atgaaggctg cagttgtccg tcacaatcct gatgggtacg ctgatcttgt agaaaaagag    60
ttgagggcca ttaagccaaa tgaggcattg ttggatatgg aatactgcgg tgtctgtcac   120
actgacctac atgttgctgc cggagatttc ggcaacaagg cagggacagt tttaggacat   180
gaaggtatag gtattgtgaa agagattggt gccgatgtta gttctctccg agtaggtgat   240
agagtgagtg ttgcttggtt tttcgaaggg tgtggacatt gcgaatactg tgtgtcaggt   300
aacgagacat tttgccgaga agccaaaaac gctggttata gcgttgatgg tggaatggca   360
gaggaagcga tcgtggttgc agattatgcc gttaaagtcc cagatggcct agatccaata   420
gaagcatcat ctataacttg tgcaggcgtc accacttaca aagctatcaa ggtgtctggc   480
gttaagccag agactggca agttatcttc ggagctggtg gcctgggcaa cttagctatc   540
cagtacgcca aaaacgtatt tggtgcgaag gtgatcgctg tagatatcaa tcaagataag   600
ctcaatcttg ccaaaaagat aggtgctgat gtcacaatta actctggtga cgttaaccct   660
gtagacgaaa tcaaaaagat cactggcggt ttaggtgttc aatccgcgat tgtatgtgcc   720
gttgcgagaa ttgcattcga gcaggctgta gcctcactaa agcctatggg caaaatggta   780

```
gccgttgctg taccaaacac agaaatgaca ttatctgtgc caacagtcgt gtttgatgga    840
gttgaagtag caggtagtct tgttggaaca agactcgatt tggccgaagc tttccaattc    900
ggtgcagaag ggaaggttaa gcctattgtc gctaccagaa agttggagga aatcaatgac    960
atcattgatg agatgaaggc ggggaagatt gaaggtagaa tggttataga cttcacgaag   1020
caccaccacc accaccacta a                                             1041
```

<210> SEQ ID NO 195
<211> LENGTH: 346
<212> TYPE: PRT
<213> ORGANISM: Lactococcus lactis

<400> SEQUENCE: 195

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
                20                  25                  30

Met Glu Tyr Cys Gly Val Cys His Thr Asp Leu His Val Ala Ala Gly
            35                  40                  45

Asp Phe Gly Asn Lys Ala Gly Thr Val Leu Gly His Glu Gly Ile Gly
        50                  55                  60

Ile Val Lys Glu Ile Gly Ala Asp Val Ser Ser Leu Arg Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Ala Lys Asn Ala Gly
            100                 105                 110

Tyr Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Thr Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Val Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

```
Ile Ile Asp Glu Met Lys Ala Gly Lys Ile Glu Gly Arg Met Val Ile
            325                 330                 335

Asp Phe Thr Lys His His His His His His
        340                 345

<210> SEQ ID NO 196
<211> LENGTH: 1041
<212> TYPE: DNA
<213> ORGANISM: Lactococcus lactis

<400> SEQUENCE: 196
atgaaggctg cagttgtccg tcacaatcct gatgggtacg ctgatcttgt agaaaaagag      60
ttgagggcca ttaagccaaa tgaggcattg ttggatatgg aatactgcgg tgtctgtcac     120
actgacctac atgttgctgc cggagatttc ggcaacaagg cagggacagt tttaggacat     180
gaaggtatag gtattgtgaa agagattggt gccgatgtta gttctctcca agtaggtgat     240
agagtgagtg ttgcttggtt tttcgaaggg tgtggacatt gcgaatactg tgtgtcaggt     300
aacgagacat tttgccgaga attcaaaaac gctggtttta gcgttgatgg tggaatggca     360
gaggaagcga tcgtggttgc agattatgcc gttaaagtcc cagatggcct agatccaata     420
gaagcatcat ctataacttg tgcaggcgtc accacttaca aagctatcaa ggtgtctggc     480
gttaagccag gagactggca gttatcttc ggagctggtg gcctgggcaa cttagctatc     540
cagtacgcca aaaacgtatt tggtgcgaag gtgatcgctg tagatatcaa tcaagataag     600
ctcaatcttg ccaaaaagat aggtgctgat gtcacaatta actctggtga cgttaaccct     660
gtagacgaaa tcaaaaagat cactggcggt ttaggtgttc aatccgcgat gtatgtgcc     720 gttgcgagaa ttgcattcga gcaggctgta gcctcactaa agcctatggg caaaatggta     780
gccgttgctg taccaaacac agaaatgaca ttatctgtgc aaacagtcgt gtttgatgga     840
gttgaagtag caggtagtct tgttggaaca agactcgatt tggccgaagc tttccaattc     900
ggtgcagaag gaaggttaa gcctattgtc gctaccagaa agttggagga aatcaatgac     960
atcattgatg agatgaaggc ggggaagatt gaaggtagaa tggttataga cttcacgaag    1020
caccaccacc accaccacta a                                              1041

<210> SEQ ID NO 197
<211> LENGTH: 346
<212> TYPE: PRT
<213> ORGANISM: Lactococcus lactis

<400> SEQUENCE: 197

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Phe Lys Asn Ala Gly
            100                 105                 110
```

```
Phe Ser Val Asp Gly Gly Met Ala Glu Glu Ala Ile Val Val Ala Asp
            115                 120                 125

Tyr Ala Lys Val Pro Asp Gly Leu Asp Pro Ile Glu Ala Ser Ser
        130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
            195                 200                 205

Ala Asp Val Thr Ile Asn Ser Gly Asp Val Asn Pro Val Asp Glu Ile
            210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Val Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
            290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335

Asp Phe Thr Lys His His His His His His
            340                 345

<210> SEQ ID NO 198
<211> LENGTH: 1041
<212> TYPE: DNA
<213> ORGANISM: Lactococcus lactis

<400> SEQUENCE: 198
atgaaagcag cagtagtaag acacaatcca gatggttatg cggaccttgt tgaaaaggaa      60
cttcgagcaa tcaaacctaa tgaagctttg cttgacatgg agtattgtgg agtctgtcat     120
accgatttgc acgttgcagc aggtgatttt ggcaacaaag cagggactgt tcttggtcat     180
gaaggaattg gaattgtcaa agaaattgga gctgatgtaa gctcgcttca agttggtgat     240
cgggtttcag tggcttggtt ctttgaagga tgtggtcact gtaatactg tgtatctggt     300 aatgaaactt tttgtcgaga agttaaaaat gcaggatttt cagttgatgg cggaatggct     360
gaagaagcaa ttgttgttgc cgattatgct gtcaaagttc ctgacggact tgacccaatt     420
gaagctagct caattacttg tgctggagta acaacttaca aagcaatcaa agtatcagga     480
gtaaaacctg gtgattggca agtaattttt ggtgctggag acttggaaa tttagcaatt     540 caatatgcta aaaatgtttt tggagcaaaa gtaattgctg ttgatattaa tcaagataaa     600
ttaaatttag ctaaaaaaat tggagctgat gtggcaatca attctggtga tgtaaatcca     660
gttgatgaaa ttaaaaaaat aactggcggc ttaggggtgc aaagtgcaat agtttgtgct     720
gttgcaagga ttgcttttga acaagcggtt gcttctttga acctatggg caaaatggtt     780
```

```
gctgtggcag tacccaatac tgagatgact ttatcagttc aacagttgt ttttgacgga    840 gtggaggttg caggttcact tgtcggaaca agacttgact tggcagaagc ttttcaattt    900
ggagcagaag gtaaggtaaa accaattgtt gcgacacgca aactggaaga atcaatgat    960 attattgatg aaatgaaggc aggaaaaatt gaaggccgaa tggtcattga ttttactaaa   1020
caccaccacc accaccacta a                                             1041
```

<210> SEQ ID NO 199
<211> LENGTH: 346
<212> TYPE: PRT
<213> ORGANISM: Lactococcus lactis

<400> SEQUENCE: 199

```
Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Phe Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Ala Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Val Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
```

325                 330                 335
Asp Phe Thr Lys His His His His His His
            340                 345

<210> SEQ ID NO 200
<211> LENGTH: 1041
<212> TYPE: DNA
<213> ORGANISM: Lactococcus lactis

<400> SEQUENCE: 200
atgaaagcag cagtagtaag acacaatcca gatggttatg cggaccttgt tgaaaggaa      60 cttcgagcaa tcaaacctaa tgaagctttg cttgacatgg agtattgtgg agtctgtcat    120
accgatttgc acgttgcagc aggtgatttt ggcaacaaag cagggactgt tcttggtcat    180
gaaggaattg gaattgtcaa agaaattgga gctgatgtaa gctcgctttc tgttggtgat    240
cgggtttcag tggcttggtt ctttgaagga tgtggtcact gtgaatactg tgtatctggt    300
aatgaaactt tttgtcgaga agttaaaaat gcaggatttt cagttgatgg cggaatggct    360
gaagaagcaa ttgttgttgc cgattatgct gtcaaagttc ctgacggact tgacccaatt    420
gaagctagct caattacttg tgctggagta acaacttaca aagcaatcaa agtatcagga    480
gtaaaacctg gtgattggca agtaattttt ggtgctggag acttggaaa tttagcaatt    540 caatatgcta aaaatgtttt tggagcaaaa gtaattgctg ttgatattaa tcaagataaa    600
ttaaatttag ctaaaaaaat tggagctgat gtgacaatca attctggtga tgtaaatcca    660
gttgatgaaa ttaaaaaaat aactggcggc ttaggggtgc aaagtgcaat agtttgtgct    720
gttgcaagga ttgcttttga acaagcggtt gcttctttga aacctatggg caaaatggtt    780
gctgtggcag tacccaatac tgagatgact ttatcagttc aacagttgt ttttgacgga    840 gtggaggttg caggttcact tgtcggaaca agacttgact tggcagaagc ttttcaattt    900
ggagcagaag gtaaggtaaa accaattgtt gcgacacgca aactggaaga aatcaatgat    960
attattgatg aaatgaaggc aggaaaaatt gaaggccgaa tggtcattga ttttactaaa   1020
caccaccacc accaccacta a                                              1041

<210> SEQ ID NO 201
<211> LENGTH: 346
<212> TYPE: PRT
<213> ORGANISM: Lactococcus lactis

<400> SEQUENCE: 201

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Ser Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Phe Ser Val Asp Gly Gly Met Ala Glu Glu Ala Ile Val Val Ala Asp

```
            115                 120                 125
Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Thr Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Val Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335

Asp Phe Thr Lys His His His His His His
            340                 345

<210> SEQ ID NO 202
<211> LENGTH: 1041
<212> TYPE: DNA
<213> ORGANISM: Lactococcus lactis

<400> SEQUENCE: 202
atgaaagcag cagtagtaag acacaatcca gatggttatg cggaccttgt tgaaaaggaa      60
cttcgagcaa tcaaacctaa tgaagctttg cttgacatgg agtattgtgg agtctgtcat     120
accgatttgc acgttgcagc aggtgatttt ggcaacaaag cagggactgt tcttggtcat     180
gaaggaattg gaattgtcaa agaaattgga gctgatgtaa gctcgcttcg agttggtgat     240
cgggtttcag tggcttggtt ctttgaagga tgtggtcact gtgaatactg tgtatctggt     300
aatgaaactt tttgtcgaga gttaaaaaat gcaggatttt cagttgatgg cggaatggct     360
gaagaagcaa ttgttgttgc cgattatgct gtcaaagttc ctgacggact tgacccaatt     420
gaagctagct caattacttg tgctggagta acaacttaca agcaatcaa gtatcagga      480 gtaaaacctg gtgattggca agtaattttt ggtgctggag acttggaaa tttagcaatt     540 caatatgcta aaaatgtttt tggagcaaaa gtaattgctg ttgatattaa tcaagataaa     600
ttaaatttag ctaaaaaaat tggagctgat gtggcaatca attctggtga tgtaaatcca     660
gttgatgaaa ttaaaaaaat aactggcggc ttaggggtgc aaagtgcaat agtttgtgct     720
gttgcaagga ttgcttttga acaagcggtt gcttctttga aacctatggg caaaatggtt     780
gctgtggcag tacccaatac tgagatgact ttatcagttc caacagttgt ttttgacgga     840
```

```
gtggaggttg caggttcact tgtcggaaca agacttgact tggcagaagc ttttcaattt    900
ggagcagaag gtaaggtaaa accaattgtt gcgacacgca aactggaaga aatcaatgat    960
attattgatg aaatgaaggc aggaaaaatt gaaggccgaa tggtcattga ttttactaaa   1020
caccaccacc accaccacta a                                             1041
```

<210> SEQ ID NO 203
<211> LENGTH: 346
<212> TYPE: PRT
<213> ORGANISM: Lactococcus lactis

<400> SEQUENCE: 203

```
Met Lys Ala Ala Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Arg Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Phe Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Ala Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Val Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335
```

Asp Phe Thr Lys His His His His His His
            340                 345

<210> SEQ ID NO 204
<211> LENGTH: 1041
<212> TYPE: DNA
<213> ORGANISM: Lactococcus lactis

<400> SEQUENCE: 204

| | | | | | |
|---|---|---|---|---|---|
| atgaaagcag | cagtagtaag | acacaatcca | gatggttatg | cggaccttgt | tgaaaaggaa | 60 |
| cttcgagcaa | tcaaacctaa | tgaagctttg | cttgacatgg | agtattgtgg | agtctgtcat | 120 |
| accgatttgc | acgttgcagc | aggtgatttt | ggcaacaaag | cagggactgt | tcttggtcat | 180 |
| gaaggaattg | gaattgtcaa | agaaattgga | gctgatgtaa | gctcgctttc | tgttggtgat | 240 |
| cgggtttcag | tggcttggtt | ctttgaagga | tgtggtcact | gtgaatactg | tgtatctggt | 300 |
| aatgaaactt | tttgtcgaga | agttaaaaat | gcaggatttt | cagttgatgg | cggaatggct | 360 |
| gaagaagcaa | ttgttgttgc | cgattatgct | gtcaaagttc | ctgacggact | tgacccaatt | 420 |
| gaagctagct | caattacttg | tgctggagta | acaacttaca | aagcaatcaa | agtatcagga | 480 |
| gtaaaacctg | gtgattggca | agtaattttt | ggtgctggag | gacttggaaa | tttagcaatt | 540 |
| caatatgcta | aaaatgtttt | tggagcaaaa | gtaattgctg | ttgatattaa | tcaagataaa | 600 |
| ttaaatttag | ctaaaaaaat | tggagctgat | gtggtaatca | attctggtga | tgtaaatcca | 660 |
| gttgatgaaa | ttaaaaaaat | aactggcggc | ttaggggtgc | aaagtgcaat | agtttgtgct | 720 |
| gttgcaagga | ttgcttttga | acaagcggtt | gcttctttga | aacctatggg | caaaatggtt | 780 |
| gctgtggcag | tacccaatac | tgagatgact | ttatcagttc | aacagttgt | ttttgacgga | 840 |
| gtggaggttg | caggttcact | tgtcggaaca | agacttgact | tggcagaagc | ttttcaattt | 900 |
| ggagcagaag | gtaaggtaaa | accaattgtt | gcgacacgca | aactggaaga | aatcaatgat | 960 |
| attattgatg | aaatgaaggc | aggaaaaatt | gaaggccgaa | tggtcattga | ttttactaaa | 1020 |
| caccaccacc | accaccacta | a | | | | 1041 |

<210> SEQ ID NO 205
<211> LENGTH: 346
<212> TYPE: PRT
<213> ORGANISM: Lactococcus lactis

<400> SEQUENCE: 205

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Ser Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Phe Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
            165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
            195                 200                 205

Ala Asp Val Val Ile Asn Ser Gly Asp Val Asn Pro Val Asp Glu Ile
210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
            245                 250                 255

Gly Lys Met Val Ala Val Ala Val Pro Asn Thr Glu Met Thr Leu Ser
            260                 265                 270

Val Pro Thr Val Val Phe Asp Gly Val Glu Val Ala Gly Ser Leu Val
            275                 280                 285

Gly Thr Arg Leu Asp Leu Ala Glu Ala Phe Gln Phe Gly Ala Glu Gly
290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
            325                 330                 335

Asp Phe Thr Lys His His His His His His
            340                 345

<210> SEQ ID NO 206
<211> LENGTH: 1023
<212> TYPE: DNA
<213> ORGANISM: Lactococcus lactis

<400> SEQUENCE: 206
atgaaggctg cagttgtccg tcacaatcct gatgggtacg ctgatcttgt agaaaaagag      60
ttgagggcca ttaagccaaa tgaggcattg ttggatatgg aatactgcgg tgtctgtcac     120
actgacctac atgttgctgc cggagattac ggcaacaagg cagggacagt tttaggacat     180
gaaggtatag gtattgtgaa agagattggt gccgatgtta gttctctcca gtaggtgat     240
agagtgagtg ttgcttggtt tttcgaaggg tgtggacatt gcgaatactg tgtgtcaggt     300
aacgagacat tttgccgaga agtcaaaaac gctggttata gcgttgatgg tggaatggca     360
gaggaagcaa tcgtggttgc agattatgcc gtcaaagtcc cagatggcct agatccaata     420
gaagcatcat ctataacttg tgcaggcgtc accacttaca aagctatcaa ggtgtctggc     480
gttaagccag agactggcag agttatcttc ggagctggtg gcctgggcaa cttagctatc     540
cagtacgcca aaaacgtatt tggtgcgaag gtgatcgctg tagatatcaa tcaagataag     600
ctcaatcttg ccaaaaagat aggtgctgat gtcatcatta ctctggtga cgttaaccct     660
gtagacgaaa tcaaaaagat cactggcggt ttaggtgttc aatccgcgat tgtatgtgcc     720
gttgcgagaa ttgcattcga gcaggctgta gcctcactaa agcctatggg caaaatggta     780
gccgttgctt tgccaaacac agaaatgaca ttatctgtgc caacagtcgt gtttgatgga     840

```
gttgaagtag caggtagtct tgttggaaca agactcgatt tggccgaagc tttccaattc      900
ggtgcagaag ggaaggttaa gcctattgtc gctaccagaa agttggagga aatcaatgac      960
atcattgatg agatgaaggc ggggaagatt gaaggtagaa tggttataga cttcacgaag     1020
taa                                                                   1023

<210> SEQ ID NO 207
<211> LENGTH: 1023
<212> TYPE: DNA
<213> ORGANISM: Lactococcus lactis

<400> SEQUENCE: 207
atgaaggctg cagttgtccg tcacaatcct gatgggtacg ctgatcttgt agaaaaagag       60
ttgagggcca ttaagccaaa tgaggcattg ttggatatgg aatactgcgg tgtctgtcac      120
actgacctac atgttgctgc cggagattac ggcaacaagg cagggacagt tttaggacat      180
gaaggtatag gtattgtgaa agagattggt gccgatgtta gttctctcca agtaggtgat      240
agagtgagtg ttgcttggtt tttcgaaggg tgtggacatt gcgaatactg tgtgtcaggt      300
aacgagacat tttgccgaga agtcaaaaac gctggttata gcgttgatgg tggaatggca      360
gaggaagcga tcgtggttgc agattatgcc gttaaagtcc cagatggcct agatccaata      420
gaagcatcat ctataacttg tgcaggcgtc accacttaca aagctatcaa ggtgtctggc      480
gttaagccag agactggca agttatcttc ggagctggtg gcctgggcaa cttagctatc      540
cagtacgcca aaaacgtatt tggtgcgaag gtgatcgctg tagatatcaa tcaagataag      600
ctcaatcttg ccaaaaagat aggtgctgat gtcatcatta actctggtga cgtttaccct      660
gtagacgaaa tcaaaaagat cactggcggt ttaggtgttc aatccgcgat tgtatgtgcc      720
gttgcgagaa ttgcattcga gcaggctgta gcctcactaa agcctatggg caaaatggta      780
gccgttgctg tgccaaacac agaaatgaca ttatctgtgc aacagtcgt gtttgatgga      840 gttgaagtag caggtagtct tgttggaaca agactcgatt tggccgaagc tttccaattc      900
ggtgcagaag ggaaggttaa gcctattgtc gctaccagaa agttggagga aatcaatgac      960
atcattgatg agatgaaggc ggggaagatt gaaggtagaa tggttataga cttcacgaag     1020
taa                                                                   1023

<210> SEQ ID NO 208
<211> LENGTH: 340
<212> TYPE: PRT
<213> ORGANISM: Lactococcus lactis

<400> SEQUENCE: 208

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Tyr Gly Asn Lys Ala Gly Thr Val Leu Gly His Glu Gly Ile Gly
    50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
```

```
                100                 105                 110
Tyr Ser Val Asp Gly Gly Met Ala Glu Glu Ala Ile Val Val Ala Asp
            115                 120                 125
Tyr Ala Val Lys Val Pro Asp Gly Leu Asp Pro Ile Glu Ala Ser Ser
        130                 135                 140
Ile Thr Cys Ala Gly Val Thr Thr Tyr Lys Ala Ile Lys Val Ser Gly
145                 150                 155                 160
Val Lys Pro Gly Asp Trp Gln Val Ile Phe Gly Ala Gly Leu Gly
                165                 170                 175
Asn Leu Ala Ile Gln Tyr Ala Lys Asn Val Phe Gly Ala Lys Val Ile
            180                 185                 190
Ala Val Asp Ile Asn Gln Asp Lys Leu Asn Leu Ala Lys Lys Ile Gly
        195                 200                 205
Ala Asp Val Ile Ile Asn Ser Gly Asp Val Tyr Pro Val Asp Glu Ile
        210                 215                 220
Lys Lys Ile Thr Gly Gly Leu Gly Val Gln Ser Ala Ile Val Cys Ala
225                 230                 235                 240
Val Ala Arg Ile Ala Phe Glu Gln Ala Val Ala Ser Leu Lys Pro Met
                245                 250                 255
Gly Lys Met Val Ala Val Ala Val Pro Asn Thr Glu Met Thr Leu Ser
                260                 265                 270
Val Pro Thr Val Val Phe Asp Gly Val Glu Val Ala Gly Ser Leu Val
            275                 280                 285
Gly Thr Arg Leu Asp Leu Ala Glu Ala Phe Gln Phe Gly Ala Glu Gly
        290                 295                 300
Lys Val Lys Pro Ile Val Ala Thr Arg Lys Leu Glu Glu Ile Asn Asp
305                 310                 315                 320
Ile Ile Asp Glu Met Lys Ala Gly Lys Ile Glu Gly Arg Met Val Ile
                325                 330                 335
Asp Phe Thr Lys
        340

<210> SEQ ID NO 209
<211> LENGTH: 1023
<212> TYPE: DNA
<213> ORGANISM: Lactococcus lactis

<400> SEQUENCE: 209
atgaaggctg cagttgtccg tcacaatcct gatgggtacg ctgatcttgt agaaaaagag    60
ttgagggcca ttaagccaaa tgaggcattg ttggatatgg aatactgcgg tgtctgtcac   120
actgacctac atgttgctgc cggagatttc ggcaacaagg cagggacagt tttaggacat   180
gaaggtatag gtattgtgaa agagattggt gccgatgtta gttctctcca gtaggtgat    240 agagtgagtg ttgcttggtt tttcgaaggg tgtggacatt gcgaatactg tgtgtcaggt   300
aacgagacat tttgccgaga agtcaaaaac gctggttata gcgttgatgg tggaatggca   360
gaggaagcga tcgtggttgc agattatgcc gttaaagtcc cagatggcct agatccaata   420
gaagcatcat ctataacttg tgcaggcgtc accacttaca agctatcaa ggtgtctggc    480 gttaagccag gagactggca agttatcttc ggagctggtg gcctgggcaa cttagctatc   540
cagtacgcca aaaacgtatt tggtgcgaag gtgatcgctg tagatatcaa tcaagataag   600
ctcaatcttg ccaaaaagat aggtgctgat gtcacaatta actctggtga cgttaaccct   660
gtagacgaaa tcaaaaagat cactggcggt ttaggtgttc aatccgcgat tgtatgtgcc   720
```

-continued

```
gttgcgagaa ttgcattcga gcaggctgta gcctcactaa agcctatggg caaaatggta    780
gccgttgctc tgccaaacac agaaatgaca ttatctgtgc caacagtcgt gtttgatgga    840
gttgaagtag caggtagtct tgttggaaca agactcgatt tggccgaagc tttccaattc    900
ggtgcagaag gaaggttaa gcctattgtc gctaccagaa agttggagga aatcaatgac    960
atcattgatg agatgaaggc ggggaagatt gaaggtagaa tggttataga cttcacgaag   1020
taa                                                                 1023
```

```
<210> SEQ ID NO 210
<211> LENGTH: 340
<212> TYPE: PRT
<213> ORGANISM: Lactococcus lactis

<400> SEQUENCE: 210
```

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Tyr Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Thr Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Leu Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
            325                 330                 335

Asp Phe Thr Lys
            340

<210> SEQ ID NO 211
<211> LENGTH: 1023
<212> TYPE: DNA
<213> ORGANISM: Lactococcus lactis

<400> SEQUENCE: 211
atgaaggctg cagttgtccg tcacaatcct gatgggtacg ctgatcttgt agaaaaagag    60
ttgagggcca ttaagccaaa tgaggcattg ttggatatgg aatactgcgg tgtctgtcac   120
actgacctac atgttgctgc cggagatttc ggcaacaagg cagggacagt tttaggacat   180
gaaggtatag gtattgtgaa agagattggt gccgatgtta gttctctcca agtaggtgat   240
agagtgagtg ttgcttggtt tttcgaaggg tgtggacatt gcgaatactg tgtgtcaggt   300
aacgagacat tttgccgaga agtcaaaaac gctggttata gcgttgatgg tggaatggca   360
gaggaagcga tcgtggttgc agattatgcc gttaaagtcc cagatggcct agatccaata   420
gaagcatcat ctataacttg tgcaggcgtc accacttaca aagctatcaa ggtgtctggc   480
gttaagccag agactggca agttatcttc ggagctggtg gcctgggcaa cttagctatc   540
cagtacgcca aaacgtatt tggtgcgaag gtgatcgctg tagatatcaa tcaagataag   600
ctcaatcttg ccaaaaagat aggtgctgat gtcacaatta actctggtga cgttaaccct   660
gtagacgaaa tcaaaagat cactggcggt ttaggtgttc aatccgcgat tgtatgtgcc   720
gttgcgagaa ttgcattcga gcaggctgta gcctcactaa agcctatggg caaaatggta   780
gccgttgctg taccaaacac agaaatgaca ttatctgtgc aacagtcgt gtttgatgga   840 gttgaagtag caggtagtct tgttggaaca agactcgatt tggccgaagc tttccaattc   900
ggtgcagaag ggaaggttaa gcctattgtc gctaccagaa agttggagga atcaatgac   960 atcattgatg agatgaaggc ggggaagatt gaaggtagaa tggttataga cttcacgaag  1020
taa                                                                 1023

<210> SEQ ID NO 212
<211> LENGTH: 340
<212> TYPE: PRT
<213> ORGANISM: Lactococcus lactis

<400> SEQUENCE: 212

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Tyr Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Thr Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Val Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335

Asp Phe Thr Lys
        340

<210> SEQ ID NO 213
<211> LENGTH: 1023
<212> TYPE: DNA
<213> ORGANISM: Lactococcus lactis

<400> SEQUENCE: 213

| | | |
|---|---|---|
| atgaaggctg cagttgtccg tcacaatcct gatgggtacg ctgatcttgt agaaaaagag | 60 |
| ttgagggcca ttaagccaaa tgaggcattg ttggatatgg aatactgcgg tgtctgtcac | 120 |
| actgacctac atgttgctgc cggagatttc ggcaacaagg cagggacagt tttaggacat | 180 |
| gaaggtatag gtattgtgaa agagattggt gccgatgtta gttctctccg agtaggtgat | 240 |
| agagtgagtg ttgcttggtt tttcgaaggg tgtggacatt gcgaatactg tgtgtcaggt | 300 |
| aacgagacat tttgccgaga agccaaaaac gctggttata gcgttgatgg tggaatggca | 360 |
| gaggaagcga tcgtggttgc agattatgcc gttaaagtcc cagatggcct agatccaata | 420 |
| gaagcatcat ctataacttg tgcaggcgtc accacttaca aagctatcaa ggtgtctggc | 480 |
| gttaagccag agactggca agttatcttc ggagctggtg gcctgggcaa cttagctatc | 540 |
| cagtacgcca aaaacgtatt tggtgcgaag gtgatcgctg tagatatcaa tcaagataag | 600 |
| ctcaatcttg ccaaaaagat aggtgctgat gtcacaatta actctggtga cgttaaccct | 660 |
| gtagacgaaa tcaaaaagat cactggcggt ttaggtgttc aatccgcgat tgtatgtgcc | 720 |
| gttgcgagaa ttgcattcga gcaggctgta gcctcactaa agcctatggg caaaatggta | 780 |

-continued

```
gccgttgctg taccaaacac agaaatgaca ttatctgtgc caacagtcgt gtttgatgga    840
gttgaagtag caggtagtct tgttggaaca agactcgatt tggccgaagc tttccaattc    900
ggtgcagaag ggaaggttaa gcctattgtc gctaccagaa agttggagga aatcaatgac    960
atcattgatg agatgaaggc ggggaagatt gaaggtagaa tggttataga cttcacgaag   1020
taa                                                                 1023
```

<210> SEQ ID NO 214
<211> LENGTH: 340
<212> TYPE: PRT
<213> ORGANISM: Lactococcus lactis

<400> SEQUENCE: 214

```
Met Lys Ala Ala Val Arg His Asn Pro Asp Gly Tyr Ala Asp Leu
1               5                  10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Arg Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Ala Lys Asn Ala Gly
            100                 105                 110

Tyr Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Thr Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Val Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320
```

```
Ile Ile Asp Glu Met Lys Ala Gly Lys Ile Glu Gly Arg Met Val Ile
            325                 330                 335

Asp Phe Thr Lys
            340

<210> SEQ ID NO 215
<211> LENGTH: 1023
<212> TYPE: DNA
<213> ORGANISM: Lactococcus lactis

<400> SEQUENCE: 215
atgaaggctg cagttgtccg tcacaatcct gatgggtacg ctgatcttgt agaaaaagag      60
ttgagggcca ttaagccaaa tgaggcattg ttggatatgg aatactgcgg tgtctgtcac     120
actgacctac atgttgctgc cggagatttc ggcaacaagg cagggacagt tttaggacat     180
gaaggtatag gtattgtgaa agagattggt gccgatgtta gttctctcca agtaggtgat     240
agagtgagtg ttgcttggtt tttcgaaggg tgtggacatt gcgaatactg tgtgtcaggt     300
aacgagacat tttgccgaga attcaaaaac gctggtttta gcgttgatgg tggaatggca     360
gaggaagcga tcgtggttgc agattatgcc gttaaagtcc cagatggcct agatccaata     420
gaagcatcat ctataacttg tgcaggcgtc accacttaca aagctatcaa ggtgtctggc     480
gttaagccag gagactggca agttatcttc ggagctggtg gcctgggcaa cttagctatc     540
cagtacgcca aaaacgtatt tggtgcgaag gtgatcgctg tagatatcaa tcaagataag     600
ctcaatcttg ccaaaaagat aggtgctgat gtcacaatta actctggtga cgttaaccct     660
gtagacgaaa tcaaaaagat cactggcggt ttaggtgttc aatccgcgat gtatgtgcc     720 gttgcgagaa ttgcattcga gcaggctgta gcctcactaa agcctatggg caaaatggta     780
gccgttgctg taccaaacac agaaatgaca ttatctgtgc caacagtcgt gtttgatgga     840
gttgaagtag caggtagtct tgttggaaca agactcgatt tggccgaagc tttccaattc     900
ggtgcagaag gaaggttaa gcctattgtc gctaccagaa agttggagga aatcaatgac     960
atcattgatg agatgaaggc ggggaagatt gaaggtagaa tggttataga cttcacgaag    1020
taa                                                                  1023

<210> SEQ ID NO 216
<211> LENGTH: 340
<212> TYPE: PRT
<213> ORGANISM: Lactococcus lactis

<400> SEQUENCE: 216

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Phe Lys Asn Ala Gly
            100                 105                 110
```

```
Phe Ser Val Asp Gly Gly Met Ala Glu Glu Ala Ile Val Val Ala Asp
        115                 120                 125
Tyr Ala Lys Val Pro Asp Gly Leu Asp Pro Ile Glu Ala Ser Ser
    130                 135                 140
Ile Thr Cys Ala Gly Val Thr Thr Tyr Lys Ala Ile Lys Val Ser Gly
145                 150                 155                 160
Val Lys Pro Gly Asp Trp Gln Val Ile Phe Gly Ala Gly Leu Gly
                165                 170                 175
Asn Leu Ala Ile Gln Tyr Ala Lys Asn Val Phe Gly Ala Lys Val Ile
                180                 185                 190
Ala Val Asp Ile Asn Gln Asp Lys Leu Asn Leu Ala Lys Lys Ile Gly
            195                 200                 205
Ala Asp Val Thr Ile Asn Ser Gly Asp Val Asn Pro Val Asp Glu Ile
        210                 215                 220
Lys Lys Ile Thr Gly Gly Leu Gly Val Gln Ser Ala Ile Val Cys Ala
225                 230                 235                 240
Val Ala Arg Ile Ala Phe Glu Gln Ala Val Ala Ser Leu Lys Pro Met
                245                 250                 255
Gly Lys Met Val Ala Val Ala Val Pro Asn Thr Glu Met Thr Leu Ser
                260                 265                 270
Val Pro Thr Val Val Phe Asp Gly Val Glu Val Ala Gly Ser Leu Val
            275                 280                 285
Gly Thr Arg Leu Asp Leu Ala Glu Ala Phe Gln Phe Gly Ala Glu Gly
        290                 295                 300
Lys Val Lys Pro Ile Val Ala Thr Arg Lys Leu Glu Glu Ile Asn Asp
305                 310                 315                 320
Ile Ile Asp Glu Met Lys Ala Gly Lys Ile Glu Gly Arg Met Val Ile
                325                 330                 335
Asp Phe Thr Lys
        340

<210> SEQ ID NO 217
<211> LENGTH: 1023
<212> TYPE: DNA
<213> ORGANISM: Lactococcus lactis

<400> SEQUENCE: 217
atgaaagcag cagtagtaag acacaatcca gatggttatg cggaccttgt tgaaaaggaa      60
cttcgagcaa tcaaacctaa tgaagctttg cttgacatgg agtattgtgg agtctgtcat     120
accgatttgc acgttgcagc aggtgatttt ggcaacaaag cagggactgt tcttggtcat     180
gaaggaattg gaattgtcaa agaaattgga gctgatgtaa gctcgcttca agttggtgat     240
cgggtttcag tggcttggtt ctttgaagga tgtggtcact gtgaatactg tgtatctggt     300
aatgaaactt tttgtcgaga agttaaaaat gcaggatttt cagttgatgg cggaatggct     360
gaagaagcaa ttgttgttgc cgattatgct gtcaaagttc ctgacggact tgacccaatt     420
gaagctagct caattacttg tgctggagta acaacttaca aagcaatcaa agtatcagga     480
gtaaaacctg gtgattggca agtaattttt ggtgctggag gacttggaaa tttagcaatt     540
caatatgcta aaaatgtttt tggagcaaaa gtaattgctg ttgatattaa tcaagataaa     600
ttaaatttag ctaaaaaaat tggagctgat gtggcaatca attctggtga tgtaaatcca     660
gttgatgaaa ttaaaaaaat aactggcggc ttaggggtgc aaagtgcaat agtttgtgct     720
gttgcaagga ttgcttttga acaagcggtt gcttctttga aacctatggg caaaatggtt     780
```

```
gctgtggcag tacccaatac tgagatgact ttatcagttc aacagttgt ttttgacgga    840 gtggaggttg caggttcact tgtcggaaca agacttgact tggcagaagc ttttcaattt    900
ggagcagaag gtaaggtaaa accaattgtt gcgacacgca aactggaaga atcaatgat    960 attattgatg aaatgaaggc aggaaaaatt gaaggccgaa tggtcattga ttttactaaa   1020
taa                                                                 1023
```

<210> SEQ ID NO 218
<211> LENGTH: 340
<212> TYPE: PRT
<213> ORGANISM: Lactococcus lactis

<400> SEQUENCE: 218

```
Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
                20                  25                  30

Met Glu Tyr Cys Gly Val Cys His Thr Asp Leu His Val Ala Ala Gly
            35                  40                  45

Asp Phe Gly Asn Lys Ala Gly Thr Val Leu Gly His Glu Gly Ile Gly
        50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Phe Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Ala Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Val Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
```

```
<210> SEQ ID NO 219
<211> LENGTH: 1041
<212> TYPE: DNA
<213> ORGANISM: Lactococcus lactis

<400> SEQUENCE: 219
atgaaagcag cagtagtaag acacaatcca gatggttatg cggaccttgt tgaaaaggaa      60
cttcgagcaa tcaaacctaa tgaagctttg cttgacatgg agtattgtgg agtctgtcat     120
accgatttgc acgttgcagc aggtgatttt ggcaacaaag cagggactgt tcttggtcat     180
gaaggaattg gaattgtcaa agaaattgga gctgatgtaa gctcgctttc tgttggtgat     240
cgggtttcag tggcttggtt cttttgaagga tgtggtcact gtgaatactg tgtatctggt     300
aatgaaactt tttgtcgaga agttaaaaat gcaggatttt cagttgatgg cggaatggct     360
gaagaagcaa ttgttgttgc cgattatgct gtcaaagttc ctgacggact tgacccaatt     420
gaagctagct caattacttg tgctggagta acaacttaca aagcaatcaa agtatcagga     480
gtaaaacctg gtgattggca gtaatttttt ggtgctggag acttggaaa tttagcaatt     540
caatatgcta aaaatgtttt tggagcaaaa gtaattgctg ttgatattaa tcaagataaa     600
ttaaatttag ctaaaaaaat tggagctgat gtgacaatca attctggtga tgtaaatcca     660
gttgatgaaa ttaaaaaaat aactggcggc ttaggggtgc aaagtgcaat agtttgtgct     720
gttgcaagga ttgcttttga acaagcggtt gcttctttga aacctatggg caaaatggtt     780
gctgtggcag tacccaatac tgagatgact ttatcagttc aacagttgt ttttgacgga     840
gtggaggttg caggttcact tgtcggaaca agacttgact tggcagaagc ttttcaattt     900
ggagcagaag gtaaggtaaa accaattgtt gcgacacgca aactggaaga aatcaatgat     960
attattgatg aaatgaaggc aggaaaaatt gaaggccgaa tggtcattga ttttactaaa    1020
caccaccacc accaccacta a                                              1041

<210> SEQ ID NO 220
<211> LENGTH: 340
<212> TYPE: PRT
<213> ORGANISM: Lactococcus lactis

<400> SEQUENCE: 220

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Ser Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Phe Ser Val Asp Gly Gly Met Ala Glu Glu Ala Ile Val Val Ala Asp
```

Asp Phe Thr Lys
        340

```
                115                 120                 125
Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Thr Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Val Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335

Asp Phe Thr Lys
            340

<210> SEQ ID NO 221
<211> LENGTH: 1023
<212> TYPE: DNA
<213> ORGANISM: Lactococcus lactis

<400> SEQUENCE: 221
atgaaagcag cagtagtaag acacaatcca gatggttatg cggaccttgt tgaaaaggaa      60
cttcgagcaa tcaaacctaa tgaagctttg cttgacatgg agtattgtgg agtctgtcat     120
accgatttgc acgttgcagc aggtgatttt ggcaacaaag cagggactgt tcttggtcat     180
gaaggaattg gaattgtcaa agaaattgga gctgatgtaa gctcgcttcg agttggtgat     240
cgggtttcag tggcttggtt cttttgaagga tgtggtcact gtgaatactg tgtatctggt     300
aatgaaactt tttgtcgaga agttaaaaat gcaggatttt cagttgatgg cggaatggct     360
gaagaagcaa ttgttgttgc cgattatgct gtcaaagttc ctgacggact tgacccaatt     420
gaagctagct caattacttg tgctggagta acaacttaca aagcaatcaa agtatcagga     480
gtaaaacctg gtgattggca agtaattttt ggtgctggag acttggaaa tttagcaatt     540 caatatgcta aaaatgtttt tggagcaaaa gtaattgctg ttgatattaa tcaagataaa     600
ttaaatttag ctaaaaaaat tggagctgat gtggcaatca attctggtga tgtaaatcca     660
gttgatgaaa ttaaaaaaat aactggcggc ttaggggtgc aaagtgcaat agtttgtgct     720
gttgcaagga ttgctttga caagcggtt gcttctttga aacctatggg caaaatggtt     780
gctgtggcag tacccaatac tgagatgact ttatcagttc caacagttgt ttttgacgga     840
```

```
gtggaggttg caggttcact tgtcggaaca agacttgact tggcagaagc ttttcaattt    900
ggagcagaag gtaaggtaaa accaattgtt gcgacacgca aactggaaga aatcaatgat    960
attattgatg aaatgaaggc aggaaaaatt gaaggccgaa tggtcattga ttttactaaa   1020
taa                                                                 1023
```

<210> SEQ ID NO 222
<211> LENGTH: 340
<212> TYPE: PRT
<213> ORGANISM: Lactococcus lactis

<400> SEQUENCE: 222

```
Met Lys Ala Ala Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Arg Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Phe Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Ala Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Val Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335
```

Asp Phe Thr Lys
            340

<210> SEQ ID NO 223
<211> LENGTH: 1023
<212> TYPE: DNA
<213> ORGANISM: Lactococcus lactis

<400> SEQUENCE: 223

```
atgaaagcag cagtagtaag acacaatcca gatggttatg cggaccttgt tgaaaaggaa      60
cttcgagcaa tcaaacctaa tgaagctttg cttgacatgg agtattgtgg agtctgtcat     120
accgatttgc acgttgcagc aggtgatttt ggcaacaaag cagggactgt tcttggtcat     180
gaaggaattg gaattgtcaa agaaattgga gctgatgtaa gctcgctttc tgttggtgat     240
cgggtttcag tggcttggtt ctttgaagga tgtggtcact gtgaatactg tgtatctggt     300
aatgaaactt tttgtcgaga agttaaaaat gcaggatttt cagttgatgg cggaatggct     360
gaagaagcaa ttgttgttgc cgattatgct gtcaaagttc ctgacggact tgacccaatt     420
gaagctagct caattacttg tgctggagta acaacttaca aagcaatcaa agtatcagga     480
gtaaaacctg gtgattggca agtaattttt ggtgctggag acttggaaa tttagcaatt     540
caatatgcta aaaatgtttt tggagcaaaa gtaattgctg ttgatattaa tcaagataaa     600
ttaaatttag ctaaaaaaat tggagctgat gtggtaatca attctggtga gtaaatccca     660
gttgatgaaa ttaaaaaaat aactggcggc ttaggggtgc aaagtgcaat agtttgtgct     720
gttgcaagga ttgcttttga acaagcggtt gcttctttga aacctatggg caaaatggtt     780
gctgtggcag tacccaatac tgagatgact ttatcagttc aacagttgt ttttgacgga     840
gtggaggttg caggttcact tgtcggaaca agacttgact tggcagaagc ttttcaattt     900
ggagcagaag gtaaggtaaa accaattgtt gcgacacgca aactggaaga aatcaatgat     960
attattgatg aaatgaaggc aggaaaaatt gaaggccgaa tggtcattga tttttactaa    1020
taa                                                                   1023
```

<210> SEQ ID NO 224
<211> LENGTH: 340
<212> TYPE: PRT
<213> ORGANISM: Lactococcus lactis

<400> SEQUENCE: 224

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Ser Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Phe Ser Val Asp Gly Gly Met Ala Glu Glu Ala Ile Val Val Ala Asp
        115                 120                 125

-continued

```
Tyr Ala Val Lys Val Pro Asp Gly Leu Asp Pro Ile Glu Ala Ser Ser
            130                 135                 140
Ile Thr Cys Ala Gly Val Thr Thr Tyr Lys Ala Ile Lys Val Ser Gly
145                 150                 155                 160
Val Lys Pro Gly Asp Trp Gln Val Ile Phe Gly Ala Gly Gly Leu Gly
                165                 170                 175
Asn Leu Ala Ile Gln Tyr Ala Lys Asn Val Phe Gly Ala Lys Val Ile
            180                 185                 190
Ala Val Asp Ile Asn Gln Asp Lys Leu Asn Leu Ala Lys Lys Ile Gly
        195                 200                 205
Ala Asp Val Val Ile Asn Ser Gly Asp Val Asn Pro Val Asp Glu Ile
    210                 215                 220
Lys Lys Ile Thr Gly Gly Leu Gly Val Gln Ser Ala Ile Val Cys Ala
225                 230                 235                 240
Val Ala Arg Ile Ala Phe Glu Gln Ala Val Ala Ser Leu Lys Pro Met
                245                 250                 255
Gly Lys Met Val Ala Val Ala Val Pro Asn Thr Glu Met Thr Leu Ser
            260                 265                 270
Val Pro Thr Val Val Phe Asp Gly Val Glu Val Ala Gly Ser Leu Val
        275                 280                 285
Gly Thr Arg Leu Asp Leu Ala Glu Ala Phe Gln Phe Gly Ala Glu Gly
    290                 295                 300
Lys Val Lys Pro Ile Val Ala Thr Arg Lys Leu Glu Glu Ile Asn Asp
305                 310                 315                 320
Ile Ile Asp Glu Met Lys Ala Gly Lys Ile Glu Gly Arg Met Val Ile
                325                 330                 335
Asp Phe Thr Lys
            340

<210> SEQ ID NO 225
<211> LENGTH: 24
<212> TYPE: DNA
<213> ORGANISM: Artificial Sequence
<220> FEATURE:
<223> OTHER INFORMATION: Primer XX7

<400> SEQUENCE: 225
ggagaaaacc catatgtcgt ttac                                          24

<210> SEQ ID NO 226
<211> LENGTH: 25
<212> TYPE: DNA
<213> ORGANISM: Artificial Sequence
<220> FEATURE:
<223> OTHER INFORMATION: Primer XX9

<400> SEQUENCE: 226
gcagccgaac gctcgagggc ggccg                                         25

<210> SEQ ID NO 227
<211> LENGTH: 48
<212> TYPE: DNA
<213> ORGANISM: Artificial Sequence
<220> FEATURE:
<223> OTHER INFORMATION: Primer His_Not1_1947_rev

<400> SEQUENCE: 227
ctcgagcggc cgcttagtgg tggtggtggt ggtgtttagt aaaatcaa                48
```

<210> SEQ ID NO 228
<211> LENGTH: 26
<212> TYPE: DNA
<213> ORGANISM: Artificial Sequence
<220> FEATURE:
<223> OTHER INFORMATION: Primer Sal1_for

<400> SEQUENCE: 228
gaaagcatag caatctaatc taagtt                                    26

<210> SEQ ID NO 229
<211> LENGTH: 31
<212> TYPE: DNA
<213> ORGANISM: Artificial Sequence
<220> FEATURE:
<223> OTHER INFORMATION: Primer adhAcoSc_SalIin_for

<400> SEQUENCE: 229
gtttgtcgac atgaaggctg cagttgtccg t                              31

<210> SEQ ID NO 230
<211> LENGTH: 60
<212> TYPE: DNA
<213> ORGANISM: Artificial Sequence
<220> FEATURE:
<223> OTHER INFORMATION: Primer adhAcoSC_NotIin_his_rev

<400> SEQUENCE: 230
tcgagcggcc gcttagtggt ggtggtggtg gtgcttcgtg aagtctataa ccattctacc    60

<210> SEQ ID NO 231
<211> LENGTH: 51
<212> TYPE: DNA
<213> ORGANISM: Artificial Sequence
<220> FEATURE:
<223> OTHER INFORMATION: Primer pGV1994ep_for

<400> SEQUENCE: 231
cggtcttcaa ttctcaagt ttcagtttca tttttcttgt tctattacaa c          51

<210> SEQ ID NO 232
<211> LENGTH: 35
<212> TYPE: DNA
<213> ORGANISM: Artificial Sequence
<220> FEATURE:
<223> OTHER INFORMATION: Primer pGV1994ep_rev

<400> SEQUENCE: 232
ctaactcctt cctttcggt tagagcggat gtggg                           35

<210> SEQ ID NO 233
<211> LENGTH: 30
<212> TYPE: DNA
<213> ORGANISM: Artificial Sequence
<220> FEATURE:
<223> OTHER INFORMATION: Primer RecombADHY50_for

<400> SEQUENCE: 233
tgctgccgga gattwcggca acaaggcagg                                30

<210> SEQ ID NO 234
<211> LENGTH: 30
<212> TYPE: DNA
<213> ORGANISM: Artificial Sequence
<220> FEATURE:
<223> OTHER INFORMATION: Primer RecombADHY50_rev

<400> SEQUENCE: 234
cctgccttgt tgccgwaatc tccggcagca                              30

<210> SEQ ID NO 235
<211> LENGTH: 30
<212> TYPE: DNA
<213> ORGANISM: Artificial Sequence
<220> FEATURE:
<223> OTHER INFORMATION: Primer RecombADHL264_for

<400> SEQUENCE: 235
atggtagccg ttgctktacc aaacacagaa                              30

<210> SEQ ID NO 236
<211> LENGTH: 30
<212> TYPE: DNA
<213> ORGANISM: Artificial Sequence
<220> FEATURE:
<223> OTHER INFORMATION: Primer RecombADHL264_rev

<400> SEQUENCE: 236
ttctgtgttt ggtamagcaa cggctaccat                              30

<210> SEQ ID NO 237
<211> LENGTH: 40
<212> TYPE: DNA
<213> ORGANISM: Artificial Sequence
<220> FEATURE:
<223> OTHER INFORMATION: Primer RecombADHI212_Y219_for

<400> SEQUENCE: 237
gctgatgtca yaattaactc tggtgacgtt waccctgtag                   40

<210> SEQ ID NO 238
<211> LENGTH: 40
<212> TYPE: DNA
<213> ORGANISM: Artificial Sequence
<220> FEATURE:
<223> OTHER INFORMATION: Primer RecombADHI212_Y219_rev

<400> SEQUENCE: 238
ctacagggtw aacgtcacca gagttaattr tgacatcagc                   40

<210> SEQ ID NO 239
<211> LENGTH: 25
<212> TYPE: DNA
<213> ORGANISM: Artificial Sequence
<220> FEATURE:
<223> OTHER INFORMATION: Primer NNKADHF50_for
<220> FEATURE:
<221> NAME/KEY: misc_feature
<222> LOCATION: (14)..(15)
<223> OTHER INFORMATION: n is a, c, g, or t

<400> SEQUENCE: 239
tgctgccgga gatnnkggca acaag                                   25

<210> SEQ ID NO 240
<211> LENGTH: 25
<212> TYPE: DNA
<213> ORGANISM: Artificial Sequence
<220> FEATURE:
<223> OTHER INFORMATION: Primer NNKADHF50_rev
<220> FEATURE:
<221> NAME/KEY: misc_feature
<222> LOCATION: (13)..(14)

<223> OTHER INFORMATION: n is a, c, g, or t

<400> SEQUENCE: 240
gccttgttgc cmnnatctcc ggcag					25

<210> SEQ ID NO 241
<211> LENGTH: 26
<212> TYPE: DNA
<213> ORGANISM: Artificial Sequence
<220> FEATURE:
<223> OTHER INFORMATION: Primer NNKADHR77_for
<220> FEATURE:
<221> NAME/KEY: misc_feature
<222> LOCATION: (13)..(14)
<223> OTHER INFORMATION: n is a, c, g, or t

<400> SEQUENCE: 241
gttagttctc tcnnkgtagg tgatag					26

<210> SEQ ID NO 242
<211> LENGTH: 26
<212> TYPE: DNA
<213> ORGANISM: Artificial Sequence
<220> FEATURE:
<223> OTHER INFORMATION: Primer NNKADHR77_rev
<220> FEATURE:
<221> NAME/KEY: misc_feature
<222> LOCATION: (17)..(18)
<223> OTHER INFORMATION: n is a, c, g, or t

<400> SEQUENCE: 242
cactctatca cctacmnnga gagaac					26

<210> SEQ ID NO 243
<211> LENGTH: 26
<212> TYPE: DNA
<213> ORGANISM: Artificial Sequence
<220> FEATURE:
<223> OTHER INFORMATION: Primer NNKADHA108_for
<220> FEATURE:
<221> NAME/KEY: misc_feature
<222> LOCATION: (16)..(17)
<223> OTHER INFORMATION: n is a, c, g, or t

<400> SEQUENCE: 243
acattttgcc gagaannkaa aaacgc					26

<210> SEQ ID NO 244
<211> LENGTH: 26
<212> TYPE: DNA
<213> ORGANISM: Artificial Sequence
<220> FEATURE:
<223> OTHER INFORMATION: Primer NNKADHA108_rev
<220> FEATURE:
<221> NAME/KEY: misc_feature
<222> LOCATION: (14)..(15)
<223> OTHER INFORMATION: n is a, c, g, or t

<400> SEQUENCE: 244
accagcgttt ttmnnttctc ggcaaa					26

<210> SEQ ID NO 245
<211> LENGTH: 26
<212> TYPE: DNA
<213> ORGANISM: Artificial Sequence
<220> FEATURE:
<223> OTHER INFORMATION: Primer NNKADHF113_for
<220> FEATURE:
<221> NAME/KEY: misc_feature
<222> LOCATION: (16)..(17)
<223> OTHER INFORMATION: n is a, c, g, or t

<400> SEQUENCE: 245
gtcaaaaacg ctggtnnkag cgttga         26

<210> SEQ ID NO 246
<211> LENGTH: 26
<212> TYPE: DNA
<213> ORGANISM: Artificial Sequence
<220> FEATURE:
<223> OTHER INFORMATION: Primer NNKADHF113_rev
<220> FEATURE:
<221> NAME/KEY: misc_feature
<222> LOCATION: (14)..(15)
<223> OTHER INFORMATION: n is a, c, g, or t

<400> SEQUENCE: 246
accatcaacg ctmnnaccag cgtttt         26

<210> SEQ ID NO 247
<211> LENGTH: 26
<212> TYPE: DNA
<213> ORGANISM: Artificial Sequence
<220> FEATURE:
<223> OTHER INFORMATION: Primer NNKADHT212_for
<220> FEATURE:
<221> NAME/KEY: misc_feature
<222> LOCATION: (18)..(19)
<223> OTHER INFORMATION: n is a, c, g, or t

<400> SEQUENCE: 247
agataggtgc tgatgtcnnk attaac         26

<210> SEQ ID NO 248
<211> LENGTH: 26
<212> TYPE: DNA
<213> ORGANISM: Artificial Sequence
<220> FEATURE:
<223> OTHER INFORMATION: Primer NNKADHT212_rev
<220> FEATURE:
<221> NAME/KEY: misc_feature
<222> LOCATION: (12)..(13)
<223> OTHER INFORMATION: n is a, c, g, or t

<400> SEQUENCE: 248
cagagttaat mnngacatca gcacct         26

<210> SEQ ID NO 249
<211> LENGTH: 26
<212> TYPE: DNA
<213> ORGANISM: Artificial Sequence
<220> FEATURE:
<223> OTHER INFORMATION: Primer NNKADHV264_for
<220> FEATURE:
<221> NAME/KEY: misc_feature
<222> LOCATION: (14)..(15)
<223> OTHER INFORMATION: n is a, c, g, or t

<400> SEQUENCE: 249
ggtagccgtt gctnnkccaa acacag         26

<210> SEQ ID NO 250
<211> LENGTH: 26
<212> TYPE: DNA
<213> ORGANISM: Artificial Sequence
<220> FEATURE:
<223> OTHER INFORMATION: Primer NNKADHV264_rev
<220> FEATURE:

```
<221> NAME/KEY: misc_feature
<222> LOCATION: (16)..(17)
<223> OTHER INFORMATION: n is a, c, g, or t

<400> SEQUENCE: 250
atttctgtgt ttggmnnagc aacggc                                          26

<210> SEQ ID NO 251
<211> LENGTH: 30
<212> TYPE: DNA
<213> ORGANISM: Artificial Sequence
<220> FEATURE:
<223> OTHER INFORMATION: Primer Recomb2F50Minilib_for

<400> SEQUENCE: 251
gttgcagcag gtgattdkgg caacaaagca                                      30

<210> SEQ ID NO 252
<211> LENGTH: 30
<212> TYPE: DNA
<213> ORGANISM: Artificial Sequence
<220> FEATURE:
<223> OTHER INFORMATION: Primer Recomb2F50Minilib_rev

<400> SEQUENCE: 252
tgctttgttg ccmhaatcac ctgctgcaac                                      30

<210> SEQ ID NO 253
<211> LENGTH: 30
<212> TYPE: DNA
<213> ORGANISM: Artificial Sequence
<220> FEATURE:
<223> OTHER INFORMATION: Primer Recomb2Q77Gen5_for3

<400> SEQUENCE: 253
tgatgtaagc tcgcttcaag ttggtgatcg                                      30

<210> SEQ ID NO 254
<211> LENGTH: 30
<212> TYPE: DNA
<213> ORGANISM: Artificial Sequence
<220> FEATURE:
<223> OTHER INFORMATION: Primer Recomb2Q77Gen5_rev4

<400> SEQUENCE: 254
cgatcaccaa cttgaagcga gcttacatca                                      30

<210> SEQ ID NO 255
<211> LENGTH: 30
<212> TYPE: DNA
<213> ORGANISM: Artificial Sequence
<220> FEATURE:
<223> OTHER INFORMATION: Primer Recomb2R77Gen5_for5

<400> SEQUENCE: 255
tgatgtaagc tcgcttcgag ttggtgatcg                                      30

<210> SEQ ID NO 256
<211> LENGTH: 30
<212> TYPE: DNA
<213> ORGANISM: Artificial Sequence
<220> FEATURE:
<223> OTHER INFORMATION: Primer Recomb2R77Gen5_rev6

<400> SEQUENCE: 256
cgatcaccaa ctcgaagcga gcttacatca                                      30
```

<210> SEQ ID NO 257
<211> LENGTH: 30
<212> TYPE: DNA
<213> ORGANISM: Artificial Sequence
<220> FEATURE:
<223> OTHER INFORMATION: Primer Recomb2S77Gen5_for7

<400> SEQUENCE: 257
tgatgtaagc tcgctttctg ttggtgatcg                                      30

<210> SEQ ID NO 258
<211> LENGTH: 30
<212> TYPE: DNA
<213> ORGANISM: Artificial Sequence
<220> FEATURE:
<223> OTHER INFORMATION: Primer Recomb2S77Gen5_rev8

<400> SEQUENCE: 258
cgatcaccaa cagaaagcga gcttacatca                                      30

<210> SEQ ID NO 259
<211> LENGTH: 30
<212> TYPE: DNA
<213> ORGANISM: Artificial Sequence
<220> FEATURE:
<223> OTHER INFORMATION: Primer Recomb2Y113 Gen5_for9

<400> SEQUENCE: 259
ttaaaaatgc aggatattca gttgatggcg                                      30

<210> SEQ ID NO 260
<211> LENGTH: 30
<212> TYPE: DNA
<213> ORGANISM: Artificial Sequence
<220> FEATURE:
<223> OTHER INFORMATION: Primer Recomb2Y113 Gen5_rev10

<400> SEQUENCE: 260
cgccatcaac tgaatatcct gcatttttaa                                      30

<210> SEQ ID NO 261
<211> LENGTH: 30
<212> TYPE: DNA
<213> ORGANISM: Artificial Sequence
<220> FEATURE:
<223> OTHER INFORMATION: Primer Recomb2F113 Gen5_for11

<400> SEQUENCE: 261
ttaaaaatgc aggattttca gttgatggcg                                      30

<210> SEQ ID NO 262
<211> LENGTH: 30
<212> TYPE: DNA
<213> ORGANISM: Artificial Sequence
<220> FEATURE:
<223> OTHER INFORMATION: Primer Recomb2F113 Gen5_rev12

<400> SEQUENCE: 262
cgccatcaac tgaaaatcct gcatttttaa                                      30

<210> SEQ ID NO 263
<211> LENGTH: 30
<212> TYPE: DNA
<213> ORGANISM: Artificial Sequence

```
<220> FEATURE:
<223> OTHER INFORMATION: Primer Recomb2G113 Gen5_for13

<400> SEQUENCE: 263
ttaaaaatgc aggagggtca gttgatggcg                                30

<210> SEQ ID NO 264
<211> LENGTH: 30
<212> TYPE: DNA
<213> ORGANISM: Artificial Sequence
<220> FEATURE:
<223> OTHER INFORMATION: Primer Recomb2G113 Gen5_rev14

<400> SEQUENCE: 264
cgccatcaac tgaccctcct gcatttttaa                                30

<210> SEQ ID NO 265
<211> LENGTH: 30
<212> TYPE: DNA
<213> ORGANISM: Artificial Sequence
<220> FEATURE:
<223> OTHER INFORMATION: Primer Recomb2T212 Mini_for15

<400> SEQUENCE: 265
gagctgatgt gryaatcaat tctggtgatg                                30

<210> SEQ ID NO 266
<211> LENGTH: 30
<212> TYPE: DNA
<213> ORGANISM: Artificial Sequence
<220> FEATURE:
<223> OTHER INFORMATION: Primer Recomb2T212 Mini_rev16

<400> SEQUENCE: 266
catcaccaga attgattryc acatcagctc                                30

<210> SEQ ID NO 267
<211> LENGTH: 30
<212> TYPE: DNA
<213> ORGANISM: Artificial Sequence
<220> FEATURE:
<223> OTHER INFORMATION: Primer Recomb2V264 Mini_for17

<400> SEQUENCE: 267
tggttgctgt ggcaktaccc aatactgaga                                30

<210> SEQ ID NO 268
<211> LENGTH: 30
<212> TYPE: DNA
<213> ORGANISM: Artificial Sequence
<220> FEATURE:
<223> OTHER INFORMATION: Primer Recomb2V264 Mini_rev18

<400> SEQUENCE: 268
tctcagtatt gggtamtgcc acagcaacca                                30
```

US 9,012,189 B2

MODIFIED ALCOHOL DEHYDROGENASES FOR THE PRODUCTION OF FUELS AND CHEMICALS

CROSS REFERENCE TO RELATED APPLICATIONS

This application claims priority to U.S. Provisional Application Ser. No. 61/304,069, filed Feb. 12, 2010; U.S. Provisional Application Ser. No. 61/308,568, filed Feb. 26, 2010; U.S. Provisional Application Ser. No. 61/282,641, filed Mar. 10, 2010; U.S. Provisional Application Ser. No. 61/352,133, filed Jun. 7, 2010; U.S. Provisional Application Ser. No. 61/411,885, filed Nov. 9, 2010; and U.S. Provisional Application Ser. No. 61/430,801, filed Jan. 7, 2011, each of which is herein incorporated by reference in its entirety for all purposes.

ACKNOWLEDGMENT OF GOVERNMENTAL SUPPORT

This invention was made with government support under Contract No. 2009-10006-05919, awarded by the United States Department of Agriculture, and under Contract No. W911 NF-09-2-0022, awarded by the United States Army Research Laboratory. The government has certain rights in the invention.

TECHNICAL FIELD

Recombinant microorganisms and methods of producing such organisms are provided. Also provided are methods of producing beneficial metabolites including fuels, chemicals, and amino acids by contacting a suitable substrate with recombinant microorganisms and enzymatic preparations therefrom.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GEVO_045_04US_SeqList_ST25.txt, date recorded: Feb. 9, 2011, file size: 305 kilobytes).

BACKGROUND

The ability of microorganisms to convert pyruvate to beneficial metabolites including fuels, chemicals, and amino acids has been widely described in the literature in recent years. See, e.g., Alper et al., 2009, *Nature Microbiol. Rev.* 7: 715-723. Recombinant engineering techniques have enabled the creation of microorganisms that express biosynthetic pathways capable of producing a number of useful products, such as valine, isoleucine, leucine, and panthothenic acid (vitamin B5). In addition, fuels such as isobutanol have been produced recombinantly in microorganisms expressing a heterologous metabolic pathway (See, e.g., WO/2007/050671 to Donaldson et al., and WO/2008/098227 to Liao, et al.). Although engineered microorganisms represent potentially useful tools for the renewable production of fuels, chemicals, and amino acids, many of these microorganisms have fallen short of commercial relevance due to their low performance characteristics, including low productivity, low titers, and low yields.

One of the primary reasons for the sub-optimal performance observed in many existing microorganisms is the undesirable conversion of pathway intermediates to unwanted by-products. The present inventors have identified various by-products, including 2,3-dihydroxy-2-methylbutanoic acid (DH2MB) (CAS #14868-24-7), 2-ethyl-2,3-dihydroxybutyrate, 2,3-dihydroxy-2-methyl-butanonate, isobutyrate, 3-methyl-1-butyrate, 2-methyl-1-butyrate, and propionate, which are derived from various intermediates of biosynthetic pathways used to produce fuels, chemicals, and amino acids. The accumulation of these by-products negatively impacts the synthesis and yield of desirable metabolites in a variety of fermentation reactions. Until now, the enzymatic activities responsible for the production of these unwanted by-products had not been characterized. More particularly, the present application shows that the activities of a 3-ketoacid reductase (3-KAR) and an aldehyde dehydrogenase (ALDH) allow for the formation of these by-products from important biosynthetic pathway intermediates.

The present invention results from the study of these enzymatic activities and shows that the suppression of the 3-KAR and/or ALDH enzymes considerably reduces or eliminates the formation of unwanted by-products, and concomitantly improves the yields and titers of beneficial metabolites. The present application shows moreover, that enhancement of the 3-KAR and/or ALDH enzymatic activities can be used to increase the production of various by-products, such 2,3-dihydroxy-2-methylbutanoic acid (DH2MB), 2-ethyl-2,3-dihydroxybutyrate, 2,3-dihydroxy-2-methyl-butanonate, isobutyrate, 3-methyl-1-butyrate, 2-methyl-1-butyrate, and propionate.

SUMMARY OF THE INVENTION

The present inventors have discovered that unwanted by-products can accumulate during various fermentation processes, including fermentation of the biofuel candidate, isobutanol. The accumulation of these unwanted by-products results from the undesirable conversion of pathway intermediates including the 3-keto acids, acetolactate and 2-aceto-2-hydroxybutyrate, and/or aldehydes, such as isobutyraldehyde, 1-butanal, 1-propanal, 2-methyl-1-butanal, and 3-methyl-1-butanal. The conversion of these intermediates to unwanted by-products can hinder the optimal productivity and yield of a 3-keto acid- and/or aldehyde-derived products. Therefore, the present inventors have developed methods for reducing the conversion of 3-keto acid and/or aldehyde intermediates to various fermentation by-products during processes where a 3-keto acid and/or an aldehyde acts as a pathway intermediate.

In a first aspect, the present invention relates to a recombinant microorganism comprising a biosynthetic pathway of which a 3-keto acid and/or an aldehyde is/are intermediate(s), wherein said recombinant microorganism is (a) substantially free of an enzyme catalyzing the conversion of a 3-keto acid to a 3-hydroxyacid; (b) substantially free of an enzyme catalyzing the conversion of an aldehyde to an acid by-product; (c) engineered to reduce or eliminate the expression or activity of an enzyme catalyzing the conversion of a 3-keto acid to a 3-hydroxyacid; and/or (d) engineered to reduce or eliminate the expression or activity of an enzyme catalyzing the conversion of an aldehyde to acid by-product. In one embodiment, the 3-keto acid is acetolactate. In another embodiment, the 3-keto acid is 2-aceto-2-hydroxybutyrate.

In one embodiment, the invention is directed to a recombinant microorganism comprising a biosynthetic pathway which uses the 3-keto acid, acetolactate, as an intermediate, wherein said recombinant microorganism is engineered to reduce or eliminate the expression or activity of an enzyme catalyzing the conversion of acetolactate to the corresponding 3-hydroxyacid, DH2MB. In some embodiments, the enzyme catalyzing the conversion of acetolactate to DH2MB is a 3-ketoacid reductase (3-KAR).

In one embodiment, the invention is directed to a recombinant microorganism comprising a biosynthetic pathway which uses the 3-keto acid, 2-aceto-2-hydroxybutyrate, as an intermediate, wherein said recombinant microorganism is engineered to reduce or eliminate the expression or activity of an enzyme catalyzing the conversion of acetolactate to the corresponding 3-hydroxyacid, 2-ethyl-2,3-dihydroxybutanoate. In some embodiments, the enzyme catalyzing the conversion of 2-aceto-2-hydroxybutyrate to 2-ethyl-2,3-dihydroxybutanoate is a 3-ketoacid reductase (3-KAR).

In one embodiment, the invention is directed to a recombinant microorganism comprising a biosynthetic pathway which uses an aldehyde as an intermediate, wherein said recombinant microorganism is engineered to reduce or eliminate the expression or activity of an enzyme catalyzing the conversion of the aldehyde to an acid by-product. In some embodiments, the enzyme catalyzing the conversion of the aldehyde to an acid by-product is an aldehyde dehydrogenase (ALDH).

In one embodiment, the invention is directed to a recombinant microorganism comprising a biosynthetic pathway which uses both a 3-keto acid and an aldehyde as intermediates, wherein said recombinant microorganism is (a) engineered to reduce or eliminate the expression or activity of an enzyme catalyzing the conversion of a 3-keto acid intermediate to a 3-hydroxyacid by-product; and (b) engineered to reduce or eliminate the expression or activity of an enzyme catalyzing the conversion of an aldehyde intermediate to an acid by-product. In one embodiment, the 3-keto acid is acetolactate and the 3-hydroxyacid by-product is DH2MB. In another embodiment, the 3-keto acid is 2-aceto-2-hydroxybutyrate and the 3-hydroxyacid by-product is 2-ethyl-2,3-dihydroxybutanoate. In some embodiments, the enzyme catalyzing the conversion of acetolactate to DH2MB is a 3-ketoacid reductase (3-KAR). In some other embodiments, the enzyme catalyzing the conversion of 2-aceto-2-hydroxybutyrate to 2-ethyl-2,3-dihydroxybutanoate is a 3-ketoacid reductase (3-KAR). In some other embodiments, the enzyme catalyzing the conversion of the aldehyde to an acid by-product is an aldehyde dehydrogenase (ALDH). In yet some other embodiments, the enzyme catalyzing the conversion of acetolactate to DH2MB is a 3-ketoacid reductase (3-KAR) and the enzyme catalyzing the conversion of the aldehyde to an acid by-product is an aldehyde dehydrogenase (ALDH). In yet some other embodiments, the enzyme catalyzing the conversion of 2-aceto-2-hydroxybutyrate to 2-ethyl-2,3-dihydroxybutanoate is a 3-ketoacid reductase (3-KAR) and the enzyme catalyzing the conversion of the aldehyde to an acid by-product is an aldehyde dehydrogenase (ALDH).

In various embodiments described herein, the recombinant microorganisms of the invention may comprise a reduction or deletion of the activity or expression of one or more endogenous proteins involved in catalyzing the conversion of a 3-keto acid intermediate to a 3-hydroxyacid by-product. In one embodiment, the activity or expression of one or more endogenous proteins involved in catalyzing the conversion of a 3-keto acid intermediate to a 3-hydroxyacid by-product is reduced by at least about 50%. In another embodiment, the activity or expression of one or more endogenous proteins involved in catalyzing the conversion of a 3-keto acid intermediate to a 3-hydroxyacid by-product is reduced by at least about 60%, by at least about 65%, by at least about 70%, by at least about 75%, by at least about 80%, by at least about 85%, by at least about 90%, by at least about 95%, or by at least about 99% as compared to a recombinant microorganism not comprising a reduction or deletion of the activity or expression of one or more endogenous proteins involved in catalyzing the conversion of a 3-keto acid intermediate to a 3-hydroxyacid by-product. In one embodiment, the 3-keto acid intermediate is acetolactate and the 3-hydroxyacid by-product is DH2MB. In another embodiment, the 3-keto acid intermediate is 2-aceto-2-hydroxybutyrate and the 3-hydroxyacid by-product is 2-ethyl-2,3-dihydroxybutanoate.

In various embodiments described herein, the protein involved in catalyzing the conversion of a 3-keto acid intermediate to a 3-hydroxyacid by-product is a ketoreductase. In an exemplary embodiment, the ketoreductase is a 3-ketoacid reductase (3-KAR). In another embodiment, the protein is a short chain alcohol dehydrogenase. In yet another embodiment, the protein is a medium chain alcohol dehydrogenase. In yet another embodiment, the protein is an aldose reductase. In yet another embodiment, the protein is a D-hydroxyacid dehydrogenase. In yet another embodiment, the protein is a lactate dehydrogenase. In yet another embodiment, the protein is selected from the group consisting of YAL060W, YJR159W, YGL157W, YBL114W, YOR120W, YKL055C, YBR159W, YBR149W, YDL168W, YDR368W, YLR426W, YCR107W, YIL124W, YML054C, YOL151W, YMR318C, YMR226C, YBR046C, YHR104W, YIR036C, YDL174C, YDR541C, YBR145W, YGL039W, YCR105W, YDL124W, YIR035C, YFL056C, YNL274C, YLR255C, YGL185C, YGL256W, YJR096W, YMR226C, YJR155W, YPL275W, YOR388C, YLR070C, YMR083W, YER081W, YJR139C, YDL243C, YPL113C, YOL165C, YML086C, YMR303C, YDL246C, YLR070C, YHR063C, YNL331C, YFL057C, YIL155C, YOL086C, YAL061W, YDR127W, YPR127W, YCI018W, YIL074C, YIL124W, and YEL071W genes of *S. cerevisiae* and homologs thereof.

In one embodiment, the endogenous protein is a 3-ketoacid reductase (3-KAR). In an exemplary embodiment, the 3-ketoacid reductase is the *S. cerevisiae* YMR226C (SEQ ID NO: 1) protein, used interchangeably herein with "TMA29". In some embodiments, the endogenous protein may be the *S. cerevisiae* YMR226C (SEQ ID NO: 1) protein or a homolog or variant thereof. In one embodiment, the homolog may be selected from the group consisting of *Vanderwaltomzyma polyspora* (SEQ ID NO: 2), *Saccharomyces castellii* (SEQ ID NO: 3), *Candida glabrata* (SEQ ID NO: 4), *Saccharomyces bayanus* (SEQ ID NO: 5), *Zygosaccharomyces rouxii* (SEQ ID NO: 6), *Kluyveromyces lactis* (SEQ ID NO: 7), *Ashbya gossypii* (SEQ ID NO: 8), *Saccharomyces kluyveri* (SEQ ID NO: 9), *Kluyveromyces thermotolerans* (SEQ ID NO: 10), *Kluyveromyces waltii* (SEQ ID NO: 11), *Pichia stipitis* (SEQ ID NO: 12), *Debaromyces hansenii* (SEQ ID NO: 13), *Pichia pastoris* (SEQ ID NO: 14), *Candida dubliniensis* (SEQ ID NO: 15), *Candida albicans* (SEQ ID NO: 16), *Yarrowia lipolytica* (SEQ ID NO: 17), *Issatchenkia orientalis* (SEQ ID NO: 18), *Aspergillus nidulans* (SEQ ID NO: 19), *Aspergillus niger* (SEQ ID NO: 20), *Neurospora crassa* (SEQ ID NO: 21), *Schizosaccharomyces pombe* (SEQ ID NO: 22), and *Kluyveromyces marxianus* (SEQ ID NO: 23).

In one embodiment, the recombinant microorganism includes a mutation in at least one gene encoding for a 3-ketoacid reductase resulting in a reduction of 3-ketoacid reductase activity of a polypeptide encoded by said gene. In another embodiment, the recombinant microorganism includes a partial deletion of gene encoding for a 3-ketoacid reductase resulting in a reduction of 3-ketoacid reductase activity of a polypeptide encoded by the gene. In another embodiment, the recombinant microorganism comprises a complete deletion of a gene encoding for a 3-ketoacid reductase resulting in a reduction of 3-ketoacid reductase activity of a polypeptide encoded by the gene. In yet another embodiment, the recombinant microorganism includes a modification of the regulatory region associated with the gene encoding for a 3-ketoacid reductase resulting in a reduction of expression of a polypeptide encoded by said gene. In yet another embodiment, the recombinant microorganism comprises a modification of the transcriptional regulator resulting in a reduction of transcription of a gene encoding for a 3-ketoacid reductase. In yet another embodiment, the recombinant microorganism comprises mutations in all genes encoding for a 3-ketoacid reductase resulting in a reduction of activity of a polypeptide encoded by the gene(s). In one embodiment, the 3-ketoacid reductase activity or expression is reduced by at least about 50%. In another embodiment, the 3-ketoacid reductase activity or expression is reduced by at least about 60%, by at least about 65%, by at least about 70%, by at least about 75%, by at least about 80%, by at least about 85%, by at least about 90%, by at least about 95%, or by at least about 99% as compared to a recombinant microorganism not comprising a reduction of the 3-ketoacid reductase activity or expression. In one embodiment, said 3-ketoacid reductase is encoded by the *S. cerevisiae* TMA29 (YMR226C) gene or a homolog thereof.

In various embodiments described herein, the recombinant microorganisms of the invention may comprise a reduction or deletion of the activity or expression of one or more endogenous proteins involved in catalyzing the conversion of an aldehyde to an acid by-product. In one embodiment, the activity or expression of one or more endogenous proteins involved in catalyzing the conversion of an aldehyde to an acid by-product is reduced by at least about 50%. In another embodiment, the activity or expression of one or more endogenous proteins involved in catalyzing the conversion of an aldehyde to an acid by-product is reduced by at least about 60%, by at least about 65%, by at least about 70%, by at least about 75%, by at least about 80%, by at least about 85%, by at least about 90%, by at least about 95%, or by at least about 99% as compared to a recombinant microorganism not comprising a reduction or deletion of the activity or expression of one or more endogenous proteins involved in catalyzing the conversion of an aldehyde to an acid by-product.

In various embodiments described herein, the endogenous protein involved in catalyzing the conversion of an aldehyde to an acid by-product is an aldehyde dehydrogenase (ALDH). In one embodiment, the aldehyde dehydrogenase is encoded by a gene selected from the group consisting of ALD2, ALD3, ALD4, ALD5, ALD6, and HFD1, and homologs and variants thereof. In an exemplary embodiment, the aldehyde dehydrogenase is the *S. cerevisiae* ALD6 (SEQ ID NO: 25) protein. In some embodiments, the aldehyde dehydrogenase is the *S. cerevisiae* ALD6 (SEQ ID NO: 25) protein or a homolog or variant thereof. In one embodiment, the homolog is selected from the group consisting of *Saccharomyces castelli* (SEQ ID NO: 26), *Candida glabrata* (SEQ ID NO: 27), *Saccharomyces bayanus* (SEQ ID NO: 28), *Kluyveromyces lactis* (SEQ ID NO: 29), *Kluyveromyces thermotolerans* (SEQ ID NO: 30), *Kluyveromyces waltii* (SEQ ID NO: 31), *Saccharomyces cerevisiae* YJ789 (SEQ ID NO: 32), *Saccharomyces cerevisiae* JAY291 (SEQ ID NO: 33), *Saccharomyces cerevisiae* EC1118 (SEQ ID NO: 34), *Saccharomyces cerevisiae* DBY939 (SEQ ID NO: 35), *Saccharomyces cerevisiae* AWRI1631 (SEQ ID NO: 36), *Saccharomyces cerevisiae* RM11-1a (SEQ ID NO: 37), *Pichia pastoris* (SEQ ID NO: 38), *Kluyveromyces marxianus* (SEQ ID NO: 39), *Schizosaccharomyces pombe* (SEQ ID NO: 40), and *Schizosaccharomyces pombe* (SEQ ID NO: 41).

In one embodiment, the recombinant microorganism includes a mutation in at least one gene encoding for an aldehyde dehydrogenase resulting in a reduction of aldehyde dehydrogenase activity of a polypeptide encoded by said gene. In another embodiment, the recombinant microorganism includes a partial deletion of gene encoding for an aldehyde dehydrogenase resulting in a reduction of aldehyde dehydrogenase activity of a polypeptide encoded by the gene. In another embodiment, the recombinant microorganism comprises a complete deletion of a gene encoding for an aldehyde dehydrogenase resulting in a reduction of aldehyde dehydrogenase activity of a polypeptide encoded by the gene. In yet another embodiment, the recombinant microorganism includes a modification of the regulatory region associated with the gene encoding for an aldehyde dehydrogenase resulting in a reduction of expression of a polypeptide encoded by said gene. In yet another embodiment, the recombinant microorganism comprises a modification of the transcriptional regulator resulting in a reduction of transcription of a gene encoding for an aldehyde dehydrogenase. In yet another embodiment, the recombinant microorganism comprises mutations in all genes encoding for an aldehyde dehydrogenase resulting in a reduction of activity of a polypeptide encoded by the gene(s). In one embodiment, the aldehyde dehydrogenase activity or expression is reduced by at least about 50%. In another embodiment, the aldehyde dehydrogenase activity or expression is reduced by at least about 60%, by at least about 65%, by at least about 70%, by at least about 75%, by at least about 80%, by at least about 85%, by at least about 90%, by at least about 95%, or by at least about 99% as compared to a recombinant microorganism not comprising a reduction of the aldehyde dehydrogenase activity or expression. In one embodiment, said aldehyde dehydrogenase is encoded by the *S. cerevisiae* ALD6 gene or a homolog thereof.

In various embodiments described herein, the recombinant microorganism may comprise a biosynthetic pathway which uses a 3-keto acid as an intermediate. In one embodiment, the 3-keto acid intermediate is acetolactate. The biosynthetic pathway which uses acetolactate as an intermediate may be selected from a pathway for the biosynthesis of isobutanol, 2-butanol, 1-butanol, 2-butanone, 2,3-butanediol, acetoin, diacetyl, valine, leucine, pantothenic acid, isobutylene, 3-methyl-1-butanol, 4-methyl-1-pentanol, and coenzyme A. In another embodiment, the 3-keto acid intermediate is 2-aceto-2-hydroxybutyrate. The biosynthetic pathway which uses 2-aceto-2-hydroxybutyrate as an intermediate may be selected from a pathway for the biosynthesis of 2-methyl-1-butanol, isoleucine, 3-methyl-1-pentanol, 4-methyl-1-hexanol, and 5-methyl-1-heptanol.

In various embodiments described herein, the recombinant microorganism may comprise a biosynthetic pathway which uses an aldehyde as an intermediate. The biosynthetic pathway which uses an aldehyde as an intermediate may be selected from a pathway for the biosynthesis of isobutanol, 1-butanol, 2-methyl-1-butanol, 3-methyl-1-butanol, 1-propanol, 1-pentanol, 1-hexanol, 3-methyl-1-pentanol, 4-methyl-1-pentanol, 4-methyl-1-hexanol, and 5-methyl-1-heptanol. In various embodiments described herein, the aldehyde intermediate may be selected from isobutyraldehyde, 1-butanal, 2-methyl-1-butanal, 3-methyl-1-butanal, 1-propanal, 1-pentanal, 1-hexanal, 3-methyl-1-pentanal, 4-methyl-1-pentanal, 4-methyl-1-hexanal, and 5-methyl-1-heptanal.

In various embodiments described herein, the recombinant microorganism may comprise a biosynthetic pathway which uses a 3-keto acid and an aldehyde as intermediates. In one embodiment, the 3-keto acid intermediate is acetolactate. The biosynthetic pathway which uses acetolactate and an aldehyde as intermediates may be selected from a pathway for the biosynthesis of isobutanol, 1-butanol, and 3-methyl-1-butanol. In another embodiment, the 3-keto acid intermediate is 2-aceto-2-hydroxybutyrate. The biosynthetic pathway which uses 2-aceto-2-hydroxybutyrate and an aldehyde as intermediates may be selected from a pathway for the biosynthesis of 2-methyl-1-butanol, 3-methyl-1-pentanol, 4-methyl-1-hexanol, and 5-methyl-1-heptanol.

In one embodiment, the invention is directed to a recombinant microorganism for producing isobutanol, wherein said recombinant microorganism comprises an isobutanol producing metabolic pathway and wherein said microorganism is engineered to reduce or eliminate the expression or activity of an enzyme catalyzing the conversion of acetolactate to DH2MB. In some embodiments, the enzyme catalyzing the conversion of acetolactate to DH2MB is a 3-ketoacid reductase (3-KAR). In a specific embodiment, the 3-ketoacid reductase is encoded by the S. cerevisiae TMA29 (YMR226C) gene or a homolog thereof.

In another embodiment, the invention is directed to a recombinant microorganism for producing isobutanol, wherein said recombinant microorganism comprises an isobutanol producing metabolic pathway and wherein said microorganism is engineered to reduce or eliminate the expression or activity of an enzyme catalyzing the conversion of isobutyraldehyde to isobutyrate. In some embodiments, the enzyme catalyzing the conversion of isobutyraldehyde to isobutyrate is an aldehyde dehydrogenase. In a specific embodiment, the aldehyde dehydrogenase is encoded by the S. cerevisiae ALD6 gene or a homolog thereof.

In yet another embodiment, the invention is directed to a recombinant microorganism for producing isobutanol, wherein said recombinant microorganism comprises an isobutanol producing metabolic pathway and wherein said microorganism is (i) engineered to reduce or eliminate the expression or activity of an enzyme catalyzing the conversion of acetolactate to DH2MB and (ii) engineered to reduce or eliminate the expression or activity of an enzyme catalyzing the conversion of isobutyraldehyde to isobutyrate. In some embodiments, the enzyme catalyzing the conversion of acetolactate to DH2MB is a 3-ketoacid reductase (3-KAR). In a specific embodiment, the 3-ketoacid reductase is encoded by the S. cerevisiae TMA29 (YMR226C) gene or a homolog thereof. In some embodiments, the enzyme catalyzing the conversion of isobutyraldehyde to isobutyrate is an aldehyde dehydrogenase. In a specific embodiment, the aldehyde dehydrogenase is encoded by the S. cerevisiae ALD6 gene or a homolog thereof.

In one embodiment, the isobutanol producing metabolic pathway comprises at least one exogenous gene that catalyzes a step in the conversion of pyruvate to isobutanol. In another embodiment, the isobutanol producing metabolic pathway comprises at least two exogenous genes that catalyze steps in the conversion of pyruvate to isobutanol. In yet another embodiment, the isobutanol producing metabolic pathway comprises at least three exogenous genes that catalyze steps in the conversion of pyruvate to isobutanol. In yet another embodiment, the isobutanol producing metabolic pathway comprises at least four exogenous genes that catalyze steps in the conversion of pyruvate to isobutanol. In yet another embodiment, the isobutanol producing metabolic pathway comprises at five exogenous genes that catalyze steps in the conversion of pyruvate to isobutanol.

In one embodiment, one or more of the isobutanol pathway genes encodes an enzyme that is localized to the cytosol. In one embodiment, the recombinant microorganisms comprise an isobutanol producing metabolic pathway with at least one isobutanol pathway enzyme localized in the cytosol. In another embodiment, the recombinant microorganisms comprise an isobutanol producing metabolic pathway with at least two isobutanol pathway enzymes localized in the cytosol. In yet another embodiment, the recombinant microorganisms comprise an isobutanol producing metabolic pathway with at least three isobutanol pathway enzymes localized in the cytosol. In yet another embodiment, the recombinant microorganisms comprise an isobutanol producing metabolic pathway with at least four isobutanol pathway enzymes localized in the cytosol. In an exemplary embodiment, the recombinant microorganisms comprise an isobutanol producing metabolic pathway with five isobutanol pathway enzymes localized in the cytosol.

In various embodiments described herein, the isobutanol pathway genes encodes enzyme(s) selected from the group consisting of acetolactate synthase (ALS), ketol-acid reductoisomerase (KARI), dihydroxyacid dehydratase (DHAD), 2-keto-acid decarboxylase (KIVD), and alcohol dehydrogenase (ADH).

In another aspect, the recombinant microorganism may be engineered to reduce the conversion of isobutanol to isobutyraldehyde by reducing and/or eliminating the expression of one or more alcohol dehydrogenases. In a specific embodiment, the alcohol dehydrogenase is encoded by a gene selected from the group consisting of ADH1, ADH2, ADH3, ADH4, ADH5, ADH6, and ADH7, and homologs and variants thereof.

In another aspect, the present invention relates to modified alcohol dehydrogenase (ADH) enzymes that exhibit an enhanced ability to convert isobutyraldehyde to isobutanol. In general, cells expressing these improved ADH enzymes will produce increased levels of isobutanol during fermentation reactions. While the modified ADH enzymes of the present invention have utility in isobutanol-producing fermentation reactions, it will be understood by those skilled in the art equipped with this disclosure that the modified ADH enzymes also have usefulness in fermentation reactions producing other alcohols such as 1-propanol, 2-propanol, 1-butanol, 2-butanol, 1-pentanol, 2-methyl-1-butanol, and 3-methyl-1-butanol.

In certain aspects, the invention is directed to alcohol dehydrogenases (ADHs), which have been modified to enhance the enzyme's ability to convert isobutyraldehyde to isobutanol. Examples of such ADHs include enzymes having one or more mutations at positions corresponding to amino acids selected from: (a) tyrosine 50 of the L. lactis AdhA (SEQ ID NO: 185); (b) glutamine 77 of the L. lactis AdhA (SEQ ID NO: 185); (c) valine 108 of the L. lactis AdhA (SEQ ID NO: 185); (d) tyrosine 113 of the L. lactis AdhA (SEQ ID NO: 185); (e) isoleucine 212 of the L. lactis AdhA (SEQ ID NO: 185); and (f) leucine 264 of the L. lactis AdhA (SEQ ID NO: 185), wherein AdhA (SEQ ID NO: 185) is encoded by the L. lactis alcohol dehydrogenase (ADH) gene adhA (SEQ ID NO: 184) or a codon-optimized version thereof (SEQ ID NO: 206).

In one embodiment, the modified ADH enzyme contains a mutation at the amino acid corresponding to position 50 of the L. lactis AdhA (SEQ ID NO: 185). In another embodiment, the modified ADH enzyme contains a mutation at the amino acid corresponding to position 77 of the L. lactis AdhA (SEQ ID NO: 185). In yet another embodiment, the modified ADH enzyme contains a mutation at the amino acid corresponding to position 108 of the *L. lactis* AdhA (SEQ ID NO: 185). In yet another embodiment, the modified ADH enzyme contains a mutation at the amino acid corresponding to position 113 of the *L. lactis* AdhA (SEQ ID NO: 185). In yet another embodiment, the modified ADH enzyme contains a mutation at the amino acid corresponding to position 212 of the *L. lactis* AdhA (SEQ ID NO: 185). In yet another embodiment, the modified ADH enzyme contains a mutation at the amino acid corresponding to position 264 of the *L. lactis* AdhA (SEQ ID NO: 185).

In one embodiment, the ADH enzyme contains two or more mutations at the amino acids corresponding to the positions described above. In another embodiment, the ADH enzyme contains three or more mutations at the amino acids corresponding to the positions described above. In yet another embodiment, the ADH enzyme contains four or more mutations at the amino acids corresponding to the positions described above. In yet another embodiment, the ADH enzyme contains five or more mutations at the amino acids corresponding to the positions described above. In yet another embodiment, the ADH enzyme contains six mutations at the amino acids corresponding to the positions described above.

In one specific embodiment, the invention is directed to ADH enzymes wherein the tyrosine at position 50 is replaced with a phenylalanine or tryptophan residue. In another specific embodiment, the invention is directed to ADH enzymes wherein the glutamine at position 77 is replaced with an arginine or serine residue. In another specific embodiment, the invention is directed to ADH enzymes wherein the valine at position 108 is replaced with a serine or alanine residue. In another specific embodiment, the invention is directed to ADH enzymes wherein the tyrosine at position 113 is replaced with a phenylalanine or glycine residue. In another specific embodiment, the invention is directed to ADH enzymes wherein the isoleucine at position 212 is replaced with a threonine or valine residue. In yet another specific embodiment, the invention is directed to ADH enzymes wherein the leucine at position 264 is replaced with a valine residue. In one embodiment, the ADH enzyme contains two or more mutations at the amino acids corresponding to the positions described in these specific embodiments. In another embodiment, the ADH enzyme contains three or more mutations at the amino acids corresponding to the positions described in these specific embodiments. In yet another embodiment, the ADH enzyme contains four or more mutations at the amino acids corresponding to the positions described in these specific embodiments. In yet another embodiment, the ADH enzyme contains five or more mutations at the amino acids corresponding to the positions described in these specific embodiments. In yet another embodiment, the ADH enzyme contains six mutations at the amino acids corresponding to the positions described in these specific embodiments.

In certain exemplary embodiments, the ADH enzyme comprises a sequence selected SEQ ID NO: 189, SEQ ID NO: 191, SEQ ID NO: 193, SEQ ID NO: 195, SEQ ID NO: 197, SEQ ID NO: 199, SEQ ID NO: 201, SEQ ID NO: 203, SEQ ID NO: 205, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, and homologs or variants thereof comprising corresponding mutations as compared to the wild-type or parental enzyme.

As alluded to in the preceding paragraph, further included within the scope of the invention are ADH enzymes, other than the *L. lactis* AdhA (SEQ ID NO: 185), which contain alterations corresponding to those set out above. Such ADH enzymes may include, but are not limited to, the ADH enzymes listed in Table 97.

In some embodiments, the ADH enzymes to be modified are NADH-dependent ADH enzymes. Examples of such NADH-dependent ADH enzymes are described in commonly owned and co-pending U.S. Patent Publication No. 2010/0143997, which is herein incorporated by reference in its entirety for all purposes. In some embodiments, genes originally encoding NADPH-utilizing ADH enzymes are modified to switch the co-factor preference of the enzyme to NADH.

As described herein, the modified ADHs will generally exhibit an enhanced ability to convert isobutyraldehyde to isobutanol as compared to the wild-type or parental ADH. Preferably, the catalytic efficiency ($k_{cat}/K_M$) of the modified ADH enzyme is enhanced by at least about 5% as compared to the wild-type or parental ADH. More preferably, the catalytic efficiency of the modified ADH enzyme is enhanced by at least about 15% as compared to the wild-type or parental ADH. More preferably, the catalytic efficiency of the modified ADH enzyme is enhanced by at least about 25% as compared to the wild-type or parental ADH. More preferably, the catalytic efficiency of the modified ADH enzyme is enhanced by at least about 50% as compared to the wild-type or parental ADH. More preferably, the catalytic efficiency of the modified ADH enzyme is enhanced by at least about 75% as compared to the wild-type or parental ADH. More preferably, the catalytic efficiency of the modified ADH enzyme is enhanced by at least about 100% as compared to the wild-type or parental ADH. More preferably, the catalytic efficiency of the modified ADH enzyme is enhanced by at least about 200% as compared to the wild-type or parental ADH. More preferably, the catalytic efficiency of the modified ADH enzyme is enhanced by at least about 500% as compared to the wild-type or parental ADH. More preferably, the catalytic efficiency of the modified ADH enzyme is enhanced by at least about 1000% as compared to the wild-type or parental ADH. More preferably, the catalytic efficiency of the modified ADH enzyme is enhanced by at least about 2000% as compared to the wild-type or parental ADH. More preferably, the catalytic efficiency of the modified ADH enzyme is enhanced by at least about 3000% as compared to the wild-type or parental ADH. Most preferably, the catalytic efficiency of the modified ADH enzyme is enhanced by at least about 3500% as compared to the wild-type or parental ADH.

In additional aspects, the invention is directed to modified ADH enzymes that have been codon optimized for expression in certain desirable host organisms, such as yeast and *E. coli*. In other aspects, the present invention is directed to recombinant host cells comprising a modified ADH enzyme of the invention. According to this aspect, the present invention is also directed to methods of using the modified ADH enzymes in any fermentation process, where the conversion of isobutyraldehyde to isobutanol is desired. In one embodiment according to this aspect, the modified ADH enzymes may be suitable for enhancing a host cell's ability to produce isobutanol. In another embodiment according to this aspect, the modified ADH enzymes may be suitable for enhancing a host cell's ability to produce 1-propanol, 2-propanol, 1-butanol, 2-butanol, 1-pentanol, 2-methyl-1-butanol, and 3-methyl-1-butanol.

In various embodiments described herein, the recombinant microorganisms comprising a modified ADH may be further engineered to express an isobutanol producing metabolic pathway. In one embodiment, the recombinant microorganism may be engineered to express an isobutanol producing metabolic pathway comprising at least one exogenous gene. In one embodiment, the recombinant microorganism may be engineered to express an isobutanol producing metabolic pathway comprising at least two exogenous genes. In another embodiment, the recombinant microorganism may be engineered to express an isobutanol producing metabolic pathway comprising at least three exogenous genes. In another embodiment, the recombinant microorganism may be engineered to express an isobutanol producing metabolic pathway comprising at least four exogenous genes. In another embodiment, the recombinant microorganism may be engineered to express an isobutanol producing metabolic pathway comprising five exogenous genes. Thus, the present invention further provides recombinant microorganisms that comprise an isobutanol producing metabolic pathway and methods of using said recombinant microorganisms to produce isobutanol.

In various embodiments described herein, the isobutanol pathway enzyme(s) is/are selected from acetolactate synthase (ALS), ketol-acid reductoisomerase (KARI), dihydroxyacid dehydratase (DHAD), 2-keto-acid decarboxylase (KIVD), and alcohol dehydrogenase (ADH).

In various embodiments described herein, the isobutanol pathway enzymes may be derived from a prokaryotic organism. In alternative embodiments described herein, the isobutanol pathway enzymes may be derived from a eukaryotic organism. An exemplary metabolic pathway that converts pyruvate to isobutanol may be comprised of a acetohydroxy acid synthase (ALS) enzyme encoded by, for example, alsS from *B. subtilis*, a ketol-acid reductoisomerase (KARI) encoded by, for example ilvC from *E. coli*, a dihydroxy-acid dehydratase (DHAD), encoded by, for example, ilvD from *L. lactis*, a 2-keto-acid decarboxylase (KIVD) encoded by, for example kivD from *L. lactis*, and an alcohol dehydrogenase (ADH) (e.g. a modified ADH described herein), encoded by, for example, adhA from *L. lactis* with one or more mutations at positions Y50, Q77, V108, Y113, I212, and L264 as described herein.

In various embodiments described herein, the recombinant microorganisms may be microorganisms of the *Saccharomyces* clade, *Saccharomyces sensu stricto* microorganisms, Crabtree-negative yeast microorganisms, Crabtree-positive yeast microorganisms, post-WGD (whole genome duplication) yeast microorganisms, pre-WGD (whole genome duplication) yeast microorganisms, and non-fermenting yeast microorganisms.

In some embodiments, the recombinant microorganisms may be yeast recombinant microorganisms of the *Saccharomyces* clade.

In some embodiments, the recombinant microorganisms may be *Saccharomyces sensu stricto* microorganisms. In one embodiment, the *Saccharomyces sensu stricto* is selected from the group consisting of *S. cerevisiae, S. kudriavzevii, S. mikatae, S. bayanus, S. uvarum. S. carocanis* and hybrids thereof.

In some embodiments, the recombinant microorganisms may be Crabtree-negative recombinant yeast microorganisms. In one embodiment, the Crabtree-negative yeast microorganism is classified into a genera selected from the group consisting of *Saccharomyces, Kluyveromyces, Pichia, Issatchenkia, Hansenula*, or *Candida*. In additional embodiments, the Crabtree-negative yeast microorganism is selected from *Saccharomyces kluyveri, Kluyveromyces lactis, Kluyveromyces marxianus, Pichia anomala, Pichia stipitis, Hansenula anomala, Candida utilis* and *Kluyveromyces waltii*.

In some embodiments, the recombinant microorganisms may be Crabtree-positive recombinant yeast microorganisms. In one embodiment, the Crabtree-positive yeast microorganism is classified into a genera selected from the group consisting of *Saccharomyces, Kluyveromyces, Zygosaccharomyces, Debaryomyces, Candida, Pichia* and *Schizosaccharomyces*. In additional embodiments, the Crabtree-positive yeast microorganism is selected from the group consisting of *Saccharomyces cerevisiae, Saccharomyces uvarum, Saccharomyces bayanus, Saccharomyces paradoxus, Saccharomyces castelli, Kluyveromyces thermotolerans, Candida glabrata, Z. bailli, Z. rouxii, Debaryomyces hansenii, Pichia pastorius, Schizosaccharomyces pombe*, and *Saccharomyces uvarum*.

In some embodiments, the recombinant microorganisms may be post-WGD (whole genome duplication) yeast recombinant microorganisms. In one embodiment, the post-WGD yeast recombinant microorganism is classified into a genera selected from the group consisting of *Saccharomyces* or *Candida*. In additional embodiments, the post-WGD yeast is selected from the group consisting of *Saccharomyces cerevisiae, Saccharomyces uvarum, Saccharomyces bayanus, Saccharomyces paradoxus, Saccharomyces castelli*, and *Candida glabrata*.

In some embodiments, the recombinant microorganisms may be pre-WGD (whole genome duplication) yeast recombinant microorganisms. In one embodiment, the pre-WGD yeast recombinant microorganism is classified into a genera selected from the group consisting of *Saccharomyces, Kluyveromyces, Candida, Pichia, Issatchenkia, Debaryomyces, Hansenula, Pachysolen, Yarrowia* and *Schizosaccharomyces*. In additional embodiments, the pre-WGD yeast is selected from the group consisting of *Saccharomyces kluyveri, Kluyveromyces thermotolerans, Kluyveromyces marxianus, Kluyveromyces waltii, Kluyveromyces lactis, Candida tropicalis, Pichia pastoris, Pichia anomala, Pichia stipitis, Issatchenkia orientalis, Issatchenkia occidentalis, Debaryomyces hansenii, Hansenula anomala, Pachysolen tannophilis, Yarrowia lipolytica*, and *Schizosaccharomyces pombe*.

In some embodiments, the recombinant microorganisms may be microorganisms that are non-fermenting yeast microorganisms, including, but not limited to those, classified into a genera selected from the group consisting of *Tricosporon, Rhodotorula, Myxozyma*, or *Candida*. In a specific embodiment, the non-fermenting yeast is *C. xestobii*.

In another aspect, the present invention provides methods of producing beneficial metabolites including fuels, chemicals, and amino acids using a recombinant microorganism as described herein. In one embodiment, the method includes cultivating the recombinant microorganism in a culture medium containing a feedstock providing the carbon source until a recoverable quantity of the metabolite is produced and optionally, recovering the metabolite. In one embodiment, the microorganism produces the metabolite from a carbon source at a yield of at least about 5 percent theoretical. In another embodiment, the microorganism produces the metabolite at a yield of at least about 10 percent, at least about 15 percent, about least about 20 percent, at least about 25 percent, at least about 30 percent, at least about 35 percent, at least about 40 percent, at least about 45 percent, at least about 50 percent, at least about 55 percent, at least about 60 percent, at least about 65 percent, at least about 70 percent, at least about 75 percent, at least about 80 percent, at least about 85 percent, at least about 90 percent, at least about 95 percent, or at least about 97.5 percent theoretical. In one embodiment, the metabolite may be derived from a biosynthetic pathway which uses a 3-keto acid as an intermediate. In one embodiment, the 3-keto acid intermediate is acetolactate. Accordingly, the metabolite may be derived from a biosynthetic pathway which uses acetolactate as an intermediate, including, but not limited to, isobutanol, 2-butanol, 1-butanol, 2-butanone, 2,3-butanediol, acetoin, diacetyl, valine, leucine, pantothenic acid, isobutylene, 3-methyl-1-butanol, 4-methyl-1-pentanol, and coenzyme A. In another embodiment, the 3-keto acid intermediate is 2-aceto-2-hydroxybutyrate. Accordingly, the metabolite may be derived from a biosynthetic pathway which uses 2-aceto-2-hydroxybutyrate as an intermediate, including, but not limited to, 2-methyl-1-butanol, isoleucine, 3-methyl-1-pentanol, 4-methyl-1-hexanol, and 5-methyl-1-heptanol. In another embodiment, the metabolite may be derived from a biosynthetic pathway which uses an aldehyde as an intermediate, including, but not limited to, isobutanol, 1-butanol, 2-methyl-1-butanol, 3-methyl-1-butanol, 1-propanol, 1-pentanol, 1-hexanol, 3-methyl-1-pentanol, 4-methyl-1-pentanol, 4-methyl-1-hexanol, and 5-methyl-1-heptanol. In yet another embodiment, the metabolite may be derived from a biosynthetic pathway which uses acetolactate and an aldehyde as intermediates, including, but not limited to, isobutanol, 1-butanol, and 3-methyl-1-butanol biosynthetic pathways. In yet another embodiment, the metabolite may be derived from a biosynthetic pathway which uses 2-aceto-2-hydroxybutyrate and an aldehyde as intermediates, including, but not limited to, 2-methyl-1-butanol, 3-methyl-1-pentanol, 4-methyl-1-hexanol, and 5-methyl-1-heptanol biosynthetic pathways.

In one embodiment, the recombinant microorganism is grown under aerobic conditions. In another embodiment, the recombinant microorganism is grown under microaerobic conditions. In yet another embodiment, the recombinant microorganism is grown under anaerobic conditions.

BRIEF DESCRIPTION OF DRAWINGS

Illustrative embodiments of the invention are illustrated in the drawings, in which.

DETAILED DESCRIPTION

Figure 1:
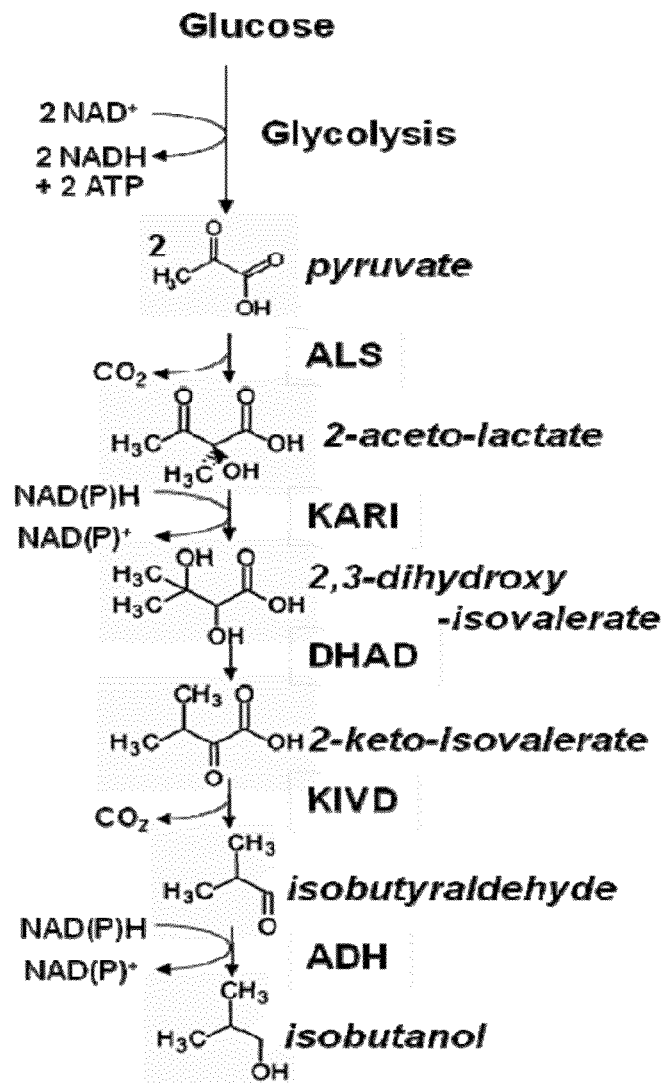
FIG. 1 illustrates an exemplary embodiment of an isobutanol pathway.

As used herein and in the appended claims, the singular forms "a," "an," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "genus" is defined as a taxonomic group of related species according to the Taxonomic Outline of Bacteria and Archaea (Garrity, G.M.,Lilburn, T.G., Cole, JR., Harrison, S.H., Euzehy, J., and Tindall, B.J. (2007) The Taxonomic Outline of Bacteria and Archaea. TOBA Release 7.7, Mar. 2007. Michigan State University Board of Trustees.

The term "species" is defined as a collection of closely related organisms with greater than 97% 16S ribosomal RNA sequence homology and greater than 70% genomic hybridization and sufficiently different from all other organisms so as to be recognized as a distinct unit.

The terms "recombinant microorganism," "modified microorganism," and "recombinant host cell" are used interchangeably herein and refer to microorganisms that have been genetically modified to express or overexpress endogenous polynucleotides, to express heterologous polynucleotides, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra. The polynucleotide generally encodes a target enzyme involved in a metabolic pathway for producing a desired metabolite. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "overexpression" refers to an elevated level (e.g., aberrant level) of mRNAs encoding for a protein(s) (e.g., an TMA29 protein or homolog thereof), and/or to elevated levels of protein(s) (e.g., TMA29) in cells as compared to similar corresponding unmodified cells expressing basal levels of mRNAs (e.g., those encoding Aft proteins) or having basal levels of proteins. In particular embodiments, TMA29, or homologs thereof, may be overexpressed by at least 2-fold, 3-fold, 4-fold, 5-fold, 6-fold, 8-fold, 10-fold, 12-fold, 15-fold or more in microorganisms engineered to exhibit increased TMA29 mRNA, protein, and/or activity.

As used herein and as would be understood by one of ordinary skill in the art, "reduced activity and/or expression" of a protein such as an enzyme can mean either a reduced specific catalytic activity of the protein (e.g. reduced activity) and/or decreased concentrations of the protein in the cell (e.g. reduced expression), while "deleted activity and/or expression" or "eliminated activity and/or expression" of a protein such as an enzyme can mean either no or negligible specific catalytic activity of the enzyme (e.g. deleted activity) and/or no or negligible concentrations of the enzyme in the cell (e.g. deleted expression).

The term "wild-type microorganism" describes a cell that occurs in nature, i.e. a cell that has not been genetically modified. A wild-type microorganism can be genetically modified to express or overexpress a first target enzyme. This microorganism can act as a parental microorganism in the generation of a microorganism modified to express or overexpress a second target enzyme. In turn, the microorganism modified to express or overexpress a first and a second target enzyme can be modified to express or overexpress a third target enzyme.

Accordingly, a "parental microorganism" functions as a reference cell for successive genetic modification events. Each modification event can be accomplished by introducing a nucleic acid molecule in to the reference cell. The introduction facilitates the expression or overexpression of a target enzyme. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of heterologous polynucleotides encoding a target enzyme in to a parental microorganism The term "engineer" refers to any manipulation of a microorganism that results in a detectable change in the microorganism, wherein the manipulation includes but is not limited to inserting a polynucleotide and/or polypeptide heterologous to the microorganism and mutating a polynucleotide and/or polypeptide native to the microorganism.

The term "mutation" as used herein indicates any modification of a nucleic acid and/or polypeptide which results in an altered nucleic acid or polypeptide. Mutations include, for example, point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, a nonsense mutation, an insertion, or a deletion of part or all of a gene. In addition, in some embodiments of the modified microorganism, a portion of the microorganism genome has been replaced with a heterologous polynucleotide. In some embodiments, the mutations are naturally-occurring. In other embodiments, the mutations are identified and/or enriched through artificial selection pressure. In still other embodiments, the mutations in the microorganism genome are the result of genetic engineering.

The term "biosynthetic pathway", also referred to as "metabolic pathway", refers to a set of anabolic or catabolic biochemical reactions for converting one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

As used herein, the term "isobutanol producing metabolic pathway" refers to an enzyme pathway which produces isobutanol from pyruvate.

The term "heterologous" as used herein with reference to molecules and in particular enzymes and polynucleotides, indicates molecules that are expressed in an organism other than the organism from which they originated or are found in nature, independently of the level of expression that can be lower, equal or higher than the level of expression of the molecule in the native microorganism.

On the other hand, the term "native" or "endogenous" as used herein with reference to molecules, and in particular enzymes and polynucleotides, indicates molecules that are expressed in the organism in which they originated or are found in nature, independently of the level of expression that can be lower equal or higher than the level of expression of the molecule in the native microorganism. It is understood that expression of native enzymes or polynucleotides may be modified in recombinant microorganisms.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a biofuel in a fermentation process. However, a feedstock may contain nutrients other than a carbon source.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, such as any biomass derived sugar, but also intermediate and end product metabolites used in a pathway associated with a recombinant microorganism as described herein.

The term "C2-compound" as used as a carbon source for engineered yeast microorganisms with mutations in all pyruvate decarboxylase (PDC) genes resulting in a reduction of pyruvate decarboxylase activity of said genes refers to organic compounds comprised of two carbon atoms, including but not limited to ethanol and acetate.

The term "fermentation" or "fermentation process" is defined as a process in which a microorganism is cultivated in a culture medium containing raw materials, such as feedstock and nutrients, wherein the microorganism converts raw materials, such as a feedstock, into products.

The term "volumetric productivity" or "production rate" is defined as the amount of product formed per volume of medium per unit of time. Volumetric productivity is reported in gram per liter per hour (g/L/h).

The term "specific productivity" or "specific production rate" is defined as the amount of product formed per volume of medium per unit of time per amount of cells. Specific productivity is reported in gram or milligram per liter per hour per OD (g/L/h/OD).

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product. For example, the theoretical yield for one typical conversion of glucose to isobutanol is 0.41 g/g. As such, a yield of isobutanol from glucose of 0.39 g/g would be expressed as 95% of theoretical or 95% theoretical yield.

The term "titer" is defined as the strength of a solution or the concentration of a substance in solution. For example, the titer of a biofuel in a fermentation broth is described as g of biofuel in solution per liter of fermentation broth (g/L).

"Aerobic conditions" are defined as conditions under which the oxygen concentration in the fermentation medium is sufficiently high for an aerobic or facultative anaerobic microorganism to use as a terminal electron acceptor.

In contrast, "anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of the fermentation until oxygen is unavailable to the microorganism as a terminal electron acceptor. Methods for the production of isobutanol under anaerobic conditions are described in commonly owned and co-pending publication, US 2010/0143997, the disclosures of which are herein incorporated by reference in its entirety for all purposes.

"Aerobic metabolism" refers to a biochemical process in which oxygen is used as a terminal electron acceptor to make energy, typically in the form of ATP, from carbohydrates. Aerobic metabolism occurs e.g. via glycolysis and the TCA cycle, wherein a single glucose molecule is metabolized completely into carbon dioxide in the presence of oxygen.

In contrast, "anaerobic metabolism" refers to a biochemical process in which oxygen is not the final acceptor of electrons contained in NADH. Anaerobic metabolism can be divided into anaerobic respiration, in which compounds other than oxygen serve as the terminal electron acceptor, and substrate level phosphorylation, in which the electrons from NADH are utilized to generate a reduced product via a "fermentative pathway."

In "fermentative pathways", NAD(P)H donates its electrons to a molecule produced by the same metabolic pathway that produced the electrons carried in NAD(P)H. For example, in one of the fermentative pathways of certain yeast strains, NAD(P)H generated through glycolysis transfers its electrons to pyruvate, yielding ethanol. Fermentative pathways are usually active under anaerobic conditions but may also occur under aerobic conditions, under conditions where NADH is not fully oxidized via the respiratory chain. For example, above certain glucose concentrations, Crabtree positive yeasts produce large amounts of ethanol under aerobic conditions.

The term "byproduct" or "by-product" means an undesired product related to the production of an amino acid, amino acid precursor, chemical, chemical precursor, biofuel, or biofuel precursor.

The term "substantially free" when used in reference to the presence or absence of enzymatic activities (3-KAR, ALDH, PDC, GPD, etc.) in carbon pathways that compete with the desired metabolic pathway (e.g., an isobutanol-producing metabolic pathway) means the level of the enzyme is substantially less than that of the same enzyme in the wild-type host, wherein less than about 50% of the wild-type level is preferred and less than about 30% is more preferred. The activity may be less than about 20%, less than about 10%, less than about 5%, or less than about 1% of wild-type activity. Microorganisms which are "substantially free" of a particular enzymatic activity (3-KAR, ALDH, PDC, GPD, etc.) may be created through recombinant means or identified in nature.

The term "non-fermenting yeast" is a yeast species that fails to demonstrate an anaerobic metabolism in which the electrons from NADH are utilized to generate a reduced product via a fermentative pathway such as the production of ethanol and $CO_2$ from glucose. Non-fermentative yeast can be identified by the "Durham Tube Test" (J. A. Barnett, R. W. Payne, and D. Yarrow. 2000. Yeasts Characteristics and Identification. $3^{rd}$ edition. p. 28-29. Cambridge University Press, Cambridge, UK) or by monitoring the production of fermentation productions such as ethanol and $CO_2$.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "operon" refers to two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

"Transformation" refers to the process by which a vector is introduced into a host cell. Transformation (or transduction, or transfection), can be achieved by any one of a number of means including chemical transformation (e.g. lithium acetate transformation), electroporation, microinjection, biolistics (or particle bombardment-mediated delivery), or *agrobacterium* mediated transformation.

The term "enzyme" as used herein refers to any substance that catalyzes or promotes one or more chemical or biochemical reactions, which usually includes enzymes totally or partially composed of a polypeptide, but can include enzymes composed of a different molecule including polynucleotides.

The term "protein," "peptide," or "polypeptide" as used herein indicates an organic polymer composed of two or more amino acidic monomers and/or analogs thereof. As used herein, the term "amino acid" or "amino acidic monomer" refers to any natural and/or synthetic amino acids including glycine and both D or L optical isomers. The term "amino acid analog" refers to an amino acid in which one or more individual atoms have been replaced, either with a different atom, or with a different functional group. Accordingly, the term polypeptide includes amino acidic polymer of any length including full length proteins, and peptides as well as analogs and fragments thereof. A polypeptide of three or more amino acids is also called a protein oligomer or oligopeptide The term "homolog," used with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. (Thus, the term "homologous proteins" is defined to mean that the two proteins have similar amino acid sequences).

The term "analog" or "analogous" refers to nucleic acid or protein sequences or protein structures that are related to one another in function only and are not from common descent or do not share a common ancestral sequence. Analogs may differ in sequence but may share a similar structure, due to convergent evolution. For example, two enzymes are analogs or analogous if the enzymes catalyze the same reaction of conversion of a substrate to a product, are unrelated in sequence, and irrespective of whether the two enzymes are related in structure.

Recombinant Microorganisms with Reduced By-Product Accumulation

Yeast cells convert sugars to produce pyruvate, which is then utilized in a number of pathways of cellular metabolism. In recent years, yeast cells have been engineered to produce a number of desirable products via pyruvate-driven biosynthetic pathways. In many of these biosynthetic pathways, the initial pathway step is the conversion of endogenous pyruvate to a 3-keto acid.

As used herein, a "3-keto acid" refers to an organic compound which contains a carboxylic acid moiety on the C1 carbon and a ketone moiety on the C3 carbon. For example, acetolactate and 2-hydroxy-2-methyl-3-oxobutanoic acid are 3-keto acids with a ketone group at the C3 carbon (See, e.g., FIG. 2).

Figure 18:
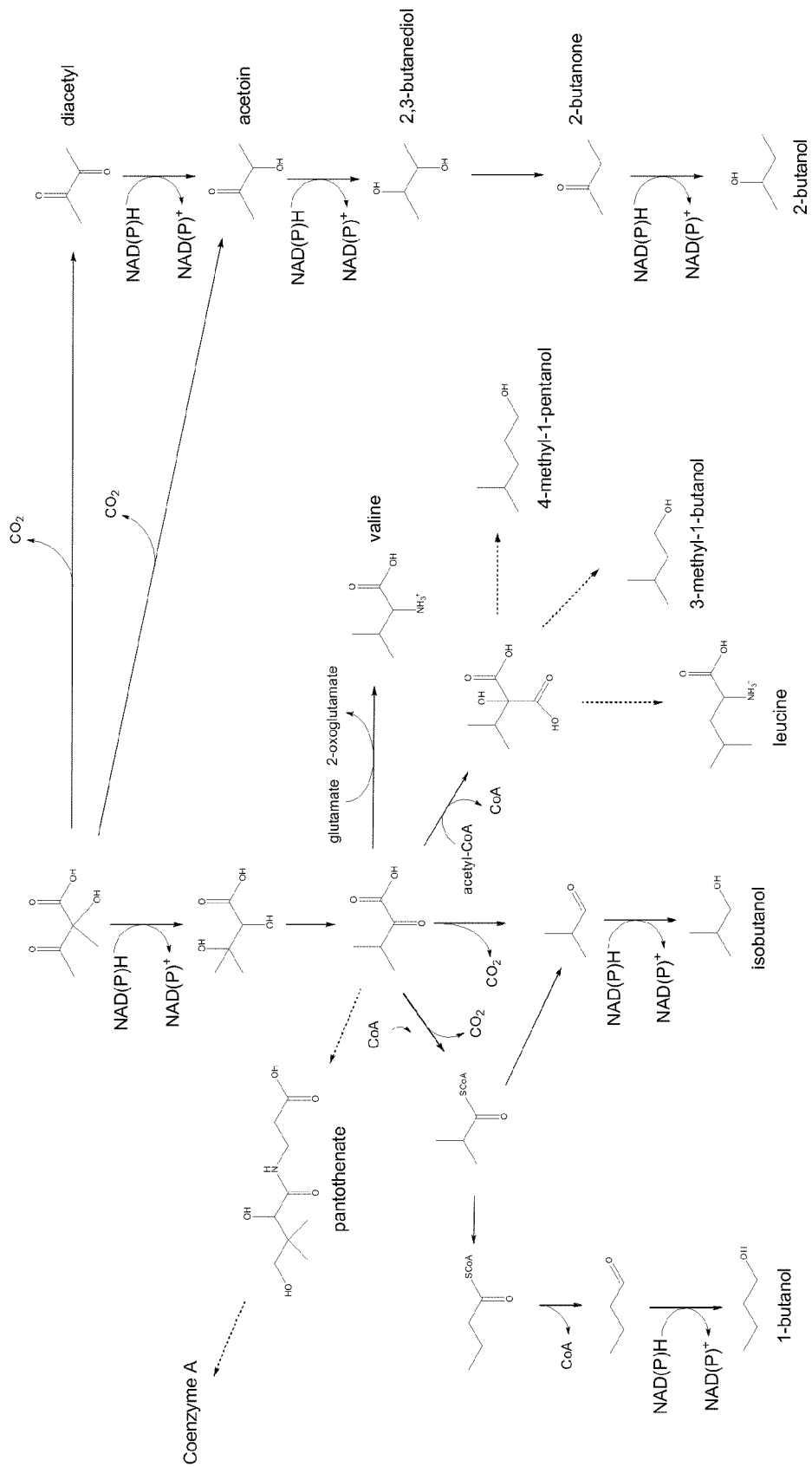
FIG. 18 illustrates biosynthetic pathways utilizing acetolactate as an intermediate. Biosynthetic pathways for the production of 1-butanol, isobutanol, 3-methyl-1-butanol, and 4-methyl-1-pentanol use both acetolactate and an aldehyde as an intermediate.

An example of a 3-keto acid which is common to many biosynthetic pathways is acetolactate, which is formed from pyruvate by the action of the enzyme acetolactate synthase (also known as acetohydroxy acid synthase). Amongst the biosynthetic pathways using acetolactate as intermediate include pathways for the production of isobutanol, 2-butanol, 1-butanol, 2-butanone, 2,3-butanediol, acetoin, diacetyl, valine, leucine, pantothenic acid, isobutylene, 3-methyl-1-butanol, 4-methyl-1-pentanol, and coenzyme A. Engineered biosynthetic pathways for the synthesis of these beneficial acetolactate-derived metabolites are found in Table 1 and FIG. 18.

Each of the biosynthetic pathways listed in Table 1 shares the common 3-keto acid intermediate, acetolactate. Therefore, the product yield from these biosynthetic pathways will in part depend upon the amount of acetolactate that is available to downstream enzymes of said biosynthetic pathways.

Figure 19:
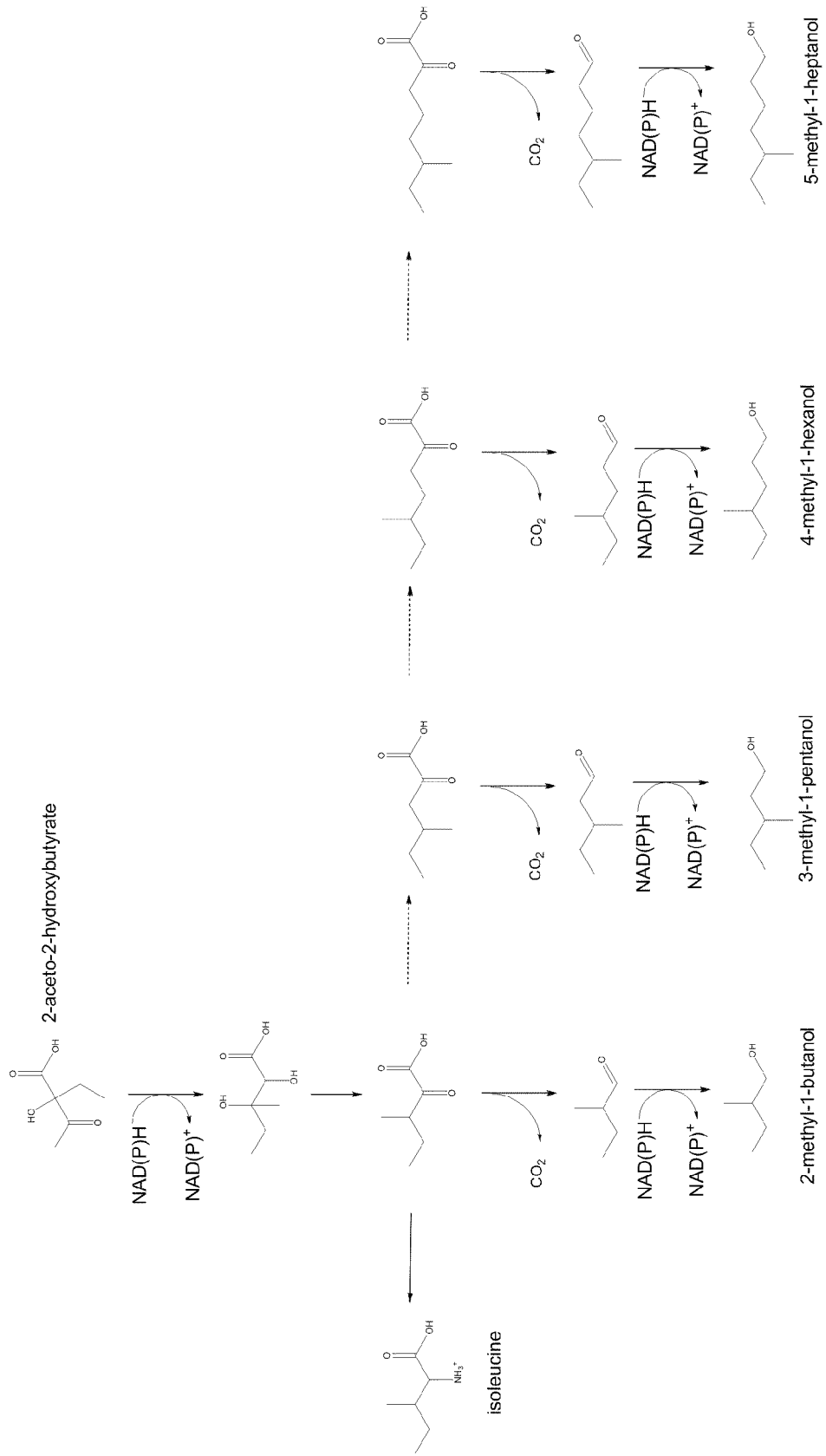
FIG. 19 illustrates biosynthetic pathways utilizing 2-aceto-2-hydroxybutyrate as an intermediate. Biosynthetic pathways for the production of 2-methyl-1-butanol, 3-methyl-1-pentanol, 4-methyl-1-hexanol, and 5-methyl-1-heptanol use both 2-aceto-2-hydroxybutyrate and an aldehyde as an intermediate.

Another example of a 3-keto acid which is common to many biosynthetic pathways is 2-aceto-2-hydroxybutyrate, which is formed from pyruvate and 2-ketobutyrate by the action of the enzyme acetolactate synthase (also known as acetohydroxy acid synthase). Amongst the biosynthetic pathways using 2-aceto-2-hydroxybutyrate as intermediate include pathways for the production of 2-methyl-1-butanol, isoleucine, 3-methyl-1-pentanol, 4-methyl-1-hexanol, and 5-methyl-1-heptanol. Engineered biosynthetic pathways for the synthesis of these beneficial 2-aceto-2-hydroxybutyrate-derived metabolites are found in Table 2 and FIG. 19.

TABLE 2

Biosynthetic Pathways Utilizing 2-Aceto-2-Hydroxybutyrate as an Intermediate

| Biosynthetic Pathway | Reference[a] |
|---|---|
| 2-Methyl-1-Butanol | WO/2008/098227 (Liao et al.), WO/2009/076480 (Picataggio et al.), and Atsumi et al., 2008, *Nature* 451: 86-89 |
| Isoleucine | McCourt et al., 2006, *Amino Acids* 31: 173-210 |
| 3-Methyl-1-Pentanol | WO/2010/045629 (Liao et al.), Zhang et al., 2008, *Proc Natl Acad Sci* USA 105: 20653-20658 |
| 4-Methyl-1-Hexanol | W WO/2010/045629 (Liao et al.), Zhang et al., 2008, *Proc Natl Acad Sci* USA 105: 20653-20658 |
| 5-Methyl-1-Heptanol | WO/2010/045629 (Liao et al.), Zhang et al., 2008, *Proc Natl Acad Sci* USA 105: 20653-20658 |

[a]The contents of each of the references in this table are herein incorporated by reference in their entireties for all purposes.

Each of the biosynthetic pathways listed in Table 2 shares the common 3-keto acid intermediate, 2-aceto-2-hydroxybu-

TABLE 1

Biosynthetic Pathways Utilizing Acetolactate as an Intermediate

| Biosynthetic Pathway | Reference[a] |
|---|---|
| Isobutanol | US 2009/0226991 (Feldman et al.), US 2011/0020889 (Feldman et al.), and US 2010/0143997 (Buelter et al.) |
| 1-Butanol | WO/2010/017230 (Lynch), WO/2010/031772 (Wu et al.), and KR2011002130 (Lee et al.) |
| 2-Butanol | WO/2007/130518 (Donaldson et al.), WO/2007/130521 (Donaldson et al.), and WO/2009/134276 (Donaldson et al.) |
| 2-Butanone | WO/2007/130518 (Donaldson et al.), WO/2007/130521 (Donaldson et al.), and WO/2009/134276 (Donaldson et al.) |
| 2-3-Butanediol | WO/2007/130518 (Donaldson et al.), WO/2007/130521 (Donaldson et al.), and WO/2009/134276 (Donaldson et al.) |
| Acetoin | WO/2007/130518 (Donaldson et al.), WO/2007/130521 (Donaldson et al.), and WO/2009/134276 (Donaldson et al.) |
| Diacetyl | Gonzalez et al., 2000, *J. Biol. Chem* 275: 35876-85 and Ehsani et al., 2009, *App. Environ. Micro.* 75: 3196-205 |
| Valine | WO/2001/021772 (Yocum et al.) and McCourt et al., 2006, *Amino Acids* 31: 173-210 |
| Leucine | WO/2001/021772 (Yocum et al.) and McCourt et al., 2006, *Amino Acids* 31: 173-210 |
| Pantothenic Acid | WO/2001/021772 (Yocum et al.) |
| 3-Methyl-1-Butanol | WO/2008/098227 (Liao et al.), Atsumi et al., 2008, *Nature* 451: 86-89, and Connor et al., 2008, *Appl. Environ. Microbiol.* 74: 5769-5775 |
| 4-Methyl-1-Pentanol | WO/2010/045629 (Liao et al.), Zhang et al., 2008, *Proc Natl Acad Sci* USA 105: 20653-20658 |
| Coenzyme A | WO/2001/021772 (Yocum et al.) |

[a]The contents of each of the references in this table are herein incorporated by reference in their entireties for all purposes.

tyrate. Therefore, the product yield from these biosynthetic pathways will in part depend upon the amount of acetolactate that is available to downstream enzymes of said biosynthetic pathways.

Figure 20:
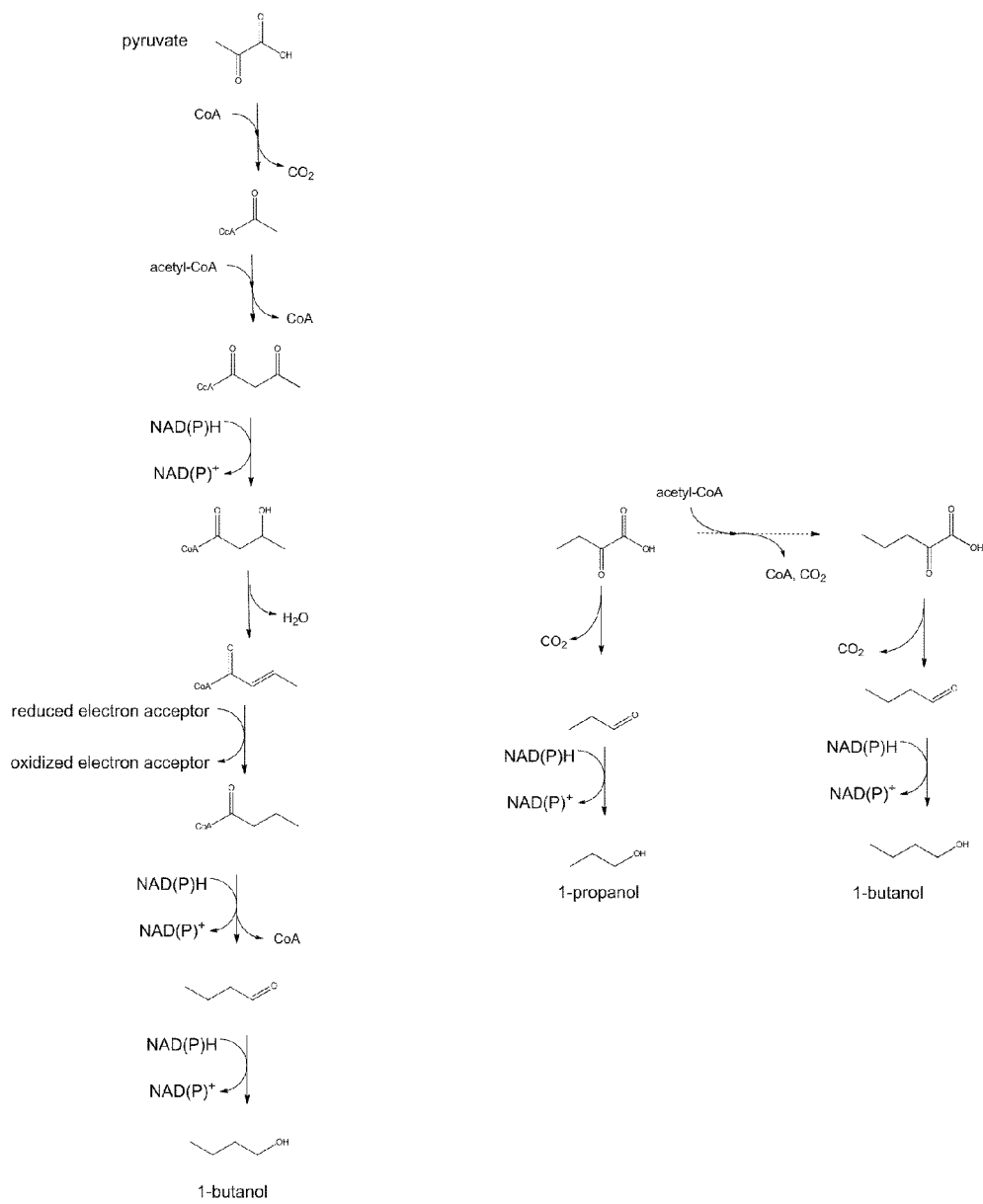
FIG. 20 illustrates additional biosynthetic pathways utilizing an aldehyde as an intermediate.

Likewise, yeast cells can be engineered to produce a number of desirable products via biosynthetic pathways that utilize an aldehyde as a pathway intermediate. Engineered biosynthetic pathways comprising an aldehyde intermediate include biosynthetic pathways for the production of isobutanol, 1-butanol, 2-methyl-1-butanol, 3-methyl-1-butanol, 1-propanol, 1-pentanol, 1-hexanol, 3-methyl-1-pentanol, 4-methyl-1-pentanol, 4-methyl-1-hexanol, and 5-methyl-1-heptanol (See Table 3 and FIGS. 18, 19, and 20).

including, but not limited to, those listed in Tables 1-3. The present inventors have found that suppressing these newly-characterized enzymatic activities considerably reduces or eliminates the formation of unwanted by-products, and concomitantly improves the yields and titers of beneficial metabolites.

Reduced Accumulation of 3-Hydroxyacids from 3-Keto Acids

As described herein, the present inventors have discovered that unwanted by-products, 3-hydroxyacids, can accumulate during fermentation reactions with microorganisms comprising a pathway involving a 3-keto acid intermediate.

TABLE 3

Biosynthetic Pathways Utilizing an Aldehyde as an Intermediate

| Biosynthetic Pathway | Aldehyde Intermediate | Reference[a] |
|---|---|---|
| Isobutanol | Isobutyraldehyde | US 2009/0226991 (Feldman et al.), US 2011/0020889 (Feldman et al.), and US 2010/0143997 (Buelter et al.) |
| 1-Butanol | 1-Butanal | WO/2010/017230 (Lynch), WO/2010/031772 (Wu et al.), WO/2010/045629 (Liao et al.), WO/2007/041269 (Donaldson et al.), WO/2008/052991 (Raamsdonk et al.), WO/2008/143704 (Buelter et al.), and WO/2008/080124 (Gunawardena et al.) |
| 2-Methyl-1-Butanol | 2-Methyl-1-Butanal | WO/2008/098227 (Liao et al.), WO/2009/076480 (Picataggio et al.), and Atsumi et al., 2008, *Nature* 451: 86-89 |
| 3-Methyl-1-Butanol | 3-Methyl-1-Butanal | WO/2008/098227 (Liao et al.), Atsumi et al., 2008, *Nature* 451: 86-89, and Connor et al., 2008, *Appl. Environ. Microbiol.* 74: 5769-5775 |
| 1-Propanol | 1-Propanal | WO/2008/098227 (Liao et al.) |
| 1-Pentanol | 1-Pentanal | WO/2010/045629 (Liao et al.), Zhang et al., 2008, *Proc Natl Acad Sci* USA 105: 20653-20658 |
| 1-Hexanol | 1-Hexanal | WO/2010/045629 (Liao et al.), Zhang et al., 2008, *Proc Natl Acad Sci* USA 105: 20653-20658 |
| 3-Methyl-1-Pentanol | 3-Methyl-1-Pentanal | WO/2010/045629 (Liao et al.), Zhang et al., 2008, *Proc Natl Acad Sci* USA 105: 20653-20658 |
| 4-Methyl-1-Pentanol | 4-Methyl-1-Pentanal | WO/2010/045629 (Liao et al.), Zhang et al., 2008, *Proc Natl Acad Sci* USA 105: 20653-20658 |
| 4-Methyl-1-Hexanol | 4-Methyl-1-Hexanal | WO/2010/045629 (Liao et al.), Zhang et al., 2008, *Proc Natl Acad Sci* USA 105: 20653-20658 |
| 5-Methyl-1-Heptanol | 5-Methyl-1-Heptanal | WO/2010/045629 (Liao et al.), Zhang et al., 2008, *Proc Natl Acad Sci* USA 105: 20653-20658 |

[a]The contents of each of the references in this table are herein incorporated by reference in their entireties for all purposes.

Each of the biosynthetic pathways listed in Table 3 have an aldehyde intermediate. For example, the aldehyde intermediate in the isobutanol producing metabolic pathway is isobutyraldehyde (See FIG. 1), while pathways for the production of 1-butanol, 2-methyl-1-butanol, 3-methyl-1-butanol, 1-propanol, 1-pentanol, 1-hexanol, 3-methyl-1-pentanol, 4-methyl-1-pentanol, 4-methyl-1-hexanol, and 5-methyl-1-heptanol utilize 1-butanal, 2-methyl-1-butanal, 3-methyl-1-butanal, 1-propanal, 1-pentanal, 1-hexanal, 3-methyl-1-pentanal, 4-methyl-1-pentanal, 4-methyl-1-hexanal, and 5-methyl-1-heptanol as aldehyde intermediates, respectively. Therefore, the product yield in biosynthetic pathways that utilize these aldehyde intermediates will in part depend upon the amount of the aldehyde intermediate that is available to downstream enzymes of said biosynthetic pathways.

As described herein, the present inventors have discovered the enzymatic activities responsible for the accumulation of unwanted by-products derived from 3-keto acid and/or aldehyde intermediates. Specifically, they have determined that a 3-ketoacid reductase and an aldehyde dehydrogenase are responsible for the conversion of 3-keto acids and aldehydes, respectively, to unwanted by-products. The activities of these enzymes are shown to hinder the optimal productivity and yield of 3-keto acid- and/or aldehyde-derived products, As used herein, a "3-hydroxyacid" is an organic compound which contains a carboxylic acid moiety on the C1 carbon and an alcohol moiety on the C3 carbon. 3-hydroxyacids can be obtained from 3-keto acids by chemical reduction of the 3-keto acid ketone moiety to an alcohol moiety. For example, reduction of the ketone moiety in acetolactate or 2-hydroxy-2-methyl-3-oxobutanoic acid results in the formation of 3-hydroxyacid 2,3-dihydroxy-2-methylbutanoic acid (DH2MB) (See, e.g., FIG. 2).

The present inventors have discovered that the 3-hydroxyacid by-product, 2,3-dihydroxy-2-methylbutanoic acid (CAS # 14868-24-7) (DH2MB), accumulates during fermentation reactions with microorganisms comprising biosynthetic pathways involving the 3-keto acid intermediate, acetolactate. The accumulation of this by-product was found to hinder optimal productivity and yield of the biosynthetic pathway's target metabolite. The present inventors found that the production of DH2MB is caused by the reduction of acetolactate. To reduce or eliminate the activity responsible for the production of DH2MB, the corresponding enzymatic activity catalyzing this reaction had to be identified and reduced or eliminated. The inventors have found in *S. cerevisiae* that one such enzyme catalyzing the conversion of acetolactate to DH2MB is YMR226C (also known as TMA29). This the first report of a protein in yeast that converts acetolactate to DH2MB.

The present inventors have also discovered that the 3-hydroxyacid by-product, 2-ethyl-2,3-dihydroxybutanoate, accumulates during fermentation reactions with microorganisms comprising biosynthetic pathways involving the 3-keto acid intermediate, 2-aceto-2-hydroxybutyrate. The accumulation of this by-product was found to hinder optimal productivity and yield of the biosynthetic pathway's target metabolite. The present inventors found that the production of 2-ethyl-2,3-dihydroxybutanoate is caused by the reduction of 2-aceto-2-hydroxybutyrate. To reduce or eliminate the activity responsible for the production of 2-ethyl-2,3-dihydroxybutanoate, the corresponding enzymatic activity catalyzing this reaction had to be identified and reduced or eliminated. The inventors have found in *S. cerevisiae*, the enzyme YMR226C (also known as TMA29) which catalyzes the conversion of acetolactate to DH2MB also catalyzes the conversion of 2-aceto-2-hydroxybutyrate to 2-ethyl-2,3-dihydroxybutanoate. This the first report of a protein in yeast that converts 2-aceto-2-hydroxybutyrate to 2-ethyl-2,3-dihydroxybutanoate.

The present inventors describe herein multiple strategies for reducing the conversion of the 3-keto acid intermediate to the corresponding 3-hydroxyacid by-product, a process which is accompanied by an increase in the yield of desirable metabolites. In one embodiment, the 3-keto acid intermediate is acetolactate and the corresponding 3-hydroxyacid is DH2MB. As described herein, reducing the conversion of acetolactate to DH2MB enables the increased production of beneficial metabolites such as isobutanol, 2-butanol, 1-butanol, 2-butanone, 2,3-butanediol, acetoin, diacetyl, valine, leucine, pantothenic acid, isobutylene, 3-methyl-1-butanol, 4-methyl-1-pentanol, and coenzyme A which are derived from biosynthetic pathways which use acetolactate as an intermediate. In another embodiment, the 3-keto acid intermediate is 2-aceto-2-hydroxybutyrate and the corresponding 3-hydroxyacid is 2-ethyl-2,3-dihydroxybutanoate. As described herein, reducing the conversion of 2-aceto-2-hydroxybutyrate to 2-ethyl-2,3-dihydroxybutanoate enables the increased production of beneficial metabolites such as 2-methyl-1-butanol, isoleucine, 3-methyl-1-pentanol, 4-methyl-1-hexanol, and 5-methyl-1-heptanol.

Accordingly, one aspect of the invention is directed to a recombinant microorganism comprising a biosynthetic pathway which uses a 3-keto acid as an intermediate, wherein said recombinant microorganism is substantially free of an enzyme that catalyzes the conversion of the 3-keto acid intermediate to a 3-hydroxyacid by-product. In one embodiment, the 3-keto acid intermediate is acetolactate and the 3-hydroxyacid by-product is DH2MB. In another embodiment, the 3-keto acid intermediate is 2-aceto-2-hydroxybutyrate and the 3-hydroxyacid by-product is 2-ethyl-2,3-dihydroxybutanoate.

In another aspect, the invention is directed to a recombinant microorganism comprising a biosynthetic pathway which uses a 3-keto acid as an intermediate, wherein said recombinant microorganism is engineered to reduce or eliminate the expression or activity of an enzyme catalyzing the conversion of the 3-keto acid intermediate to a 3-hydroxyacid by-product. In one embodiment, the 3-keto acid intermediate is acetolactate and the 3-hydroxyacid by-product is DH2MB. In another embodiment, the 3-keto acid intermediate is 2-aceto-2-hydroxybutyrate and the 3-hydroxyacid by-product is 2-ethyl-2,3-dihydroxybutanoate.

Figure 2:
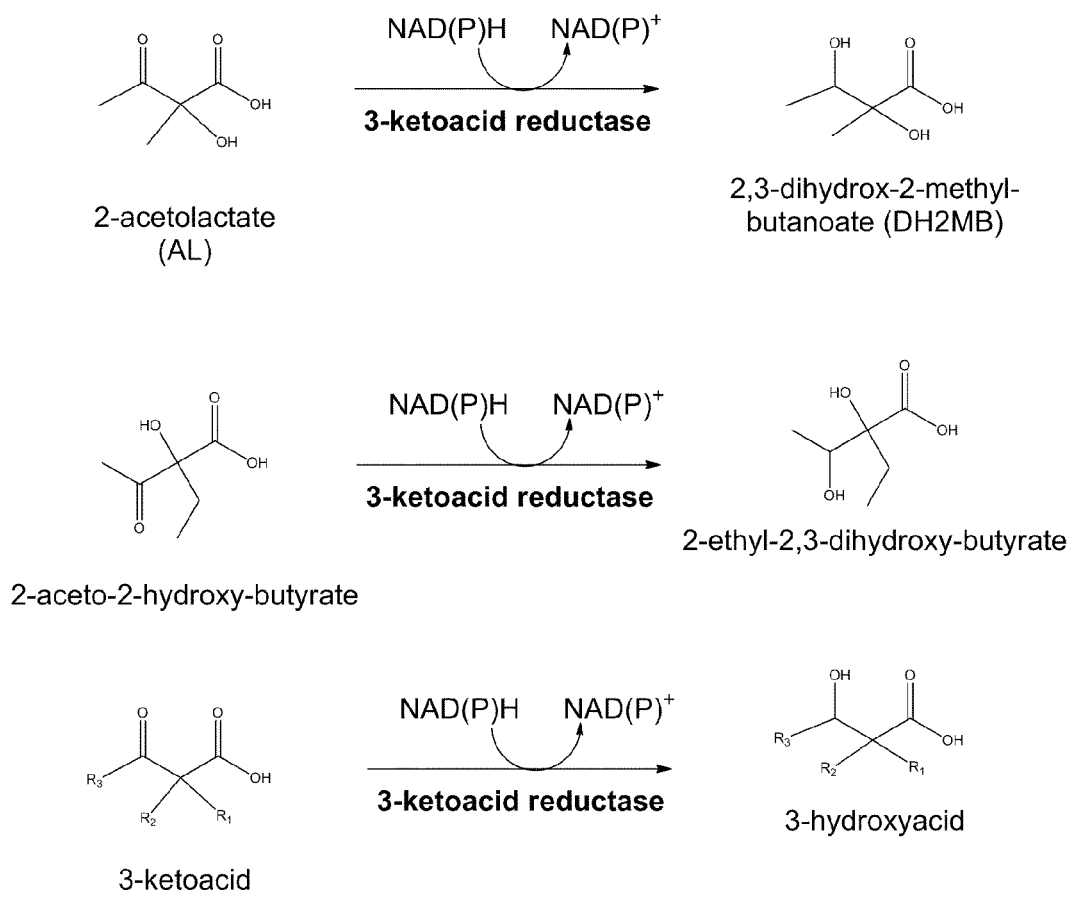
FIG. 2 illustrates exemplary reactions capable of being catalyzed by 3-ketoacid reductases.
Figure 3:
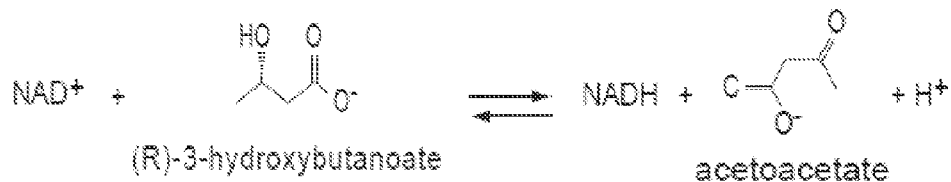
FIG. 3 illustrates a non-limiting list of exemplary 3-ketoacid reductases and their corresponding enzyme classification numbers.
Figure 3:
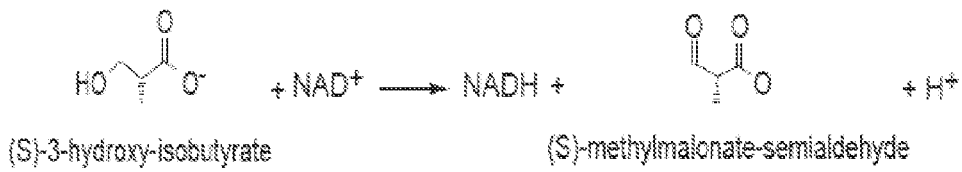
Figure 3:
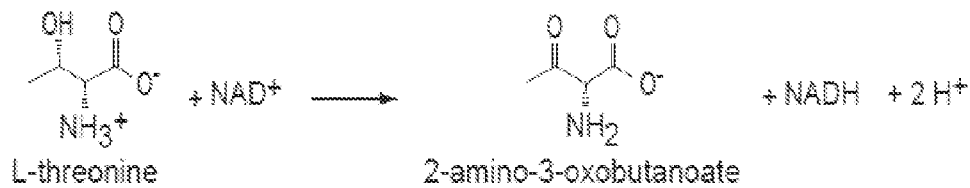
Figure 3:
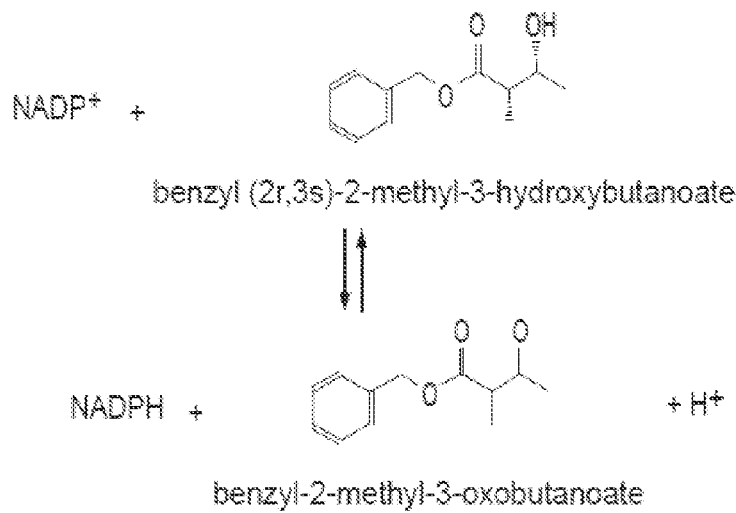
Figure 3:
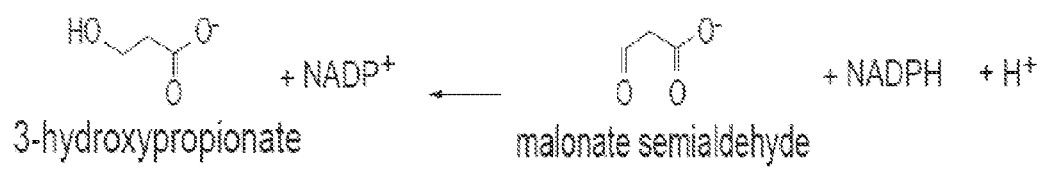

In various embodiments described herein, the protein involved in catalyzing the conversion of the 3-keto acid intermediate to the 3-hydroxyacid by-product is a ketoreductase. In an exemplary embodiment, the ketoreductase is a 3-ketoacid reductase (3-KAR). As used herein, the term "3-ketoacid reductase" refers to a ketoreductase (i.e. ketone reductase) active towards the 3-oxo group of a 3-keto acid. An illustration of exemplary reactions capable of being catalyzed by 3-ketoacid reductases is shown in FIG. 2. Suitable 3-ketoacid reductases are generally found in the enzyme classification subgroup 1.1.1.X, the final digit X being dependent upon the substrate. A non-limiting list of exemplary 3-ketoacid reductases and their corresponding enzyme classification number is shown in FIG. 3.

In an exemplary embodiment, the 3-ketoacid reductase is the *S. cerevisiae* YMR226C (SEQ ID NO: 1) protein, used interchangeably herein with "TMA29". In some embodiments, the 3-ketoacid reductase is the *S. cerevisiae* YMR226C (SEQ ID NO: 1) protein or a homolog or variant thereof. In one embodiment, the homolog may be selected from the group consisting of *Vanderwaltomzyma polyspora* (SEQ ID NO: 2), *Saccharomyces castellii* (SEQ ID NO: 3), *Candida glabrata* (SEQ ID NO: 4), *Saccharomyces bayanus* (SEQ ID NO: 5), *Zygosaccharomyces rouxii* (SEQ ID NO: 6), *K. lactis* (SEQ ID NO: 7), *Ashbya gossypii* (SEQ ID NO: 8), *Saccharomyces kluyveri* (SEQ ID NO: 9), *Kluyveromyces thermotolerans* (SEQ ID NO: 10), *Kluyveromyces waltii* (SEQ ID NO: 11), *Pichia stipitis* (SEQ ID NO: 12), *Debaromyces hansenii* (SEQ ID NO: 13), *Pichia pastoris* (SEQ ID NO: 14), *Candida dubliniensis* (SEQ ID NO: 15), *Candida albicans* (SEQ ID NO: 16), *Yarrowia lipolytica* (SEQ ID NO: 17), *Issatchenkia orientalis* (SEQ ID NO: 18), *Aspergillus nidulans* (SEQ ID NO: 19), *Aspergillus niger* (SEQ ID NO: 20), *Neurospora crassa* (SEQ ID NO: 21), *Schizosaccharomyces pombe* (SEQ ID NO: 22), and *Kluyveromyces marxianus* (SEQ ID NO: 23).

In one embodiment, the recombinant microorganism of the invention includes a mutation in at least one gene encoding for a 3-ketoacid reductase resulting in a reduction of 3-ketoacid reductase activity of a polypeptide encoded by said gene. In another embodiment, the recombinant microorganism includes a partial deletion of a gene encoding for a 3-ketoacid reductase gene resulting in a reduction of 3-ketoacid reductase activity of a polypeptide encoded by the gene. In another embodiment, the recombinant microorganism comprises a complete deletion of a gene encoding for a 3-ketoacid reductase resulting in a reduction of 3-ketoacid reductase activity of a polypeptide encoded by the gene. In yet another embodiment, the recombinant microorganism includes a modification of the regulatory region associated with the gene encoding for a 3-ketoacid reductase resulting in a reduction of expression of a polypeptide encoded by said gene. In yet another embodiment, the recombinant microorganism comprises a modification of the transcriptional regulator resulting in a reduction of transcription of gene encoding for a 3-ketoacid reductase. In yet another embodiment, the recombinant microorganism comprises mutations in all genes encoding for a 3-ketoacid reductase resulting in a reduction of activity of a polypeptide encoded by the gene(s). In one embodiment, said 3-ketoacid reductase gene is the *S. cerevisiae* TMA29 (YMR226C) gene or a homolog thereof. As would be understood in the art, naturally occurring homologs of TMA29 in yeast other than *S. cerevisiae* can similarly be inactivated using the methods of the present invention. TMA29 homologs and methods of identifying such TMA29 homologs are described herein.

As is understood by those skilled in the art, there are several additional mechanisms available for reducing or disrupting the activity of a protein such as 3-ketoacid reductase, including, but not limited to, the use of a regulated promoter, use of a weak constitutive promoter, disruption of one of the two copies of the gene in a diploid yeast, disruption of both copies of the gene in a diploid yeast, expression of an anti-sense nucleic acid, expression of an siRNA, over expression of a negative regulator of the endogenous promoter, alteration of the activity of an endogenous or heterologous gene, use of a heterologous gene with lower specific activity, the like or combinations thereof.

As described herein, the recombinant microorganisms of the present invention are engineered to produce less of the 3-hydroxyacid by-product than an unmodified parental microorganism. In one embodiment, the recombinant microorganism produces the 3-hydroxyacid by-product from a carbon source at a carbon yield of less than about 20 percent. In another embodiment, the microorganism is produces the 3-hydroxyacid by-product from a carbon source at a carbon yield of less than about 10, less than about 5, less than about 2, less than about 1, less than about 0.5, less than about 0.1, or less than about 0.01 percent. In one embodiment, the 3-hydroxyacid by-product is DH2MB, derived from the 3-keto acid, acetolactate. In another embodiment, the 3-hydroxyacid by-product is 2-ethyl-2,3-dihydroxybutanoate, derived from the 3-keto acid, 2-aceto-2-hydroxybutyrate.

In one embodiment, the 3-hydroxyacid by-product carbon yield derived from the 3-ketoacid is reduced by at least about 50% in a recombinant microorganism as compared to a parental microorganism that does not comprise a reduction or deletion of the activity or expression of one or more endogenous proteins involved in catalyzing the conversion of the 3-ketoacid intermediate to the 3-hydroxyacid by-product. In another embodiment, the 3-hydroxyacid by-product derived from the 3-ketoacid is reduced by at least about 60%, by at least about 65%, by at least about 70%, by at least about 75%, by at least about 80%, by at least about 85%, by at least about 90%, by at least about 95%, by at least about 99%, by at least about 99.9%, or by at least about 100% as compared to a parental microorganism that does not comprise a reduction or deletion of the activity or expression of one or more endogenous proteins involved in catalyzing the conversion of the 3-ketoacid to the 3-hydroxyacid by-product. In one embodiment, the 3-hydroxyacid by-product is DH2MB, derived from the 3-keto acid, acetolactate. In another embodiment, the 3-hydroxyacid by-product is 2-ethyl-2,3-dihydroxybutanoate, derived from the 3-keto acid, 2-aceto-2-hydroxybutyrate.

In an additional embodiment, the yield of a desirable fermentation product is increased in the recombinant microorganisms comprising a reduction or elimination of the activity or expression of one or more endogenous proteins involved in catalyzing the conversion of the 3-ketoacid intermediate to the 3-hydroxyacid by-product. In one embodiment, the yield of a desirable fermentation product is increased by at least about 1% as compared to a parental microorganism that does not comprise a reduction or elimination of the activity or expression of one or more endogenous proteins involved in catalyzing the conversion of the 3-ketoacid intermediate to the 3-hydroxyacid by-product. In another embodiment, the yield of a desirable fermentation product is increased by at least about 5%, by at least about 10%, by at least about 25%, or by at least about 50% as compared to a parental microorganism that does not comprise a reduction or elimination of the activity or expression of one or more endogenous proteins involved in catalyzing the conversion of the 3-ketoacid intermediate to the 3-hydroxyacid by-product. In one embodiment, the 3-hydroxyacid by-product is DH2MB, derived from the 3-keto acid, acetolactate. Accordingly, in one embodiment, the desirable fermentation product is derived from any biosynthetic pathway in which acetolactate acts as an intermediate, including, but not limited to, isobutanol, 2-butanol, 1-butanol, 2-butanone, 2,3-butanediol, acetoin, diacetyl, valine, leucine, pantothenic acid, isobutylene, 3-methyl-1-butanol, 4-methyl-1-pentanol, and coenzyme A. In another embodiment, the 3-hydroxyacid by-product is 2-ethyl-2,3-dihydroxybutanoate, derived from the 3-keto acid, 2-aceto-2-hydroxybutyrate. Accordingly, in another embodiment, the desirable fermentation product is derived from any biosynthetic pathway in which 2-aceto-2-hydroxybutyrate acts as an intermediate, including, but not limited to, 2-methyl-1-butanol, isoleucine, 3-methyl-1-pentanol, 4-methyl-1-hexanol, and 5-methyl-1-heptanol.

In further embodiments, additional enzymes potentially catalyzing the conversion of a 3-ketoacid intermediate to a 3-hydroxyacid by-product are deleted from the genome of a recombinant microorganism comprising a biosynthetic pathway which uses a 3-ketoacid as an intermediate. Endogenous yeast genes with the potential to convert of a 3-ketoacid intermediate to a 3-hydroxyacid by-product include ketoreductases, short chain alcohol dehydrogenases, medium chain alcohol dehydrogenases, members of the aldose reductase family, members of the D-hydroxyacid dehydrogenase family, alcohol dehydrogenases, and lactate dehydrogenases. In one embodiment, the 3-hydroxyacid by-product is DH2MB, derived from the 3-keto acid, acetolactate. In another embodiment, the 3-hydroxyacid by-product is 2-ethyl-2,3-dihydroxybutanoate, derived from the 3-keto acid, 2-aceto-2-hydroxybutyrate.

Methods for identifying additional enzymes catalyzing the conversion of a 3-ketoacid intermediate to a 3-hydroxyacid by-product are outlined as follows: endogenous yeast genes coding for ketoreductases, short chain alcohol dehydrogenases, medium chain alcohol dehydrogenases, members of the aldose reductase family, members of the D-hydroxyacid dehydrogenase family, alcohol dehydrogenases, and lactate dehydrogenases are deleted from the genome of a yeast strain comprising a biosynthetic pathway in which a 3-ketoacid (e.g., acetolactate or 2-aceto-2-hydroxybutyrate) is an intermediate. These deletion strains are compared to the parent strain by fermentation and analysis of the fermentation broth for the presence and concentration of the corresponding 3-hydroxyacid by-product (e.g., DH2MB or 2-ethyl-2,3-dihydroxybutanoate, derived from acetolactate and 2-aceto-2-hydroxybutyrate, respectively). In *S. cerevisiae*, deletions that reduce the production of the 3-hydroxyacid by-product are combined by construction of strains carrying multiple deletions. Candidate genes can include, but are not limited to, YAL060W, YJR159W, YGL157W, YBL114W, YOR120W, YKL055C, YBR159W, YBR149W, YDL168W, YDR368W, YLR426W, YCR107W, YILL24W, YML054C, YOL151W, YMR318C, YBR046C, YHR104W, YIR036C, YDL174C, YDR541C, YBR145W, YGL039W, YCR105W, YDL124W, YIR035C, YFL056C, YNL274C, YLR255C, YGL185C, YGL256W, YJR096W, YJR155W, YPL275W, YOR388C, YLR070C, YMR083W, YER081W, YJR139C, YDL243C, YPL113C, YOL165C, YML086C, YMR303C, YDL246C, YLR070C, YHR063C, YNL331C, YFL057C, YIL155C, YOL086C, YAL061W, YDR127W, YPR127W, YCL018W, YIL074C, YIL124W, and YEL071W. Many of these deletion strains are available commercially (for example Open Biosystems YSC1054). These deletion strains are transformed with a plasmid pGV2435 from which the ALS gene (e.g., the

*B. subtilis* alsS) is expressed under the control of the CUP1 promoter. The transformants are cultivated in YPD medium containing 150 g/L glucose in shake flasks at 30° C., 75 rpm in a shaking incubator for 48 hours. After 48 h samples from the shake flasks are analyzed by HPLC for the concentration of the 3-hydroxyacid by-product (e.g., DH2MB and 2-ethyl-2,3-dihydroxybutanoate, derived from acetolactate and 2-aceto-2-hydroxybutyrate, respectively). As would be understood in the art, naturally occurring homologs of 3-ketoacid reductase genes (e.g., TMA29) in yeast other than *S. cerevisiae* can similarly be inactivated. 3-ketoacid reductase gene (e.g., TMA29) homologs and methods of identifying such 3-ketoacid reductase gene homologs are described herein.

Another way to screen the deletion library is to incubate yeast cells with the 3-ketoacid intermediate (e.g., acetolactate or 2-aceto-2-hydroxybutyrate) and analyze the broth for the production of the corresponding 3-hydroxyacid by-product (e.g., DH2MB or 2-ethyl-2,3-dihydroxybutanoate, derived from acetolactate and 2-aceto-2-hydroxybutyrate, respectively).

Some of the listed genes are the result of tandem duplication or whole genome duplication events and are expected to have similar substrate specificities. Examples are YAL061W (BDH1), and YAL060W (BDH2), YDR368W (YPR1) and YOR120W (GCY1). Deletion of just one of the duplicated genes is likely not to result in a phenotype. These gene pairs have to be analyzed in strains carrying deletions in both genes.

An alternative approach to find additional endogenous activity responsible for the production of the 3-hydroxyacid by-product (e.g., DH2MB or 2-ethyl-2,3-dihydroxybutanoate, derived from acetolactate and 2-aceto-2-hydroxybutyrate, respectively) is to analyze yeast strains that overexpress the genes suspected of encoding the enzyme responsible for production of the 3-hydroxyacid by-product. Such strains are commercially available for many of the candidate genes listed above (for example Open Biosystems YSC3870). The ORF overexpressing strains are processed in the same way as the deletion strains. They are transformed with a plasmid for ALS expression and screened for 3-hydroxyacid by-product (e.g., DH2MB or 2-ethyl-2,3-dihydroxybutanoate) production levels. To narrow the list of possible genes causing the production of the 3-hydroxyacid by-product (e.g., DH2MB or 2-ethyl-2,3-dihydroxybutanoate), their expression can be analyzed in fermentation samples. Genes that are not expressed during a fermentation that produced the 3-hydroxyacid by-product (e.g., DH2MB or 2-ethyl-2,3-dihydroxybutanoate) can be excluded from the list of possible targets. This analysis can be done by extraction of RNA from fermenter samples and submitting these samples to whole genome expression analysis, for example, by Roche NimbleGen.

As described herein, strains that naturally produce low levels of one or more 3-hydroxyacid by-products can also have applicability for producing increased levels of desirable fermentation products that are derived from biosynthetic pathways comprising a 3-ketoacid intermediate. As would be understood by one skilled in the art equipped with the instant disclosure, strains that naturally produce low levels of one or more 3-hydroxyacid by-products may inherently exhibit low or undetectable levels of endogenous enzyme activity, resulting in the reduced conversion of 3-ketoacids to 3-hydroxyacids, a trait favorable for the production of a desirable fermentation product such as isobutanol. Described herein are several approaches for identifying a native host microorganism which is substantially free of 3-ketoacid reductase activity. For example, one approach to finding a host microorganism which exhibits inherently low or undetectable endogenous enzyme activity responsible for the production of the 3-hydroxyacid by-product (e.g., DH2MB or 2-ethyl-2,3-dihydroxybutanoate) is to analyze yeast strains by incubating the yeast cells with a 3-keto acid (e.g., acetolactate or 2-aceto-2-hydroxybutyrate) and analyze the broth for the production of the corresponding 3-hydroxyacid by-product (e.g., DH2MB or 2-ethyl-2,3-dihydroxybutanoate, derived from acetolactate and 2-aceto-2-hydroxybutyrate, respectively).

The recombinant microorganisms described herein which produce a beneficial metabolite derived from a biosynthetic pathway which uses a 3-keto acid as an intermediate may be further engineered to reduce or eliminate enzymatic activity for the conversion of pyruvate to products other than the 3-keto acid (e.g., acetolactate and/or 2-aceto-2-hydroxybutyrate). In one embodiment, the enzymatic activity of pyruvate decarboxylase (PDC), lactate dehydrogenase (LDH), pyruvate oxidase, pyruvate dehydrogenase, and/or glycerol-3-phosphate dehydrogenase (GPD) is reduced or eliminated.

In a specific embodiment, the beneficial metabolite is produced in a recombinant PDC-minus GPD-minus yeast microorganism that overexpresses an acetolactate synthase (ALS) gene. In another specific embodiment, the ALS is encoded by the *B. subtilis* alsS.

Reduced Accumulation of Acid By-Products from Aldehyde Intermediates

As described further in the Examples, the present inventors have also discovered that unwanted acid by-products (e.g., isobutyrate in the case of isobutanol), can accumulate during fermentation reactions with microorganisms comprising a pathway involving an aldehyde intermediate (e.g., isobutyraldehyde in the case of isobutanol).

As used herein, an "acid by-product" refers to an organic compound which contains a carboxylic acid moiety. An acid by-product can be obtained by the oxidation of an aldehyde. For example, the oxidation of isobutyraldehyde results in the formation of isobutyric acid (See, e.g., FIG. 4).

The present inventors have found that accumulation of these acid by-products hinders the optimal productivity and yield of the biosynthetic pathway which utilize aldehyde intermediates. The present inventors found that the production of these acid by-products is caused by dehydrogenation of the corresponding aldehyde. To reduce or eliminate the activity responsible for the production of the acid by-product, the corresponding enzymatic activity catalyzing this reaction had to be identified and reduced or eliminated. The inventors have found in *S. cerevisiae* that one such enzyme catalyzing the conversion of aldehydes to acid by-products is aldehyde dehydrogenase.

The present inventors describe herein multiple strategies for reducing acid by-product formation, a process which is accompanied by an increase in the yield of desirable metabolites such as isobutanol, 1-butanol, 2-methyl-1-butanol, 3-methyl-1-butanol, 1-propanol, 1-pentanol, 1-hexanol, 3-methyl-1-pentanol, 4-methyl-1-pentanol, 4-methyl-1-hexanol, and 5-methyl-1-heptanol.

Accordingly, one aspect of the invention is directed to a recombinant microorganism comprising a biosynthetic pathway which uses an aldehyde as an intermediate, wherein said recombinant microorganism is substantially free of an enzyme that catalyzes the conversion of an aldehyde to an acid by-product.

In another aspect, the invention is directed to a recombinant microorganism comprising a biosynthetic pathway which uses an aldehyde as an intermediate, wherein said recombinant microorganism is engineered to reduce or eliminate the expression or activity of one or more enzymes catalyzing the conversion of the aldehyde to an acid by-product.

In one embodiment, the aldehyde intermediate is isobutyraldehyde and the acid by-product is isobutyrate. In another embodiment, the aldehyde intermediate is 1-butanal and the acid by-product is butyrate. In yet another embodiment, the aldehyde intermediate is 2-methyl-1-butanal and the acid by-product is 2-methyl-1-butyrate. In yet another embodiment, the aldehyde intermediate is 3-methyl-1-butanal and the acid by-product is 3-methyl-1-butyrate. In yet another embodiment, the aldehyde intermediate is 1-propanal and the acid by-product is propionate. In yet another embodiment, the aldehyde intermediate is 1-pentanal and the acid by-product is pentanoate. In yet another embodiment, the aldehyde intermediate is 1-hexanal and the acid by-product is hexanoate. In yet another embodiment, the aldehyde intermediate is 3-methyl-1-pentanal and the acid by-product is 3-methyl-1-pentanoate. In yet another embodiment, the aldehyde intermediate is 4-methyl-1-pentanal and the acid by-product is 4-methyl-1-pentanoate. In yet another embodiment, the aldehyde intermediate is 4-methyl-1-hexanal and the acid by-product is 4-methyl-1-hexanoate. In yet another embodiment, the aldehyde intermediate is 5-methyl-1-heptanal and the acid by-product is 5-methyl-1-heptanoate.

In various embodiments described herein, the protein involved in catalyzing the conversion of an aldehyde to acid by-product is an aldehyde dehydrogenase (ALDH).

As used herein, the term "aldehyde dehydrogenase" refers to an enzyme catalyzing the reaction:

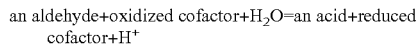

Figure 4:
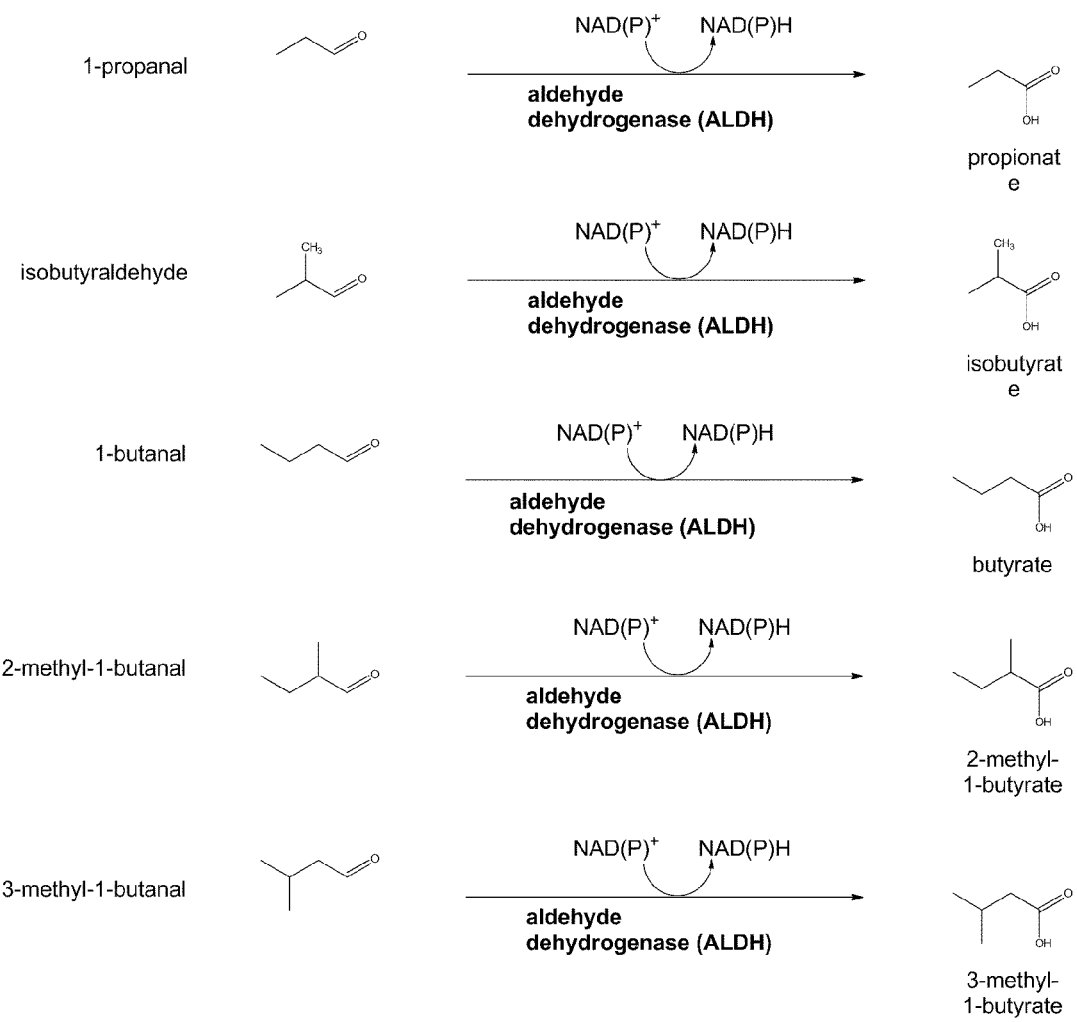
FIG. 4 illustrates exemplary reactions capable of being catalyzed by aldehyde dehydrogenases.

An illustration of exemplary reactions capable of being catalyzed by aldehyde dehydrogenases is shown in FIG. 4. Suitable aldehyde dehydrogenases are generally found in the enzyme classification subgroup EC 1.2.1.X, wherein the final digit X is dependent upon the substrate or the cofactor. For example, EC 1.2.1.3 catalyzes the following reaction: an aldehyde+$NAD^+$+$H_2O$=an acid+NADH+$H^+$); EC 1.2.1.4 catalyzes the following reaction: an aldehyde+$NADP^+$+$H_2O$=an acid+NADPH+$H^+$); and EC 1.2.1.5 catalyzes the following reaction: an aldehyde+$NAD(P)^+$+$H_2O$=an acid+NAD(P)H+$H^+$.

As described herein, the protein involved in catalyzing the conversion of an aldehyde to an acid by-product is an aldehyde dehydrogenase (ALDH). In one embodiment, the aldehyde dehydrogenase is encoded by a gene selected from the group consisting of ALD2, ALD3, ALD4, ALD5, ALD6, and HFD1, and homologs and variants thereof. In an exemplary embodiment, the aldehyde dehydrogenase is the S. cerevisiae aldehyde dehydrogenase ALD6 (SEQ ID NO: 25) or a homolog or variant thereof. In one embodiment, the homolog may be selected from the group consisting of Saccharomyces castelli (SEQ ID NO: 26), Candida glabrata (SEQ ID NO: 27), Saccharomyces bayanus (SEQ ID NO: 28), Kluyveromyces lactis (SEQ ID NO: 29), Kluyveromyces thermotolerans (SEQ ID NO: 30), Kluyveromyces waltii (SEQ ID NO: 31), Saccharomyces cerevisiae YJ789 (SEQ ID NO: 32), Saccharomyces cerevisiae JAY291 (SEQ ID NO: 33), Saccharomyces cerevisiae EC1118 (SEQ ID NO: 34), Saccharomyces cerevisiae DBY939 (SEQ ID NO: 35), Saccharomyces cerevisiae AWRI1631 (SEQ ID NO: 36), Saccharomyces cerevisiae RM11-1a (SEQ ID NO: 37), Pichia pastoris (SEQ ID NO: 38), Kluyveromyces marxianus (SEQ ID NO: 39), Schizosaccharomyces pombe (SEQ ID NO: 40), and Schizosaccharomyces pombe (SEQ ID NO: 41).

In one embodiment, the recombinant microorganism includes a mutation in at least one gene encoding for an aldehyde dehydrogenase resulting in a reduction of aldehyde dehydrogenase activity of a polypeptide encoded by said gene. In another embodiment, the recombinant microorganism includes a partial deletion of gene encoding for an aldehyde dehydrogenase resulting in a reduction of aldehyde dehydrogenase activity of a polypeptide encoded by the gene. In another embodiment, the recombinant microorganism comprises a complete deletion of a gene encoding for an aldehyde dehydrogenase resulting in a reduction of aldehyde dehydrogenase activity of a polypeptide encoded by the gene. In yet another embodiment, the recombinant microorganism includes a modification of the regulatory region associated with the gene encoding for an aldehyde dehydrogenase resulting in a reduction of expression of a polypeptide encoded by said gene. In yet another embodiment, the recombinant microorganism comprises a modification of the transcriptional regulator resulting in a reduction of transcription of a gene encoding for an aldehyde dehydrogenase. In yet another embodiment, the recombinant microorganism comprises mutations in all genes encoding for an aldehyde dehydrogenase resulting in a reduction of activity of a polypeptide encoded by the gene(s). In one embodiment, said aldehyde dehydrogenase is encoded by a gene selected from the group consisting of ALD2, ALD3, ALD4, ALD5, ALD6, and HFD1, and homologs and variants thereof. As would be understood in the art, naturally occurring homologs of aldehyde dehydrogenase in yeast other than S. cerevisiae can similarly be inactivated using the methods of the present invention. Aldehyde dehydrogenase homologs and methods of identifying such aldehyde dehydrogenase homologs are described herein.

As is understood by those skilled in the art, there are several additional mechanisms available for reducing or disrupting the activity of a protein such as aldehyde dehydrogenase, including, but not limited to, the use of a regulated promoter, use of a weak constitutive promoter, disruption of one of the two copies of the gene in a diploid yeast, disruption of both copies of the gene in a diploid yeast, expression of an antisense nucleic acid, expression of an siRNA, over expression of a negative regulator of the endogenous promoter, alteration of the activity of an endogenous or heterologous gene, use of a heterologous gene with lower specific activity, the like or combinations thereof.

As would be understood by one skilled in the art, the activity or expression of more than one aldehyde dehydrogenase can be reduced or eliminated. In one specific embodiment, the activity or expression of ALD4 and ALD6 or homologs or variants thereof is reduced or eliminated. In another specific embodiment, the activity or expression of ALD5 and ALD6 or homologs or variants thereof is reduced or eliminated. In yet another specific embodiment, the activity or expression of ALD4, ALD5, and ALD6 or homologs or variants thereof is reduced or eliminated. In yet another specific embodiment, the activity or expression of the cytosolically localized aldehyde dehydrogenases ALD2, ALD3, and ALD6 or homologs or variants thereof is reduced or eliminated. In yet another specific embodiment, the activity or expression of the mitochondrially localized aldehyde dehydrogenases, ALD4 and ALD5 or homologs or variants thereof, is reduced or eliminated.

As described herein, the recombinant microorganisms of the present invention are engineered to produce less of the acid by-product than an unmodified parental microorganism. In one embodiment, the recombinant microorganism produces the acid by-product from a carbon source at a carbon yield of less than about 50 percent as compared to a parental microorganism. In another embodiment, the microorganism is produces the acid by-product from a carbon source from a carbon source at a carbon yield of less than about 25, less than about 10, less than about 5, less than about 1, less than about 0.5, less than about 0.1, or less than about 0.01 percent as compared to a parental microorganism. In one embodiment, the acid by-product is isobutyrate, derived from isobutyraldehyde, an intermediate of the isobutanol biosynthetic pathway. In another embodiment, the acid by-product is butyrate, derived from 1-butanal, an intermediate of the 1-butanol biosynthetic pathway. In yet another embodiment, the acid by-product is 2-methyl-1-butyrate, derived from 2-methyl-1-butanal, an intermediate of the 2-methyl-1-butanol biosynthetic pathway. In yet another embodiment, the acid by-product is 3-methyl-1-butyrate, derived from 3-methyl-1-butanal, an intermediate of the 3-methyl-1-butanol biosynthetic pathway. In yet another embodiment, the acid by-product is propionate, derived from 1-propanal, an intermediate of the 1-propanol biosynthetic pathway. In yet another embodiment, the acid by-product is pentanoate, derived from 1-pentanal, an intermediate of the 1-pentanol biosynthetic pathway. In yet another embodiment, the acid by-product is hexanoate, derived from 1-hexanal, an intermediate of the 1-hexanol biosynthetic pathway. In yet another embodiment, the acid by-product is 3-methyl-1-pentanoate, derived from 3-methyl-1-pentanal, an intermediate of the 3-methyl-1-pentanol biosynthetic pathway. In yet another embodiment, the acid by-product is 4-methyl-1-pentanoate, derived from 4-methyl-1-pentanal, an intermediate of the 4-methyl-1-pentanol biosynthetic pathway. In yet another embodiment, the acid by-product is 4-methyl-1-hexanoate, derived from 4-methyl-1-hexanal, an intermediate of the 4-methyl-1-hexanol biosynthetic pathway. In yet another embodiment, the acid by-product is 5-methyl-1-heptanoate, derived from 5-methyl-1-heptanal, an intermediate of the 5-methyl-1-heptanol biosynthetic pathway.

In one embodiment, the acid by-product carbon yield from the corresponding aldehyde is reduced by at least about 50% in a recombinant microorganism as compared to a parental microorganism that does not comprise a reduction or deletion of the activity or expression of one or more proteins involved in catalyzing the conversion of an aldehyde to an acid by-product. In another embodiment, the acid by-product carbon yield from acetolactate is reduced by at least about 60%, by at least about 65%, by at least about 70%, by at least about 75%, by at least about 80%, by at least about 85%, by at least about 90%, by at least about 95%, by at least about 99%, by at least about 99.9%, or by at least about 100% as compared to a parental microorganism that does not comprise a reduction or deletion of the activity or expression of one or more proteins involved in catalyzing the conversion of an aldehyde to an acid by-product. In one embodiment, the acid by-product is isobutyrate, derived from isobutyraldehyde, an intermediate of the isobutanol biosynthetic pathway. In another embodiment, the acid by-product is butyrate, derived from 1-butanal, an intermediate of the 1-butanol biosynthetic pathway. In yet another embodiment, the acid by-product is 2-methyl-1-butyrate, derived from 2-methyl-1-butanal, an intermediate of the 2-methyl-1-butanol biosynthetic pathway. In yet another embodiment, the acid by-product is 3-methyl-1-butyrate, derived from 3-methyl-1-butanal, an intermediate of the 3-methyl-1-butanol biosynthetic pathway. In yet another embodiment, the acid by-product is propionate, derived from 1-propanal, an intermediate of the 1-propanol biosynthetic pathway. In yet another embodiment, the acid by-product is pentanoate, derived from 1-pentanal, an intermediate of the 1-pentanol biosynthetic pathway. In yet another embodiment, the acid by-product is hexanoate, derived from 1-hexanal, an intermediate of the 1-hexanol biosynthetic pathway. In yet another embodiment, the acid by-product is 3-methyl-1-pentanoate, derived from 3-methyl-1-pentanal, an intermediate of the 3-methyl-1-pentanol biosynthetic pathway. In yet another embodiment, the acid by-product is 4-methyl-1-pentanoate, derived from 4-methyl-1-pentanal, an intermediate of the 4-methyl-1-pentanol biosynthetic pathway. In yet another embodiment, the acid by-product is 4-methyl-1-hexanoate, derived from 4-methyl-1-hexanal, an intermediate of the 4-methyl-1-hexanol biosynthetic pathway. In yet another embodiment, the acid by-product is 5-methyl-1-heptanoate, derived from 5-methyl-1-heptanal, an intermediate of the 5-methyl-1-heptanol biosynthetic pathway.

In an additional embodiment, the yield of a desirable fermentation product is increased in the recombinant microorganisms comprising a reduction or elimination of the activity or expression of one or more proteins involved in catalyzing the conversion of an aldehyde to acid by-product. In one embodiment, the yield of a desirable fermentation product is increased by at least about 1% as compared to a parental microorganism that does not comprise a reduction or elimination of the activity or expression of one or more endogenous proteins involved in catalyzing the conversion of an aldehyde to acid by-product. In another embodiment, the yield of a desirable fermentation product is increased by at least about 5%, by at least about 10%, by at least about 25%, or by at least about 50% as compared to a parental microorganism that does not comprise a reduction or elimination of the activity or expression of one or more endogenous proteins involved in catalyzing the conversion of an aldehyde to acid by-product. As described herein, the desirable fermentation product may be derived from any biosynthetic pathway in which an aldehyde acts as an intermediate, including, but not limited to, isobutanol, 1-butanol, 2-methyl-1-butanol, 3-methyl-1-butanol, 1-propanol, 1-pentanol, 1-hexanol, 3-methyl-1-pentanol, 4-methyl-1-pentanol, 4-methyl-1-hexanol, and 5-methyl-1-heptanol biosynthetic pathways.

Methods for identifying additional enzymes catalyzing the conversion of an aldehyde to acid by-product are outlined as follows: endogenous yeast genes coding for putative aldehyde and alcohol dehydrogenases are deleted from the genome of a yeast strain. These deletion strains are compared to the parent strain by enzymatic assay. Many of these deletion strains are available commercially (for example Open Biosystems YSC1054).

Another way to screen the deletion library is to incubate yeast cells with an aldehyde (e.g., isobutyraldehyde or 1-butanal) and analyze the broth for the production of the corresponding acid by-product (e.g., isobutyrate or butyrate, derived from isobutyraldehyde or 1-butanal, respectively).

An alternative approach to find additional endogenous activity responsible for the production of the acid by-product (e.g., isobutyrate or butyrate, derived from isobutyraldehyde or 1-butanal, respectively) is to analyze yeast strains that overexpress the genes suspected of encoding the enzyme responsible for production of the acid by-product. Such strains are commercially available for many of the candidate genes listed above (for example Open Biosystems YSC3870). The ORF overexpressing strains are screened for increased acid by-product production levels. Alternatively, the cell lysates of the ORF overexpressing strains are assayed for increased aldehyde oxidation activity. To narrow the list of possible genes causing the production of acid by-products, their expression can be analyzed in fermentation samples. Genes that are not expressed during a fermentation that produces an acid by-product can be excluded from the list of possible targets. This analysis can be done by extraction of RNA from fermenter samples and submitting these samples to whole genome expression analysis, for example, by Roche NimbleGen.

As described herein, strains that naturally produce low levels of one or more acid by-products can also have applicability for producing increased levels of desirable fermentation products that are derived from biosynthetic pathways comprising an aldehyde intermediate. As would be understood by one skilled in the art equipped with the instant disclosure, strains that naturally produce low levels of one or more acid by-products may inherently exhibit low or undetectable levels of endogenous enzyme activity, resulting in the reduced conversion of aldehydes to acid by-products, a trait favorable for the production of a desirable fermentation product such as isobutanol. Described herein are several approaches for identifying a native host microorganism which is substantially free of aldehyde dehydrogenase activity. For example, one approach to finding a host microorganism which exhibits inherently low or undetectable endogenous enzyme activity responsible for the production of the acid by-product (e.g., isobutyrate or butyrate) is to analyze yeast strains by incubating the yeast cells with an aldehyde (e.g., isobutyraldehyde or 1-butanal) and analyze the broth for the production of the corresponding acid by-product (e.g., isobutyrate or butyrate, derived from isobutyraldehyde or 1-butanal, respectively).

As described above, one strategy reducing the production of the acid by-product, isobutyrate, is to reduce or eliminate the activity or expression of one or more endogenous aldehyde dehydrogenase proteins present in yeast that may be converting isobutyraldehyde to isobutyrate.

Another strategy for reducing the production of isobutyrate is the reduction or elimination of activity or expression of one more endogenous yeast alcohol dehydrogenases. Reducing the expression of or deleting one or more alcohol dehydrogenases including, but not limited to, S. cerevisiae ADH1, ADH2, ADH3, ADH4, ADH5, ADH6, ADH7, and SFA1, and homologs or variants thereof, will generally lead to a reduced production of isobutyrate and a concomitant increase in isobutanol yield. The reduction and/or deletion of additional dehydrogenases are envisioned herein and are considered within the scope of the present invention. These dehydrogenases include additional alcohol dehydrogenases such as S. cerevisiae BDH1, BDH2, SOR1, SOR2, and XYL1, and homologs or variants thereof, as well as aryl alcohol dehydrogenases such as AAD3, AAD4, AAD6, AAD10, AAD14, AAD15, AAD16, and YPL088W, and homologs or variants thereof.

In another embodiment, the invention provides recombinant microorganisms engineered to reduce and/or deletion one or more additional genes encoding carbonyl/aldehyde reductases. These carbonyl/aldehyde reductases include S. cerevisiae ARI1, YPR1, TMA29, YGL039W, and UGA2, and homologs or variants thereof.

An additional strategy described herein for reducing the production of the by-product isobutyrate is to reduce or eliminate the activity or expression of endogenous proteins present in yeast that may be producing isobutyrate from the isobutanol pathway intermediate 2-ketoisovalerate. Such enzymes are generally referred to as ketoacid dehydrogenases (KDH). Elimination or reduction of the activity or expression of these endogenous proteins can reduce or eliminate the production of the unwanted byproduct, isobutyrate. KDH enzyme activity has been identified in S. cerevisiae (Dickinson, J. R., and I. W. Dawes, 1992, The catabolism of branched-chain amino acids occurs via a 2-oxoacid dehydrogenase in S. cerevisiae. J. Gen. Microbiol. 138: 2029-2033). Reducing the expression of or deleting one or more ketoacid dehydrogenases and homologs or variants thereof, will generally lead to a reduced production of isobutyrate and a concomitant increase in isobutanol yield.

The reduction in expression of or deletion of genes in S. cerevisiae and other yeast can be achieved by methods known to those of skill in the art, such as allelic replacement or exchange, as well as gene disruption by the insertion of another gene or marker cassette.

Another strategy described herein for reducing the production of the by-product isobutyrate is to increase the activity and/or expression of an alcohol dehydrogenase (ADH) responsible for the conversion of isobutyraldehyde to isobutanol. This strategy prevents competition by endogenous enzymes for the isobutanol pathway intermediate, isobutyraldehyde. An increase in the activity and/or expression of the alcohol dehydrogenase may be achieved by various means. For example, alcohol dehydrogenase activity can be increased by utilizing a promoter with increased promoter strength, by increasing the copy number of the alcohol dehydrogenase gene, or by utilizing an alternative or modified alcohol dehydrogenase with increased specific activity.

An alternative strategy described herein for reducing the production of the by-product isobutyrate is to utilize an alcohol dehydrogenase (ADH) in the isobutanol pathway responsible for the conversion of isobutyraldehyde to isobutanol which exhibits a decrease in Michaelis-Menten constant ($K_M$). This strategy also prevents competition by endogenous enzymes for the isobutanol pathway intermediate, isobutyraldehyde.

Another strategy described herein for reducing the production of the by-product isobutyrate is to utilize an alcohol dehydrogenase (ADH) in the isobutanol pathway responsible for the conversion of isobutyraldehyde to isobutanol which exhibits increased activity and a decrease in Michaelis-Menten constant ($K_M$). This strategy also prevents competition by endogenous enzymes for the isobutanol pathway intermediate, isobutyraldehyde.

Further, by utilizing a modified ADH enzyme, the present inventors may establish a situation in which the forward reaction (i.e. the isobutyraldehyde conversion to isobutanol) is the favored reaction over the reverse reaction (i.e. the conversion of isobutanol to isobutyraldehyde).

The strategies described above generally lead to a decrease in isobutyrate yield, which is accompanied by an increase in isobutanol yield. Hence, the above strategies are useful for decreasing the isobutyrate yield and/or titer and for increasing the ratio of isobutanol yield over isobutyrate yield.

In one embodiment, the isobutyrate yield (mol isobutyrate per mol glucose) is less than about 5%. In another embodiment, the isobutyrate yield (mol isobutyrate per mol glucose) is less than about 1%. In yet another embodiment, the isobutyrate yield (mol isobutyrate per mol glucose) is less than about 0.5%, less than about 0.1%, less than about 0.05%, or less than about 0.01%.

In one embodiment, the isobutanol to isobutyrate yield ratio is at least about 2. In another embodiment, the isobutanol to isobutyrate yield is at least about 5. In yet another embodiment, the isobutanol to isobutyrate yield ratio at least about 20, at least about 100, at least about 500, or at least about 1000.

The recombinant microorganisms described herein which produce a beneficial metabolite derived from a biosynthetic pathway which uses an aldehyde as an intermediate may be further engineered to reduce or eliminate enzymatic activity for the conversion of pyruvate to products other than a 3-keto acid (e.g., acetolactate and/or 2-aceto-2-hydroxybutyrate). In one embodiment, the enzymatic activity of pyruvate decarboxylase (PDC), lactate dehydrogenase (LDH), pyruvate oxidase, pyruvate dehydrogenase, and/or glycerol-3-phosphate dehydrogenase (GPD) is reduced or eliminated.

In a specific embodiment, the beneficial metabolite is produced in a recombinant PDC-minus GPD-minus yeast microorganism that overexpresses an acetolactate synthase (ALS) gene. In another specific embodiment, the ALS is encoded by the B. subtilis alsS.

Reduced Accumulation of 3-Hydroxyacid By-Products and Acid By-Products

The present inventors describe herein multiple strategies for reducing the conversion of a 3-keto acid intermediate to a corresponding 3-hydroxyacid by-product, a process which is accompanied by an increase in the yield of desirable metabolites. The present inventors also describe herein multiple strategies for reducing the conversion of an aldehyde intermediate to a corresponding acid by-product, a process which is accompanied by a further increase in the yield of desirable metabolites.

Accordingly, in one aspect, the invention is directed to a recombinant microorganism comprising a biosynthetic pathway which uses a 3-keto acid as an intermediate and an aldehyde as an intermediate, wherein said recombinant microorganism is (i) substantially free of an enzyme that catalyzes the conversion of the 3-keto acid intermediate to a 3-hydroxyacid by-product and (ii) substantially free of an enzyme that catalyzes the conversion of an aldehyde to an acid by-product. In one embodiment, the 3-keto acid intermediate is acetolactate. The biosynthetic pathway which uses acetolactate and an aldehyde as intermediates may be selected from a pathway for the biosynthesis of isobutanol, 1-butanol, and 3-methyl-1-butanol. In another embodiment, the 3-keto acid intermediate is 2-aceto-2-hydroxybutyrate. The biosynthetic pathway which uses 2-aceto-2-hydroxybutyrate and an aldehyde as intermediates may be selected from a pathway for the biosynthesis of 2-methyl-1-butanol, 3-methyl-1-pentanol, 4-methyl-1-hexanol, and 5-methyl-1-heptanol.

In another aspect, the invention is directed to a recombinant microorganism comprising a biosynthetic pathway which uses a 3-keto acid as an intermediate and an aldehyde as an intermediate, wherein said recombinant microorganism is (i) engineered to reduce or eliminate the expression or activity of an enzyme catalyzing the conversion of the 3-keto acid intermediate to a 3-hydroxyacid by-product and (ii) engineered to reduce or eliminate the expression or activity of one or more enzymes catalyzing the conversion of the aldehyde to an acid by-product. In one embodiment, the 3-keto acid intermediate is acetolactate. The biosynthetic pathway which uses acetolactate and an aldehyde as intermediates may be selected from a pathway for the biosynthesis of isobutanol, 1-butanol, and 3-methyl-1-butanol. In another embodiment, the 3-keto acid intermediate is 2-aceto-2-hydroxybutyrate. The biosynthetic pathway which uses 2-aceto-2-hydroxybutyrate and an aldehyde as intermediates may be selected from a pathway for the biosynthesis of 2-methyl-1-butanol, 3-methyl-1-pentanol, 4-methyl-1-hexanol, and 5-methyl-1-heptanol.

In various embodiments described herein, the protein involved in catalyzing the conversion of the 3-keto acid intermediate to the 3-hydroxyacid by-product is a ketoreductase. In an exemplary embodiment, the ketoreductase is a 3-ketoacid reductase (3-KAR). In a further exemplary embodiment, the 3-ketoacid reductase is the S. cerevisiae YMR226C (SEQ ID NO: 1) protein or a homolog or variant thereof. In one embodiment, the homolog may be selected from the group consisting of Vanderwaltomzyma polyspora (SEQ ID NO: 2), Saccharomyces castellii (SEQ ID NO: 3), Candida glabrata (SEQ ID NO: 4), Saccharomyces bayanus (SEQ ID NO: 5), Zygosaccharomyces rouxii (SEQ ID NO: 6), K. lactis (SEQ ID NO: 7), Ashbya gossypii (SEQ ID NO: 8), Saccharomyces kluyveri (SEQ ID NO: 9), Kluyveromyces thermotolerans (SEQ ID NO: 10), Kluyveromyces waltii (SEQ ID NO: 11), Pichia stipitis (SEQ ID NO: 12), Debaromyces hansenii (SEQ ID NO: 13), Pichia pastoris (SEQ ID NO: 14), Candida dubliniensis (SEQ ID NO: 15), Candida albicans (SEQ ID NO: 16), Yarrowia lipolytica (SEQ ID NO: 17), Issatchenkia orientalis (SEQ ID NO: 18), Aspergillus nidulans (SEQ ID NO: 19), Aspergillus niger (SEQ ID NO: 20), Neurospora crassa (SEQ ID NO: 21), Schizosaccharomyces pombe (SEQ ID NO: 22), and Kluyveromyces marxianus (SEQ ID NO: 23).

In various embodiments described herein, the protein involved in catalyzing the conversion of an aldehyde to an acid by-product is an aldehyde dehydrogenase (ALDH). In one embodiment, the aldehyde dehydrogenase is encoded by a gene selected from the group consisting of ALD2, ALD3, ALD4, ALD5, ALD6, and HFD1, and homologs and variants thereof. In an exemplary embodiment, the aldehyde dehydrogenase is the S. cerevisiae aldehyde dehydrogenase ALD6 (SEQ ID NO: 25) or homolog or variant thereof. In one embodiment, the homolog may be selected from the group consisting of Saccharomyces castelli (SEQ ID NO: 26), Candida glabrata (SEQ ID NO: 27), Saccharomyces bayanus (SEQ ID NO: 28), Kluyveromyces lactis (SEQ ID NO: 29), Kluyveromyces thermotolerans (SEQ ID NO: 30), Kluyveromyces waltii (SEQ ID NO: 31), Saccharomyces cerevisiae YJ789 (SEQ ID NO: 32), Saccharomyces cerevisiae JAY291 (SEQ ID NO: 33), Saccharomyces cerevisiae EC1118 (SEQ ID NO: 34), Saccharomyces cerevisiae DBY939 (SEQ ID NO: 35), Saccharomyces cerevisiae AWRI1631 (SEQ ID NO: 36), Saccharomyces cerevisiae RM11-1a (SEQ ID NO: 37), Pichia pastoris (SEQ ID NO: 38), Kluyveromyces marxianus (SEQ ID NO: 39), Schizosaccharomyces pombe (SEQ ID NO: 40), and Schizosaccharomyces pombe (SEQ ID NO: 41).

The recombinant microorganisms described herein which produce a beneficial metabolite derived from a biosynthetic pathway which uses a 3-keto acid and an aldehyde as an intermediate may be further engineered to reduce or eliminate enzymatic activity for the conversion of pyruvate to products other than a 3-keto acid (e.g., acetolactate and/or 2-aceto-2-hydroxybutyrate). In one embodiment, the enzymatic activity of pyruvate decarboxylase (PDC), lactate dehydrogenase (LDH), pyruvate oxidase, pyruvate dehydrogenase, and/or glycerol-3-phosphate dehydrogenase (GPD) is reduced or eliminated.

In a specific embodiment, the beneficial metabolite is produced in a recombinant PDC-minus GPD-minus yeast microorganism that overexpresses an acetolactate synthase (ALS) gene. In another specific embodiment, the ALS is encoded by the B. subtilis alsS.

Figure 5:
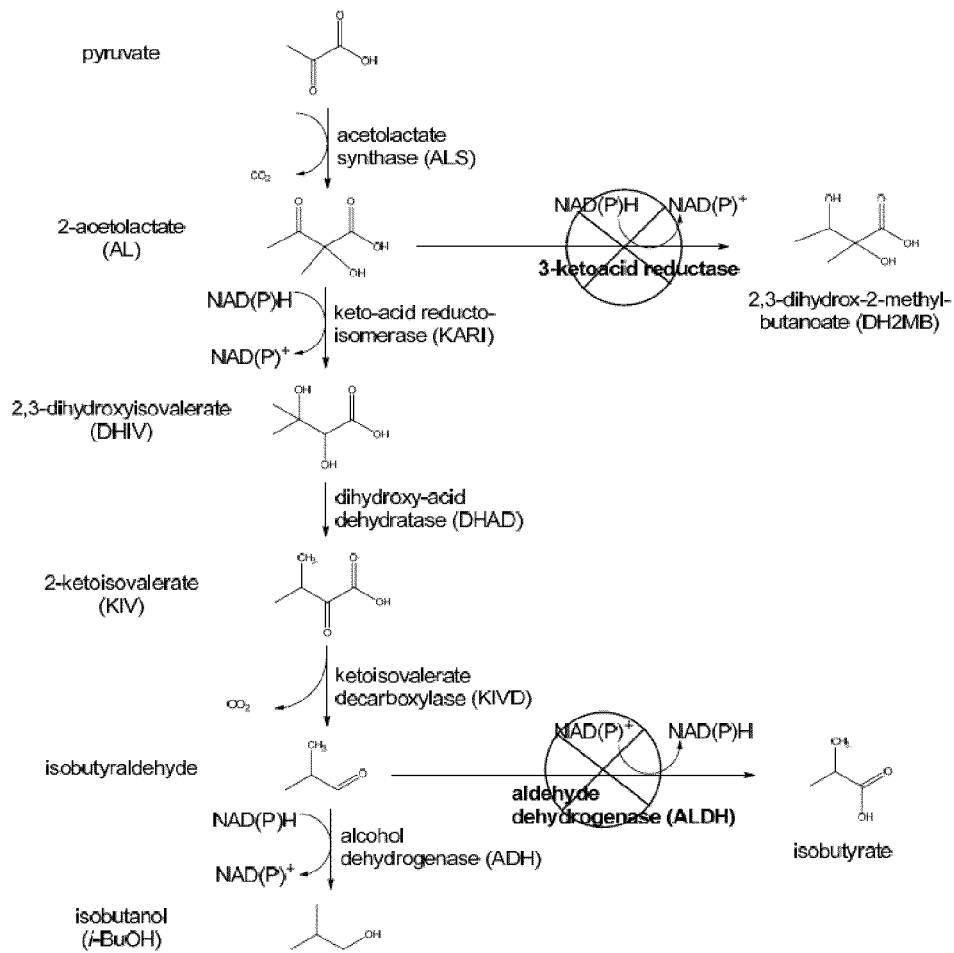
FIG. 5 illustrates a strategy for reducing the production of DH2MB and isobutyrate in isobutanol-producing recombinant microorganisms.

Illustrative Embodiments of Strategies for Reducing Accumulation of 3-Hydroxyacid by-Products and/or Acid by-Products In a specific illustrative embodiment, the recombinant microorganism comprises an isobutanol producing metabolic pathway of which acetolactate and isobutyraldehyde are intermediates, wherein said recombinant microorganism is substantially free of enzymes catalyzing the conversion of the acetolactate intermediate to DH2MB and of the isobutyraldehyde intermediate to isobutyrate. In another specific embodiment, the recombinant microorganism comprises an isobutanol producing metabolic pathway of which acetolactate and isobutyraldehyde are intermediates, wherein said recombinant microorganism is (i) engineered to reduce or eliminate the expression or activity of one or more enzymes catalyzing the conversion of acetolactate to DH2MB and (ii) engineered to reduce or eliminate the expression or activity of one or more enzymes catalyzing the conversion of isobutyraldehyde to isobutyrate. In one embodiment, the enzyme catalyzing the conversion of acetolactate to DH2MB is a 3-ketoacid reductase (3-KAR). In another embodiment, the enzyme catalyzing the conversion of isobutyraldehyde to isobutyrate is an aldehyde dehydrogenase (ALDH). A non-limiting example of such a pathway in which a 3-ketoacid reductase (3-KAR) and an aldehyde dehydrogenase (ALDH) are eliminated is depicted in FIG. 5.

Figure 6:
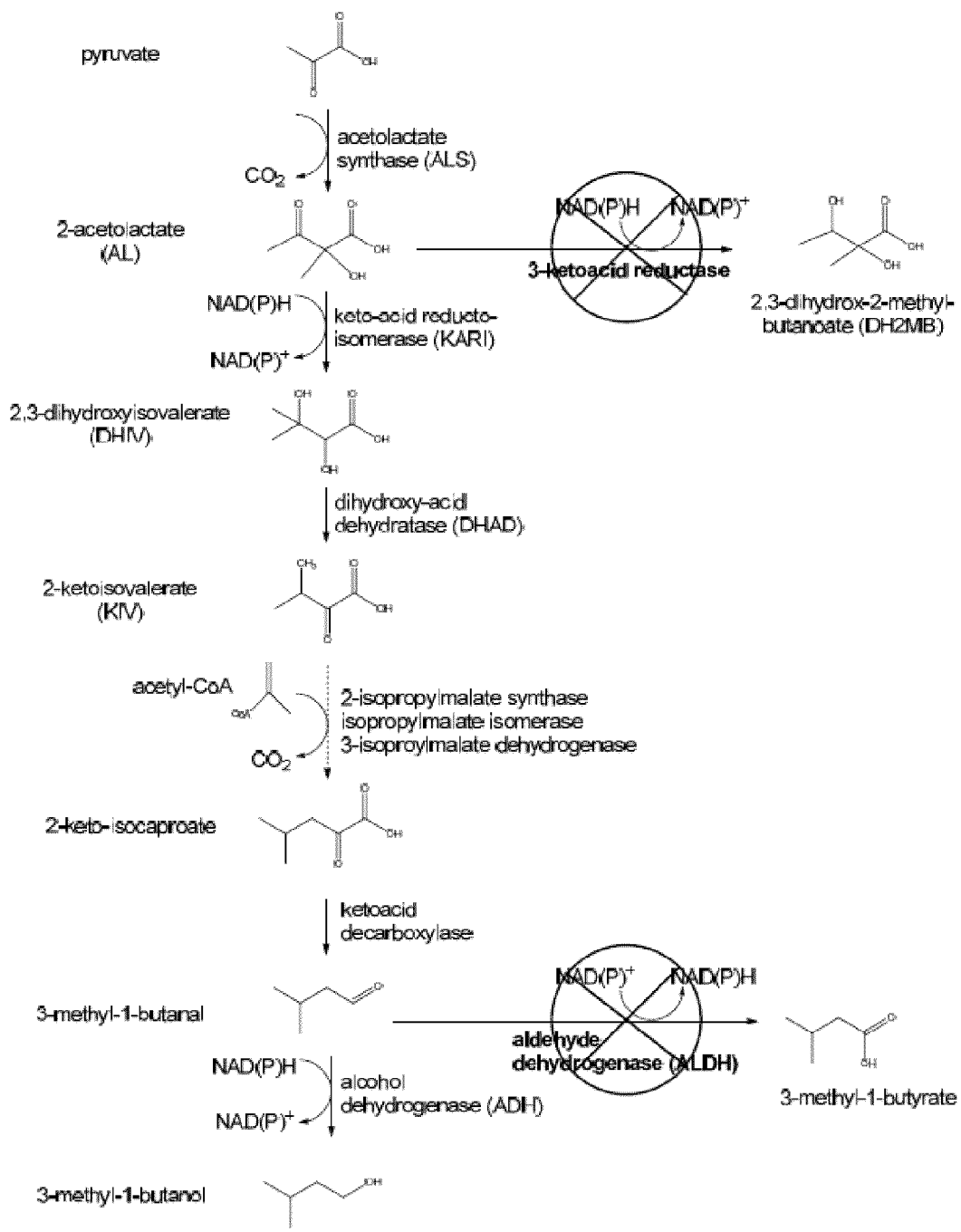
FIG. 6 illustrates a strategy for reducing the production of DH2MB and 3-methyl-1-butyrate in 3-methyl-1-butanol-producing recombinant microorganisms.

In a further specific illustrative embodiment, the recombinant microorganism comprises a 3-methyl-1-butanol producing metabolic pathway of which acetolactate and 3-methyl-1-butanal are intermediates, wherein said recombinant microorganism is substantially free of enzymes catalyzing the conversion of the acetolactate intermediate to DH2MB and of the 3-methyl-1-butanal intermediate to 3-methyl-1-butyrate. In another specific embodiment, the recombinant microorganism comprises a 3-methyl-1-butanol producing metabolic pathway of which acetolactate and 3-methyl-1-butanal are intermediates, wherein said recombinant microorganism is (i) engineered to reduce or eliminate the expression or activity of one or more enzymes catalyzing the conversion of acetolactate to DH2MB and (ii) engineered to reduce or eliminate the expression or activity of one or more enzymes catalyzing the conversion of 3-methyl-1-butanal to 3-methyl-1-butyrate. In one embodiment, the enzyme catalyzing the conversion of acetolactate to DH2MB is a 3-ketoacid reductase (3-KAR). In another embodiment, the enzyme catalyzing the conversion of 3-methyl-1-butanal to 3-methyl-1-butyrate is an aldehyde dehydrogenase (ALDH). A non-limiting example of such a pathway in which a 3-ketoacid reductase (3-KAR) and an aldehyde dehydrogenase (ALDH) are eliminated is depicted in FIG. 6.

Figure 7:
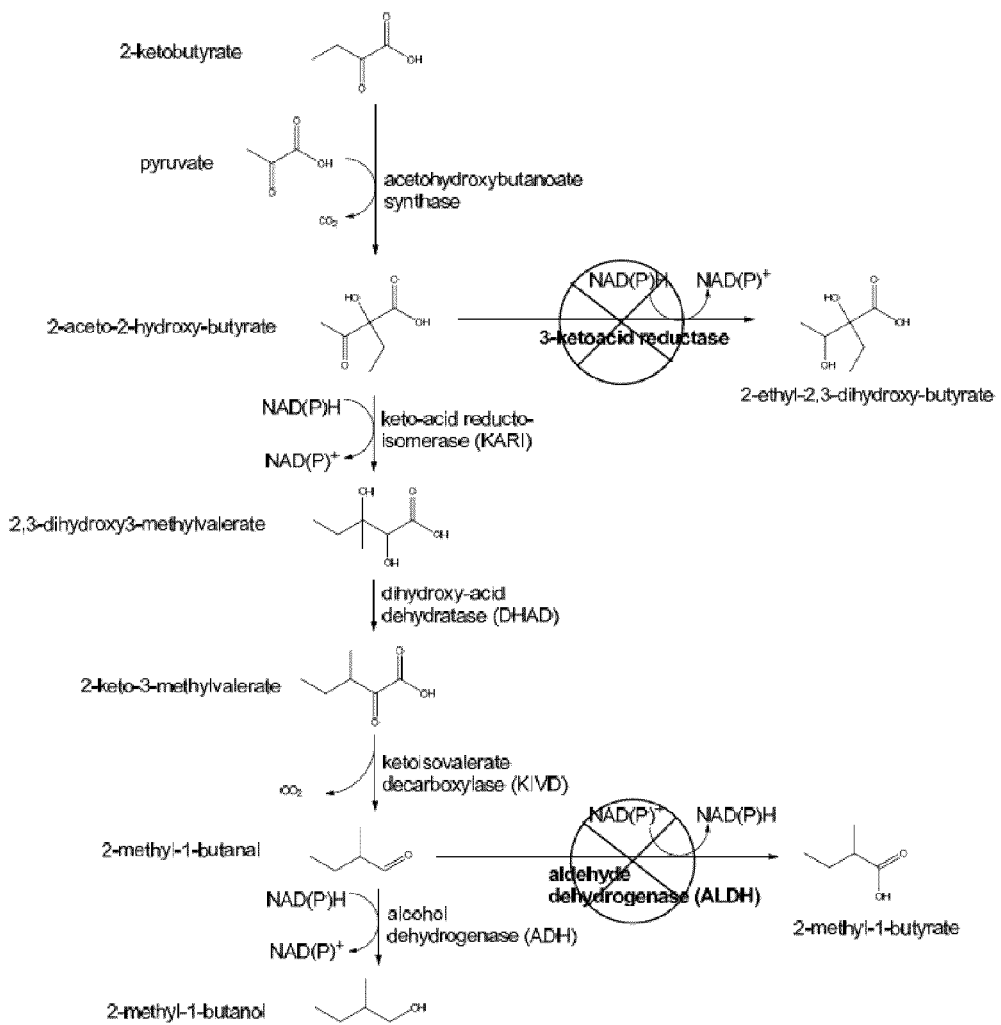
FIG. 7 illustrates a strategy for reducing the production of 2-ethyl-2,3-dihydroxybutyrate and 2-methyl-1-butyrate in 2-methyl-1-butanol producing recombinant microorganisms.

In a further specific illustrative embodiment, the recombinant microorganism comprises a 2-methyl-1-butanol producing metabolic pathway of which acetolactate and 2-methyl-1-butanal are intermediates, wherein said recombinant microorganism is substantially free of enzymes catalyzing the conversion of the 2-aceto-2-hydroxybutyrate intermediate to 2-ethyl-2,3-dihydroxybutyrate and of the 2-methyl-1-butanal intermediate to 2-methyl-1-butyrate. In another specific embodiment, the recombinant microorganism comprises a 2-methyl-1-butanol producing metabolic pathway of which 2-aceto-2-hydroxybutyrate and 2-methyl-1-butanal are intermediates, wherein said recombinant microorganism is (i) engineered to reduce or eliminate the expression or activity of one or more enzymes catalyzing the conversion of 2-aceto-2-hydroxybutyrate to 2-ethyl-2,3-dihydroxybutyrate and (ii) engineered to reduce or eliminate the expression or activity of one or more enzymes catalyzing the conversion of 2-methyl-1-butanal to 2-methyl-1-butyrate. In one embodiment, the enzyme catalyzing the conversion of 2-aceto-2-hydroxybutyrate to 2-ethyl-2,3-dihydroxybutyrate is a 3-ketoacid reductase (3-KAR). In another embodiment, the enzyme catalyzing the conversion of 2-methyl-1-butanal to 2-methyl-1-butyrate is an aldehyde dehydrogenase (ALDH). A non-limiting example of such a pathway in which a 3-ketoacid reductase (3-KAR) and an aldehyde dehydrogenase (ALDH) are eliminated is depicted in FIG. 7.

Overexpression of Enzymes Converting DH2MB into Isobutanol Pathway Intermediates A different approach to reduce or eliminate the production of 2,3-dihydroxy-2-methylbutanoic acid (CAS# 14868-24-7) in isobutanol producing yeast is to overexpress an enzyme that converts DH2MB into an isobutanol pathway intermediate. One way to accomplish this is through the use of an enzyme that catalyzes the interconversion of DH2MB and acetolactate, but favors the oxidation of DH2MB. Therefore, in one embodiment, the present invention provides a recombinant microorganism for producing isobutanol, wherein said recombinant microorganism overexpresses an endogenous or heterologous protein capable of converting DH2MB into acetolactate.

In one embodiment, the endogenous or heterologous protein kinetically favors the oxidative reaction. In another embodiment, the endogenous or heterologous protein has a low $K_M$ for DH2MB and a high $K_M$ for acetolactate. In yet another embodiment, the endogenous or heterologous protein has a low $K_M$ for the oxidized form of its cofactor and a high $K_M$ for the corresponding reduced form of its cofactor. In yet another embodiment, the endogenous or heterologous protein has a higher $k_{cat}$ for the oxidative reaction than for the reductive direction. This endogenous or heterologous protein should preferably have the ability to use a redox cofactor with a high concentration of its oxidized form versus its reduced form.

In one embodiment, the endogenous or heterologous protein is encoded by a gene selected from the group consisting of YAL060W, YJR159W, YGL157W, YBL114W, YOR120W, YKL055C, YBR159W, YBR149W, YDL168W, YDR368W, YLR426W, YCR107W, YILL24W, YML054C, YOL151W, YMR318C, YBR046C, YHR104W, YIR036C, YDL174C, YDR541C, YBR145W, YGL039W, YCR105W, YDL124W, YIR035C, YFL056C, YNL274C, YLR255C, YGL185C, YGL256W, YJR096W, YJR155W, YPL275W, YOR388C, YLR070C, YMR083W, YER081W, YJR139C, YDL243C, YPL113C, YOL165C, YML086C, YMR303C, YDL246C, YLR070C, YHR063C, YNL331C, YFL057C, YIL155C, YOL086C, YAL061W, YDR127W, YPR127W, YCL018W, YIL074C, YIL124W, and YEL071W. In addition, heterologous genes can be overexpressed in isobutanol producing yeast. For examples beta-hydroxy acid dehydrogenases (EC1.1.1.45 and EC1.1.1.60) would be candidates for overexpression.

In another embodiment, the endogenous or heterologous protein kinetically that favors the reductive reaction is engineered to favor the oxidative reaction. In another embodiment, the protein is engineered to have a low $K_M$ for DH2MB and a high $K_M$ for acetolactate. In yet another embodiment, the protein is engineered to have a low $K_M$ for the oxidized form of its cofactor and a high $K_M$ for the corresponding reduced form of its cofactor. In yet another embodiment, the protein is engineered to have a higher $k_{cat}$ for the oxidative reaction than for the reductive direction. This engineered protein should preferably have the ability to use a redox cofactor with a high concentration of its oxidized form versus its reduced form.

Alternatively, an enzyme could be overexpressed that isomerizes DH2MB into DHIV. This approach represents a novel pathway for the production of isobutanol from pyruvate. Thus, in one embodiment, the present invention provides a recombinant microorganism for producing isobutanol, wherein said recombinant microorganism overexpresses an endogenous or heterologous protein capable of converting DH2MB into 2,3-dihydroxyisovalerate.

Overexpression of Enzymes Converting 2-Ethyl-2,3-Dihydroxybutanoate into Biosynthetic Pathway Intermediates A different approach to reduce or eliminate the production of 2-ethyl-2,3-dihydroxybutanoate in yeast is to overexpress an enzyme that converts 2-ethyl-2,3-dihydroxybutanoate into a biosynthetic pathway intermediate. This approach is useful for any biosynthetic pathway which uses 2-aceto-2-hydroxybutyrate as an intermediate, including, but not limited to, 2-methyl-1-butanol, isoleucine, 3-methyl-1-pentanol, 4-methyl-1-hexanol, and 5-methyl-1-heptanol. One way to accomplish this is through the use of an enzyme that catalyzes the interconversion of 2-ethyl-2,3-dihydroxybutanoate and 2-aceto-2-hydroxybutyrate, but favors the oxidation of 2-ethyl-2,3-dihydroxybutanoate. Therefore, in one embodiment, the present invention provides a recombinant microorganism for producing a product selected from 2-methyl-1-butanol, isoleucine, 3-methyl-1-pentanol, 4-methyl-1-hexanol, and 5-methyl-1-heptanol wherein said recombinant microorganism overexpresses an endogenous or heterologous protein capable of converting 2-ethyl-2,3-dihydroxybutanoate into 2-aceto-2-hydroxybutyrate.

In one embodiment, the endogenous or heterologous protein kinetically favors the oxidative reaction. In another embodiment, the endogenous or heterologous protein has a low $K_M$ for 2-ethyl-2,3-dihydroxybutanoate and a high $K_M$ for 2-aceto-2-hydroxybutyrate. In yet another embodiment, the endogenous or heterologous protein has a low $K_M$ for the oxidized form of its cofactor and a high $K_M$ for the corresponding reduced form of its cofactor. In yet another embodiment, the endogenous or heterologous protein has a higher $k_{cat}$ for the oxidative reaction than for the reductive direction. This endogenous or heterologous protein should preferably have the ability to use a redox cofactor with a high concentration of its oxidized form versus its reduced form.

In one embodiment, the endogenous or heterologous protein is encoded by a gene selected from the group consisting of YAL060W, YJR159W, YGL157W, YBL114W, YOR120W, YKL055C, YBR159W, YBR149W, YDL168W, YDR368W, YLR426W, YCR107W, YILL24W, YML054C, YOL151W, YMR318C, YBR046C, YHR104W, YIR036C, YDL174C, YDR541C, YBR145W, YGL039W, YCR105W, YDL124W, YIR035C, YFL056C, YNL274C, YLR255C, YGL185C, YGL256W, YJR096W, YJR155W, YPL275W, YOR388C, YLR070C, YMR083W, YER081W, YJR139C, YDL243C, YPL113C, YOL165C, YML086C, YMR303C, YDL246C, YLR070C, YHR063C, YNL331C, YFL057C, YIL155C, YOL086C, YAL061W, YDR127W, YPR127W, YCL018W, YIL074C, YIL124W, and YEL071W. In addition, heterologous genes can be overexpressed in isoleucine producing yeast. For examples beta-hydroxy acid dehydrogenases (EC1.1.1.45 and EC1.1.1.60) would be candidates for overexpression.

Alternatively an enzyme could be overexpressed that isomerizes 2-ethyl-2,3-dihydroxybutanoate into 2,3-dihydroxy-3-methylvalerate. This approach represents a novel pathway for the production of 2-methyl-1-butanol, isoleucine, 3-methyl-1-pentanol, 4-methyl-1-hexanol, and 5-methyl-1-heptanol from pyruvate. Thus, in one embodiment, the present invention provides a recombinant microorganism for producing a product selected from 2-methyl-1-butanol, isoleucine, 3-methyl-1-pentanol, 4-methyl-1-hexanol, and 5-methyl-1-heptanol, wherein said recombinant microorganism overexpresses an endogenous or heterologous protein capable of converting 2-ethyl-2,3-dihydroxybutanoate into α,β-dihydroxy-β-methylvalerate.

Use of Overexpressed Ketol-Acid Reductoisomerase (KARI) and/or Modified Ketol-Acid Reductoisomerase (KARI) to Reduce the Production of DH2MB As described herein, the conversion of acetolactate to DH2MB competes with the isobutanol pathway for the intermediate acetolactate. In the current yeast isobutanol production strains, ketol-acid reductoisomerase (KARI) catalyzes the conversion of acetolactate to DHIV.

In one embodiment, the present invention provides recombinant microorganisms having an overexpressed ketol-acid reductoisomerase (KARI), which catalyzes the conversion of acetolactate to 2,3-dihydroxyisovalerate (DHIV). The overexpression of KARI has the effect of reducing DH2MB production. In one embodiment, the KARI has at least 0.01 U/mg of activity in the lysate. In another embodiment, the KARI has at least 0.03 U/mg of activity in the lysate. In yet another embodiment, the KARI has at least 0.05, 0.1, 0.5, 1, 2, 5, or 10 U/mg of activity in the lysate.

In a preferred embodiment, the overexpressed KARI is engineered to exhibit a reduced $K_M$ for acetolactate as compared to a wild-type or parental KARI. The use of the modified KARI with lower $K_M$ for acetolactate is expected to reduce the production of the by-product DH2MB. A KARI with lower substrate $K_M$ is identified by screening homologs. In the alternative, the KARI can be engineered to exhibit reduced $K_M$ by directed evolution using techniques known in the art.

In each of these embodiments, the KARI may be a variant enzyme that utilizes NADH (rather than NADPH) as a cofactor. Such enzymes are described in the commonly owned and co-pending publication, US 2010/0143997, which is herein incorporated by reference in its entirety for all purposes.

Use of Overexpressed Dihydroxy Acid Dehydratase (DHAD) to Reduce the Production of DH2MB As described herein, the present inventors have found that overexpression of the isobutanol pathway enzyme, dihydroxyacid dehydratase (DHAD), reduces the production of the by-product, DH2MB.

Accordingly, in one embodiment, the present invention provides recombinant microorganisms having an dihydroxyacid dehydratase (DHAD), which catalyzes the conversion of 2,3-dihydroxyisovalerate (DHIV) to 2-ketoisovalerate (KIV). The overexpression of DHAD has the effect of reducing DH2MB production. In one embodiment, the DHAD has at least 0.01 U/mg of activity in the lysate. In another embodiment, the DHAD has at least 0.03 U/mg of activity in the lysate. In yet another embodiment, the DHAD has at least 0.05, 0.1, 0.5, 1, 2, 5, or 10 U/mg of activity in the lysate.

Recombinant Microorganisms for the Production of 3-Hydroxyacids

The present invention provides in additional aspects recombinant microorganisms for the production of 3-hydroxyacids as a product or a metabolic intermediate. In one embodiment, these 3-hydroxyacid-producing recombinant microorganisms express acetolactate synthase (ALS) and a 3-ketoacid reductase catalyzing the reduction of 2-acetolactate to DH2MB. In another embodiment, these 3-hydroxyacid-producing recombinant microorganisms express acetolactate synthase (ALS) and a 3-ketoacid reductase catalyzing the reduction of 2-aceto-2-hydroxybutyrate into 2-ethyl-2,3-dihydroxybutyrate.

These 3-hydroxyacid-producing recombinant microorganisms may be further engineered to reduce or eliminate enzymatic activity for the conversion of pyruvate to products other than acetolactate. In one embodiment, the enzymatic activity of pyruvate decarboxylase (PDC), lactate dehydrogenase (LDH), pyruvate oxidase, pyruvate dehydrogenase, and/or glycerol-3-phosphate dehydrogenase (GPD) is reduced or eliminated.

In a specific embodiment, DH2MB is produced in a recombinant PDC-minus GPD-minus yeast microorganism that overexpresses an ALS gene and expresses a 3-ketoacid reductase. In one embodiment, the 3-ketoacid reductase is natively expressed. In another embodiment, the 3-ketoacid reductase is heterologously expressed. In yet another embodiment, the 3-ketoacid reductase is overexpressed. In a specific embodiment, the 3-ketoacid reductase is encoded by the S. cerevisiae TMA29 gene or a homolog thereof. In another specific embodiment, the ALS is encoded by the B. subtilis AlsS.

In another specific embodiment, 2-ethyl-2,3-dihydroxybutyrate is produced in a recombinant PDC-minus GPD-minus yeast microorganism that overexpresses an ALS gene and expresses a 3-ketoacid reductase. In one embodiment, the 3-ketoacid reductase is natively expressed. In another embodiment, the 3-ketoacid reductase is heterologously expressed. In yet another embodiment, the 3-ketoacid reductase is overexpressed. In a specific embodiment, the 3-ketoacid reductase is encoded by the S. cerevisiae TMA29 gene or a homolog thereof. In another specific embodiment, the ALS is encoded by the B. subtilis AlsS.

In accordance with these additional aspects, the present invention also provides a method of producing 2,3-dihydroxy-2-methylbutanoic acid (DH2MB), comprising: (a) providing a DH2MB-producing recombinant microorganism that expresses acetolactate synthase (ALS) and a 3-ketoacid reductase catalyzing the reduction of 2-acetolactate to DH2MB, and (b) cultivating said recombinant microorganism in a culture medium containing a feedstock providing the carbon source, until a recoverable quantity of DH2MB is produced.

In accordance with these additional aspects, the present invention also provides a method of producing 2-ethyl-2,3-dihydroxybutyrate, comprising: (a) providing a 2-ethyl-2,3-dihydroxybutyrate-producing recombinant microorganism that expresses acetolactate synthase (ALS) and a 3-ketoacid reductase catalyzing the reduction of 2-aceto-2-hydroxybutyrate to 2-ethyl-2,3-dihydroxybutyrate, and (b) cultivating said recombinant microorganism in a culture medium containing a feedstock providing the carbon source, until a recoverable quantity of 2-ethyl-2,3-dihydroxybutyrate is produced.

Recombinant Microorganisms for the Production of Acid Products

The present invention provides in additional aspects recombinant microorganisms for the production of acid products derived from aldehydes. In one embodiment, these acid product producing recombinant microorganisms express an aldehyde dehydrogenase catalyzing the conversion of an aldehyde to a corresponding acid product. These acid product producing recombinant microorganisms may be further engineered to reduce or eliminate competing enzymatic activity for the undesirable conversion of metabolites upstream of the desired acid product.

In a specific embodiment, the acid product is produced in a recombinant yeast microorganism that overexpresses an aldehyde dehydrogenase. In one embodiment, the aldehyde dehydrogenase is natively expressed. In another embodiment, the aldehyde dehydrogenase is heterologously expressed. In yet another embodiment, the aldehyde dehydrogenase is overexpressed. In a specific embodiment, the aldehyde dehydrogenase is encoded by the S. cerevisiae ALD6 gene or a homolog thereof.

In accordance with this additional aspect, the present invention also provides a method of producing an acid product, comprising: (a) providing an acid product-producing recombinant microorganism that expresses an aldehyde dehydrogenase catalyzing the conversion of an aldehyde to acid product, and (b) cultivating said recombinant microorganism in a culture medium containing a feedstock providing the carbon source, until a recoverable quantity of the desired acid product is produced.

The Microorganism in General

The recombinant microorganisms provided herein can express a plurality of heterologous and/or native enzymes involved in pathways for the production of beneficial metabolites such as isobutanol, 2-butanol, 1-butanol, 2-butanone, 2,3-butanediol, acetoin, diacetyl, valine, leucine, pantothenic acid, isobutylene, 3-methyl-1-butanol, coenzyme A, 2-methyl-1-butanol, isoleucine, 1-pentanol, 1-hexanol, 3-methyl-1-pentanol, 4-methyl-1-pentanol, 4-methyl-1-hexanol, 5-methyl-1-heptanol, and 1-propanol from a suitable carbon source. A non-limiting list of beneficial metabolites produced in engineered biosynthetic pathways is found herein at Tables 1-3.

As described herein, "engineered" or "modified" microorganisms are produced via the introduction of genetic material into a host or parental microorganism of choice and/or by modification of the expression of native genes, thereby modifying or altering the cellular physiology and biochemistry of the microorganism. Through the introduction of genetic material and/or the modification of the expression of native genes the parental microorganism acquires new properties, e.g., the ability to produce a new, or greater quantities of, an intracellular and/or extracellular metabolite. As described herein, the introduction of genetic material into and/or the modification of the expression of native genes in a parental microorganism results in a new or modified ability to produce beneficial metabolites such as isobutanol, 2-butanol, 1-butanol, 2-butanone, 2,3-butanediol, acetoin, diacetyl, valine, leucine, pantothenic acid, isobutylene, 3-methyl-1-butanol, coenzyme A, 2-methyl-1-butanol, isoleucine, 1-pentanol, 1-hexanol, 3-methyl-1-pentanol, 4-methyl-1-pentanol, 4-methyl-1-hexanol, 5-methyl-1-heptanol, and 1-propanol from a suitable carbon source. The genetic material introduced into and/or the genes modified for expression in the parental microorganism contains gene(s), or parts of genes, coding for one or more of the enzymes involved in a biosynthetic pathway for the production of one or more metabolites selected from isobutanol, 2-butanol, 1-butanol, 2-butanone, 2,3-butanediol, acetoin, diacetyl, valine, leucine, pantothenic acid, isobutylene, 3-methyl-1-butanol, coenzyme A, 2-methyl-1-butanol, isoleucine, 1-pentanol, 1-hexanol, 3-methyl-1-pentanol, 4-methyl-1-pentanol, 4-methyl-1-hexanol, 5-methyl-1-heptanol, and 1-propanol and may also include additional elements for the expression and/or regulation of expression of these genes, e.g., promoter sequences.

In addition to the introduction of a genetic material into a host or parental microorganism, an engineered or modified microorganism can also include alteration, disruption, deletion or knocking-out of a gene or polynucleotide to alter the cellular physiology and biochemistry of the microorganism. Through the alteration, disruption, deletion or knocking-out of a gene or polynucleotide the microorganism acquires new or improved properties (e.g., the ability to produce a new metabolite or greater quantities of an intracellular metabolite, to improve the flux of a metabolite down a desired pathway, and/or to reduce the production of by-products).

Recombinant microorganisms provided herein may also produce metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate), an intermediate (e.g., 2-ketoisovalerate), or an end product (e.g., isobutanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias."

Optimized coding sequences containing codons preferred by a particular prokaryotic or eukaryotic host (Murray et al., 1989, *Nucl Acids Res.* 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996, *Nucl Acids Res.* 24: 216-8). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites are encompassed by the microorganisms and methods provided herein.

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, *Methods in Mol Biol* 25: 365-89).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See commonly owned and co-pending application US 2009/0226991. A typical algorithm used comparing a molecule sequence to a database containing a large number of sequences from different organisms is the computer program BLAST. When searching a database containing sequences from a large number of different organisms, it is typical to compare amino acid sequences. Database searching using amino acid sequences can be measured by algorithms described in commonly owned and co-pending application US 2009/0226991.

It is understood that a range of microorganisms can be modified to include a recombinant metabolic pathway suitable for the production of beneficial metabolites from acetolactate- and/or aldehyde intermediate-requiring biosynthetic pathways. In various embodiments, microorganisms may be selected from yeast microorganisms. Yeast microorganisms for the production of a metabolite such as isobutanol, 2-butanol, 1-butanol, 2-butanone, 2,3-butanediol, acetoin, diacetyl, valine, leucine, pantothenic acid, isobutylene, 3-methyl-1-butanol, coenzyme A, 2-methyl-1-butanol, isoleucine, 1-pentanol, 1-hexanol, 3-methyl-1-pentanol, 4-methyl-1-pentanol, 4-methyl-1-hexanol, 5-methyl-1-heptanol, and 1-propanol may be selected based on certain characteristics:

One characteristic may include the property that the microorganism is selected to convert various carbon sources into beneficial metabolites such as isobutanol, 2-butanol, 1-butanol, 2-butanone, 2,3-butanediol, acetoin, diacetyl, valine, leucine, pantothenic acid, isobutylene, 3-methyl-1-butanol, coenzyme A, 2-methyl-1-butanol, isoleucine, 1-pentanol, 1-hexanol, 3-methyl-1-pentanol, 4-methyl-1-pentanol, 4-methyl-1-hexanol, 5-methyl-1-heptanol, and 1-propanol. The term "carbon source" generally refers to a substance suitable to be used as a source of carbon for prokaryotic or eukaryotic cell growth. Examples of suitable carbon sources are described in commonly owned and co-pending application US 2009/0226991. Accordingly, in one embodiment, the recombinant microorganism herein disclosed can convert a variety of carbon sources to products, including but not limited to glucose, galactose, mannose, xylose, arabinose, lactose, sucrose, and mixtures thereof.

The recombinant microorganism may thus further include a pathway for the production of isobutanol, 2-butanol, 1-butanol, 2-butanone, 2,3-butanediol, acetoin, diacetyl, valine, leucine, pantothenic acid, isobutylene, 3-methyl-1-butanol, coenzyme A, 2-methyl-1-butanol, isoleucine, 1-pentanol, 1-hexanol, 3-methyl-1-pentanol, 4-methyl-1-pentanol, 4-methyl-1-hexanol, 5-methyl-1-heptanol, and 1-propanol from five-carbon (pentose) sugars including xylose. Most yeast species metabolize xylose via a complex route, in which xylose is first reduced to xylitol via a xylose reductase (XR) enzyme. The xylitol is then oxidized to xylulose via a xylitol dehydrogenase (XDH) enzyme. The xylulose is then phosphorylated via a xylulokinase (XK) enzyme. This pathway operates inefficiently in yeast species because it introduces a redox imbalance in the cell. The xylose-to-xylitol step uses NADH as a cofactor, whereas the xylitol-to-xylulose step uses NADPH as a cofactor. Other processes must operate to restore the redox imbalance within the cell. This often means that the organism cannot grow anaerobically on xylose or other pentose sugars. Accordingly, a yeast species that can efficiently ferment xylose and other pentose sugars into a desired fermentation product is therefore very desirable.

Thus, in one aspect, the recombinant microorganism is engineered to express a functional exogenous xylose isomerase. Exogenous xylose isomerases functional in yeast are known in the art. See, e.g., Rajgarhia et al., US2006/0234364, which is herein incorporated by reference in its entirety. In an embodiment according to this aspect, the exogenous xylose isomerase gene is operatively linked to promoter and terminator sequences that are functional in the yeast cell. In a preferred embodiment, the recombinant microorganism further has a deletion or disruption of a native gene that encodes for an enzyme (e.g., XR and/or XDH) that catalyzes the conversion of xylose to xylitol. In a further preferred embodiment, the recombinant microorganism also contains a functional, exogenous xylulokinase (XK) gene operatively linked to promoter and terminator sequences that are functional in the yeast cell. In one embodiment, the xylulokinase (XK) gene is overexpressed.

In one embodiment, the microorganism has reduced or no pyruvate decarboxylase (PDC) activity. PDC catalyzes the decarboxylation of pyruvate to acetaldehyde, which is then reduced to ethanol by ADH via an oxidation of NADH to NAD+. Ethanol production is the main pathway to oxidize the NADH from glycolysis. Deletion of this pathway increases the pyruvate and the reducing equivalents (NADH) available for the biosynthetic pathway. Accordingly, deletion of PDC genes can further increase the yield of desired metabolites.

In another embodiment, the microorganism has reduced or no glycerol-3-phosphate dehydrogenase (GPD) activity. GPD catalyzes the reduction of dihydroxyacetone phosphate (DHAP) to glycerol-3-phosphate (G3P) via the oxidation of NADH to NAD+. Glycerol is then produced from G3P by Glycerol-3-phosphatase (GPP). Glycerol production is a secondary pathway to oxidize excess NADH from glycolysis. Reduction or elimination of this pathway would increase the pyruvate and reducing equivalents (NADH) available for the biosynthetic pathway. Thus, deletion of GPD genes can further increase the yield of desired metabolites.

In yet another embodiment, the microorganism has reduced or no PDC activity and reduced or no GPD activity. PDC-minus/GPD-minus yeast production strains are described in commonly owned and co-pending publications, US 2009/0226991 and US 2011/0020889, both of which are herein incorporated by reference in their entireties for all purposes.

In one embodiment, the yeast microorganisms may be selected from the "*Saccharomyces* Yeast Clade", as described in commonly owned and co-pending application US 2009/0226991.

The term "*Saccharomyces sensu stricto*" taxonomy group is a cluster of yeast species that are highly related to *S. cerevisiae* (Rainieri et al., 2003, *J. Biosci Bioengin* 96: 1-9). *Saccharomyces sensu stricto* yeast species include but are not limited to *S. cerevisiae, S. kudriavzevii, S. mikatae, S. bayanus, S. uvarum, S. carocanis* and hybrids derived from these species (Masneuf et al., 1998, *Yeast* 7: 61-72).

An ancient whole genome duplication (WGD) event occurred during the evolution of the hemiascomycete yeast and was discovered using comparative genomic tools (Kellis et al., 2004, *Nature* 428: 617-24; Dujon et al., 2004, *Nature* 430:35-44; Langkjaer et al., 2003, *Nature* 428: 848-52; Wolfe et al., 1997, *Nature* 387: 708-13). Using this major evolutionary event, yeast can be divided into species that diverged from a common ancestor following the WGD event (termed "post-WGD yeast" herein) and species that diverged from the yeast lineage prior to the WGD event (termed "pre-WGD yeast" herein).

Accordingly, in one embodiment, the yeast microorganism may be selected from a post-WGD yeast genus, including but not limited to *Saccharomyces* and *Candida*. The favored post-WGD yeast species include: *S. cerevisiae, S. uvarum, S. bayanus, S. paradoxus, S. castelli*, and *C. glabrata*.

In another embodiment, the yeast microorganism may be selected from a pre-whole genome duplication (pre-WGD) yeast genus including but not limited to *Saccharomyces, Kluyveromyces, Candida, Pichia, Issatchenkia, Debaryomyces, Hansenula, Yarrowia and, Schizosaccharomyces*. Representative pre-WGD yeast species include: *S. kluyveri, K. thermotolerans, K. marxianus, K. waltii, K. lactis, C. tropicalis, P. pastoris, P. anomala, P. stipitis, I. orientalis, I. occidentalis, I. scutulata, D. hansenii, H. anomala, Y. lipolytica*, and *S. pombe*.

A yeast microorganism may be either Crabtree-negative or Crabtree-positive as described in described in commonly owned and co-pending application US 2009/0226991. In one embodiment the yeast microorganism may be selected from yeast with a Crabtree-negative phenotype including but not limited to the following genera: *Saccharomyces, Kluyveromyces, Pichia, Issatchenkia, Hansenula,* and *Candida*. Crabtree-negative species include but are not limited to: *S. kluyveri, K. lactis, K. marxianus, P. anomala, P. stipitis, I. orientalis, I. occidentalis, I. scutulata, H. anomala,* and *C. utilis*. In another embodiment, the yeast microorganism may be selected from yeast with a Crabtree-positive phenotype, including but not limited to *Saccharomyces, Kluyveromyces, Zygosaccharomyces, Debaryomyces, Pichia* and *Schizosaccharomyces*. Crabtree-positive yeast species include but are not limited to: *S. cerevisiae, S. uvarum, S. bayanus, S. paradoxus, S. castelli, K. thermotolerans, C. glabrata, Z. bailli, Z. rouxii, D. hansenii, P. pastorius,* and *S. pombe*.

Another characteristic may include the property that the microorganism is that it is non-fermenting. In other words, it cannot metabolize a carbon source anaerobically while the yeast is able to metabolize a carbon source in the presence of oxygen. Nonfermenting yeast refers to both naturally occurring yeasts as well as genetically modified yeast. During anaerobic fermentation with fermentative yeast, the main pathway to oxidize the NADH from glycolysis is through the production of ethanol. Ethanol is produced by alcohol dehydrogenase (ADH) via the reduction of acetaldehyde, which is generated from pyruvate by pyruvate decarboxylase (PDC). In one embodiment, a fermentative yeast can be engineered to be non-fermentative by the reduction or elimination of the native PDC activity. Thus, most of the pyruvate produced by glycolysis is not consumed by PDC and is available for the isobutanol pathway. Deletion of this pathway increases the pyruvate and the reducing equivalents available for the biosynthetic pathway. Fermentative pathways contribute to low yield and low productivity of desired metabolites such as isobutanol. Accordingly, deletion of PDC genes may increase yield and productivity of desired metabolites such as isobutanol.

In some embodiments, the recombinant microorganisms may be microorganisms that are non-fermenting yeast microorganisms, including, but not limited to those, classified into a genera selected from the group consisting of *Tricosporon, Rhodotorula, Myxozyma,* or *Candida*. In a specific embodiment, the non-fermenting yeast is *C. xestobii*.

Isobutanol-Producing Yeast Microorganisms

As described herein, in one embodiment, a yeast microorganism is engineered to convert a carbon source, such as glucose, to pyruvate by glycolysis and the pyruvate is converted to isobutanol via an isobutanol producing metabolic pathway (See, e.g., WO/2007/050671, WO/2008/098227, and Atsumi et al., 2008, Nature 45: 86-9). Alternative pathways for the production of isobutanol have been described in WO/2007/050671 and in Dickinson et al., 1998, *J Biol Chem* 273:25751-6.

Accordingly, in one embodiment, the isobutanol producing metabolic pathway to convert pyruvate to isobutanol can be comprised of the following reactions:

1. 2 pyruvate→acetolactate+$CO_2$
2. acetolactate+NAD(P)H→2,3-dihydroxyisovalerate+$NAD(P)^+$
3. 2,3-dihydroxyisovalerate→alpha-ketoisovalerate
4. alpha-ketoisovalerate→isobutyraldehyde+$CO_2$
5. isobutyraldehyde+NAD(P)H→isobutanol+NAD(P)+

These reactions are carried out by the enzymes 1) Acetolactate Synthase (ALS), 2) Ketol-acid Reducto-Isomerase (KARI), 3) Dihydroxy-acid dehydratase (DHAD), 4) Ketoisovalerate decarboxylase (KIVD), and 5) an Alcohol dehydrogenase (ADH) (FIG. 1). In another embodiment, the yeast microorganism is engineered to overexpress these enzymes. For example, these enzymes can be encoded by native genes. Alternatively, these enzymes can be encoded by heterologous genes. For example, ALS can be encoded by the alsS gene of *B. subtilis*, alsS of *L. lactis*, or the ilvK gene of *K. pneumonia*. For example, KARI can be encoded by the ilvC genes of *E. coli, C. glutamicum, M. maripaludis,* or *Piromyces* sp E2. For example, DHAD can be encoded by the ilvD genes of *E. coli, C. glutamicum,* or *L. lactis*. For example, KIVD can be encoded by the kivD gene of *L. lactis*. ADH can be encoded by ADH2, ADH6, or ADH7 of *S. cerevisiae* or adhA of *L. lactis*.

In one embodiment, pathway steps 2 and 5 may be carried out by KARI and ADH enzymes that utilize NADH (rather than NADPH) as a co-factor. Such enzymes are described in the commonly owned and co-pending publication, US 2010/0143997, which is herein incorporated by reference in its entirety for all purposes. The present inventors have found that utilization of NADH-dependent KARI and ADH enzymes to catalyze pathway steps 2 and 5, respectively, surprisingly enables production of isobutanol under anaerobic conditions. Thus, in one embodiment, the recombinant microorganisms of the present invention may use an NADH-dependent KARI to catalyze the conversion of acetolactate (+NADH) to produce 2,3-dihydroxyisovalerate. In another embodiment, the recombinant microorganisms of the present invention may use an NADH-dependent ADH to catalyze the conversion of isobutyraldehyde (+NADH) to produce isobutanol. In yet another embodiment, the recombinant microorganisms of the present invention may use both an NADH-dependent KARI to catalyze the conversion of acetolactate (+NADH) to produce 2,3-dihydroxyisovalerate, and an NADH-dependent ADH to catalyze the conversion of isobutyraldehyde (+NADH) to produce isobutanol.

In another embodiment, the yeast microorganism may be engineered to have increased ability to convert pyruvate to isobutanol. In one embodiment, the yeast microorganism may be engineered to have increased ability to convert pyruvate to isobutyraldehyde. In another embodiment, the yeast microorganism may be engineered to have increased ability to convert pyruvate to keto-isovalerate. In another embodiment, the yeast microorganism may be engineered to have increased ability to convert pyruvate to 2,3-dihydroxyisovalerate. In another embodiment, the yeast microorganism may be engineered to have increased ability to convert pyruvate to acetolactate.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum*, *Kluyveromyces* spp., including *K. thermotolerans, K. lactis,* and *K. marxianus*, *Pichia* spp., *Hansenula* spp., including *H. polymorpha*, *Candida* spp., *Trichosporon* spp., *Yamadazyma* spp., including *Y.* spp. *stipitis, Torulaspora pretoriensis, Issatchenkia orientalis,*

*Schizosaccharomyces* spp., including *S. pombe*, *Cryptococcus* spp., *Aspergillus* spp., *Neurospora* spp., or *Ustilago* spp. Sources of genes from anaerobic fungi include, but not limited to, *Piromyces* spp., *Orpinomyces* spp., or *Neocallimastix* spp. Sources of prokaryotic enzymes that are useful include, but not limited to, *Escherichia. coli, Zymomonas mobilis, Staphylococcus aureus, Bacillus* spp., *Clostridium* spp., *Corynebacterium* spp., *Pseudomonas* spp., *Lactococcus* spp., *Enterobacter* spp., and *Salmonella* spp.

In one embodiment, the invention is directed to a recombinant microorganism for producing isobutanol, wherein said recombinant microorganism comprises an isobutanol producing metabolic pathway and wherein said microorganism is engineered to reduce or eliminate the expression or activity of an enzyme catalyzing the conversion of acetolactate to DH2MB. In some embodiments, the enzyme catalyzing the conversion of acetolactate to DH2MB is a 3-ketoacid reductase (3-KAR). In a specific embodiment, the 3-ketoacid reductase is encoded by the *S. cerevisiae* TMA29 (YMR226C) gene or a homolog thereof. In one embodiment, the homolog may be selected from the group consisting of *Vanderwaltomzyma polyspora* (SEQ ID NO: 2), *Saccharomyces castellii* (SEQ ID NO: 3), *Candida glabrata* (SEQ ID NO: 4), *Saccharomyces bayanus* (SEQ ID NO: 5), *Zygosaccharomyces rouxii* (SEQ ID NO: 6), *Kluyveromyces lactis* (SEQ ID NO: 7), *Ashbya gossypii* (SEQ ID NO: 8), *Saccharomyces kluyveri* (SEQ ID NO: 9), *Kluyveromyces thermotolerans* (SEQ ID NO: 10), *Kluyveromyces waltii* (SEQ ID NO: 11), *Pichia stipitis* (SEQ ID NO: 12), *Debaromyces hansenii* (SEQ ID NO: 13), *Pichia pastoris* (SEQ ID NO: 14), *Candida dubliniensis* (SEQ ID NO: 15), *Candida albicans* (SEQ ID NO: 16), *Yarrowia lipolytica* (SEQ ID NO: 17), *Issatchenkia orientalis* (SEQ ID NO: 18), *Aspergillus nidulans* (SEQ ID NO: 19), *Aspergillus niger* (SEQ ID NO: 20), *Neurospora crassa* (SEQ ID NO: 21), *Schizosaccharomyces pombe* (SEQ ID NO: 22), and *Kluyveromyces marxianus* (SEQ ID NO: 23).

In another embodiment, the invention is directed to a recombinant microorganism for producing isobutanol, wherein said recombinant microorganism comprises an isobutanol producing metabolic pathway and wherein said microorganism is engineered to reduce or eliminate the expression or activity of an enzyme catalyzing the conversion of isobutyraldehyde to isobutyrate. In some embodiments, the enzyme catalyzing the conversion of isobutyraldehyde to isobutyrate is an aldehyde dehydrogenase. In an exemplary embodiment, the aldehyde dehydrogenase is the *S. cerevisiae* aldehyde dehydrogenase ALD6 (SEQ ID NO: 25) or a homolog or variant thereof. In one embodiment, the homolog is selected from the group consisting of *Saccharomyces castelli* (SEQ ID NO: 26), *Candida glabrata* (SEQ ID NO: 27), *Saccharomyces bayanus* (SEQ ID NO: 28), *Kluyveromyces lactis* (SEQ ID NO: 29), *Kluyveromyces thermotolerans* (SEQ ID NO: 30), *Kluyveromyces waltii* (SEQ ID NO: 31), *Saccharomyces cerevisiae* YJ789 (SEQ ID NO: 32), *Saccharomyces cerevisiae* JAY291 (SEQ ID NO: 33), *Saccharomyces cerevisiae* EC1118 (SEQ ID NO: 34), *Saccharomyces cerevisiae* DBY939 (SEQ ID NO: 35), *Saccharomyces cerevisiae* AWRI1631 (SEQ ID NO: 36), *Saccharomyces cerevisiae* RM11-1a (SEQ ID NO: 37), *Pichia pastoris* (SEQ ID NO: 38), *Kluyveromyces marxianus* (SEQ ID NO: 39), *Schizosaccharomyces pombe* (SEQ ID NO: 40), and *Schizosaccharomyces pombe* (SEQ ID NO: 41).

In yet another embodiment, the invention is directed to a recombinant microorganism for producing isobutanol, wherein said recombinant microorganism comprises an isobutanol producing metabolic pathway and wherein said microorganism is (i) engineered to reduce or eliminate the expression or activity of an enzyme catalyzing the conversion of acetolactate to DH2MB and (ii) engineered to reduce or eliminate the expression or activity of an enzyme catalyzing the conversion of isobutyraldehyde to isobutyrate. In some embodiments, the enzyme catalyzing the conversion of acetolactate to DH2MB is a 3-ketoacid reductase (3-KAR). In a specific embodiment, the 3-ketoacid reductase is encoded by the *S. cerevisiae* TMA29 (YMR226C) gene or a homolog or variant thereof. In one embodiment, the homolog is selected from the group consisting of *Vanderwaltomzyma polyspora* (SEQ ID NO: 2), *Saccharomyces castellii* (SEQ ID NO: 3), *Candida glabrata* (SEQ ID NO: 4), *Saccharomyces bayanus* (SEQ ID NO: 5), *Zygosaccharomyces rouxii* (SEQ ID NO: 6), *Kluyveromyces lactis* (SEQ ID NO: 7), *Ashbya gossypii* (SEQ ID NO: 8), *Saccharomyces kluyveri* (SEQ ID NO: 9), *Kluyveromyces thermotolerans* (SEQ ID NO: 10), *Kluyveromyces waltii* (SEQ ID NO: 11), *Pichia stipitis* (SEQ ID NO: 12), *Debaromyces hansenii* (SEQ ID NO: 13), *Pichia pastoris* (SEQ ID NO: 14), *Candida dubliniensis* (SEQ ID NO: 15), *Candida albicans (SEQ ID NO:* 16), *Yarrowia lipolytica* (SEQ ID NO: 17), *Issatchenkia orientalis* (SEQ ID NO: 18), *Aspergillus nidulans* (SEQ ID NO: 19), *Aspergillus niger* (SEQ ID NO: 20), *Neurospora crassa* (SEQ ID NO: 21), *Schizosaccharomyces pombe* (SEQ ID NO: 22), and *Kluyveromyces marxianus* (SEQ ID NO: 23). In some embodiments, the enzyme catalyzing the conversion of isobutyraldehyde to isobutyrate is an aldehyde dehydrogenase. In a specific embodiment, the aldehyde dehydrogenase is the *S. cerevisiae* aldehyde dehydrogenase ALD6 (SEQ ID NO: 25) or a homolog or variant thereof. In one embodiment, the homolog is selected from the group consisting of *Saccharomyces castelli* (SEQ ID NO: 26), *Candida glabrata* (SEQ ID NO: 27), *Saccharomyces bayanus* (SEQ ID NO: 28), *Kluyveromyces lactis* (SEQ ID NO: 29), *Kluyveromyces thermotolerans* (SEQ ID NO: 30), *Kluyveromyces waltii* (SEQ ID NO: 31), *Saccharomyces cerevisiae* YJ789 (SEQ ID NO: 32), *Saccharomyces cerevisiae* JAY291 (SEQ ID NO: 33), *Saccharomyces cerevisiae* EC1118 (SEQ ID NO: 34), *Saccharomyces cerevisiae* DBY939 (SEQ ID NO: 35), *Saccharomyces cerevisiae* AWRI1631 (SEQ ID NO: 36), *Saccharomyces cerevisiae* RM11-1a (SEQ ID NO: 37), *Pichia pastoris* (SEQ ID NO: 38), *Kluyveromyces marxianus* (SEQ ID NO: 39), *Schizosaccharomyces pombe* (SEQ ID NO: 40), and *Schizosaccharomyces pombe* (SEQ ID NO: 41).

In one embodiment, the isobutanol producing metabolic pathway comprises at least one exogenous gene that catalyzes a step in the conversion of pyruvate to isobutanol. In another embodiment, the isobutanol producing metabolic pathway comprises at least two exogenous genes that catalyze steps in the conversion of pyruvate to isobutanol. In yet another embodiment, the isobutanol producing metabolic pathway comprises at least three exogenous genes that catalyze steps in the conversion of pyruvate to isobutanol. In yet another embodiment, the isobutanol producing metabolic pathway comprises at least four exogenous genes that catalyze steps in the conversion of pyruvate to isobutanol. In yet another embodiment, the isobutanol producing metabolic pathway comprises at five exogenous genes that catalyze steps in the conversion of pyruvate to isobutanol.

In one embodiment, one or more of the isobutanol pathway genes encodes an enzyme that is localized to the cytosol. In one embodiment, the recombinant microorganisms comprise an isobutanol producing metabolic pathway with at least one isobutanol pathway enzyme localized in the cytosol. In another embodiment, the recombinant microorganisms comprise an isobutanol producing metabolic pathway with at least two isobutanol pathway enzymes localized in the cytosol. In yet another embodiment, the recombinant microorganisms comprise an isobutanol producing metabolic pathway with at least three isobutanol pathway enzymes localized in the cytosol. In yet another embodiment, the recombinant microorganisms comprise an isobutanol producing metabolic pathway with at least four isobutanol pathway enzymes localized in the cytosol. In an exemplary embodiment, the recombinant microorganisms comprise an isobutanol producing metabolic pathway with five isobutanol pathway enzymes localized in the cytosol. Isobutanol producing metabolic pathways in which one or more genes are localized to the cytosol are described in commonly owned and co-pending U.S. application Ser. No. 12/855,276, which is herein incorporated by reference in its entirety for all purposes.

Expression of Modified Alcohol Dehydrogenases in the Production of Isobutanol

Another strategy described herein for reducing the production of the by-product isobutyrate is to increase the activity and/or expression of an alcohol dehydrogenase (ADH) responsible for the conversion of isobutyraldehyde to isobutanol. This strategy prevents competition by endogenous enzymes for the isobutanol pathway intermediate, isobutyraldehyde. An increase in the activity and/or expression of ADH may be achieved by various means. For example, ADH activity can be increased by utilizing a promoter with increased promoter strength or by increasing the copy number of the alcohol dehydrogenase gene.

In alternative embodiments, the production of the by-product isobutyrate may be reduced by utilizing an ADH with increased specific activity for isobutyraldehyde. Such ADH enzymes with increased specific activity for isobutyraldehyde may be identified in nature, or may result from modifications to the ADH enzyme, such as the modifications described herein. In some embodiments, these modifications will produce a decrease in the Michaelis-Menten constant ($K_M$) for isobutyraldehyde. Through the use of such modified ADH enzymes, competition by endogenous enzymes for isobutyraldehyde is further limited. In one embodiment, the isobutyrate yield (mol isobutyrate per mol glucose) in a recombinant microorganism comprising a modified ADH as described herein is less than about 5%. In another embodiment, the isobutyrate yield (mol isobutyrate per mol glucose) in a recombinant microorganism comprising a modified ADH as described herein is less than about 1%. In yet another embodiment, the isobutyrate yield (mol isobutyrate per mol glucose) in a recombinant microorganism comprising a modified ADH as described herein is less than about 0.5%, less than about 0.1%, less than about 0.05%, or less than about 0.01%.

Further, by utilizing a modified ADH enzyme, the present inventors may establish a situation in which the forward reaction (i.e. the isobutyraldehyde conversion to isobutanol) is the favored reaction over the reverse reaction (i.e. the conversion of isobutanol to isobutyraldehyde).

The strategies described above generally lead to a decrease in isobutyrate yield, which is accompanied by an increase in isobutanol yield. Hence, the above strategies are useful for decreasing the isobutyrate yield and/or titer and for increasing the ratio of isobutanol yield over isobutyrate yield.

Accordingly, in one aspect, the present application describes the generation of modified ADHs with enhanced activity that can facilitate improved isobutanol production when co-expressed with the remaining four isobutanol pathway enzymes. In one embodiment according to this aspect, the present application is directed to recombinant microorganisms comprising one or more modified ADHs. In one embodiment, the recombinant microorganism is further engineered to reduce or eliminate the expression or activity of an enzyme catalyzing the conversion of acetolactate to DH2MB as described herein. In another embodiment, the recombinant microorganism is further engineered to reduce or eliminate the expression or activity of an enzyme catalyzing the conversion of isobutyraldehyde to isobutyrate as described herein.

In addition to the isobutanol biosynthetic pathway, other biosynthetic pathways utilize ADH enzymes for the conversion of an aldehyde to an alcohol. For example, ADH enzymes convert various aldehydes to alcohols as part of biosynthetic pathways for the production of 1-propanol, 2-propanol, 1-butanol, 2-butanol, 1-pentanol, 2-methyl-1-butanol, 3- and methyl-1-butanol.

As used herein, the terms "ADH" or "ADH enzyme" or "alcohol dehydrogenase" are used interchangeably herein to refer to an enzyme that catalyzes the conversion of isobutyraldehyde to isobutanol. ADH sequences are available from a vast array of microorganisms, including, but not limited to, *L. lactis* (SEQ ID NO: 175), *Streptococcus pneumoniae*, *Staphylococcus aureus*, and *Bacillus cereus*. ADH enzymes modifiable by the methods of the present invention include, but are not limited to those, disclosed in commonly owned and co-pending U.S. Patent Publication No. 2010/0143997. A representative list of ADH enzymes modifiable by the methods described herein can be found in Table 97.

Modified ADH Enzymes

In accordance with the invention, any number of mutations can be made to the ADH enzymes, and in one embodiment, multiple mutations can be made to result in an increased ability to convert isobutyraldehyde to isobutanol. Such mutations include point mutations, frame shift mutations, deletions, and insertions, with one or more (e.g., one, two, three, four, five, or six, etc.) point mutations preferred. In an exemplary embodiment, the modified ADH enzyme comprises one or more mutations at positions corresponding to amino acids selected from: (a) tyrosine 50 of the *L. lactis* AdhA (SEQ ID NO: 185); (b) glutamine 77 of the *L. lactis* AdhA (SEQ ID NO: 185); (c) valine 108 of the *L. lactis* AdhA (SEQ ID NO: 185); (d) tyrosine 113 of the *L. lactis* AdhA (SEQ ID NO: 185); (e) isoleucine 212 of the *L. lactis* AdhA (SEQ ID NO: 185); and (f) leucine 264 of the *L. lactis* AdhA (SEQ ID NO: 185), wherein AdhA (SEQ ID NO: 185) is encoded by the *L. lactis* alcohol dehydrogenase (ADH) gene adhA (SEQ ID NO: 184) or a codon-optimized version thereof (SEQ ID NO: 206).

Mutations may be introduced into the ADH enzymes of the present invention using any methodology known to those skilled in the art. Mutations may be introduced randomly by, for example, conducting a PCR reaction in the presence of manganese as a divalent metal ion cofactor. Alternatively, oligonucleotide directed mutagenesis may be used to create the modified ADH enzymes which allows for all possible classes of base pair changes at any determined site along the encoding DNA molecule. In general, this technique involves annealing an oligonucleotide complementary (except for one or more mismatches) to a single stranded nucleotide sequence coding for the ADH enzyme of interest. The mismatched oligonucleotide is then extended by DNA polymerase, generating a double-stranded DNA molecule which contains the desired change in sequence in one strand. The changes in sequence can, for example, result in the deletion, substitution, or insertion of an amino acid. The double-stranded polynucleotide can then be inserted into an appropriate expression vector, and a mutant or modified polypeptide can thus be produced. The above-described oligonucleotide directed mutagenesis can, for example, be carried out via PCR.

Enzymes for use in the compositions and methods of the invention include any enzyme having the ability to convert isobutyraldehyde to isobutanol. Such enzymes include, but are not limited to, the *L. lactis* AdhA, the *S. pneumoniae* AdhA, the *S. aureus* AdhA, and the *Bacillus cereus* AdhA, amongst others. Additional ADH enzymes modifiable by the methods of the present invention include, but are not limited to those, disclosed in commonly owned and co-pending U.S. Patent Publication No. 2010/0143997. A representative list of ADH enzymes modifiable by the methods described herein can be found in Table 16. As will be understood by one of ordinary skill in the art, modified ADH enzymes may be obtained by recombinant or genetic engineering techniques that are routine and well-known in the art. Modified ADH enzymes can, for example, be obtained by mutating the gene or genes encoding the ADH enzyme of interest by site-directed or random mutagenesis. Such mutations may include point mutations, deletion mutations, and insertional mutations. For example, one or more point mutations (e.g., substitution of one or more amino acids with one or more different amino acids) may be used to construct modified ADH enzymes of the invention.

The invention further includes homologous ADH enzymes which are 5%, 10%, 20%, 30%, 40%, 50%, 60%, 70%, 75%, 80%, 85%, 90%, 95%, 96%, 97%, 98%, or 99% identical at the amino acid level to a wild-type ADH enzyme (e.g., *L. lactis* AdhA or *E. coli* AdhA) and exhibit an increased ability to convert isobutyraldehyde to isobutanol. Also included within the invention are ADH enzymes, which are 50%, 60%, 70%, 75%, 80%, 85%, 90%, 95%, 96%, 97%, 98%, or 99% identical at the amino acid level to an ADH enzyme comprising the amino acid sequence set out in SEQ ID NO: 185 and exhibit an increased ability to convert isobutyraldehyde to isobutanol as compared to the unmodified wild-type enzyme. The invention also includes nucleic acid molecules, which encode the above-described ADH enzymes.

The invention also includes fragments of ADH enzymes which comprise at least 50, 100, 150, 200, 250, 300, 350, 400, 450, 500, 550, or 600 amino acid residues and retain one or more activities associated with ADH enzymes. Such fragments may be obtained by deletion mutation, by recombinant techniques that are routine and well-known in the art, or by enzymatic digestion of the ADH enzyme(s) of interest using any of a number of well-known proteolytic enzymes. The invention further includes nucleic acid molecules, which encode the above described modified ADH enzymes and ADH enzyme fragments.

By a protein or protein fragment having an amino acid sequence at least, for example, 50% "identical" to a reference amino acid sequence, it is intended that the amino acid sequence of the protein is identical to the reference sequence except that the protein sequence may include up to 50 amino acid alterations per each 100 amino acids of the amino acid sequence of the reference protein. In other words, to obtain a protein having an amino acid sequence at least 50% identical to a reference amino acid sequence, up to 50% of the amino acid residues in the reference sequence may be deleted or substituted with another amino acid, or a number of amino acids up to 50% of the total amino acid residues in the reference sequence may be inserted into the reference sequence. These alterations of the reference sequence may occur at the amino (N—) and/or carboxy (C—) terminal positions of the reference amino acid sequence and/or anywhere between those terminal positions, interspersed either individually among residues in the reference sequence and/or in one or more contiguous groups within the reference sequence. As a practical matter, whether a given amino acid sequence is, for example, at least 50% identical to the amino acid sequence of a reference protein can be determined conventionally using known computer programs such as those described above for nucleic acid sequence identity determinations, or using the CLUSTAL W program (Thompson, J. D., et al., *Nucleic Acids Res.* 22:4673 4680 (1994)).

In one aspect, amino acid substitutions are made at one or more of the above identified positions (i.e., amino acid positions equivalent or corresponding to Y50, Q77, V108, Y113, I212, or L264 of *L. lactis* AdhA (SEQ ID NO: 185)). Thus, the amino acids at these positions may be substituted with any other amino acid including Ala, Asn, Arg, Asp, Cys, Gln, Glu, Gly, His, Ile, Leu, Lys, Met, Phe, Pro, Ser, Thr, Trp, Tyr, and Val. A specific example of a ADH enzyme which exhibits an increased ability to convert isobutyraldehyde to isobutanol is an ADH in which (1) the tyrosine at position 50 has been replaced with a phenylalanine or tryptophan residue, (2) the glutamine at position 77 has been replaced with an arginine or serine residue, (3) the valine at position 108 has been replaced with a serine or alanine residue, (4) the tyrosine at position 113 has been replaced with a phenylalanine or glycine residue, (5), the isoleucine at position 212 has been replaced with a threonine or valine residue, and/or (6) the leucine at position 264 is replaced with a valine residue.

Polypeptides having the ability to convert isobutyraldehyde to isobutanol for use in the invention may be isolated from their natural prokaryotic or eukaryotic sources according to standard procedures for isolating and purifying natural proteins that are well-known to one of ordinary skill in the art (see, e.g., Houts, G. E., et al., *J. Virol.* 29:517 (1979)). In addition, polypeptides having the ability to convert isobutyraldehyde to isobutanol may be prepared by recombinant DNA techniques that are familiar to one of ordinary skill in the art (see, e.g., Kotewicz, M. L., et al., *Nucl. Acids Res.* 16:265 (1988); Soltis, D. A., and Skalka, A. M., *Proc. Natl. Acad. Sci. USA* 85:3372 3376 (1988)).

In one aspect of the invention, modified ADH enzymes are made by recombinant techniques. To clone a gene or other nucleic acid molecule encoding an ADH enzyme which will be modified in accordance with the invention, isolated DNA which contains the ADH enzyme gene or open reading frame may be used to construct a recombinant DNA library. Any vector, well known in the art, can be used to clone the ADH enzyme of interest. However, the vector used must be compatible with the host in which the recombinant vector will be transformed.

Prokaryotic vectors for constructing the plasmid library include plasmids such as those capable of replication in *E. coli* such as, for example, pBR322, ColE1, pSC101, pUC-vectors (pUC18, pUC19, etc.: In: Molecular Cloning, A Laboratory Manual, Cold Spring Harbor Laboratory Press, Cold Spring Harbor, N.Y. (1982); and Sambrook et al., In: Molecular Cloning A Laboratory Manual (2d ed.) Cold Spring Harbor Laboratory Press, Cold Spring Harbor, N.Y. (1989)). *Bacillus* plasmids include pC194, pUB110, pE194, pC221, pC217, etc. Such plasmids are disclosed by Glyczan, T. In: The Molecular Biology Bacilli, Academic Press, York (1982), 307 329. Suitable *Streptomyces* plasmids include pIJ101 (Kendall et al., *J. Bacteriol.* 169:4177 4183 (1987)). *Pseudomonas* plasmids are reviewed by John et al., (Rad. Insec. Dis. 8:693 704 (1986)), and Igaki, (Jpn. J. Bacteriol. 33:729 742 (1978)). Broad-host range plasmids or cosmids, such as pCP13 (Darzins and Chakrabarty, *J. Bacteriol.* 159:9 18 (1984)) can also be used for the present invention.

Suitable hosts for cloning the ADH nucleic acid molecules of interest are prokaryotic hosts. One example of a prokaryotic host is *E. coli*. However, the desired ADH nucleic acid molecules of the present invention may be cloned in other prokaryotic hosts including, but not limited to, hosts in the genera *Escherichia, Bacillus, Streptomyces, Pseudomonas, Salmonella, Serratia*, and *Proteus*.

Eukaryotic hosts for cloning and expression of the ADH enzyme of interest include yeast and fungal cells. A particularly preferred eukaryotic host is yeast. Expression of the desired ADH enzyme in such eukaryotic cells may require the use of eukaryotic regulatory regions which include eukaryotic promoters. Cloning and expressing the ADH nucleic acid molecule in eukaryotic cells may be accomplished by well known techniques using well known eukaryotic vector systems.

In accordance with the invention, one or more mutations may be made in any ADH enzyme of interest in order to increase the ability of the enzyme to convert isobutyraldehyde to isobutanol, or confer other properties described herein upon the enzyme, in accordance with the invention. Such mutations include point mutations, frame shift mutations, deletions, and insertions. Preferably, one or more point mutations, resulting in one or more amino acid substitutions, are used to produce ADH enzymes having an enhanced ability to convert isobutyraldehyde to isobutanol. In a preferred aspect of the invention, one or more mutations at positions equivalent or corresponding to position Y50 (e.g., Y50W or Y50F), Q77 (e.g., Q77S or Q77R), V108 (e.g. V108S or V108A), Y113 (e.g., Y113F or Y113G), I212 (e.g., I212T or I212V), and/or L264 (e.g. L264V) of the *L. lactis* AdhA (SEQ ID NO: 185) enzyme may be made to produce the desired result in other ADH enzymes of interest.

The corresponding positions of the ADH enzymes identified herein (e.g. the *L. lactis* AdhA of SEQ ID NO: 185) may be readily identified for other ADH enzymes by one of skill in the art. Thus, given the defined region and the assays described in the present application, one with skill in the art can make one or a number of modifications, which would result in an increased ability to convert isobutyraldehyde to isobutanol in any ADH enzyme of interest.

In a preferred embodiment, the modified ADH enzymes have from 1 to 6 amino acid substitutions selected from positions corresponding to Y50, Q77, V108, Y113, I212, or L264 as compared to the wild-type ADH enzymes. In other embodiments, the modified ADH enzymes have additional amino acid substitutions at other positions as compared to the respective wild-type ADH enzymes. Thus, modified ADH enzymes may have at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 different residues in other positions as compared to the respective wild-type ADH enzymes. As will be appreciated by those of skill in the art, the number of additional positions that may have amino acid substitutions will depend on the wild-type ADH enzyme used to generate the variants. Thus, in some instances, up to 50 different positions may have amino acid substitutions.

It is understood that various microorganisms can act as "sources" for genetic material encoding ADH enzymes suitable for use in a recombinant microorganism provided herein. For example, In addition, genes encoding these enzymes can be identified from other fungal and bacterial species and can be expressed for the modulation of this pathway. A variety of organisms could serve as sources for these enzymes, including, but not limited to, *Lactococcus* sp., including *L. lactis, Lactobacillus* sp., including *L. brevis, L. buchneri, L. hilgardii, L. fermentum, L. reuteri, L. vaginalis, L. antri, L. oris*, and *L. coleohominis, Pediococcus* sp., including *P. acidilactici, Bacillus* sp., including *B. cereus, B. thuringiensis, B. coagulans, B. anthracis, B. weihenstephanensis, B. mycoides*, and *B. amyloliquefaciens, Leptotrichia* sp., including *L. goodfellowii, L. buccalis*, and *L. hofstadii, Actinobacillus* sp., including *A. pleuropneumoniae, Streptococcus* sp., including *S. sanguinis, S. parasanguinis, S. gordonii, S. pneumoniae*, and *S. mitis, Streptobacillus* sp., including *S. moniliformis, Staphylococcus* sp., including *S. aureus, Eikenella* sp., including *E. corrodens, Weissella* sp., including *W. paramesenteroides, Kingella* sp., including *K. oralis*, and *Rothia* sp., including *R. dentocariosa*, and *Exiguobacterium* sp.

The nucleotide sequences for several ADH enzymes are known. For instance, the sequences of ADH enzymes are available from a vast array of microorganisms, including, but not limited to, *L. lactis* (SEQ ID NO: 185), *S. pneumoniae, S. aureus*, and *Bacillus cereus*. ADH enzymes modifiable by the methods of the present invention include, but are not limited to those, disclosed in commonly owned and co-pending U.S. Patent Publication No. 2010/0143997. A representative list of ADH enzymes modifiable by the methods described herein can be found in Table 97.

In addition, any method can be used to identify genes that encode for ADH enzymes with a specific activity. Generally, homologous or analogous genes with similar activity can be identified by functional, structural, and/or genetic analysis. In most cases, homologous or analogous genes with similar activity will have functional, structural, or genetic similarities. Techniques known to those skilled in the art may be suitable to identify homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous genes, proteins, or enzymes, techniques may include, but not limited to, cloning a gene by PCR using primers based on a published sequence of a gene/enzyme or by degenerate PCR using degenerate primers designed to amplify a conserved region among a gene. Further, one skilled in the art can use techniques to identify homologous or analogous genes, proteins, or enzymes with functional homology or similarity. Techniques include examining a cell or cell culture for the catalytic efficiency or the specific activity of an enzyme through in vitro enzyme assays for said activity, then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or analogous genes with similar activity, techniques also include comparison of data concerning a candidate gene or enzyme with databases such as BRENDA, KEGG, or MetaCYC. The candidate gene or enzyme may be identified within the above mentioned databases in accordance with the teachings herein. Furthermore, enzymatic activity can be determined phenotypically.

Methods of Making ADH Enzymes with Enhanced Catalytic Efficiency

The present invention further provides methods of engineering ADH enzymes to enhance their catalytic efficiency.

One approach to increasing the catalytic efficiency of ADH enzymes is by saturation mutagenesis with NNK libraries. These libraries may be screened for increases in catalytic efficiency in order to identify, which single mutations contribute to an increased ability to convert isobutyraldehyde to isobutanol. Combinations of mutations at aforementioned residues may be investigated by any method. For example, a combinatorial library of mutants may be designed based on the results of the saturation mutagenesis studies.

Another approach is to use random oligonucleotide mutagenesis to generate diversity by incorporating random mutations, encoded on a synthetic oligonucleotide, into the enzyme. The number of mutations in individual enzymes within the population may be controlled by varying the length of the target sequence and the degree of randomization during synthesis of the oligonucleotides. The advantages of this more defined approach are that all possible amino acid mutations and also coupled mutations can be found.

If the best variants from the experiments described above do not display sufficient activity, directed evolution via error-prone PCR may be used to obtain further improvements. Error-prone PCR mutagenesis of the ADH enzyme may be performed followed by screening for ADH activity.

Enhanced ADH Catalytic Efficiency

In one aspect, the catalytic efficiency of the modified ADH enzyme is enhanced. As used herein, the phrase "catalytic efficiency" refers to the property of the ADH enzyme that allows it to convert isobutyraldehyde to isobutanol.

In one embodiment, the catalytic efficiency of the modified ADH is enhanced as compared to the wild-type or parental ADH. Preferably, the catalytic efficiency of the modified ADH enzyme is enhanced by at least about 5% as compared to the wild-type or parental ADH. More preferably, the catalytic efficiency of the modified ADH enzyme is enhanced by at least about 15% as compared to the wild-type or parental ADH. More preferably, the catalytic efficiency of the modified ADH enzyme is enhanced by at least about 25% as compared to the wild-type or parental ADH. More preferably, the catalytic efficiency of the modified ADH enzyme is enhanced by at least about 50% as compared to the wild-type or parental ADH. More preferably, the catalytic efficiency of the modified ADH enzyme is enhanced by at least about 75% as compared to the wild-type or parental ADH. More preferably, the catalytic efficiency of the modified ADH enzyme is enhanced by at least about 100% as compared to the wild-type or parental ADH. More preferably, the catalytic efficiency of the modified ADH enzyme is enhanced by at least about 200% as compared to the wild-type or parental ADH. More preferably, the catalytic efficiency of the modified ADH enzyme is enhanced by at least about 500% as compared to the wild-type or parental ADH. More preferably, the catalytic efficiency of the modified ADH enzyme is enhanced by at least about 1000% as compared to the wild-type or parental ADH. More preferably, the catalytic efficiency of the modified ADH enzyme is enhanced by at least about 2000% as compared to the wild-type or parental ADH. More preferably, the catalytic efficiency of the modified ADH enzyme is enhanced by at least about 3000% as compared to the wild-type or parental ADH. Most preferably, the catalytic efficiency of the modified ADH enzyme is enhanced by at least about 3500% as compared to the wild-type or parental ADH.

Gene Expression of Modified ADH Enzymes

Provided herein are methods for the expression of one or more of the modified ADH enzyme genes involved the production of beneficial metabolites and recombinant DNA expression vectors useful in the method. Thus, included within the scope of the disclosure are recombinant expression vectors that include such nucleic acids. The term expression vector refers to a nucleic acid that can be introduced into a host microorganism or cell-free transcription and translation system. An expression vector can be maintained permanently or transiently in a microorganism, whether as part of the chromosomal or other DNA in the microorganism or in any cellular compartment, such as a replicating vector in the cytoplasm. An expression vector also comprises a promoter that drives expression of an RNA, which typically is translated into a polypeptide in the microorganism or cell extract. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host microorganisms containing the vector can be identified and/or selected, may also be present in an expression vector. Selectable markers, i.e., genes that confer antibiotic resistance or sensitivity, are used and confer a selectable phenotype on transformed cells when the cells are grown in an appropriate selective medium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433), can also be used. For *E. coli* expression vectors, it is useful to include an *E. coli* origin of replication, such as from pUC, p1 P, p1, and pBR.

Thus, recombinant expression vectors contain at least one expression system, which, in turn, is composed of at least a portion of a biosynthetic gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

Moreover, methods for expressing a polypeptide from a nucleic acid molecule that are specific to a particular microorganism (i.e. a yeast microorganism) are well known. For example, nucleic acid constructs that are used for the expression of heterologous polypeptides within *Kluyveromyces* and *Saccharomyces* are well known (see, e.g., U.S. Pat. Nos. 4,859,596 and 4,943,529, each of which is incorporated by reference herein in its entirety for *Kluyveromyces* and, e.g., Gellissen et al., Gene 190(1):87-97 (1997) for *Saccharomyces*. Yeast plasmids have a selectable marker and an origin of replication, also known as Autonomously Replicating Sequences (ARS). In addition certain plasmids may also contain a centromeric sequence. These centromeric plasmids are generally a single or low copy plasmid. Plasmids without a centromeric sequence and utilizing either a 2 micron (*S. cerevisiae*) or 1.6 micron (*K. lactis*) replication origin are high copy plasmids. The selectable marker can be either prototrophic, such as HIS3, TRP1, LEU2, URA3 or ADE2, or antibiotic resistance, such as, bar, ble, hph, or kan.

A nucleic acid of the disclosure can be amplified using cDNA, mRNA synthetic DNA, or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated nucleic acid molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Although the effect of an amino acid change varies depending upon factors such as phosphorylation, glycosylation, intra-chain linkages, tertiary structure, and the role of the amino acid in the active site or a possible allosteric site, it is generally preferred that the substituted amino acid is from the same group as the amino acid being replaced. To some extent the following groups contain amino acids, which are interchangeable: the basic amino acids lysine, arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids.

Methods in General
Identification of 3-Ketoacid Reductase Homologs

Any method can be used to identify genes that encode for enzymes with 3-ketoacid reductase activity, including, but not limited to *S. cerevisiae* TMA29. Generally, genes that are homologous or similar to 3-ketoacid reductases such as TMA29 can be identified by functional, structural, and/or genetic analysis. In most cases, homologous or similar genes and/or homologous or similar enzymes will have functional, structural, or genetic similarities.

The *S. cerevisiae* gene TMA29 is also known as YMR226C. The open reading frame (ORF) YMR226C is found on the *S. cerevisiae* Chromosome XIII at positions 722395 . . . 721592. The chromosomal location of YMR226C is a region that is highly syntenic to chromosomes in many related yeast [Byrne, K. P. and K. H. Wolfe (2005) "The Yeast Gene Order Browser: combining curated homology and syntenic context reveals gene fate in polyploid species." Genome Res. 15(10):1456-61. Scannell, D. R., K. P. Byrne, J. L. Gordon, S. Wong, and K. H. Wolfe (2006) "Multiple rounds of speciation associated with reciprocal gene loss in polyploidy yeasts." *Nature* 440: 341-5. Scannell, D. R., A. C. Frank, G. C. Conant, K. P. Byrne, M. Woolfit, and K. H. Wolfe (2007) "Independent sorting-out of thousands of duplicated gene pairs in two yeast species descended from a whole-genome duplication." *Proc Natl Acad Sci USA* 104: 8397-402.]

For example, locations of the syntenic versions of YMR226C from other yeast species can be found on Chromosome 13 in *Candida glabrata*, Chromosome 1 in *Zygosaccharomyces rouxii*, Chromosome 2 in *K. lactis*, Chromosome 6 in *Ashbya gossypii*, Chromosome 8 in *S. kluyveri*, Chromosome 4 in *K. thermotolerance* and Chromosome 8 from the inferred ancestral yeast species [Gordon, J. L., K. P. Byrne, and K. H. Wolfe (2009) "Additions, losses, and rearrangements on the evolutionary route from a reconstructed ancestor to the modern *Saccharomyces cerevisiae* genome." *PLoS Genet.* 5: e1000485.]

Using this syntenic relationship, species-specific versions of this gene are readily identified and examples can be found in Table 4.

TABLE 4

YMR226C and homologs thereof.

| Species | Gene Name | SEQ ID NO: |
|---|---|---|
| S. cerevisiae | YMR226C | 1 |
| K. polyspora | Kpol_1043p53 | 2 |
| S. castellii | Scas_594.12d | 3 |
| C. glabrata | CAGL0M11242g | 4 |
| S. bayanus | Sbay_651.2 | 5 |
| Z. rouxii | ZYRO0A05742p | 6 |
| K. lactis | KLLA0B08371g | 7 |
| A. gossypii | AFR561Wp | 8 |
| S. kluyveri | SAKL0H04730g | 9 |
| K. thermotolerans | KLTH0D13002p | 10 |
| K. waltii | Kwal_26.9160 | 11 |

In addition to synteny, fungal homologs to the *S. cerevisiae* TMA29 gene may be identified by one skilled in the art through tools such as BLAST and sequence alignment. These other homologs may be deleted in a similar manner from the respective yeast species to eliminate the accumulation of the 3-hydroxyacid by-product. Examples of homologous proteins can be found in *Vanderwaltomzyma polyspora* (SEQ ID NO: 2), *Saccharomyces castellii* (SEQ ID NO: 3), *Candida glabrata* (SEQ ID NO: 4), *Saccharomyces bayanus* (SEQ ID NO: 5), *Zygosaccharomyces rouxii* (SEQ ID NO: 6), *K. lactis* (SEQ ID NO: 7), *Ashbya gossypii* (SEQ ID NO: 8), *Saccharomyces kluyveri* (SEQ ID NO: 9), *Kluyveromyces thermotolerans* (SEQ ID NO: 10), *Kluyveromyces waltii* (SEQ ID NO: 11), *Pichia stipitis* (SEQ ID NO: 12), *Debaromyces hansenii* (SEQ ID NO: 13), *Pichia pastoris* (SEQ ID NO: 14), *Candida dubliniensis* (SEQ ID NO: 15), *Candida albicans* (SEQ ID NO: 16), *Yarrowia lipolytica* (SEQ ID NO: 17), *Issatchenkia orientalis* (SEQ ID NO: 18), *Aspergillus nidulans* (SEQ ID NO: 19), *Aspergillus niger* (SEQ ID NO: 20),

*Neurospora crassa* (SEQ ID NO: 21), *Schizosaccharomyces pombe* (SEQ ID NO: 22), and *Kluyveromyces marxianus* (SEQ ID NO: 23).

Techniques known to those skilled in the art may be suitable to identify additional homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous genes, proteins, or enzymes, techniques may include, but not limited to, cloning a dehydratase gene by PCR using primers based on a published sequence of a gene/enzyme or by degenerate PCR using degenerate primers designed to amplify a conserved region among dehydratase genes. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K. *Branched-Chain Amino Acids* Methods Enzymology, 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein.

Identification of Aldehyde Dehydrogenase Homologs

Any method can be used to identify genes that encode for enzymes with aldehyde dehydrogenase activity, including, but not limited, to the *S. cerevisiae* ALD6. Generally, genes that are homologous or similar to aldehyde dehydrogenases such as ALD6 can be identified by functional, structural, and/or genetic analysis. In most cases, homologous or similar genes and/or homologous or similar enzymes will have functional, structural, or genetic similarities.

The *S. cerevisiae* gene ALD6 is also known by its systematic name YPL061W. The open reading frame (ORF) YPL061W is found on the *S. cerevisiae* Chromosome XVI at positions 432585 . . . 434087. The chromosomal location of YPL061W is a region that is highly syntenic to chromosomes in many related yeast [Byrne, K. P. and K. H. Wolfe (2005) "The Yeast Gene Order Browser: combining curated homology and syntenic context reveals gene fate in polyploid species." *Genome Res.* 15: 1456-61. Scannell, D. R., K. P. Byrne, J. L. Gordon, S. Wong, and K. H. Wolfe (2006) "Multiple rounds of speciation associated with reciprocal gene loss in polyploidy yeasts." *Nature* 440: 341-5. Scannell, D. R., A. C. Frank, G. C. Conant, K. P. Byrne, M. Woolfit, and K. H. Wolfe (2007) "Independent sorting-out of thousands of duplicated gene pairs in two yeast species descended from a whole-genome duplication." *Proc Natl Acad Sci USA* 104: 8397-402.]

For example, locations of the syntenic versions of YPL061W from other yeast species can be found on Chromosome 8 in *Candida glabrata*, Chromosome 5 in *K. lactis*, Chromosome 5 in *K. thermotolerans* and Chromosome 8 from the inferred ancestral yeast species [Gordon, J. L., K. P. Byrne, and K. H. Wolfe (2009) "Additions, losses, and rearrangements on the evolutionary route from a reconstructed ancestor to the modern *Saccharomyces cerevisiae* genome." *PLoS Genet.* 5: e1000485.].

Using this syntenic relationship, species-specific versions of this gene are readily identified and examples can be found in Table 5.

TABLE 5

ALD6 and homologs thereof.

| Species | Gene Name | SEQ ID NO: |
|---|---|---|
| S. cerevisiae | YPL061W | 25 |
| S. castellii | Scas_664.24 | 26 |
| C. glabrata | CAGL0H05137g | 27 |
| S. bayanus | Sbay_623.4 | 28 |
| K. lactis | KLLA0E23057 | 29 |
| K. thermotolerans | KLTH0E12210g | 30 |
| K. waltii | Kwal_27.119760 | 31 |

In addition to synteny, fungal homologs to the *S. cerevisiae* ALD6 gene may be identified by one skilled in the art through tools such as BLAST and sequence alignment. These other homologs may be deleted in a similar manner from the respective yeast species to eliminate the accumulation of the aldehyde by-product. Examples of homologous proteins can be found in *Saccharomyces castelli* (SEQ ID NO: 26), *Candida glabrata* (SEQ ID NO: 27), *Saccharomyces bayanus* (SEQ ID NO: 28), *Kluyveromyces lactis* (SEQ ID NO: 29), *Kluyveromyces thermotolerans* (SEQ ID NO: 30), *Kluyveromyces waltii* (SEQ ID NO: 31), *Saccharomyces cerevisiae* YJ789 (SEQ ID NO: 32), *Saccharomyces cerevisiae* JAY291 (SEQ ID NO: 33), *Saccharomyces cerevisiae* EC1118 (SEQ ID NO: 34), *Saccharomyces cerevisiae* DBY939 (SEQ ID NO: 35), *Saccharomyces cerevisiae* AWRI1631 (SEQ ID NO: 36), *Saccharomyces cerevisiae* RM11-1a (SEQ ID NO: 37), *Pichia pastoris* (SEQ ID NO: 38), *Kluyveromyces marxianus* (SEQ ID NO: 39), *Schizosaccharomyces pombe* (SEQ ID NO: 40), and *Schizosaccharomyces pombe* (SEQ ID NO: 41).

Identification of an ADH or KDH in a Microorganism

Any method can be used to identify genes that encode for enzymes with alcohol dehydrogenase (ADH) or ketoacid dehydrogenase (KDH) activity. Alcohol dehydrogenase (ADH) can catalyze the reversible conversion of isobutanol to isobutyraldehyde. Ketoacid dehydrogenases (KDH) can catalyze the conversion of 2-ketoisovalerate to isobutyryl-CoA, which can be converted further to isobutyrate by the action of transacetylase and carboxylic acid kinase enzymes. Generally, genes that are homologous or similar to known alcohol dehydrogenases and ketoacid dehydrogenases can be identified by functional, structural, and/or genetic analysis. In most cases, homologous or similar alcohol dehydrogenase genes and/or homologous or similar alcohol dehydrogenase enzymes will have functional, structural, or genetic similarities. Likewise, homologous or similar ketoacid dehydrogenase genes and/or homologous or similar ketoacid dehydrogenase enzymes will have functional, structural, or genetic similarities.

Identification of PDC and GPD in a Yeast Microorganism

Any method can be used to identify genes that encode for enzymes with pyruvate decarboxylase (PDC) activity or glycerol-3-phosphate dehydrogenase (GPD) activity. Suitable methods for the identification of PDC and GPD are described in commonly owned and co-pending publications, US 2009/0226991 and US 2011/0020889, both of which are herein incorporated by reference in their entireties for all purposes.

Genetic Insertions and Deletions

Any method can be used to introduce a nucleic acid molecule into yeast and many such methods are well known. For example, transformation and electroporation are common methods for introducing nucleic acid into yeast cells. See, e.g., Gietz et al., 1992, *Nuc Acids Res.* 27: 69-74; Ito et al., 1983, *J. Bacteriol.* 153: 163-8; and Becker et al., 1991, *Methods in Enzymology* 194: 182-7.

In an embodiment, the integration of a gene of interest into a DNA fragment or target gene of a yeast microorganism occurs according to the principle of homologous recombination. According to this embodiment, an integration cassette containing a module comprising at least one yeast marker gene and/or the gene to be integrated (internal module) is flanked on either side by DNA fragments homologous to those of the ends of the targeted integration site (recombinogenic sequences). After transforming the yeast with the cassette by appropriate methods, a homologous recombination between the recombinogenic sequences may result in the internal module replacing the chromosomal region in between the two sites of the genome corresponding to the recombinogenic sequences of the integration cassette. (Orr-Weaver et al., 1981, *PNAS USA* 78: 6354-58).

In an embodiment, the integration cassette for integration of a gene of interest into a yeast microorganism includes the heterologous gene under the control of an appropriate promoter and terminator together with the selectable marker flanked by recombinogenic sequences for integration of a heterologous gene into the yeast chromosome. In an embodiment, the heterologous gene includes an appropriate native gene desired to increase the copy number of a native gene(s). The selectable marker gene can be any marker gene used in yeast, including but not limited to, HIS3, TRP1, LEU2, URA3, bar, ble, hph, and kan. The recombinogenic sequences can be chosen at will, depending on the desired integration site suitable for the desired application.

In another embodiment, integration of a gene into the chromosome of the yeast microorganism may occur via random integration (Kooistra et al., 2004, Yeast 21: 781-792).

Additionally, in an embodiment, certain introduced marker genes are removed from the genome using techniques well known to those skilled in the art. For example, URA3 marker loss can be obtained by plating URA3 containing cells in FOA (5-fluoro-orotic acid) containing medium and selecting for FOA resistant colonies (Boeke et al., 1984, *Mol. Gen. Genet.* 197: 345-47).

The exogenous nucleic acid molecule contained within a yeast cell of the disclosure can be maintained within that cell in any form. For example, exogenous nucleic acid molecules can be integrated into the genome of the cell or maintained in an episomal state that can stably be passed on ("inherited") to daughter cells. Such extra-chromosomal genetic elements (such as plasmids, mitochondrial genome, etc.) can additionally contain selection markers that ensure the presence of such genetic elements in daughter cells. Moreover, the yeast cells can be stably or transiently transformed. In addition, the yeast cells described herein can contain a single copy, or multiple copies of a particular exogenous nucleic acid molecule as described above.

Reduction of Enzymatic Activity

Yeast microorganisms within the scope of the invention may have reduced enzymatic activity such as reduced 3-ketoacid reductase, PDC, ALDH, or glycerol-3-phosphate dehydrogenase (GPD) activity. The term "reduced" as used herein with respect to a particular enzymatic activity refers to a lower level of enzymatic activity than that measured in a comparable yeast cell of the same species. The term reduced also refers to the elimination of enzymatic activity as compared to a comparable yeast cell of the same species. Thus, yeast cells lacking 3-ketoacid reductase, PDC, ALDH or glycerol-3-phosphate dehydrogenase (GPD) activity are considered to have reduced 3-ketoacid reductase, PDC, ALDH or glycerol-3-phosphate dehydrogenase (GPD) activity since most, if not all, comparable yeast strains have at least some 3-ketoacid reductase, PDC, ALDH, or glycerol-3-phosphate dehydrogenase (GPD) activity. Such reduced enzymatic activities can be the result of lower enzyme concentration, lower specific activity of an enzyme, or a combination thereof. Many different methods can be used to make yeast having reduced enzymatic activity. For example, a yeast cell can be engineered to have a disrupted enzyme-encoding locus using common mutagenesis or knock-out technology. See, e.g., Methods in Yeast Genetics (1997 edition), Adams, Gottschling, Kaiser, and Stems, Cold Spring Harbor Press (1998). In addition, certain point-mutation(s) can be introduced which results in an enzyme with reduced activity. Also included within the scope of this invention are yeast strains which when found in nature, are substantially free of one or more activities selected from 3-ketoacid reductase, PDC, ALDH, or glycerol-3-phosphate dehydrogenase (GPD) activity.

Alternatively, antisense technology can be used to reduce enzymatic activity. For example, yeast can be engineered to contain a cDNA that encodes an antisense molecule that prevents an enzyme from being made. The term "antisense molecule" as used herein encompasses any nucleic acid molecule that contains sequences that correspond to the coding strand of an endogenous polypeptide. An antisense molecule also can have flanking sequences (e.g., regulatory sequences). Thus antisense molecules can be ribozymes or antisense oligonucleotides. A ribozyme can have any general structure including, without limitation, hairpin, hammerhead, or axhead structures, provided the molecule cleaves RNA.

Yeast having a reduced enzymatic activity can be identified using many methods. For example, yeast having reduced 3-ketoacid reductase, PDC, ALDH, or glycerol-3-phosphate dehydrogenase (GPD) activity can be easily identified using common methods, which may include, for example, measuring glycerol formation via liquid chromatography.

Overexpression of Heterologous Genes

Methods for overexpressing a polypeptide from a native or heterologous nucleic acid molecule are well known. Such methods include, without limitation, constructing a nucleic acid sequence such that a regulatory element promotes the expression of a nucleic acid sequence that encodes the desired polypeptide. Typically, regulatory elements are DNA sequences that regulate the expression of other DNA sequences at the level of transcription. Thus, regulatory elements include, without limitation, promoters, enhancers, and the like. For example, the exogenous genes can be under the control of an inducible promoter or a constitutive promoter. Moreover, methods for expressing a polypeptide from an exogenous nucleic acid molecule in yeast are well known. For example, nucleic acid constructs that are used for the expression of exogenous polypeptides within *Kluyveromyces* and *Saccharomyces* are well known (see, e.g., U.S. Pat. Nos. 4,859,596 and 4,943,529, for *Kluyveromyces* and, e.g., Gellissen et al., Gene 190(1):87-97 (1997) for *Saccharomyces*). Yeast plasmids have a selectable marker and an origin of replication. In addition certain plasmids may also contain a centromeric sequence. These centromeric plasmids are generally a single or low copy plasmid. Plasmids without a centromeric sequence and utilizing either a 2 micron (*S. cerevisiae*) or 1.6 micron (*K. lactis*) replication origin are high copy plasmids. The selectable marker can be either prototrophic, such as HIS3, TRP1, LEU2, URA3 or ADE2, or antibiotic resistance, such as, bar, ble, hph, or kan.

In another embodiment, heterologous control elements can be used to activate or repress expression of endogenous genes. Additionally, when expression is to be repressed or eliminated, the gene for the relevant enzyme, protein or RNA can be eliminated by known deletion techniques.

As described herein, any yeast within the scope of the disclosure can be identified by selection techniques specific to the particular enzyme being expressed, over-expressed or repressed. Methods of identifying the strains with the desired phenotype are well known to those skilled in the art. Such methods include, without limitation, PCR, RT-PCR, and nucleic acid hybridization techniques such as Northern and Southern analysis, altered growth capabilities on a particular substrate or in the presence of a particular substrate, a chemical compound, a selection agent and the like. In some cases, immunohistochemistry and biochemical techniques can be used to determine if a cell contains a particular nucleic acid by detecting the expression of the encoded polypeptide. For example, an antibody having specificity for an encoded enzyme can be used to determine whether or not a particular yeast cell contains that encoded enzyme. Further, biochemical techniques can be used to determine if a cell contains a particular nucleic acid molecule encoding an enzymatic polypeptide by detecting a product produced as a result of the expression of the enzymatic polypeptide. For example, transforming a cell with a vector encoding acetolactate synthase and detecting increased acetolactate concentrations compared to a cell without the vector indicates that the vector is both present and that the gene product is active. Methods for detecting specific enzymatic activities or the presence of particular products are well known to those skilled in the art. For example, the presence of acetolactate can be determined as described by Hugenholtz and Starrenburg, 1992, *Appl. Micro. Biot.* 38:17-22.

Increase of Enzymatic Activity

Yeast microorganisms of the invention may be further engineered to have increased activity of enzymes (e.g., increased activity of enzymes involved in an isobutanol producing metabolic pathway). The term "increased" as used herein with respect to a particular enzymatic activity refers to a higher level of enzymatic activity than that measured in a comparable yeast cell of the same species. For example, overexpression of a specific enzyme can lead to an increased level of activity in the cells for that enzyme. Increased activities for enzymes involved in glycolysis or the isobutanol pathway would result in increased productivity and yield of isobutanol.

Methods to increase enzymatic activity are known to those skilled in the art. Such techniques may include increasing the expression of the enzyme by increased copy number and/or use of a strong promoter, introduction of mutations to relieve negative regulation of the enzyme, introduction of specific mutations to increase specific activity and/or decrease the Km for the substrate, or by directed evolution. See, e.g., Methods in Molecular Biology (vol. 231), ed. Arnold and Georgiou, Humana Press (2003).

Methods of Using Recombinant Microorganisms for High-Yield Fermentations

For a biocatalyst to produce a beneficial metabolite most economically, it is desirable to produce said metabolite at a high yield. Preferably, the only product produced is the desired metabolite, as extra products (i.e. by-products) lead to a reduction in the yield of the desired metabolite and an increase in capital and operating costs, particularly if the extra products have little or no value. These extra products also require additional capital and operating costs to separate these products from the desired metabolite.

In one aspect, the present invention provides a method of producing a beneficial metabolite derived from a recombinant microorganism comprising a biosynthetic pathway.

In one embodiment, the method includes cultivating a recombinant microorganism comprising a biosynthetic pathway which uses a 3-ketoacid as an intermediate in a culture medium containing a feedstock providing the carbon source until a recoverable quantity of the beneficial metabolite is produced and optionally, recovering the metabolite. In one embodiment, the 3-ketoacid intermediate is acetolactate. In an exemplary embodiment, said recombinant microorganism is engineered to reduce or eliminate the expression or activity of an enzyme catalyzing the conversion of acetolactate to DH2MB. The beneficial metabolite may be derived from any biosynthetic pathway which uses acetolactate as intermediate, including, but not limited to, biosynthetic pathways for the production of isobutanol, 2-butanol, 1-butanol, 2-butanone, 2,3-butanediol, acetoin, diacetyl, valine, leucine, pantothenic acid, isobutylene, 3-methyl-1-butanol, 4-methyl-1-pentanol, and coenzyme A. In a specific embodiment, the beneficial metabolite is isobutanol. In another embodiment, the 3-ketoacid intermediate is 2-aceto-2-hydroxybutyrate. In an exemplary embodiment, said recombinant microorganism is engineered to reduce or eliminate the expression or activity of an enzyme catalyzing the conversion of 2-aceto-2-hydroxybutyrate to 2-ethyl-2,3-dihydroxybutyrate. The beneficial metabolite may be derived from any biosynthetic pathway which uses 2-aceto-2-hydroxybutyrate as intermediate, including, but not limited to, biosynthetic pathways for the production of 2-methyl-1-butanol, isoleucine, 3-methyl-1-pentanol, 4-methyl-1-hexanol, and 5-methyl-1-heptanol.

In another embodiment, the method includes cultivating a recombinant microorganism comprising a biosynthetic pathway which uses an aldehyde as an intermediate in a culture medium containing a feedstock providing the carbon source until a recoverable quantity of the beneficial metabolite is produced and optionally, recovering the metabolite. In an exemplary embodiment, said recombinant microorganism is engineered to reduce or eliminate the expression or activity of an enzyme catalyzing the conversion of an aldehyde to acid by-product. The beneficial metabolite may be derived from any biosynthetic pathway which uses an aldehyde as intermediate, including, but not limited to, biosynthetic pathways for the production of isobutanol, 1-butanol, 2-methyl-1-butanol, 3-methyl-1-butanol, 1-propanol, 1-pentanol, 1-hexanol, 3-methyl-1-pentanol, 4-methyl-1-pentanol, 4-methyl-1-hexanol, and 5-methyl-1-heptanol. In a specific embodiment, the beneficial metabolite is isobutanol.

In another embodiment, the method includes cultivating a recombinant microorganism comprising a biosynthetic pathway which uses acetolactate and an aldehyde as intermediates in a culture medium containing a feedstock providing the carbon source until a recoverable quantity of the beneficial metabolite is produced and optionally, recovering the metabolite. In an exemplary embodiment, said recombinant microorganism is engineered to (i) reduce or eliminate the expression or activity of an enzyme catalyzing the conversion of acetolactate to DH2MB and (ii) reduce or eliminate the expression or activity of an enzyme catalyzing the conversion of an aldehyde to acid by-product. The beneficial metabolite may be derived from any biosynthetic pathway which uses acetolactate and an aldehyde as intermediate, including, but not limited to, biosynthetic pathways for the production of isobutanol, 1-butanol, and 3-methyl-1-butanol. In a specific embodiment, the beneficial metabolite is isobutanol.

In another embodiment, the method includes cultivating a recombinant microorganism comprising a biosynthetic pathway which uses 2-aceto-2-hydroxybutyrate and an aldehyde as intermediates in a culture medium containing a feedstock providing the carbon source until a recoverable quantity of the beneficial metabolite is produced and optionally, recovering the metabolite. In an exemplary embodiment, said recombinant microorganism is engineered to (i) reduce or eliminate the expression or activity of an enzyme catalyzing the conversion of 2-aceto-2-hydroxybutyrate to 2-ethyl-2,3-dihydroxybutyrate and (ii) reduce or eliminate the expression or activity of an enzyme catalyzing the conversion of an aldehyde to acid by-product. The beneficial metabolite may be derived from any biosynthetic pathway which uses 2-aceto-2-hydroxybutyrate and an aldehyde as intermediate, including, but not limited to, biosynthetic pathways for the production of 2-methyl-1-butanol, 3-methyl-1-pentanol, 4-methyl-1-hexanol, and 5-methyl-1-heptanol.

In another embodiment, the present invention provides a method of producing a beneficial metabolite derived from an alcohol dehydrogenase (ADH)-requiring biosynthetic pathway. In one embodiment, the method includes cultivating a recombinant microorganism comprising a modified ADH described herein in a culture medium containing a feedstock providing the carbon source until a recoverable quantity of the beneficial metabolite is produced and optionally, recovering the metabolite. The beneficial metabolite may be derived from any ADH-requiring biosynthetic pathway, including, but not limited to, biosynthetic pathways for the production of 1-propanol, 2-propanol, 1-butanol, 2-butanol, 1-pentanol, 2-methyl-1-butanol, and 3-methyl-1-butanol. In a specific embodiment, the beneficial metabolite is isobutanol.

In a method to produce a beneficial metabolite from a carbon source, the yeast microorganism is cultured in an appropriate culture medium containing a carbon source. In certain embodiments, the method further includes isolating the beneficial metabolite from the culture medium. For example, isobutanol may be isolated from the culture medium by any method known to those skilled in the art, such as distillation, pervaporation, or liquid-liquid extraction.

In one embodiment, the recombinant microorganism may produce the beneficial metabolite from a carbon source at a yield of at least 5 percent theoretical.

In another embodiment, the microorganism may produce the beneficial metabolite from a carbon source at a yield of at least about 10 percent, at least about 15 percent, about least about 20 percent, at least about 25 percent, at least about 30 percent, at least about 35 percent, at least about 40 percent, at least about 45 percent, at least about 50 percent, at least about 55 percent, at least about 60 percent, at least about 65 percent, at least about 70 percent, at least about 75 percent, at least about 80 percent, at least about 85 percent, at least about 90 percent, at least about 95 percent, or at least about 97.5% theoretical. In a specific embodiment, the beneficial metabolite is isobutanol.

This invention is further illustrated by the following examples that should not be construed as limiting. The contents of all references, patents, and published patent applications cited throughout this application, as well as the Figures and the Sequence Listing, are incorporated herein by reference for all purposes.

EXAMPLES

General Methods for Examples 1-26

Sequences: Amino acid and nucleotide sequences disclosed herein are shown in Table 6.

TABLE 6

Amino Acid and Nucleotide Sequences of Enzymes and Genes Disclosed in Various Examples.

| Enz. | Source | Gene (SEQ ID NO) | Corresponding Protein (SEQ ID NO) |
|---|---|---|---|
| ALS | B. subtilis | Bs_alsS1_coSc (SEQ ID NO: 42) | Bs_AlsS1 (SEQ ID NO: 43) |
| KARI | E. coli | Ec_ilvC_coSc$^{Q110V}$ (SEQ ID NO: 44) | Ec_IlvC$^{Q110V}$ (SEQ ID NO: 45) |
|  | E. coli | Ec_ilvC_coSc$^{P2D1-A1}$ (SEQ ID NO: 46) | Ec_ilvC_coSc$^{P2D1-A1}$ (SEQ ID NO: 47) |
| KIVD | L. lactis | Ll_kivD2_coEc (SEQ ID NO: 48) | Ll_Kivd2 (SEQ ID NO: 49) |
| DHAD | L. lactis | Ll_ilvD_coSc (SEQ ID NO: 50) | Ll_IlvD (SEQ ID NO: 51) |
|  | S. cerevisiae | Sc_ILV3ΔN (SEQ ID NO: 52) | Sc_Ilv3ΔN (SEQ ID NO: 53) |
| ADH | D. melanogaster | Dm_ADH (SEQ ID NO: 54) | Dm_Adh (SEQ ID NO: 55) |
|  | L. lactis | Ll_adhA (SEQ ID NO: 56) | Ll_AdhA (SEQ ID NO: 57) |
|  | L. lactis | Ll_adhA_coSc$^{his6}$ (SEQ ID NO: 58) | Ll_AdhA$^{his6}$ (SEQ ID NO: 59) |
|  | L. lactis | Ll_adhA$^{RE1}$_coSc$^{his6}$ (SEQ ID NO: 60) | Ll_AdhA$^{RE1-his6}$ (SEQ ID NO: 61) |

Media: Medium used was standard yeast medium (see, for example Sambrook, J., Russel, D. W. Molecular Cloning, A Laboratory Manual. 3rd ed. 2001, Cold Spring Harbor, N.Y.: Cold Spring Harbor Laboratory Press and Guthrie, C. and Fink, G. R. eds. Methods in Enzymology Part B: Guide to Yeast Genetics and Molecular and Cell Biology 350:3-623 (2002)). YP medium contains 1% (w/v) yeast extract, 2% (w/v) peptone. YPD is YP containing 2% glucose unless specified otherwise. YPE is YP containing 25 mL/L ethanol. SC medium is 6.7 g/L Difco™ Yeast Nitrogen Base, 14 g/L Sigma™ Synthetic Dropout Media supplement (includes amino acids and nutrients excluding histidine, tryptophan, uracil, and leucine), 0.076 g/L histidine, 0.076 g/L tryptophan, 0.380 g/L leucine, and 0.076 g/L uracil. SCD is containing 2% (w/v) glucose unless otherwise noted. Dropout versions of SC and SCD media are made by omitting one or more of histidine (-H), tryptophan (-W), leucine (-L), or uracil (-U). Solid versions of the above described media contain 2% (w/v) agar.

Cloning techniques: Standard molecular biology methods for cloning and plasmid construction were generally used, unless otherwise noted (Sambrook, J., Russel, D. W. *Molecular Cloning, A Laboratory Manual.* 3 ed. 2001, Cold Spring Harbor, N.Y.: Cold Spring Harbor Laboratory Press). Cloning techniques included digestion with restriction enzymes, PCR to generate DNA fragments (KOD Hot Start Polymerase, Cat# 71086, Merck, Darmstadt, Germany), ligations of two DNA fragments using the DNA Ligation Kit (Mighty Mix Cat# TAK 6023, Clontech Laboratories, Madison, Wis.), and bacterial transformations into competent *E. coli* cells (Xtreme Efficiency DH5a Competent Cells, Cat# ABP-CE-CC02096P, Allele Biotechnology, San Diego, Calif.). Plasmid DNA was purified from *E. coli* cells using the Qiagen QIAprep Spin Miniprep Kit (Cat# 27106, Qiagen, Valencia, Calif.). DNA was purified from agarose gels using the Zymoclean Gel DNA Recovery Kit (Zymo Research, Orange, Calif.; Catalog #D4002) according to manufacturer's protocols.

Colony PCR: Yeast colony PCR used the FailSafe™ PCR System (EPICENTRE® Biotechnologies, Madison, Wis.; Catalog #FS99250) according to manufacturer's protocols. A PCR cocktail containing 15 µL of Master Mix E buffer, 10.5 µL water, 2 µL of each primer at 10 µM concentration, 0.5 µL polymerase enzyme mix from the kit was added to a 0.2 mL PCR tube for each sample (30 µL each). For each candidate a small amount of cells was added to the reaction tube using a sterile pipette tip. Presence of the positive PCR product was assessed using agarose gel electrophoresis.

SOE PCR: The PCR reactions were incubated in a thermocycler using the following PCR conditions: 1 cycle of 94° C.×2 min, 35 cycles of 94° C.×30 s, 53° C.×30 s, 72° C.×2 min and 1 cycle of 72° C.×10 min. A master mix was made such that each reaction contained the following: 3 µL $MgSO_4$ (25 mM), 5 µL 10×KOD buffer, 5 µL 50% DMSO, 5 µL dNTP mix (2 mM each), 1 µL KOD, 28 µL $dH_2O$, 1.5 µL forward primer (10 µM), 1.5 µL reverse primer (10 µM), 0.5 µL template (plasmid or genomic DNA).

Genomic DNA Isolation: The Zymo Research ZR Fungal/Bacterial DNA Kit (Zymo Research Orange, Calif.; Catalog #D6005) was used for genomic DNA isolation according to manufacturer's protocols with the following modifications. Following resuspension of pellets, 200 µL was transferred to 2 separate ZR BashingBead™ Lysis Tubes (to maximize yield). Following lysis by bead beating, 400 µL of supernatant from each of the ZR BashingBead™ Lysis Tubes was transferred to 2 separate Zymo-Spin™ IV Spin Filters and centrifuged at 7,000 rpm for 1 min. Following the spin, 1.2 mL of Fungal/Bacterial DNA Binding Buffer was added to each filtrate. In 800 µl aliquots, filtrate from both filters was transferred to a single Zymo-Spin™ IIC Column in a collection tube and centrifuged at 10,000×g for 1 min. For the elution step, instead of eluting in 100 µL of EB (elution buffer, Qiagen), 50 µL of EB was added, incubated 1 min then the columns were centrifuged for 1 min. This elution step was repeated for a final elution volume of 100 µL.

*S. cerevisiae* Transformations. *S. cerevisiae* strains were grown in YPD containing 1% ethanol. Transformation-competent cells were prepared by resuspension of *S. cerevisiae* cells in 100 mM lithium acetate. Once the cells were prepared, a mixture of DNA (final volume of 15 µL with sterile water), 72 µL 50% PEG, 10 µL 1M lithium acetate, and 3 µL of denatured salmon sperm DNA (10 mg/mL) was prepared for each transformation. In a 1.5 mL tube, 15 µL of the cell suspension was added to the DNA mixture (100 µL), and the transformation suspension was vortexed for 5 short pulses. The transformation was incubated for 30 min at 30° C., followed by incubation for 22 min at 42° C. The cells were collected by centrifugation (18,000×g, 10 seconds, 25° C.). The cells were resuspended in 350 µL YPD and after an overnight recovery shaking at 30° C. and 250 rpm, the cells were spread over YPD plates containing 0.2 g/L G418 selective plates. Transformants were then single colony purified onto G418 selective plates.

*K. marxianus* transformations: *K. marxianus* strains were grown in 3 mL of an appropriate culture medium at 250 rpm and 30° C. overnight. The following day, cultures were diluted in 50 mL of the same medium and grown to an $OD_{600}$ of between 1 and 4. The cells were collected in a sterile 50 mL conical tube by centrifugation (1600×g, 5 min at room temperature). The cells were resuspended in 10 mL of electroporation buffer (10 mM Tris-C1, 270 mM sucrose, 1 mM $MgCl_2$, pH 7.5), and collected at 1600×g for 5 min at room temperature. The cells were resuspended in 10 mL IB (YPE, 25 mM DTT, 20 mM HEPES, pH 8.0; prepared fresh by diluting 100 µL of 2.5 M DTT and 200 µL of 1 mM HEPES, pH 8.0 into 10 mL of YPD). The cells were incubated for 30 min, 250 rpm, 30° C. (tube standing vertical). The cells were collected at 1600×g for 5 min at room temperature and resuspended in 10 mL of chilled electroporation buffer. The cells were pelleted at 1600×g for 5 min at 4° C. The cells were resuspended in 1 mL of chilled electroporation buffer and transferred to a microfuge tube. The cells were collected by centrifugation at >10,000×g for 20 sec at 4° C. The cells were resuspended in appropriate amount of chilled electroporation buffer for a final biomass concentration of 30-38 $OD_{600}$/mL. 400 µL of cells was added to a chilled electroporation cuvette (0.4 cm gap), 50 µL of SOE PCR product (or water control) was added and mixed by pipetting up and down, and the cuvette was incubated on ice for 30 min. The samples were electroporated at 1.8 kV, 1000 Ohm, 25 µF. The samples were then transferred to a 50 mL tube with 1 mL of an appropriate culture medium, and the samples were incubated for overnight at 250 rpm at 30° C. After incubation the cells were plated onto appropriate agar plates.

*K. lactis* transformations: *K. lactis* strains were grown in 3 mL YPD at 250 rpm and 30° C. overnight. The following day, cultures were diluted in 50 mL YPD and allowed to grow until they reached an $OD_{600}$ of ~0.8. Cells from 50 mL YPD cultures were collected by centrifugation (2700 rcf, 2 min, 25° C.). The cells were washed with 50 mL sterile water and collected by centrifugation at 2700 rcf for 2 min at RT. The cells were washed again with 25 mL sterile water and collected by centrifugation at 2700 rcf for 2 min at RT. The cells were resuspended in 1 mL 100 mM lithium acetate and transferred to a 1.5 mL Eppendorf tube. The cells were collected by centrifugation for 10 sec at 18,000 rcf at RT. The cells were resuspended in a volume of 100 mM lithium acetate that was approximately 4× the volume of the cell pellet. A volume of 10-15 µL of DNA, 72 µL 50% PEG (3350), 10 µL 1 M lithium acetate, 3 µL denatured salmon sperm DNA, and sterile water were combined to a final volume of 100 µL for each transformation. In a 1.5 mL tube, 15 µL of the cell suspension was added to the DNA mixture and the transformation suspension was vortexed with 5 short pulses. The transformation was incubated for 30 min at 30° C., followed by incubation for 22 min at 42° C. The cells were collected by centrifugation for 10 sec at 18,000 rcf at RT. The cells were resuspended in 400 µL of an appropriate medium and spread over agar plates containing an appropriate medium to select for transformed cells.

Analytical Chemistry:

Gas Chromatography (method GC1). Analysis of volatile organic compounds, including ethanol and isobutanol was performed on a Agilent 5890/6890/7890 gas chromatograph fitted with an Agilent 7673 Autosampler, a ZB-FFAP column (J&W; 30 m length, 0.32 mm ID, 0.25 µM film thickness) or equivalent connected to a flame ionization detector (FID). The temperature program was as follows: 200° C. for the injector, 300° C. for the detector, 100° C. oven for 1 minute, 70° C./minute gradient to 230° C., and then hold for 2.5 min. Analysis was performed using authentic standards (>99%, obtained from Sigma-Aldrich, and a 5-point calibration curve with 1-pentanol as the internal standard.

High Performance Liquid Chromatography (method LC1): Analysis of organic acid metabolites including 2,3-dihydroxyisovalerate (DHIV), 2,3-dihydroxy-2-methylbutanoic acid (DH2MB), isobutyrate and glucose was performed on an Agilent 1200 or equivalent High Performance Liquid Chromatography system equipped with a Bio-Rad Micro-guard Cation H Cartridge and two Phenomenex Rezex RFQ-Fast Fruit H+ (8%), 100×7.8-mm columns in series, or equivalent. Organic acid metabolites were detected using an Agilent 1100 or equivalent UV detector (210 nm) and a refractive index detector. The column temperature was 60° C. This method was isocratic with 0.0180 N $H_2SO_4$ in Milli-Q water as mobile phase. Flow was set to 1.1 mL/min. Injection volume was 20 µL and run time was 16 min. Quantitation of organic acid metabolites was performed using a 5-point calibration curve with authentic standards (>99% or highest purity available), with the exception of DHIV (2,3-dihydroxy-3-methyl-butanoate, CAS 1756-18-9), which was synthesized according to Cioffi et al. (Cioffi, E. et al. *Anal Biochem* 1980, 104, pp. 485) and DH2MB which quantified based on the assumption that DHIV and DH2MB exhibit the same response factor. In this method, DHIV and DH2MB co-elute, hence their concentrations are reported as the sum of the two concentrations.

Figure 8:
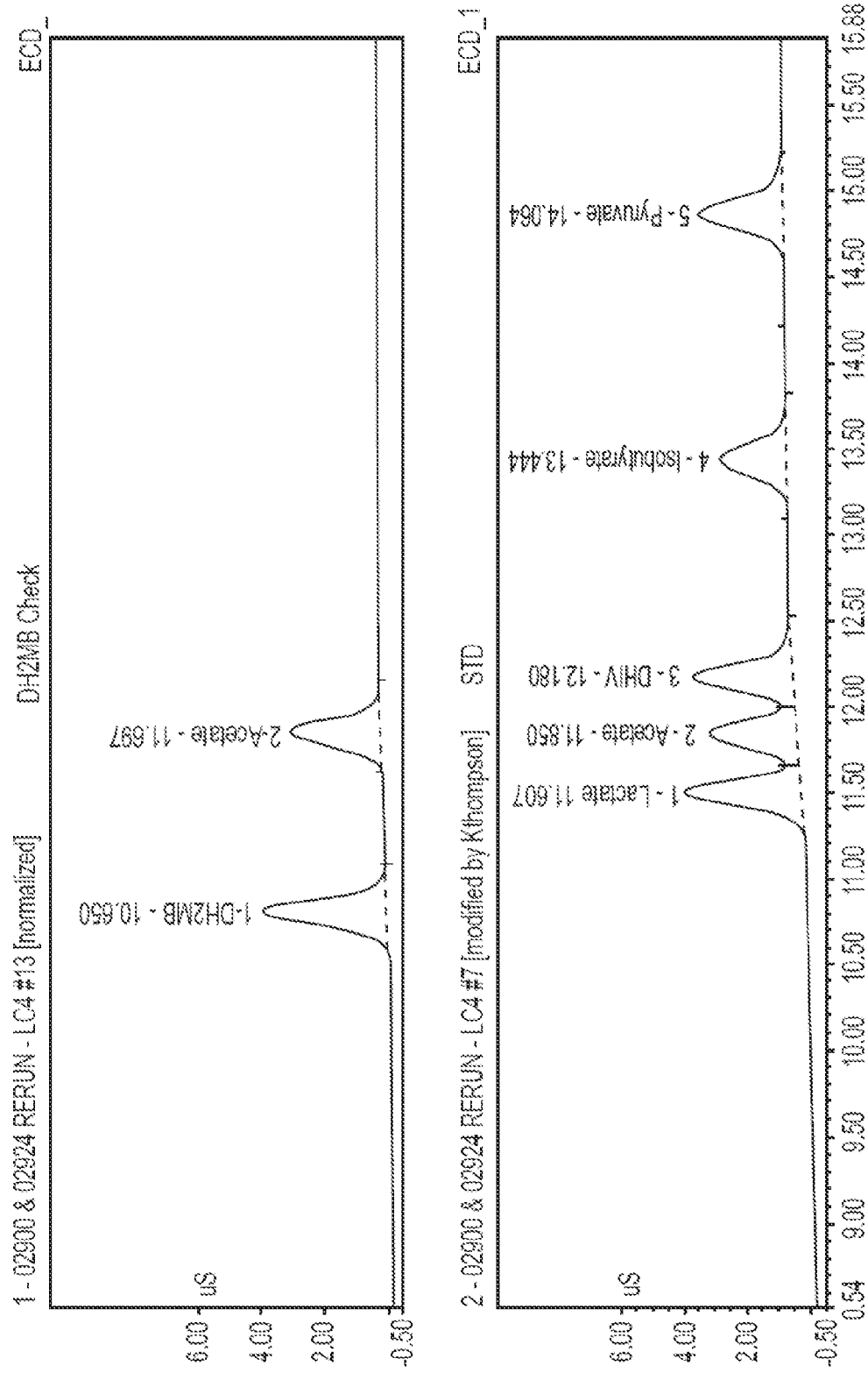
FIG. 8 illustrates a stacked overlay of LC4 chromatograms showing a sample containing DH2MB and acetate (top) and a sample containing acetate and DHIV (bottom). Elution order: DH2MB followed by acetate (top); lactate, acetate, DHIV, isobutyrate, pyruvate (bottom).

High Performance Liquid Chromatography (method LC4): Analysis of oxo acids, including 2,3-dihydroxyisovalerate (DHIV, CAS 1756-18-9), 2,3-dihydroxy-2-methylbutyrate acid (DH2MB), lactate, acetate, acetolactate, isobutyrate, and pyruvate) was performed on a Agilent-1100 High Performance Liquid Chromatography system equipped with an IonPac AS11-HC Analytical column (Dionex: 9 µm, 4.6×250 mm) coupled with an IonPac AG11-HC guard column (Dionex: 13 µm, 4.6×50 mm) and an IonPac ATC-3 Anion Trap column (Dionex: 9×24 mm). Acetolactate was detected using a UV detector at 225 nm, while all other analytes were detected using a conductivity detector (ED50-suppressed conductivity with ASRS 4 mm in AutoSuppression recycle mode, 200 mA suppressor current). The column temperature was 35° C. Injection size was 10 µL. This method used the following elution profile: 0.25 mM NaOH for 3 min, followed by a linear gradient from 0.25 to 5 mM NaOH in 22 min and a second linear gradient from 5 mM to 38.25 mM in 0.1 min, followed by 38.25 mM NaOH for 4.9 min and a final linear gradient from 38.25 mM to 0.25 mM for 0.1 min before re-equilibrating at 0.25 mM NaOH for 7 min. Flow was set at 2 mL/min. Analysis was performed using a 4-point calibration curve with authentic standards (>99%, or highest purity available), with the following exceptions: DHIV was synthesized according to Cioffi et al. (Cioffi, E. et al. *Anal Biochem* 1980, 104, pp. 485). DH2MB was synthesized as described in Example 8 and quantified based on the assumption that DHIV and DH2MB exhibit the same response factor. Racemic acetolactate was made by hydrolysis of Ethyl-2-acetoxy-2-methylacetoacetate (EAMMA) with NaOH (Krampitz, L. O. *Methods in Enzymology* 1957, 3, 277-283.). In this method, DHIV and DH2MB are separated (FIG. 8).

Enzyme Assays

Determination of protein concentration: Protein concentration: (of yeast lysate or of purified protein) was determined using the BioRad Bradford Protein Assay Reagent Kit (Cat# 500-0006, BioRad Laboratories, Hercules, Calif.) and using BSA for the standard curve. A standard curve for the assay was made using a dilution series of a standard protein stock of 500 µg/mL BSA. An appropriate dilution of cell lysate was made in water to obtain $OD_{595}$ measurements of each lysate that fell within linear range of the BioRad protein standard curve. Ten µL of the lysate dilution was added to 500 µL of diluted BioRad protein assay dye, samples were mixed by vortexing, and incubated at room temperature for 6 min. Samples were transferred to cuvettes and read at 595 nm in a spectrophotometer. The linear regression of the standards was used to calculate the protein concentration of each sample.

Alcohol Dehydrogenase (ADH) Assay. Cells were thawed on ice and resuspended in lysis buffer (100 mM Tris-HCl pH 7.5). 1000 µL of glass beads (0.5 mm diameter) were added to a 1.5 mL Eppendorf tube and 875 µL of cell suspension was added. Yeast cells were lysed using a Retsch MM301 mixer mill (Retsch Inc. Newtown, Pa.), mixing 6×1 min each at full speed with 1 min incubations on ice between each bead-beating step. The tubes were centrifuged for 10 min at 23,500×g at 4° C. and the supernatant was removed for use. These lysates were held on ice until assayed. Yeast lysate protein concentrations were determined as described.

Dilutions of the samples were made such that an activity reading could be obtained. Generally the samples from strains expected to have low ADH activity were diluted 1:5 in lysis buffer (100 mM Tris-HCl pH 7.5) and the samples from strains with expected high ADH activity such as strains where the ADH gene is expressed from a high copy number plasmid were diluted 1:40 to 1:100. Reactions were performed in triplicate using 10 µL of appropriately diluted cell extract with 90 µL of reaction buffer (100 mM Tris-HCl, pH 7.5; 150 µM NADH; 11 mM isobutyraldehyde) in a 96-well plate in a SpectraMax® 340PC multi-plate reader (Molecular Devices, Sunnyvale, Calif.). The reaction was followed at 340 nm for 5 minutes, with absorbance readings every 10 seconds. The reactions were performed at 30° C. The reactions were performed in complete buffer and also in buffer with no substrate.

Isobutyraldehyde Oxidation Assay (ALD6 assay): Cell pellets were thawed on ice and resuspended in lysis buffer (10 mM sodium phosphate pH7.0, 1 mM dithiothreitol, 5% w/v glycerol). One mL of glass beads (0.5 mm diameter) was added to a 1.5 mL Eppendorf tube for each sample and 850 µL of cell suspension were added. Yeast cells were lysed using a Retsch MM301 mixer mill (Retsch Inc. Newtown, Pa.), mixing 6×1 min each at full speed with 1 min incubation on ice between. The tubes were centrifuged for 10 min at 21,500×g at 4° C. and the supernatant was transferred to a fresh tube. Extracts were held on ice until assayed. Yeast lysate protein concentrations were determined as described.

The method used to measure enzyme activity of enzymes catalyzing the oxidation of isobutyraldehyde to isobutyrate in cell lysates was modified from Meaden et al. 1997, Yeast 13: 1319-1327 and Postma et al. 1988, *Appl. Environ. Microbiol.* 55: 468-477. Briefly, for each sample, 10 µL of undiluted cell lysate was added to 6 wells of a UV microtiter plate. Three wells received 90 µL assay buffer containing 50 mM HEPES-NaOH at pH 7.5, 0.4 mM $NADP^+$, 3.75 mM $MgCl_2$, and 0.1 mM, 1 mM, or 10 mM isobutyraldehyde. The other 3 wells received 90 µL of no substrate buffer (same as assay buffer but without isobutyraldehyde). The buffers were mixed with the lysate in the wells by pipetting up and down. The reactions were then monitored at 340 nm for 5 minutes, with absorbance readings taken every 10 seconds in a SpectraMax® 340PC plate reader (Molecular Devices, Sunnyvale, Calif.). The reactions were performed at 30° C. The $V_{max}$ for each sample was determined by subtracting the background reading of the no substrate control. A no lysate control was also performed in triplicate for each substrate concentration.

ALS Assay: For ALS assays described in Examples 1-18, cells were thawed on ice and resuspended in lysis buffer (50 mM potassium phosphate buffer pH 6.0 and 1 mM $MgSO_4$). 1000 µL of glass beads (0.5 mm diameter) were added to a 1.5 mL Eppendorf tube and 875 µL of cell suspension was added. Yeast cells were lysed using a Retsch MM301 mixer mill (Retsch Inc. Newtown, Pa.), mixing 6×1 min each at full speed with 1 min incubations on ice between each bead-beating step. The tubes were centrifuged for 10 min at 23,500×g at 4° C. and the supernatant was removed for use. These lysates were held on ice until assayed. Protein content of the lysates was measured as described. All ALS assays were performed in triplicate for each lysate, both with and without substrate. To assay each lysate, 15 µL of lysate was mixed with 135 µL of buffer (50 mM potassium phosphate buffer pH 6.0, 1 mM $MgSO_4$, 1 mM thiamin-pyrophosphate, 110 mM pyruvate), and incubated for 15 minutes at 30° C. Buffers were prepared at room temperature. A no substrate control (buffer without pyruvate) and a no lysate control (lysis buffer instead of lysate) were also included. After incubation 21.5 µL of 35% $H_2SO_4$ was added to each reaction and incubated at 37° C. for 1 h.

For ALS assays described in Examples 19-25, cells were thawed on ice and resuspended in lysis buffer (100 mM $NaPO_4$ pH 7.0, 5 mM $MgCl_2$ and 1 mM DTT). One mL of glass beads (0.5 mm diameter) were added to a 1.5 mL Eppendorf tube and 800 µL of the cell suspension was added to the tube containing glass beads. Yeast cells were lysed using a Retsch MM301 mixer mill (Retsch Inc. Newtown, Pa.) and a cooling block by mixing six times for 1 min each at 30 cycles/second with 1 min icing in between mixing. The tubes were centrifuged for 10 min at 21,500×g at 4° C. and the supernatant was removed. Extracts were held on ice until assayed. Yeast lysate protein concentration was determined using the BioRad Bradford Protein Assay Reagent Kit (Cat# 500-0006, BioRad Laboratories, Hercules, Calif.) and using BSA for the standard curve as described. All ALS assays were performed in triplicate for each lysate. All buffers, lysates and reaction tubes were pre-cooled on ice. To assay each lysate, 15 µL of lysate (diluted with lysis buffer as needed) was mixed with 135 µL of assay buffer (50 mM KPi, pH 7.0, 1 mM $MgSO_4$, 1 mM thiamin-pyrophosphate, 110 mM pyruvate), and incubated for 15 min at 30° C. A no substrate control (buffer without pyruvate) and a no lysate control (lysis buffer instead of lysate) were also included. After incubation each reaction was mixed with 21.5 µL of 35% $H_2SO_4$, incubated at 37° C. for 1 h and centrifuged for 5 min at 5,000×g to remove any insoluble precipitants.

All assay samples were analyzed for the assay substrate (pyruvate) and product (acetoin) via high performance liquid chromatography an HP-1200 High Performance Liquid Chromatography system equipped with two Restek RFQ 150×4.6 mm columns in series. Organic acid metabolites were detected using an HP-1100 UV detector (210 nm) and refractive index. The column temperature was 60° C. This method was isocratic with 0.0180 N $H_2SO_4$ (in Milli-Q water) as mobile phase. Flow was set to 1.1 mL/min. Injection volume was 20 µL and run time was 8 min. Analysis was performed using authentic standards (>99%, obtained from Sigma-Aldrich) and a 5-point calibration curve.

TMA29 enzyme assay: Cell pellets were thawed on ice and resuspended in lysis buffer (10 mM sodium phosphate pH 7.0, 1 mM dithiothreitol, 5% w/v glycerol). One mL of glass beads (0.5 mm diameter) was added to a 1.5 mL Eppendorf tube for each sample and 850 µL of cell suspension were added. Yeast cells were lysed using a Retsch MM301 mixer mill (Retsch Inc. Newtown, Pa.), mixing 6×1 min each at full speed with 1 min incubation on ice between. The tubes were centrifuged for 10 min at 21,500×g at 4° C. and the supernatant was transferred to a fresh tube. Extracts were held on ice until assayed. Yeast lysate protein concentration was determined using the BioRad Bradford Protein Assay Reagent Kit (Cat# 500-0006, BioRad Laboratories, Hercules, Calif.) and using BSA for the standard curve as described.

Enzymatic synthesis of (S)-2-acetolactate ((S)-AL) was performed in an anaerobic flask. The reaction was carried out in a total volume of 55 mL containing 20 mM potassium phosphate pH 7.0, 1 mM $MgCl_2$, 0.05 mM thiamine pyrophosphate (TPP), and 200 mM sodium pyruvate. The synthesis was initiated by the addition of 65 units of purified *B. subtilis* AlsS, and the reaction was incubated at 30° C. in a static incubator for 7.5 h.

Chemical synthesis of racemic 2-acetolactate ((R/S)-2-AL) was performed by mixing 50 µL of ethyl-2-acetoxy-2-methylacetoacetate (EAMMA) with 990 µL of water. 260 µL of 2 N NaOH was then added in 10 µL increments with 15 seconds of vortexing after each addition. The solution was then mixed on an orbital shaker for 20 minutes.

Chemical synthesis of racemic AHB ((R/S)-AHB) was performed by mixing 50 µL of ethyl-2-acetoxy-2-ethyl-3-oxobutanoate with 990 µL of water. 2 N NaOH was then added in 10 µL increments with 15 seconds of vortexing after each addition. The NaOH was added until the pH of the solution was 12 (~180 µL of 2 N NaOH). The solution was then mixed on an orbital shaker for 20 minutes.

For determination of (S)-AL, (R/S)-AL or (R/S)-AHB reduction activity, 10 µL of undiluted cell lysate was added to 6 wells of a UV microtiter plate. Three wells received 90 µL assay buffer containing 100 mM $KPO_4$ at pH 7.0, 150 µM NADPH, and 5 mM (S)-AL or 10 mM (R/S)-AL or 10 mM (R/S)-AHB as substrate. The other 3 wells received 90 µL of assay buffer but without substrate. The buffers were mixed with the lysate in the wells by pipetting up and down. The reactions were then monitored at 340 nm, with absorbance readings taken every 10 seconds in a SpectraMax® 340PC plate reader (Molecular Devices, Sunnyvale, Calif.). The reactions were performed at 30° C. The (S)-AL, (R/S)-AL or (R/S)-AHB reduction activity for each sample was determined by subtracting the background reading of the no substrate control. A no lysate control was also performed in triplicate.

DHAD Enzyme Assay: Cell pellets were thawed on ice and resuspended in lysis buffer (50 mM Tris pH 8.0, 5 mM $MgSO_4$, and G Biosciences Yeast/Fungal ProteaseArrest™ (St. Louis, Mo., USA, Catalog #788-333)). One mL of glass beads (0.5 mm diameter) was added to a 1.5 mL Eppendorf tube for each sample and 850 µL of cell suspension were added. Yeast cells were lysed using a Retsch MM301 mixer mill (Retsch Inc. Newtown, Pa.), mixing 6×1 min each at full speed with 1 min incubation on ice between. The tubes were centrifuged for 10 min at 21,500×g at 4° C. and the supernatant was transferred to a fresh tube. Extracts were held on ice until assayed. Yeast lysate protein concentration was determined as described. Protein from each sample was diluted in DHAD assay buffer (50 mM Tris pH8, 5 mM $MgSO_4$) to a final concentration of 0.5 µg/µL. Three samples of each lysate were assayed, along with no lysate controls. 10 µL of each sample (or DHAD assay buffer) was added to 0.2 mL PCR tubes. Using a multi-channel pipette, 90 µL of the substrate was added to each tube (substrate mix was prepared by adding 4 mL DHAD assay buffer to 0.5 mL 100 mM DHIV). Samples were put in a thermocycler (Eppendorf Mastercycler) at 35° C. for 30 min followed by a 5 min incubation at 95° C. Samples were cooled to 4° C. on the thermocycler, then centrifuged at 3000×g for 5 minutes. Finally, 75 μL of supernatant was transferred to new PCR tubes and analyzed by HPLC as follows 100 μL DNPH reagent (12 mM 2,4-Dinitrophenyl Hydrazine 10 mM Citric Acid pH 3.0 80% Acetonitrile 20% MilliQ $H_2O$) was added to 100 μL of each sample. Samples were incubated for 30 min at 70° C. in a thermocycler (Eppendorf, Mastercycler). Analysis of keto-isovalerate and isobutyraldehyde was performed on an HP-1200 High Performance Liquid Chromatography system equipped with an Eclipse XDB C-18 reverse phase column (Agilent) and a C-18 reverse phase column guard (Phenomenex). Ketoisovalerate and isobutyraldehyde were detected using an HP-1100 UV detector (210 nm). The column temperature was 50° C. This method was isocratic with 70% acetonitrile to water as mobile phase with 2.5% dilute phosphoric acid (4%). Flow was set to 3 mL/min. Injection size was 10 μL and run time is 2 min.

Example 1

Increased Isobutanol/Isobutyrate Ratio by Increasing ADH Activity in S. cerevisiae The purpose of this example is to demonstrate that increased alcohol dehydrogenase activity results in an increased isobutanol yield, a decreased isobutyrate yield, and an increase in the ratio of isobutanol yield to isobutyrate yield.

Strains and plasmids disclosed in this example are shown in Tables 7 and 8, respectively.

TABLE 7

Genotype of Strains Disclosed in Example 1.

| GEVO Number | Genotype |
|---|---|
| GEVO2843 | S. cerevisiae, MATa ura3 leu2 his3 trp1 pdc1Δ::$P_{CUP1}$:[Bs_alsS1_coSc:$T_{CYC1}$: $P_{PGK1}$: Ll_kivD2: $P_{ENO2}$: Sp_HIS5] pdc5Δ::[LEU2: bla: $P_{TEF1}$: ILV3ΔN: $P_{TDH3}$: Ec_ilvC_coSc$^{Q110V}$] pdc6Δ::[URA3: bla: $P_{TEF1}$: Ll_kivD2: $P_{TDH3}$: Dm_ADH] {evolved for C2 supplement-independence, glucose tolerance and faster growth} |

TABLE 8

Plasmids Disclosed in Example 1.

| Plasmid Name | Relevant Genes/Usage | Genotype |
|---|---|---|
| pGV2011 | 2μ plasmid expressing KARI, and DHAD | $P_{TDH3}$:Ec_ilvC_coSc$^{Q110V}$, $P_{TEF1}$:Ll_ilvD_coSc, 2μ ori, bla, G418R |
| pGV2485 | 2μ plasmid expressing KARI, DHAD, and ADH | $P_{TDH3}$:Ec_ilvC_coSc$^{Q110V}$, $P_{TEF1}$:Ll_ilvD_coSc, $P_{ENO2}$:Ll_adhA, 2μ ori, bla, G418R |

S. cerevisiae strain GEVO2843, which expresses a single alcohol dehydrogenase (D. melanogaster ADH, Dm_ADH) from its chromosomal DNA was transformed with 2μ plasmids pGV2011 carrying only the KARI and DHAD (Ec_ilvC_Q110V and Ll_ilvD_coSc, respectively) or pGV2485 carrying the KARI, DHAD and ADH (Ec_ilvC_Q110V, Ll_ilvD_coSc, and Ll_adhA, respectively) as described.

To start fermentation cultures, small overnight cultures of the transformed strains were started in YPD medium containing 1% ethanol and 0.2 g/L G418 and incubated overnight at 30° C. and 250 rpm. Three biological replicates of each strain were tested. The next morning, the $OD_{600}$ of these cultures was determined and an appropriate amount used to inoculate 50 mL of the same medium in a 50 mL baffled flask to an $OD_{600}$ of approximately 0.1. These precultures were incubated at 30° C. and 250 rpm overnight. When the cultures had reached an $OD_{600}$ of approximately 5-6 they were centrifuged at 2700 rpm for 5 min at 25° C. in 50 mL Falcon tubes. The cells from one 50 mL culture (one clone) were resuspended in YPD containing 8% glucose, 0.2 g/L G418, 1% (v/v) ethanol (containing 3 g/L ergosterol and 132 g/L Tween-80), and buffered at pH 6.5 with 200 mM MES. The cultures were then transferred into 250 mL unbaffled flasks and incubated at 30° C. and 75 rpm.

At the 72 h timepoint, samples from each fermentation flask were taken for determining $OD_{600}$, ADH activity, and for analysis by GC1 and LC1. To prepare samples for GC1 and LC1 analysis, an appropriate volume of cell culture was spun in a microcentrifuge for 10 minutes at maximum speed and the supernatant was removed for GC1 and LC1 analysis. Cell pellets were prepared for ADH assays by centrifuging 14 mL of culture medium at 3000×g for 5 minutes at 4° C. The supernatant was removed and the cells washed in 3 mL cold, sterile water. The tubes were then centrifuged as per above for 2 minutes, the supernatant removed, and the tubes reweighed to determine total cell weight. The Falcon tubes were stored at −80° C. ADH assays were performed as described.

Table 9 shows the $OD_{600}$ for each strain during the course of the fermentation. During the 72 h of this fermentation, the $OD_{600}$ of the strains were similar: they started at an $OD_{600}$ of around 7 and ended at an $OD_{600}$ of around 9. The in vitro ADH enzymatic activity of lysates from GEVO2843 transformed with the two plasmids was measured for the 72 h timepoint. Table 9 shows the ADH activity in the lysates as measured in vitro. The strain carrying the plasmid with no ADH (pGV2011) showed an activity of about 0.04 U/mg. The strain carrying the plasmid with the Ll_adhA gene, (pGV2485), had approximately 7-fold more ADH activity.

TABLE 9

$OD_{600}$ and Alcohol Dehydrogenase Activity of Strain GEVO2843 Transformed with Plasmids pGV2011 or pGV2485 After 72 h of Fermentation.

| GEVO2843 transformed with | $OD_{600}$ | ADH activity [U/mg] |
|---|---|---|
| pGV2011 | 8.5 | 0.04 |
| pGV2485 | 9.1 | 0.29 |

Isobutanol and isobutyrate titers after 72 h of fermentation are shown in Table 10. The isobutanol titer in the strain with low ADH activity of 0.04 U/mg was significantly lower compared to the strain with high ADH activity of 0.29 U/mg. The isobutyrate titer in the strain with low ADH activity of 0.04

U/mg was significantly higher compared to the strain with high ADH activity of 0.29 U/mg. Table 6 also shows the yield for isobutyrate and isobutanol after 72 h of fermentation. The isobutanol yield in the strain with low ADH activity of 0.04 U/mg was significantly lower compared to the strain with high ADH activity of 0.29 U/mg. The isobutyrate yield in the strain with low ADH activity of 0.04 U/mg was significantly higher compared to the strain with high ADH activity of 0.29 U/mg.

mids pGV2543 carrying KARI, DHAD, KIVD and his-tagged, codon-optimized wild-type ADH (Ec_ilvC$^{Q110V}$, Ll_ilvD_coSc, and Ll_adhA_coSc$^{his6}$, respectively) or pGV2545 carrying KARI, DHAD, KIVD and his-tagged, codon-optimized mutant ADH (Ec_ilvC$^{Q110V}$, Ll_ilvD_coSc, and Ll_adhA$^{RE1}$_coSc$^{his6}$, respectively). These strains were cultured and evaluated for ADH enzyme activity and the production of extracellular metabolites by GC1 and LC1 as described.

TABLE 10

Titers and Yields for Isobutanol and Isobutyrate in Strain GEVO2843 Transformed with Plasmids pGV2011 or pGV2485 After 72 h of Fermentation.

| | Isobutanol titer [g/L] | Isobutyrate titer [g/L] | isobutanol yield [mol/mol glucose] | Isobutryate yield [mol/mol glucose] | Yield ratio (isobutanol/isobutyrate) |
|---|---|---|---|---|---|
| pGV2011 | 3.2 | 3.8 | 0.22 | 0.22 | 1.0 |
| pGV2485 | 4.7 | 1.9 | 0.33 | 0.11 | 3.0 |

Example 2

Further Increased Isobutanol/Isobutyrate Ratio by Use of Variant ADH Ll AdhA$^{RE1}$ in *S. cerevisiae*

The purpose of this example is to demonstrate that expression of an alcohol dehydrogenase with increased $k_{cat}$ and decreased $K_M$ results in a further increase in isobutanol yield, decrease in isobutyrate yield, and increase in the ratio of isobutanol yield to isobutyrate yield.

TABLE 11

Genotype of Strains Disclosed in Example 2.

| GEVO Number | Genotype |
|---|---|
| GEVO2843 | *S. cerevisiae*, MATa ura3 leu2 his3 trp1 pdc1Δ::P$_{CUP1}$:[Bs_alsS1_coSc:T$_{CYC1}$: P$_{PGK1}$: Ll_kivD2: P$_{ENO2}$: Sp_HIS5] pdc5Δ::[LEU2: bla: P$_{TEF1}$: ILV3ΔN: P$_{TDH3}$: Ec_ilvC_coSc$^{Q110V}$] pdc6Δ::[URA3: bla: P$_{TEF1}$: Ll_kivD2: P$_{TDH3}$: Dm_ADH] {evolved for C2 supplement-independence, glucose tolerance and faster growth} |

TABLE 12

Plasmids Disclosed in Example 2.

| Plasmid Name | Relevant Genes/Usage | Genotype |
|---|---|---|
| pGV2543 | 2μ plasmid expressing KARI, DHAD, KIVD, and ADH (Ll_AdhA$^{his6}$) | P$_{TDH3}$:Ec_ilvC_coSc$^{Q110V}$, P$_{TEF1}$:Ll_ilvD_coSc, P$_{PGK1}$:Ll_kivD_coEc, P$_{ENO2}$: Ll_AdhA$^{his6}$, 2μ ori, bla, G418R |
| pGV2545 | 2μ plasmid expressing KARI, DHAD, KIVD, and ADH (Ll_AdhA$^{RE1-his6}$) | P$_{TDH3}$:Ec_ilvC_coSc$^{Q110V}$, P$_{TEF1}$:Ll_ilvD_coSc, P$_{PGK1}$:Ll_kivD_coEc, P$_{ENO2}$: Ll_AdhA$^{RE1-his6}$, 2μ ori, bla, G418R |

*S. cerevisiae* strain GEVO2843, which expresses a single alcohol dehydrogenase (*D. melanogaster* ADH, Dm_ADH) from its chromosomal DNA was transformed with 2μ plas- The kinetic parameters of the gene products of Ll_adhA_coSc$^{his6}$ Ll_adhA$^{RE1}$_coSc$^{his6}$ (Ll_adhA$^{his6}$ and Ll_adhA$^{RE1-his6}$, respectively) are shown in Table 13.

TABLE 13

Comparison of Kinetic Parameters of Wild-Type Ll_adhA$^{his6}$ with Modified Ll_adhA$^{RE1}$ Measured for Isobutyraldehyde with NADH as Cofactor.

| Variant | $K_M$ [mM isobutyraldehyde] | $k_{cat}$ [s$^{-1}$] | $k_{cat}/K_M$ [M$^{-1}$ * s$^{-1}$] |
|---|---|---|---|
| Ll_adhA$^{his6}$ | 11.7 | 51 | 4400 |
| Ll_adhA$^{RE1-his6}$ | 1.6 | 84 | 49700 |

Table 14 shows the OD$_{600}$ for each strain during the course of the fermentation. During the 72 h of this fermentation, the OD$_{600}$ of the strains were similar: they started at an OD$_{600}$ of around 6 and ended at an OD$_{600}$ of around 9. The in vitro ADH enzymatic activity of lysates from GEVO2843 transformed with the two plasmids was measured for the 72 h timepoint. Table 14 shows the ADH activity in the lysates as measured in vitro as described above. The strain carrying the plasmid with Ll_adhA_coSc$^{his6}$ (pGV2543) showed an activity of about 0.38 U/mg. The strain carrying the plasmid with the Ll_adhA$^{RE1}$_coSc$^{his6}$ gene, (pGV2545), had approximately 7-fold more ADH activity.

TABLE 14

OD$_{600}$, and Alcohol Dehydrogenase Activity of Strain GEVO2843 Transformed with Plasmids pGV2543 or pGV2545 After 72 h of Fermentation.

| GEVO2843 transformed with | OD$_{600}$ | ADH activity [U/mg] |
|---|---|---|
| pGV2543 | 8.5 | 0.38 |
| pGV2545 | 8.8 | 2.46 |

Isobutanol and isobutyrate titers and yield after 72 h of fermentation are shown in Table 15. The isobutanol titer and yield in the strain carrying pGV2543 was lower compared to the strain carrying pGV2545. The isobutyrate titer and yield in the strain carrying pGV2543 was significantly higher compared to the strain carrying pGV2545.

TABLE 15

Titers and Yields for Isobutanol and Isobutyrate in Strain GEVO2843 Transformed with Plasmids pGV2453 or pGV2485 After 72 h of Fermentation.

| GEVO2843 transformed with | Isobutanol [g/L] | Isobutyrate [g/L] | isobutanol yield [mol/mol glucose] | Isobutryate yield [mol/mol glucose] | Yield ratio (Isobutanol/isobutyrate) |
|---|---|---|---|---|---|
| pGV2543 | 4.6 | 1.3 | 0.28 | 0.06 | 4 |
| pGV2545 | 4.9 | 0.3 | 0.29 | 0.01 | 20 |

Example 3

Further Increased Isobutanol/Isobutyrate Ratio in *S. cerevisiae* by Expression of RE1

The purpose of this example is to demonstrate that expression of an alcohol dehydrogenase with increased $k_{cat}$ and decreased $K_M$ results in an increase in isobutanol yield and a decrease in isobutyrate yield in fermentations performed in fermenter vessels.

A fermentation was performed to compare performance of *S. cerevisiae* strains GEVO3519 and GEVO3523. Isobutanol and isobutyrate titers and yields were measured during the fermentation. GEVO3519 carries a 2μ plasmid pGV2524 that contains genes encoding the following enzymes: KARI, DHAD, KIVD and his-tagged, codon-optimized wild-type *Lactococcus lactis* ADH. GEVO3523 carries a 2μ plasmid pGV2524 that contains genes encoding the following enzymes: KARI, DHAD, KIVD and an improved variant of the his-tagged, codon-optimized *Lactococcus* lactis ADH having decreased $K_M$ and increased $k_{cat}$. These strains were evaluated for isobutanol, isobutyraldehyde, glucose consumption by LC1 and GC1, as well as for $OD_{600}$ during a fermentation in DasGip fermenter vessels.

TABLE 16

Genotype of Strains Disclosed in Example 3.

| GEVO Number | Genotype |
|---|---|
| GEVO3128 | *S. cerevisiae*, MATa ura3 leu2 his3 trp1<br>gpd2Δ::[$T_{Kl\_URA3\_short}$:$P_{FBA1}$:Kl_URA3:$T_{Kl\_URA3}$]<br>gpd1Δ::$P_{ccw12}$:hph<br>pdc1Δ::[$P_{CUP1}$:Bs_alsS1_coSc:$T_{CYC1}$:$P_{PGK1}$:Ll_kivDkivD2:$P_{ENO2}$:Sp_HIS5]<br>pdc5Δ::[LEU2:bla:$P_{TEF1}$; ILV3ΔN:$P_{TDH3}$:Ec_ilvC_coSc$^{Q110V}$]<br>pdc6Δ::[$P_{TEF1}$:Ll_ilvD:$P_{TDH3}$:Ec_ilvC_coSc$^{P2D1-A1}$:$P_{ENO2}$:Ll_adhA:$P_{FBA1}$:Sc_TRP1]<br>{evolved for C2 supplement-independence, glucose tolerance and faster growth} |
| GEVO3519 | GEVO3128 transformed with plasmid pGV2524 |
| GEVO3523 | GEVO3128 transformed with plasmid pGV2546 |

TABLE 17

Plasmids Disclosed in Example 3.

| Plasmid Name | Relevant Genes/ Usage | Genotype |
|---|---|---|
| pGV2524 | 2μ plasmid | $P_{TDH3}$:Ec_ilvC_coSc$^{P2D1-A1}$,<br>$P_{TEF1}$:Ll_ilvD_coSc,<br>$P_{PGK1}$:Ll_kivD2_coEc<br>$P_{ENO2}$:Ll_adhA_coSc$^{his6}$,<br>2μ ori, bla, G418R |
| pGV2546 | 2μ plasmid | $P_{TDH3}$:Ec_ilvC_coSc$^{P2D1-A1}$,<br>$P_{TEF1}$:Ll_ilvD_coSc, |

TABLE 17-continued

Plasmids Disclosed in Example 3.

| Plasmid Name | Relevant Genes/ Usage | Genotype |
|---|---|---|
| | | $P_{PGK1}$:Ll_kivD2_coEc<br>$P_{ENO2}$:Ll_adhA_coSc$^{RE1-his6}$,<br>2μ ori, bla, G418R |

*S. cerevisiae* strain GEVO3128 was transformed with either 2μ plasmid pGV2524 or pGV2546, to generate strains GEVO3519 and GEVO3523, respectively as described. Inoculum cultures of GEVO3519 and GEVO3523 were started by inoculating 500 mL baffled flasks containing 80 mL of YPD medium 0.2 g/L G418 antibiotic, 1% v/v ethanol, and 0.019 g/L tryptophan. The cultures were incubated for approximately 34 h. The orbital shaker was set at 250 rpm and 30° C. in both experiments. Similar cell mass was achieved for GEVO3519 and GEVO3523 strains. The cell density achieved after incubation was 8.0 $OD_{600}$. Batch fermentations were conducted in YPD medium containing 80 g/L glucose, 0.2 g/L G418, 1% v/v ethanol, and 0.019 g/L tryptophan using 2 L top drive motor DasGip vessels with a working volume of 0.9 L per vessel. Vessels were sterilized, along with the appropriate dissolved oxygen and pH probes, for 60 minutes at 121° C. Dissolved oxygen probes were calibrated post sterilization in order to allow for polarization, however, pH probes were calibrated prior to sterilization. The pH was controlled at pH 6.0 using 6N KOH and 2N $H_2SO_4$. During the growth phase of the culture the oxygen transfer rate (OTR) was 10 mM/h and during the production phase of the culture the OTR was 0.2 mM/h.

Table 18 shows the isobutanol titer and yield (as % theoretical) as calculated for the production phase of the culture. Both isobutanol titer and yield are increased in strain GEVO3523 carrying the alcohol dehydrogenase with decreased $K_M$ and increased $k_{cat}$. Table 18 also shows the isobutyrate titer, reported as maximum titer reached, and yield as carbon yield in %. Both isobutyrate titer and yield are decreased in strain GEVO3523 carrying the alcohol dehydrogenase with decreased $K_M$ and increased $k_{cat}$.

TABLE 18

Isobutanol and Isobutyrate Titers and Yields.

| Strain | Isobutanol titer [g/L] | Isobutanol yield [% theor.] | Isobutyrate titer [g/L] | Isobutyrate yield [% C-yield] |
|---|---|---|---|---|
| GEVO3519 | 3.9 ± 0.4 | 50.5 ± 2.1 | 0.82 ± 0.04 | 4.0 ± 0.0 |
| GEVO3523 | 5.0 ± 0.3 | 59.5 ± 2.1 | 0.40 ± 0.01 | 2.0 ± 0.0 |

Example 4

Decreased Isobutyrate and Acetate Production in Fermentations with Deletion of ALD6 Gene in *S. cerevisiae*

The following example illustrates that deletion of the ALD6 gene leads to a decrease in isobutyrate and acetate production in fermentations.

Construction of ALD6 Deletion Strains: PCR was used to generate a DNA fragment that contained a deletion allele of ALD6 for deletion of ALD6 from *S. cerevisiae*. One PCR reaction amplified a DNA fragment (A) comprising the upstream flanking region of ALD6 and a region of overlap at the 3' end of the DNA fragment with the 5' end of the $P_{Sc\_CCW12}$ promoter region from pGV1954, using primers oGV2834 and oGV2835. Another PCR reaction amplified a DNA fragment (D) comprising the downstream flanking region of ALD6 and a region of overlap at the 5' end of the DNA fragment with the 3' end of the hph hygromycin resistance ORF from pGV2074, using primers oGV2836 and oGV2837. Another PCR reaction amplified a DNA fragment (B) comprising the $P_{Sc\_CCW12}$ promoter region from pGV1954 with a region of overlap at the 5' end of the DNA fragment with the 3' end of the upstream flanking region of ALD6 (fragment A) and a region at the 3' end of the DNA fragment with the 5' end of the hph hygromycin resistance ORF from pGV2074, using primers oGV2631 and oGV2632. Another PCR reaction amplified a DNA fragment (C) comprising the hph hygromycin resistance ORF from pGV2074 with a region of overlap at the 5' end of the DNA fragment with the 3' end of the $P_{Sc\_CCW12}$ promoter region from pGV1954 (fragment B) and a region of overlap at the 3' end of the DNA fragment with the 5' end of the downstream flanking region of ALD6 (fragment D), using primers oGV2633 and oGV2634. DNA fragments A and B were combined by PCR using primers oGV2834 and oGV2632 to generate DNA fragment AB and DNA fragments C and D were combined by PCR using primers oGV2633 and oGV2837 to generate DNA fragment CD. DNA fragments AB and CD were combined by PCR using primers oGV2834 and oGV2837 to generate the final DNA fragment ABCD that contained the deletion allele of ALD6.

TABLE 19

Primer Sequences Disclosed in Example 4.

| oGV No. | Sequence |
|---|---|
| oGV968 | ACTCGCCGATAGTGGAAACCGACG (SEQ ID NO: 62) |
| oGV1965 | CAAACTGTGATGGACGACACC (SEQ ID NO: 63) |
| oGV2631 | CAATACGTTATGCCGTAATGAAG (SEQ ID NO: 64) |
| oGV2632 | GCTTTTTACCCATTATTGATATAGTGTTTAAGCGAATG (SEQ ID NO: 65) |
| oGV2633 | CACTATATCAATAATGGGTAAAAAGCCTGAACTCAC (SEQ ID NO: 66) |
| oGV2634 | TTATTCCTTTGCCCTCGGACG (SEQ ID NO: 67) |
| oGV2680 | TGCACTGCTGTCTTCACTTC (SEQ ID NO: 68) |
| oGV2796 | TGTCAGCGCTTCAGACTC (SEQ ID NO: 69) |
| oGV2797 | AAGTATTTTTAAGGATTCGCTC (SEQ ID NO: 70) |
| oGV2798 | CTTCATTACGGCATAACGTATTGAAGTATTTTTAAGGATTCGCTC (SEQ ID NO: 71) |
| oGV2800 | CGTCCGAGGGCAAAGGAATAAGATAGTTATCATTATGTAAGTGCG (SEQ ID NO: 72) |
| oGV2801 | GGGAGTTTAGCAATCAGC (SEQ ID NO: 73) |
| oGV2802 | TGGTTGACCCGCAAACTTC (SEQ ID NO: 74) |

TABLE 19-continued

Primer Sequences Disclosed in Example 4.

| oGV No. | Sequence |
|---|---|
| oGV2803 | ACAATCTCCCTGTCTCCTCCC (SEQ ID NO: 75) |
| oGV2804 | AAGGTGATTTGGCACAAATTTTAC (SEQ ID NO: 76) |
| oGV2805 | GGTACAATTCTGTCCTGAATTGTAG (SEQ ID NO: 77) |
| oGV2806 | AGGTCCTAGAAATCCCTTAAG (SEQ ID NO: 78) |
| oGV2808 | CTTCATTACGGCATAACGTATTGCGATATCAGTATACAAGGTAGGC (SEQ ID NO: 79) |
| oGV2810 | CGTCCGAGGGCAAAGGAATAAGGATTTAAGATGAGTGGTATTGG (SEQ ID NO: 80) |
| oGV2811 | TGTTCGTAACTTTTGTCATCAC (SEQ ID NO: 81) |
| oGV2812 | TCAGCATGCGGAACAATTG (SEQ ID NO: 82) |
| oGV2813 | TCCACACGGTATCATACGATC (SEQ ID NO: 83) |
| oGV2814 | GCGGTCGACAAGTTCAATATG (SEQ ID NO: 84) |
| oGV2815 | TACTGAGCCGCCAACCTTAGTA (SEQ ID NO: 85) |
| oGV2816 | CATAACTATACCCGTACGCAG (SEQ ID NO: 86) |
| oGV2818 | CTTCATTACGGCATAACGTATTGAGCGTAGATCTACTGAACATGC (SEQ ID NO: 87) |
| oGV2820 | CGTCCGAGGGCAAAGGAATAACATGAGATTGTCAAAGAGG (SEQ ID NO: 88) |
| oGV2821 | CACCAGGCTTATTGATGACC (SEQ ID NO: 89) |
| oGV2822 | CATTACCGGCAGTTGCTC (SEQ ID NO: 90) |
| oGV2824 | TATGACAGTGCCTATCAAGC (SEQ ID NO: 91) |
| oGV2825 | AATGGGTTCTACCAGTATC (SEQ ID NO: 92) |
| oGV2826 | AAGCCGGGAACGTGCGTAAC (SEQ ID NO: 93) |
| oGV2827 | CTTCATTACGGCATAACGTATTGGGAACGCGTAATGGTGCTTG (SEQ ID NO: 94) |
| oGV2828 | CGTCCGAGGGCAAAGGAATAACCCGAGTTGACTGCTCATTG (SEQ ID NO: 95) |
| oGV2829 | AATACTCGCCGAGGCGTAGG (SEQ ID NO: 96) |
| oGV2830 | TTGGAGCTGGGAGGTAAATC (SEQ ID NO: 97) |
| oGV2831 | TGCGGCTAACCCATATTGAG (SEQ ID NO: 98) |
| oGV2832 | TACGCTGAGCGTAGTACAAC (SEQ ID NO: 99) |

TABLE 19-continued

Primer Sequences Disclosed in Example 4.

| oGV No. | Sequence |
|---|---|
| oGV2833 | TAAAGCGCTGGGTGGACAACCG<br>(SEQ ID NO: 100) |
| oGV2834 | GCACCGAGACGTCATTGTTG<br>(SEQ ID NO: 101) |
| oGV2835 | CTTCATTACGGCATAACGTATTGTAAACACGCCAGGCTTGACC<br>(SEQ ID NO: 102) |
| oGV2836 | CGTCCGAGGGCAAAGGAATAATCCATTCGGTGGTGTTAAGC<br>(SEQ ID NO: 103) |
| oGV2837 | ATGGCGAAATGGCAGTACTC<br>(SEQ ID NO: 104) |
| oGV2838 | ACCAACGACCCAAGAATC<br>(SEQ ID NO: 105) |
| oGV2839 | CTTTGCGACAGTGACAAC<br>(SEQ ID NO: 106) |
| oGV2840 | CCTCACGTAAGGGCATGATAG<br>(SEQ ID NO: 107) |
| oGV2841 | GCATTGCAGCGGTATTGTCAGG<br>(SEQ ID NO: 108) |
| oGV2842 | CAGCAGCCACATAGTATACC<br>(SEQ ID NO: 109) |
| oGV2843 | CTTCATTACGGCATAACGTATTGAGCCGTCGTTTGACATGTTG<br>(SEQ ID NO: 110) |
| oGV2844 | CGTCCGAGGGCAAAGGAATAACGCTCCATTTGGAGGGATCG<br>(SEQ ID NO: 111) |
| oGV2845 | GAATGCGCTTGCTGCTAGGG<br>(SEQ ID NO: 112) |
| oGV2846 | CAGCTCTTGCTGCAGGTAACAC<br>(SEQ ID NO: 113) |
| oGV2847 | GGCACAATCTTGGAGCCGTTAG<br>(SEQ ID NO: 114) |
| oGV2848 | ACCAAGCCATCAAGGTTGTC<br>(SEQ ID NO: 115) |
| oGV2849 | TGGGTGATGGTTTGGCGAATGC<br>(SEQ ID NO: 116) |
| oGV2896 | GAAATGATGACATGTGGAAATATAACAG<br>(SEQ ID NO: 117) |

Strains to demonstrate decreased isobutyrate and acetate production by deletion of ALD6 were constructed by transformation of GEVO3198 with the ABCD DNA fragment that contained the deletion allele of ALD6. Transformants were selected for resistance to 0.1 g/L hygromycin and transformant colonies were screened by colony PCR for the correct integration of the ABCD DNA fragment using primer pairs oGV2840/oGV2680, oGV968/oGV2841, and oGV2838/oGV2839. Strains GEVO3711, GEVO3712 and GEVO3713 were identified by this colony PCR as having ALD6 deleted by correct integration of the ABCD DNA fragment.

Strains containing an isobutanol production pathway to demonstrate decreased isobutyrate and acetate production by deletion of ALD6 were constructed by transformation of GEVO3711, GEVO3712 and GEVO3713 with a 2μ origin of replication plasmid, pGV2247, carrying genes expressing KARI, DHAD, KIVD and ADH (Ec_ilvC_coSc$^{P2D1-A1}$, Ll_ilvD_coSc, Ll_kivD2_coEc, and Ll_adhA, respectively). Transformants were selected for resistance to 0.2 g/L G418 and 0.1 g/L hygromycin and purified by re-streaking onto media containing 0.1 g/L hygromycin and 0.2 g/L G418, generating strains GEVO3714, GEVO3715 and GEVO3716. An ALD6 control strain containing an isobutanol production pathway, GEVO3466, was generated by transformation of GEVO3198 with plasmid pGV2247. Transformants were selected for resistance to 0.2 g/L G418 and purified by re-streaking onto media containing 0.2 g/L G418.

Construction of ald2Δ, ald3Δ, ald4Δ, ald5Δ and hfd1Δ Deletion Strains: PCR was used to generate separate DNA fragments that contained individual deletion alleles of ALD2, ALD3, ALD4, ALD5 and HFD1 for deletion of ALD2, ALD3, ALD4, ALD5 and HFD1 individually from S. cerevisiae in separate strains. Additionally, PCR was used to generate a DNA fragment that contained a deletion allele covering both ALD2 and ALD3, which are adjacent genes in the *S. cerevisiae* genome, for deletion of ALD2 and ALD3 together (ald2Δ ald3Δ) from *S. cerevisiae* in an individual strain. Four-component fragments containing the upstream flanking region, the $P_{Sc\_CCW12}$ promoter region from pGV1954, the hph hygromycin resistance ORF from pGV2074 and the downstream flanking region for each individual gene were generated by PCR as for the generation of the ABCD fragment for deletion of ALD6 except using the primer pairs listed in Table 20. The four-component fragment for deletion of ALD2 and ALD3 together contained the upstream flanking region from ALD2 and the downstream flanking region from ALD3 and was similarly constructed by PCR using the primer pairs listed in Table 20. The $P_{Sc\_CCW12}$ promoter region from pGV1954 was always amplified with primer pair oGV2631/oGV2632 and the hph hygromycin resistance ORF from pGV2074 was always amplified with primer pair oGV2633/oGV2634.

TABLE 20

Primers Used to Amplify Upstream and Downstream Regions for Gene Deletions.

| Gene Deletion | Primer Pairs for Upstream Region | Primer Pairs for Downstream Region |
| --- | --- | --- |
| ald2Δ | oGV2796/oGV2797, oGV2796/oGV2798 | oGV2800/oGV2801 |
| ald3Δ | oGV2806/oGV2808 | oGV2810/oGV2811 |
| ald2Δ ald3Δ | oGV2796/oGV2798 | oGV2810/oGV2811 |
| ald4Δ | oGV2816/oGV2818 | oGV2820/oGV2821 |
| ald5Δ | oGV2826/oGV2827 | oGV2828/oGV2829 |
| ald6Δ | oGV2834/oGV2835 | oGV2836/oGV2837 |
| hfd1Δ | oGV2842/oGV2843 | oGV2844/oGV2845 |

Strains with deletion of ALD2, ALD3, ALD4, ALD5 and HFD1 individually and with deletion of ALD2 and ALD3 together were constructed by transformation of GEVO3198 or GEVO3466 with the individual four-component DNA fragment that contained the individual deletion allele of ALD2, ALD3, ALD4, ALD5 or HFD1 or with the four-component DNA fragment that contained the deletion allele of ALD2 and ALD3 together. Transformants were selected for resistance to 0.1 g/L hygromycin and transformant colonies were screened by colony PCR for the correct integration of the four-component DNA fragment using the primer pairs listed in Table 21. Strain GEVO3567 was identified by this colony PCR as having ALD2 correctly deleted; strain GEVO3568 was identified by this colony PCR as having ALD3 correctly deleted; strain GEVO3569 was identified by this colony PCR as having ALD2 and ALD3 together correctly deleted; strain GEVO3579 was identified by this colony PCR as having ALD4 correctly deleted; strains GEVO3705, GEVO3706 and GEVO3707 were identified by this colony PCR as having ALD5 correctly deleted; and strains GEVO3720, GEVO3721 and GEVO3722 were identified by this colony PCR as having HFD1 correctly deleted.

Strains containing an isobutanol production pathway and with deletion of ALD2, ALD3 and ALD5 individually or with deletion of ALD2 and ALD3 together were constructed by transformation of strains GEVO3567, GEVO3568, GEVO3569, GEVO3705, GEVO3706 and GEVO3707 with plasmid pGV2247. Transformants were selected for resistance to 0.2 g/L G418 and 0.1 g/L hygromycin and purified by re-streaking onto media containing 0.1 g/L hygromycin and 0.2 g/L G418, generating strains GEVO3586, GEVO3587, GEVO3588, GEVO3590, GEVO3591, GEVO3592, GEVO3593, GEVO3594, GEVO3595, GEVO3708, GEVO3709 and GEVO3710. Strains GEVO3579, GEVO3720, GEVO3721 and GEVO3722 were generated from GEVO3466 and therefore contained plasmid pGV2247.

TABLE 21

Primers Used to Screen Colonies for Verification of Gene Deletions.

| Gene Deletion | Primer Pairs |
| --- | --- |
| ald2Δ | oGV2802/oGV2632, oGV968/oGV2803, oGV2804/oGV2805 |
| ald3Δ | oGV2812/oGV2632, oGV968/oGV2813, oGV2814/oGV2815 |
| ald2Δ | oGV2802/oGV2632, oGV968/oGV2813, oGV2804/oGV2805, |
| ald3Δ | oGV2814/oGV2815 |
| ald4Δ | oGV2822/oGV2632, oGV968/oGV2896, oGV2824/oGV2825 |
| ald5Δ | oGV2832/oGV2680, oGV1965/oGV2833, oGV2830/oGV2831 |
| ald6Δ | oGV2840/oGV2680, oGV968/oGV2841, oGV2838/oGV2839 |
| hfd1Δ | oGV2848/oGV2680, oGV968/oGV2849, oGV2846/oGV2847 |

TABLE 22

Genotype of Strains Disclosed in Example 4.

| GEVO No. | Genotype |
| --- | --- |
| GEVO3198 | MATa ura3 leu2 his3 trp1 <br> gpd1Δ::[$T_{Kl\_URA3}$] gpd2 Δ::[$T_{Kl\_URA3\_short}$:$P_{FBA1}$:Kl_URA3:$T_{Kl\_URA3}$] <br> pdc1Δ::[$P_{CUP1}$:Bs_alsS_coSc:$T_{CYC1}$:$P_{PGK1}$:Ll_kivD2_coEc:$P_{ENO2}$:Sp_HIS5] <br> pdc5Δ::[LEU2:bla:$P_{TEF1}$:Sc_ILV3ΔN:$P_{TDH3}$-Ec_ilvC_coSc$^{Q110V}$] <br> pdc6Δ::[$P_{TEF1}$:Ll_ilvD_coSc:$P_{TDH3}$:Ec_ilvC_coSc$^{P2D1-A1}$:$P_{ENO2}$:Ll_adhA:$P_{FBA1}$:Sc_TRP1] <br> {evolved for C2 supplement-independence, glucose tolerance and faster growth} |
| GEVO3466 | MATa ura3 leu2 his3 trp1 <br> gpd1Δ::[$T_{Kl\_URA3}$] gpd2 Δ::[$T_{Kl\_URA3\_short}$:$P_{FBA1}$:Kl_URA3:$T_{Kl\_URA3}$] <br> pdc1Δ::[$P_{CUP1}$:Bs_alsS_coSc:$T_{CYC1}$:$P_{PGK1}$:Ll_kivD2_coEc:$P_{ENO2}$:Sp_HIS5] <br> pdc5Δ::[LEU2:bla:$P_{TEF1}$:Sc_ILV3ΔN:$P_{TDH3}$-Ec_ilvC_coSc$^{Q110V}$] <br> pdc6Δ::[$P_{TEF1}$:Ll_ilvD_coSc:$P_{TDH3}$:Ec_ilvC_coSc$^{P2D1-A1}$:$P_{ENO2}$:Ll_adhA:$P_{FBA1}$:Sc_TRP1] <br> {evolved for C2 supplement-independence, glucose tolerance and faster growth}: <br> transformed with pGV2247 |
| GEVO3567 | MATa ura3 leu2 his3 trp1 gpd1Δ::[$T_{Kl\_URA3}$] gpd2 Δ::[$T_{Kl\_URA3\_short}$:$P_{FBA1}$:Kl_URA3:$T_{Kl\_URA3}$] <br> pdc1Δ::[$P_{CUP1}$:Bs_alsS_coSc:$T_{CYC1}$:$P_{PGK1}$:Ll_kivD2_coEc:$P_{ENO2}$:Sp_HIS5] <br> pdc5Δ::[LEU2:bla:$P_{TEF1}$:Sc_ILV3ΔN:$P_{TDH3}$-Ec_ilvC_coSc$^{Q110V}$] <br> pdc6Δ::[$P_{TEF1}$:Ll_ilvD_coSc:$P_{TDH3}$:Ec_ilvC_coSc$^{P2D1-A1}$:$P_{ENO2}$:Ll_adhA:$P_{FBA1}$:Sc_TRP1] <br> ald2Δ::$P_{Sc\_CCW12}$:hph {evolved for C2 supplement-independence, glucose tolerance and faster growth} |

TABLE 22-continued

Genotype of Strains Disclosed in Example 4.

| GEVO No. | Genotype |
|---|---|
| GEVO3568 | MATa ura3 leu2 his3 trp1 gpd1Δ::[$T_{Kl\_URA3}$] gpd2 Δ::[$T_{Kl\_URA3\_short}$:$P_{FBA1}$:Kl_URA3-$T_{Kl\_URA3}$] pdc1Δ::[$P_{CUP1}$:Bs_alsS_coSc:$T_{CYC1}$:$P_{PGK1}$:Ll_kivD2_coEc:$P_{ENO2}$:Sp_HIS5] pdc5Δ::[LEU2:bla:$P_{TEF1}$:Sc_ILV3ΔN:$P_{TDH3}$-Ec_ilvC_coSc$^{Q110V}$] pdc6Δ::[$P_{TEF1}$:Ll_ilvD_coSc:$P_{TDH3}$:Ec_ilvC_coSc$^{P2D1-A1}$:$P_{ENO2}$:Ll_adhA:$P_{FBA1}$:Sc_TRP1] ald3Δ::$P_{Sc\_CCW12}$-hph {evolved for C2 supplement-independence, glucose tolerance and faster growth} |
| GEVO3569 | MATa ura3 leu2 his3 trp1 gpd1Δ::[$T_{Kl\_URA3}$] gpd2 Δ::[$T_{Kl\_URA3\_short}$:$P_{FBA1}$:Kl_URA3-$T_{Kl\_URA3}$] pdc1Δ::[$P_{CUP1}$:Bs_alsS_coSc:$T_{CYC1}$:$P_{PGK1}$:Ll_kivD2_coEc:$P_{ENO2}$:Sp_HIS5] pdc5Δ::[LEU2:bla:$P_{TEF1}$:Sc_ILV3ΔN:$P_{TDH3}$-Ec_ilvC_coSc$^{Q110V}$] pdc6Δ::[$P_{TEF1}$:Ll_ilvD_coSc:$P_{TDH3}$:Ec_ilvC_coSc$^{P2D1-A1}$:$P_{ENO2}$:Ll_adhA:$P_{FBA1}$:Sc_TRP1] ald2Δ :ald3Δ::$P_{Sc\_CCW12}$-hph {evolved for C2 supplement-independence, glucose tolerance and faster growth} |
| GEVO3579 | MATa ura3 leu2 his3 trp1 gpd1Δ::[$T_{Kl\_URA3}$] gpd2 Δ::[$T_{Kl\_URA3\_short}$:$P_{FBA1}$:Kl_URA3-$T_{Kl\_URA3}$] pdc1Δ::[$P_{CUP1}$:Bs_alsS_coSc:$T_{CYC1}$:$P_{PGK1}$:Ll_kivD2_coEc:$P_{ENO2}$:Sp_HIS5] pdc5Δ::[LEU2:bla:$P_{TEF1}$:Sc_ILV3ΔN:$P_{TDH3}$-Ec_ilvC_coSc$^{Q110V}$] pdc6Δ::[$P_{TEF1}$:Ll_ilvD_coSc:$P_{TDH3}$:Ec_ilvC_coSc$^{P2D1-A1}$:$P_{ENO2}$:Ll_adhA:$P_{FBA1}$:Sc_TRP1] ald4Δ::$P_{Sc\_CCW12}$-hph {evolved for C2 supplement-independence, glucose tolerance and faster growth}; transformed with pGV2247 |
| GEVO3586, GEVO3587 and GEVO3588 | MATa ura3 leu2 his3 trp1 gpd1Δ::[$T_{Kl\_URA3}$] gpd2 Δ::[$T_{Kl\_URA3\_short}$:$P_{FBA1}$:Kl_URA3-$T_{Kl\_URA3}$] pdc1Δ::[$P_{CUP1}$:Bs_alsS_coSc:$T_{CYC1}$:$P_{PGK1}$:Ll_kivD2_coEc:$P_{ENO2}$:Sp_HIS5] pdc5Δ::[LEU2:bla:$P_{TEF1}$:Sc_ILV3ΔN:$P_{TDH3}$-Ec_ilvC_coSc$^{Q110V}$] pdc6Δ::[$P_{TEF1}$:Ll_ilvD_coSc:$P_{TDH3}$:Ec_ilvC_coSc$^{P2D1-A1}$:$P_{ENO2}$:Ll_adhA:$P_{FBA1}$:Sc_TRP1] ald2Δ: ald3Δ::$P_{Sc\_CCW12}$-hph {evolved for C2 supplement-independence, glucose tolerance and faster growth}; transformed with pGV2247 |
| GEVO3590, GEVO3591 and GEVO3592 | MATa ura3 leu2 his3 trp1 gpd1Δ::[$T_{Kl\_URA3}$] gpd2 Δ::[$T_{Kl\_URA3\_short}$:$P_{FBA1}$:Kl_URA3-$T_{Kl\_URA3}$] pdc1Δ::[$P_{CUP1}$:Bs_alsS_coSc:$T_{CYC1}$:$P_{PGK1}$:Ll_kivD2_coEc:$P_{ENO2}$:Sp_HIS5] pdc5Δ::[LEU2:bla:$P_{TEF1}$:Sc_ILV3ΔN:$P_{TDH3}$-Ec_ilvC_coSc$^{Q110V}$] pdc6Δ::[$P_{TEF1}$:Ll_ilvD_coSc:$P_{TDH3}$:Ec_ilvC_coSc$^{P2D1-A1}$:$P_{ENO2}$:Ll_adhA:$P_{FBA1}$:Sc_TRP1] ald2Δ::$P_{Sc\_CCW12}$-hph {evolved for C2 supplement-independence, glucose tolerance and faster growth}; transformed with pGV2247 |
| GEVO3593, GEVO3594 and GEVO3595 | MATa ura3 leu2 his3 trp1 gpd1::$T_{Kl\_URA3}$ gpd2::$T_{Kl\_URA3\_short}$-$P_{FBA1}$-Kl_URA3-$T_{Kl\_URA3}$ pdc1::$P_{CUP1}$-Bs_alsS-coSc-$T_{CYC1}$-$P_{PGK1}$-Ll_kivD2_coEc-$P_{ENO2}$-Sp_HIS5 pdc5::LEU2-bla-$P_{TEF1}$-Sc_ILV3ΔN-$P_{TDH3}$-Ec_ilvC_coSc$^{Q110V}$ pdc6::$P_{TEF1}$-Ll_ilvD_coSc-$P_{TDH3}$-Ec_ilvC_coSc$^{P2D1-A1}$-$P_{ENO2}$-Ll_adhA-$P_{FBA1}$-Sc_TRP1 ald3Δ::$P_{Sc\_CCW12}$-hph {evolved for C2 supplement-independence, glucose tolerance and faster growth}; transformed with pGV2247 |
| GEVO3705, GEVO3706 and GEVO3707 | MATa ura3 leu2 his3 trp1 gpd1Δ::[$T_{Kl\_URA3}$] gpd2 Δ::[$T_{Kl\_URA3\_short}$:$P_{FBA1}$:Kl_URA3-$T_{Kl\_URA3}$] pdc1Δ::[$P_{CUP1}$:Bs_alsS_coSc:$T_{CYC1}$:$P_{PGK1}$:Ll_kivD2_coEc:$P_{ENO2}$:Sp_HIS5] pdc5Δ::[LEU2:bla:$P_{TEF1}$:Sc_ILV3ΔN:$P_{TDH3}$-Ec_ilvC_coSc$^{Q110V}$] pdc6Δ::[$P_{TEF1}$:Ll_ilvD_coSc:$P_{TDH3}$:Ec_ilvC_coSc$^{P2D1-A1}$:$P_{ENO2}$:Ll_adhA:$P_{FBA1}$:Sc_TRP1] ald5Δ::$P_{Sc\_CCW12}$-hph {evolved for C2 supplement-independence, glucose tolerance and faster growth} |
| GEVO3708, GEVO3709 and GEVO3710 | MATa ura3 leu2 his3 trp1 gpd1Δ::[$T_{Kl\_URA3}$] gpd2 Δ::[$T_{Kl\_URA3\_short}$:$P_{FBA1}$:Kl_URA3-$T_{Kl\_URA3}$] pdc1Δ::[$P_{CUP1}$:Bs_alsS_coSc:$T_{CYC1}$:$P_{PGK1}$:Ll_kivD2_coEc:$P_{ENO2}$:Sp_HIS5] pdc5Δ::[LEU2:bla:$P_{TEF1}$:Sc_ILV3ΔN:$P_{TDH3}$-Ec_ilvC_coSc$^{Q110V}$] pdc6Δ::[$P_{TEF1}$:Ll_ilvD_coSc:$P_{TDH3}$:Ec_ilvC_coSc$^{P2D1-A1}$:$P_{ENO2}$:Ll_adhA:$P_{FBA1}$:Sc_TRP1] ald5Δ::$P_{Sc\_CCW12}$-hph {evolved for C2 supplement-independence, glucose tolerance and faster growth}; transformed with pGV2247 |
| GEVO3711, GEVO3712 and GEVO3713 | MATa ura3 leu2 his3 trp1 gpd1Δ::[$T_{Kl\_URA3}$] gpd2 Δ::[$T_{Kl\_URA3\_short}$:$P_{FBA1}$:Kl_URA3-$T_{Kl\_URA3}$] pdc1Δ::[$P_{CUP1}$:Bs_alsS_coSc:$T_{CYC1}$:$P_{PGK1}$:Ll_kivD2_coEc:$P_{ENO2}$:Sp_HIS5] pdc5Δ::[LEU2:bla:$P_{TEF1}$:Sc_ILV3ΔN:$P_{TDH3}$-Ec_ilvC_coSc$^{Q110V}$] pdc6Δ::[$P_{TEF1}$:Ll_ilvD_coSc:$P_{TDH3}$:Ec_ilvC_coSc$^{P2D1-A1}$:$P_{ENO2}$:Ll_adhA:$P_{FBA1}$:Sc_TRP1] ald6Δ::$P_{Sc\_CCW12}$-hph {evolved for C2 supplement-independence, glucose tolerance and faster growth} |
| GEVO3714, GEVO3715 and GEVO3716 | MATa ura3 leu2 his3 trp1 gpd1Δ::[$T_{Kl\_URA3}$] gpd2 Δ::[$T_{Kl\_URA3\_short}$:$P_{FBA1}$:Kl_URA3-$T_{Kl\_URA3}$] pdc1Δ::[$P_{CUP1}$:Bs_alsS_coSc:$T_{CYC1}$:$P_{PGK1}$:Ll_kivD2_coEc:$P_{ENO2}$:Sp_HIS5] pdc5Δ::[LEU2:bla:$P_{TEF1}$:Sc_ILV3ΔN:$P_{TDH3}$-Ec_ilvC_coSc$^{Q110V}$] pdc6Δ::[$P_{TEF1}$:Ll_ilvD_coSc:$P_{TDH3}$:Ec_ilvC_coSc$^{P2D1-A1}$:$P_{ENO2}$:Ll_adhA:$P_{FBA1}$:Sc_TRP1] ald6Δ::$P_{Sc\_CCW12}$-hph {evolved for C2 supplement-independence, glucose tolerance and faster growth}; transformed with pGV2247 |
| GEVO3720, GEVO3721 and GEVO3722 | MATa ura3 leu2 his3 trp1 gpd1Δ::[$T_{Kl\_URA3}$] gpd2 Δ::[$T_{Kl\_URA3\_short}$:$P_{FBA1}$:Kl_URA3-$T_{Kl\_URA3}$] pdc1Δ::[$P_{CUP1}$:Bs_alsS_coSc:$T_{CYC1}$:$P_{PGK1}$:Ll_kivD2_coEc:$P_{ENO2}$:Sp_HIS5] pdc5Δ::[LEU2:bla:$P_{TEF1}$:Sc_ILV3ΔN:$P_{TDH3}$-Ec_ilvC_coSc$^{Q110V}$] pdc6Δ::[$P_{TEF1}$:Ll_ilvD_coSc:$P_{TDH3}$:Ec_ilvC_coSc$^{P2D1-A1}$:$P_{ENO2}$:Ll_adhA:$P_{FBA1}$:Sc_TRP1] hfd1Δ::$P_{Sc\_CCW12}$-hph {evolved for C2 supplement-independence, glucose tolerance and faster growth}: transformed with pGV2247 |

TABLE 23

Plasmids Disclosed in Example 4.

| Plasmid Name | Genotype |
|---|---|
| pGV2247 | $P_{TEF1}$:Ll_ilvD_coSc $P_{TDH3}$:Ec_ilvC_coSc$^{P2D1-A1}$ $P_{PGK1}$:Ll_kivD2_coEc $P_{ENO2}$: Ll_adhA 2μ-ori, pUC-ori, bla, G418R. |

Shake Flask Fermentations: Fermentations were performed to compare the performance of GEVO3466 to strains containing the ald2Δ, ald3Δ, ald2Δ ald3Δ, ald4Δ, ald5Δ, hfd1Δ and ald6Δ deletion mutations. Yeast strains were inoculated from cell patches or from purified single colonies from YPD agar plates containing 0.2 g/L G418 into 3 mL of YPD containing 0.2 g/L G418 and 1% v/v ethanol medium in 14 mL round-bottom snap-cap tubes. The cultures were incubated overnight up to 24 h shaking at an angle at 250 rpm at 30° C. Separately for each strain, these overnight cultures were used to inoculate 50 mL of YPD containing 0.2 g/L G418 and 1% v/v ethanol medium in a 250 mL baffled flask with a sleeve closure to an $OD_{600}$ of 0.1. These flask cultures were incubated overnight up to 24 h shaking at 250 rpm at 30° C. The cells from these flask cultures were harvested separately for each strain by centrifugation at 3000×g for 5 minutes and each cell pellet resuspended separately in 5 mL of YPD containing 80 g/L glucose, 1% v/v stock solution of 3 g/L ergosterol and 132 g/L Tween 80 dissolved in ethanol, 200 mM MES buffer, pH 6.5, and 0.2 g/L G418 medium. Each cell suspension was used to inoculate 50 mL of YPD containing 80 g/L glucose, 1% v/v stock solution of 3 g/L ergosterol and 132 g/L Tween 80 dissolved in ethanol, 200 mM MES buffer, pH 6.5, and 0.2 g/L G418 medium in a 250 mL non-baffled flask with a vented screw-cap to an $OD_{600}$ of approximately 5. These fermentations were incubated shaking at 250 rpm at 30° C. Periodically, samples from each shake flask fermentation were removed to measure $OD_{600}$ and to prepare for gas chromatography (GC1) analysis, for isobutanol and other metabolites, and for high performance liquid chromatography (LC1) analysis for organic acids and glucose. Samples of 2 mL were removed into a microcentrifuge tube and centrifuged in a microcentrifuge for 10 min at maximum rpm. One mL of the supernatant was analysis of extracellular metabolites by GC1 and LC1 as described.

Deletion of ALD6 decreased isobutyrate and acetate production in shake flask fermentations: The 52 h shake flask fermentation results for GEVO3466 and the ald6Δ strains GEVO3714, GEVO3715 and GEVO3716 are summarized in Table 24. The ald6Δ strains GEVO3714, GEVO3715 and GEVO3716 produced 71% less isobutyrate than the ALD6 strain GEVO3466. The ald6Δ strains GEVO3714, GEVO3715 and GEVO3716 also produced 86% less acetate than the ALD6 strain GEVO3466. Isobutanol yield in the ald6Δ strains GEVO3714, GEVO3715 and GEVO3716 was not appreciably different than the ALD6 strain GEVO3466. Isobutanol titer in the ald6Δ strains GEVO3714, GEVO3715 and GEVO3716 was 23% higher than the ALD6 strain GEVO3466.

TABLE 24

Shake Flask Fermentation Results Demonstrating Decreased Isobutyrate and Acetate Production by Deletion of ALD6

| Strain | Isobutanol Titer [g/L] | Isobutanol Yield [% theoretical] | Isobutyrate Produced [g/L] | Acetate Produced [g/L] |
|---|---|---|---|---|
| GEVO3466 (ALD6) | 2.6 ± 0.1 | 44 ± 2 | 0.48 ± 0.06 | 0.59 ± 0.04 |
| GEVO3714, GEVO3715 and GEVO3716 (ald6Δ) | 3.2 ± 0.2 | 42 ± 2 | 0.14 ± 0.06 | 0.08 ± 0.01 |

The 72 h shake flask fermentation results for GEVO3466 and the ald2Δ, ald3Δ, ald2Δ, ald3Δ, ald4Δ, ald5Δ and hfd1Δ strains are summarized in Table 25 and Table 26. Strains with deletions in ALD3, ALD2 and ALD3 together or ALD4 had no decrease in isobutyrate production compared with the wild-type ALDH strain GEVO3466. Strains with deletions in ALD2, ALD5 or HFD1 had no appreciable decrease in isobutyrate production compared with the wild-type ALDH strain GEVO3466. Strains with deletions of both ALD2 and ALD3 together produced 19% less acetate than the wild-type ALDH strain GEVO3466 but strains with individual deletions of ALD2, ALD3, ALD4, ALD5 or HFD1 had no appreciable decrease in acetate production compared with the wild-type ALD strain GEVO3466.

TABLE 25

Shake Flask Fermentation Results Demonstrating No Decrease in Isobutyrate and Acetate production by Deletion of ALD2, ALD3, ALD4 or ALD2 and ALD3 Together.

| Strain | Isobutanol Titer [g/L] | Isobutanol Yield [% theoretical] | Isobutyrate Produced [g/L] | Acetate Produced [g/L] |
|---|---|---|---|---|
| GEVO3466 (wild-type) | 5.1 ± 0.1 | 42 ± 2 | 1.24 ± 0.15 | 0.95 ± 0.07 |
| GEVO3590, GEVO3591 and GEVO3592 (ald2Δ) | 5.2 ± 0.2 | 45 ± 2 | 1.21 ± 0.06 | 0.85 ± 0.07 |
| GEVO3593, GEVO3594 and GEVO3595 (ald3Δ) | 5.5 ± 0.6 | 45 ± 6 | 1.34 ± 0.16 | 0.91 ± 0.07 |
| GEVO3596, GEVO3597 and GEVO3598 (ald2Δ ald3Δ) | 6.8 ± 0.1 | 51 ± 1 | 1.41 ± 0.09 | 0.77 ± 0.08 |
| GEVO3579 (ald4Δ) | 5.6 ± 0.7 | 46 ± 6 | 1.34 ± 0.13 | 0.89 ± 0.15 |

TABLE 26

Shake Flask Fermentation Results Demonstrating No Decrease in Isobutyrate and Acetate Production by Deletion of ALD5 or HFD1.

| Strain | Isobutanol Titer [g/L] | Isobutanol Yield [% theoretical] | Isobutyrate Produced [g/L] | Acetate Produced [g/L] |
|---|---|---|---|---|
| GEVO3466 (wild-type) | 4.0 ± 0.4 | 44 ± 7 | 0.47 ± 0.04 | 0.75 ± 0.05 |

TABLE 26-continued

Shake Flask Fermentation Results Demonstrating No Decrease in Isobutyrate and Acetate Production by Deletion of ALD5 or HFD1.

| Strain | Isobutanol Titer [g/L] | Isobutanol Yield [% theoretical] | Isobutyrate Produced [g/L] | Acetate Produced [g/L] |
|---|---|---|---|---|
| GEVO3708, GEVO3709 and GEVO3710 (ald5Δ) | 3.8 ± 0.8 | 46 ± 15 | 0.41 ± 0.04 | 0.64 ± 0.08 |
| GEVO3720, GEVO3721 and GEVO3722 (hfd1Δ) | 4.4 ± 1.0 | 54 ± 14 | 0.40 ± 0.07 | 0.56 ± 0.18 |

Fermentations in benchtop fermenters: Fermentations in benchtop fermenters were performed to compare the performance of GEVO3466 (ALD6) to GEVO3714 and GEVO3715 (ald6Δ). Glucose consumption, isobutanol production, isobutyrate production, and $OD_{600}$ were measured during the fermentation. For these fermentations, purified strains from streak plates were transferred to 500 mL baffled flasks containing 80 mL of YPD medium containing 1% v/v ethanol, 100 μM $CuSO_4 \cdot 5H_2O$ and 0.2 g/L G418 and incubated for 32 h at 30° C. in an orbital shaker at 250 rpm. The flask cultures were transferred to individual 2 L top drive motor fermenter vessels with a working volume of 0.9 L of YPD medium containing 80 g/L glucose, 1% v/v ethanol, 100 μM $CuSO_4 \cdot 5H_2O$ and 0.2 g/L G418 per vessel for a starting $OD_{600}$ of 0.5. Fermenters were operated at 30° C. and pH 6.0 controlled with 6N KOH and 2N $H_2SO_4$ in a 2-phase aerobic condition based on oxygen transfer rate (OTR). Initially, fermenters were operated at a growth phase OTR of 10 mM/h by fixed agitation of 700 rpm and an air overlay of 5 sL/h. Cultures were grown for 24 h to approximately 9-10 $OD_{600}$ then immediately switched to a production aeration OTR=2.0 mM/h by reducing agitation from 700 rpm to 450 rpm for the period of 24 h to 86.5 h. Periodically, samples from each fermenter were removed to measure $OD_{600}$ and to prepare for gas chromatography (GC1) analysis, for isobutanol and other metabolites, and for high performance liquid chromatography (LC1) analysis for organic acids and glucose. Samples of 2 mL were removed into a microcentrifuge tube and centrifuged in a microcentrifuge for 10 min at maximum rpm. One mL of the supernatant was submitted for GC1 and LC1 analysis as described.

Deletion of ALD6 decreased isobutyrate and acetate production and increased isobutanol yield in benchtop fermenter fermentations: The 86.5 h benchtop fermenter fermentation results are summarized in Table 27. The ald6Δ strains GEVO3714 and GEVO3715 produced 38% less isobutyrate than the ALD6 strain GEVO3466. The ald6Δ strains GEVO3714 and GEVO3715 also produced 61% less acetate than the ALD6 strain GEVO3466. Isobutanol yield in the ald6Δ strains GEVO3714 and GEVO3715 was 25% higher than the ALD6 strain GEVO3466. Isobutanol titer in the ald6Δ strains GEVO3714 and GEVO3715 was also 35% higher than the ALD6 strain GEVO3466.

TABLE 27

Benchtop Fermenter Fermentation Results Demonstrating Decreased Isobutyrate and Acetate Production and Increased Isobutanol Yield by Deletion of ALD6.

| Strain | Isobutanol Titer [g/L] | Isobutanol Yield [% theoretical] | Isobutyrate Produced [g/L] | Acetate Produced [g/L] |
|---|---|---|---|---|
| GEVO3466 (ALD6) | 8.2 ± 0.1 | 32 ± 1 | 2.1 ± 0.1 | 2.3 ± 0.3 |
| GEVO3714 and GEVO3715 (ald6Δ) | 11.1 ± 0.1 | 40 ± 0 | 1.3 ± 0.1 | 0.9 ± 0.1 |

Example 5

Determination of ALD6 Activity in *S. cerevisiae*

The following example illustrates that the isobutyraldehyde oxidation activity is significantly decreased in an ald6Δ strain.

TABLE 28

Genotype of Strains Disclosed in Example 5.

| GEVO # | Genotype | Source |
|---|---|---|
| GEVO3527 | MATα his3Δ-1 leu2Δ lys2Δ ura3Δ | ATCC# 201389 (BY4742) |
| GEVO3940 | MATα his3Δ-1 leu2Δlys2Δ ura3Δ ald6Δ::kan$^R$ | OpenBiosystems cat# YSC1054 (Yeast MATalpha collection) |

Yeast strains GEVO3940 from which the ALD6 (YPL061W) gene was deleted and its parent GEVO3527 were each cultured in triplicate by inoculating 3 mL of YPD medium in a 14 mL culture tube in triplicate for each strain. Cultures were started from patches on YPD agar plate for GEVO3527 and on YPD agar plates containing 0.2 g/L G418 plates for GEVO3940. The cultures were incubated overnight at 30° C. and 250 rpm. The next day, the $OD_{600}$ of the overnight cultures were measured and the volume of each culture to inoculate a 50 mL culture to an $OD_{600}$ of 0.1 was calculated. The calculated volume of each culture was used to inoculate 50 mL of YPD in a 250 mL baffled flask and the cultures were incubated at 30° C. and 250 rpm. The cells were harvested during mid-log phase at ODs of 1.6-2.1 after 7 h of growth. The cultures were transferred to pre-weighed 50 mL Falcon tubes and cells were collected by centrifugation for 5 minutes at 3000×g. After removal of the medium, cells were washed with 10 mL MilliQ $H_2O$. After removal of the water, the cells were centrifuged again at 3000×g for 5 minutes and the remaining water was carefully removed using a 1 mL pipette tip. The cell pellets were weighed and then stored at −80° C. until they were lysed and assayed for isobutyraldehyde oxidation activity as described.

As shown in Table 29, the specific activity of *S. cerevisiae* ALD6 in GEVO3527 lysates for the oxidation of 10 mM isobutyraldehyde was 13.9 mU/mg. The same strain with an ALD6 deletion had a specific activity of 0.6 mU/mg which is 22-fold less. The specific activity of *S. cerevisiae* ALD6 in GEVO3527 lysates for the oxidation of 1.0 mM isobutyraldehyde was 17.6 mU/mg. The same strain with an ALD6 deletion had a specific activity of 2.1 mU/mg which is 8-fold less. The specific activity of *S. cerevisiae* ALD6 in GEVO3527 lysates for the oxidation of 0.1 mM isobutyraldehyde was 6.7 mU/mg. The same strain with an ALD6 deletion had a specific activity of 1.3 mU/mg which is 5-fold less. These data demonstrate that the endogenous ALD6 enzyme is responsible for the isobutyrate byproduct of the isobutanol pathway in S. cerevisiae

TABLE 29

Specific Isobutyraldehyde Oxidation Activities of Strains GEVO3527 and GEVO3940 Using Various Isobutyraldehyde Concentrations. Specific Activities were Measured in Lysates From 3 Parallel Cultures of GEVO3527 and GEVO3940. Shown are the Averages and Standard Deviations of the Activities Measured in the Biological Replicate Cultures.

| Strain | Activity [mU/mg total protein] measured with isobutyraldehyde | | |
|---|---|---|---|
|  | 0.1 mM Isobutyraldehyde | 1.0 mM Isobutyraldehyde | 10 mM Isobutyraldehyde |
| GEVO3527 | 6.7 ± 0.4 | 17.6 ± 1.2 | 13.9 ± 0.4 |
| GEVO3940 | 1.3 ± 0.2 | 2.1 ± 0.2 | 0.6 ± 0.1 |

Example 6

Further Decreased Isobutyrate Production with Deletion of ALD6 Gene and Overexpression of an Improved Alcohol Dehydrogenase in S. cerevisiae The following example illustrates that the combination of an ALD6 deletion and overexpression of an ADH with improved kinetic properties leads to a further decrease in isobutyrate production and to a further increase in isobutanol production.

Isobutyrate is a byproduct of isobutyraldehyde metabolism in yeast and can comprise a significant fraction of the carbon yield. The following yeast strains were constructed: GEVO3466 was constructed by transforming strain GEVO3198 with a 2μ plasmid, pGV2247, carrying genes encoding the following enzymes: KARI, DHAD, KIVD and wild-type ADH (Ec_ilvC_coSc$^{P2D1-A1}$, Ll_ilvD_coSc, Ll_kivD2_coEc, and Ll_adhA, respectively). GEVO3198 expresses a single copy of alcohol dehydrogenase (L. lactis ADH, Ll_adhA) from its chromosomal DNA. The second strain, of which biological replicates are termed GEVO3714 and GEVO3715, was constructed by transforming two independent strains, GEVO3711 and GEVO3712, with a 2μ plasmid pGV2247 carrying genes encoding the following enzymes: KARI, DHAD, KIVD and wild-type ADH (Ec_ilvC_coSc$^{P2D1-A1}$, Ll_ilvD_coSc, Ll_kivD2_coEc, and Ll_adhA, respectively). GEVO3711 and 3712 express a single alcohol dehydrogenase (L. lactis ADH, Ll_adhA) and have the ALD6 gene deleted from the chromosomal DNA. A third strain, of which biological replicates are termed GEVO3855 and GEVO3856, was constructed by transforming a strain, GEVO3711, with 2μ plasmid pGV2602 carrying genes encoding the following enzymes: KARI, DHAD, KIVD and a mutant ADH (Ec_ilvC_coSc$^{P2D1-A1-his6}$, Ll_ilvD_coSc, Ll_kivD2_coEc, and Ll_adhA$^{RE1}$, respectively).

TABLE 30

Genotype of Strains Disclosed in Example 6.

| GEVO No. | Genotype |
|---|---|
| GEVO3198 | MATa ura3 leu2 his3 trp1<br>gpd1Δ::T$_{Kl\_URA3}$<br>gpd2Δ::[T$_{Kl\_URA3\_short}$:P$_{FBA1}$:Kl_URA3:T$_{Kl\_URA3}$]<br>pdc1Δ::[P$_{CUP1}$:Bs_alsS_coSc:T$_{CYC1}$:P$_{PGK1}$:Ll_kivDkivD:P$_{ENO2}$:Sp_HIS5]<br>pdc5Δ::[LEU2:bla:P$_{TEF1}$:ILV3ΔN:P$_{TDH3}$:Ec_ilvC_coSc$^{Q110V}$]<br>pdc6Δ::[P$_{TEF}$:Ll_ilvD:P$_{TDH3}$:Ec_ilvC_coSc$^{P2D1-A1}$:P$_{ENO2}$:Ll_adhA:P$_{FBA1}$:Sc_TRP1]<br>{evolved for C2 supplement-independence, glucose tolerance and faster growth} |
| GEVO3466 | MATa ura3 leu2 his3 trp1 gpd1Δ::T$_{Kl\_URA3}$<br>gpd2Δ::[T$_{Kl\_URA3\_short}$:P$_{FBA1}$:Kl_URA3:T$_{Kl\_URA3}$]<br>pdc1Δ::[P$_{CUP1}$:Bs_alsS_coSc:T$_{CYC1}$:P$_{PGK1}$:Ll_kivDkivD:P$_{ENO2}$:Sp_HIS5]<br>pdc5Δ::[LEU2:bla:P$_{TEF1}$:ILV3ΔN:P$_{TDH3}$:Ec_ilvC_coSc$^{Q110V}$]<br>pdc6Δ::[P$_{TEF}$:Ll_ilvD:P$_{TDH3}$:Ec_ilvC_coSc$^{P2D1-A1}$:P$_{ENO2}$:Ll_adhA:P$_{FBA1}$:Sc_TRP1]<br>Transformed with pGV2247 {evolved for C2 supplement-independence, glucose tolerance and faster growth} |
| GEVO3711, GEVO3712 | MATa ura3 leu2 his3 trp1 gpd1Δ::T$_{Kl\_URA3}$<br>gpd2Δ::[T$_{Kl\_URA3\_short}$:P$_{FBA1}$:Kl_URA3:T$_{Kl\_URA3}$]<br>pdc1Δ::[P$_{CUP1}$:Bs_alsS_coSc:T$_{CYC1}$:P$_{PGK1}$:Ll_kivD:P$_{ENO2}$:Sp_HIS5]<br>pdc5Δ::[LEU2:bla:P$_{TEF1}$:ILV3ΔN:P$_{TDH3}$:Ec_ilvC_coSc$^{Q110V}$]<br>pdc6Δ::[P$_{TEF}$:Ll_ilvD:P$_{TDH3}$:Ec_ilvC_coSc$^{P2D1-A1}$:P$_{ENO2}$:Ll_adhA:P$_{FBA1}$:Sc_TRP1]<br>ald6Δ::P$_{CCW12}$: hph {evolved for C2 supplement-independence, glucose tolerance and faster growth} |
| GEVO3714, GEVO3715 | MATa ura3 leu2 his3 trp1 gpd1Δ::T$_{Kl\_URA3}$<br>gpd2Δ::[T$_{Kl\_URA3\_short}$:P$_{FBA1}$:Kl_URA3:T$_{Kl\_URA3}$]<br>pdc1Δ::[P$_{CUP1}$:Bs_alsS_coSc:T$_{CYC1}$:P$_{PGK1}$:Ll_kivD:P$_{ENO2}$:Sp_HIS5]<br>pdc5Δ::[LEU2:bla:P$_{TEF1}$:ILV3ΔN:P$_{TDH3}$:Ec_ilvC_coSc$^{Q110V}$]<br>pdc6Δ::[P$_{TEF}$:Ll_ilvD:P$_{TDH3}$:Ec_ilvC_coSc$^{P2D1-A1}$:P$_{ENO2}$:Ll_adhA:P$_{FBA1}$:Sc_TRP1]<br>ald6Δ::P$_{CCW12}$: hph Transformed with pGV2247 {evolved for C2 supplement-independence, glucose tolerance and faster growth} |
| GEVO3855, GEVO3856 | MATa ura3 leu2 his3 trp1 gpd1Δ::T$_{Kl\_URA3}$<br>gpd2Δ::[T$_{Kl\_URA3\_short}$:P$_{FBA1}$:Kl_URA3:T$_{Kl\_URA3}$]<br>pdc1Δ::[P$_{CUP1}$:Bs_alsS_coSc:T$_{CYC1}$:P$_{PGK1}$:Ll_kivD:P$_{ENO2}$:Sp_HIS5]<br>pdc5Δ::[LEU2:bla:P$_{TEF1}$:ILV3ΔN:P$_{TDH3}$:Ec_ilvC_coSc$^{Q110V}$]<br>pdc6Δ::[P$_{TEF}$:Ll_ilvD:P$_{TDH3}$:Ec_ilvC_coSc$^{P2D1-A1}$:P$_{ENO2}$:Ll_adhA:P$_{FBA1}$:Sc_TRP1]<br>ald6Δ::P$_{CCW12}$: hph Transformed with pGV2602 {evolved for C2 supplement-independence, glucose tolerance and faster growth} |

TABLE 31

Plasmids Disclosed in Example 6.

| Plasmid Name | Genotype |
|---|---|
| pGV2247 | $P_{TEF1}$:Ll_ilvD_coSc, $P_{TDH3}$:Ec_ilvC_coSc$^{P2D1-A1}$, $P_{PGK1}$:Ll_kivD2_coEc, $P_{ENO2}$: Ll_adhA. 2μ-ori, pUC-ori, bla, G418R. |
| pGV2602 | $P_{TEF1}$:Ll_ilvD_coSc, $P_{TDH3}$:Ec_ilvC_coSc$^{P2D1-A1\text{-}his6}$, $P_{PGK1}$:Ll_kivD2_coEc, $P_{ENO2}$: Ll_adhA$^{RE1}$. 2μ-ori, pUC-ori, bla, G418R. |

Two different sets of fermentations were performed. Fermentation set A was performed to compare the performance of GEVO3466 (Ll_adhA) to GEVO3714-GEVO3715 (Ll_adhA, ald6Δ). Fermentation set B was performed to compare the performance of GEVO3714 (Ll_adhA, ald6Δ) to GEVO3855-GEVO3856 (Ll_adhA$^{RE1}$, ald6Δ) respectively. Glucose consumption, isobutanol production, isobutyrate production, and $OD_{600}$ were measured during the fermentation. For these fermentations, single isolate cell colonies grown on YPD agar plates were transferred to 500 mL baffled flasks containing 80 mL of YPD medium containing 1% v/v Ethanol, 100 μM $CuSO_4.5H_2O$, and 0.2 g/L G418 and incubated for 32 h at 30° C. in an orbital shaker at 250 rpm. The flask cultures were transferred to individual 2 L top drive motor fermenter vessels with a working volume of 0.9 L of YPD medium containing 80 g/L glucose, 1% v/v Ethanol, 100 μM $CuSO_4.5H_2O$, and 0.2 g/L G418 per vessel for a starting $OD_{600}$ of 0.5. Fermenters were operated at 30° C. and pH 6.0 controlled with 6N KOH in a 2-phase aerobic condition based on oxygen transfer rate (OTR). Initially, fermenters were operated at a growth phase OTR of 10 mM/h by fixed agitation of 700 rpm and an air overlay of 5 sL/h in both experiments. Cultures were grown for 24 h to approximately 9-10 $OD_{600}$ then immediately switched to production aeration conditions for 48.5 h. In the first experiment, an OTR of 2.5-3.0 mM/h was sustained by reducing agitation from 700 rpm to 425 rpm while in the second experiment, an OTR of 2.0-2.5 mM/h was sustained by reducing agitation from 700 rpm to 400 rpm. Periodically, samples from each fermenter were removed to measure $OD_{600}$ and to prepare for gas chromatography (GC1) and liquid chromatography (LC1) analysis. For GC1 and LC1, 2 mL sample was removed into an Eppendorf tube and centrifuged in a microcentrifuge for 10 min at maximum. One mL of the supernatant was analyzed by GC1 (isobutanol, other metabolites) and one mL analyzed by high performance liquid chromatography (LC1) for organic acids and glucose.

The 72.5 h data from two separate fermentation sets A and B are summarized in Tables 32 and 33. Fermentation set A compared GEVO3466 (WT ADH) to GEVO3714 and 3715 (WT ADH, ald6Δ) while the fermentation set B compared GEVO3714 (WT ADH, ald6Δ) to GEVO3855 and 3856 (Ll_adhA$^{RE1}$, ald6Δ)

The data referring to fermentation set A (Table 32) show that isobutanol titer and theoretical yield in the strain carrying Ll_adhA with the ALD6 gene deletion was 1.4- and 1.3-fold higher, respectively, compared to the strain carrying Ll_adhA without the ALD6 gene deletion. The strain carrying Ll_adhA without ALD6 gene deletion (GEVO3466) had an isobutyrate yield (gram isobutyrate produced/gram glucose consumed) of 0.040 g/g while the strains carrying Ll_adhA with the ALD6 gene deletion (GEVO3714, GEVO3715) had a lower isobutyrate yield of 0.017 g/g. The strain carrying the *L. lactis* adhA without the ALD6 gene deletion produced 2.3 g/L acetate while the strain carrying the *L. lactis* adhA with the ALD6 gene deletion produced 0.6 g/L acetate.

TABLE 32

Data from Fermentation Set A.

| Strain | $OD_{600}$ | Isobutanol produced [g/L] | Isobutyrate produced [g/L] | Isobutanol yield [% theoretical] | Isobutyrate yield [g/g] | Acetate produced [g/L] |
|---|---|---|---|---|---|---|
| GEVO3466 (WT ADH) | 9.7 ± 0.1 | 7.4 ± 0.6 | 1.7 ± 0.0 | 48.1 ± 2.6 | 0.040 ± 0.004 | 2.3 ± 0.1 |
| GEVO3714, GEVO3715 (WT ADH, ALD6Δ) | 10.0 ± 0.7 | 10.4 ± 0.1 | 0.8 ± 0.1 | 55.3 ± 0.6 | 0.017 ± 0.003 | 0.6 ± 00.1 |

The data referring to fermentation set B (Table 33) show that isobutanol titer and theoretical yield in the strain carrying *L. lactis* adhA$^{RE1}$ with the ALD6 gene deletion was 1.2 and 1.1-fold higher, respectively, compared to the strain carrying *L. lactis* adhA with the ALD6 gene deletion. The strains carrying *L. lactis* adhA$^{RE1}$ with the ALD6 gene deletion (GEVO3855, GEVO3856) had the lowest isobutyrate yield (gram isobutyrate produced/gram glucose consumed), 0.005 g/g, and produced 0.0 g/L acetate compared to the strain carrying *L. lactis* adhA with ALD6 gene deletion (GEVO3714) which had a higher isobutyrate yield of 0.014 g/g and a similar acetate titer of 0.0 g/L (Table 33).

TABLE 33

Data from Fermentation Set B.

| Strain | $OD_{600}$ | Isobutanol produced [g/L] | Isobutyrate produced [g/L] | Isobutanol yield [% theoretical] | Isobutyrate yield [g/g] | Acetate produced [g/L] |
|---|---|---|---|---|---|---|
| GEVO3714, (WT ADH, ALD6Δ) | 9.7 ± 0.2 | 10.3 ± 0.1 | 0.8 ± 0.0 | 46.5 ± 1.6 | 0.014 ± 0.000 | 0.0 ± 0.0 |

TABLE 33-continued

Data from Fermentation Set B.

| Strain | $OD_{600}$ | Isobutanol produced [g/L] | Isobutyrate produced [g/L] | Isobutanol yield [% theoretical] | Isobutyrate yield [g/g] | Acetate produced [g/L] |
|---|---|---|---|---|---|---|
| GEVO3855, GEVO3856 (LL_adhA$^{RE1}$, ALD6Δ) | 9.9 ± 0.3 | 12.0 ± 0.0 | 0.3 ± 0.0 | 51.5 ± 0.8 | 0.005 ± 0.000 | 0.0 ± 0.0 |

Example 7

Identification of DH2MB as a By-Product of Isobutanol Fermentation

During fermentation of isobutanol-producing yeast strains, it was found that an unknown peak, co-eluting with 2,3-dihydroxy isovalerate (DHIV) on method LC1, and quantitated on this basis, was acting as a sink for a substantial portion of the carbon being utilized.

Initially, it was believed this peak was solely 2,3-dihydroxyisovalerate (DHIV), but subsequent studies indicated that KARI product inhibition would have occurred at these levels of DHIV, making such concentrations impossible. Additional experiments showed that this recovered peak was not reactive with DHAD in enzyme assays, thus eliminating the possibility that significant amounts of DHIV were present.

High Performance Liquid Chromatography LC1: Analysis of organic acid metabolites was performed on an Agilent-1200 High Performance Liquid Chromatography system equipped with two Rezex RFQ-Fast Fruit H+ (8%)150×4.6 mm columns (Phenomenex) in series. Organic acid metabolites were detected using an Agilent-1100 UV detector (210 nm) and refractive index (RI) detector. The column temperature was 60° C. This method was isocratic with 0.0128 N $H_2SO_4$ (25% 0.0512 N $H_2SO_4$ in Milli-Q water) as mobile phase. Flow was set to 1.1 mL/min. Injection volume was 20 µL and run time was 16 min.

High Performance Liquid Chromatography LC3: For samples containing a maximum of 10 mM aldehydes, ketones and ketoacid intermediates (combined), DNPH reagent was added to each sample in a 1:1 ratio. 100 µL DNPH reagent (12 mM 2,4-Dinitrophenyl Hydrazine 20 mM Citric Acid pH 3.0 80% Acetonitrile 20% MilliQ $H_2O$) was added to 100 µL of each sample. Samples were incubated for 30 min at 70° C. in a thermo-cycler (Eppendorf, Mastercycler). Analysis of acetoin, diacetyl, ketoisovalerate and isobutyraldehyde was performed on an Agilent-1200 High Performance Liquid Chromatography system equipped with an Eclipse XDB C-18 150×4 mm; 5 µm particle size reverse phase column (Agilent) and a C-18 reverse phase guard column (Phenomenex). All analytes were detected using an Agilent-1100 UV detector (360 nm). The column temperature was 50° C. This method was isocratic with 60% acetonitrile 2.5% phosphoric acid (0.4%), 37.5% water as mobile phase. Flow was set to 2 mL/min. Injection size was 10 µL and run time is 10 min.

High Performance Liquid Chromatography LC4: Analysis of oxo acids was performed on a Agilent-1100 High Performance Liquid Chromatography system equipped with an IonPac AS11-HC Analytical, IonPac AG11-HC guard column (3-4 mm for IonPac ATC column, Dionex) or equivalent and an IonPac ATC-1 Anion Trap column or equivalent. Oxo acids were detected using a conductivity detector (ED50-suppressed conductivity, Suppressor type: ASRS 4 mm in Auto-Suppression recycle mode, Suppressor current: 300 mA). The column temperature was 35° C. This method used the following elution profile: Hold at 0.25 mM for 3 min; linear gradient to 5 mM at 25 min; linear gradient to 38.5 mM at 25.1 min, hold at 38.5 mM for 4.9 min; linear gradient to 0.25 mM at 30.1 min; hold for 7 min to equilibrate. Flow was set at 2 mL/min. Injection size is 5 µL and run time is 37.1 min.

GC-MS: Varian 3800CP GC system equipped with a single quad 320MS; DB-5 ms column; 1079 injection port at 250° C.; constant flow 1.0 mL/min at 100 split ration; oven profile: initial temperature, 40° C., hold for 5 min, ramp of 20° C./min up to 235° C. and hold for 2 minutes; combiPAL autosampler delivering 0.5 µL of sample; collected masses of 35 to 100. BSTFA Derivation: (1) Evaporate sample to dryness under nitrogen in a GC vial; (2) add 0.5 mL of Acetonitrile and 0.5 mL of BSTFA reagent; (3) Incubate at 50° C. for 30 minutes; (4) Inject onto GC-MS.

LC-MS: For the LC-MS analysis of the LC1 peak fraction the sample was injected into an Agilent 1100 Series high-performance liquid chromatographic (HPLC) system that was equipped with a multiple wavelength detector and an LC/MSD Trap mass spectrometer (ion trap). The separations were monitored by mass spectrometry to provide identification for the component in the sample. The mass spectrometer was operated in the atmospheric pressure chemical ionization (APCI) mode for sample injection. The analyses were conducted using the positive and negative APCI modes. Detection of the "unknown" was only observed in the negative ionization mode. The analysis was conducted using MSn to obtain fragmentation data on the sample analyte. Separations were achieved using a 4.6×150 mm Agilent Zorbax SB C-18 column with 5 µm particles. The sample was run using an isocratic method which used an eluent of 90% HPLC water and 10% methanol. A 10 µL injection was used for the analysis of the sample solution. The sample was also analyzed bypassing the chromatographic column.

DHIV and its isomer, DH2MB, elute at the same retention time on LC1. The peak related to these compounds is separated from other compounds in the fermentation samples. The peak was collected from the HPLC and used for further analysis.

The signal ratio of the RI detector signal to UV detector signal seen in LC1 for DHIV (and DH2MB) is characteristic of common organic acids (e.g. lactate, acetate, etc.); conjugated acids (e.g., pyruvate) have very different RI/UV signal ratios. The recovered "peak DHIV" had the characteristics of a non-conjugated acid:

Ratio (RI/UV): Recovered DHIV/DH2MB peak (130); DHIV Std (150); Pyruvate (14).

The lack of a carbonyl moiety in the "mystery peak" was confirmed by the complete lack of reaction between the recovered peak fraction from LC1 and DNPH: no adduct peaks were evident in the LC3 chromatographic system.

Figure 9:
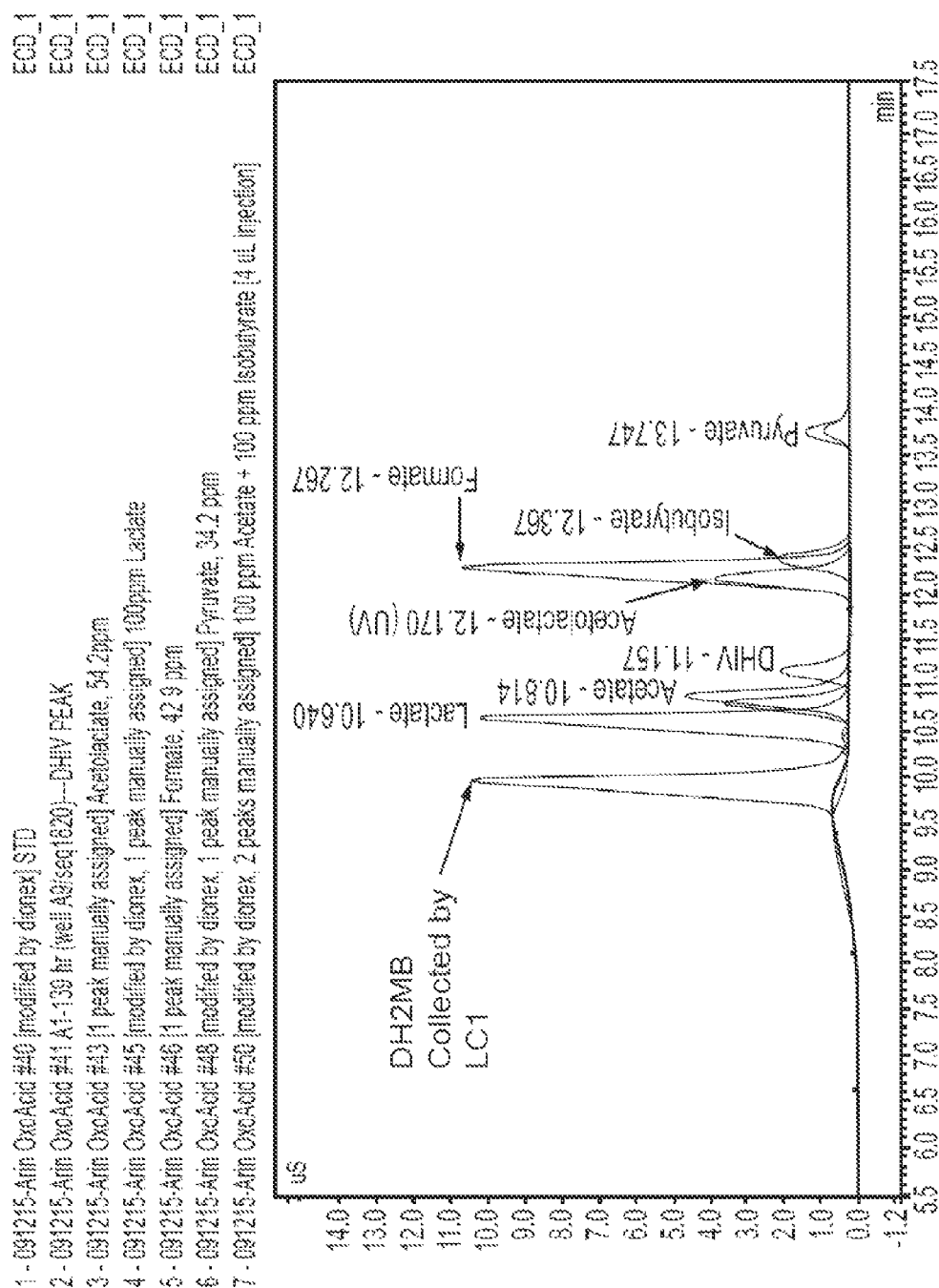
FIG. 9 illustrates a chromatogram for sample fraction collected at retention time corresponding to DHIV collected on LC1 and analyzed by LC4 on an AS-11 Column with Conductivity Detection.

The recovered peak fraction from LC1 was then analyzed by method LC4, which runs under alkaline conditions, and is capable of separating DHIV and acetolactate. That result is shown in FIG. 9, together with an overlay of standard mixtures. This clearly shows the separation between DH2MB (as it was subsequently identified), and DHIV. Some pyruvate was also brought along in the collection of the DH2MB peak.

Figure 10:
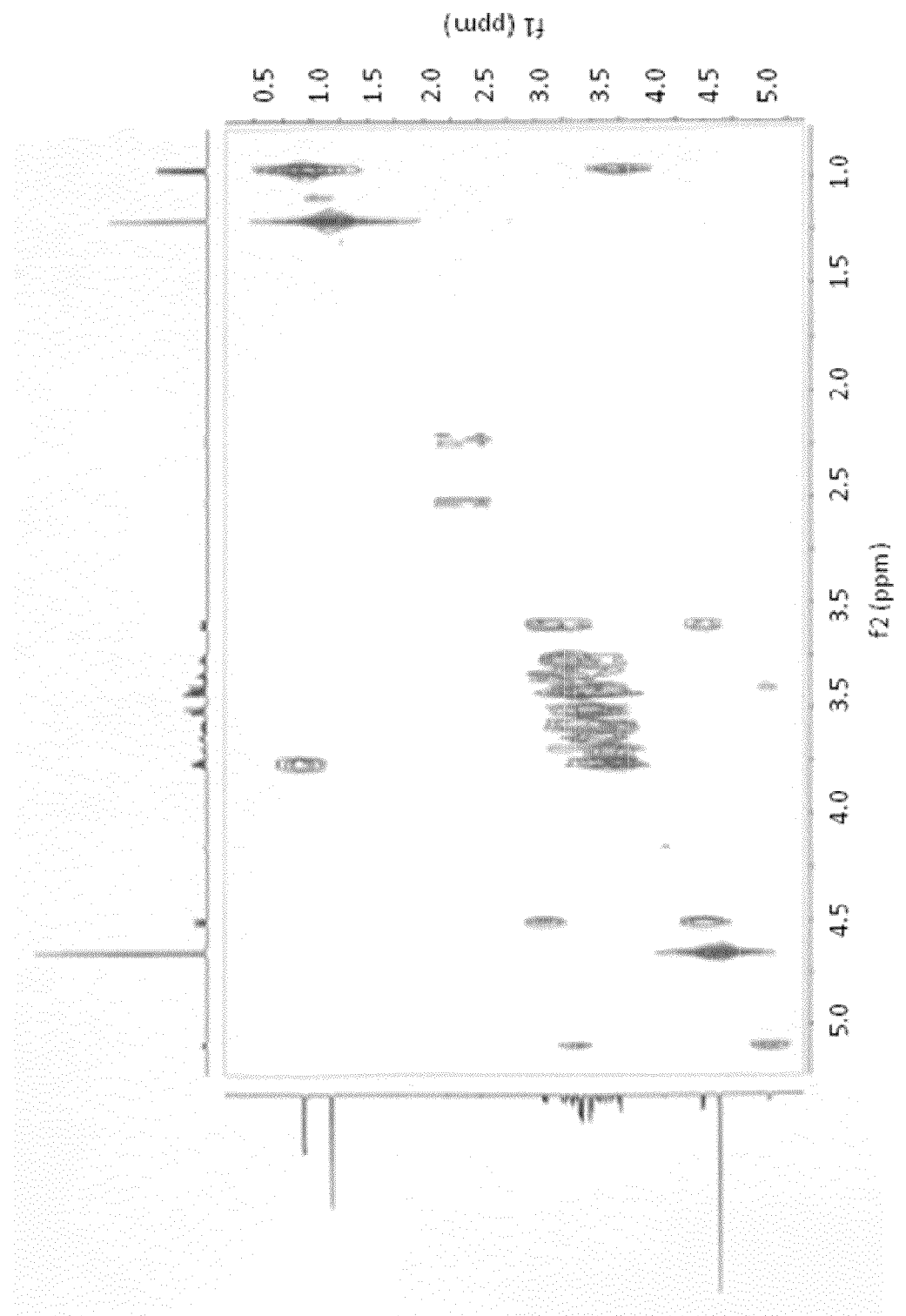
FIG. 10 illustrates a 1H-COSY spectrum of the peak isolated from LC1. The spectrum indicates that DH2MB methyl protons (doublet) at 0.95 ppm are coupled to methine proton (quartet) at 3.7 ppm.
Figure 11:
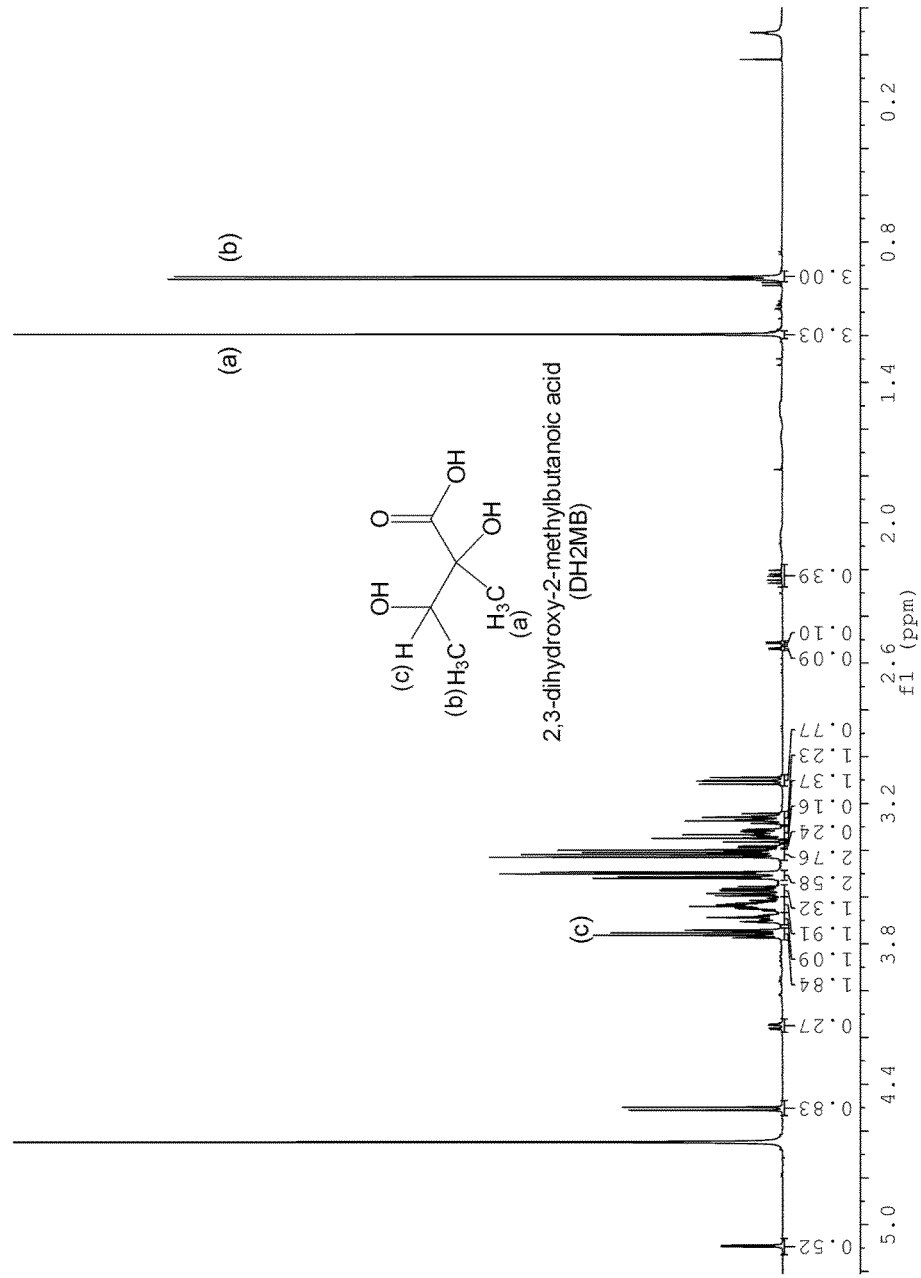
FIG. 11 illustrates a 1H-NMR spectrum of the peak isolated from LC1. The spectrum indicates the presence of DH2MB: a singlet of methyl protons (a) at 1.2 ppm with integral value 3, a doublet of methyl protons (b) at 0.95 ppm with integral value 3 and a quartet of methine proton (c) at 3.7 ppm with integral value of 1.84. Integral value of methine proton (c) is greater than 1 due to overlap with glucose resonance in the same region.

NMR Analysis: The sample peak recovered from method LC1 was neutralized and lyophilized and sent for NMR analysis. The 2-D connectivity analysis by 1H-COSY NMR (FIG. 10) and the proton NMR spectrum (FIG. 11) yielded good results.

2-D analysis of "mystery peak" eluting with DHIV (FIG. 10): One methyl group, shifted downfield, is not split by any adjacent protons, where the methyl group at 0.95 ppm is split into a doublet by one proton adjacent to a hydroxyl. That proton, in turn, is split into a quartet by the adjacent methyl group. Complex patterns between 3.1 and 3.7 ppm indicate the different anomers of glucose carried along during the peak collection of "DHIV".

The assignments of the NMR peaks are shown in the spectrum below (FIG. 11), clearly indicating that the identity of the "mystery peak" is 2,3-dihydroxy-2-butyrate (DH2MB).

The $^1$H NMR and COSY spectra support the presence of 2,3-dihydroxy-2-methylbutanoic acid, a structural isomer of dihydroxyisovaleric acid. Other signals in these spectra support the presence of anomeric proteins and, therefore, a sugar component. Furthermore, complex grouping of signals between 3.1-3.8 ppm are often observed with oligosaccharides. The 13C NMR spectrum is very weak and appears to be an attached proton test (APT) experiment based on the signal at 45 ppm that falls below the base line.

Figure 12:
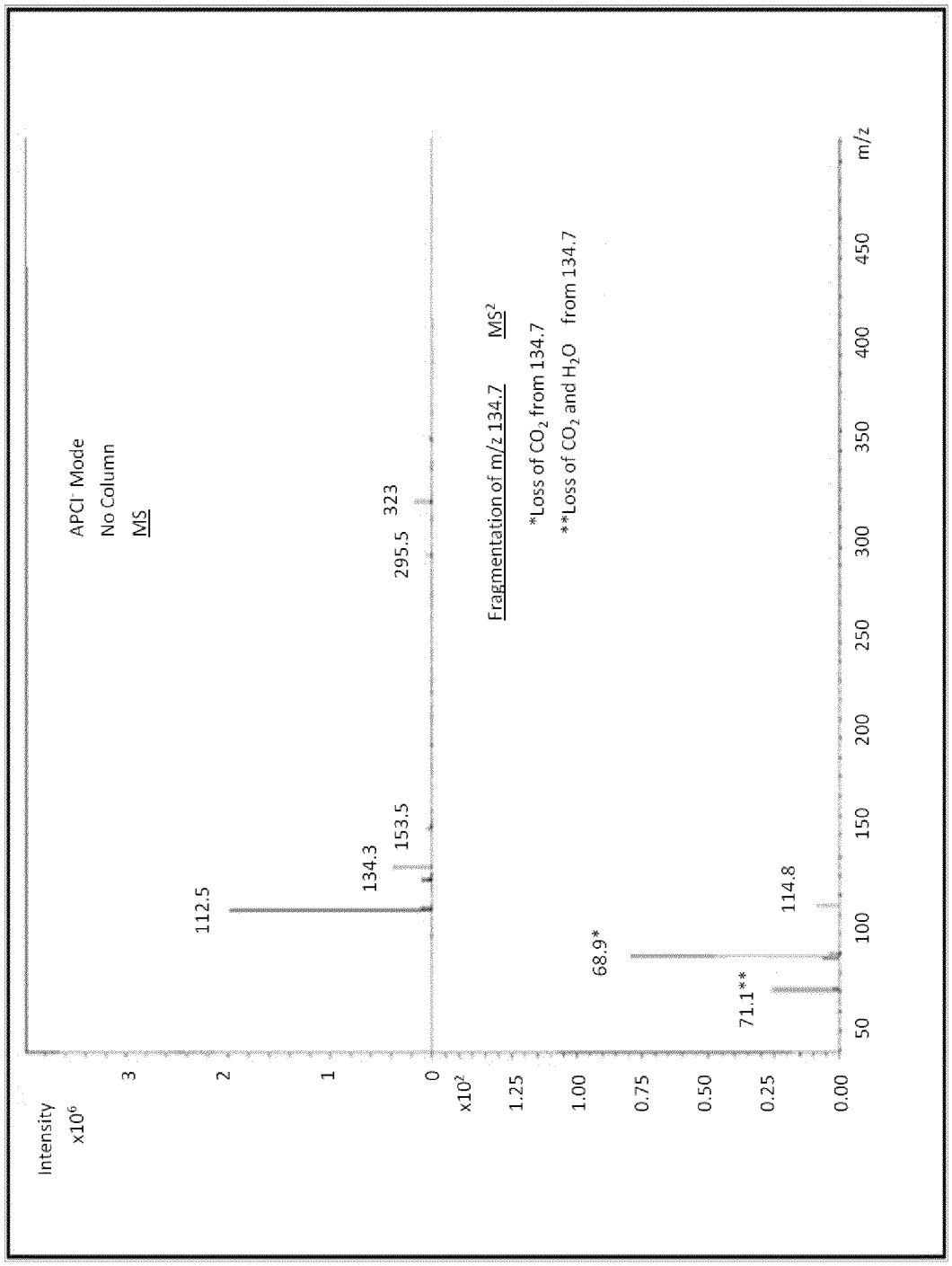
FIG. 12 illustrates a LC-MS analysis of the peak isolated from LC1. Several molecular ions were identified in the sample as indicated at the top portion of the figure. Further fragmentation (MS2) of 134 molecular ion indicated that isolated LC1 fraction contains hydroxyl carboxylic acid by characteristic loss of $CO_2$ (*) and $H_2O+CO_2$ (**).

LC-MS was also carried out on the LC1 peak fraction. The LC-MS was sufficient to demonstrate that the compound had a mass of 134 (both DHIV and DH2MB) (FIG. 12).

Figure 13:
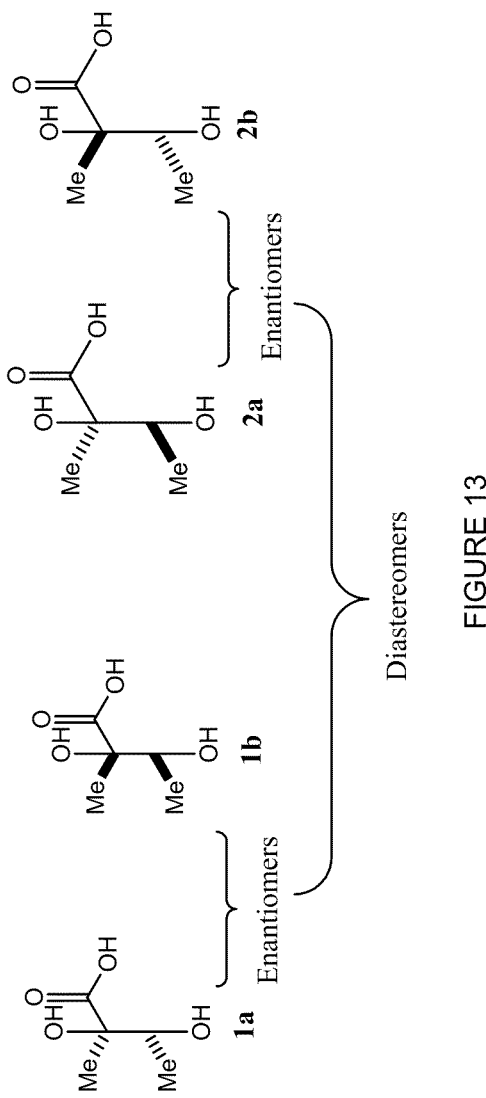
FIG. 13 illustrates the diastereomeric and enantiomeric structures of 2,3-dihydroxy-2-methylbutanoic acid (2R,3S)-1a, (2S,3R)-1b, (2R,3R)-2a, (2S,3S)-2b.

This analysis conclusively identified the unknown by-product as 2,3-dihydroxy-2-methylbutanoic acid (CAS # 14868-24-7). This compound exists in 4 different stereoisomeric forms. 2,3-dihydroxy-2-methylbutanoic acid exists as a set of cis and trans diastereomers, each of which exists as a set of enantiomers. The four compounds are shown in FIG. 13.

As described herein, DH2MB is derived from (2S)-2-hydroxy-2-methyl-3-oxobutyrate (acetolactate). The product of this reaction would be either (2S,3R)-2,3-Dihydroxy-2-methylbutanoic acid, (2S,3S)-2,3-Dihydroxy-2-methylbutanoic acid or a mixture of the two diastereomers depending on the stereoselectivity of the endogenous enzyme(s) catalyzing this conversion.

Example 8

Production and Purification of DH2MB

The purpose of this example is to illustrate how DH2MB was produced and purified.

An engineered *S. cerevisiae* CEN.PK2 strain comprising ALS activity (GEVO3160, *S. cerevisiae* CEN.PK2: MATa ura3 leu2 his3 trp1 gpd1Δ::$P_{CCW12}$: Hph gpd2Δ::$T_{KI\_URA3\_short}$:$P_{FBA1}$: KI_URA3:$T_{KI\_URA3}$ pdc1Δ:: $P_{CUP1}$: Bs_alsS_coSc: $T_{CYC1}$: $P_{PGK1}$: Ll_kivD: $P_{ENO2\_Sp\_}$HIS5 pdc5Δ::LEU2: bla: $P_{TEF1}$: ILV3ΔN: $P_{TDH3}$: ilvC_coSc Q110V pdc6Δ::$P_{TEF1}$: Ll_ilvD_$P_{TDH3}$: Ec_ilvC_coSc P2D1-A1: $P_{ENO2}$: Ll_adhA: $P_{FBA1}$: Sc_TRP1 {evolved for C2 supplement-independence, glucose tolerance and faster growth} expressing plasmid pGV2247 (2-micron, G418 resistant plasmid for the expression of Ec_ilvC_P2D1-A1, Ll_ilvD, Ll_kivD2, and Ll_adhA) was used to produce approximately 10 g/L DH2MB in a batch fermentation using a 2 L top drive motor DasGip vessels filled with 1 L culture medium (10 g/L yeast extract, 20 g/L peptone, 80 g/L glucose, 1% v/v Ethanol, 100 μM CuSO$_4$.5H$_2$O, 0.2 g/L G418) at 30° C., pH6.0, and an OTR of approximately 10 mmol/h.

The cell-free fermentation broth was acidified to pH 2 using concentrated H$_2$SO$_4$. Acidified broth was concentrated to 350 mL under reduced pressure (0-100 mbar) using Büchi Rotovapor R-215. The flask containing broth was heated in the water bath to 20-30° C. during evaporation. A 70 mL volume of MeOH was added to concentrated broth and mixture was transferred to a 500 mL liquid-liquid extractor (Sigma-Aldrich cat. # Z562432), which was set up according to manufacturer's specifications for continuous extraction with ethyl acetate (EtOAc). Continuous extraction was carried out for 3 days replacing the EtOAc extract daily with fresh EtOAc.

Following extraction, the first two batches of DH2MB extract in EtOAc were combined and dried with anhydrous MgSO$_4$ followed by filtration. Dry extract was concentrated under vacuum to 500 mL and was treated with 3 g of activated charcoal (Fluka cat# 05105) for 30 min by stirring at room temperature. The decolorized solution was filtered and concentrated to approximately 50 mL under vacuum (0-100 mbar) using Büchi Rotovapor R-215). The Solution was incubated at 4° C. for two days. Obtained crystals were filtered and washed with ice-cold diethylether and acetone. Crystals were dried using lyophilizer under reduced pressure (0.05 mbar) for one day.

Figure 14:
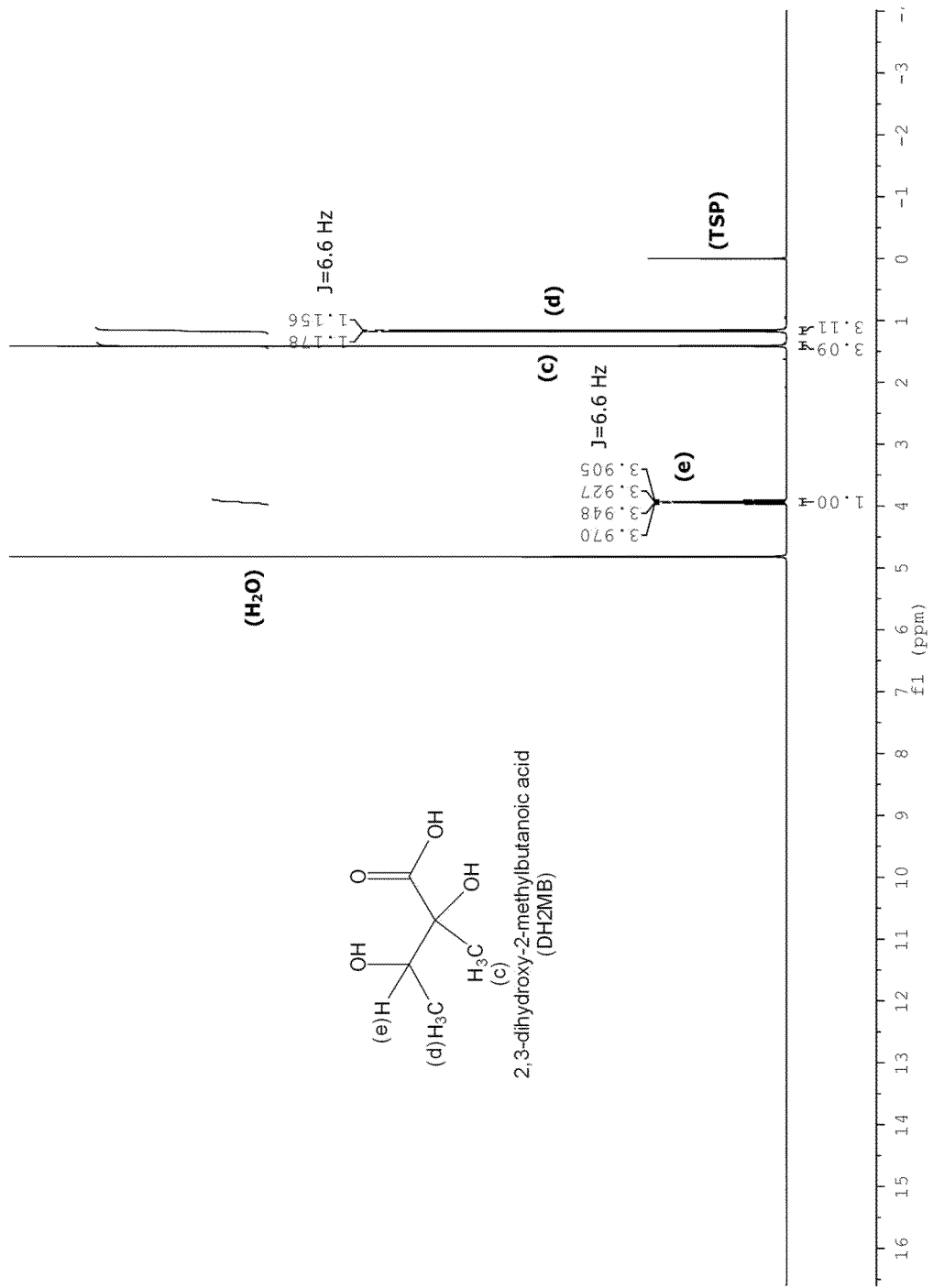
FIG. 14 illustrates the 1H spectrum of crystallized DH2MB in $D_2O$. $^1H$ NMR (TSP) 1.1 (d, 6.5 Hz, 3H), 1.3 (s, 3H), 3.9 (q, 6.5 Hz, 3H)
Figure 15:
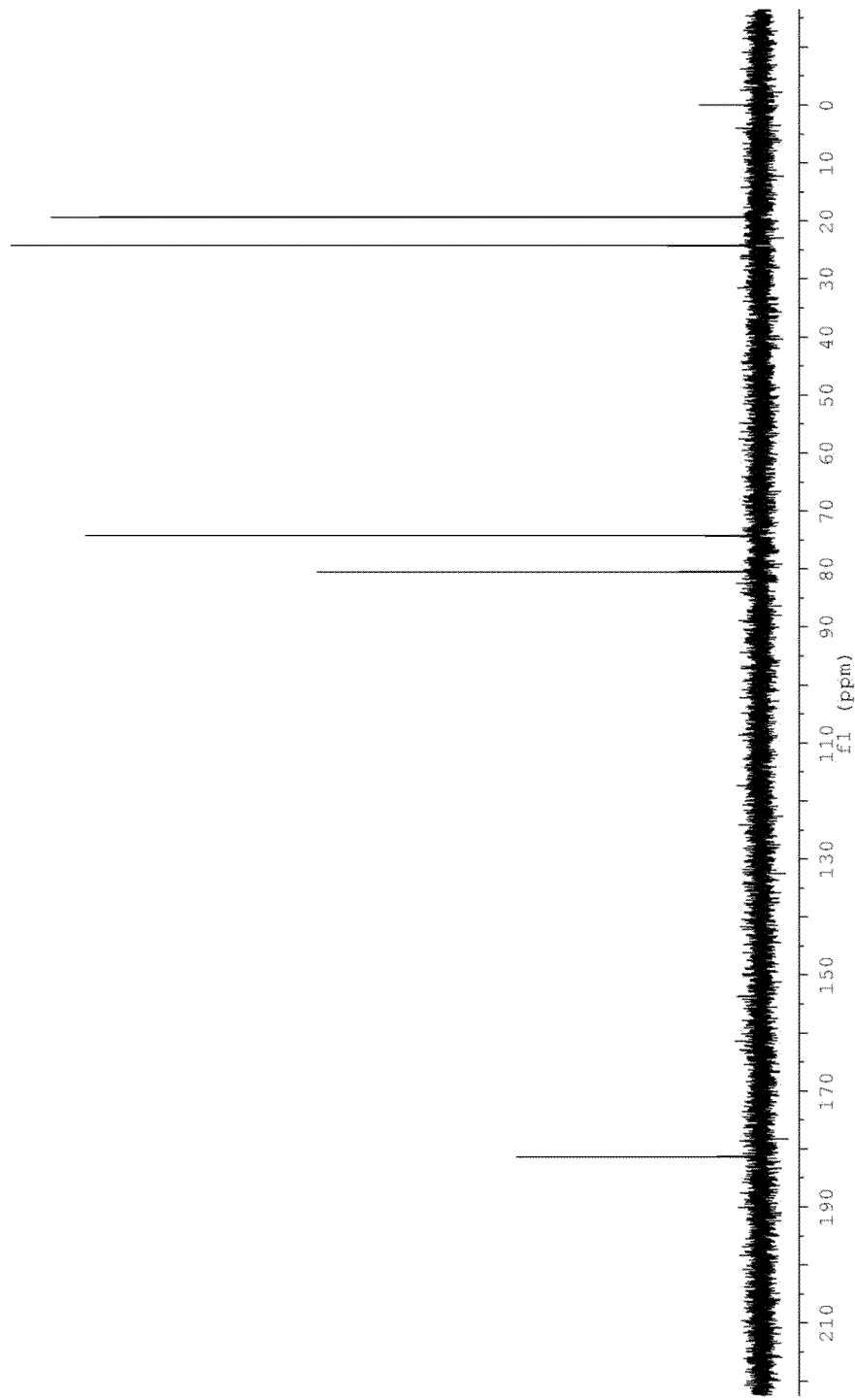
FIG. 15 illustrates the 13C spectrum of crystallized DH2MB in $D_2O$. The spectrum indicates five different carbon resonances one of them being characteristic carboxylic acid resonance at 181 ppm.

Isolated DH2MB was analyzed by 1H (FIG. 14) and 13C (FIG. 15) NMR. 1H NMR (TSP) 1.1 (d, 6.5 Hz, 3H), 1.3 (s, 3H), 3.9 (q, 6.5 Hz, 3H). A 13C spectrum indicated five different carbon atoms present in the sample. Resonance at 181 ppm indicated carboxylic acid carbon present in the sample. In conclusion, based on NMR spectra one could estimate a 99% purity of isolated DH2MB.

Example 9

Impact of DH2MB Production on Isobutanol Yield in Fermentation

The purpose of this example is to demonstrate that DH2MB accumulates to substantial levels in yeast strains comprising ALS and TMA29 activity.

Strains and plasmids disclosed in this example are shown in Tables 34 and 35, respectively.

TABLE 34

| Genotype of *S. cerevisiae* Strain GEVO3160. | |
|---|---|
| Strain | Genotype |
| GEVO3160 | MATa ura3 leu2 his3 trp1 gpd1Δ::[$P_{CCW12}$: hph] gpd2Δ::[$T_{KI\_URA3\_short}$:$P_{FBA1}$: KI_URA3:$T_{KI\_URA3}$] pdc1Δ:: [$P_{CUP1}$: Bs_alsS_coSc: $T_{CYC1}$: $P_{PGK1}$: Ll_kivD: $P_{ENO2}$: Sp_HIS5] pdc5Δ::[LEU2: bla: $P_{TEF}$-ILV3ΔN: $P_{TDH3}$: Ec_ilvC_coSc$^{Q110V}$] pdc6Δ::[$P_{TEF1}$: Ll_ilvD_$P_{TDH3}$: Ec_ilvC_coSc$^{P2D1-A1}$: $P_{ENO2}$: Ll_adhA: $P_{FBA1}$: Sc_TRP1]{evolved for C2 supplement-independence, glucose tolerance and faster growth} pGV2247 |

TABLE 35

Genotype of Plasmid pGV2247.

| Plasmid | Genotype |
|---------|----------|
| pGV2247 | $P_{Sc\_TEF1}$: Ll_ilvD_coSc, $P_{Sc\_TDH3}$: Ec_ilvC_coSc$^{P2D1A1}$, $P_{Sc\_TPI1}$: G418R, $P_{Sc\_PGK1}$: Ll_kivD_coEc, $P_{Sc\_ENO2}$: Ll_adhA, 2μ, AP$^r$, PMB1 |

S. cerevisiae strain GEVO3160 was transformed with pGV2247 as described. A fermentation was performed to characterize the transformed strain. A single isolate cell colony grown on a YPD agar plate containing 0.2 g/L G418 were transferred 5 mL of YPD medium containing 80 g/L glucose, 1% v/v ethanol, 100 μM CuSO$_4$.5H$_2$O, and 0.2 g/L G418 and incubated for 24 h at 30° C., 250 rpm. Next, this culture was transferred to 500 mL baffled flasks containing 80 mL of the same medium and incubated for 24 h at 30° C. in an orbital shaker at 250 rpm. The flask culture was transferred to a 2 L top drive motor fermenter vessel with a working volume of 0.9 L of the same medium for a starting OD$_{600}$ of 0.5. The fermenter was operated at 30° C. and pH 6.0 controlled with 6N KOH in a 2-phase aerobic condition based on oxygen transfer rate (OTR). Initially, the fermenter was operated at a growth phase OTR of 10 mM/h by fixed agitation of 700 rpm and an air overlay of 5 sL/h in both experiments. The cultures was grown for about 20 h to an OD$_{600}$ of approximately 8, and then immediately switched to production aeration. An OTR of 1 mM/h was sustained by reducing agitation from 700 rpm to 350 rpm. After 93 h post inoculation, one replicate vessel from each strain was further reduced to an OTR=0.3 mM/h by decreasing the agitation from 350 rpm to 180 rpm. Periodically, samples from each fermenter were removed to measure OD$_{600}$ and to prepare for gas chromatography (GC1) and liquid chromatography (LC1) analysis. For GC1 and LC1, 2 mL sample was removed into an Eppendorf tube and centrifuged in a microcentrifuge for 10 min at maximum. One mL of the supernatant was analyzed by GC1 (isobutanol, other metabolites) and one mL analyzed by high performance liquid chromatography (LC1) for organic acids and glucose.

Figure 16:
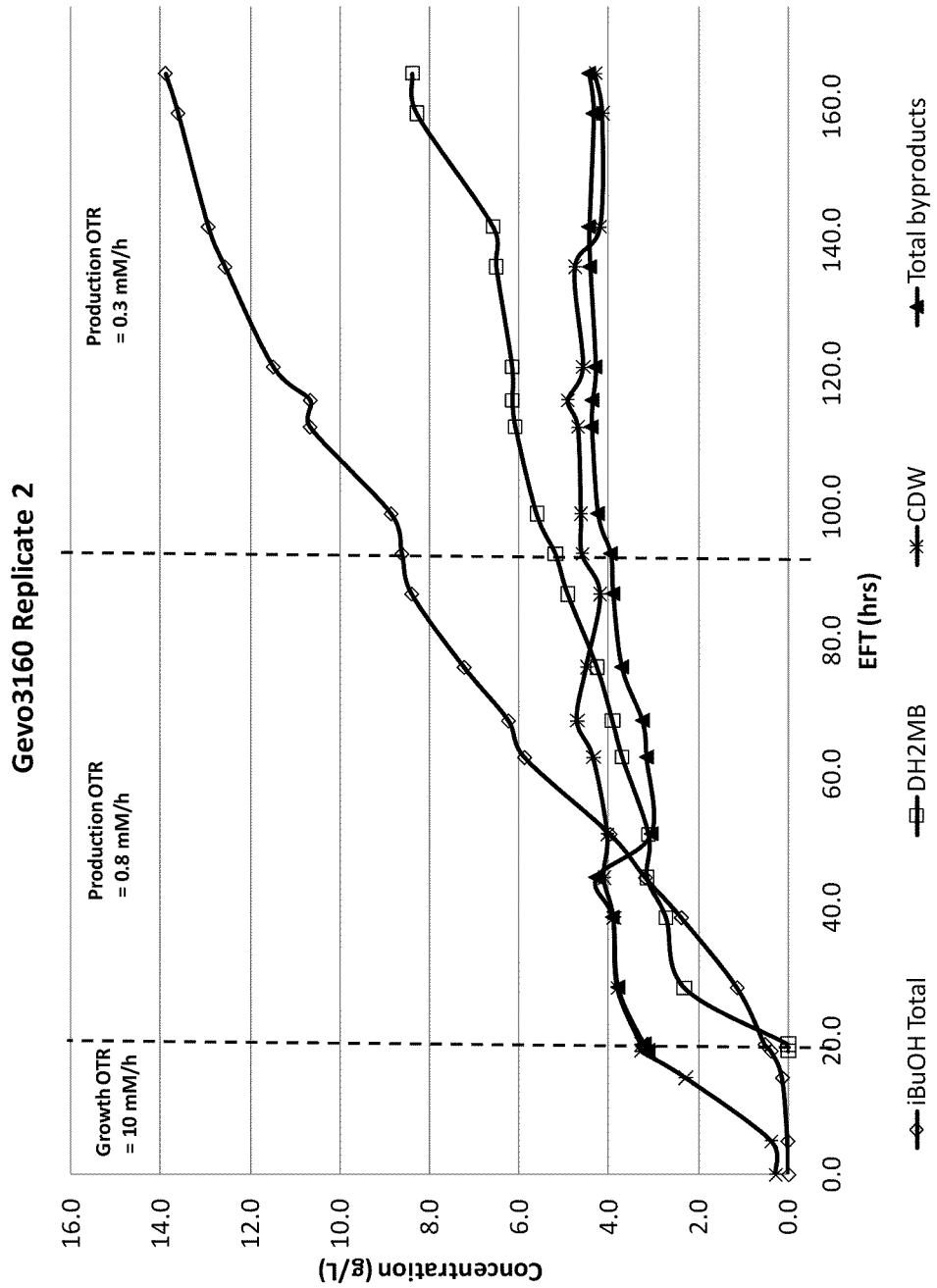
FIG. 16 illustrates the fermentation profile of isobutanol and by-products from a single fermentation with GEVO3160. Production aeration was reduced from an OTR of 0.8 mM/h to 0.3 mM/h at 93 h post inoculation. Open diamond=iBuOH, square=unknown quantified as DH2MB, asterisk=cell dry weight (cdw), and closed triangle=total byproducts.

FIG. 16 depicts the product and by-product profiles of S. cerevisiae GEVO3160 transformed with pGV2247. These profiles are representative for isobutanol producing Pdc-minus, Gpd-minus yeast strains. Pdc-minus/Gpd-minus yeast production strains are described in commonly owned and co-pending publications, US 2009/0226991 and US 2011/0020889, both of which are herein incorporated by reference in their entireties for all purposes. FIG. 16 shows that isobutanol (13.9 g/L) and the unknown compound quantified as "DHIV" and now identified as DH2MB (8.4 g/L) are the primary products produced during microaerobic production OTR. Assuming that the quantitation using the response factor of DHIV leads to an accurate quantitation of DH2MB, approximately 12-13% of the carbon consumed is diverted into production of DH2MB. If the acetolactate that is converted into DH2MB would instead be converted into isobutanol then the isobutanol yield over the entire time of the fermentation shown in FIG. 16 would be significantly higher.

Example 10

ALS Expression is Necessary for DH2MB Production

The purpose of this example is to demonstrate that exogenously expressed ALS activity is required for DH2MB accumulation in S. cerevisiae.

This experiment was performed to determine whether ALS is required for the production of DH2MB. The strains used in this experiment were GEVO1187 (S. cerevisiae CEN.PK2; MATa ura3-52 leu2-3_112 his3Δ1 trp1-289 ADE2) and GEVO2280 (S. cerevisiae CEN.PK2; MATa ura3 leu2 his3 trp1 ADE2 pdc1Δ::P$_{CUP1-1}$:Bs_alsS2:TRP1). Prior to fermentations, both strains were transformed with the 2 micron plasmid pGV2082 (P$_{TDH3}$:Ec_ilvC_coSc$^{Q110V}$, P$_{TEF1}$:Ll_ilvD_coSc, P$_{PGK1}$:Ll_kivD_coEc, and P$_{ENO2}$:Dm_ADH, 2μ ori, bla, G418R) as described.

To measure ALS activity, yeast cell extracts from GEVO1187 and GEVO2280 were prepared. Cells were grown to an OD$_{600}$ of about 1, induced with 1 mM CuSO$_4$ for 2 hours and then harvested. To prepare cells for assays, 50 ml of cells was collected by centrifugation at 2700×g. After removal of the media, cells were resuspended in sterile dH$_2$O, centrifuged at 2700×g and the remaining media was carefully removed with a 1 ml pipette tip. The cell pellets were weighed (empty tubes were preweighed) and then frozen at −80° C. until use. Cell lysates were made using the following SOP as described below. Cells were thawed on ice and resuspended in lysis buffer (250 mM KPO$_4$ pH 7.5, 10 mM MgCl$_2$ and 1 mM DTT) such that the result was a 20% cell suspension by mass. A volume of 1000 μl of glass beads (0.5 mm diameter) were added to a 1.5 ml Eppendorf tube and 875 μl of cell suspension was added. Yeast cells were lysed using a Retsch MM301 mixer mill (Retsch Inc. Newtown, Pa.) by mixing 6×1 min each at full speed with 1 min icing steps between. The tubes were centrifuged for 10 min at 23,500×g at 4° C. and the supernatant was removed. Extracts were held on ice until assayed. The lysate protein concentration was determined using the BioRad Bradford Protein Assay Reagent Kit (Cat# 500-0006, BioRad Laboratories, Hercules, Calif.) and using BSA for the standard curve as described. Briefly, all ALS assays were performed in triplicate for each lysate, both with and without substrate. To assay each lysate, 100 μL of lysate diluted 1:2 with lysis buffer was mixed with 900 μL of buffer (50 mM potassium phosphate buffer pH 6.0, 1 mM MgSO$_4$, 1 mM thiamin-pyrophosphate, 110 mM pyruvate), and incubated for 15 minutes at 30° C. Buffers were prepared at room temperature. A no substrate control (buffer without pyruvate) and a no lysate control (lysis buffer instead of lysate) were also included. After incubation 175 μL from each reaction was mixed with 25 μL 35% H$_2$SO$_4$ and incubated at 37° C. for 30 min. Samples were submitted to analytics for analysis by LC1. Using this method, it was determined that the wild-type strain GEVO1187 had no detectable ALS activity while the ALS-expressing strain GEVO2280 had 0.65 units/mg lysate ALS activity.

The performance of the two strains (with or without the heterologous ALS integrated expression construct) was compared using the following shake flask fermentation conditions. Strains were patched onto YPD plates containing 0.2 mg/mL G418. After overnight growth, cells were removed from the plate with a sterile toothpick and resuspended in 4 mL of YPD with 0.2 g/L G418. The OD$_{600}$ was determined for each culture. Cells were added to 50 mL YP with 50 g/L dextrose and 0.2 mg/mL G418 such that a final OD$_{600}$ of 0.1 was obtained. To induce the CUP1 promoter driving ALS expression, 1 mM copper sulfate was added at the 24 hour time point. Unused media was stored at 4° C. to act as medium blank for GC and LC, and to act as the t=0 sample for the fermentation. At t=24, 48 and 72 hours samples were prepared for analysis by GC1 and at 72 hours samples were additionally analyzed by LC1. At 24 and 48 hours a 1:10 dilution of the supernatant of each culture was analyzed by YSI. If needed 50% glucose containing 0.2 g/L G418 was added to a final concentration of 100 g/L glucose. Fermentations were performed at 30° C. shaking at 250 RPM.

The DH2MB titer reached at 72 hours of a shake flask fermentation was determined using LC1 method for both the WT strain (BUD1187) without ALS and the strain expressing the $P_{CUP1}$:Bs_alsS2 at PDC1 (BUD2280). Each strain was transformed with the 4-component plasmid pGV2082. The fermentation was performed as described. Without exogenous ALS expression, the strain produced no DH2MB, whereas the strain with ALS expression produced up to 1.4 g/L DH2MB plus DHIV.

Example 11

Only ALS Expression is Necessary for DH2MB Production

The purpose of this example is to demonstrate that ALS activity alone is responsible for DH2MB accumulation in *S. cerevisiae*.

This experiment was performed to determine whether ALS alone or in combination with a KARI, DHAD, KIVD, ADH expressing plasmid is responsible for the production of DH2MB. The strain used in this experiment was GEVO2618 (MATa ura3 leu2 his3 trp1 pdc1Δ::[$P_{CUP1}$: Bs_alsS1_coSc: TRP1). The plasmids tested in this experiment were pGV2227 which contains the remaining four pathway genes (-$P_{TEF1}$:Ll_ilvD_coSc: $P_{TDH3}$:EC_ilvC_coSc$^{Q110V}$:$P_{Sc\_TPI1}$: G418: $P_{PGK1}$: Ll_kivD2_coEc:PDC1-3' region: $P_{ENO2}$: Ll_adhA 2μ bla, pUC-ori), and pGV2020, the empty vector control ($P_{Sc\_TEF1}$, $P_{Sc\_TPI1}$, G418R, APr, 2μ).

Shake flask cultures of GEVO2618 transformed with pGV2020 and GEVO2618 transformed with pGV2227 were started in YPD (15% glucose) containing 200 mM MES pH6.5, and 0.4 g/L G418 at an OD600~0.1, and were run at 30° C. and 75 rpm in a shaking incubator. Samples were taken at 24 h and 48 h and the samples were analyzed for metabolite levels by HPLC (LC1) and GC (GC1). After 48 hours, all glucose was consumed from the media by both strains. The strain containing the empty vector (GEVO2618+pGV2020) produced 4.6 g/L of DHIV+DH2MB representing 3.8% yield. The strain containing the vector expressing additional four pathway genes (GEVO2618+pGV2227), produced a similar titer of 5.6 g/L DHIV+DH2MB representing 3.1% yield.

Example 12

Effect of Increased KARI Activity on DH2MB production

The purpose of this example is to demonstrate that increased KARI activity results in decreased in DH2MB production in yeast comprising ALS activity.

Strains and plasmids disclosed in this example are shown in Tables 36 and 37, respectively.

TABLE 36

Genotype of Strains Disclosed in Example 12.

| Strain | Genotype |
| --- | --- |
| GEVO2843 | *S. cerevisiae*, MATa ura3 leu2 his3 trp1 pdc1Δ::$P_{CUP1}$:[Bs_alsS1_coSc:$T_{CYC1}$: $P_{PGK1}$: Ll_kivD2: $P_{ENO2}$: Sp_HIS5] pdc5Δ::[LEU2: bla: $P_{TEF1}$: ILV3ΔN: $P_{TDH3}$: Ec_ilvC_coSc$^{Q110V}$] |

TABLE 36-continued

Genotype of Strains Disclosed in Example 12.

| Strain | Genotype |
| --- | --- |
| | pdc6Δ::[URA3: bla: $P_{TEF1}$: Ll_kivD2: $P_{TDH3}$: Dm_ADH] {evolved for C2 supplement-independence, glucose tolerance and faster growth} |

TABLE 37

Plasmids Disclosed in Example 12.

| Plasmid | Genotype |
| --- | --- |
| pGV2196 | CEN, ARS, hph, bla, pUC-ori. |
| pGV2377 | $P_{TEF1}$: Ll_ilvD_coSc, $P_{ScPGK1}$: Ll_kivD_coEc, $P_{ScENO2}$: Ll_adhA, 2μ ori, pUC ori, bla, G418R |
| pGV2466 | $P_{TEF1}$: Ll_ilvD_coSc, $P_{ScTDH3}$: Ec_ilvC_coSc$^{his6}$, $P_{ScPGK1}$: Ll_kivD_coEc, $P_{ScENO2}$: Ll_adhA, 2μ ori, pUC ori, bla, G418R |
| pGV2398 | $P_{TEF1}$: Ll_ilvD_coSc, $P_{ScTDH3}$: Ec_ilvC_coSc$^{Q110V\text{-}his6}$, $P_{ScPGK1}$: Ll_kivD_coEc, $P_{ScENO2}$:Ll_adhA, 2μ ori, pUC ori, bla, G418R |
| pGV2400 | $P_{TEF1}$: Ll_ilvD_coSc, $P_{ScTDH3}$: Ec_ilvC_coSc$^{P2D1\text{-}A1\text{-}his6}$, $P_{ScPGK1}$: Ll_kivD_coEc, $P_{ScENO2}$: Ll_adhA, 2μ ori, pUC ori, bla, G418R |
| pGV2406 | $P_{Sc\_TEF1}$. EC_ilvC_coSc$^{Q110V\text{-}his6}$, CEN, ARS, hph, bla, pUC ori. |

*S. cerevisiae* strain GEVO2843 was transformed with 2μ plasmids pGV2377, pGV2466, pGV2398, and pGV2400 as described to determine if expression of wild-type or engineered KARIs led to a greater accumulation of DH2MB.

Precultures of GEVO2843 transformed with the 2μ plasmids (pGV2377, 2466, 2398, 2400) were started in YPD containing 1% ethanol and 0.2 g/L G418 and incubated overnight at 30° C. and 250 rpm. These precultures were used to inoculate 50 mL of the same medium in a baffled flask and incubated at 30° C. and 250 rpm until reaching an OD$_{600}$ of ~5. They were pelleted in 50 mL Falcon tubes at 2700 rcf for 5 minutes at 25° C. Next, the cells from each 50 mL culture were resuspended in 50 mL YPD containing 8% glucose, 1% (v/v) ethanol, ergosterol, Tween-80, 0.2 g/L G418, and 200 mM MES, pH6.5. The cultures were added to 250 mL unbaffled flasks and placed in an incubator at 30° C. and 75 rpm. Samples were taken after 72 h to determine OD$_{600}$ and to analyze the fermentation broth for extracellular metabolites via GC1 and LC1 analysis.

Table 38 shows that the strain transformed with pGV2377 (Not overexpressing any KARI gene from plasmid) produced the highest carbon yield of 15% for combined DH2MB+ DHIV, while the strains with pGV2466 (containing Ec_ilvC_coSc$^{his6}$), pGV2398 (containing Ec_ilvC_coSc$^{Q110V\text{-}his6}$), and pGV2400 (containing Ec_ilvC_coSc$^{P2D1\text{-}A1\text{-}his6}$) had similar combined DH2MB+DHIV carbon yields of 8-10%. Likewise, the strain transformed with pGV2377 produced isobutanol at the lowest carbon yield of 6%. The remaining strains comprising KARI genes on a plasmid produced isobutanol at higher carbon yields. The observation that decreased DH2MB production correlates with increased isobutanol production is consistent with the finding that DH2MB is produced from acetolactate via a reaction that does not involve KARI.

TABLE 38

Isobutanol and Combined DH2MB + DHIV Carbon Yields

| Strain | Plasmid | KARI | Isobutanol carbon yield [%] | DH2MB + DHIV carbon yield [%] |
|---|---|---|---|---|
| GEVO2843 | pGV2377 | n/a | 6 | 15 |
| GEVO2843 | pGV2466 | Ec_ilvC_coSc$^{his6}$ | 18 | 8 |
| GEVO2843 | pGV2398 | Ec_ilvC_coSc$^{Q110V-his6}$ | 15 | 8 |
| GEVO2843 | pGV2400 | Ec_ilvC_coSc$^{P2D1-A1-his6}$ | 18 | 10 |

A second experiment was performed in which strains expressed either no KARI from a plasmid, a low level of KARI, or a high level of KARI. In this experiment the KARI activity of cell lysates was measured.

S. cerevisiae strain GEVO2843 was transformed as described with combinations of plasmids as described in Table 37; the no KARI strain contained pGV2377+pGV2196 and had no plasmid-borne KARI, the low KARI strain contained pGV2377+pGV2406 and expressed KARI from a low copy plasmid, and the high KARI strain contained pGV2398+pGV2196 and expressed KARI from a high copy plasmid. Fermentations and sampling were performed as described. GC1 and LC1 methods were performed as described. Cells for KARI assays were lysed as described except that lysis buffer was 250 mM $KPO_4$ pH 7.5, 10 mM $MgCl_2$ and 1 mM DTT. The protein concentration of lysates was determined as described.

To measure in vitro KARI activity, acetolactate substrate was made by mixing 50 μl of ethyl-2 acetoxy-2-methyl-acetoacetate with 990 ul of water. Next 10 μl of 2 N NaOH was sequentially added, with vortex mixing between additions for 15 sec, until 260 μl of NaOH was added. The acetolactate was agitated at room temperature for 20 min and held on ice. NADPH was prepared in 0.01N NaOH to a concentration of 50 mM. The concentration was determined by reading the OD of a diluted sample at 340 nm in a spectrophotometer and using the molar extinction coefficient of 6.22 $M^{-1}cm^{-1}$ to calculate the precise concentration. Three buffers were prepared and held on ice. Reaction buffer contained 250 mM $KPO_4$ pH 7.5, 10 mM $MgCl_2$, 1 mM DTT, 10 mM acetolactate, and 0.2 mM NADPH. No substrate buffer was missing the acetolactate. No NADPH buffer was missing the NADPH. Reactions were performed in triplicate using 10 μl of cell extract with 90 μl of reaction buffer in a 96-well plate in a SpectraMax 340PC multi-plate reader (Molecular Devices, Sunnyvale, Calif.). The reaction was followed at 340 nm by measuring a kinetic curve for 5 minutes, with OD readings every 10 seconds at 30° C. The Vmax for each extract was determined after subtracting the background reading of the no substrate control from the reading in complete buffer.

Table 39 shows data for KARI activity, as well as carbon yield in % for isobutanol and combined DH2MB+DHIV. As KARI activity increased the isobutanol carbon yield increased and the combined DH2MB+DHIV carbon yield decreased.

TABLE 39

KARI Activity, Isobutanol and Combined DH2MB + DHIV Carbon Yields.

| Strain | Plasmid | KARI activity μmol/min/mg | Isobutanol carbon yield [%] | DH2MB + DHIV carbon yield [%] |
|---|---|---|---|---|
| GEVO2843 | pGV2377 + pGV2196 | 0.011 ± .002 | 5 | 19 |

TABLE 39-continued

KARI Activity, Isobutanol and Combined DH2MB + DHIV Carbon Yields.

| Strain | Plasmid | KARI activity μmol/min/mg | Isobutanol carbon yield [%] | DH2MB + DHIV carbon yield [%] |
|---|---|---|---|---|
| GEVO2843 | pGV2377 + pGV2406 | 0.030* | 11* | 16* |
| GEVO2843 | pGV2398 + pGV2196 | 0.151 ± .005 | 19 | 11 |

*This data comprises only one sample

Example 13

Effect of Increased DHAD Activity

The purpose of this example is to demonstrate that increased DHAD activity results in decreased in DH2MB production in yeast comprising ALS activity.

Strains and plasmids disclosed in this example are shown in Tables 40 and 41, respectively.

GEVO2843 was transformed with different pairs of plasmids. Strain A contains pGV2227 plus pGV2196. Strain B contains pGV2284 plus pGV2196. Strain C contains pGV2284 plus pGV2336. Single transformants of BUD2843 with one of the three 2-plasmid combinations were single colony purified on YPD plates containing hygromycin, and the patched cells were used to inoculate 3 mL YPD containing 1% ethanol (v/v), 0.2 g/L G418, and 0.1 g/L hygromycin. The cultures were incubated at 30° C., 250 rpm overnight prior to their use to inoculate 3 mL YPD containing 1% ethanol (v/v), 0.2 g/L G418, and 0.1 g/L hygromycin. These cultures were incubated at 30° C., 250 rpm overnight. The following day, the cultures were used to inoculate 50 ml YPD containing 8% glucose, 200 mM MES pH6.5, Ergosterol, and TWEEN™ 80 to an $OD_{600}$ of approximately 0.1. These cultures were incubated at 30° C., 250 rpm overnight. The following day the cultures were diluted in 50 mL of the same medium to an $OD_{600}$ of ~0.1. The cultures were incubated at 30° C., 250rpm, and 1.5 mL samples were removed after 0, 24, 47, 70, and 92 hours of incubation. The samples were prepared for GC and LC analysis as described. After 92 hours, the remainder of all samples was centrifuged and the pellets were weighed and stored at −80° C. DHAD assays were performed with lysates prepared. from the frozen pellets as described. LC1 and GC1 analysis was performed as described.

TABLE 40

Genotype of Strains Disclosed in Example 13.

| Strain | Genotype |
|---|---|
| GEVO2843 | MATa ura3 leu2 his3 trp1<br>pdc1Δ::[$P_{CUP1}$:Bs_alsS_coSc:$T_{CYC1}$:$P_{PGK1}$:Ll_kivD:$P_{ENO2}$:Sp_HIS5] pdc5<br>Δ::[LEU2:bla:$P_{TEF1}$:Sc_ILV3ΔN:$P_{TDH3}$:Ec_ilvC_coSc$^{Q110V}$]<br>pdc6Δ::[URA3:bla:$P_{TEF1}$:Ll_kivD:$P_{TDH3}$:DmADH]<br>{evolved for C2 supplement-independence, glucose tolerance and faster growth} |

TABLE 41

Plasmids Disclosed in Example 13.

| Plasmids | Genotype |
|---|---|
| pGV2227 | $P_{Sc\_TEF1}$: Ll_ilvD_coSc, $P_{Sc\_TDH3}$: Ec_ilvC_coSc$^{Q110V}$, $P_{Sc\_TPI1}$: G418, $P_{Sc\_PGK1}$: Ll_kivD_coEc, $P_{Sc\_ENO2}$: Ll_adhA, 2μ, AP$^r$, PMB1 |
| pGV2284 | $P_{Sc\_TEF1}$, $P_{Sc\_TDH3}$: Ec_ilvC_coSc$^{P2D1-A1}$, $P_{Sc\_TPI1}$: G418, $P_{Sc\_PGK1}$: Ll_kivD_coEc, $P_{Sc\_ENO2}$: Ll_adhA, 2μ, AP$^r$, PMB1 |
| pGV2196 | $P_{Sc\_PGK1}$ $P_{Sc\_TEF1}$, $P_{Sc\_TPI1}$: hph, CEN, AP$^r$, pUC ORI |
| pGV2336 | $P_{Sc\_ENO}$, $T_{ScPDC6}$ $P_{Sc\_PGK}$, $P_{Sc\_TEF1}$: Ll_ilvD_coSc $P_{Sc\_TDH3}$, $P_{Sc\_TPI1}$: hph, CEN, AP$^r$, pUC ORI |

Table 42 shows the DHAD activity, isobutanol yield and the combined DHIV+DH2MB yield. The strain transformed with pGV2284+pGV2196 (no DHAD expressed from a plasmid) produced the highest carbon yield of 19% for combined DH2MB+DHIV and the lowest carbon yield of isobutanol at 9%. The strain transformed with pGV2227+pGV2196 (highest DHAD expression from a plasmid) had the lowest carbon yield of 9% for combined DH2MB+DHIV and the highest carbon yield for isobutanol at 18%. The strain transformed with pGV2284+pGV2336 (low copy DHAD expression from a plasmid) had an intermediate carbon yield of 16% for combined DH2MB+DHIV and of 12% for isobutanol.

TABLE 42

DHAD Activities, Isobutanol and Combined DH2MB + DHIV Carbon Yields at 92 hrs Fermentation.

| Strain | Plasmids | DHAD activity | Isobutanol carbon yield [%] | DH2MB + DHIV carbon yield [%] |
|---|---|---|---|---|
| A | pGV2227 + pGV2196 | 0.29 ± 0.05 | 18 | 9 |
| B | pGV2284 + pGV2196 | 0.05 ± 0.00 | 9 | 19 |
| C | pGV2284 + pGV2336 | 0.08 ± 0.01 | 12 | 16 |

In a second experiment, GEVO2843 was transformed with different pairs of plasmid (Table 43) and assessed in a shake flask fermentation as above. Strain D contains pGV2196 plus pGV2589. Strain E contains pGV2529 plus pGV2589. Strain F contains pGV2196 plus pGV2485. The strain transformed with pGV2196+pGV2589 (no plasmid-borne DHAD) produced 1.25 g/L isobutanol and 5.67 g/L DH2MB+DHIV. The strain with DHAD expressed from a high-copy plasmid (pGV2196+pGV2485) produced 2.74 g/L isobutanol and 3.71 g/L DH2MB+DHIV, indicating that an increase in DHAD expression led to a decrease in DH2MB+DHIV accumulation. The strain with DHAD expressed from a low-copy plasmid (pGV2529+pGV2485) produced an intermediate level of both metabolites, consistent with an intermediate level of DHAD activity.

TABLE 43

Additional Plasmids Disclosed in Example 13.

| Plasmid | Genotype |
|---|---|
| 2196 | $P_{Sc\_PGK1}$, $P_{Sc\_TEF1}$, $P_{Sc\_TPI1}$hPh, CEN, AP$^r$, pUC ORI |
| 2529 | $P_{Sc\_PGK1}$, $P_{Sc\_TEF1}$Ll_ilvD_coSc4, $P_{Sc\_TPI1}$hph, CEN, AP$^r$, pUC ORI |
| 2589 | $P_{Sc\_TDH3}$Ec_ilvC_coSc_Q110V, $P_{Sc\_TPI1}$G418R, $P_{Sc\_ENO2}$Ll_adhA, 2μ, AP$^r$, PMB1 |

TABLE 44

DHAD activities, Isobutanol Titer and Yield, and Combined DH2MB + DHIV Titers at 72 hrs Fermentation.

| Strain | Plasmid(s) | Plasmid-borne DHAD | Isobutanol Titer (g/L) | Isobutanol Yield (%) | DH2MB + DHIV (g/L) |
|---|---|---|---|---|---|
| D | pGV2196 + pGV2589 | None | 1.25 ± 0.27 | 16.1 | 5.67 ± 0.29 |
| E | pGV2529 + pGV2589 | Low-copy | 2.15 ± 0.05 | 24.8 | 5.00 ± 0.20 |
| F | pGV2196 + pGV2485 | High-copy | 2.74 ± 0.22 | 31.0 | 3.71 ± 0.11 |

Example 14

Deletion of TMA29 in *S. cerevisiae* by Targeted Deletion

The following example illustrates that deletion of the TMA29 gene from the *S. cerevisiae* genome eliminates the production of DH2MB when acetolactate synthase is overexpressed.

Several reductase enzyme candidates that may catalyze the production of DH2MB were identified in the *S. cerevisiae* genome, including the TMA29 gene product. The genes encoding these reductases were deleted in the *S. cerevisiae* strain GEVO2618, a strain known to produce g/L quantities of DH2MB, using integration of a URA3 marker. Fermentations were performed with these strains to determine if deleting any of the candidate genes, including TMA29, reduced or eliminated the production of DH2MB.

Strains, plasmids, and primer sequences are listed in Tables 45, 46, and 47, respectively.

TABLE 45

Genotype of Strains Disclosed in Example 14.

| GEVO No. | Genotype |
| --- | --- |
| GEVO1187 | S. cerevisiae CEN.PK2 MATa ura3-52 leu2-3_112 his3Δ1 trp1-289 ADE2 |
| GEVO2618 | S. cerevisiae, MATa ura3 leu2 his3 trp1 pdc1Δ::[P$_{CUP1-1}$: Bs_alsS1_coSc: TRP1]. |
| GEVO3638 | S. cerevisiae, MATa ura3 leu2 his3 trp1 pdc1Δ::[P$_{CUP1-1}$: Bs_alsS1_coSc: TRP1] tma29Δ::[T$_{Kl\_URA3\_short}$: P$_{FBA1}$: Kl_URA3: T$_{Kl\_URA3}$] |
| GEVO3639 | S. cerevisiae, MATa ura3 leu2 his3 trp1 pdc1Δ::[P$_{CUP1-1}$: Bs_alsS1_coSc: TRP1] tma29Δ::[T$_{Kl\_URA3\_short}$: P$_{FBA1}$: Kl_URA3: T$_{Kl\_URA3}$] |
| GEVO3640 | S. cerevisiae, MATa ura3 leu2 his3 trp1 pdc1Δ::[P$_{CUP1-1}$: Bs_alsS1_coSc: TRP1] tma29Δ::[T$_{Kl\_URA3\_short}$: P$_{FBA1}$: Kl_URA3:T$_{Kl\_URA3}$] |

TABLE 46

Plasmids Disclosed in Example 14.

| Plasmid Name | Genotype |
| --- | --- |
| pGV1299 | Kl_URA3, bla, pUC-ori. |
| pGV2129 | Kl_URA3-5', bla. |

TABLE 47

Oligonucleotide Sequences Disclosed in Example 14.

| oGV # | Sequence |
| --- | --- |
| 893 | GGATGTGAAGTCGTTGACACAG (SEQ ID NO: 118) |
| 2231 | TTGAAACGTTGGGTCCATAC (SEQ ID NO: 119) |
| 2232 | TTCACCGTGTGCTAGAGAAC (SEQ ID NO: 120) |
| 2862 | TTATACAGGAAACTTAATAGAACAAATC (SEQ ID NO: 121) |
| 2867 | TGAAACAGCATGGCGCATAG (SEQ ID NO: 122) |
| 2869 | CTGTGTCAACGACTTCACATCCGAGGTAACGAGGAACAAGCC (SEQ ID NO: 123) |
| 2870 | TTTCGCCGGTATATTCCGTAG (SEQ ID NO: 124) |
| 2891 | GTTCTATTAAGTTTCCTGTATAACGGCATTGTTCACCAGAATGTC (SEQ ID NO: 125) |
| 2902 | TCCCGACGGCTGCTAGAATG (SEQ ID NO: 126) |
| 2904 | CGCTCCCCATTAATTATACA (SEQ ID NO: 127) |
| 2913 | GAAAGGCTCTTGGCAGTGAC (SEQ ID NO: 128) |
| 2914 | GCCCTGGTGCAATTAGAATG (SEQ ID NO: 129) |
| 2915 | TGCAGAGGGTGATGAGTAAG (SEQ ID NO: 130) |
| 2916 | GGCCAAAGGTAAGGAGAACG (SEQ ID NO: 131) |

Strain Construction: S. cerevisiae strains GEVO3638, GEVO3639, and GEVO3640 were constructed by transforming GEVO2618 with bipartite integration SOE PCR products to replace TMA29 with a URA3 marker. Primers to amplify 5' and 3' targeting sequences for reductase genes were designed with a 20 bp sequence homologous to a URA3 fragment. This was done so that SOE PCR could be used to create fragments containing the URA3 marker and homologous regions flanking the reductase gene of interest. PCR was performed on an Eppendorf Mastercycler® (Cat# 71086, Novagen, Madison Wis.). The following PCR program was followed for primer sets used to generate SOE PCR fragments: 94° C. for 2 min then 30 cycles of (94° C. 30 sec, 53° C. 30 sec, 72° C. 1.5 min) then 72° C. for 10 min. The following primer pairs and templates were used for the first step of the SOE reactions.

To generate the 5' URA3 fragment, oGV2232 and oGV2862 were used to amplify the 5' URA3 fragment using pGV2129 as template. The 1364 bp fragment was purified by gel electrophoresis. To generate the 3' URA3 fragment, oGV2231 and oGV893 were used to amplify the 3' URA3 fragment using pGV1299 as template. The 1115 bp fragment was purified by gel electrophoresis.

To generate the 5' TMA29 fragment, oGV2867 and oGV2891 were used to amplify the 5' TMA29 fragment using S. cerevisiae S288c genomic DNA as template. The S. cerevisiae S288c strain was purchased from ATCC (ATCC#204508). The 412 bp fragment was purified by gel electrophoresis. To generate the 3' TMA29 fragment, oGV2869 and oGV2870 were used to amplify the 3' TMA29 fragment using S. cerevisiae S288c genomic DNA as template. The 305 bp fragment was purified by gel electrophoresis.

The following primer pairs and templates were used to generate the SOE PCR products. To generate the 5' TMA29 SOE PCR product, oGV2232 and oGV2867 were used. The 5' URA3 fragment and the 5' TMA29 fragment were used as template. To generate the 3' TMA29 SOE PCR product, oGV2231 and oGV2870 were used. The 3' URA3 fragment and the 3' TMA29 fragment were used as template.

Transformation of S. cerevisiae strain GEVO2618 with the bipartite integration SOE PCR products was performed as described. Following transformation, the cells were collected by centrifugation (18,000×g, 10 seconds, 25° C.) and resuspended in 400 µL SCD-HLWU media. Integrative transformants were selected by plating the transformed cells on SCD-Ura agar medium. Once the transformants were single colony purified they were maintained on SCD-Ura plates.

Colony PCR was used to verify correct integration. To screen for the correct 5'-end, the URA3: TMA29 5' junction primers oGV2915 and oGV2902 were used to give an expected band at 991 bp. To screen for the correct 3'-end, the URA3: TMA29 3' junction primers oGV2904 and oGV2916 were used to give an expected band at 933 bp. To screen deletion of the TMA29 gene primers oGV2913 and oGV2914 were used, expecting a lack of a 288 bp if the CDS was deleted.

Fermentations: Fermentations were conducted with tma29Δ strains GEVO3638, GEVO3639, and GEVO3640 and the parent TMA29 strain GEVO2618. Cultures were started in YPD shaking at 30° C. and 250 rpm. After four doublings, the $OD_{600}$ was determined for each culture. Cells were added to 50 mL YPD with 15% glucose such that a final $OD_{600}$ of 0.05 was obtained. At t=24 h, 2 mL of media was removed and 25 μL used at a 1:40 dilution to determine $OD_{600}$. The remaining culture was centrifuged in a microcentrifuge at maximum speed for 10 min and 1 mL of supernatant was removed and submitted for LC1 and LC4 analysis. At t=48 h, 2 mL of media was removed and 25 μL used at a 1:40 dilution to determine $OD_{600}$. 1 mL of supernatant was submitted for LC1 analysis. In addition, 14 mL was collected by centrifugation at 2700×g. After removal of the media, cells were resuspended in sterile $dH_2O$, centrifuged at 2700×g and the remaining medium was carefully removed with a 1 mL pipette tip. The cell pellets were weighed (empty tubes were preweighed) and then frozen at −80° C. until thawed for ALS assays as described.

The production of DH2MB is dependent on heterologous ALS expression, for instance the Bs_alsS1_coSc gene. The ALS activity of cell lysates was measured as described to demonstrate that the TMA29 deletion had no impact on ALS expression and/or activity. The ALS activity of extracts from the strains carrying the TMA29 deletion is not less than, and is slightly more than the activity of extracts from the parent strain. The results at 24 h (48 h for ALS activity) are summarized in Table 48 and clearly demonstrate the lack of DH2MB production in the strain with the TMA29 deletion. LC4 analysis confirmed that GEVO3527 did not produce DHIV.

TABLE 48

Production of DH2MB in Strain with TMA29 Deletion.

| Strain | $OD_{600}$ | Glucose consumed by LC1 [g/L] | DH2MB by LC1 [g/L] | ALS activity [U/mg] |
|---|---|---|---|---|
| GEVO2618 | 9.2 ± 0.9 | 61.56 ± 12.0 | 1.51 ± 0.1 | 0.44 ± 0.06 |
| GEVO3638, GEVO3639, GEVO3640 (tma29Δ) | 12.5 ± 5.0 | 68.44 ± 12.5 | 0.00 ± 0.0 | 0.57 ± 0.04 |

Example 15

Deletion of TMA29 in *S. cerevisiae* by Deletion Library

The following example illustrates that deletion of the TMA29 gene from the *S. cerevisiae* genome eliminates the production of DH2MB when acetolactate synthase is overexpressed.

Strains, ORF deletions, and plasmids are listed in Tables 49, 50, and 51.

TABLE 49

Genotype of Strains Disclosed in Example 15.

| GEVO # | Genotype/Source |
|---|---|
| GEVO3527 | *S. cerevisiae* BY4742: MATa his3Δ1 leu2Δ0 lys2Δ0 ura3Δ0/ATCC #201389, purchased from ATCC 10801 University Boulevard Manassas, VA 20110-2209 |

TABLE 50

ORF Deletion Disclosed in Example 15.

| ORF deletion | Gene name | Source |
|---|---|---|
| YMR226C | TMA29 | Deletion library was obtained from Open Biosystems, cat # YSC 1054 |

TABLE 51

Plasmid Disclosed in Example 15.

| Plasmid | Relevant Genes |
|---|---|
| pGV2435 | $P_{ScCUP1}$: Bs_alsS1_coSc:$P_{ScTPI1}$:hph:$T_{ScCYC1}$, CEN/ARS, bla, pUC-ori |

A commercial library of *S. cerevisiae* strains which has one gene/ORF deleted per strain was used to screen for a deletion that might catalyze the production of DH2MB. The candidate strain containing the deletion of the TMA29 (i.e., YMR226C) ORF was selected. Since exogenous ALS expression is required for production of DH2MB, a CEN plasmid (pGV2435) containing the Bs_alsS1_coSc gene driven by the CUP1 promoter was transformed into the strains as described. Transformations were recovered overnight at 30° C., 250 rpm before plating onto YPD plates containing 0.2 g/L hygromycin. Transformants were then patched onto YPD plates containing 0.2 g/L hygromycin and incubated at 30° C.

Fermentations were performed with these strains to determine if deleting TMA29 (YMR226C) reduced or eliminated the production of DH2MB. Three independent transformants of each strain were used to inoculate fermentation precultures which were grown overnight to saturation in YPD containing 0.2 g/L hygromycin at 30° C. and 250 rpm. The next day, the $OD_{600}$ of the precultures was measured and the volume of overnight culture needed to inoculate a 50 mL culture to an $OD_{600}$ of 0.1 was calculated for each culture. 50 mL of YPD containing 150 g/L glucose, 200 mM MES, pH 6.5, and 0.2 g/L hygromycin in a 250 mL non-baffled flask were inoculated with the calculated amount of overnight culture. Cells were incubated at 30° C. and 75 rpm in an orbital shaker. At 24 h, all cultures were fed an additional 75 g/L of glucose by addition of 8.8 mL of a 50% glucose solution to each flask and then returned to incubation at 30° C. and 75 rpm. At 72 h, 1.5 mL was sampled from each flask (750 μL divided between two Eppendorf tubes). The $OD_{600}$ was measured for each culture (1:40 dilution in $H_2O$). The cells were removed from samples by centrifugation at ≥14000×g for 10 minutes in a microcentrifuge. The supernatants from the samples were collected and stored at 4° C. until analysis by LC1, and the cell pellets were stored at −80° C. until thawed for ALS assays as described.

There was some variation in the growth between the two strains, with $OD_{600}$ values of 13.7 for GEVO3527 and 15.7 for the TMA29 deletion strain at 72 h (Table 52). The strains consumed the same amount of glucose of around 223 g/L by 72 h (Table 52). GEVO3527 produced 2.8 g/L of DH2MB by 72 h. The YMR226C deletion strain (tma29Δ) did not produce detectable levels of DH2MB. The specific DH2MB titer for GEVO3527 was 0.2 g/L/OD; the YMR226C deletion strain (tma29Δ) did not produce detectable levels of DH2MB. LC4 analysis confirmed that GEVO3527 did not produce DHIV.

TABLE 52

Cell Growth, Glucose Consumed, and DH2MB Production at 72 h.

| Strain | $OD_{600}$ | Glucose consumed by LC1 [g/L] | DH2MB titer by LC1 [g/L] | Specific DH2MB titer [g/L/OD] |
|---|---|---|---|---|
| GEVO3527 | 13.7 ± 0.3 | 223.3 ± 0.6 | 2.8 ± 0.1 | 0.2 ± 0.01 |
| TMA29Δ | 15.7 ± 5.5 | 223.9 ± 0.2 | 0.0 ± 0.0 | 0.0 ± 0.0 |

Example 16

Improved Isobutanol Rate, Yield, and Titer with Deletion of TMA29 Gene in S. cerevisiae The following example illustrates that deletion of the TMA29 gene from the *S. cerevisiae* genome leads to an increase in productivity, yield, and titer of the desired product, isobutanol. In addition, it leads to a decrease in DH2MB productivity, yield and titer.

DH2MB is a byproduct of acetolactate metabolism in yeast. In isobutanol fermentations, DH2MB can comprise 10% or greater of the carbon yield. Strains with wild-type TMA29 produce DH2MB in the presence of expressed acetolactate synthase (ALS), encoded by Bs_alsS1_coSc (SEQ ID NO: 23). Strains deleted for TMA29 do not produce DH2MB in the presence of expressed Bs_alsS1_coSc. A yeast strain deleted for all PDC and GPD genes that expresses ALS (Bs_alsS1_coSc) from the chromosome was deleted for TMA29 and transformed with a high copy four-component isobutanol pathway plasmid, pGV2550 with genes for DHAD (Ll_ilvD_coSc), KARI (Ec_ilvC_coSc$^{P2D1-A1-his6}$), KIVD (Ll_kivD2_coEc) and ADH (Ll_adhA_coSc$^{RE1-his6}$). Isobutanol titer, yield and productivity of this strain were compared to that of the parent strain that was not deleted for the TMA29 gene, in both a shake flask fermentation and in fermenters. Strains and plasmids are listed in Tables 53 and 54, respectively.

TABLE 54

Plasmids Disclosed in Example 16.

| Plasmid Name | Genotype |
|---|---|
| pGV1299 | Kl_URA3, bla, pUC-ori. |
| pGV2129 | Kl_URA3-5', bla, pUC ori |
| pGV2550 | P$_{ScTEF1}$:Ll_ilvD_coS, P$_{ScTDH3}$:Ec_ilvC_coSc$^{P2D1-A1-his6}$:-P$_{ScPGK1}$:Ll_kivD2_coEc:P$_{ScENO2}$:Ll_adhA_coSc$^{RE1-his6}$, 2μ-ori, pUC-ori, bla, G418R. |

Yeast strain construction: GEVO3663 was constructed by transforming GEVO3351 with the bipartite integration SOE PCR products described in Example 14 to replace TMA29 with a URA3 marker as described, except after transformation the cells were resuspended in 350 μL SCD-Ura media before being spread to SCD-Ura plates.

*S. cerevisiae* strains GEVO3690, GEVO3691, and GEVO3692 were constructed by transforming GEVO3351 with plasmid pGV2550. *S. cerevisiae* strains GEVO3694, GEVO3695, and GEVO3697 were constructed by transforming GEVO3663 with plasmid pGV2250 Briefly, competent cells were prepared by removing cells from a fresh plate into 100 μL 100 mM lithium acetate. The cell suspension was incubated at room temperature for 30 min. Plasmid DNA was transformed as described. After transformation, the cells were resuspended in 400 μL YPD containing 1% ethanol and incubated at 30° C. for 6 h shaking at 250 rpm. The cells were then spread onto YPD plates containing 0.2 g/L G418. Transformants were single colony purified onto YPD plates containing 0.2 g/L G418 plates. Once the transformants were single colony purified they were maintained on YPD plates containing 0.2 g/L G418.

TABLE 53

Genotype of Strains Disclosed in Example 16.

| GEVO No. | Genotype |
|---|---|
| GEVO1187 | *S. cerevisiae* CEN.PK2 MATa ura3 leu2 his3 trp1 ADE2 |
| GEVO3351 | MATa ura3 leu2 his3 trp1 gpd1Δ::[TKl_URA3] gpd2 Δ::TKl_URA3 |
| | pdc1 Δ::[P$_{CUP1}$:Bs_alsS1_coSc:T$_{CYC1}$:P$_{PGK1}$:Ll_kivD-P$_{ENO2}$:Sp_HIS5] |
| | pdc5 Δ::[LEU2; bla; P$_{TEF1}$:ILV3ΔN; P$_{TDH3}$; ilvC_coSc$^{Q110V}$] |
| | pdc6 Δ::[P$_{TEF}$-Ll_ilvD:P$_{TDH3}$:Ec_ilvC_coSc$^{P2D1-A1}$:P$_{ENO2}$:Ll_adhA:P$_{FBA1}$:Sc_TRP1] |
| | {evolved for C2 supplement-independence, glucose tolerance and faster growth} |
| GEVO3663 | MATa ura3 leu2 his3 trp1 gpd1::T$_{Kl\_URA3}$ gpd1Δ::[T$_{Kl\_URA3}$] gpd2 Δ::T$_{Kl\_URA3}$ |
| | pdc1 Δ::[P$_{CUP1}$:Bs_alsS1_coSc:T$_{CYC1}$:P$_{PGK1}$:Ll_kivD-P$_{ENO2}$:Sp_HIS5] |
| | pdc5 Δ::[LEU2; bla; P$_{TEF1}$:ILV3ΔN; P$_{TDH3}$; ilvC_coSc$^{Q110V}$] |
| | pdc6 Δ::[P$_{TEF}$-Ll_ilvD:P$_{TDH3}$:Ec_ilvC_coSc$^{P2D1-A1}$:P$_{ENO2}$:Ll_adhA:P$_{FBA1}$:Sc_TRP1] |
| | tma29Δ::[T$_{Kl\_URA3\_short}$: P$_{FBA1}$:Kl_URA3: T$_{Kl\_URA3}$] {evolved for C2 supplement-independence, glucose tolerance and faster growth} |
| GEVO3690, GEVO3691, GEVO 3692 | MATa ura3 leu2 his3 trp1 gpd1Δ::[T$_{Kl\_URA3}$] gpd2 Δ::T$_{Kl}$_URA3 |
| | pdc1 Δ::[P$_{CUP1}$:Bs_alsS1_coSc:T$_{CYC1}$:P$_{PGK1}$:Ll_kivD-P$_{ENO2}$:Sp_HIS5] |
| | pdc5 Δ::[LEU2; bla; P$_{TEF1}$:ILV3ΔN; P$_{TDH3}$; ilvC_coSc$^{Q110V}$] |
| | pdc6 Δ::[P$_{TEF}$-Ll_ilvD:P$_{TDH3}$:Ec_ilvC_coSc$^{P2D1-A1}$:P$_{ENO2}$:Ll_adhA:P$_{FBA1}$:Sc_TRP1] |
| | Transformed with pGV2550 {evolved for C2 supplement-independence, glucose tolerance and faster growth} |
| GEVO3694, GEVO3695, GEVO3696, GEVO3697 | MATa ura3 leu2 his3 trp1 gpd1Δ::[T$_{Kl\_URA3}$] gpd2 Δ::T$_{Kl}$_URA3 |
| | pdc1 Δ::[P$_{CUP1}$:Bs_alsS1_coSc:T$_{CYC1}$:P$_{PGK1}$:Ll_kivD-P$_{ENO2}$:Sp_HIS5] |
| | pdc5 Δ::[LEU2; bla; P$_{TEF1}$:ILV3ΔN; P$_{TDH3}$; ilvC_coSc$^{Q110V}$] |
| | pdc6 Δ::[P$_{TEF}$-Ll_ilvD:P$_{TDH3}$:Ec_ilvC_coSc$^{P2D1-A1}$:P$_{ENO2}$:Ll_adhA:P$_{FBA1}$:Sc_TRP1] |
| | tma29Δ::[T$_{Kl\_URA3\_short}$: P$_{FBA1}$:Kl_URA3: T$_{Kl\_URA3}$]Transformed with pGV2550 {evolved for C2 supplement-independence, glucose tolerance and faster growth} |

Fermentations: A shake flask fermentation was performed comparing performance of GEVO3690-GEVO3692 (TMA29) to GEVO3694-GEVO3695 and GEVO3697 (tma29Δ). Cultures (3 mL) were started in YPD containing 1% ethanol and 0.2 g/L G418 and incubated overnight at 30° C. and 250 rpm. The $OD_{600}$ of these cultures was measured after about 20 h. An appropriate amount of each culture was used to inoculate 50 mL of YPD containing 1% ethanol and 0.2 g/L G418 in a 250 mL baffled flask to an $OD_{600}$ of approximately 0.1. These precultures were incubated at 30° C. and 250 rpm overnight. When the cultures had reached an $OD_{600}$ of approximately 5 they were centrifuged at 2700 rcf for 5 min at 25° C. in 50 mL Falcon tubes. The cells from each 50 mL culture were resuspended in 50 mL of fermentation media as described. The cultures were then transferred to 250 mL unbaffled screw-cap flasks with small vents and incubated at 30° C. and 75 rpm. At 24 and 48 h, samples from each flask were removed to measure $OD_{600}$ and to prepare for GC1 analysis. For GC1, 2 mL sample was removed into an Eppendorf tube and centrifuged in a microcentrifuge for 10 min at maximum. One mL of the supernatant was analyzed by GC1. At 72 h the same procedures were used to collect cells for $OD_{600}$ and GC analysis and in addition the samples were analyzed by high performance liquid chromatography (LC1) for organic acids, including DH2MB and DHIV, and glucose.

The results at 72 h are summarized in Table 55. Isobutanol titer, yield and rate increase with deletion of the TMA29 gene, while DH2MB production decreases.

flask cultures were transferred to individual 2 L top drive motor fermenter vessels with a working volume of 1.2 L of 80 mL of YP medium with 20 g/L glucose, 1% v/v Ethanol, 100 μM $CuSO_4.5H_2O$, and 0.2 g/L G418 for a starting $OD_{600}$ of 0.2. Fermenters were operated at 30° C. and pH 6, controlled with 6N KOH in a two-phase aerobic fermentation. Initially, fermenters were operated at a growth phase oxygen transfer rate (OTR) of 10 mM/h by fixed agitation of 850 rpm and an air overlay of 5 sL/h. Cultures were grown for 31 h to approximately 6-7$OD_{600}$ then immediately switched to a production aeration OTR of 0.5 mM/h by reducing agitation from 850 rpm to 300 rpm for the remainder of the fermentation of 111 h. Periodically, samples from each fermenter were removed to measure $OD_{600}$ and to prepare for gas chromatography (GC1) analysis. For GC, 2 mL sample was removed into an Eppendorf tube and centrifuged in a microcentrifuge for 10 min at maximum. One mL of the supernatant was analyzed by GC1 (isobutanol, other metabolites). At 72 h the same procedures were used to collect cells for $OD_{600}$ and GC analysis and in addition the samples were analyzed by high performance liquid chromatography (LC1) for organic acids and glucose.

The results at 111 h are summarized in Table 56. Isobutanol titer, yield, and rate increased with deletion of the TMA29 gene. DH2MB production decreased to undetectable levels.

TABLE 55

Isobutanol Titer, Yield, and Rate Increase at 72 h.

| Strain | $OD_{600}$ | Glucose consumed [g/L] | Isobutanol produced [g/L] | Isobutanol yield [% theoretical] | Isobutanol rate [g/L/h] | DH2MB produced [g/L] |
|---|---|---|---|---|---|---|
| GEVO3690, GEVO3691, GEVO3692 | 8.3 ± 0.3 | 29.8 ± 1.3 | 5.5 ± 0.4 | 45.1 ± 4 | 0.08 | 3.1 |
| GEVO3694, GEVO3695, GEVO3697 (TMA29Δ) | 8.3 ± 0.7 | 33.4 ± 1.0 | 7.6 ± 0.2 | 55.1 ± 2 | 0.11 | 0.03 |

In addition, the performance of GEVO3690-GEVO3691 (TMA29) to GEVO3694-GEVO3696 (tma29Δ) was also compared in fermentations performed in fermenter vessels. Plated cultures were transferred to 500 mL baffled flasks containing 80 mL of YP medium with 20 g/L glucose, 1% v/v Ethanol, 100 μM $CuSO_4.5H_2O$, and 0.2 g/L G418 and incubated for 34.5 h at 30° C. in an orbital shaker at 250 rpm. The

TABLE 56

Isobutanol Titer, Yield, and Rate Increase at 111 h.

| Strain | $OD_{600}$ | Glucose consumed[a] [g/L] | Isobutanol produced[a] [g/L] | DH2MB produced[a] [g/L] | Isobutanol yield[b] [% theor.] | Isobutanol rate[b] [g/L/h] |
|---|---|---|---|---|---|---|
| GEVO3690 GEVO3691, (TMA29+) | 7.2 ± 0.7 | 29.7 ± 1.1 | 8.6 ± 0.1 | 2.9 | 62.4 ± 3 | 0.09 |
| GEVO3694, GEVO3695, GEVO3696 (TMA29Δ) | 7.4 ± 1.3 | 35.7 ± 3.9 | 12.3 ± 1.2 | 0 | 75.0 ± 0.01 | 0.14 |

[a]Glucose, isobutanol, and DH2MB titers are the final titers, i.e. at 111 h of fermentation.
[b]Isobutanol yield and rate are calculated based on the production phase only, i.e. from 31 to 111 h of fermentation.

Example 17

Determination of TMA29 Activity in *S. cerevisiae*

The following example illustrates that the (S)-2-acetolactate reduction activity is significantly decreased in a tma29Δ strain.

TABLE 57

Genotype of Strains Disclosed in Example 17.

| GEVO # | Genotype | Source |
|---|---|---|
| GEVO3527 | MATα his3Δ-1 leu2Δ lys2Δ ura3Δ | ATCC# 201389 (BY4742) |
| GEVO3939 | MATα his3Δ-1 leu2Δ lys2Δ ura3Δ tma29::kan$^R$ | OpenBiosystems cat# YSC1054 (Yeast MATalpha collection) |

Yeast strains GEVO3939 from which the TMA29 (YMR226C) gene was deleted and its parent GEVO3527 were each cultured in triplicate by inoculating 3 mL of YPD in a 14 mL culture tube in triplicate for each strain. Cultures were started from patches on YPD agar plate for GEVO3527 and on YPD plates containing 0.2 g/L G418 for GEVO3939 and GEVO3940. The cultures were incubated overnight at 30° C. and 250 rpm. The next day, the OD$_{600}$ of the overnight cultures were measured and the volume of each culture to inoculate a 50 mL culture to an OD$_{600}$ of 0.1 was calculated. The calculated volume of each culture was used to inoculate 50 mL of YPD in a 250 mL baffled flask and the cultures were incubated at 30° C. and 250 rpm.

The cells were harvested during mid-log phase at ODs of 1.6-2.1 after 7 h of growth. The cultures were transferred to pre-weighed 50 mL Falcon tubes and cells were collected by centrifugation for 5 minutes at 3000×g. After removal of the medium, cells were washed with 10 mL MilliQ H$_2$O. After removal of the water, the cells were centrifuged again at 3000×g for 5 minutes and the remaining water was carefully removed using a 1 mL pipette tip. The cell pellets were weighed and then stored at −80° C. until further use.

Cell pellets were thawed on ice and resuspended in lysis buffer (10 mM sodium phosphate pH7.0, 1 mM dithiothreitol, 5% w/v glycerol) such that the result was a 20% cell suspension by mass. One mL of glass beads (0.5 mm diameter) was added to a 1.5 mL Eppendorf tube for each sample and 850 μL of cell suspension were added. Yeast cells were lysed using a Retsch MM301 mixer mill (Retsch Inc. Newtown, Pa.), mixing 6×1 min each at full speed with 1 min incubation on ice between. The tubes were centrifuged for 10 min at 21,500×g at 4° C. and the supernatant was transferred to a fresh tube. Extracts were held on ice until they were assayed using the TMA29 assay as described.

The specific activity of *S. cerevisiae* TMA29 in GEVO3527 lysates, a wild-type MATa *S. cerevisiae* strain, for the reduction of (S)-2-acetolactate was 6.9±0.2 mU/mg. The tma29Δ strain GEVO3939 had a specific activity of 0.7±0.3 mU/mg. The wild-type GEVO3527 strain had about a 10-fold higher specific TMA29 activity than the deletion strain.

Example 18

Determination of TMA29 Activity in *Kluyveromyces lactis*

The following example illustrates that the (S)-2-acetolactate reduction activity is significantly decreased in a tma29Δ strain.

TABLE 58

Genotype of Strains Disclosed in Example 18.

| GEVO # | Genotype |
|---|---|
| GEVO1287 | *Kluyveromyces lactis*, MATα uraA1 trp1 leu2 lysA1 ade1 lac4-8 [pKD1] |
| GEVO1742 | *Kluyveromyces lactis*, MATalpha uraA1 trp1 leu2 lysA1 ade1 lac4-8 [pKD1] pdc1Δ::kan |
| GEVO4458 | *Kluyveromyces lactis*, MATalpha uraA1 trp1 leu2 lysA1 ade1 lac4-8 [pKD1] pdc1Δ::kan tma29Δ::hph |

TABLE 59

Oligonucleotide Sequences Disclosed in Example 18.

| oGV # | Sequence |
|---|---|
| 821 | CGGGTAATTAACGACACCCTAGAGG (SEQ ID NO: 132) |
| 2320 | GGCTGTGTAGAAGTACTCGCCGATAG (SEQ ID NO: 133) |
| 3065 | AAAAAGGAGTAGAAACATTTTGAAGCTATGCGTTGATAAGGGCAACAACGTTAGTATC (SEQ ID NO: 134) |
| 3066 | ATACTAACGTTGTTGCCCTTATCAACGCATAGCTTCAAAATGTTTCTACTCCTTTTTTAC (SEQ ID NO: 135) |
| 3067 | TCAAATTTTTCTTTTTTTTCTGTACAGTTACCCAAGCTGTTTTGCCTATTTTCAAAGC (SEQ ID NO: 136) |
| 3068 | GCTTTGAAAATAGGCAAAACAGCTTGGGTAACTGTACAGAAAAAAAAGAAAAATTTG (SEQ ID NO: 137) |

TABLE 59-continued

Oligonucleotide Sequences Disclosed
in Example 18.

| oGV # | Sequence |
|---|---|
| 3069 | AGTTCAAATCAGTTCGAGGATAATTTAAG<br>(SEQ ID NO: 138) |
| 3070 | TTAATAAATGCTCAAAAGAAAAAAGGCTGGCG<br>(SEQ ID NO: 139) |
| 3103 | ACCGGTGCTTCTGCAGGTATTG<br>(SEQ ID NO: 140) |
| 3106 | ATGCTTGGTTGGAAGCAAATAC<br>(SEQ ID NO: 141) |

The *K. lactis* strain GEVO4458 was constructed from GEVO1742 as follows. DNA constructs were made to delete the TMA29 locus of *K. lactis* using SOE PCR. The 5' targeting sequence was amplified by PCR using GEVO1287 genomic DNA as template with primers oGV3103 and oGV3065. The 376 bp fragment was purified by gel electrophoresis. The 3' targeting sequence was amplified by PCR using GEVO1287 genomic DNA as template with primers oGV3106 and oGV3067. The 405 bp fragment was gel purified. The Hph marker was amplified by PCR using pGV2701 ($P_{TEF1}$-Hph, CEN/ARS, pUC-ori, bla) as template with primers oGV3066 and oGV3068. The 1,165 bp fragment was gel purified. Next the 5' targeting sequence and the hph marker were joined together using PCR products described as template. The reaction was amplified using primers oGV3068 and oGV3103. The 1,984 bp fragment was gel purified. Next the 5' targeting sequence plus Hph marker PCR fragment was joined with the 3' targeting sequence using PCR with primers oGV3103 and oGV3106. The 2,331 bp was gel purified and used for transformation. Yeast DNA was isolated using the Zymo Research ZR Fungal/Bacterial DNA Kit (Zymo Research Orange, Calif.; Catalog #D6005). GEVO1287 was grown to saturation in 12.5 mL of YPD in baffled 125 mL flasks. The entire culture was collected in 15 mL Falcon tubes and cells collected at 2700 rcf for 5 min. Genomic DNA was isolated according to the manufacturer's instructions. The DNA concentration was measured and all genomic DNA preps were diluted to a final concentration of 25 ng/µL.

GEVO1742 was transformed as follows. 50 mL YPD medium in 250 mL baffled flasks were inoculated with GEVO1742 cells from a fresh plate. The cultures were incubated overnight at 30° C. and 250 rpm. The next morning the culture was diluted 1:50 in YPD medium and allowed to grow for 6 h. Cells were collected by centrifugation at 2700 rcf for 2 min at 30° C. Cells were washed by fully resuspending cells with 50 mL sterile MilliQ water. Cells were collected by centrifugation at 2700 rcf for 2 min at 30° C. Cells were washed by resuspending with 25 mL sterile MilliQ water. Cells were collected by centrifugation at 2700 rcf for 2 min at 30° C. Cells were resuspended in 1 mL 100 mM lithium acetate, transferred to an Eppendorf tube and collected by centrifuging at 14,000 rcf for 10 seconds. The supernatant was removed and the cells were resuspended with 4× the pellet volume in 100 mM LiOAc. A mixture of DNA (15 µL of PCR product), 72 µL 50% PEG, 10 µL 1 M lithium acetate, and 3 µL of denatured salmon sperm DNA (10 mg/mL) was prepared for each transformation. In a 1.5 mL tube, 15 µL of the cell suspension was added to the DNA mixture (170 µL), and the transformation suspension was vortexed for 5 short pulses. The transformation was incubated for 30 min at 30° C., followed by incubation for 22 min at 42° C. The cells were collected by centrifugation (18,000×g, 10 sec, 25° C.). The cells were resuspended in 400 µL YPD medium and allowed to recover overnight at 30° C. and 250 rpm. The following morning, the cells were spread onto YPE plates 1% (w/v) yeast extract, 2% (w/v) peptone, 25 mL/L ethanol) supplemented with 0.1 g/L Hygromycin. Transformants were single colony purified onto YPE plates supplemented with 0.1 g/L Hygromycin.

The single colony isolates were patched onto YPE supplemented with 0.1 g/L Hygromycin plates and the patches were screened for the correct integration by colony PCR. Presence of the correct PCR product was confirmed using agarose gel electrophoresis. To screen for the internal TMA29 coding region, primers oGV3103 and oGV3106 were used. To screen the 5' integration junction, primers oGV3069 and oGV821 were used. To screen the 3' integration junction, primers oGV2320 and oGV3070 were used.

Yeast cells were cultured by inoculating 3 mL of YPD medium (1% (w/v) yeast extract, 2% (w/v) peptone, 2% (w/v) glucose) in a 14 mL culture tube in triplicate for each strain. Cultures were started from patches on a YPD plate 1% (w/v) yeast extract, 2% (w/v) peptone, 2% (w/v) glucose, 2% agar). The cultures were incubated overnight at 30° C. and 250 rpm. The next day, the $OD_{600}$ of the overnight cultures were measured and the volume of each culture to inoculate a 50 mL culture to an $OD_{600}$ of 0.1 was calculated. The calculated volume of each culture was used to inoculate 50 mL of YPD in a 250 mL baffled flask and the cultures were incubated at 30° C. and 250 rpm overnight. Cells were harvested during mid-log phase at ODs of 1.8-2.2. The cultures were transferred to pre-weighed 50 mL Falcon tubes and cells were collected by centrifugation for 5 min at 3000×g. After removal of the medium, cells were washed with 10 mL MilliQ $H_2O$. After removal of the water, the cells were centrifuged again at 3000×g for 5 min and the remaining water was carefully removed with a 1 mL pipette tip. The cell pellets were weighed and then stored at −80'C.

Cell pellets were thawed on ice and resuspended in lysis buffer (10 mM sodium phosphate pH7.0, 1 mM dithiothreitol, 5% w/v glycerol) such that the result was a 20% cell suspension by mass. One mL of glass beads (0.5 mm diameter) was added to a 1.5 mL Eppendorf tube for each sample and 850 µL of cell suspension were added. Yeast cells were lysed using a Retsch MM301 mixer mill (Retsch Inc. Newtown, Pa.), mixing 6×1 min each at full speed with 1 min incubation on ice between. The tubes were centrifuged for 10 min at 21,500×g at 4° C. and the supernatant was transferred to a fresh tube. Extracts were held on ice until they were assayed using the TMA29 assay as described.

The specific activity of Gevo1742 with the TMA29 gene for the reduction of (S)-2-acetolactate was 0.0043±0.0005 µmol/min/mg lysate. The specific activity of Gevo4459 deleted for the TMA29 gene was 0.0019±0.0003 µmol/min/mg lysate.

Example 19

Increased Isobutanol Yield in Strains Comprising an ALD6 Deletion, a TMA29 Deletion and an Alcohol Dehydrogenase with Increased $k_{cat}$ and Decreased $K_m$ in S. cerevisiae The following example illustrates that the combination of an ALD6 deletion, TMA29 deletion and overexpression of a gene encoding an ADH with improved kinetic properties leads to increased isobutanol production and theoretical yield.

A S. cerevisiae CEN.PK2 strain, GEVO3991, was constructed by transforming a S. cerevisiae CEN.PK2 strain, GEVO3956, which expresses an improved alcohol dehydrogenase (L. lactis ADH*, Ll_ADH*) and a decarboxylase (L. lactis KIVD, Ll_kivD2) from its chromosomal DNA with a 2µ plasmid, pGV2603 ($P_{TDH3}$:Ec_ilvC_coSc$^{P2D1-A1-his6}$, $P_{TEF1}$:Ll_ilvD_coSc, $P_{ENO2}$:Ll_adhA$^{RE1}$,2µ-ori, pUC-ori, bla, G418R), expressing genes encoding enzymes: KARI, DHAD, and the improved ADH (EC_ilvC_coSc$^{P2D1-A1-his6}$ Ll_ilvD_coSc, and Ll_adhA$^{RE1}$, respectively).

MgSO$_4$, and 0.2 g/L G418 and incubated for 30 h at 30° C. in an orbital shaker at 250 rpm. The flask cultures were transferred to four individual 2 L top drive motor fermenter vessels with a working volume of 0.9 L of YPD containing 80 g/L glucose, 5 g/L ethanol, 0.5 g/L MgSO$_4$, and 0.2 g/L G418 per vessel for a starting OD$_{600}$ of 0.3. Fermenters were operated at 30° C. and pH 6.0 controlled with 6N KOH in a 2-phase aerobic condition based on oxygen transfer rate (OTR). Initially, fermenters were operated at a growth phase OTR of 10 mM/h by fixed agitation of 700 rpm and an air overlay of 5 sL/h. Cultures were grown for 22.5 h to approximately 10-11 OD$_{600}$ then immediately switched to production aeration conditions for 40.7 h. Cell density during production phase approached 13-14 OD$_{600}$. The production phase was operated at an OTR of 0.5 mM/h by fixed agitation of 300 rpm. Periodically, samples from each fermenter were removed to measure OD$_{600}$ and to prepare for gas chromatography (GC) and liquid chromatography (LC) analysis. For GC and LC, 2 mL sample was removed into an Eppendorf tube and centrifuged in a microcentrifuge for 10 min at maximum. One mL of the supernatant was analyzed by GC1 (isobutanol, other metabolites) and one mL analyzed by high performance liquid chromatography (LC1) for organic acids and glucose as described.

GEVO3991 achieved a cell density of 13.8 during the 22.5 h growth phase. The isobutanol produced during the entire duration of the experiment (63.2 h) was 18.6±0.9 g/L with 0.84±0.10 g/L isobutyrate and 0.15±0.02 g/L acetate produced. The theoretical isobutanol yield achieved during the production phase of the experiment (22.5-63.5 h) was

TABLE 60

Genotype of Strains Disclosed in Example 19.

| GEVO No. | Genotype |
|---|---|
| GEVO3991 | MATa ura3 leu2 his3 trp1<br>ald6Δ::[$P_{ENO2}$:Ll_adhA$^{RE1}$:$P_{FBA1}$:Sc_TRP1<br>gpd1Δ::T$_{Kl\_URA3}$<br>gpd2Δ::T$_{Kl\_URA3}$<br>tma29Δ::T$_{Kl\_URA3}$<br>pdc1Δ::[$P_{PDC1}$:Ll_kivD2_coSc5:$P_{FBA1}$:LEU2:T$_{LEU2}$:$P_{ADH1}$:Bs_alsS1_coSc:T$_{CYC1}$:$P_{PGK1}$:Ll_kivD2_coEc: $P_{ENO2}$:Sp_HIS5]<br>pdc5Δ::T$_{Kl\_URA3}$<br>pdc6Δ::$P_{TDH3}$:Sc_AFT1:$P_{ENO2}$:Ll_adhA$^{RE1}$:T-$_{Kl\_URA3\_short}$:<br>$P_{FBA1}$:Kl_URA3:T$_{Kl\_URA3}$]{evolved for C2 supplement-independence, glucose tolerance and faster growth},<br>[pGV2603] |
| GEVO3956 | MATa ura3 leu2 his3 trp1 ald6Δ::[$P_{ENO2}$:Ll_adhA$^{RE1}$:$P_{FBA1}$:Sc_TRP1<br>gpd1Δ::T$_{Kl\_URA3}$<br>gpd2Δ::T$_{Kl\_URA3}$<br>tma29Δ::T$_{Kl\_URA3}$<br>pdc1Δ::[$P_{PDC1}$:Ll_kivD2_coSc5:$P_{FBA1}$:LEU2:T$_{LEU2}$:$P_{ADH1}$:Bs_alsS1_coSc:T$_{CYC1}$:$P_{PGK1}$:Ll_kivD2_coEc: $P_{ENO2}$:Sp_HIS5]<br>pdc5Δ::T$_{Kl\_URA3}$<br>pdc6Δ::$P_{TDH3}$:Sc_AFT1:$P_{ENO2}$:Ll_adhA$^{RE1}$:T-$_{Kl\_URA3\_short}$:<br>$P_{FBA1}$:Kl_URA3:T$_{Kl\_URA3}$]{evolved for C2 supplement-independence, glucose tolerance and faster growth} |

A fermentation was performed to determine the performance of GEVO3991 (Ll_adhA$^{RE1}$, ALD6Δ, TMA29Δ) in four replicate fermenters. Glucose consumption, isobutanol production, isobutyrate production, acetate production and OD$_{600}$ were measured during the fermentation. For these fermentations, single isolate cell colonies grown on YPD agar plates were transferred to 500 mL baffled flasks containing 80 mL of YPD containing 80 g/L glucose, 5 g/L ethanol, 0.5 g/L 80.3±1.1% while the isobutyrate yield was only 0.013±0.001 g/g glucose. The production of DH2MB was not detected.

In addition, three independent transformants of GEVO3991 were also characterized in shake flasks. The strain was grown overnight in 3 mL of YPD containing 1% ethanol and 0.2 g/L G418 at 30° C. at 250 rpm. These cultures were diluted to an OD$_{600}$ of 0.1 in 50 mL of the same medium in a baffled 250 mL flask and grown overnight. The OD$_{600}$ was measured and a volume of cells approximately equal to 250 $OD_{600}$ was collected for each culture b centrifugation at 2700 ref for 2 minutes and the cells were resuspended in 50 mL of fermentation medium (YPD containing 80 g/L glucose, 0.03 g/L ergosterol, 1.32 g/L TWEEN™ 80, 1% v/v ethanol, 200 mM MES, pH6.5), and transferred to an unbaffled vented screw cap 250 mL flask. The $OD_{600}$ was checked and the cultures were placed at 30° C. at 75 rpm to initiate the microaerobic fermentation. Samples for liquid chromatography (LC), gas chromatography (GC) analysis and $OD_{600}$ were taken at roughly 24 h intervals. The samples (2 mL) were centrifuged at 18,000 x g for 10 min and 1.5 mL, of the clarified supernatant was used for analysis by GC 1 and LC1.

Fermentations started at an $OD_{600}$ of about 4. The cells grew to an $OD_{600}$ of about 8 by 72 h of microaerobic fermentation. After 72 h, the isobutanol titer was 12.3 g/L and the isobutanol yield was 67.2% of theoretical. Isobutyrate titer and yield were low: 0.6 g/L isobutyrate was produced at a yield of 0.013 g/g glucose. The production of DH2MB was not detected.

Example 20

Effect of TMA29 Deletion in *K. marxianus*

The purpose of this example is to demonstrate that the deletion of TMA29 in a *Kluyveromyces marxianus* strain comprising ALS activity results in reduced DH2MB production.

Strains, plasmids, and oligonucleotide sequences disclosed in this example are listed in Tables 61, 62, and 63, respectively.

TABLE 61

Genotype of Strains Disclosed in Example 20.

| GEVO No. | Genotype |
|---|---|
| 1947 | ura3-delta2, derived from strain NRRL-Y-7571 *Kluyveromyces marxianus* (E. C. Hansen) van der Walt (1971) |
| 2348 | ura3-delta2 pdc1Δ::G418R, $P_{Sc\_PDC1}$:31COX4 MTS:Bs_alsS:$P_{Sc\_FBA1}$:URA3 ura3-delta2 |
| 6403, 6404 | ura3-delta2 pdc1Δ::G418R, $P_{Sc\_PDC1}$:31COX4 MTS:alsS: $P_{Sc\_FBA1}$:URA3 ura3-delta2 tma29Δ::$P_{Sc\_TEF1}$-hph |

TABLE 62

Plasmid Disclosed in Example 20.

| Plasmid Name | Relevant Genes/Usage | Genotype |
|---|---|---|
| pGV2701 | For SOE PCR to give the hph fragment | $P_{TEF1}$:hph, CEN, pUC ori, bla |

TABLE 63

Oligonucleotide Sequences Disclosed in Example 20.

| Primer | Sequence |
|---|---|
| 3498 | ATGTCTCAAGGTAGAAGAGCTG (SEQ ID NO: 142) |
| 3137 | GGAGTAGAAACATTTTGAAGCTATGTATATCTTCTGAATCAATTGCACCGAC (SEQ ID NO: 143) |
| 3140 | CAAATTTTTCTTTTTTTTCTGTACAGAGAGGTATGATTAATACCAATGTCTTGGG (SEQ ID NO: 144) |
| 3499 | TCATTCACCACGGTAAATGTGG (SEQ ID NO: 145) |
| 3138 | GTCGGTGCAATTGATTCAGAAGATATACATAGCTTCAAAATGTTTCTACTCC (SEQ ID NO: 146) |
| 3139 | GTATTAATCATACCTCTCTGTACAGAAAAAAAAGAAAAATTTGAAATATAAATAACG (SEQ ID NO: 147) |
| 3501 | GAAGGAAATTCCAGTCTCCTAGTTCCTTTGAACAC (SEQ ID NO: 148) |
| 2320 | GGCTGTGTAGAAGTACTCGCCGATAG (SEQ ID NO: 149) |
| 3500 | CAGAACAATCAATCAACGAACGAACGACCCACCC (SEQ ID NO: 150) |
| 821 | CGGGTAATTAACGACACCCTAGAGG (SEQ ID NO: 151) |
| 3141 | AAGGAGATGCTTGGTTTGTAGCAAACACC (SEQ ID NO: 152) |

Strain Construction: The *K. marxianus* TMA29 gene homolog encoding the *K. marxianus* TMA29 protein (SEQ ID NO: 23) was deleted from parent *K. marxianus* strain GEVO2348 as follows, resulting in strains GEVO6403 and GEVO6404.

Genomic DNA was isolated from GEVO1947 as described. Constructs were made to integrate the *E. coli* hph (hygromycin resistance) cassette into the TMA29 locus of GEVO2348 by SOE PCR as described. PCR step #1 consisted of three reactions resulting in the 5' TMA29 targeting sequence, the 3' TMA29 targeting sequence, and the hph marker. The 5' targeting sequence was amplified from prepared GEVO1947 genomic DNA with primers oGV3498 and oGV3137. The 385 bp fragment was purified by gel electrophoresis. The 3' targeting sequence was amplified from prepared GEVO1947 genomic DNA with primers oGV3140 and oGV3499. The 473 bp fragment was gel purified. The $P_{TEF1}$:hph:$T_{CYC1(partial)}$ cassette was amplified from pGV2701 with primers oGV3138 and oGV3139. The 1,651 bp fragment was gel purified. The final SOE PCR step joined the 3 products from step #1 (5' targeting sequence/hph marker/3' targeting sequence). The reaction was amplified using primers oGV3498 and oGV3499. The 2,414 bp fragment was gel purified as described and used for transformation of GEVO2348 as described. Medium used to grow the cells for the transformation was YPE. Following the transformation, 150 µL of the transformation culture was spread onto YPE plates containing 0.1 g/L hygromycin. The plates were incubated at 30° C. and transformed colonies were single colony isolated and then patched for colony PCR on YPE plates containing 0.1 g/L hygromycin.

Yeast Colony PCR was used to screen for the appropriate 3' integration junction, 5' integration junction, as well as lack of the TMA29 coding region as described. The proper 3' integration junction was confirmed using primers oGV3501 and 2320. The proper 5' integration junction was confirmed using primers oGV3500 and oGV0821 were used. Finally, to screen for deletion of the TMA29 internal coding region, primers oGV3500 and oGV3141 were used.

Fermentation: Shake flask fermentations was performed in triplicate for each of the strains GEVO2348 (TMA29), GEVO6403 (tma29Δ), and GEVO6404 (tma29Δ) as described to determine if deletion of TMA29 in strains expressing Bs_alsS would result in diminished production of DH2MB. Single colony isolated transformants of tma29Δ strains were patched to YPE plates containing 0.1 g/L hygromycin, while parent strains were patched to YPE plates. Cells from the patches were used to inoculate 3 mL cultures of YPE. Cultures were incubated overnight at 30° C. and 250 rpm. After overnight incubation, the $OD_{600}$ of these cultures was determined by diluting 1:40 in water. The appropriate amount of culture was added to 50 mL of YPE to obtain an $OD_{600}$ of 0.1 in 250 mL baffled flasks and incubated at 30° C. and 250 rpm. After a 24 h incubation, the $OD_{600}$ of these cultures was determined by diluting 1:40 in water. The appropriate amount of culture was added to 50 mL of YPD containing 8% glucose and 200 mM MES, pH 6.5 to obtain an $OD_{600}$ of 5. Fermentation cultures were incubated at 30° C. and 75 rpm in unbaffled 250 mL flasks. One 15 mL aliquot of medium was also collected to use as a blank for LC4 analysis and was kept at 4° C. until sample submission. After 72 h, 1.5 mL of culture was removed and samples were prepared as above for $OD_{600}$ and LC4 analysis. In addition, samples for enzyme assays were harvested at 72 h by transferring 80 OD's of the appropriate sample to two 15 mL Falcon tubes centrifuged at 3000×g for 5 min at 4° C. Pellets were resuspended in 3 mL cold, sterile water and were centrifuged at 5000×g for 2 min at 4° C. in a swinging bucket rotor in the tabletop centrifuge. The water was removed by vacuum aspirator. The conical tubes were stored at −80° C.

The in vitro ALS enzymatic activities of the lysates were measured as described. Table 64 shows the average in vitro ALS enzymatic activity of lysates from the strains after 72 h. ALS activity is measurable in GEVO2348 (average of 3.14 Units/mg lysate) as well as in both tma29Δ strains GEVO6403 and GEVO6404 (averages of 1.63 and 1.58 Units/mg lysate respectively).

Table 64 also shows the DH2MB and DHIV titers by LC4 for these strains. GEVO2348 (TMA29) strains produced average DH2MB titers of 0.89 g/L while DHIV was not detected. The DH2MB titers were significantly decreased in the tma29Δ strains GEVO6403 and GEVO6404 which measured at 0.16 and 0.15 g/L respectively. While the ALS activity is decreased in the tma29Δ strains, this does not account for the >80% decrease in DH2MB titers in the deletion strains. For example, one technical replicate of GEVO2348 exhibited an ALS activity of 2.5 Units/mg lysate and produced 0.83 g/L DH2MB while one of the technical replicates of the tma29Δ strain GEVO6404 has similar activity of 1.9 Units/mg lysate and produced only 0.16 g/L DH2MB.

TABLE 64

ALS Activity, DH2MB and DHIV titers, and Percent DH2MB Decrease in tma29Δ Strains After 72 h Fermentation.

| Strain | TMA29 | ALS Activity (U/mg lysate) | DH2MB by LC4 (g/L) | DHIV by LC4 (g/L) | DH2MB decrease (%) |
|---|---|---|---|---|---|
| GEVO2348 | + | 3.1 ± 0.5 | 0.89 ± 0.07 | n.d. | |
| GEVO6403 | Δ | 1.6 ± 0.2 | 0.16 ± 0.02 | n.d. | 82% |
| GEVO6404 | Δ | 1.6 ± 0.3 | 0.15 ± 0.01 | n.d. | 83% | n.d. = not detected

Example 21

Effect of TMA29 Deletion in *Kluyveromyces lactis*

The purpose of this example is to demonstrate that the deletion of TMA29 in a *Kluyveromyces lactis* strain comprising ALS activity results in reduced DH2MB production.

Strains, plasmids, and oligonucleotide primers disclosed in this example are listed in Tables 65, 66, and 67, respectively.

TABLE 65

Genotype of Strains Disclosed in Example 21.

| GEVO Number | Genotype |
|---|---|
| 1742 | MATalpha uraA1 trp1 leu2 lysA1 ade1 lac4-8 [pKD1] pdc1::kan, derived from *K. lactis* strain ATCC 200826 (*Kluyveromyces lactis* (Dombrowski) van der Walt, teleomorph) |

TABLE 65-continued

Genotype of Strains Disclosed in Example 21.

| GEVO Number | Genotype |
|---|---|
| 4458 | MATalpha uraA1 trp1 leu2 lysA1 ade1 lac4-8 [pKD1] pdc1::kan tma29::hph |
| 6310, 6311, 6312 | MATalpha uraA1 trp1 leu2 lysA1 ade1 lac4-8 [pKD1] pdc1::kan [pGV1429] |
| 6313, 6314, 6315 | MATalpha uraA1 trp1 leu2 lysA1 ade1 lac4-8 [pKD1] pdc1::kan [pGV1645] |
| 6316, 6317 | MATalpha uraA1 trp1 leu2 lysA1 ade1 lac4-8 [pKD1] pdc1::kan + random integration of Bs_alsS:TRP1 |
| 6318, 6319, 6320 | MATalpha uraA1 trp1 leu2 lysA1 ade1 lac4-8 [pKD1] pdc1::kan tma29::hph [pGV1429] |
| 6321, 6322, 6323 | MATalpha uraA1 trp1 leu2 lysA1 ade1 lac4-8 [pKD1] pdc1::kan tma29::hph [pGV1645] |
| 6324, 6325 | MATalpha uraA1 trp1 leu2 lysA1 ade1 lac4-8 [pKD1] pdc1::kan tma29::hph + random integration of Bs_alsS:TRP1 |

TABLE 66

Plasmids Disclosed in Example 21.

| Plasmid Name | Relevant Genes/Usage | Genotype |
|---|---|---|
| pGV1429 | High copy 1.6 µ empty vector containing TRP1 | 1.6 µ-ori, PMB1 ori, bla, TRP1 |
| pGV1645 | High copy 1.6 µ vector containing TRP1 and Bs_alsS | 1.6 µ-ori, PMB1 ori, bla, TRP1, Bs_alsS |
| pGV1726 (linearized with AhdI) | Vector containing TRP1 and Bs_alsS | PMB1 ori, bla, TRP1, Bs_alsS |

TABLE 67

Oligonucleotide Sequences Disclosed in Example 21.

| Primer | Sequence |
|---|---|
| oGV3065 | AAAAAGGAGTAGAAACATTTTGAAGCTATGCGTTGATAAGGGCAACAACGTTAGTATC (SEQ ID NO: 153) |
| oGV3066 | ATACTAACGTTGTTGCCCTTATCAACGCATAGCTTCAAAATGTTTCTACTCCTTTTTTAC (SEQ ID NO: 154) |
| oGV3067 | TCAAATTTTTCTTTTTTTTCTGTACAGTTACCCAAGCTGTTTTGCCTATTTTCAAAGC (SEQ ID NO: 155) |
| oGV3068 | GCTTTGAAAATAGGCAAAACAGCTTGGGTAACTGTACAGAAAAAAAAGAAAAATTTG (SEQ ID NO: 156) |
| oGV3103 | ACCGGTGCTTCTGCAGGTATTG (SEQ ID NO: 157) |
| oGV3106 | ATGCTTGGTTGGAAGCAAATAC (SEQ ID NO: 158) |
| oGV1321 | AATCATATCGAACACGATGC (SEQ ID NO: 159) |
| oGV1324 | AGCTGGTCTGGTGATTCTAC (SEQ ID NO: 160) |

Strain Construction: The *K. lactis* TMA29 gene homolog encoding the *K. lactis* TMA29 protein (SEQ ID NO: 7) was deleted from parent *K. lactis* strain GEVO1742 as follows, resulting in strain GEVO4458 as described in Example 18.

*K. lactis* strains GEVO1742 (parent, TMA29) and GEVO4458 (tma29Δ) were transformed with plasmid pGV1429 (empty control vector), pGV1645 (expressing Bs_alsS) or with AhdI linearized plasmid pGV1726 (resulting in random integration of Bs_alsS) as described, resuspended in 400 µL of 1.25×SC-HWLU and spread over SCD-W plates to select for transformed cells. Random integration of AhdI linearized pGV1726 in both GEVO1742 and tma29Δ strain GEVO4458 was confirmed by colony PCR with primers oGV1321 and oGV1324 that are specific to the internal Bs_alsS coding region as described. Strains GEVO6316, GEVO6317, GEVO6324, and GEVO6325 were positive for the gene integration.

Fermentation: A shake flask fermentation was performed on the various GEVO strains (Table 65) as described to determine if deletion of TMA29 in strains expressing Bs_alsS would result in diminished production of DH2MB. Single colony isolated transformants were patched to SCD-W plates, non transformed parents were patched onto YPD. Cells from the patches were used to inoculate 3 mL cultures in either YPD (parent strains and integrated strains) or 3 mL SCD-W. Cultures were incubated overnight at 30° C. and 250 rpm. After overnight incubation, the $OD_{600}$ of these cultures was determined by diluting 1:40 in water. The appropriate amount of culture was added to 50 mL of YPD containing 5% glucose or SCD-W containing 5% glucose to obtain an $OD_{600}$ of 0.1 in 250 mL baffled flasks and incubated at 30° C. and 250 rpm. After 24 h incubation, the $OD_{600}$ of these cultures was determined by diluting 1:40 in water. The appropriate amount of culture was added to 50 mL of YPD containing 8% glucose, 200 mM MES pH 6.5 or SCD-W containing 8% glucose to obtain an $OD_{600}$ of 5. When 250 OD's were not available to start the fermentation, the entire 50 mL culture was used. Fermentation cultures were incubated at 30° C. and 75 rpm in unbaffled 250 mL flasks. A 15 mL conical tube was also collected for media blanks for LC1 and LC4 analysis as described and kept at 4° C. until sample submission. At the 72 h timepoint, 1.5 mL of culture was collected. $OD_{600}$ values were determined and samples were prepared for LC1 and LC4 analysis by centrifuging for 10 min at 14,000 rpm and removing 1 mL of the supernatant to be analyzed. In addition samples for enzyme assays were harvested at the 72 h timepoint. 60 OD's of the appropriate sample were transferred into a 15 mL Falcon tube and centrifuged at 3000×g for 5 min at 4° C. Pellets were resuspended in 3 mL cold, sterile water and transferred to 3, 1.5 mL Eppendorf tubes (1 mL each) to make 3×20 OD replicates. The tubes were centrifuged at 5000×g for 2 min at 4° C. in a swinging bucket rotor in the tabletop centrifuge. The water was removed by vacuum aspirator. The Eppendorf tubes were stored at −80° C.

The in vitro ALS enzymatic activities of the lysates were measured as described. Table 68 shows the average in vitro ALS enzymatic activity of lysates from the strains after 72 h. ALS activity was measurable only in strains with Bs_alsS randomly integrated (GEVO6316, GEVO6317, GEVO6324, 6325) or expressed from plasmid (GEVO6313-6315, GEVO6321-6323). ALS activity in strains with Bs_alsS integrated is lower than in strains expressing Bs_alsS from plasmid. However, the activity of 0.25 Units/mg lysate in the TMA29 strains with integrated Bs_alsS (GEVO6316, GEVO6317) was still enough to produce a titer 1.06 g/L of combined DHIV+DH2MB.

Table 68 shows the combined DHIV+DH2MB titers for the various strains after 72 h of fermentation based on LC1 analysis. Strain GEVO1742 (parent, TMA29) strains produced measurable combined DHIV+DH2MB titers only when Bs_alsS was randomly integrated (1.06 g/L) or expressed from plasmid pGV1645 (0.45 g/L). These DHIV+DH2MB titers were abolished in the tma29Δ strain GEVO4458 when expressing Bs_alsS via random integration (GEVO6324, GEVO6325) or plasmid (GEVO6321-6323). LC4 analysis indicated that the majority of the combined DHIV+DH2MB titer was in fact DH2MB.

Example 22

Effect of TMA29 Deletion in *I. orientalis*

The following example illustrates that deletion of the *I. orientalis* TMA29 gene results in decreased TMA29 activity and also results in decrease in DH2MB production in strains comprising ALS activity.

TABLE 69

Genotype of Strains Disclosed in Example 22.

| GEVO # | Relevant Genotype |
|---|---|
| GEVO4450 | ura3Δ/ura3Δ<br>pdc1-1Δ::Ll_kivD: $T_{ScCYC1}$: loxP: $P_{ENO1}$: Bs_alsS/<br>pdc1-2Δ::Ll_kivD: $T_{ScCYC1}$: loxP: $P_{ENO1}$: Bs_alsS<br>TMA29/TMA29 |
| GEVO12425 | ura3Δ/ura3Δ<br>pdc1-1Δ:: Ll_kivD: $T_{ScCYC1}$: loxP: $P_{ENO1}$:<br>Bs_alsS pdc1-2Δ:: Ll_kivD: loxP<br>TMA29/TMA29 |
| GEVO6155 | ura3Δ/ura3Δ<br>pdc1-1Δ::Ll_kivD: $T_{ScCYC1}$: loxP: $P_{ENO1}$: Bs_alsS<br>pdc1-2Δ::Ll_kivD: loxP<br>TMA29/<br>tma29Δ::$P_{PDC}$:Ll_adhA$^{RE1}$: $P_{TDH3}$: Ec_ilvC$^{P2D1-A1}$: loxP:<br>URA3: loxP: $P_{ENO1}$: Ll_ilvD |
| GEVO6158 | ura3Δ/ura3Δ<br>pdc1-1Δ:: Ll_kivD: $T_{ScCYC1}$: loxP: $P_{ENO1}$: Bs_alsS<br>pdc1-2Δ:: Ll_kivD: loxP<br>tma29Δ:: $P_{PDC}$: Ll_adhA$^{RE1}$: $P_{TDH3}$:<br>Ec_ilvC$^{P2D1-A1}$_coCB:<br>loxP: URA3: loxP: $P_{ENO1}$: Ll_ilvD/<br>tma29Δ:: $P_{PDC}$: Ll_adhA$^{RE1}$:<br>$P_{TDH3}$:Ec_ilvC$^{P2D1-A1}$: loxP: URA3: loxP:<br>$P_{ENO1}$: Ll_ilvD |
| GEVO12473 | ura3Δ/ura3Δ<br>pdc1-1Δ:: Ll_kivD: $T_{ScCYC1}$: loxP: $P_{ENO1}$: Bs_alsS<br>pdc1-2Δ:: Ll_kivD: loxP<br>tma29Δ:: loxP: URA3: loxP/<br>tma29Δ::loxP: MEL5: loxP |
| GEVO12474 | ura3Δ/ura3Δ<br>pdc1-1Δ:: Ll_kivD: $T_{ScCYC1}$: loxP: $P_{ENO1}$: Bs_alsS<br>pdc1-2Δ:: Ll_kivD: loxP<br>tma29Δ:: loxP: URA3: loxP/<br>tma29Δ:: loxP: MEL5: loxP |

Strain Construction: Issatchenkia orientalis strains derived from PTA-6658 were constructed that were wild-type for the TMA29 gene (GEVO4450, GEVO12425), heterozygous for deletion of one copy of the TMA29 gene (GEVO6155), or completely deleted for the TMA29 gene (GEVO6158,

TABLE 68

ALS Activity, Combined DHIV + DH2MB Titer, and Percentage of DH2MB of Combined DHIV + DH2MB Titer.

| Strain | Parent Strain | Plasmid Integrated (I), plasmid (P), or control (C) | TMA29 | ALS | ALS Activity (U/mg lysate) | DHIV + DH2MB by LC1 (g/L) | % DH2MB in DH2MB + DHIV by LC4 |
|---|---|---|---|---|---|---|---|
| GEVO1742 | | none | + | − | 0.00 ± 0.00 | 0.00 ± 0.00 | n/a |
| GEVO6316, 6317 | GEVO1742 | pGV1726 (I) | + | + | 0.25 ± 0.06 | 1.06 ± 0.23 | 80.0 ± 3.7 |
| GEVO4458 | GEVO1742 | none | Δ | − | 0.00 ± 0.00 | 0.00 ± 0.00 | n/a |
| GEVO6324, 6325 | GEVO4458 | pGV1726 (I) | Δ | + | 0.86 ± 0.28 | 0.00 ± 0.00 | n/a |
| GEVO6310-6312 | GEVO1742 | pGV1429 (C) | + | − | 0.00 ± 0.00 | 0.00 ± 0.00 | n/a |
| GEVO6313-6315 | GEVO1742 | pGV1645 (P) | + | + | 6.12 ± 1.09 | 0.45 ± 0.02 | 87.2 ± 2.3 |
| GEVO6318-6320 | GEVO4458 | pGV1429 (C) | Δ | − | 0.00 ± 0.00 | 0.00 ± 0.00 | n/a |
| GEVO6321-6323 | GEVO4458 | pGV1645 (P) | Δ | + | 1.23 ± 0.45 | 0.00 ± 0.00 | n/a | n/a = not applicable, samples had no detectable peak by LC1 so were not analyzed by LC4

GEVO12473, GEVO12474) using standard yeast genetics and molecular biology methods. These strains also carry a copy of the Bacillus subtilis alsS gene.

TMA29 Enzyme Assay: For the TMA29 in vitro assay, *I. orientalis* strains GEVO4450 (TMA29/TMA29), GEVO6155 (tma29Δ/TMA29), and GEVO6158 (complete tma29Δ/tma29Δ) were grown by inoculating 25 mL YPD in 125 mL baffled flasks with cells from a fresh YPD plate. Cultures were grown overnight at 30° C. and 250 rpm. These cultures were used to inoculate 50 mL of YPD in 250 mL baffled flasks to an $OD_{600}$ of 0.05. The cultures were grown at 30° C. and 250 rpm until they had reached an $OD_{600}$ of approximately 5-8 (late log phase). Cells were harvested by collecting 80 ODs of cells in a 50 mL Falcon tube and centrifuging at 2,700×g for 3 min. After removal of supernatant, cells were placed on ice and washed with 5 mL cold water. Cells were centrifuged at 2,700×g for 3 min and the water was removed. The cell pellets were stored at −80° C. until use. Additionally, the same strains were grown by inoculating 3 mL of YPD from fresh plates and growing for 8 h at 30° C. and 250 rpm. These cultures were used to inoculate 50 mL of YPD in 250 mL baffled flasks to an $OD_{600}$ of 0.01 and the cultures were grown at 30° C. and 250 rpm until they reached an $OD_{600}$ of approximately 4-8. This culture was used to inoculate 50 mL of YPD containing 8% glucose, 200 mM MES pH 6.5 to a final $OD_{600}$ of 4-5 by centrifuging an appropriate amount of culture at 2,700×g for 3 min in a 50 mL Falcon tube and then resuspending the cell pellet in 50 mL of the stated medium. Cells were incubated in 250 mL non-baffled flasks at 30° C. and 75 rpm for 48 h (fermentation phase). Eighty OD cell pellets were harvested as described. Cells were resuspended, lysed and assayed for TMA29 activity as described.

Table 70 shows the specific TMA29 activity of lysates of *I. orientalis* strains GEVO4450, 6155, and 6158 in U/mg of total protein. Specific TMA29 activity is reduced in GEVO6155 (tma29/TMA29) and GEVO6158 (complete tma29 deletion) as compared to GEVO4450 (TMA29/TMA29).

TABLE 70

TMA29 Activity in *I. orientalis* Strains.

| STRAIN | TMA29 activity Late log phase [U/mg total protein] | TMA29 activity 48 h fermentation phase [U/mg total protein] |
|---|---|---|
| GEVO4450 | 0.0048 ± .0010 | .0027 ± .0003 |
| GEVO6155 | 0.0025 ± .0008 | .0010 ± .0001 |
| GEVO6158 | 0.0023 ± .0003 | .0010 ± .0003 |

Fermentation: For the fermentation, *I. orientalis* strains GEVO12425 (TMA29/TMA29), GEVO12473 (tma29/tma29), and GEVO12474 (tma29/tma29) were grown by inoculating 12 mL YPD in 125 mL baffled flasks with cells from a fresh YPD plate. Cultures were grown overnight at 30° C. and 250 rpm. The $OD_{600}$ of the 12 mL overnight cultures were determined and the appropriate amount was used to inoculate 50 mL YPD containing 5% glucose in 250 mL baffled flasks to an $OD_{600}$ of 0.1. The flasks were incubated at 30° C. and 250 rpm overnight. The $OD_{600}$ of the 50 mL cultures was determined. The appropriate amount of culture was centrifuged at 2700 rcf for 5 min at 25° C. in 50 mL Falcon tubes and the supernatant removed. The cells from each 50 mL culture were resuspended in 50 mL YPD containing 8% glucose, 200 mM MES, pH 6.5. The cultures were then transferred to 250 mL unbaffled screw-cap flasks and incubated at 30° C. and 75 rpm. At 72 h samples from each flask were removed, the $OD_{600}$ was measured and samples prepared for LC4 analysis by transferring 1 mL sample to an Eppendorf tube and centrifuging at 18,000×g, 10 seconds, 25° C. After centrifugation, 0.75 mL of supernatant was transferred to a microtiter plate and analyzed by LC4. Also at 72 h cells for enzyme assays were collected by transferring 80 ODs to 15 mL Falcon tubes as described. Cells for ALS assays were resuspended, lysed, and assayed as described.

Table 71 shows the DH2MB production and ALS activities for GEVO12425, 12473, and 12474 at 72 h. The DH2MB titer was determined by LC4. The ALS activity was similar in all strains.

TABLE 71

DH2MB Production and ALS Activity in *I. orientalis* Strains at 72 h Fermentation.

| STRAIN | DH2MB by LC4 [g/L] | ALS activity [U/mg] |
|---|---|---|
| GEVO12425 | 1.87 ± 0.60 | 4.6 ± 1.1 |
| GEVO12473 | 0.08 ± 0.01 | 4.0 ± 0.1 |
| GEVO12474 | 0.07 ± 0.00 | 3.1 ± 1.1 |

Example 23

Effect of TMA29 deletion in *S. pombe*

The following example illustrates that the (S)-2-acetolactate reduction activity is significantly decreased in an *S. pombe* tma29Δ strain compared to an *S. pombe* TMA29 strain.

TABLE 72

Genotype of strains disclosed in Example 23.

| GEVO # | Genotype | Source |
|---|---|---|
| GEVO6444 | h+ ade6-M216, ura4-D18, leu1-32 | Bioneer strain BG_0000H8 |
| GEVO6445 | h+ SPAC521.03Δ::kanMX4, ade6-M216, ura4-D18, leu1-32 TMA29 homolog (SEQ ID NO: 22) deleted | Bioneer strain BG_1772H |

Yeast strains GEVO6444 which has an intact TMA29 gene (SEQ ID NO: 161) and GEVO6445 which has the TMA29 gene deleted, were grown overnight in 12 mL YPD in 125 mL baffled flasks at 250 rpm and 30° C. The next day, $OD_{600}$ values were determined and technical triplicate cultures were started in 50 mL YPD with 5% glucose at an $OD_{600}$ of approximately 0.3. Cultures were allowed to grow at 250 rpm and 30° C. throughout the day. At the end of the day, the cultures were diluted in YPD with 5% glucose to an $OD_{600}$ of approximately 0.15 and incubated overnight at 250 rpm and 30° C. The cells were harvested upon reaching an $OD_{600}$ of between 4 and 6. To harvest pellets for enzyme assays 80 ODs of the appropriate sample were transferred into two 15 mL Falcon tube (for duplicate samples) and centrifuged at 3000×g for 5 min at 4° C. Pellets were resuspended in 3 mL cold, sterile water and were centrifuged at 5000×g for 2 min at 4° C. in a swinging bucket rotor in the tabletop centrifuge. The water was removed by vacuum aspirator. The pellets were stored at −80° C. Lysates were prepared and TMA29 enzyme assays were performed as described.

The specific activity of S. pombe GEVO6444 lysates for the reduction of (S)-2-acetolactate was 0.018±0.002 U/mg total protein. Lysates of the tma29Δ strain GEVO6445 had a specific activity of 0.001±0.002 U/mg total protein.

Example 24

Effect of ALD6 Deletion in K. marxianus

The purpose of this example is to demonstrate that the deletion of ALD6 in a *Kluyveromyces marxianus* strain results in reduced isobutyraldehyde oxidation activity and isobutyrate production.

Strains, plasmids, and oligonucleotide primers disclosed in this example are listed in Tables 73, 74, and 75, respectively

TABLE 73

Genotype of *K. marxianus* Strains Disclosed in Example 24.

| GEVO Number | Genotype |
|---|---|
| GEVO1947 | ura3-delta2 |
| GEVO6264, GEVO6265 | ura3-delta2 ald6Δ::$P_{TEF1}$-hph |
| GEVO2087 | ura3-delta2, PDC1, $P_{Sc\_PDC1}$:31COX4 MTS:alsS:$P_{Sc\_TDH3}$:kivD co HMI1 MTS:$P_{Sc\_ADH1}$:ADH7:$P_{Sc\_FBA1}$:URA3 |
| GEVO6270 | ura3-delta2, PDC1, $P_{Sc\_PDC1}$:31COX4 MTS:alsS:$P_{Sc\_TDH3}$:kivD co HMI1 |

TABLE 73-continued

Genotype of *K. marxianus* Strains Disclosed in Example 24.

| GEVO Number | Genotype |
|---|---|
| GEVO6271 | MTS:$P_{Sc\_ADH1}$:ADH7:$P_{Sc\_FBA1}$:URA3 ald6Δ:: $P_{TEF1}$-hph |

TABLE 74

Plasmids Disclosed in Example 24.

| Plasmid Name | Relevant Genes/Usage | Genotype |
|---|---|---|
| pGV2701 | For SOE PCR to give the hph fragment | $P_{TEF1}$:hph, CEN, pUC ori, bla |

TABLE 75

Oligonucleotide Sequences Disclosed in Example 24.

| Primer | Sequence |
|---|---|
| oGV3490 | GTCAAGATTGTTGAACAAAAGCC (SEQ ID NO: 162) |
| oGV3492 | GAGTAAAAAAGGAGTAGAAACATTTTGAAGCTATGGTTTAGTGGGGTTGGGGAAGCTGGC (SEQ ID NO: 163) |
| oGV3493 | CAAATTTTTCTTTTTTTTCTGTACAGGCCAACATCAAGAAGACTATTCCAAACTTGGTC (SEQ ID NO: 164) |
| oGV3495 | TGTATGATTCGAAAGCTTCTTCACC (SEQ ID NO: 165) |
| oGV3491 | GCCAGCTTCCCCAACCCCACTAAACCATAGCTTCAAAATGTTTCTACTCCTTTTTTACTC (SEQ ID NO: 166) |
| oGV3494 | GACCAAGTTTGGAATAGTCTTCTTGATGTTGGCCTGTACAGAAAAAAAAGAAAAATTTG (SEQ ID NO: 167) |
| oGV3497 | TTACTCGAGCTTGATTCTGAC (SEQ ID NO: 168) |
| oGV2320 | GGCTGTGTAGAAGTACTCGCCGATAG (SEQ ID NO: 169) |
| oGV3496 | ATGTCTTCATCACTAGCAGAG (SEQ ID NO: 170) |
| oGV0821 | CGGGTAATTAACGACACCCTAGAGG (SEQ ID NO: 171) |
| oGV0706 | GGTTGGTATTCCAGCTGGTGTCG (SEQ ID NO: 172) |

Strain Construction: The *K. marxianus* ALD6 gene homolog encoding the *K. marxianus* ALD6 protein (SEQ ID NO: 39) was deleted from parent *K. marxianus* strains GEVO1947 and GEVO2087 as follows, resulting in strains GEVO6264/GEVO6265, and GEVO6270/GEVO6271 respectively.

Genomic DNA was isolated from GEVO1947 as described. Constructs were made to integrate the *E. coli* hph (hygromycin resistance) cassette into the ALD6 locus of GEVO1947 and GEVO2087 by SOE PCR as described. PCR step #1 consisted of three reactions: the 5' ALD6 targeting sequence, the 3' ALD6 targeting sequence, and the hph marker. The 5' targeting sequence was amplified from prepared GEVO1947 genomic DNA with primers oGV3490 and oGV3492. The 635 bp fragment was purified by gel electrophoresis. The 3' targeting sequence was amplified from prepared GEVO1947 genomic DNA with primers oGV3493 and oGV3495. The 645 bp fragment was gel purified. The $P_{TEF1}$:hph:$T_{CYC1(partial)}$ cassette was amplified from pGV2701 with primers oGV3491 and oGV3494. The 1,665 bp fragment was gel purified. The final SOE PCR step joined the 3 products from step #1 (5' ALD6 targeting sequence/hph/marker/3' ALD6 targeting sequence). The reaction was amplified using primers oGV3490 and oGV3495. The 2,826 bp fragment was gel purified and used for transformations of GEVO1947 and GEVO2087 as described. Medium used to grow cells for the transformation was YPD. Following the transformation, 150 μL of each transformation culture was spread onto YPD plates supplemented with 0.2 g/L hygromycin. The plates were incubated at 30° C. Transformed colonies were patched for initial colony PCR screening, then single colony isolated and repatched on YPD plates supplemented with 0.2 g/L hygromycin.

Yeast Colony PCR was used to screen for the appropriate 3' integration junction, 5' integration junction, as well as lack of the ALD6 coding region as described. The proper 3' integration junction was confirmed using primers oGV3497 and oGV2320. The proper 5' integration junction was confirmed using primers oGV3496 and oGV0821. Finally, deletion of the ALD6 internal coding region was confirmed using primers oGV3495 and oGV0706.

Fermentation: A shake flask fermentation with 2 g/L isobutyraldehyde was performed as described using technical triplicates of the ald6Δ strains GEVO6264/GEVO6265 and GEVO6270/GEVO6271 and their corresponding ALD6 parent strains GEVO1947 and GEVO2087.

Single colony isolated transformants of confirmed ald6Δ strains were patched to YPD plates supplemented with 0.2 g/L hygromycin plates and parents were patched to YPD plates. Cells from the patches were used to inoculate technical triplicate 3 mL cultures of YPD. Cultures were incubated overnight at 30° C. and 250 rpm. After overnight incubation, the $OD_{600}$ of these cultures was determined by diluting 1:40 in water. The appropriate amount of culture was added to 50 mL of YPD with 5% glucose to obtain an $OD_{600}$ of 0.1 in 250 mL baffled flasks and cultures were incubated at 30° C. and 250 rpm. After 24 h incubation, the $OD_{600}$ of these cultures was determined by diluting 1:40 in water. The appropriate amount of culture was added to 50 mL of YPD containing 8% glucose, 200 mM MES pH 6.5, and 2 g/L isobutyraldehyde to obtain an $OD_{600}$ of 5. Fermentation cultures were incubated at 30° C. and 75 rpm in unbaffled 250 mL flasks. Unused media was collected as a media blank for LC analysis and kept at 4° C. until sample submission. At 48 h, samples from each of the flasks were taken as follows. 1.5 mL of culture was removed into 1.5 mL Eppendorf tubes. $OD_{600}$ values were determined and samples were prepared for LC1 analysis. Each tube was centrifuged for 10 min at 14,000 rpm and the supernatant was analyzed by LC1. In addition samples for enzyme assays were harvested after 48 h. 80 ODs of the appropriate sample were transferred into two 15 mL Falcon tube (for duplicate samples) and centrifuged at 3000×g for 5 min at 4° C. Pellets were resuspended in 3 mL cold, sterile water and were centrifuged at 5000×g for 2 min at 4° C. in a swinging bucket rotor. The water was removed by vacuum aspirator. The conical tubes were stored at −80° C.

Table 76 shows the isobutyrate titer after 48 h of fermentation. The ALD6 parent strain GEVO1947 produced average total and specific isobutyrate titers of 0.19 g/L and 0.013 g/L/OD, respectively. These total and specific isobutyrate titers were significantly decreased in the ald6Δ strain GEVO6264 (0.06 g/L and 0.004 g/L/OD respectively), and also in the ald6Δ strain GEVO6265 (0.05 g/L and 0.003 g/L/OD respectively). The ALD6 parent strain GEVO2087 produced total and specific isobutyrate titers of 0.15 g/L and 0.008 g/L/OD, respectively. The total and specific isobutyrate titers were significantly decreased in the ald6Δ strain GEVO6270 (0.05 g/L and 0.003 g/L/OD), and also in the ald6Δ strain GEVO6271 (0.08 g/L and 0.005 g/L/OD, respectively).

TABLE 76

Isobutyrate Production of ALD6 Parent Strains and ald6Δ Strains Derived From Said ALD6 Parent Strains.

| Strain | Parent Strain | ALD6 | Isobutyraldehyde Feed Fermentation (48 hr) | |
|---|---|---|---|---|
| | | | Isobutyrate Titer (g/L) | Isobutyrate Decrease (%) |
| GEVO1947 | | + | 0.19 ± 0.05 | |
| GEVO6264 | GEVO1947 | − | 0.06 ± 0.02 | 68% |
| GEVO6265 | GEVO1947 | − | 0.05 ± 0.02 | 74% |
| GEVO2087 | | + | 0.15 ± 0.03 | |
| GEVO6270 | GEVO2087 | − | 0.05 ± 0.03 | 67% |
| GEVO6271 | GEVO2087 | − | 0.08 ± 0.02 | 47% |

Example 25

Effect of ALD6 Deletion in *K. lactis*

The purpose of this example is to demonstrate that the deletion of ALD6 in a *Kluyveromyces lactis* strain results in reduced isobutyraldehyde oxidation activity and isobutyrate production.

Strains, plasmids, and oligonucleotide primers disclosed in this example are listed in Tables 77, 78, and 79, respectively.

TABLE 77

Genotype of *K. lactis* Strains Disclosed in Example 25.

| GEVO Number | Genotype |
|---|---|
| GEVO1287 | MATα uraA1 trp1 leu2 lysA1 ade1 lac4-8 [pKD1], *Kluyveromyces lactis* (Dombrowski) van der Walt, teleomorph, ATCC 200826 |
| GEVO6242 | MATα uraA1 trp1 leu2 lysA1 ade1 lac4-8 [pKD1] ald6Δ::$P_{TEF1}$-hph |
| GEVO1830 | MATα uraA1 trp1 leu2 lysA1 ade1 lac4-8 [pKD1] pdc1::kan:Ec_ilvC_ΔN:Ec_ilvDΔN_coKl::Sc_LEU2 integrated}{Ll_kivD; Sc_Adh7:Km_URA3 randomly integrated} {$P_{Sc\_CUP1-1}$:Bs_alsS:TRP1 random integrated} |
| GEVO6244, GEVO6245 | MATα uraA1 trp1 leu2 lysA1 ade1 lac4-8 [pKD1] pdc1::kan:Ec_ilvC_ΔN:Ec_ilvDΔN_coKl::Sc_LEU2 integrated} {Ll_kivD; Sc_Adh7:Km_URA3 integrated} {$P_{Sc\_CUP1-1}$:Bs_alsS:TRP1 random integrated} ald6Δ::$P_{TEF1}$-hph |

TABLE 78

Plasmid Disclosed in Example 25.

| Plasmid Name | Genotype |
|---|---|
| pGV2701 | $P_{TEF1}$:hph, CEN, pUC ori, bla |

TABLE 79

Oligonucleotide Sequences Disclosed in Example 25.

| Primer | Sequence |
|---|---|
| oGV3502 | GAAACACAGTGGATTAGTGCTGTC (SEQ ID NO: 173) |
| oGV3504 | GAAGAGTAAAAAAGGAGTAGAAACATTTTGAAGCTATGCTCTTTGTAATTGTTGTTGGTG (SEQ ID NO: 174) |
| oGV3505 | CAAATTTTTCTTTTTTTTCTGTACAAACAGAGTCCATCCGTTTGAAACTGATTGCATGTC (SEQ ID NO: 175) |
| oGV3507 | TCAAATTCTATTATCGCGCGGG (SEQ ID NO: 176) |
| oGV3503 | CACCAACAACAATTACAAAGAGCATAGCTTCAAAATGTTTCTACTCCTTTTTTACTCTTC (SEQ ID NO: 177) |
| oGV3506 | GACATGCAATCAGTTTCAAACGGATGGACTCTGTTTGTACAGAAAAAAAAGAAAAATTTG (SEQ ID NO: 178) |
| oGV3509 | CTCCTCCGTTGCAGAACAAGGCTTTG (SEQ ID NO: 179) |
| oGV2320 | GGCTGTGTAGAAGTACTCGCCGATAG (SEQ ID NO: 180) |
| oGV3508 | CGGTGTTAAGTGCCAGAAATTGGTTG (SEQ ID NO: 181) |
| oGV0821 | CGGGTAATTAACGACACCCTAGAGG (SEQ ID NO: 182) |
| oGV3510 | CGGCGTACTCGACGTCTTGAGAAGTAG (SEQ ID NO: 183) |

Strain Construction: The *K. lactis* ALD6 gene homolog encoding the *K. lactis* ALD6 protein (SEQ ID NO: 29) was deleted from parent *K. lactis* strains GEVO1287 and GEVO1830 as follows, resulting in strains GEVO6242 and GEVO6244/GEVO6245, respectively.

Genomic DNA was isolated from GEVO1287 as described. Constructs were made to integrate the *E. coli* hph (hygromycin resistance) cassette into the ALD6 locus of GEVO1287 and GEVO1830 by SOE PCR as described. PCR step #1 consisted of three reactions: the 5' ALD6 targeting sequence, the 3' ALD6 targeting sequence, and the hph marker. The 5' targeting sequence was amplified from prepared GEVO1287 genomic DNA with primers oGV3502 and oGV3504. The 639 bp fragment was purified by gel electrophoresis. The 3' targeting sequence was amplified from prepared GEVO1287 genomic DNA with primers oGV3505 and oGV3507. The 628 bp fragment was gel purified. The $P_{TEF1}$:hph:$T_{CYC1(partial)}$ cassette was amplified from pGV2701 with primers oGV3503 and oGV3506. The 1,663 bp fragment was gel purified. The final SOE PCR step joined the 3 products from step #1 (5' targeting sequence/hph marker/3' targeting sequence). The reaction was amplified using primers oGV3502 and oGV3507. The 2,810 bp fragment was gel purified and used for transformations of GEVO1287 and GEVO1830 as described. Colonies were selected for hygromycin resistance on YPD plates supplemented with 0.1 g/L hygromycin. Yeast Colony PCR was used to screen for the appropriate 3' integration junction, 5' integration junction, as well as lack of the ALD6 coding region as described. The proper 3' integration junction was confirmed using primers oGV3509 and oGV2320. The proper 5' integration junction was confirmed using primers oGV3508 and oGV0821. Finally, deletion of the ALD6 internal coding region was confirmed using primers oGV3508 and oGV3510.

Fermentation: A first shake flask fermentation with 2 g/L isobutyraldehyde in the medium was performed using technical triplicates of the ald6Δ strain GEVO6242 and the ALD6 wild-type parent strain GEVO1287. Single colony isolated transformants of confirmed ald6Δ deletion strains were patched to YPD plates supplemented with 0.1 g/L hygromycin plates, parent strains were patched onto YPD. Cells from the patches were used to inoculate technical triplicate 3 mL cultures of YPD. Cultures were incubated overnight at 30° C. and 250 rpm. After overnight incubation, the $OD_{600}$ of these cultures was determined by diluting 1:40 in water. The appropriate amount of culture was added to 50 mL of YPD with 5% glucose to obtain an $OD_{600}$ of 0.1 in 250 mL baffled flasks and cultures were incubated at 30° C. and 250 rpm. After 24 h incubation, the $OD_{600}$ of these cultures was determined by diluting 1:40 in water. The appropriate amount of culture was added to 50 mL of YPD containing 8% glucose, 200 mM MES pH 6.5, and 2 g/L isobutyraldehyde to obtain an $OD_{600}$ of 5. Fermentation cultures were incubated at 30° C. and 75 rpm in unbaffled 250 mL flasks. Unused media was collected as a media blank for LC1 analysis and kept at 4° C. until sample submission. At 24 h, samples from each of the flasks were taken as follows. 1.5 mL of culture was removed into 1.5 mL Eppendorf tubes. $OD_{600}$ values were determined and samples were prepared for LC1 analysis as described. Each tube was centrifuged for 10 min at 14,000 rpm and the supernatant was collected for analysis by LC1 as described.

A second shake flask fermentation with 2 g/L isobutyraldehyde was performed as described using the ald6Δ deletion strains GEVO6244/GEVO6245 and their corresponding ALD6 parent strain GEVO1830. This fermentation was sampled at 24 and 48 h as described. Table 80 shows the isobutyrate titer for both of these fermentations. Isobutyrate titers are significantly decreased in the ald6Δ strains compared to the ALD6 parent strains.

TABLE 80

Isobutyrate Production of ALD6 Parent Strains and ald6Δ Strains Derived From Said ALD6 Parent Strains.

| Strain | Isobutyraldehyde Feed Fermentation (24 hr) | | Isobutyraldehyde Feed Fermentation (48 hr) | |
|---|---|---|---|---|
| | Isobutyrate Titer (g/L) | Isobutyrate Decrease (%) | Isobutyrate Titer (g/L) | Isobutyrate Decrease (%) |
| GEVO1287 | 0.19 ± 0.03 | | n.d. | n.d. |
| GEVO6242 | 0.12 ± 0.02 | 36.8% | n.d. | n.d. |
| GEVO1830 | 0.16 ± 0.00 | | 0.12 ± 0.01 | |
| GEVO6244 | 0.06 ± 0.02 | 62.5% | 0.04 ± 0.01 | 66.7 |
| GEVO6245 | 0.07 ± 0.00 | 56.3% | 0.00 ± 0.00 | ≥79.2* | n.d. = not determined in this experiment
*based on LOQ for isobutyrate of 0.025 g/L Example 26

TMA29 Activity Towards 2-aceto-2-hydroxybutyrate

The following example illustrates that the *S. cerevisiae* TMA29 protein is active towards (S)-2-acetolactate ((S)-AL) and 2-aceto-2-hydroxybutyrate (AHB).

TABLE 81

Genotype of Strains Disclosed in Example 26.

| GEVO # | Genotype | Source |
|---|---|---|
| GEVO3527 | MATα his3Δ-1 leu2Δ lys2Δ ura3Δ | ATCC# 201389 (BY4742) |
| GEVO3939 | MATα his3Δ-1 leu2Δ lys2Δ ura3Δ tma29::kan$^R$ | OpenBiosystems cat# YSC1054 (Yeast MATalpha collection) |

Yeast strains GEVO3939 from which the TMA29 (YMR226C) gene was deleted and its parent GEVO3527 were each cultured in triplicate by inoculating 3 mL of YPD in a 14 mL culture tube in triplicate for each strain. Cultures were started from patches on YPD agar plate for GEVO3527 and on YPD plates containing 0.2 g/L G418 for GEVO3939. The cultures were incubated overnight at 30° C. and 250 rpm. The next day, the $OD_{600}$ of the overnight cultures were measured and the volume of each culture to inoculate a 50 mL culture to an $OD_{600}$ of 0.1 was calculated. The calculated volume of each culture was used to inoculate 50 mL of YPD in a 250 mL baffled flask and the cultures were incubated at 30° C. and 250 rpm.

The cells were harvested during mid-log phase at ODs of 2.2-2.7 after 8 h of growth. The cultures were transferred to pre-weighed 50 mL Falcon tubes and cells were collected by centrifugation for 5 minutes at 3000×g. After removal of the medium, cells were washed with 10 mL MilliQ $H_2O$. After removal of the water, the cells were centrifuged again at 3000×g for 5 minutes and the remaining water was carefully removed using a 1 mL pipette tip. The cell pellets were weighed and then stored at −80° C. until further use.

Cell pellets were thawed on ice and resuspended in lysis buffer (10 mM sodium phosphate pH7.0, 1 mM dithiothreitol, 5% w/v glycerol) such that the result was a 20% cell suspension by mass. One mL of glass beads (0.5 mm diameter) was added to a 1.5 mL Eppendorf tube for each sample and 850 μL of cell suspension were added. Yeast cells were lysed using a Retsch MM301 mixer mill (Retsch Inc. Newtown, Pa.), mixing 6×1 min each at full speed with 1 min incubation on ice between. The tubes were centrifuged for 10 min at 21,500×g at 4° C. and the supernatant was transferred to a fresh tube. Extracts were held on ice until they were assayed using the TMA29 assay as described to determine TMA29 activity towards (R/S)-AHB and (R/S)-AL.

The specific activity of *S. cerevisiae* TMA29 in GEVO3527 lysates, a wild-type MATa *S. cerevisiae* strain, for the reduction of (R/S)-AHB was 10.5±0.6 mU/mg. The tma29Δ strain GEVO3939 had a specific activity of 4.8±0.1 mU/mg. The wild-type GEVO3527 strain had about a 2-fold higher specific TMA29 activity than the deletion strain.

The specific activity of *S. cerevisiae* TMA29 in GEVO3527 lysates, a wild-type MATa *S. cerevisiae* strain, for the reduction of (R/S)-AL was 12.3±0.2 mU/mg. The tma29Δ strain GEVO3939 had a specific activity of 2.9±0.3 mU/mg. The wild-type GEVO3527 strain had about a 4-fold higher specific TMA29 activity than the deletion strain.

General Methods for Examples 27-30

Strains, plasmids, gene/amino acid sequences, and primer sequences described in Examples 27-30 are listed in Tables 82, 83, 84, and 85, respectively.

TABLE 82

Genotype of Strains Disclosed in Examples 27-30.
Genotype or reference

*E. coli* BL21(DE3) (Lucigen Corporation, Middleton, WI)
*E. coli* DH5α (Novagen, Gibbstown, NJ)
*S. cerevisiae* CEN.PK2 (Euroscarf, Frankfurt, Germany)

TABLE 83

Plasmids Disclosed in Examples 27-30.

| Gevo No. | Genotype or reference |
|---|---|
| pET22(b)+ | Novagen, Gibbstown, NJ |
| pGV1102 | $P_{Sc\_TEF1}$-HA-tag-MCS-$T_{CYC1}$, URA3, 2-micron, bla, pUC-ori |
| pGV1662 | $P_{Sc\_TEF1}$-*L. lactis* kivD-$T_{Sc\_CYC1}$, bla, ColE1 ori, URA3, 2μ ori. |
| pGV1947 | $P_{Sc\_TEF1}$-Ll_adhA-$T_{Sc\_CYC1}$ bla URA3 pMB1 ori 2μ ori |
| pGV1947his | $P_{Sc\_TEF1}$-Ll_adhA$^{his6}$-$T_{Sc\_CYC1}$ bla URA3 pMB1 ori 2μ ori |
| pET1947 | $P_{T7}$::Ll_adhA$^{his6}$, bla, oripBR322, lacI |

TABLE 83-continued

Plasmids Disclosed in Examples 27-30.

| Gevo No. | Genotype or reference |
| --- | --- |
| pGV2274 | Cloning vector containing Ll_adhA_coSc sequence (synthesized by DNA2.0, Menlo Park, CA) |
| pGV2475 | $P_{Sc\_TEF1}$-Ll_adhA_coSc$^{28E7\text{-}his6}$-$T_{Sc\_CYC1}$, bla, URA3, pMB1 ori, 2µ ori |
| pGV2476 | $P_{Sc\_TEF1}$-Ll_adhA_coSc$^{his6}$-$T_{Sc\_CYC1}$, bla, URA3, pMB1 ori, 2µ ori |
| pGV2477 | $P_{Sc\_TEF1}$-Ll_adhA_coSc$^{RE1\text{-}his6}$-$T_{Sc\_CYC1}$, bla, URA3, pMB1 ori, 2µ ori |
| pGV30C11 | $P_{Sc\_TEF1}$-Ll_adhA_coSc$^{30C11\text{-}his6}$-$T_{Sc\_CYC1}$, bla, URA3, pMB1 ori, 2µ ori |

TABLE 84

Nucleic Acid and Protein Sequences Disclosed in Examples 27-30.

| Source | Gene (SEQ ID NO) | Protein (SEQ ID NO) |
| --- | --- | --- |
| L. lactis | Ll_adhA (SEQ ID NO: 184) | Ll_AdhA (SEQ ID NO: 185) |
| L. lactis | Ll_adhA_coSc$^{his6}$ (SEQ ID NO: 186) | Ll_AdhA$^{his6}$ (SEQ ID NO: 187) |
| L. lactis | Ll_adhA_coSc$^{28E7\text{-}his6}$ (SEQ ID NO: 188) | Ll_AdhA$^{28E7\text{-}his6}$ (SEQ ID NO: 189) |
| L. lactis | Ll_adhA_coSc$^{30C11\text{-}his6}$ (SEQ ID NO: 190) | Ll_AdhA$^{30C11\text{-}his6}$ (SEQ ID NO: 191) |
| L. lactis | Ll_adhA_coSc$^{RE1\text{-}his6}$ (SEQ ID NO: 192) | Ll_AdhA$^{RE1\text{-}his6}$ (SEQ ID NO: 193) |
| L. lactis | Ll_adhA_coSc$^{7A4\text{-}his6}$ (SEQ ID NO: 194) | Ll_AdhA$^{7A4\text{-}his6}$ (SEQ ID NO: 195) |
| L. lactis | Ll_adhA_coSc$^{4A3\text{-}his6}$ (SEQ ID NO: 196) | Ll_AdhA$^{4A3\text{-}his6}$ (SEQ ID NO: 197) |
| L. lactis | Ll_adhA$^{1H7\text{-}his6}$ (SEQ ID NO: 198) | Ll_AdhA$^{1H7\text{-}his6}$ (SEQ ID NO: 199) |
| L. lactis | Ll_adhA$^{10F10\text{-}his6}$ (SEQ ID NO: 200) | Ll_AdhA$^{10F10\text{-}his6}$ (SEQ ID NO: 201) |
| L. lactis | Ll_adhA$^{8F11\text{-}his6}$ (SEQ ID NO: 202) | Ll_AdhA$^{8F11\text{-}his6}$ (SEQ ID NO: 203) |
| L. lactis | Ll_adhA$^{8D10\text{-}his6}$ (SEQ ID NO: 204) | Ll_AdhA$^{8D10\text{-}his6}$ (SEQ ID NO: 205) |
| L. lactis | Ll_adhA_coSc (SEQ ID NO: 206) | Ll_AdhA (SEQ ID NO: 185) |
| L. lactis | Ll_adhA_coSc$^{28E7}$ (SEQ ID NO: 207) | Ll_AdhA$^{28E7}$ (SEQ ID NO: 208) |
| L. lactis | Ll_adhA_coSc$^{30C11}$ (SEQ ID NO: 209) | Ll_AdhA$^{30C11}$ (SEQ ID NO: 210) |
| L. lactis | Ll_adhA_coSc$^{RE1}$ (SEQ ID NO: 211) | Ll_AdhA$^{RE1}$ (SEQ ID NO: 212) |
| L. lactis | Ll_adhA_coSc$^{7A4}$ (SEQ ID NO: 213) | Ll_AdhA$^{7A4}$ (SEQ ID NO: 214) |
| L. lactis | Ll_adhA_coSc$^{4A3}$ (SEQ ID NO: 215) | Ll_AdhA$^{4A3}$ (SEQ ID NO: 216) |
| L. lactis | Ll_adhA$^{1H7}$ (SEQ ID NO: 217) | Ll_AdhA$^{1H7}$ (SEQ ID NO: 218) |
| L. lactis | Ll_adhA$^{10F10}$ (SEQ ID NO: 219) | Ll_AdhA$^{10F10}$ (SEQ ID NO: 220) |
| L. lactis | Ll_adhA$^{8F11}$ (SEQ ID NO: 221) | Ll_AdhA$^{8F11}$ (SEQ ID NO: 222) |
| L. lactis | Ll_adhA$^{8D10}$ (SEQ ID NO: 223) | Ll_AdhA$^{8D10}$ (SEQ ID NO: 224) |

TABLE 85

Primer Sequences (shown from 5' to 3') Disclosed in Examples 27-30.

| Primer Name | Sequence* |
| --- | --- |
| XX7 | GGAGAAAACCCATATGTCGTTTAC (SEQ ID NO: 225) |
| XX9 | GCAGCCGAACGCTCGAGGGCGGCCG (SEQ ID NO: 226) |
| His_Not1_1947_rev | CTCGAGCGGCCGCTTAGTGGTGGTGGTGGTGGTGTTTAGTAAA ATCAA (SEQ ID NO: 227) |
| Sal1_for | GAAAGCATAGCAATCTAATCTAAGTT (SEQ ID NO: 228) |
| adhAcoSc_Sal1in_for | GTTTGTCGACATGAAGGCTGCAGTTGTCCGT (SEQ ID NO: 229) |
| adhAcoSC_Not1in_his_rev | TCGAGCGGCCGCTTAGTGGTGGTGGTGGTGGTGCTTCGTGAAG TCTATAACCATTCTACC (SEQ ID NO: 230) |
| pGV1994ep_for | CGGTCTTCAATTTCTCAAGTTTCAGTTTCATTTTTCTTGTTCTATT ACAAC (SEQ ID NO: 231) |
| pGV1994ep_rev | CTAACTCCTTCCTTTTCGGTTAGAGCGGATGTGGG (SEQ ID NO: 232) |

TABLE 85-continued

Primer Sequences (shown from 5' to 3') Disclosed in Examples 27-30.

| Primer Name | Sequence* |
|---|---|
| RecombADHY50_for | TGCTGCCGGAGATTWCGGCAACAAGGCAGG (SEQ ID NO: 233) |
| RecombADHY50_rev | CCTGCCTTGTTGCCGWAATCTCCGGCAGCA (SEQ ID NO: 234) |
| RecombADHL264_for | ATGGTAGCCGTTGCTKTACCAAACACAGAA (SEQ ID NO: 235) |
| RecombADHL264_rev | TTCTGTGTTTGGTAMAGCAACGGCTACCAT (SEQ ID NO: 236) |
| RecombADHI212_Y219_for | GCTGATGTCAYAATTAACTCTGGTGACGTTWACCCTGTAG (SEQ ID NO: 237) |
| RecombADHI212_Y219_rev | CTACAGGGTWAACGTCACCAGAGTTAATTRTGACATCAGC (SEQ ID NO: 238) |
| NNKADHF50_for | TGCTGCCGGAGATNNKGGCAACAAG (SEQ ID NO: 239) |
| NNKADHF50_rev | GCCTTGTTGCCMNNATCTCCGGCAG (SEQ ID NO: 240) |
| NNKADHR77_for | GTTAGTTCTCTCNNKGTAGGTGATAG (SEQ ID NO: 241) |
| NNKADHR77_rev | CACTCTATCACCTACMNNGAGAGAAC (SEQ ID NO: 242) |
| NNKADHA108_for | ACATTTGCCGAGAANNKAAAAACGC (SEQ ID NO: 243) |
| NNKADHA108_rev | ACCAGCGTTTTTMNNTTCTCGGCAAA (SEQ ID NO: 244) |
| NNKADHF113_for | GTCAAAAACGCTGGTNNKAGCGTTGA (SEQ ID NO: 245) |
| NNKADHF113_rev | ACCATCAACGCTMNNACCAGCGTTTT (SEQ ID NO: 246) |
| NNKADHT212_for | AGATAGGTGCTGATGTCNNKATTAAC (SEQ ID NO: 247) |
| NNKADHT212_rev | CAGAGTTAATMNNGACATCAGCACCT (SEQ ID NO: 248) |
| NNKADHV264_for | GGTAGCCGTTGCTNNKCCAAACACAG (SEQ ID NO: 249) |
| NNKADHV264_rev | ATTTCTGTGTTTGGMNNAGCAACGGC (SEQ ID NO: 250) |
| Recomb2F50Minilib_for | GTTGCAGCAGGTGATTDKGGCAACAAAGCA (SEQ ID NO: 251) |
| Recomb2F50Minilib_rev | TGCTTTGTTGCCMHAATCACCTGCTGCAAC (SEQ ID NO: 252) |
| Recom b2Q77Gen5_for3 | TGATGTAAGCTCGCTTCAAGTTGGTGATCG (SEQ ID NO: 253) |
| Recom b2Q77Gen5_rev4 | CGATCACCAACTTGAAGCGAGCTTACATCA (SEQ ID NO: 254) |
| Recomb2R77Gen5_for5 | TGATGTAAGCTCGCTTCGAGTTGGTGATCG (SEQ ID NO: 255) |
| Recomb2R77Gen5_rev6 | CGATCACCAACTCGAAGCGAGCTTACATCA (SEQ ID NO: 256) |
| Recomb2S77Gen5_for7 | TGATGTAAGCTCGCTTTCTGTTGGTGATCG (SEQ ID NO: 257) |

TABLE 85-continued

Primer Sequences (shown from 5' to 3') Disclosed in Examples 27-30.

| Primer Name | Sequence* |
|---|---|
| Recomb2S77Gen5_rev8 | CGATCACCAACAGAAAGCGAGCTTACATCA (SEQ ID NO: 258) |
| Recomb2Y113 GenS_for9 | TTAAAAATGCAGGATATTCAGTTGATGGCG (SEQ ID NO: 259) |
| Recomb2Y113 Gen5_rev10 | CGCCATCAACTGAATATCCTGCATTTTAA (SEQ ID NO: 260) |
| Recomb2F113 Gen5_for11 | TTAAAAATGCAGGATTTTCAGTTGATGGCG (SEQ ID NO: 261) |
| Recomb2F113 Gen5_rev12 | CGCCATCAACTGAAAATCCTGCATTTTAA (SEQ ID NO: 262) |
| Recomb2G113 Gen5_for13 | TTAAAAATGCAGGAGGGTCAGTTGATGGCG (SEQ ID NO: 263) |
| Recomb2G113 Gen5_rev14 | CGCCATCAACTGACCCTCCTGCATTTTAA (SEQ ID NO: 264) |
| Recomb2T212 Mini_for15 | GAGCTGATGTGRYAATCAATTCTGGTGATG (SEQ ID NO: 265) |
| Recomb2T212 Mini_rev16 | CATCACCAGAATTGATTRYCACATCAGCTC (SEQ ID NO: 266) |
| Recomb2V264 Mini_for17 | TGGTTGCTGTGGCAKTACCCAATACTGAGA (SEQ ID NO: 267) |
| Recomb2V264 Mini_rev18 | TCTCAGTATTGGGTAMTGCCACAGCAACCA (SEQ ID NO: 268) |

*A (Adenine), G (Guanine), C (Cytosine), T (Thymine), U (Uracil), R (Purine - A or G), Y (Pyrimidine - C or T), N (Any nucleotide), W (Weak - A or T), S (Strong - G or C), M (Amino - A or C), K (Keto - G or T), B (Not A - G or C or T), H (Not G - A or C or T), D (Not C - A or G or T), and V (Not T - A or G or C)

Media and Buffers:

SC-URA: 6.7 g/L Difco™ Yeast Nitrogen Base, 14 g/L Sigma™ Synthetic Dropout Media supplement (includes amino acids and nutrients excluding histidine, tryptophan, and leucine), 10 g/L casamino acids, 20 g/L glucose, 0.018 g/L adenine hemisulfate, and 0.076 g/L tryptophan.

SD-URA: Commercially available at MP Biomedicals (Irvine, Calif.). Composition: 1.7 g/L yeast nitrogen base (YNB), 5 g/L ammonium sulfate, 20 g/L glucose, with casamino acids without uracil CSM-URA.

YPD (yeast peptone dextrose) media: 10 g/L yeast extract, 20 g/L peptone, 20 g/L glucose.

Tris-DTT: 0.39 g 1,4-dithiothreitol per 1 mL of 1 M TrisHCl, pH 8.0, filter sterilized.

Buffer A: 20 mM Tris, 20 mM imidazol, 100 mM NaCl, 10 mM $MgCl_2$, adjusted to pH 7.4, filter sterilized.

Buffer B: 20 mM Tris, 300 mM imidazol, 100 mM NaCl, 10 mM $MgCl_2$, adjusted to pH 7.4, filter sterilized.

Buffer E: 1.2 g Tris base, 92.4 g glucose, and 0.2 g $MgCl_2$ per 1 L of deionized water, adjusted to pH 7.5, filter sterilized.

Construction of pET1947: The L. lactis adhA (Ll_adhA) gene was cloned out of pGV1947 using primers His_Not1_1947_fwd and SalI_rev and ligated into pET22b(+), yielding plasmid pET1947.

Construction of pGV2476: Plasmid pGV2274 served as template for PCR using forward primer adhAcoSc_SalIin_for and reverse primer adhAcoSC_NotIin_his_rev. The PCR product was purified, restriction digested with NotI and SalI, and ligated into pGV1662, which had been cut with NotI and SalI and purified.

Transformation of S. cerevisiae: In the evening before a planned transformation, a YPD culture was inoculated with a single S. cerevisiae CEN.PK2 colony and incubated at 30° C. and 250 rpm over night. On the next morning, a 20 mL YPD culture was started in a 250 mL Erlenmeyer flask without baffles with the overnight culture at an $OD_{600}$ of 0.1. This culture was incubated at 30° C. and 250 rpm until it reached an $OD_{600}$ of 1.3-1.5. When the culture had reached the desired $OD_{600}$, 200 µL of Tris-DTT were added, and the culture was allowed to incubate at 30° C. and 250 rpm for another 15 min. The cells were then pelleted at 4° C. and 2,500×g for 3 min. After removing the supernatant, the pellet was resuspended in 10 mL of ice-cold buffer E and spun down again as described above. Then, the cell pellet was resuspended in 1 mL of ice-cold buffer E and spun down one more time as before. After removal of the supernatant with a pipette, 200 µL of ice-cold buffer E were added, and the pellet was gently resuspended. The 6 µL of insert/backbone mixture was split in half and added to 50 µL of the cell suspension. The DNA/cell mixtures were transferred into 0.2 cm electroporation cuvettes (BIORAD) and electroporated without a pulse controller at 0.54 kV and 25 µF. Immediately, 1 mL of pre-warmed YPD was added, and the transformed cells were allowed to regenerate at 30° C. and 250 rpm in 15 mL round bottom culture tubes (Falcon). After 1 hour, the cells were spun down at 4° C. and 2,500×g for 3 min, and the pellets were resuspended in 1 mL pre-warmed SD-URA media. Different amounts of transformed cells were plated on SD-URA plates and incubated at 30° C. for 1.5 days or until the colonies were large enough to be picked with sterile toothpicks.

Plasmid Mini-Preparation of Yeast Cells: The Zymoprep™ II—Yeast Plasmid Miniprep kit (Zymo Research, Orange, Calif.) was used to prepare plasmid DNA from *S. cerevisiae* cells according to the manufacturer's protocol for liquid cultures, which was slightly altered. An aliquot of 200 μL of yeast cells was spun down at 600×g for 2 min. After decanting the supernatant, 200 μL of Solution 1 were added to resuspend the pellets. To the samples, 3 μL of Zymolyase™ were added and the cell/enzyme suspensions were gently mixed by flicking with a finger. After incubating the samples for 1 hour at 37° C., Solutions 2 and 3 were added and mixed well after each addition. The samples were then spun down at maximum speed and 4° C. for 10 min. The following clean-up over Zymo columns was performed according to the manufacturer's instructions. The plasmid DNA was eluted with 10 μL of PCR grade water. Half of this volume was used to transform *E. coli* DH5α.

Heterologous ADH expression in *E. coli*: Flasks (500 mL Erlenmeyer) containing 50 mL of Luria-Bertani (LB) medium (10 g tryptone, 10 g NaCl, 5 g yeast extract per liter) with ampicillin (final concentration 0.1 mg/mL) were inoculated to an initial $OD_{600}$ of 0.1 using 0.5 mL overnight $LB_{amp}$ culture of a single colony carrying plasmid pET1947. The 50 mL LB expression culture was allowed to grow for 3-4 h at 250 rpm and 37° C. Protein expression was induced at $OD_{600}$ of about 1 with the addition of IPTG to a final concentration of 0.5 mM. Protein expression was allowed to continue for 24 h at 225 rpm and 25° C. Cells were harvested at 5300×g and 4° C. for 10 min, and then cell pellets were frozen at −20° C. until further use.

Heterologous Expression in *S. cerevisiae* CEN.PK2: Flasks (1000 mL Erlenmeyer) filled with 100 mL of SC-URA were inoculated with 1 mL overnight culture (5 mL SC-URA inoculated with a single CEN.PK2 colony, grown at 30° C. and 250 rpm). The expression cultures were grown at 30° C. and 250 rpm for 24 hours. The cells were pelleted at 5300×g for 5 min. The supernatant was discarded and the pellets were spun again. The residual supernatant was then taken off with a pipette. The pellets were frozen at −20° C. until further use.

Heterologous Expression in CEN.PK2 in 96-Well Plates for High Throughput Assays Shallow 96-well plates, 1 mL capacity per well, filled with 300 μL of SC-URA were inoculated with single CEN.PK2 colonies carrying plasmids coding for Ll_adhA$^{his6}$ or variants thereof. Deep 96-well plates, 2 mL capacity per well, filled with 600 μL of SC-URA per well were inoculated with 50 μL of these overnight cultures. The plates were grown at 30° C. and 250 rpm for 24 h, and were then harvested at 5300×g for 5 min and 4° C. and stored at −20° C.

Preparation of ADH-Containing Extracts from *E. coli*: *E. coli* cell pellets containing expressed ADH were thawed and resuspended (0.25 g wet weight/mL buffer) in buffer A. The resuspended cells were lysed by sonication for 1 min with a 50% duty cycle and pelleted at 11000×g and 4° C. for 10 min. Extracts were stored at 4° C.

Preparation of ADH-Containing Extracts from *S. cerevisiae* CEN.PK2: *S. cerevisiae* CEN.PK2 cell pellets containing expressed ADH were thawed and weighed to obtain the wet weight of the pellets. Cells were then resuspended in buffer A such that the result was a 20% cell suspension by mass. Glass beads of 0.5 mm diameter were added to the 1000 μL-mark of (0.5 mm diameter) of a 1.5 mL Eppendorf tube, before 875 μL of cell suspension were added. Yeast cells were lysed by bead beating using a Retsch MM301 mixer mill (Retsch Inc. Newtown, Pa.), mixing 6×1 min each at full speed with 1-min icing steps between. The tubes were centrifuged for 10 min at 23,500×g and 4° C., and the supernatant was removed. Extracts were stored at 4° C.

Purification of ADH: The ADH was purified by IMAC (Immobilized metal affinity chromatography) over a 1 mL Histrap High Performance (histrap HP) column pre-charged with Nickel (GE Healthcare) using an Akta purifier FPLC system (GE Healthcare). The column was equilibrated with four column volumes (cv) of buffer A. After injecting the crude extracts onto the column, the column was washed with buffer A for 2 cvs, followed by a linear gradient to 100% elution buffer B for 15 cvs and collected in 96-well plates. The fractions containing the protein were pooled and at stored at 4° C.

ADH Cuvette Assay: ADH activity was assayed kinetically by monitoring the decrease in NADH concentration by measuring the absorbance at 340 nm. A reaction buffer was prepared containing 100 mM Tris/HCl pH 7.0, 1 mM DTT, 11 mM isobutyraldehyde, and 200 μM NADH. The reaction was initiated by addition of 100 μL of crude extract or purified protein in an appropriate dilution to 900 μL of the reaction buffer.

ADH Microtiter Plate Activity Assay: The activity measurement in microtiter plates is a downscaled cuvette assay. The total volume was 100 μL. Ten μL of crude lysates or purified enzyme, appropriately diluted, were placed in assay plates. The reaction buffer was prepared as described above (isobutyraldehyde substrate only) and 90 μL thereof were added to the enzyme solutions in the plates. The consumption of NADH was recorded at 340 nm in an infinite M200 plate reader (TECAN Trading AG, Switzerland).

ADH High-Throughput Activity Assay: Frozen yeast cell pellets in 96-well plates were thawed at room temperature for 20 min, and then 100 μL of Y-Per (Pierce, Cat# 78990) were added. Plates were vortexed briefly to resuspend the cell pellets. After a 60-min incubation period at room temperature and 130 rpm, 300 μL of 100 mM Tris-HCl (pH 7.0) were added to the plates to dilute the crude extract. Following a centrifugation step at 5,300×g and 4° C. for 10 min, 40 μL of the resulting crude extract were transferred into assay plates (flat bottom, Rainin) using a liquid handling robot. The assay plates were briefly spun down at 4,000 rpm and room temperature. Twelve mL assay buffer per plate were prepared (100 mM Tris-HCl, pH 7.0, 1 mM, 0.5 mM, 0.25 mM or 0.125 mM isobutyraldehyde, 1 mM DTT, 200 μM NADH) and 100 μL thereof were added to each well to start the reaction. The depletion of NADH was monitored at 340 nm in an infinite M200 plate reader (TECAN Trading AG, Switzerland) over 2 min.

Determination of Specific Activity Based on Data Obtained from the Activity Assays The protein concentrations of samples containing heterologously expressed *L. lactis* AdhA, such as crude extract and purified proteins, were measured using the Quick Start™ Bradford Kit (Bio-Rad, Hercules, Calif.) following the manufacturer's instructions. One unit of enzyme activity (1 U) is defined as the amount of enzyme that catalyzes the conversion of one micromole of substrate per minute under the specified conditions of the assay method.

Thermostability Measurements: $T_{50}$ values (temperature, at which 50% of the enzyme activity is retained after an incubation time of 15 min) of the parent Ll_adhA and variants thereof were measured to obtain thermostability data. Thirty μL aliquots of purified enzyme were transferred into PCR tubes. Each tube was assigned to a specific incubation temperature, which corresponded to a slot on the block of a Mastercycler®ep PCR machine (Eppendorf, Hamburg, Germany) programmed with a gradient covering a 20° C.-temperature range. The tubes were incubated for 15 min in their slots. Then, the reaction was quenched on ice. The residual activity was determined with the ADH microtiter plate activity assay as described above.

Use of His-Tags for Purification: In each of the examples described below, reference is made to an ADH enzyme comprising a his-tag. As is understood in the art, such his-tags facilitate protein purification. As would be understood by one skilled in the art equipped with the present disclosure, ADH enzymes lacking said his-tags are equally or better suited for the conversion of isobutyraldehyde to isobutanol. Examples of the modified ADH enzymes described herein which lack the purification-enabling his-tags are found in SEQ ID NOs: 206-224.

Example 27

Directed Evolution Via Random Mutagenesis

The following example illustrates a method for improving kinetic properties of an ADH and also describes the kinetic properties of such improved ADH enzymes.

Plasmid pGV2476, a derivative of plasmid pGV1662, carrying the Ll_adhA_coSc$^{his6}$ gene served as template for error prone PCR using forward primer pGV1994ep_for and reverse primer pGV1994_rev. These primers are specific to the backbone pGV1662 and bind 50 bp upstream and downstream of the ADH insert to create an overlap for homologous recombination in yeast. The compositions of the three error prone PCR reactions are summarized in Table 86. The temperature profile was the following: 95° C. 3 min initial denaturation, 95° C. 30 s denaturation, 55° C. 30 s annealing, 72° C. 2 min elongation, 25 cycles, 5 min final elongation at 72° C.

TABLE 86

PCR Conditions for the Error Prone Libraries.

|  | final MnCl$_2$ conc. [µM] | | |
| --- | --- | --- | --- |
|  | 100 | 200 | 300 |
| Template [ng] | 2 | 2 | 2 |
| primer forward [µM] | 0.2 | 0.2 | 0.2 |
| primer reverse [µM] | 0.2 | 0.2 | 0.2 |
| dNTP's [µM] | 400 | 400 | 400 |
| Taq buffer (10x stock) [µL] | 10 | 10 | 10 |
| MgCl$_2$ [µM] | 7 | 7 | 7 |
| Taq polymerase [U] | 8 | 8 | 8 |
| MnCl$_2$ (1 mM stock) [µM] | 100 | 200 | 300 |
| PCR grade water [µL] | 41.4 | 31.4 | 21.4 |

The PCR products were checked on a 1% analytical TAE agarose gel, DpnI digested for 1 h at 37° C. to remove traces of template DNA, and then cleaned up using a 1% preparative TAE agarose gel. The agarose pieces containing the PCR products were cleaned using Freeze 'n' Squeeze tubes (BIO-RAD, Hercules, Calif.; catalog #732-6166) followed by pellet paint procedure (Novagen, catalog #69049-3) according to manufacturers' protocols. In the meantime, plasmid pGV1662 was restriction digested with NotI and SalI before running out the digestion mixture on an agarose gel and pellet painting. Plasmid and insert, 500 ng each, were mixed together, precipitated with pellet paint, resuspended in 6 µL of PCR grade water, and used to transform electrocompetent *S. cerevisiae* cells as described in General Methods.

A total of 88 clones from each of the 100, 200, and 300 µM MnCl$_2$ libraries were picked into 96-well plates along with four clones containing parent plasmid pGV2476 and three clones containing pGV1102 as no-ADH control. One well was left empty and served as a sterility control. After screening these libraries as described under General Methods (Heterologous expression in CEN.PK2 in 96-well plates for high throughput assays, ADH high-throughput activity assay), the 300 µM library was chosen and an additional 4,000 clones were screened in the same way. A total of 24 variants had a more than 1.5-fold improvement compared to wild type and were chosen for a re-screen in triplicate. The top ten variants thereof were grown and expressed in 100 mL cultures as described under General Methods (Heterologous expression in *S. cerevisiae* CEN.PK2), and their specific activities in crude yeast extracts were determined as described under General Methods (ADH microtiter plate assay). Two variants, Ll_AdhA$^{28E7\text{-}his6}$ and Ll_AdhA$^{30C11\text{-}his6}$ exhibited a more than 2-fold improvement in activity (0.3 and 0.25 U/mg total lysate protein, respectively) compared to the wild-type enzyme Ll_AdhA$^{his6}$ (0.1 U/mg total lysate protein) and were characterized in greater detail.

Figure 17:
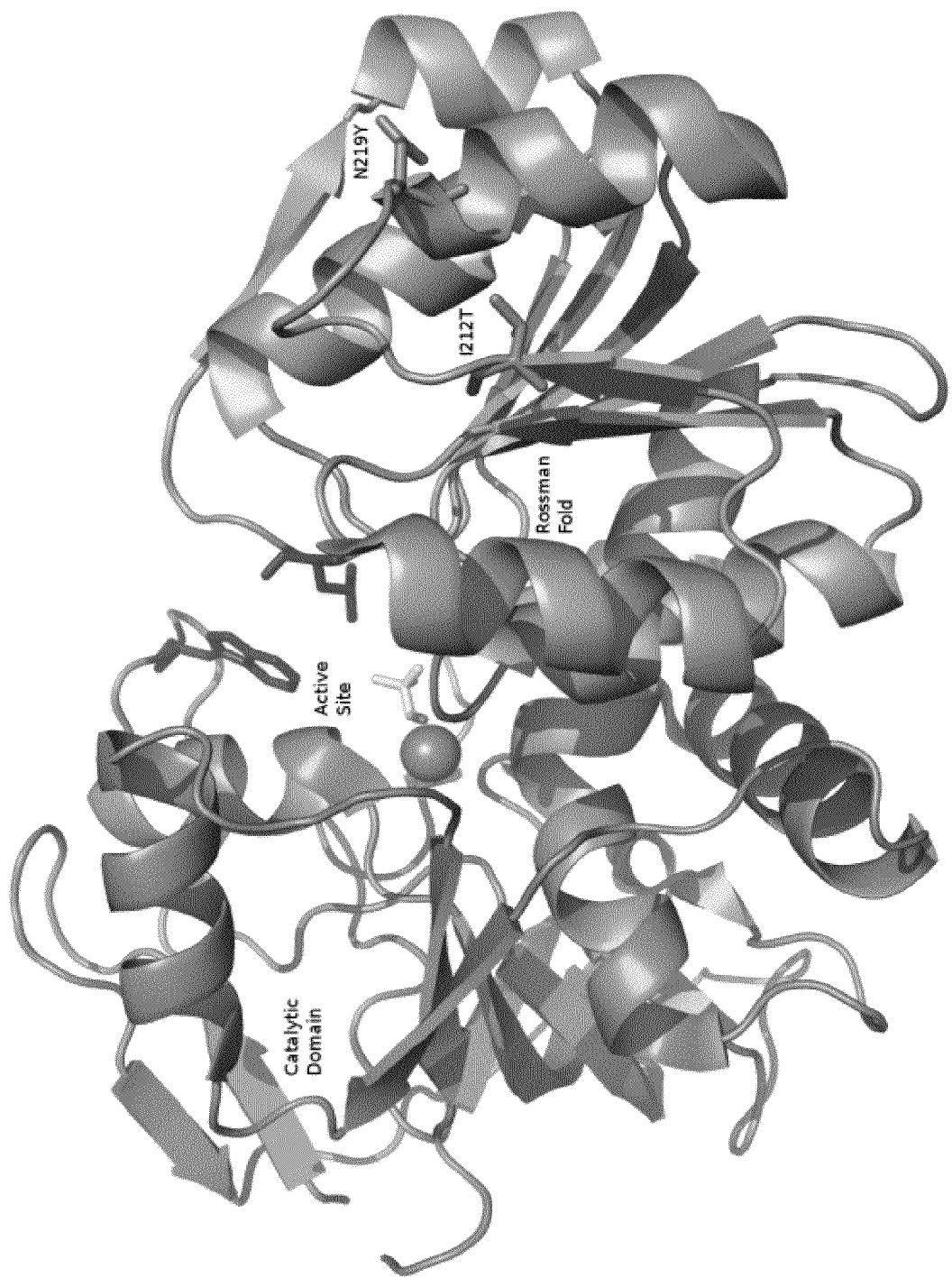
FIG. 17 illustrates a structural alignment of the L. lactis AdhA amino acid sequence with the structure of G. stearothermophilus (Pymol). Active site mutations are shown (Y50F and L264V). Mutations in the co-factor binding domain are also shown (I212T and N219Y).
Figure 17:
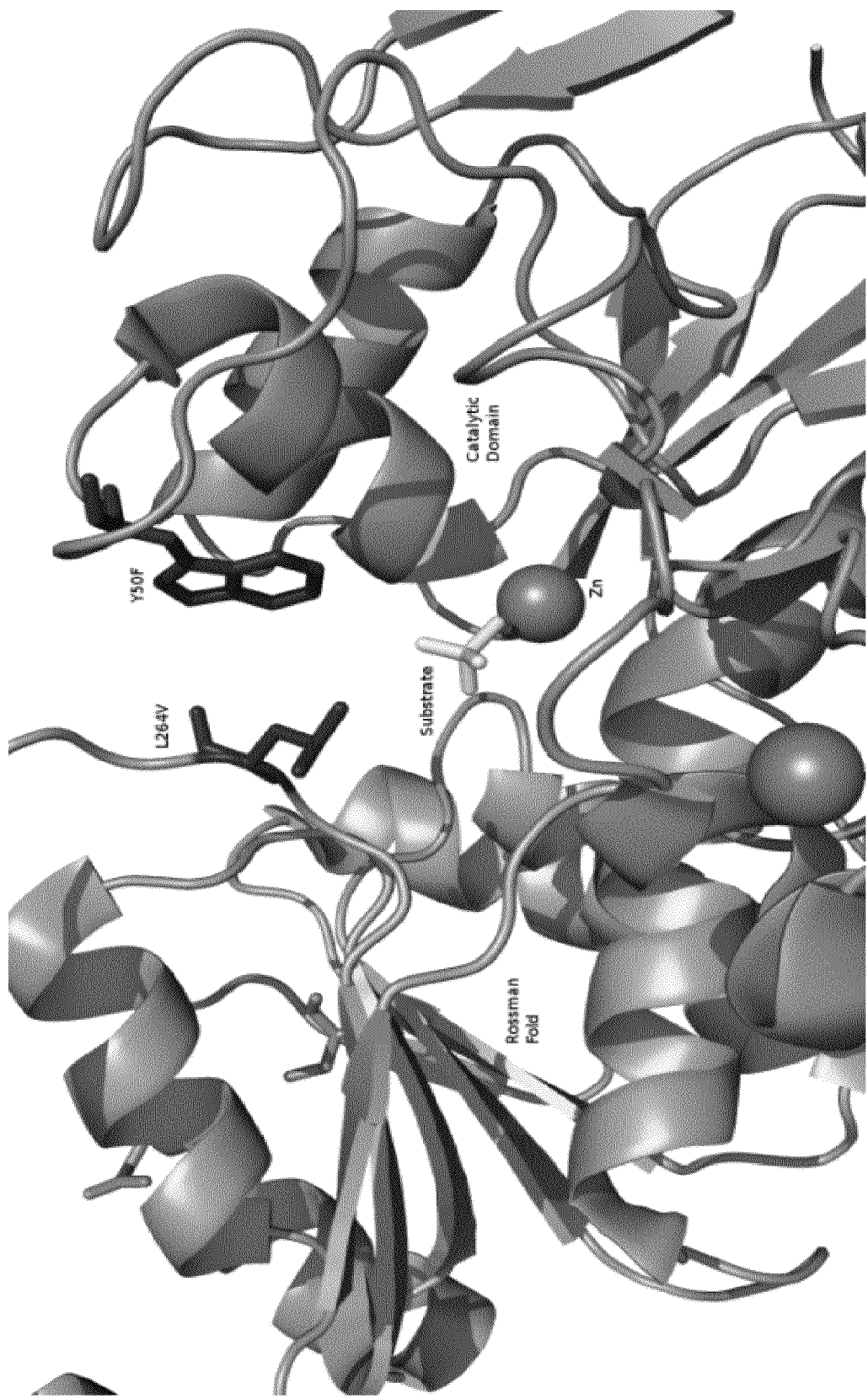

Plasmid DNA from these two variants was extracted as described under General Methods (Plasmid mini-preparation out of yeast cells) and subjected to DNA sequencing (Laragen, Los Angeles, Calif.), which revealed two mutations per variant as listed in Table 87. Two of these mutations (Y50F and L264V) are localized in close proximity to the active site which is a gap between the substrate binding domain (cyan) and the cofactor binding domain (green). Mutations I212T and N219Y are located on the surface of the cofactor binding domain (as shown in FIG. 17). In order to highlight the location of the cofactor binding site mutations, FIG. 17 entails two views on the structure alignment.

TABLE 87

List of Mutations Found in Two Improved Variants of the First Error Prone Library (Generation 1).

| Variant | Mutations |
| --- | --- |
| Ll_adhA$^{28E7\text{-}his6}$ | N219Y, L264V |
| Ll_adhA$^{30C11\text{-}his6}$ | Y50F, I212T |

The two enzyme variants, Ll_AdhA$^{28E7\text{-}his6}$ and Ll_AdhA$^{30C11\text{-}his6}$, were expressed from plasmids pGV2475 and pGV30C11, respectively on larger scale (100 mL cultures each), purified, and characterized in greater detail as described under General Methods (Heterologous expression in *S. cerevisiae* CEN.PK2, Preparation of ADH-containing extracts from *S. cerevisiae* CEN.PK2, Purification of ADH). The wild-type Ll_AdhA$^{his6}$ enzyme was expressed from plasmid pGV2476 and purified in the same way. The enzymes were characterized for the kinetic properties as described under General Methods (ADH cuvette assay). Table 88 shows the kinetic parameters measured with isobutyraldehyde and NADH. A decreased $K_M$-value was observed for both variants, while the $k_{cat}$ was only improved for Ll_AdhA$^{28E7}$.

TABLE 88

Kinetic Parameters of the Two Variants (Generation 1) on Isobutyraldehyde Compared to the Parental Enzyme.

| Variant | Crude Lysate U/mg | Purified Protein $K_M$ [mM] | U/mg | $k_{cat}$ [s$^{-1}$] | $k_{cat}/K_M$ [M$^{-1}$ * s$^{-1}$] |
|---|---|---|---|---|---|
| Ll_AdhA$^{his6}$ | 0.28 ± 0.08 | 11.7 ± 0.6 | 25 ± 0.2 | 30 | 2,800 |
| Ll_AdhA$^{28E7\text{-}his6}$ | 0.74 ± 0.15 | 2.7 ± 0.2 | 43 ± 2 | 60 | 21,000 |
| Ll_AdhA$^{30C11\text{-}his6}$ | 0.46 ± 0.2 | 3.9 ± 0.1 | 60 ± 0.2 | 80 | 20,000 |

The thermostability of the wild-type enzyme and the two variants was determined as described under General Methods (Thermostability measurements). The mutations found had a positive impact on the stability of the variants in addition to the beneficial effects on their catalytic efficiency. Table 89 summarizes the $T_{50}$s measured for the parent and the variants.

TABLE 89

Summary of the $T_{50}$s of the Parent Enzyme and the Variants.

| Variant | $T_{50}$ [° C.], 15 min |
|---|---|
| Ll_AdhA$^{his6}$ | 54.4 ± 0.5 |
| Ll_AdhA$^{28E7\text{-}his6}$ | 62.3 ± 0.3 |
| Ll_AdhA$^{30C11\text{-}his6}$ | 57.6 ± 0.6 |

Example 28

Directed Evolution Via Recombination

The following example illustrates a method for improving kinetic properties of an ADH and also illustrates the kinetic properties of such improved ADH enzymes.

A second gene library (Generation 2) was constructed to recombine beneficial mutations found in the first error prone library and the wild-type residue at each of these sites (Table 90).

TABLE 90

Amino Acid Mutations Included in the Recombination Library.

| Amino Acid Position | Wild-type | Mutations | Total # (including wild-type) |
|---|---|---|---|
| 50 | Y | F | 2 |
| 212 | I | T | 2 |
| 219 | Y | N | 2 |
| 264 | L | V | 2 |

Four PCR fragments were generated using primers RecombADHY50_rev and pGV1994ep_for (fragment 1), RecombADHY50_for and RecombADHI212_Y219_rev (fragment 2), RecombADHI212_Y219_for and RecombADHL264_rev (fragment 3), and RecombADHL264_rev and pGV1994ep_rev (fragment 4). The fragments were analyzed on an analytical 1% TAE gel, DpnI digested, separated on a 1% preparative TAE agarose gel, Freeze'n'Squeeze (BIORAD) treated, and finally pellet painted (Novagen). The clean fragments served as template for the assembly PCR. After the successful assembly PCR, the PCR products were treated as described in Example 27, mixed with pGV1662 backbone as described in Example 27, and the mixture was used to transform S. cerevisiae as described in General Methods for Examples 27-30. Eighty single clones of the recombination library were picked and compared in a high-throughput screen to the wild type and the two variants found in the error prone library.

A total of 80 single clones were picked into a 96-well plate along with the original parent and the two improved variants. After screening the recombination plate, as described under General Methods (Heterologous expression in CEN.PK2 in 96-well plates for high throughput assays, ADH high-throughput activity assay), twelve variants, all exhibiting at least two-fold higher activity compared to either parent Ll_AdhA$^{28E7\text{-}his6}$ or Ll_AdhA$^{30C11\text{-}his6}$ were grown and expressed in 100 mL cultures as described under General Methods (Heterologous expression in S. cerevisiae CEN.PK2), and their activities in crude yeast extracts were determined as described under General Methods (ADH microtiter plate assay). Two variants had very similar specific activity in crude extract. Ll_AdhA$^{RE1}$ was chosen for further modifications, as its activity was 40% better than Ll_AdhA$^{28E7\text{-}his6}$ and 64% better than Ll_AdhA$^{30C11\text{-}his6}$.

Plasmid DNA from this variant was extracted as described under General Methods (Plasmid mini-preparation out of yeast cells) and subjected to DNA sequencing (Laragen, Los Angeles, Calif.), which revealed that mutations Y50F, I212T, and L264V (found in Ll_AdhA$^{RE1}$) contributed to the observed improvements, whereas the mutation at position 219 was deleterious for the activity of the variants and was not found in any of the improved variants of the recombination library.

The variant Ll_AdhA$^{RE1\text{-}his6}$ was expressed from plasmid pGV2477, on larger scale (100 mL cultures each), purified, and characterized in greater detail as described under General Methods (Heterologous expression in S. cerevisiae CEN.PK2, Preparation of ADH-containing extracts from S. cerevisiae CEN.PK2, Purification of ADH). The wild-type Ll_AdhA$^{his6}$ enzyme was expressed from plasmid pGV2476 and purified in the same way. The enzymes were characterized for the kinetic properties as described under General Methods (ADH cuvette assay). Table 91 shows the kinetic parameters measured with isobutyraldehyde and NADH. Compared to Ll_AdhA$^{his6}$, Ll_AdhA$^{28E7\text{-}his6}$, Ll_AdhA$^{30C11\text{-}his6}$ a decreased $K_M$ and an increased $k_{cat}$ was observed for Ll_AdhA$^{RE1\text{-}his6}$.

TABLE 91

Biochemical Properties of Ll_AdhA$^{RE1}$ as Measured on Isobutyraldehyde.

| Variant | Crude Lysate U/mg | Purified Protein | | | |
|---|---|---|---|---|---|
| | | $K_M$ [mM] | U/mg | $k_{cat}$ [s$^{-1}$] | $k_{cat}/K_M$ [M$^{-1}$ * s$^{-1}$] |
| Ll_AdhA$^{his6}$ | 0.28 ± 0.08 | 11.7 ± 0.6 | 25 ± 0.2 | 30 | 2,800 |
| Ll_AdhA$^{28E7\text{-}his6}$ | 0.74 ± 0.15 | 2.7 ± 0.2 | 43 ± 2 | 60 | 21,000 |
| Ll_AdhA$^{30C11\text{-}his6}$ | 0.46 ± 0.2 | 3.9 ± 0.1 | 60 ± 0.2 | 80 | 20,000 |
| Ll_AdhA$^{RE1\text{-}his6}$ | 1.15 ± 0.2 | 1.7 ± 0.0 | 105 ± 1 | 140 | 82,000 |

Variant Ll_adhA$^{RE1\text{-}his6}$, exhibited a $T_{50}$ value of 61.6±0.1° C. which is 5 degrees higher than the $T_{50}$ of the wt and roughly 1 degree lower than the most stable parent of the recombination round, Ll_AdhA$^{28E7\text{-}his6}$.

Example 29

Directed Evolution of the L. lactis AdhA Via Random Mutagenesis, Site Saturation Mutagenesis, and Recombination The following example illustrates a method for improving kinetic properties of an ADH and also describes the kinetic properties of such improved ADH enzymes.

The Ll_adhA$^{RE1\text{-}his6}$ gene served as template for a second round of error prone PCR and screening (Generation 3). The screening assay utilized 0.125 mM isobutyraldehyde. About 3,000 clones of a library generated using error prone PCR with 200 μM MnCl$_2$ according to Example 1 above were expressed and screened in a high throughput fashion. Several hits were chosen for a rescreen in triplicate and two variants, Ll_AdhA$^{744\text{-}his6}$ and Ll_AdhA$^{443\text{-}his6}$, were identified with improved activity. The mutations of these variants are depicted in Table 92.

TABLE 92

List of Mutations Accumulated in Generation 3 Variants Ll_AdhA$^{744\text{-}his6}$ and Ll_AdhA$^{443\text{-}his6}$.

| Variant | Mutations |
|---|---|
| Ll_AdhA$^{744\text{-}his6}$ | Y50F, I212T, L264V, Q77R, V108A |
| Ll_AdhA$^{443\text{-}his6}$ | Y50F, I212T, L264V, Y113F |

The specific activities (U/mg) in lysates of Ll_AdhA$^{744\text{-}his6}$ and Ll_AdhA$^{443\text{-}his6}$, as well as the parents, were measured in biological triplicates at pH 7.0 (Table 93).

TABLE 93

Biochemical Properties of Ll_AdhA$^{744\text{-}his6}$ and Ll_AdhA$^{443\text{-}his6}$ at pH 7.0.

| Variant | Crude Lysate [U/mg] | Purified Protein | | | |
|---|---|---|---|---|---|
| | | $K_M$ [mM] | U/mg | $k_{cat}$ [s$^{-1}$] | $k_{cat}/K_M$ [M$^{-1}$ * s$^{-1}$] |
| Ll_AdhA$^{744\text{-}his6}$ | 1.14 ± 0.1 | 1.2 ± 0.2 | 88.8 ± 2.9 | 117 | 94,000 |
| Ll_AdhA$^{443\text{-}his6}$ | 1.36 ± 0.1 | 0.9 ± 0.1 | 70 ± 2.9 | 95 | 100,000 |

The $T_{50}$ values of Ll_AdhA$^{744\text{-}his6}$ (59.4° C.) and Ll_AdhA$^{443\text{-}his6}$ (57.6° C.) were both higher than Ll_AdhA$^{his6}$ and lower than Ll_AdhA$^{RE1\text{-}his6}$.

After two rounds of error prone PCR and one round of recombination, site-saturation mutagenesis was performed at each of the six sites, generating six libraries (library 50, 77, 108, 113, 212, and 264). The original parent, Ll_AdhA$^{his6}$, was used as template for each NNK fragment. Two fragments for each library were amplified using primers listed in Table 4 (pGV1994ep_for and NNKADHF50_rev for fragment 1 of library 50, NNKADHF50_for and pGV1994ep_rev for fragment 2 of library 50; pGV1994ep_for and NNKADHR77_rev for fragment 1 of library 77, NNKADHR77_for and pGV1994ep_rev for fragment 2 of library 77; pGV1994ep_for and NNKADHA108_rev for fragment 1 of library 108, NNKADHA108_for and pGV1994ep_rev for fragment 2 of library 108; pGV1994ep_for and NNKADHF113_rev for fragment 1 of library 113, NNKADHF113_for and pGV1994ep_rev for fragment 2 of library 113; pGV1994ep_for and NNKADHT212_rev for fragment 1 of library 212, NNKADHT212_for and pGV1994ep_rev for fragment 2 of library 212; pGV1994ep_for and NNKADHV264_rev for fragment 1 of library 264, NNKADHV264_for and pGV1994ep_rev for fragment 2 of library 264), and were then used as templates for assembly PCR. The assembly PCR products were treated as described before to generate the NNK libraries in yeast. Ninety clones were picked for each NNK library, and screened separately. After rescreening, nine clones from six libraries were mini-prepped from yeast, the plasmids were used to transform E. coli, and the resulting plasmids were sequenced. Their lysate activities and sequencing results are summarized in Table 94.

TABLE 94

Summary of Site Saturation Mutagenesis (Generation 4).

| Position of NNK Libraries | Variant | U/mg in Lysate | Mutation Found in NNK Library | Exemplary Mutations Found in NNK Library | Mutations for Recombination |
|---|---|---|---|---|---|
| — | Ll_adhA$^{his6}$ | 0.28 ± 0.08 | | | |
| — | Ll_AdhA$^{RE1}$ | 1.15 ± 0.20 | | | |
| 50 | 1G4 | 0.78 ± 0.02 | Y50W | F, W | C, L, F, W, Y, X |

TABLE 94-continued

Summary of Site Saturation Mutagenesis (Generation 4).

| Position of NNK Libraries | Variant | U/mg in Lysate | Mutation Found in NNK Library | Exemplary Mutations Found in NNK Library | Mutations for Recombination |
|---|---|---|---|---|---|
| 77 | 2G3 | 0.42 ± 0.00 | Q77S | R, S | Q, R, S |
| 77 | 2H2 | 0.43 ± 0.00 | — | — | — |
| 108 | 3D10 | 0.61 ± 0.01 | V108A | — | — |
| 108 | 3D12 | 0.53 ± 0.07 | V108S | — | — |
| 113 | 4A3b | 0.38 ± 0.05 | Y113G | F, G | Y, F, G |
| 113 | 4E6 | 0.30 ± 0.04 | Y113G | — | — |
| 212 | 5D2 | 0.92 ± 0.02 | I212V | T, V | A, I, T, V |
| 264 | 6E12 | 0.38 ± 0.07 | L264V | V | I, V |

A variety of mutations found in the site saturation mutagenesis libraries were recombined in a combinatorial fashion using SOE PCR and the library was constructed using non-codon optimized parent, pGV1947his. The primers described in Table 85 allowed for wild-type sequence at the six targeted sites as well. Six fragments were generated using Recomb2F50Minilib_rev and pGV1994ep_for (fragment 1), Recomb2F50Minilib_for and mix of Recomb2Q77Gen5_rev4, Recomb2R77Gen5_rev6 and Recomb2S77Gen5_rev8 (fragment 2), mix of Recomb2Q77Gen5_for 3, Recomb2R77Gen5_for 5 and Recomb2S77Gen5_for 7 and mix of Recomb2Y113 Gen5_rev10, Recomb2F113 Gen5_rev12 and Recomb2G113 Gen5_rev14 (fragment 3), mix of Recomb2Y113 Gen5_for 9, Recomb2F113 Gen5_for 11 and Recomb2G113 Gen5_for 13 and Recomb2T212 Mini_rev16 (fragment 4), Recomb2T212 Mini_for 15 and Recomb2V264 Mini_rev18 (fragment 5), and Recomb2V264 Mini_for 17 and pGV1994ep_rev (fragment 6). The fragment PCRs were analyzed on an analytical 1% TAE gel and then, the products were DpnI digested for 1 h at 37° C., separated on a 1% preparative TAE agarose gel, Freeze'n'Squeeze (BIORAD) treated, and finally pellet painted (Novagen). The clean fragments served as template for the assembly PCR. After the successful assembly PCR, homologous recombination (as described above) was used to create the library. Over a thousand individual clones were screened using an isobutyraldehyde concentration of 0.125 mM. A rescreening plate was compiled consisting of the top 60 variants and assayed with 0.125 mM isobutyraldehyde.

Ten variants were chosen for expression in 100 mL SC-URA medium to determine their specific activities in lysate. Four of them were sequenced (See Table 95 for mutations), purified, and characterized in greater detail (Table 96). The new variants showed similar specific activities in lysate as Ll_AdhA$^{RE1}$. Notably, variant 4A3 stood out as an enzyme with the high specific activity.

TABLE 95

List of Mutations in Variants from Generation 5.

| Variant | Mutations |
|---|---|
| Ll_AdhA$^{1H7\text{-}his6}$ | Y50F, I212A, L264V, Y113F |
| Ll_AdhA$^{10F10\text{-}his6}$ | Y50F, I212T, L264V, Q77S, Y113F |
| Ll_AdhA$^{8F11\text{-}his6}$ | Y50F, I212A, L264V, Q77R, Y113F |
| Ll_AdhA$^{8D10\text{-}his6}$ | Y50F, I212V, L264V, Q77S, Y113F |

TABLE 96

Biochemical Properties of Variants from Generation 5.

| Variant | Crude Lysate U/mg | $K_M$ [mM] | Purified Protein U/mg | $k_{cat}$ [s$^{-1}$] | $k_{cat}/K_M$ [M$^{-1}$ * s$^{-1}$] |
|---|---|---|---|---|---|
| Ll_AdhA$^{1H7\text{-}his6}$ | 1.12 ± 0.11 | | 39.9 ± 1.7 | | |
| Ll_AdhA$^{10F10\text{-}his6}$ | 1.15 ± 0.17 | | 75.4 ± 12.3 | | |
| Ll_AdhA$^{8F11\text{-}his6}$ | 1.09 ± 0.13 | 0.8 ± 0.2 | 41.7 ± 0.2 | 55 | 68233 |
| Ll_AdhA$^{8D10\text{-}his6}$ | 1.05 ± 0.08 | | 58.8 ± 4.5 | | |

Example 30

Engineering of Homologous ADH Enzymes

The following example illustrates how additional ADH enzymes are identified and engineered for improving kinetic properties of additional ADH enzymes.

Enzymes homologous to the L. lactis AdhA were identified through BlastP searches of publicly available databases using amino acid sequence of L. lactis AdhA (SEQ ID NO: 185) with the following search parameters: Expect threshold=10, word size=3, matrix=Blosum62, gap opening=11, gap extension=1. The top hundred hits, representing homologues with about greater than about 60% sequence identity were selected and are listed in Table 97. The sequences were aligned using the multiple sequence alignment tool AlignX, a component of Vector NTI Advance 10.3.1 with the following parameters: Gap opening pentalty=10, gap extension penalty=0.05, gap separation penalty range=8. The multiple sequence alignment showed very high levels of conservation amongst the residues corresponding to (a) tyrosine 50 of the L. lactis AdhA (SEQ ID NO: 185); (b) glutamine 77 of the L. lactis AdhA (SEQ ID NO: 185); (c) valine 108 of the L. lactis AdhA (SEQ ID NO: 185); (d) tyrosine 113 of the L. lactis AdhA (SEQ ID NO: 185); (e) isoleucine 212 of the L. lactis AdhA (SEQ ID NO: 185); and (f) leucine 264 of the L. lactis AdhA (SEQ ID NO: 185), wherein AdhA (SEQ ID NO: 185) is encoded by the *L. lactis* alcohol dehydrogenase (ADH) gene adhA (SEQ ID NO: 184) or a codon-optimized version thereof (SEQ ID NO: 206).

TABLE 97

Homologous Enzymes with >60% Sequence Identity to *L. lactis* AdhA

| Accession | Description | % Sequence Identity | E value | Total Score |
|---|---|---|---|---|
| YP_003354381.1 | alcohol dehydrogenase 1 [*Lactococcus lactis* subsp. *lactis* KF147] | 100 | 0 | 684 |
| NP_267964.1 | alcohol dehydrogenase [*Lactococcus lactis* subsp. *lactis* Il1403] | 99 | 0 | 681 |
| YP_001033251.1 | alcohol dehydrogenase [*Lactococcus lactis* subsp. *cremoris* MG1363] | 95 | 0 | 659 |
| YP_811585.1 | alcohol dehydrogenase [*Lactococcus lactis* subsp. *cremoris* SK11] | 95 | 0 | 658 |
| ZP_07367864.1 | alcohol dehydrogenase [*Pediococcus acidilactici* DSM 20284] | 69 | 2.00E−129 | 466 |
| YP_794451.1 | alcohol dehydrogenase [*Lactobacillus brevis* ATCC 367] | 66 | 1.00E−127 | 460 |
| ZP_06197454.1 | alcohol dehydrogenase [*Pediococcus acidilactici* 7_4] | 69 | 8.00E−124 | 447 |
| YP_001374103.1 | alcohol dehydrogenase [*Bacillus cereus* subsp. *cytotoxis* NVH 391-98] | 65 | 1.00E−123 | 447 |
| ZP_00741101.1 | Alcohol dehydrogenase [*Bacillus thuringiensis* serovar *israelensis* ATCC 35646] | 64 | 9.00E−123 | 444 |
| ZP_04431756.1 | Alcohol dehydrogenase GroES domain protein [*Bacillus coagulans* 36D1] | 63 | 1.00E−122 | 444 |
| ZP_04101989.1 | Alcohol dehydrogenase 1 [*Bacillus thuringiensis* serovar *berliner* ATCC 10792] | 64 | 1.00E−122 | 443 |
| ZP_03943574.1 | alcohol dehydrogenase [*Lactobacillus buchneri* ATCC 11577] | 62 | 2.00E−122 | 443 |
| YP_002338331.1 | alcohol dehydrogenase [*Bacillus cereus* AH187] | 64 | 2.00E−122 | 443 |
| ZP_04145518.1 | Alcohol dehydrogenase 1 [*Bacillus thuringiensis* serovar *tochigiensis* BGSC 4Y1] | 64 | 2.00E−122 | 443 |
| ZP_00236660.1 | alcohol dehydrogenase, propanol-preferring [*Bacillus cereus* G9241] | 64 | 2.00E−122 | 443 |
| ZP_03954717.1 | alcohol dehydrogenase [*Lactobacillus hilgardii* ATCC 8290] | 62 | 2.00E−122 | 443 |
| ZP_06011170.1 | alcohol dehydrogenase 1 [*Leptotrichia goodfellowii* F0264] | 65 | 2.00E−122 | 442 |
| ZP_07537679.1 | Alcohol dehydrogenase zinc-binding domain protein [*Actinobacillus pleuropneumoniae* serovar 9 str. CVJ13261] | 63 | 2.00E−122 | 442 |
| NP_844655.1 | alcohol dehydrogenase [*Bacillus anthracis* str. Ames] | 64 | 3.00E−122 | 442 |
| ZP_04071880.1 | Alcohol dehydrogenase 1 [*Bacillus thuringiensis* IBL 200] | 64 | 3.00E−122 | 442 |
| YP_001844344.1 | alcohol dehydrogenase [*Lactobacillus fermentum* IFO 3956] | 64 | 3.00E−122 | 442 |
| ZP_04227732.1 | Alcohol dehydrogenase 1 [*Bacillus cereus* Rock3-29] | 64 | 4.00E−122 | 442 |
| YP_002529920.1 | alcohol dehydrogenase [*Bacillus cereus* Q1] | 64 | 4.00E−122 | 442 |
| ZP_03107320.1 | putative alcohol dehydrogenase, zinc-containing [*Bacillus cereus* NVH0597-99] | 64 | 5.00E−122 | 441 |
| YP_001644942.1 | alcohol dehydrogenase [*Bacillus weihenstephanensis* KBAB4] | 64 | 5.00E−122 | 441 |
| ZP_03940565.1 | alcohol dehydrogenase [*Lactobacillus brevis* subsp. *gravesensis* ATCC 27305] | 62 | 5.00E−122 | 441 |
| ZP_05863633.1 | alcohol dehydrogenase [*Lactobacillus fermentum* 28-3-CHN] | 64 | 5.00E−122 | 441 |
| ZP_04174477.1 | Alcohol dehydrogenase 1 [*Bacillus cereus* AH1273] | 64 | 5.00E−122 | 441 |
| ZP_04168725.1 | Alcohol dehydrogenase 1 [*Bacillus mycoides* DSM 2048] | 64 | 5.00E−122 | 441 |
| ZP_03945523.1 | alcohol dehydrogenase [*Lactobacillus fermentum* ATCC 14931] | 64 | 5.00E−122 | 441 |
| YP_894846.1 | alcohol dehydrogenase [*Bacillus thuringiensis* str. Al Hakam] | 64 | 6.00E−122 | 441 |
| ZP_04273257.1 | Alcohol dehydrogenase 1 [*Bacillus cereus* BDRD-ST24] | 64 | 6.00E−122 | 441 |
| ZP_07337905.1 | alcohol dehydrogenase [*Actinobacillus pleuropneumoniae* serovar 2 str. 4226] | 63 | 6.00E−122 | 441 |
| YP_795183.1 | alcohol dehydrogenase [*Lactobacillus brevis* ATCC 367] | 64 | 6.00E−122 | 441 |
| ZP_03234447.1 | putative alcohol dehydrogenase, zinc-containing [*Bacillus cereus* H3081.97] | 64 | 7.00E−122 | 441 |
| ZP_00134308.2 | COG1064: Zn-dependent alcohol dehydrogenases [*Actinobacillus pleuropneumoniae* serovar 1 str. 4074] | 63 | 7.00E−122 | 441 |
| NP_831985.1 | alcohol dehydrogenase [*Bacillus cereus* ATCC 14579] | 64 | 7.00E−122 | 441 |
| NP_978607.1 | alcohol dehydrogenase [*Bacillus cereus* ATCC 10987] | 65 | 7.00E−122 | 441 |
| YP_002366965.1 | alcohol dehydrogenase [*Bacillus cereus* B4264] | 64 | 8.00E−122 | 441 |

TABLE 97-continued

Homologous Enzymes with >60% Sequence Identity to *L. lactis* AdhA

| Accession | Description | % Sequence Identity | E value | Total Score |
|---|---|---|---|---|
| ZP_04283955.1 | Alcohol dehydrogenase 1 [*Bacillus cereus* ATCC 4342] | 64 | 8.00E−122 | 441 |
| ZP_04218185.1 | Alcohol dehydrogenase 1 [*Bacillus cereus* Rock3-44] | 64 | 1.00E−121 | 441 |
| ZP_04186048.1 | Alcohol dehydrogenase 1 [*Bacillus cereus* AH1271] | 64 | 1.00E−121 | 441 |
| ZP_07542038.1 | Alcohol dehydrogenase zinc-binding domain protein [*Actinobacillus pleuropneumoniae* serovar 11 str. 56153] | 63 | 1.00E−121 | 440 |
| YP_003664530.1 | alcohol dehydrogenase [*Bacillus thuringiensis* BMB171] | 64 | 1.00E−121 | 440 |
| ZP_04222478.1 | Alcohol dehydrogenase 1 [*Bacillus cereus* Rock3-42] | 64 | 1.00E−121 | 440 |
| ZP_04305999.1 | Alcohol dehydrogenase 1 [*Bacillus cereus* 172560W] | 64 | 1.00E−121 | 440 |
| ZP_04317351.1 | Alcohol dehydrogenase 1 [*Bacillus cereus* ATCC 10876] | 64 | 2.00E−121 | 440 |
| YP_001035842.1 | alcohol dehydrogenase [*Streptococcus sanguinis* SK36] | 66 | 2.00E−121 | 439 |
| ZP_07336540.1 | alcohol dehydrogenase [*Actinobacillus pleuropneumoniae* serovar 6 str. Femo] | 63 | 2.00E−121 | 439 |
| ZP_03232573.1 | putative alcohol dehydrogenase, zinc-containing [*Bacillus cereus* AH1134] | 64 | 2.00E−121 | 439 |
| ZP_04084316.1 | Alcohol dehydrogenase 1 [*Bacillus thuringiensis* serovar *huazhongensis* BGSC 4BD1] | 64 | 2.00E−121 | 439 |
| YP_036379.1 | alcohol dehydrogenase [*Bacillus thuringiensis* serovar *konkukian* str. 97-27] | 64 | 2.00E−121 | 439 |
| ZP_03713785.1 | hypothetical protein EIKCOROL_01470 [*Eikenella corrodens* ATCC 23834] | 64 | 3.00E−121 | 439 |
| ZP_04300512.1 | Alcohol dehydrogenase 1 [*Bacillus cereus* MM3] | 64 | 3.00E−121 | 439 |
| ZP_04261933.1 | Alcohol dehydrogenase 1 [*Bacillus cereus* BDRD-ST196] | 64 | 3.00E−121 | 439 |
| ZP_04197309.1 | Alcohol dehydrogenase 1 [*Bacillus cereus* AH603] | 64 | 3.00E−121 | 439 |
| ZP_04289229.1 | Alcohol dehydrogenase 1 [*Bacillus cereus* R309803] | 64 | 6.00E−121 | 438 |
| YP_001449881.1 | alcohol dehydrogenase [*Streptococcus gordonii* str. Challis substr. CH1] | 64 | 1.00E−120 | 437 |
| YP_002886170.1 | Alcohol dehydrogenase zinc-binding domain protein [*Exiguobacterium* sp. AT1b] | 64 | 1.00E−120 | 437 |
| ZP_03072955.1 | Alcohol dehydrogenase GroES domain protein [*Lactobacillus reuteri* 100-23] | 63 | 3.00E−120 | 435 |
| ZP_01817011.1 | alcohol dehydrogenase, zinc-containing [*Streptococcus pneumoniae* SP3-BS71] | 65 | 5.00E−120 | 435 |
| ZP_03974464.1 | alcohol dehydrogenase [*Lactobacillus reuteri* CF48-3A] | 63 | 6.00E−120 | 434 |
| ZP_01824429.1 | alcohol dehydrogenase, zinc-containing [*Streptococcus pneumoniae* SP11-BS70] | 65 | 8.00E−120 | 434 |
| YP_002735395.1 | alcohol dehydrogenase [*Streptococcus pneumoniae* JJA] | 65 | 8.00E−120 | 434 |
| CAQ49114.1 | alcohol dehydrogenase, propanol-preferring [*Staphylococcus aureus* subsp. *aureus* ST398] | 63 | 1.00E−119 | 434 |
| ZP_01819490.1 | alcohol dehydrogenase, zinc-containing [*Streptococcus pneumoniae* SP6-BS73] | 65 | 1.00E−119 | 434 |
| ZP_01832462.1 | alcohol dehydrogenase, zinc-containing [*Streptococcus pneumoniae* SP19-BS75] | 65 | 1.00E−119 | 434 |
| ZP_01834441.1 | alcohol dehydrogenase, zinc-containing [*Streptococcus pneumoniae* SP23-BS72] | 65 | 1.00E−119 | 433 |
| ZP_07644167.1 | alcohol dehydrogenase, propanol-preferring [*Streptococcus mitis* NCTC 12261] | 65 | 1.00E−119 | 433 |
| NP_344823.1 | alcohol dehydrogenase [*Streptococcus pneumoniae* TIGR4] | 65 | 1.00E−119 | 433 |
| YP_003878532.1 | alcohol dehydrogenase, propanol-preferring [*Streptococcus pneumoniae* 670-6B] | 65 | 1.00E−119 | 433 |
| YP_001272079.1 | alcohol dehydrogenase [*Lactobacillus reuteri* DSM 20016] | 63 | 1.00E−119 | 433 |
| ZP_03960239.1 | alcohol dehydrogenase [*Lactobacillus vaginalis* ATCC 49540] | 62 | 1.00E−119 | 433 |
| ZP_07646288.1 | alcohol dehydrogenase [*Streptococcus mitis* SK564] | 65 | 2.00E−119 | 433 |
| YP_002739644.1 | alcohol dehydrogenase [*Streptococcus pneumoniae* 70585] | 65 | 2.00E−119 | 433 |
| YP_002737553.1 | alcohol dehydrogenase [*Streptococcus pneumoniae* P1031] | 65 | 2.00E−119 | 433 |
| YP_002741829.1 | alcohol dehydrogenase [*Streptococcus pneumoniae* Taiwan19F-14] | 65 | 2.00E−119 | 433 |
| ZP_05689169.1 | alcohol dehydrogenase GroES domain-containing protein [*Staphylococcus aureus* A9299] | 63 | 2.00E−119 | 432 |
| ZP_07642509.1 | alcohol dehydrogenase [*Streptococcus mitis* SK597] | 65 | 2.00E−119 | 432 |
| ZP_02718124.1 | alcohol dehydrogenase, propanol-preferring [*Streptococcus pneumoniae* CDC3059-06] | 65 | 2.00E−119 | 432 |

TABLE 97-continued

Homologous Enzymes with >60% Sequence Identity to *L. lactis* AdhA

| Accession | Description | % Sequence Identity | E value | Total Score |
|---|---|---|---|---|
| ZP_07647302.1 | alcohol dehydrogenase family protein [*Streptococcus mitis* SK321] | 65 | 2.00E−119 | 432 |
| NP_371129.1 | alcohol dehydrogenase [*Staphylococcus aureus* subsp. *aureus* Mu50] | 62 | 3.00E−119 | 432 |
| NP_645385.1 | alcohol dehydrogenase [*Staphylococcus aureus* subsp. *aureus* MW2] | 62 | 3.00E−119 | 432 |
| ZP_01826570.1 | alcohol dehydrogenase, zinc-containing [*Streptococcus pneumoniae* SP14-BS69] | 65 | 4.00E−119 | 432 |
| CBW35926.1 | alcohol dehydrogenase [*Streptococcus pneumoniae* INV104] | 65 | 4.00E−119 | 432 |
| YP_003305918.1 | Alcohol dehydrogenase zinc-binding domain protein [*Streptobacillus moniliformis* DSM 12112] | 63 | 4.00E−119 | 432 |
| YP_003445415.1 | alcohol dehydrogenase, propanol-preferring, COG1064 [*Streptococcus mitis* B6] | 64 | 4.00E−119 | 432 |
| ZP_05900148.1 | alcohol dehydrogenase, propanol-preferring [*Leptotrichia hofstadii* F0254] | 64 | 6.00E−119 | 431 |
| ZP_06901123.1 | alcohol dehydrogenase [*Streptococcus parasanguinis* ATCC 15912] | 64 | 1.00E−118 | 430 |
| ZP_05685696.1 | alcohol dehydrogenase [*Staphylococcus aureus* A9635] | 62 | 1.00E−118 | 430 |
| ZP_07728047.1 | alcohol dehydrogenase, propanol-preferring [*Streptococcus parasanguinis* F0405] | 63 | 2.00E−118 | 430 |
| ZP_04783075.1 | alcohol dehydrogenase [*Weissella paramesenteroides* ATCC 33313] | 62 | 4.00E−118 | 429 |
| YP_003163500.1 | Alcohol dehydrogenase GroES domain protein [*Leptotrichia buccalis* DSM 1135] | 63 | 7.00E−118 | 427 |
| ZP_05745418.1 | alcohol dehydrogenase [*Lactobacillus antri* DSM 16041] | 63 | 3.00E−117 | 426 |
| ZP_07729093.1 | alcohol dehydrogenase, propanol-preferring [*Lactobacillus oris* PB013-T2-3] | 63 | 4.00E−117 | 425 |
| ZP_03960690.1 | alcohol dehydrogenase [*Lactobacillus vaginalis* ATCC 49540] | 61 | 1.00E−116 | 424 |
| YP_003920444.1 | RBAM017440 [*Bacillus amyloliquefaciens* DSM7] | 60 | 2.00E−116 | 422 |
| ZP_04603652.1 | hypothetical protein GCWU000324_03153 [*Kingella oralis* ATCC 51147] | 62 | 3.00E−116 | 422 |
| ZP_05553195.1 | mycothiol-dependent formaldehyde dehydrogenase [*Lactobacillus coleohominis* 101-4-CHN] | 63 | 4.00E−116 | 422 |
| ZP_07073134.1 | alcohol dehydrogenase, propanol-preferring [*Rothia dentocariosa* M567] | 63 | 1.00E−115 | 421 |

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

What is claimed is:

1. A modified alcohol dehydrogenase (ADH) comprising one or more modifications at positions corresponding to amino acids selected from the group consisting of: (a) tyrosine 50 of the wild-type *Lactococcus lactis* AdhA (SEQ ID NO: 185); (b) glutamine 77 of the wild-type *Lactococcus lactis* AdhA (SEQ ID NO: 185); (c) valine 108 of the wild-type *Lactococcus lactis* AdhA (SEQ ID NO: 185); (d) tyrosine 113 of the wild-type *Lactococcus lactis* AdhA (SEQ ID NO: 185); (e) isoleucine 212 of the wild-type *Lactococcus lactis* AdhA (SEQ ID NO: 185); and (f) leucine 264 of the wild-type *Lactococcus lactis* AdhA (SEQ ID NO: 185), wherein said modified ADH is at least 95% identical to SEQ ID NO: 185 and has ADH activity.

2. The modified alcohol dehydrogenase (ADH) of claim 1, wherein said tyrosine 50 residue is replaced with a phenylalanine or tryptophan residue.

3. The modified alcohol dehydrogenase (ADH) of claim 1, wherein said glutamine 77 residue is replaced with an arginine or serine residue.

4. The modified alcohol dehydrogenase (ADH) of claim 1, wherein said valine 108 residue is replaced with a serine or alanine residue.

5. The modified alcohol dehydrogenase (ADH) of claim 1, wherein said tyrosine 113 residue is replaced with a phenylalanine or glycine residue.

6. The modified alcohol dehydrogenase (ADI-I) of claim 1, wherein. said isoleucine 212 residue is replaced with a threonine, alanine, or valine residue.

7. The modified alcohol dehydrogenase (ADH) of claim 1, wherein said leucine 264 residue is replaced with a valine residue.

8. The modified alcohol dehydrogenase (ADH) of claim 1, wherein the ADH is codon optimized for expression in a host cell.

9. The modified alcohol dehydrogenase (ADH) of claim 8, wherein said host cell is yeast.

10. The modified alcohol dehydrogenase (ADH) of claim 8, wherein said host cell is *Escherichia coli*.

* * * * *